US008648116B2

(12) United States Patent
Vernier et al.

(10) Patent No.: US 8,648,116 B2
(45) Date of Patent: *Feb. 11, 2014

(54) DERIVATIVES OF N-(ARYLAMINO) SULFONAMIDES INCLUDING POLYMORPHS AS INHIBITORS OF MEK AS WELL AS COMPOSITIONS, METHODS OF USE AND METHODS FOR PREPARING THE SAME

(75) Inventors: Jean-Michel Vernier, Laguna Niguel, CA (US); Colin Edward Rowlings, Encinitas, CA (US); Jean-Luc Girardet, Aliso Viejo, CA (US); Stuart Dimock, Lake Forest, CA (US); Barry Quart, Encinitas, CA (US); Jeffrey N. Miner, San Diego, CA (US)

(73) Assignee: Ardea Biosciences, Inc., San Diego, CA (US)

( * ) Notice: Subject to any disclaimer, the term of this patent is extended or adjusted under 35 U.S.C. 154(b) by 471 days.

This patent is subject to a terminal disclaimer.

(21) Appl. No.: 12/671,287

(22) PCT Filed: Jul. 28, 2008

(86) PCT No.: PCT/US2008/071392
§ 371 (c)(1),
(2), (4) Date: Sep. 7, 2010

(87) PCT Pub. No.: WO2009/018233
PCT Pub. Date: Feb. 5, 2009

(65) Prior Publication Data
US 2011/0060049 A1    Mar. 10, 2011

Related U.S. Application Data

(63) Continuation-in-part of application No. 11/830,733, filed on Jul. 30, 2007, now Pat. No. 8,101,799, and a

(51) Int. Cl.
*A61K 31/185* (2006.01)
*C07C 311/00* (2006.01)

(52) U.S. Cl.
USPC ................ 514/602; 514/601; 564/84; 564/80

(58) Field of Classification Search
USPC .......... 514/171, 249, 601, 602; 435/184, 375; 564/80, 84
See application file for complete search history.

(56) References Cited

U.S. PATENT DOCUMENTS

| 6,545,030 B1 | 4/2003 | Barrett et al. |
| 6,780,870 B2 | 8/2004 | Carter et al. |

(Continued)

FOREIGN PATENT DOCUMENTS

| WO | 2007/014011 A2 | 2/2007 |
| WO | 2007/121269 A2 | 10/2007 |

OTHER PUBLICATIONS

Cancer, Encyclopedia Britannica, 2007, Encyclopedia Britannica Online, 24, 42 pages.*

(Continued)

*Primary Examiner* — Yate K Cutliff
(74) *Attorney, Agent, or Firm* — Millen, White, Zelano & Branigan, P.C.

(57) ABSTRACT

This invention concerns N-(2-arylamino) aryl sulfonamide compounds which are inhibitors of MEK including crystalline polymorphic forms which exhibit a specific powder x-ray diffraction profile and/or a specific differential scanning calorimetry profile. This invention also concerns pharmaceutical compositions comprising the compounds described herein and methods of use of the compounds and compositions described herein, including the use in the treatment and/or prevention of cancer, hyperproliferative diseases and inflammatory conditions. The invention also concerns methods of making the compounds and compositions described herein.

25 Claims, 20 Drawing Sheets

Related U.S. Application Data continuation-in-part of application No. PCT/US2006/028326, filed on Jul. 21, 2006.

(60) Provisional application No. 61/034,466, filed on Mar. 6, 2008, provisional application No. 61/034,464, filed on Mar. 6, 2008, provisional application No. 61/044,886, filed on Apr. 14, 2008, provisional application No. 60/833,886, filed on Jul. 28, 2006, provisional application No. 60/701,814, filed on Jul. 21, 2005, provisional application No. 60/706,719, filed on Aug. 8, 2005, provisional application No. 60/731,633, filed on Oct. 28, 2005.

(56) References Cited

U.S. PATENT DOCUMENTS

| | | |
|---|---|---|
| 7,115,632 B1 | 10/2006 | Bedell et al. |
| 7,842,836 B2 | 11/2010 | Yan et al. |
| 2004/0176418 A1 | 9/2004 | Thiruvengadam et al. |
| 2007/0238710 A1 | 10/2007 | Yan et al. |

OTHER PUBLICATIONS

Punchard, N.A., et al., The Journal of Infammation, 2004, The Journal of Inflammation, pp. 1-4.*

Search Report, dated Mar. 19, 2012, issued in corresponding TW 098107166.

European Search Report from corresponding European Patent Application No. 08796733 dated Jun. 10, 2013.

M. R. Caira et al. "Crystalline Polymorphism of Organic Compounds" Topics in Current Chemistry, vol. 198, [Jan. 1998], pp. 163-208.

* cited by examiner

FIGURE 12
7 day, MTS Assay: 3 Day Growth Inhibition
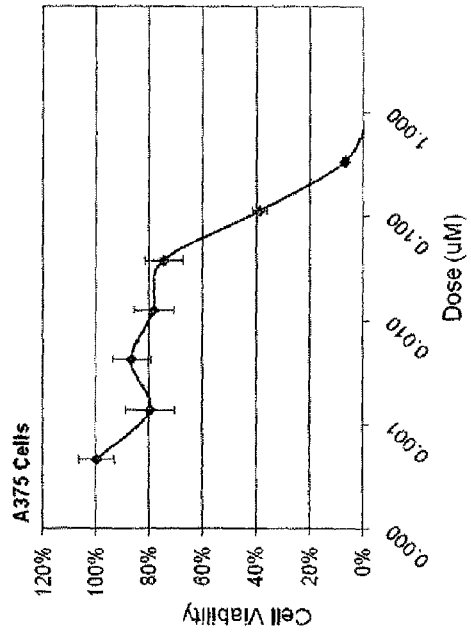
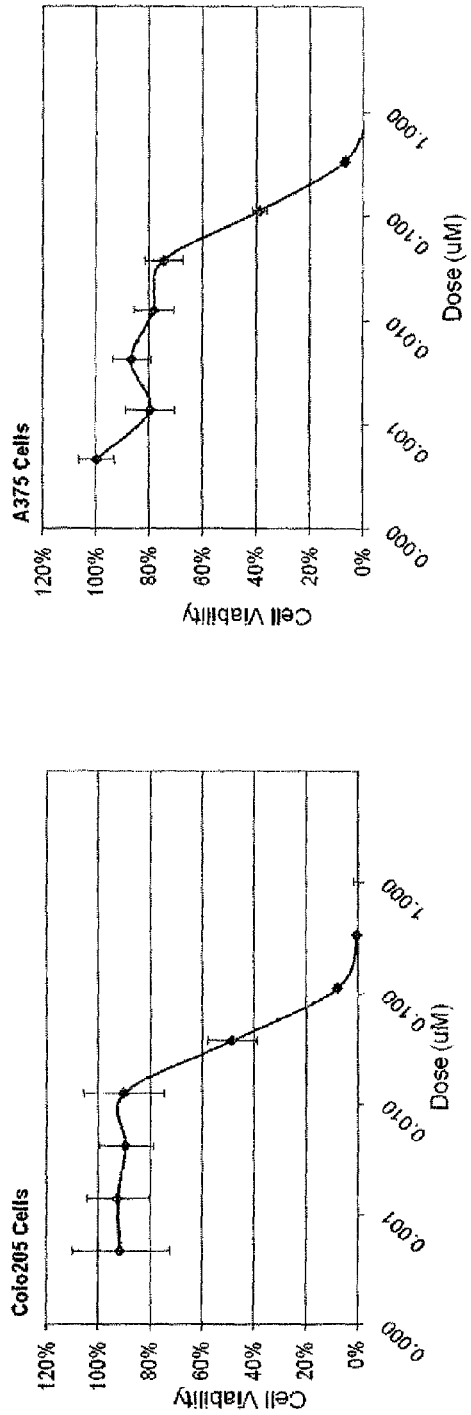
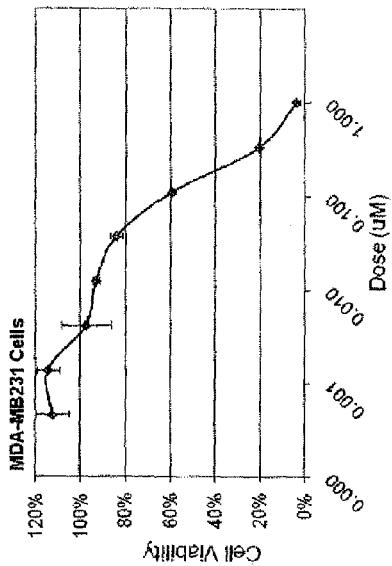

FIGURE 13
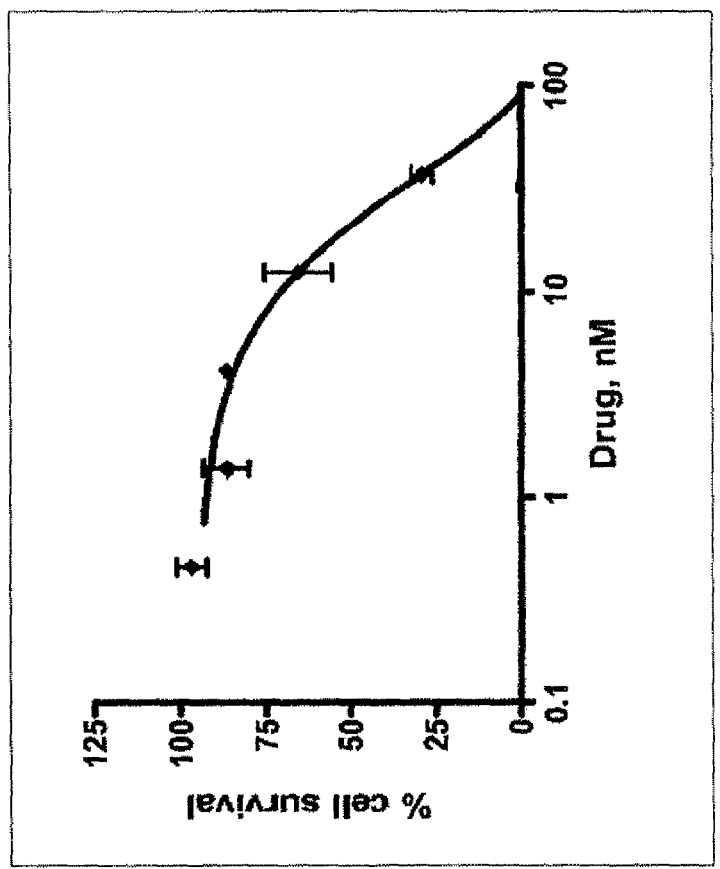
Fig 13(B)
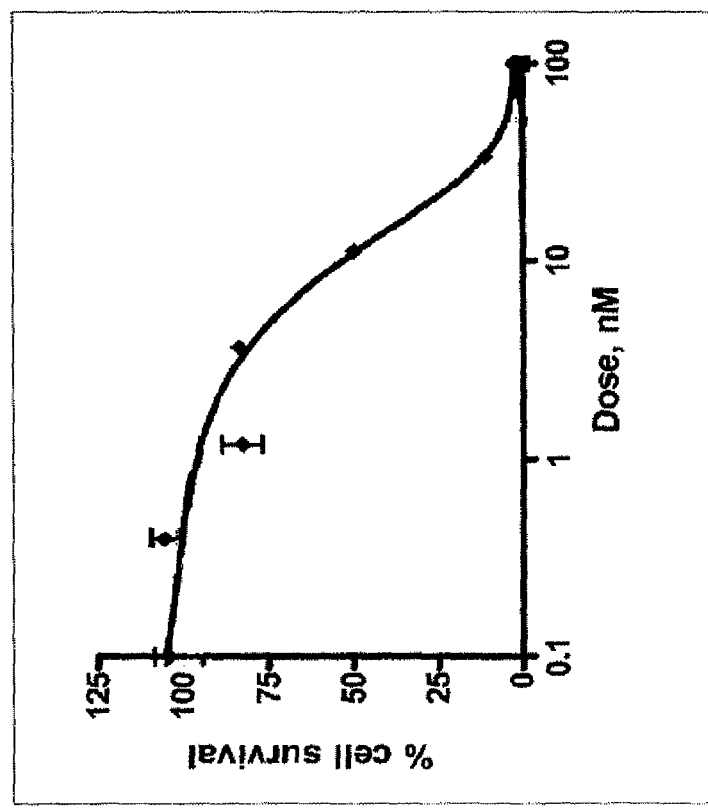
Fig 13(A)

Mean Liver Tumor Weights – tumor bearing mice only

FIGURE 20
All figures: horizontal axis = conc (uM); vertical axis = % cell death
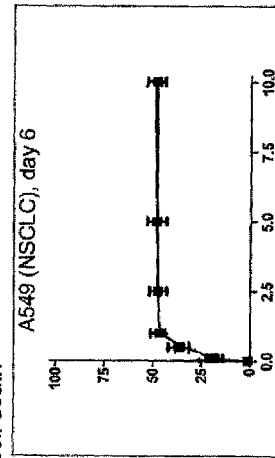
Fig 20(A)
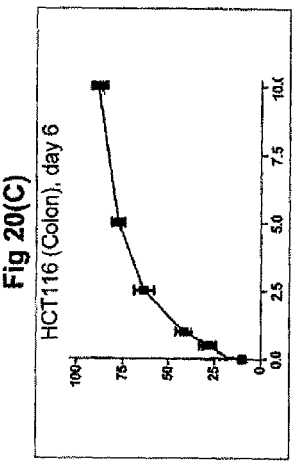
Fig 20(B)
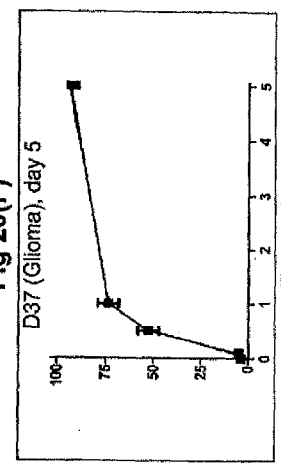
Fig 20(C)
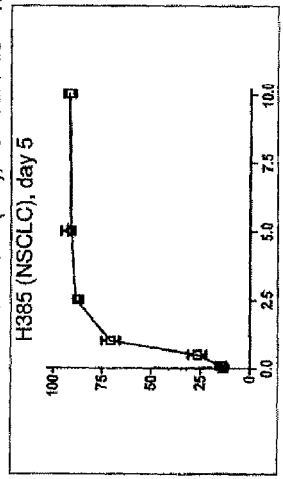
Fig 20(D)
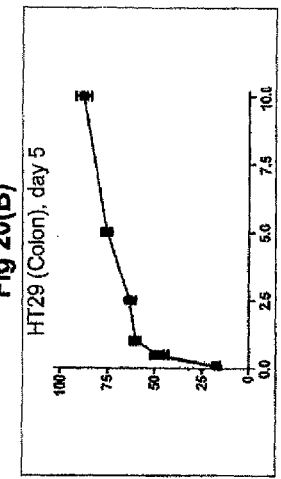
Fig 20(E)
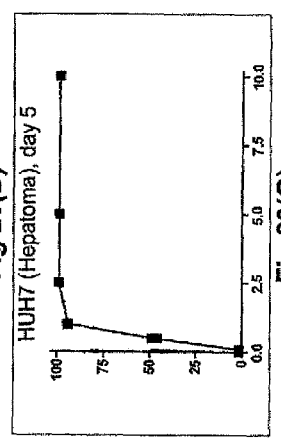
Fig 20(F)
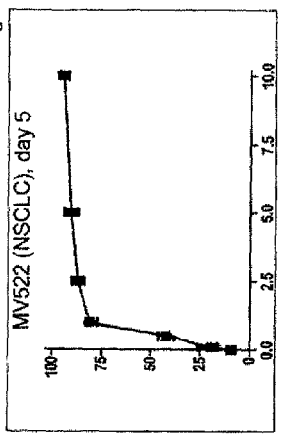
Fig 20(G)
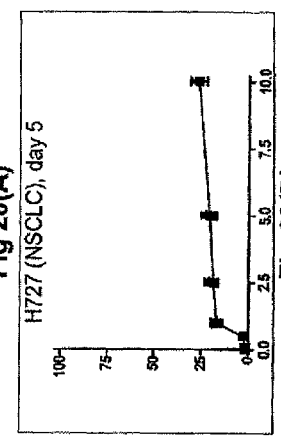
Fig 20(H)
Fig 20(I)

DERIVATIVES OF N-(ARYLAMINO) SULFONAMIDES INCLUDING POLYMORPHS AS INHIBITORS OF MEK AS WELL AS COMPOSITIONS, METHODS OF USE AND METHODS FOR PREPARING THE SAME

CROSS REFERENCE TO RELATED APPLICATIONS

This application is a National Stage Entry of PCT/US08/71392, filed Jul. 28, 2008, and claims the benefit of U.S. Provisional Application Ser. Nos. 61/044,886, filed Apr. 14, 2008, 61/034,466 filed Mar. 6, 2008, and 61/034,464 filed Mar. 6, 2008, and is a Continuation-in-Part of U.S. application Ser. No. 11/830,733, filed Jul. 30, 2007, which issued as U.S. Pat. No. 8,101,799 on Jan. 24, 2012, which claims the benefit of U.S. Provisional Application Ser. No. 60/833,886 filed Jul. 28, 2006, and which is a Continuation-in-Part of International Application Ser. No PCT/US2006/028326 filed Jul. 21, 2006, which claims the benefit of U.S. Provisional Application Ser. Nos. 60/701,814 filed Jul. 21, 2005; 60/706,719 filed Aug. 8, 2005, and to 60/731,633 filed Oct. 28, 2005, each of which is hereby incorporated by reference in the entirety, and each of whose benefit is claimed herein for the present application through the chain of applications recite above.

FIELD OF THE INVENTION

This invention concerns N-(2-arylamino) aryl sulfonamide compounds which are inhibitors of MEK including crystalline polymorphic forms which exhibit a specific powder x-ray diffraction profile and/or a specific differential scanning calorimetry profile. This invention also concerns pharmaceutical compositions comprising the compounds described herein and methods of use of the compounds and compositions described herein, including the use in the treatment and/or prevention of cancer, hyperproliferative diseases and inflammatory conditions. The invention also concerns methods of making the compounds and compositions described herein.

BACKGROUND OF THE INVENTION

Oncogenes—genes that contribute to the production of cancers—are generally mutated forms of certain normal cellular genes ("proto-oncogenes"). Oncogenes often encode abnormal versions of signal pathway components, such as receptor tyrosine kinases, serine-threonine kinases, or downstream signaling molecules. The central downstream signaling molecules are the Ras proteins, which are anchored on the inner surfaces of cytoplasmic membranes, and which hydrolyze bound guanosine triphosphate (GTP) to guanosine diphosphate (GDP). When activated by a growth factor, growth factor receptors initiate a chain of reactions that leads to the activation of guanine nucleotide exchange activity on Ras. Ras alternates between an active "on" state with a bound GTP (hereafter "Ras.GTP") and an inactive "off state with a bound GDP. The active "on" state, Ras.GTP, binds to and activates proteins that control the growth and differentiation of cells.

For example, in the "mitogen-activated protein kinase (MAP kinase) cascade," Ras.GTP leads to the activation of a cascade of serine/threonine kinases. One of several groups of kinases known to require a Ras.GTP for their own activation is the Raf family. The Raf proteins activate "MEK1" and "MEK2," abbreviations for mitogen-activated ERK-activating kinases (where ERK is extracellular signal-regulated protein kinase, another designation for MAPK). MEK1 and MEK2 are dual-function serine/threonine and tyrosine protein kinases and are also known as MAP kinase kinases. Thus, Ras.GTP activates Raf, which activates MEK1 and MEK2, which activate MAP kinase (MAPK). Activation of MAP kinase by mitogens appears to be essential for proliferation, and constitutive activation of this kinase is sufficient to induce cellular transformation. Blockade of downstream Ras signaling, as by use of a dominant negative Raf-1 protein, can completely inhibit mitogenesis, whether induced from cell surface receptors or from oncogenic, Ras mutants.

The interaction of Raf and Ras is a key regulatory step in the control of cell proliferation. To date, no substrates of MEK other than MAPK have been identified; however, recent reports indicate that MEK may also be activated by other upstream signal proteins such as MEK kinase or MEKK1 and PKC. Activated MAPK translocates and accumulates in the nucleus, where it can phosphorylate and activate transcription factors such as Elk-1 and Sap1a, leading to the enhanced expression of genes such as that for c-fos.

Once activated, Raf and other kinases phosphorylate MEK on two neighboring serine residues, $S^{218}$ and $S^{222}$ in the case of MEK1. These phosphorylations are required for activation of MEK as a kinase. In turn, MEK phosphorylates MAP kinase on two residues separated by a single amino acid: a tyrosine, $Y^{185}$ and a threonine, $T^{183}$. MEK appears to associate strongly with MAP kinase prior to phosphorylating it, suggesting that phosphorylation of MAP kinase by MEK may require a prior strong interaction between the two proteins. Two factors—MEK's unusual specificity and its requirement for a strong interaction with MAP kinase prior to phosphorylation—suggest that MEK's mechanism of action may differ sufficiently from the mechanisms of other protein kinases as to allow for selective inhibitors of MEK. Possibly, such inhibitors would operate through allosteric mechanisms rather than through the more usual mechanism involving blockage of an ATP binding site.

Thus, MEK1 and MEK2 are validated and accepted targets for anti-proliferative therapies, even when the oncogenic mutation does not affect MEK structure or expression. See, e.g., U.S. Patent Publications 2003/0149015 by Barrett et al. and 2004/0029898 by Boyle et al.

Several examples of 1-substituted-2(p-substituted-phenylamino)-aryl inhibitors of MEK have been reported. U.S. Pat. Nos. 6,440,966 and 6,750,217 and corresponding publication WO 00/42003 described carboxylic and hydroxamic acid esters and N-substituted amide derivatives of sulfonamide-substituted-2(4-iodophenylamino)-benzoic acid esters and N-substituted benzamides as functioning as MEK inhibitors. The sulfonamide may also be N-substituted.

U.S. Pat. No. 6,545,030 and corresponding publication WO 00/42029 describe MEK inhibitors that are 1-heterocyclyl-2(4-iodophenylamino)-benzene, where the heterocycle is a five-membered nitrogen-containing ring such as pyrazole, triazole, oxazole, isoxazole, and isoxazolinone. The more recent U.S. Patent Publication 2005/004186 describes related compounds in which the 4-iodo substituent of the '030 patent is replaced by a very broad genus of moieties including alkyl, alkoxy, acyloxy, alkenyl, carbamoyl, carbamoylalkyl, carboxyl, carboxylalkyl, N-acylsulfonamido, and others.

U.S. Pat. No. 6,469,004 and corresponding publication WO 00/42022 describe carboxylic and hydroxamic acid esters of a group of heterocyclo-condensed phenylene compounds, i.e., benzimidazoles, benzooxazoles, benzothiazoles, benzothiadiazoles, quinazolines, etc. The heterocycles are 7-F-6-(4-iodo-phenylamino)-5-carboxylic acid esters, carboxylic acid amides or hydroxamic acid esters. More recent publication U.S. 2005/0026970 described similar compounds in which the 4-iodo substituent was replaced by a very broad genus of structures. Related compounds are described in patent publications WO 03/077855, WO 03/77914 and US 2005/0554701. Further examples of 2-(4-iodophenylamino)-phenylhydroxamie acid esters which are reported to be useful as MEK inhibitors can be found in WO 2005/028426.

Patent Publication WO 02/06213 and corresponding U.S. application Ser. No. 10/333,399 (U.S. 2004/0054172) describe hydroxy-substituted acid esters of 1-oxamic acid-2 (4-halophenylamino)-3,4-difluorobenzene. U.S. Pat. No. 6,891,066 and corresponding publication WO 03/62191 describe similar compounds wherein the 4-halo substituent is replaced by a very broad genus of structures. Among the substituents in the 4-position were methyl, ethyl, ethynyl, and 2-hydroxyethyl. Specific related compounds are described in U.S. Pat. No. 6,770,778.

Patent Publication WO 04/083167, published Sep. 30, 2004, (in Japanese) discloses more than two thousand—but provides NMR data for only 400—1-(N-substituted sulfonyl urea)-2(2,4-dihalophenylamino)-3,4-difluorobenzenes and asserts that they useful as MEK inhibitors. Data indicating inhibition of MEK were presented for a subgroup of just twelve. In addition to a secondary or tertiary amine, these twelve compounds all contained one of the following groups: an N,N-disubstituted sulfonyl urea, N-piperazinesulfonamide, N-piperidinesulfonamide or N-pyrrolidinesulfonamide.

The MEK cascade has also been implicated in inflammatory diseases and disorders. U.S. Application Publication No. 2006/0030610 to Koch et al., U.S. Application Publication No. 2006/0140872 to Furue et al. This includes both acute and chronic inflammation disorders. Examples of such disorders are allergic contact dermatitis, rheumatoid arthritis, osteoarthritis, inflammatory bowel diseases, chronic obstructive pulmonary disorder, psoriasis, multiple sclerosis, asthma, diseases and disorders related to diabetic complications, and inflammatory complications of the cardiovascular system such as acute coronary syndrome. Among inflammatory bowel diseases are Crohn's disease and ulcerative colitis.

MBK1 and MEK2 are validated and accepted targets for anti-proliferative therapies, even when the oncogenic mutation does not affect MEK structure or expression. See, e.g., U.S. Patent Publications 2003/0149015 by Barrett et al. and 2004/0029898 by Boyle et al.

SUMMARY OF THE INVENTION

Provided herein are compounds of formula I, or pharmaceutically acceptable salts, solvates, polymorphs, esters, tautomers or prodrugs thereof:

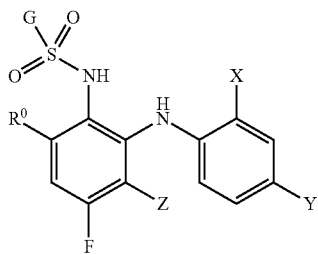

formula I wherein
Z is H or F;
X is F, Cl, $CH_3$, $CH_2OH$, $CH_2F$, $CHF_2$, or $CF_3$;
Y is I, Br, $C_1$, $CF_3$, $C_1$-$C_3$ alkyl, $C_2$-$C_3$ alkenyl, $C_2$-$C_3$ alkynyl, cyclopropyl, OMe, OEt, SMe, phenyl or Het, where Het is a 5- to 10-membered mono- or bicyclic heterocyclic group, which group is saturated, olefinic, or aromatic, containing 1-5 ring heteroatoms selected independently from N, O, and S; where
  all said phenyl or Het groups are optionally substituted with F, Cl, Br, I, acetyl, methyl, CN, $NO_2$, $CO_2H$, $C_1$-$C_3$ alkyl, $C_1$-$C_3$ alkoxy, $C_1$-$C_3$ alkyl-C(=O)—, $C_1$-$C_3$ alkyl-C(=S)—, $C_1$-$C_3$ alkoxy-C(=S)—, $C_1$-$C_3$ alkyl-C(=O)O—, $C_1$-$C_3$ alkyl-O—(C=O)—, $C_1$-$C_3$ alkyl-C(=O)NH—, $C_1$-$C_3$ alkyl-C(=NH)NH—, $C_1$-$C_3$ alkyl-NH—(C=O)—, di-$C_1$-$C_3$ alkyl-N—(C=O)—, $C_1$-$C_3$ alkyl-C(=O)N($C_1$-$C_3$ alkyl)-, $C_1$-$C_3$alkyl-S(=O)$_2$NH— or trifluoromethyl;
  all said methyl, ethyl, $C_1$-$C_3$ alkyl, and cyclopropyl groups are optionally substituted with OH;
  all said methyl groups are optionally substituted with one, two, or three F atoms;
$R^0$ is H, F, Cl, Br, I, $CH_3NH$—, $(CH_3)_2N$—, $C_1$-$C_6$ alkyl, $C_1$-$C_4$ alkoxy, $C_3$-$C_6$ cycloalkyl, $C_2$-$C_6$ alkenyl, $C_2$-$C_6$ alkynyl, phenyl, monosubstituted phenyl, O($C_1$-$C_4$ alkyl), O—C(=O)($C_1$-$C_4$ alkyl) or C(=O)O($C_1$-$C_4$ alkyl); where
  said alkyl, alkoxy, cycloalkyl, alkenyl, alkynyl and phenyl groups are optionally substituted with 1-3 substituents selected independently from F, Cl, Br, I, OH, CN, cyanomethyl, nitro, phenyl and trifluoromethyl;
  said $C_1$-$C_6$ alkyl and $C_1$-$C_4$ alkoxy groups also optionally substituted with $OCH_3$ or $OCH_2CH_3$;
G is $G_1$, $G_2$, $R_{1a}$, $R_{1b}$, $R_{1c}$, $R_{1d}$, $R_{1e}$, $Ar_1$, $Ar_2$ or $Ar_3$; where
$G_1$ is $C_1$-$C_6$ alkyl optionally substituted with one amino, $C_1$-$C_3$ alkylamino, or dialkylamino group, said dialkylamino group comprising two $C_1$-$C_4$ alkyl groups which may be identical or non-identical; or
$G_1$ is a $C_3$-$C_8$ diamino alkyl group;
$G_2$ is a 5- or 6-membered ring, which is saturated, unsaturated, or aromatic, containing 1-3 ring heteroatoms selected independently from N, O, and S, optionally substituted with 1-3 substituents selected independently from F, Cl, OH, O($C_1$-$C_3$ alkyl), $OCH_3$, $OCH_2CH_3$, $CH_3C(=O)NH$, $CH_3C(=O)O$, CN, $CF_3$, and a 5-membered aromatic heterocyclic group containing 1-4 ring heteroatoms selected independently from N, O, and S;
$R_{1a}$ is methyl, optionally substituted with 1-3 fluorine atoms or 1-3 chlorine atoms, or with OH, cyclopropoxy, or $C_1$-$C_3$ alkoxy, where said cyclopropoxy group or the $C_1$-$C_3$ alkyl moieties of said $C_1$-$C_3$ alkoxy groups are optionally substituted with one hydroxy or methoxy group, and where all $C_3$-alkyl groups within said $C_1$-$C_4$ alkoxy are optionally further substituted with a second OH group;
$R_{1b}$ is $CH(CH_3)$—$C_{1-3}$ alkyl or $C_3$-$C_6$ cycloalkyl, said alkyl and cycloalkyl groups optionally substituted with 1-3 substituents selected independently from F, Cl, Br, I, OH, $OCH_3$, and CN;
$R_{1c}$ is $(CH_2)_nO_mR'$; where
  m is 0 or 1; and where
    when m is 0, n is 1 or 2;
    when m is 1, n is 2 or 3;
  R' is $C_1$-$C_6$ alkyl, optionally substituted with 1-3 substituents selected independently from F, Cl, OH, $OCH_3$, $OCH_2CH_3$, and $C_3$-$C_6$ cycloalkyl;
$R_{1d}$ is C(A)(A')(B)—; where B is H or $C_{1-4}$ alkyl, optionally substituted with one or two OH groups;

A and A' are independently H or $C_1$-$C_4$ alkyl, optionally substituted with one or two OH groups; or A and A', together with the carbon atom to which they are attached, form a 3- to 6-member saturated ring;

$R_{1c}$ is

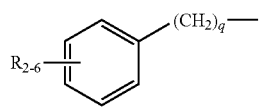

where
q is 1 or 2;

$R_2$ and $R_3$ are each independently, H, F, Cl, Br, $C_{1-13}$, $CH_2F$, $CHF_2$, $CF_3OCH_3$, $OCH_2F$, $OCHF_2$, $OCF_3$, ethyl, n-propyl, isopropyl, cyclopropyl, isobutyl, sec-butyl, tert-butyl or methylsulfonyl;

$R_4$ is H, F, Cl, Br, $CH_3$, $CH_2F$, $CHF_2$, $CF_3OCH_3$, $OCH_2F$, $OCHF_2$, $OCF_3$, ethyl, n-propyl, isopropyl, cyclopropyl, isobutyl, sec-butyl, tort-butyl, methylsulfonyl, nitro, acetamido, amidinyl, cyano, carbamoyl, methylcarbamoyl, dimethylcarbamoyl, 1,3,4-oxadiazol-2-yl, 5-methyl-1,3,4-oxadiazol, 1,3,4-thiadiazol, 5-methyl-1,3,4-thiadiazol 1H-tetrazolyl, N-morpholyl carbonyl amino, N-morpholylsulfonyl and N-pyrrolidinylcarbonylamino;

$R_5$ is H, F, Cl or methyl;
$R_6$ is H, F, Cl or methyl;
$Ar_1$ is

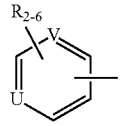

where
U and V are, independently, N, $CR_2$ or $CR_3$;

$R_2$, $R_3$ and $R_4$ are, independently, H, F, Cl, Br, $CH_3$, $CH_2F$, $CHF_2$, $CF_3OCH_3$, $OCH_2F$, $OCHF_2$, $OCF_3$, ethyl, n-propyl, isopropyl, cyclopropyl, isobutyl, sec-butyl, tert-butyl, acetamido, amidinyl, cyano, carbamoyl, methylcarbamoyl, dimethylcarbamoyl, 1,3,4-oxadiazol-2-yl, 5-methyl-1,3,4-oxadiazolyl, 1,3,4-thiadiazolyl, 5-methyl-1,3,4-thiadiazolyl, 1H-tetrazolyl, N-morpholylcarbonylamino, N-morpholylsulfonyl, N-pyrrolidinylcarbonylamino, and methylsulfortyl;

$R_5$ and $R_6$ are, independently, H, F, Cl or methyl;
$Ar_2$ is

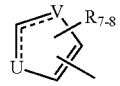

where
the dashed line represents alternative formal locations for the second ring double bond;

U is —S—, —O— or —N═, and where
when U is —O— or —S—, V is —CH═, —CCl═ or —N═;
when U is —N═, V is —CH═, —CCl═, or —N═;

$R_7$ is H or methyl;
$R_8$ is H, acetamido, methyl, F or Cl;
$Ar_3$ is

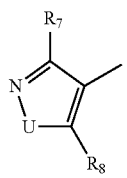

where
U is —NH—, —NCH_3— or —O—;
$R_7$ and $R_8$ are, independently, H, F, Cl, or methyl.

In some embodiments, the invention provides a compound of formula I, selected from the compounds below:

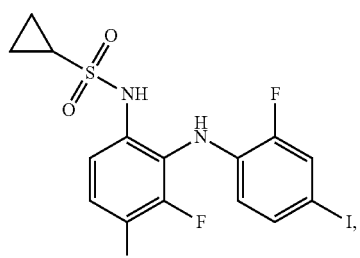

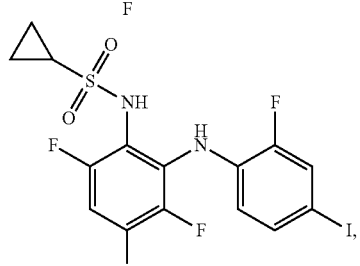

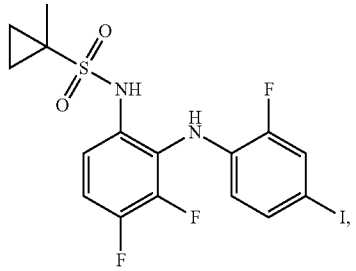

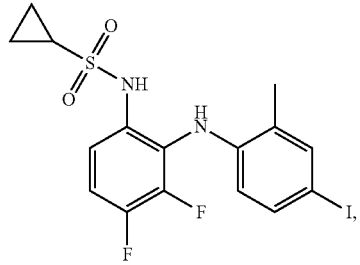

-continued
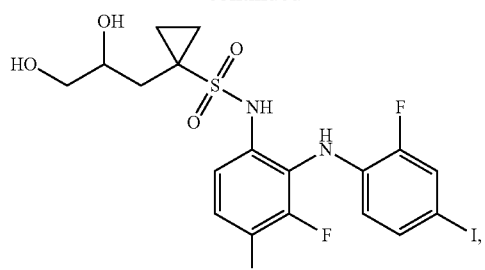
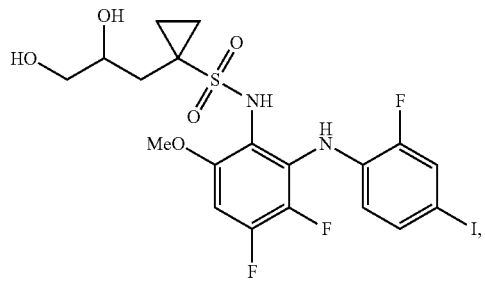
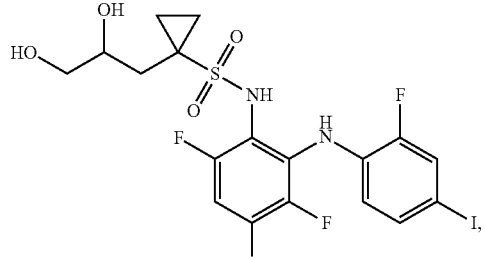
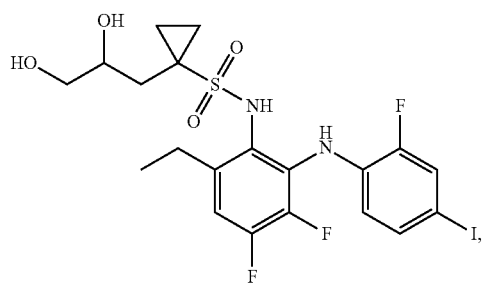
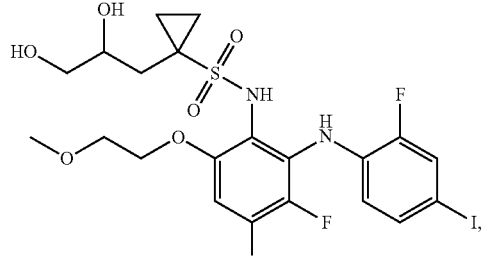
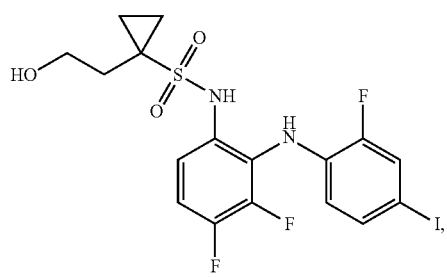
-continued
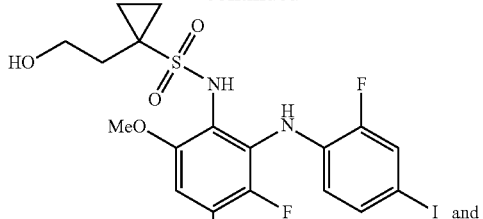
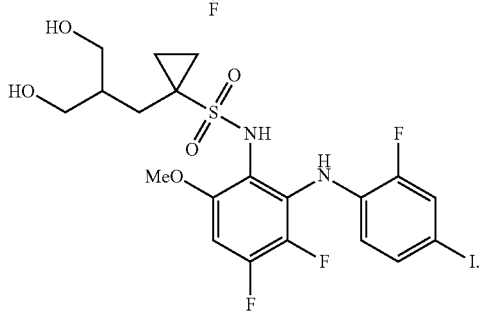
In some embodiments, the invention provides a compound of formula I, selected from:
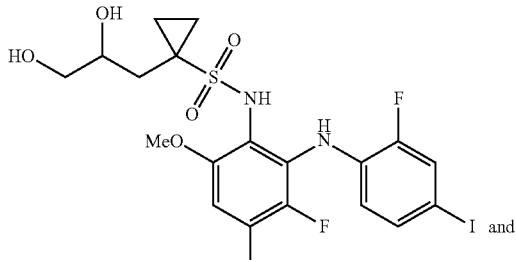
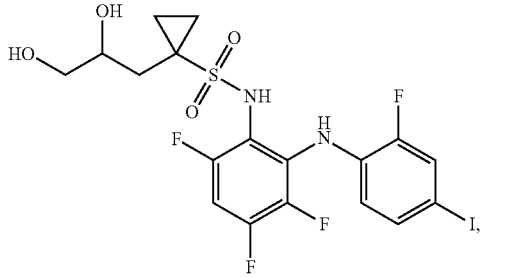
where the 2-OH carbon is in the R configuration.
In some embodiments, the invention provides a compound of formula I, selected from:
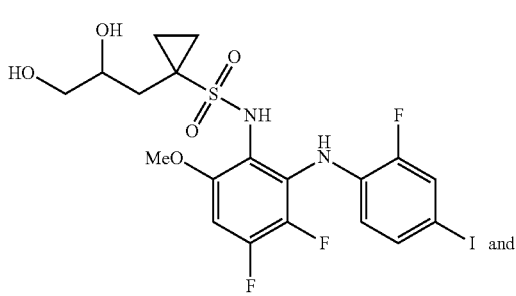

-continued

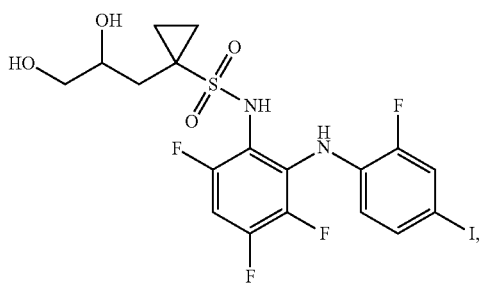

where the 2-OH carbon is in the S configuration.

In some embodiments, the invention provides a composition comprising a compound of formula I, selected from those shown below, where the 2-OH carbon is in the R configuration, substantially free of the S-isomer.

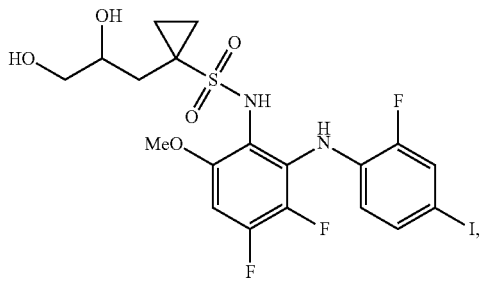

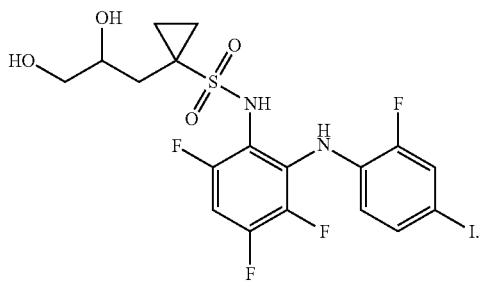

In some embodiments, the invention provides a composition comprising a compound of formula I, selected from those shown below, where the 2-OH carbon is in the S configuration, substantially free of the R-isomer.

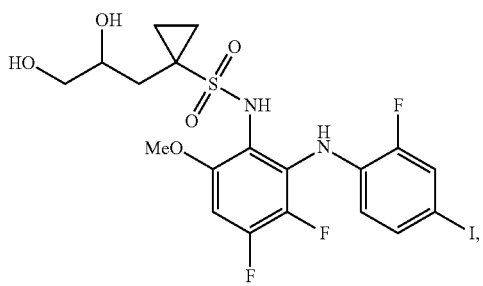

-continued

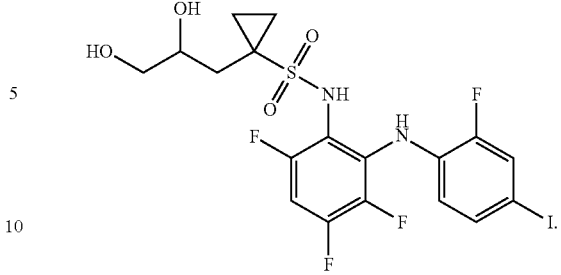

In some embodiments, this invention provides a compound of formula I, where Y is phenyl, pyridyl, or pyrazolyl. In another subgeneric embodiment, this invention provides a compound of formula I, where Y is substituted phenyl, pyridyl, or pyrazolyl. In yet another subgeneric embodiment, this invention provides a compound of formula I, where Y is Br or I. In one subgeneric embodiment, this invention provides a compound of formula I, where G is 1-piperidyl, 2-piperidyl, 3-piperidyl, or 4-piperidyl. In another subgeneric embodiment, this invention provides a compound of formula I, where G is 1-piperazyl or 2-piperazyl. In another subgeneric embodiment, this invention provides a compound of formula I, where G is morpholyl. In another subgeneric embodiment, this invention provides a compound of formula I, where G is N-methyl-2-aminoethyl. In one subgeneric embodiment, this invention provides a compound of formula I, where G is N-methyl-3-amino-n-propyl. In another subgeneric embodiment, this invention provides a compound of formula I, where G is $(CH_3)_2N$—$CH_2CH_2$—$NH$—$(CH_2)_n$—, where n is 1, 2, or 3. In another subgeneric embodiment, this invention provides a compound of formula I, where G is $(CH_3CH_2)_2N$—$CH_2CH_2$—$NH$—$(CH_2)_n$—, where n is 1 or 2. In a more specific subgeneric embodiment, this invention provides a compound of formula I, where G is I-piperidyl, 2-piperidyl, 3-piperidyl, or 4-piperidyl; $R^o$ is H, halo, or methoxy; X is F; and Y is I. In another more specific subgeneric embodiment, this invention provides a compound of formula I, where G is 1-piperazyl or 2-piperazyl; $R^o$ is H, halo, or methoxy; X is F; and Y is I In another more specific subgeneric embodiment, this invention provides a compound of formula I, where G is morpholyl; $R^o$ is H, halo, or methoxy; X is F; and Y is I. In another more specific subgeneric embodiment, this invention provides a compound of formula I, where G is N-methyl-2-aminoethyl; $R^o$ is H, halo, or methoxy; X is F; and Y is I In another more specific subgeneric embodiment, this invention provides a compound of formula I, where G is N-methyl-3-amino-n-propyl; $R^o$ is FI, halo, or methoxy; X is F; and Y is I. In another more specific subgeneric embodiment, this invention provides a compound of formula I, where G is $(CH_3)_2N$—$CH_2CH_2$—$NH$—$(CH_2)_n$—, where n is 1, 2, or 3; $R^o$ is H, halo, or methoxy; X is F; and Y is I. In another more specific subgeneric embodiment, this invention provides a compound of formula I, where G is $(CH_3CH_2)_2N$—$CH_2CH_2$—$NH$—$(CH_2)_n$—, where n is 1 or 2; $R^o$ is H, halo, or methoxy; X is F; and Y is 1.

In some embodiments, the invention provides a pharmaceutical composition comprising a compound of formula I or a pharmaceutically acceptable salt, solvate, polymorph, ester, tautomer or prodrug thereof. In some embodiments the pharmaceutical composition further comprises at least one pharmaceutically acceptable carrier.

In some embodiments, the invention provides a pharmaceutical composition comprising a compound selected from

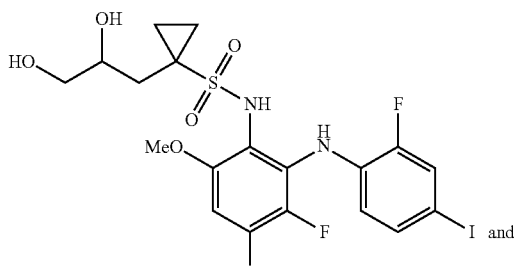

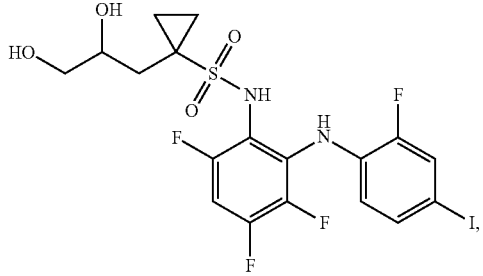

or a pharmaceutically acceptable salt, solvate, polymorph, ester, tautomer or prodrug thereof. In some embodiments, the pharmaceutical composition further comprises at least one pharmaceutically acceptable carrier. In some embodiments, the compound is in the R configuration. In some embodiments, the compound is in the R configuration, substantially free of the S-isomer. In some embodiments, the compound is in the S configuration.

In some embodiments, the compound is in the S configuration, substantially free of the R-isomer. In some embodiments, the compound is:

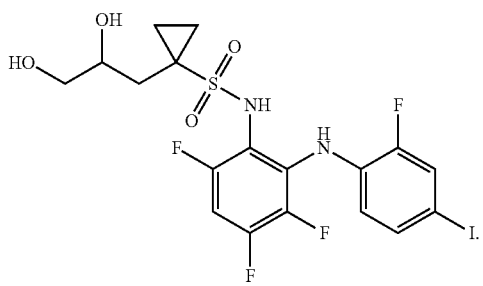 [SMILES: O=S(=O)(Nc1c(F)cc(F)c(F)c1Nc1ccc(I)cc1F)C1(CC(O)CO)CC1]

In some embodiments, the compound is:

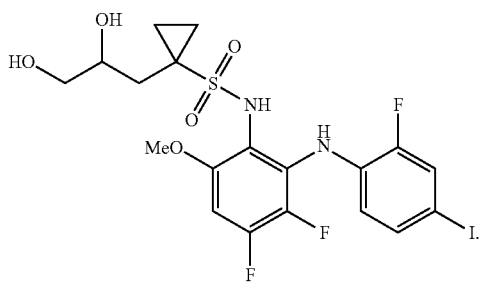

The invention also relates to a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide (also referred to herein as "Compound A" and "N-(−)-(3,4-difluoro-2-(2-fluoro-4-iodophenylamino)-6-methoxyphenyl)-1-(2,3-dihydroxypropyl) cyclopropane-1-sulfonamide"):

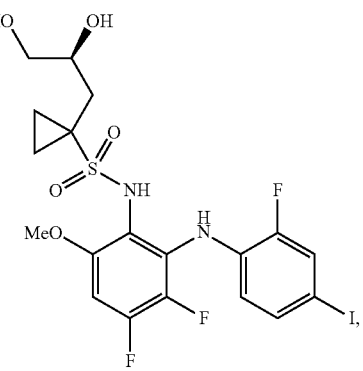

that exhibits a specific powder x-ray diffraction pattern. In some embodiments, the powder x-ray diffraction pattern contains at least 50% of the peaks shown in FIG. 5. In some embodiments, the powder x-ray diffraction pattern contains at least 70% of the peaks shown in FIG. 5. In some embodiments, the powder x-ray diffraction pattern contains at least 90% of the peaks shown in FIG. 5. In some embodiments, the powder x-ray diffraction pattern is substantially the same as the powder x-ray diffraction pattern shown in FIG. 5. Compound A has been characterized as the "S" isomer by making the R and S-MTPA esters at the secondary alcohol and comparing the proton chemical shift difference. See, e.g., Dale, J. A.; Mosher, H. S., *J. Am. Chem. Soc.*, 1973, 95, 512 and Ohtani et al., *J. Am. Chem. Soc.*, 1991, 113, 4092.

The invention also relates to N—(R)-(3,4-difluoro-2-(2-fluoro-4-iodophenylamino)-6-methoxyphenyl)-1-(2,3-dihydroxypropyl)cyclopropane-1-sulfonamide (also referred to herein as "Compound B" and "N-(+)-(3,4-difluoro-2-(2-fluoro-4-iodophenylamino)-6-methoxyphenyl)-1-(2,3-dihydroxypropyl)cyclopropane-1-sulfonamide"):

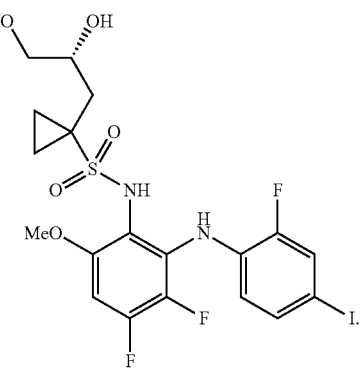

Compound B has been characterized as the "R" isomer by making the R and S-MTPA esters at the secondary alcohol and comparing the proton chemical shift difference. See, e.g., Dale, J. A.; Mosher, H. S., *J. Am. Chem. Soc.*, 1973, 95, 512 and Ohtani et al., *J. Am. Chem. Soc.*, 1991, 113, 4092.

The invention also relates to a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide:

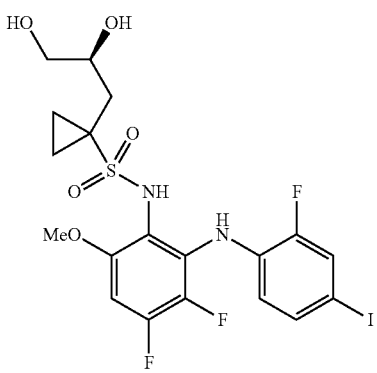 [SMILES: COc1cc(F)c(F)c(Nc2ccc(I)cc2F)c1NS(=O)(=O)C1(C[C@H](O)CO)CC1]

that exhibits a specific differential scanning calorimetry pattern. In some embodiments, the differential scanning calorimetry pattern is substantially the same as the differential scanning calorimetry pattern shown in FIG. 6.

The invention also relates to pharmaceutical compositions comprising an effective amount of crystalline polymorph form A of N—(S)-(3,4-difluoro-2-(2-fluoro-4-iodophenylamino)-6-methoxyphenyl)-1-(2,3-dihydroxypropyl) cyclopropane-1-sulfonamide and a pharmaceutically acceptable carrier or vehicle.

In some embodiments, the crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide is useful for treating or preventing cancer or an inflammatory disease. The invention further relates to methods for treating or preventing cancer or an inflammatory disease, comprising administering an effective amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide to a subject in need thereof.

In other aspects, the present invention is directed to pharmaceutical compositions comprising effective amounts of a compound of formula I or a pharmaceutically acceptable salt, solvate, polymorph, ester, tautomer or prodrug thereof. In some embodiments, the pharmaceutical compositions further comprise a pharmaceutically acceptable carrier. Such compositions may contain adjuvants, excipients, and preservatives, agents for delaying absorption, fillers, binders, adsorbents, buffers, disintegrating agents, solubilizing agents, other carriers, and other inert ingredients. Methods of formulation of such compositions are well-known in the art.

In other aspects, the present invention is directed to a pharmaceutical composition comprising a compound of formula I or a pharmaceutically acceptable salt, solvate, polymorph, ester, tautomer or prodrug thereof. In some embodiments, the pharmaceutical composition is in a form suitable for oral administration. In further or additional embodiments, the pharmaceutical composition is in the form of a tablet, capsule, pill, powder, sustained release formulation, solution, suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.002 to about 6 g/day. In further or additional embodiments the amount of compound of formula I is about 0.005 to about 5 g/day. In further or additional embodiments the amount of compound of formula I is about 0.01 to about 5 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day.

In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day.

In some embodiments, the pharmaceutical composition is for administration to a mammal. In further or additional embodiments, the mammal is human.

In further or additional embodiments, the pharmaceutical composition further comprises a pharmaceutical carrier, excipient and/or adjuvant. In further or additional embodiments, the pharmaceutical composition further comprises at least one therapeutic agent In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; anti-neoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is taxol, bortezomib or both. In further or additional embodiments, the pharmaceutical composition is administered in combination with an additional therapy. In further or additional embodiments, the additional therapy is radiation therapy, chemotherapy, surgery or any combination thereof. In further or additional embodiments, the pharmaceutical composition comprises a pharmaceutically acceptable salt of a compound of formula I.

Provided herein are compositions and methods for using a composition comprising a compound selected from:

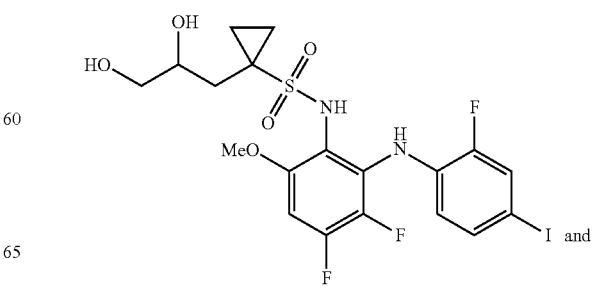

and

-continued

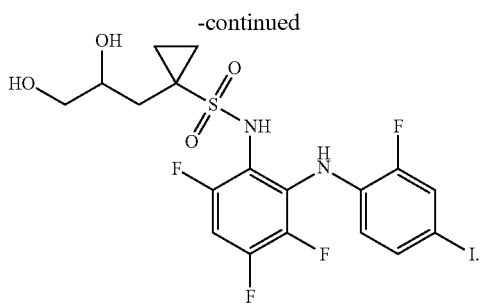

In some embodiments, the 2-OH carbon on the compound is in the R configuration. In some embodiments, the 2-OH carbon on the compound is in the S configuration. In some embodiments, composition is substantially free of the S-isomer of the compound. In some embodiments, the composition is substantially free of the R-isomer of the compound. In some embodiments, the compound contains less than 10% of the S-isomer of the compound. In some embodiments, the compound contains less than 10% of the R-isomer of the compound. In some embodiments, the compound contains less than 5% of the S-isomer of the compound. In some embodiments, the compound contains less than 5% of the R-isomer of the compound. In some embodiments, the compound contains less than 1% of the S-isomer of the compound. In some embodiments, the compound contains less than 1% of the R-isomer of the compound.

Also provided herein are compositions and methods of treating cancer or inflammation with compositions comprising about 1-100 mg of a compound having the following structure:

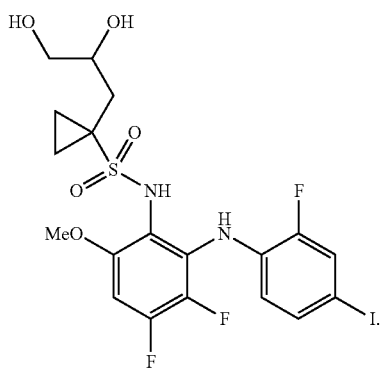 [SMILES: COc1cc(F)c(F)c(Nc2ccc(I)cc2F)c1NS(=O)(=O)C1(CC(O)CO)CC1]

In some embodiments, the composition allows for modified release of the compound. In some embodiments, the composition allows for sustained release of the compound. In some embodiments, the composition allows for delayed release of the compound. In some embodiments, the compound is present in an amount of about 1-50 tugs. In some embodiments, the compound is present in an amount of about 1-10 mgs. In some embodiments, the compound is present in an amount of about 10-20 mgs. In some embodiments, the compound is present in an amount of about 20-40 mgs. In some embodiments, the compound is present in an amount of about 40-50 mgs.

Also provided herein are compositions and methods of treating cancer or inflammation with compositions comprising: about 1-50 mg of a compound having the following structure

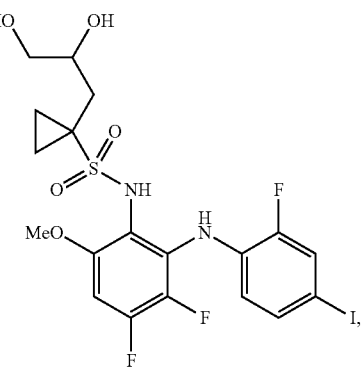

wherein the composition allows for modified release of the drug. In some embodiments, the composition further comprises microcrystalline cellulose. In some embodiments, the composition further comprises croscarmellose sodium. In some embodiments, the composition further comprises sodium lauryl sulfate. In some embodiments, the composition further comprises magnesium stearate.

Also provided here in are compositions comprising about 1 mg of a compound having the following structure:

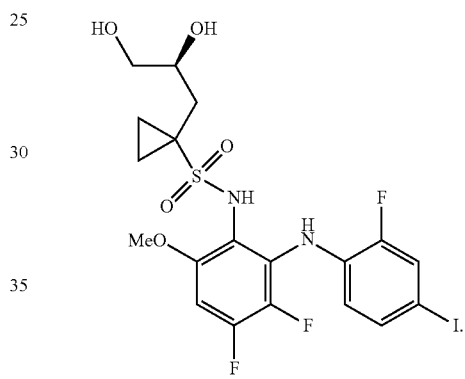

In some embodiments, the composition further comprises about 222.2 mg of microcrystalline cellulose. In some embodiments, the composition further comprises about 12.0 mg of croscarmellose sodium. In some embodiments, the composition further comprises about 2.4 mg of sodium lauryl sulfate. In some embodiments, the composition further comprises about 2.4 mg of magnesium stearate.

Also provided herein are compositions and methods of treating cancer or inflammation with compositions comprising about 10 mg of a compound having the following structure

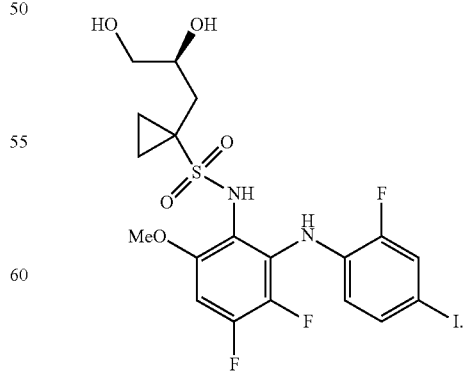

In some embodiments, the composition further comprises about 213.2 mg of microcrystalline cellulose. In some embodiments, the composition further comprises about 12.0 mg of croscarmellose sodium. In some embodiments, the composition further comprises about 2.4 mg of sodium lauryl sulfate. In some embodiments, the composition further comprises about 2.4 mg of magnesium stearate.

Also provided herein are compositions and methods of treating cancer or inflammation with compositions comprising about 20 mg of a compound having the following structure:

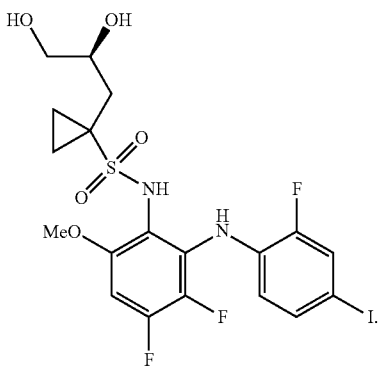 [SMILES: COc1cc(F)c(F)c(Nc2ccc(I)cc2F)c1NS(=O)(=O)C1(C[C@H](O)CO)CC1]

In some embodiments, the composition further comprises about 203.2 mg of microcrystalline cellulose. In some embodiments, the composition further comprises about 12.0 mg of croscarmellose sodium. In some embodiments, the composition further comprises about 2.4 mg of sodium lauryl sulfate. In some embodiments, the composition further comprises about 2.4 mg of magnesium stearate.

Also provided herein are compositions and methods of treating cancer or inflammation with compositions comprising about 40 mg of a compound having the following structure

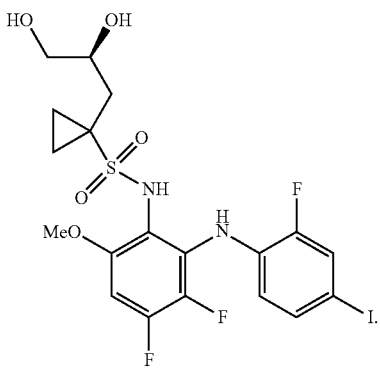 [SMILES: COc1cc(F)c(F)c(Nc2ccc(I)cc2F)c1NS(=O)(=O)C1(C[C@H](O)CO)CC1]

In some embodiments, the composition further comprises about 183.2 mg of microcrystalline cellulose. In some embodiments, the composition further comprises about 12.0 mg of croscarmellose sodium. In some embodiments, the composition further comprises about 2.4 mg of sodium lauryl sulfate. In some embodiments, the composition further comprises about 2.4 mg of magnesium stearate.

Also provided herein are compositions and methods of treating cancer or inflammation with compositions comprising: about 0.4% by weight of a compound having the following structure

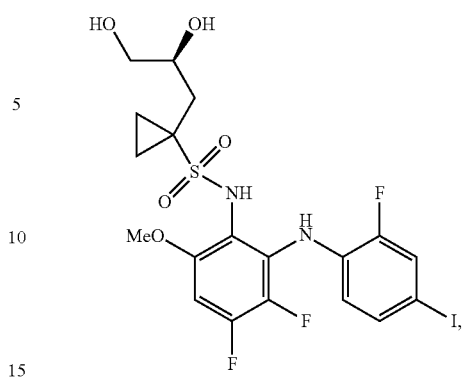

and about 99.6% by weight of a pharmaceutically acceptable carrier or vehicle. In some embodiments, the pharmaceutically acceptable carrier or vehicle comprises microcrystalline cellulose. In some embodiments, the microcrystalline cellulose is about 92.6% by weight of the composition. In some embodiments, the composition further comprises about 5% by weight croscarmellose sodium. In some embodiments, the composition further comprises about 1% by weight sodium lauryl sulfate. In some embodiments, the composition further comprises about 1% by weight magnesium stearate.

Also provided herein are compositions and methods of treating cancer or inflammation with compositions comprising about 4.2% by weight of a compound having the following structure

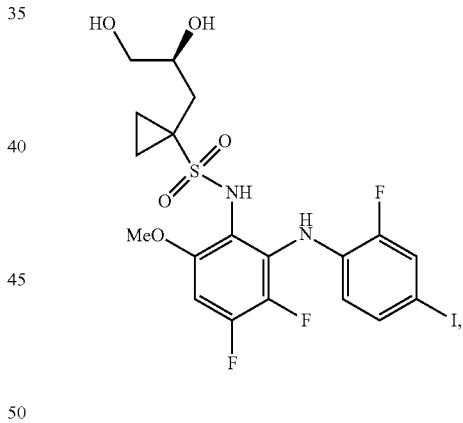

and about 95.8% by weight of a pharmaceutically acceptable carrier or vehicle. In some embodiments, the pharmaceutically acceptable carrier or vehicle comprises microcrystalline cellulose. In some embodiments, the microcrystalline cellulose is about 88.8% by weight of the composition. In some embodiments, the composition further comprises about 5% by weight croscarmellose sodium. In some embodiments, the composition further comprises about 1% by weight sodium lauryl sulfate. In some embodiments, the composition further comprises about 1% by weight magnesium stearate.

Also provided herein are compositions and methods of treating cancer or inflammation with compositions comprising from about 2% to about 10% by weight of a compound having the following structure

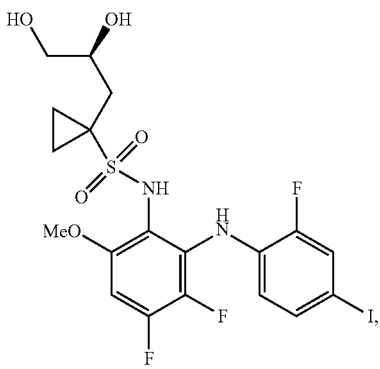

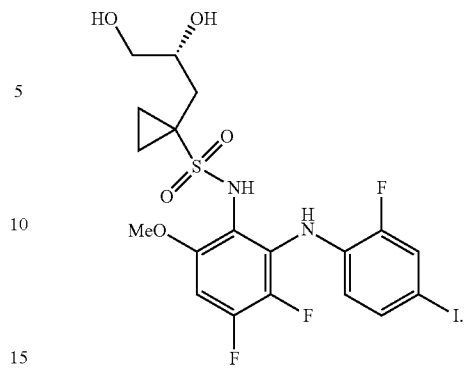

and from about 98% to about 90% by weight of a pharmaceutically acceptable carrier or vehicle. In some embodiments, the pharmaceutically acceptable carrier or vehicle further comprises microcrystalline cellulose. In some embodiments, the microcrystalline cellulose is from about 85% to about 95% by weight of the composition. In some embodiments, the composition further comprises from about 1% to about 6% by weight croscarmellose sodium. In some embodiments, the composition further comprises from about 0.1% to about 2% by weight sodium lauryl sulfate. In some embodiments, the composition further comprises from about 0.25% to about 1.5% by weight magnesium stearate.

Also provided herein are compositions and methods of treating cancer or inflammation with compositions comprising about 1 mg of a compound having the following structure In some embodiments, the composition further comprises about 213.2 mg of microcrystalline cellulose. In some embodiments, the composition further comprises about 12.0 mg of croscarmellose sodium. In some embodiments, the composition further comprises about 2.4 mg of sodium lauryl sulfate. In some embodiments, the composition further comprises about 2.4 mg of magnesium stearate.

Also provided herein are compositions and methods of treating cancer or inflammation with compositions comprising about 20 mg of a compound having the following structure:

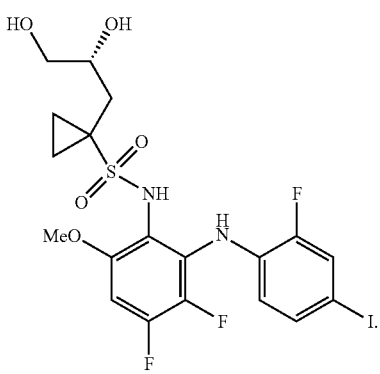 [SMILES: COc1cc(F)c(F)c(Nc2ccc(I)cc2F)c1NS(=O)(=O)C1(C[C@@H](O)CO)CC1]

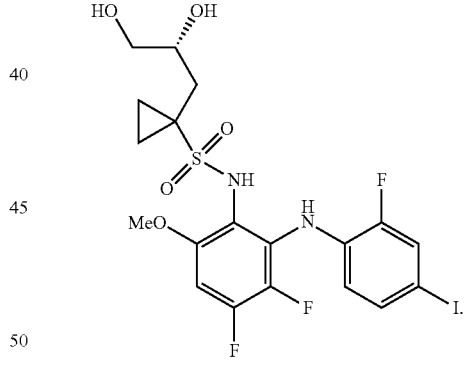

In some embodiments, the composition further comprises about 222.2 mg of microcrystalline cellulose. In some embodiments, the composition further comprises about 12.0 mg of croscarmellose sodium. In some embodiments, the composition further comprises about 2.4 mg of sodium lauryl sulfate. In some embodiments, the composition further comprises about 2.4 mg of magnesium stearate.

Also provided herein are compositions and methods of treating cancer or inflammation with compositions comprising about 10 mg of a compound having the following structure:

In some embodiments, the composition further comprises about 203.2 mg of microcrystalline cellulose. In some embodiments, the composition further comprises about 12.0 mg of croscarmellose sodium. In some embodiments, the composition further comprises about 2.4 mg of sodium lauryl sulfate. In some embodiments, the composition further comprises about 2.4 mg of magnesium stearate.

Also provided herein are compositions and methods of treating cancer or inflammation with compositions comprising about 40 mg of a compound having the following structure:

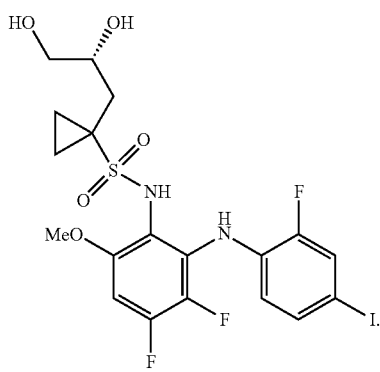 [SMILES: COc1cc(F)c(F)c(Nc2ccc(I)cc2F)c1NS(=O)(=O)C1(C[C@@H](O)CO)CC1]

In some embodiments, the composition further comprises about 183.2 mg of microcrystalline cellulose. In some embodiments, the composition further comprises about 12.0 mg of croscarmellose sodium. In some embodiments, the composition further comprises about 24 mg of sodium lauryl sulfate. In some embodiments, the composition further comprises about 2.4 mg of magnesium stearate.

Also provided herein are compositions and methods of treating cancer or inflammation with compositions comprising about 0.4% by weight of a compound having the following structure

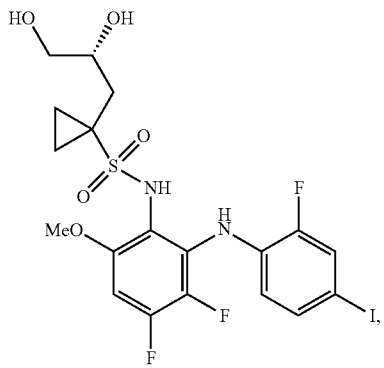

and about 99.6% by weight of a pharmaceutically acceptable carrier or vehicle. In some embodiments, the pharmaceutically acceptable carrier or vehicle comprises microcrystalline cellulose. In some embodiments, the microcrystalline cellulose is about 92.6% by weight of the composition. In some embodiments, the composition further comprises about 5% by weight croscarmellose sodium. In some embodiments, the composition further comprises about 1% by weight sodium lauryl sulfate. In some embodiments, the composition further comprises about 1% by weight magnesium stearate.

Also provided herein are compositions and methods of treating cancer or inflammation with compositions comprising about 4.2% by weight of a compound having the following structure

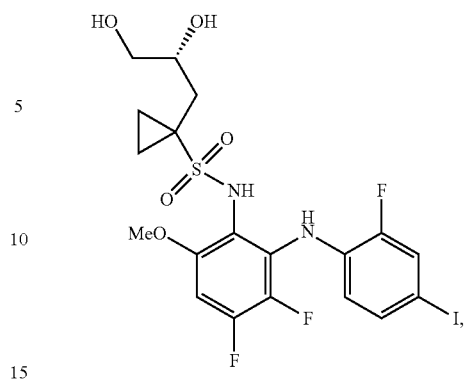

and about 95.8% by weight of a pharmaceutically acceptable carrier or vehicle. In some embodiments, the pharmaceutically acceptable carrier or vehicle comprises microcrystalline cellulose. In some embodiments, the microcrystalline cellulose is about 88.8% by weight of the composition. In some embodiments, the composition further comprises about 5% by weight croscarmellose sodium. In some embodiments, the composition further comprises about 1% by weight sodium lauryl sulfate. In some embodiments, the composition further comprises about 1% by weight magnesium stearate.

Also provided herein are compositions and methods of treating cancer or inflammation with compositions comprising from about 2% to about 10% by weight of a compound having the following structure

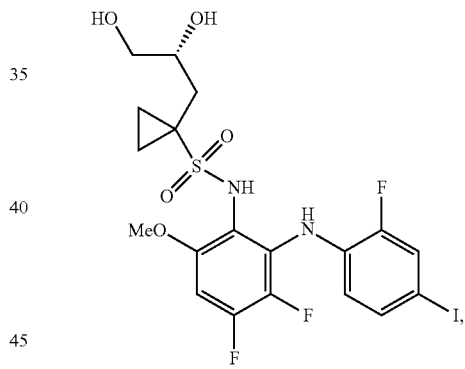

and from about 98% to about 90% by weight of a pharmaceutically acceptable carrier or vehicle. In some embodiments, the pharmaceutically acceptable carrier or vehicle comprises microcrystalline cellulose. In some embodiments, the microcrystalline cellulose is from about 85% to about 95% by weight of the composition. In some embodiments, the composition further comprises from about 1% to about 6% by weight croscarmellose sodium. In some embodiments, the composition further comprises from about 0.1% to about 2% by weight sodium lauryl sulfate. In some embodiments, the composition further comprises from about 0.25% to about 1.5% by weight magnesium stearate.

Also provided herein is a crystalline polymorph Form A of N-(−)-(3,4-difluoro-2-(2-fluoro-4-iodophenylamino)-6-methoxyphenyl)-1-(2,3-dihydroxypropyl)cyclopropane-1-sulfonamide that exhibits a powder x-ray diffraction pattern comprising at least 50% of the peaks identified in the powder x-ray diffraction pattern shown in FIG. 5 and compositions comprising this compound. In some embodiments, the crystalline polymorph Form A, wherein the powder x-ray diffraction pattern comprises at least 70% of the peaks identified in the powder x-ray diffraction pattern shown in FIG. 5. In some embodiments, the powder x-ray diffraction pattern comprises at least 90% of the peaks identified in the powder x-ray diffraction pattern shown in FIG. 5. In some embodiments, the powder x-ray diffraction pattern substantially the same as the powder x-ray diffraction pattern shown in FIG. 5. In some embodiments, the crystalline polymorph has a melting point onset as determined by differential scanning calorimetry at about 143° C. In some embodiments, the crystalline polymorph is substantially free of water. In some embodiments, the crystalline polymorph is substantially free of solvent.

Also provided herein is a crystalline polymorph Form A of N-(−)-(3,4-difluoro-2-(2-fluoro-4-iodophenylamino)-6-methoxyphenyl)-1-(2,3-dihydroxypropyl)cyclopropane-1-sulfonamide that exhibits a differential scanning calorimetry pattern substantially the same as the differential scanning calorimetry pattern shown in FIG. 6 and compositions comprising this compound. In some embodiments, the crystalline polymorph has a melting point onset as determined by differential scanning calorimetry at about 143° C. In some embodiments, the crystalline polymorph is a crystalline polymorph Form A of N-(−)-(3,4-difluoro-2-(2-fluoro-4-iodophenylamino)-6-methoxyphenyl)-1-(2,3-dihydroxypropyl)cyclopropane-1-sulfonamide that exhibits a diffeential scanning calorimetry pattern substantially the same as the differential scanning calorimetry pattern shown in FIG. 6, or said polymorph A having a melting point onset as determined by differential scanning calorimetry at about 143° C., wherein the crystalline polymorph is substantially free of water. In some embodiments, the crystalline polymorph is a crystalline polymorph Form A of N-(−)-(3,4-difluoro-2-(2-fluoro-4-iodophenylamino)-6-methoxyphenyl)-1-(2,3-dihydroxypropyl)cyclopropane-1-sulfonamide that exhibits a diffeential scanning calorimetry pattern substantially the same as the differential scanning calorimetry pattern shown in FIG. 6, or said polymorph A having a melting point onset as determined by differential scanning calorimetry at about 143° C., or said polymorph A that is substantially free of water wherein the crystalline polymorph is substantially free of solvent.

Also provided herein is a polymorphic form of N-(3,4-difluoro-2-(2-fluoro-4-iodophenylamino)-6-methoxyphenyl)-1-(2,3-dihydroxypropyl)cyclopropane-1-sulfonamide made by a method comprising the step of crystallizing amorphous N-(3,4-difluoro-2-(2-fluoro-4-iodophenylamino)-6-methoxyphenyl)-1-(2,3-dihydroxypropyl)cyclopropane-1-sulfonamide and compositions comprising this compound. In some embodiments, the crystallization step comprises crystallizing from a mixture of ethyl acetate and heptane. In some embodiments, the mixture of ethyl acetate and heptane is in a ratio of from about 1-4 parts ethyl acetate to about 2-10 parts heptane. In some embodiments, the mixture of ethyl acetate and heptane is in a ratio of from about 2 parts ethyl acetate to about 5 parts heptane.

Also provided herein are methods for inhibiting MEK enzymes comprising contacting said MEK enzyme with a compound or composition described herein, wherein the compound is present in an amount sufficient to inhibit said enzyme by at least 25%. In some embodiments, the MEK enzyme is MEK kinase. In some embodiments, said contacting occurs within a cell.

Also provided herein are methods for treating a MEK mediated disorder in an individual suffering from said disorder, comprising administering to said individual an effective amount of a compound or composition described herein. In some embodiments, the MEK inhibitor is administered in combination with an additional therapy. In some embodiments, the additional therapy is radiation therapy, non-MEK kinase inhibitor therapy, chemotherapy, surgery, Glucocorticoid, methotrexate, biological response modifiers, or any combination thereof. In some embodiments, the MEK mediated disorder is selected from the group consisting of inflammatory diseases, infections, autoimmune disorders, stroke, ischemia, cardiac disorder, neurological disorders, fibrogenetic disorders, proliferative disorders, hyperproliferative disorders, tumors, leukemias, neoplasms, cancers, carcinomas, metabolic diseases and malignant diseases. In some embodiments, the MEK mediated disorder is a hyperproliferative disease. In some embodiments, the MEK mediated disorder is cancer, tumors, leukemias, neoplasms, or carcinomas. In some embodiments, the MEK mediated disorder is an inflammatory disease. In some embodiments, said inflammatory disease is rheumatoid arthritis or multiple sclerosis.

Also provided herein are methods for the treatment or prophylaxis of a proliferative disease in an individual comprising administering to said individual an effective amount of a compound or composition described herein. In some embodiments, the proliferative disease is cancer, psoriasis, restenosis, disease, or atherosclerosis. In some embodiments, the proliferative disease is cancer. In some embodiments, the cancer is brain cancer, breast cancer, lung cancer, ovarian cancer, pancreatic cancer, prostate cancer, renal cancer, colorectal cancer, leukemia, myeloid leukemia, glioblastoma, follicular lymphona, pre-B acute leukemia, chronic lymphocytic B-leukemia, stomach cancer, mesothelioma or small cell lung cancer. In some embodiments, the method further comprises administering at least one therapeutic agent. In some embodiments, this step comprises the administration of at least one additional cancer therapy. In some embodiments, the additional therapy is radiation therapy, non-MEK kinase inhibitor therapy, chemotherapy, surgery, Glucocorticoid, methotrexate, biological response modifiers, or any combination thereof.

Also provided herein are methods for the treatment or prophylaxis of an inflammatory disease in an individual comprising administering to said individual an effective amount of a composition comprising a compound described herein. In some embodiments, the inflammatory disease is rheumatoid arthritis or multiple sclerosis.

Also provided herein are methods for degrading, inhibiting the growth of or killing cancer cells comprising contacting the cells with an amount of the compound or composition described herein effective to degrade, inhibit the growth of or kill cancer cells. In some embodiments, the cancer cells comprise brain, breast, lung, ovarian, pancreatic, prostate, renal, stomach or colorectal cancer cells.

Also provided herein are methods of inhibiting tumor size increase, reducing the size of a tumor, reducing tumor proliferation or preventing tumor proliferation in an individual comprising administering to said individual an effective amount of the compound or composition described herein to inhibit tumor size increase, reduce the size of a tumor, reduce tumor proliferation or prevent tumor proliferation. In some embodiments, the tumor occurs in the brain, breast, lung, ovaries, pancreas, prostate, kidney, stomach, colon or rectum.

Also provided herein are methods for treating or preventing ankylosing spondylitis, gout, tendonitis, bursitis or sciatica, comprising administering to a subject in need thereof an effective amount of a compound of formula (I) or a pharmaceutical salt thereof:

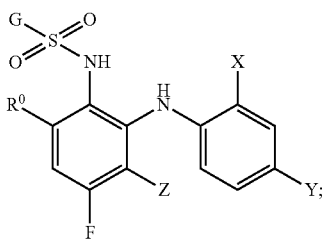

wherein:
Z is H or F;
X is F, Cl, $CH_3$, $CH_2OH$, $CH_2F$, $CHF_2$, or $CF_3$;
Y is I, Br, $C_1$, $CF_3$, $C_1$-$C_3$ alkyl, $C_2$-$C_3$ alkenyl, $C_2$-$C_3$ alkynyl, cyclopropyl, OMe, OEt, SMe, phenyl or Het, where Het is a 5- to 10-membered mono- or bicyclic heterocyclic group, which group is saturated, olefinic, or aromatic, containing 1-5 ring heteroatoms selected independently from N, O, and S; where
  all said phenyl or Het groups are optionally substituted with F, Cl, Br, I, acetyl, methyl, CN, $NO_2$, $CO_2H$, $C_1$-$C_3$ alkyl, $C_1$-$C_3$ alkoxy, $C_1$-$C_3$ alkyl-C(=O)—, $C_1$-$C_3$ alkyl-C(=S)—, $C_1$-$C_3$ alkoxy-C(=S)—, $C_1$-$C_3$ alkyl-C(=O)O—, $C_1$-$C_3$ alkyl-O—(C=O)—, $C_1$-$C_3$ alkyl-C(=O)NH—, $C_1$-$C_3$ alkyl-C(=NH)NH—, $C_1$-$C_3$ alkyl-NH—(C=O)—, di-$C_1$-$C_3$ alkyl-N—(C=O)—, $C_1$-$C_3$ alkyl-C(=O)N($C_1$-$C_3$ alkyl)-, $C_1$-$C_3$ alkyl-S(=O)$_2$NH— or trifluoromethyl;
  all said methyl, ethyl, $C_1$-$C_3$ alkyl, and cyclopropyl groups are optionally substituted with OH;
  all said methyl groups are optionally substituted with one, two, or three F atoms;
$R^0$ is H, F, Cl, Br, I, $CH_3NH$—, $(CH_3)_2N$—, $C_1$-$C_6$ alkyl, $C_1$-$C_4$ alkoxy, $C_3$-$C_6$ cycloalkyl, $C_2$-$C_5$ alkenyl, $C_2$-$C_6$ alkynyl, phenyl, monosubstituted phenyl, O($C_1$-$C_4$ alkyl), O—C(=O)($C_1$-$C_4$ alkyl) or C(=O)O($C_1$-$C_4$ alkyl); where
  said alkyl, alkoxy, cycloalkyl, alkenyl, alkynyl and phenyl groups are optionally substituted with 1-3 substituents selected independently from F, Cl, Br, I, OH, CN, cyanomethyl, nitro, phenyl and trifluoromethyl;
  said $C_1$-$C_6$ alkyl and $C_1$-$C_4$ alkoxy groups also optionally substituted with $OCH_3$ or $OCH_2CH_3$;
G is $G_1$, $G_2$, $R_{1a}$, $R_{1b}$, $R_{1c}$, $R_{1d}$, $R_{1e}$, $Ar_1$, $Ar_2$ or $Ar_3$; where
  $G_1$ is $C_1$-$C_6$ alkyl optionally substituted with one amino, $C_1$-$C_3$ alkylamino, or dialkylamino group, said dialkylamino group comprising two $C_1$-$C_4$ alkyl groups which may be identical or non-identical; or
  $G_1$ is a $C_3$-$C_8$ diamino alkyl group;
  $G_2$ is a 5- or 6-membered ring, which is saturated, unsaturated, or aromatic, containing 1-3 ring heteroatoms selected independently from N, O, and S, optionally substituted with 1-3 substituents selected independently from F, Cl, OH, O($C_1$-$C_3$ alkyl), $OCH_3$, $OCH_2CH_3$, $CH_3C$(=O)NH, $CH_3C$(=O)O, CN, $CF_3$, and a 5-membered aromatic heterocyclic group containing 1-4 ring heteroatoms selected independently from N, O, and S;
  $R_{1a}$ is methyl, optionally substituted with 1-3 fluorine atoms or 1-3 chlorine atoms, or with OH, cyclopropoxy, or $C_1$-$C_3$ alkoxy, where said cyclopropoxy group or the $C_1$-$C_3$ alkyl moieties of said $C_1$-$C_3$ alkoxy groups are optionally substituted with one hydroxy or methoxy group, and where all $C_3$— alkyl groups within said $C_1$-$C_4$ alkoxy are optionally further substituted with a second OH group;
  $R_{1b}$ is $CH(CH_3)$—$C_{1-3}$ alkyl or $C_3$-$C_6$ cycloalkyl, said alkyl and cycloalkyl groups optionally substituted with 1-3 substituents selected independently from F, Cl, Br, I, OH, $OCH_3$, and CN;
  $R_{1c}$ is $(CH_2)_6O_mR'$; where
    m is 0 or 1; and where
      when m is 0, n is 1 or 2;
      when m is 1, n is 2 or 3;
    R' is $C_1$-$C_4$ alkyl, optionally substituted with 1-3 substituents selected independently from F, Cl, OH, $OCH_3$, $OCH_2CH_3$, and $C_3$-$C_6$ cycloalkyl;
  $R_{1d}$ is C(A)(A')(B)—; where
    B is H or $C_{1-4}$ alkyl, optionally substituted with one or two OH groups;
    A and A' are independently H or $C_{1-4}$ alkyl, optionally substituted with one or two OH groups; or
    A and A', together with the carbon atom to which they are attached, form a 3- to 6-member saturated ring;
  $R_{1e}$ is

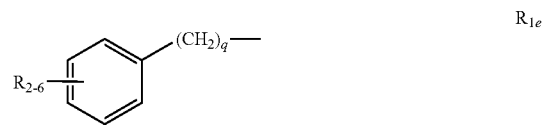

where
  q is 1 or 2;
  $R_2$ and $R_3$ are each independently, H, F, Cl, Br, $CH_3$, $CH_2F$, $CHF_2$, $CF_3OCH_3$, $OCH_2F$, $OCHF_2$, $OCF_3$, ethyl, n-propyl, isopropyl, cyclopropyl, isobutyl, sec-butyl, tert-butyl or methylsulfonyl;
  $R_4$ is H, F, Cl, Br, $CH_3$, $CH_2F$, $CHF_2$, $CF_3OCH_3$, $OCH_2F$, $OCHF_2$, $OCF_3$, ethyl, n-propyl, isopropyl, cyclopropyl, isobutyl, sec-butyl, tert-butyl, methylsulfonyl, nitro, acetamido, amidinyl, cyano, carbamoyl, methylcarbamoyl, dimethylcarbamoyl, 1,3,4-oxadiazol-2-yl, 5-methyl-1,3,4-oxadiazol, 1,3,4-thiadiazol, 5-methyl-1,3,4-thiadiazol 1H-tetrazolyl, N-morpholyl carbonyl amino, N-morpholylsulfonyl and N-pyrrolidinylcarbonylamino;
  $R_5$ is H, F, Cl or methyl;
  $R_6$ is H, F, Cl or methyl;
$Ar_1$ is

where
  U and V are, independently, N, $CR_2$ or $CR_3$;
  $R_2$, $R_3$ and $R_4$ are, independently, H, F, Cl, Br, $CH_3$, $CH_2F$, $CHF_2$, $CF_3OCH_3$, $OCH_2F$, $OCHF_2$, $OCF_3$, ethyl, n-propyl, isopropyl, cyclopropyl, isobutyl, sec-butyl, tert-butyl, acetamido, amidinyl, cyano, carbamoyl, methylcarbamoyl, dimethylcarbamoyl, 1,3,4-oxadiazol-2-yl, 5-methyl-1,3,4-oxadiazolyl, 1,3,4-thiadiazolyl, 5-methyl-1,3,4-thiadiazolyl, 1H-tetrazolyl, N-morpholylcarbonylamino, N-morpholylsulfonyl, N-pyrrolidinylcarbonylamino, and methylsulfonyl;

$R_5$ and $R_6$ are, independently, H, F, Cl or methyl;

$Ar_2$ is

where the dashed line represents alternative formal locations for the second ring double bond;

U is —S—, —O— or —N═, and where when U is —O— or —S—, V is —CH═, —CCl═ or —N═;

when U is —N═, V is —CH═, —CCl═, or —N═;

$R_7$ is H or methyl;

$R_8$ is H, acetamido, methyl, F or Cl;

$Ar_3$ is

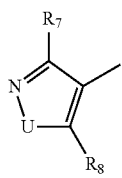

where

U is —NH—, —NCH$_3$— or —O—;

$R_7$ and $R_8$ are, independently, H, F, Cl, or methyl. In some embodiments, the compound is selected from:

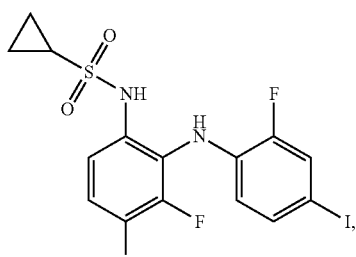

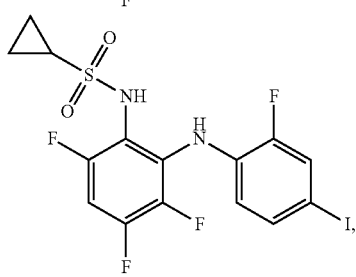

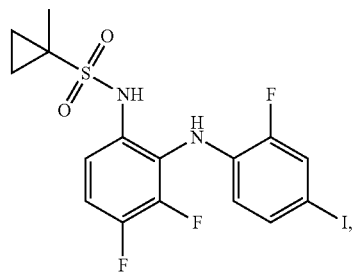

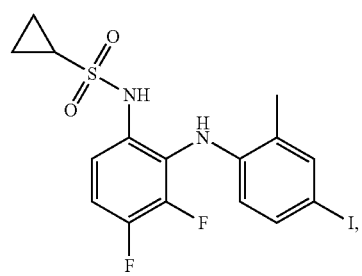

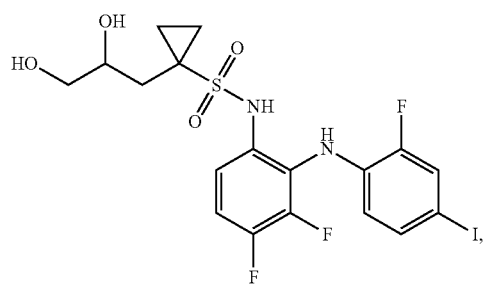

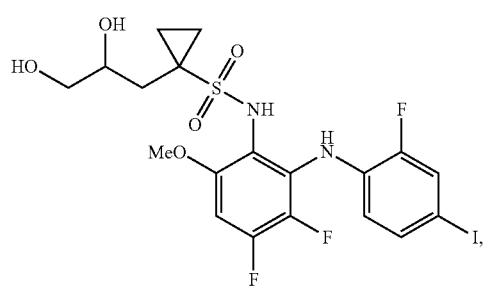

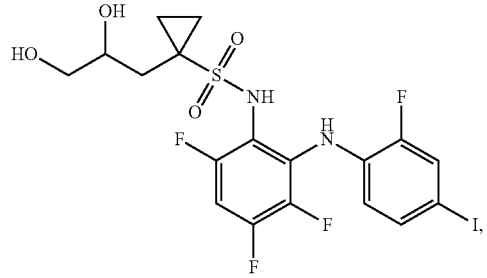

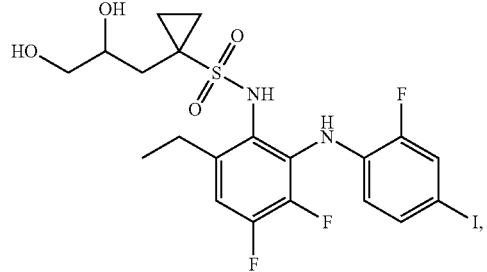

-continued

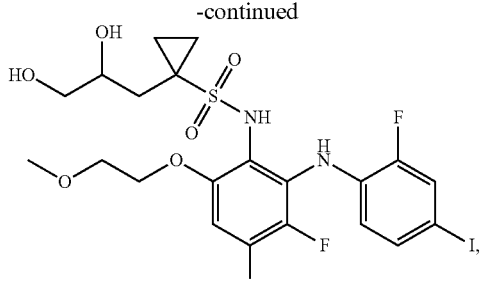

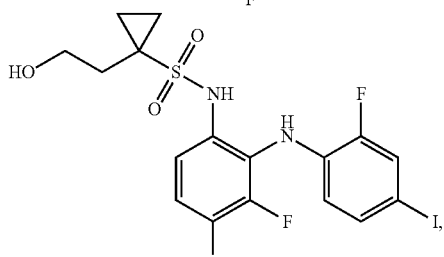

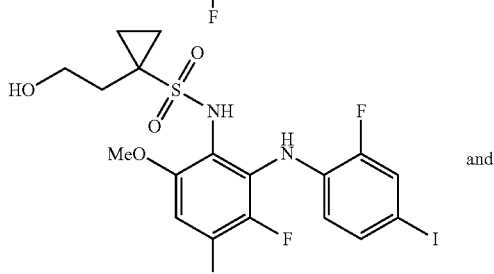

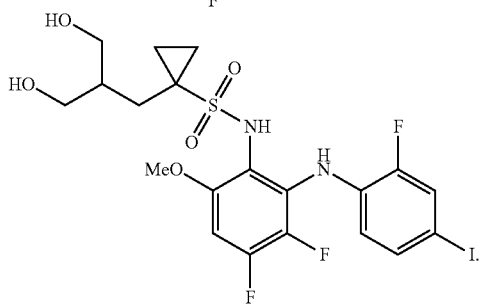

In some embodiments, the compound is selected from

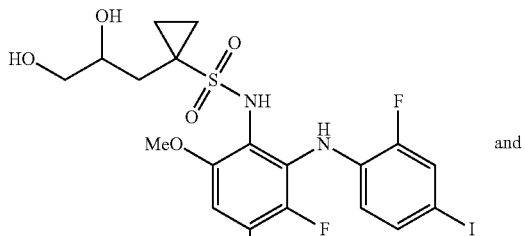

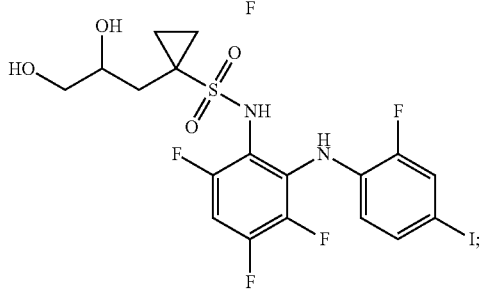

where the 2-OH carbon is in the R configuration. In some embodiments, the compound of formula (I), or a pharmaceutical salt thereof, is selected from

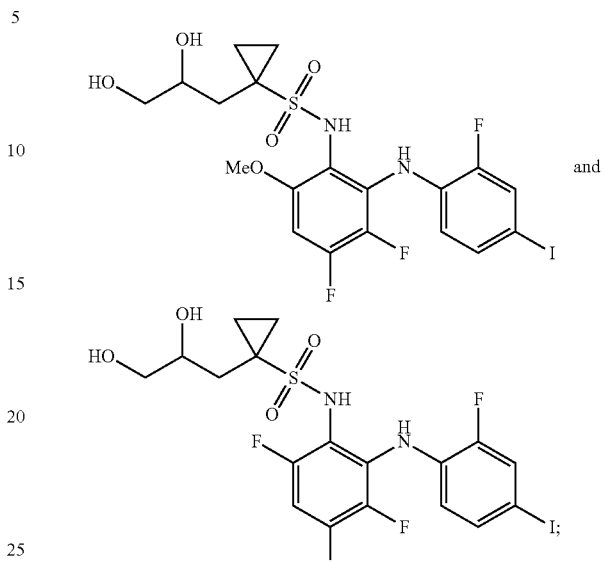

where the 2-OH carbon is in the S configuration. In some embodiments, the compound is

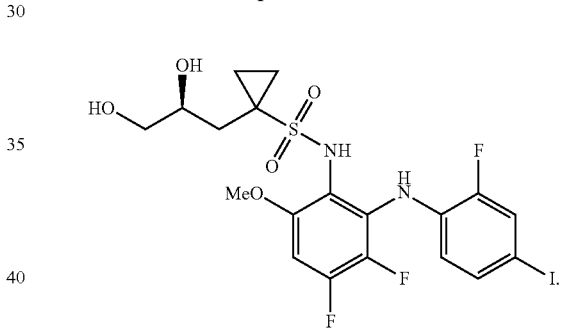

In some embodiments, the compound is

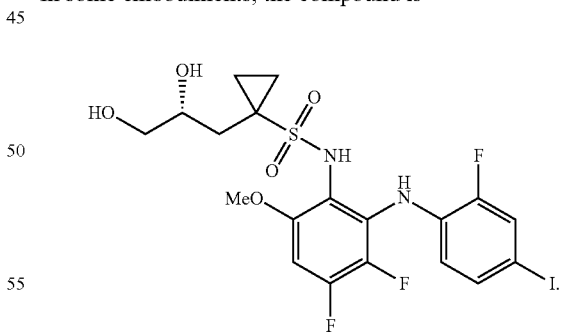

Provided herein are also methods for treating stomach cancer by administering a therapeutically effective amount of a compound or composition described herein. Provided herein are also methods for treating letikemiam melanoma, or hepatoma by administering a therapeutically effective amount of a compound or composition described herein.

Provided herein are also methods for treating non-small cell lung cancer by administering a therapeutically effective amount of a compound or composition described herein.

Provided herein are also methods for treating colon cancer by administering a therapeutically effective amount of a compound or composition described herein. Provided herein are also methods for treating CNS cancer by administering a therapeutically effective amount of a compound or composition described herein. Provided herein are also methods for treating ovarian cancer by administering a therapeutically effective amount of a compound or composition described herein. Provided herein are also methods for treating renal cancer by administering a therapeutically effective amount of a compound or composition described herein. Provided herein are also methods for treating prostate cancer by administering a therapeutically effective amount of a compound or composition described herein. Provided herein are also methods for treating breast cancer by administering a therapeutically effective amount of a compound or composition described herein. In various embodiments, these methods further comprise administering at least one additional therapeutic agent. In some embodiments, at least one additional cancer therapy is performed. In some embodiments, the additional cancer therapy is radiation therapy, chemotherapy, surgery, or any combination thereof.

Also provided herein are methods for treating or preventing psoriasis by administering a therapeutically effective amount of a compound or composition described herein in a topical dosage form.

In various embodiments, the compositions are administered orally. In some embodiments, the composition is administered once a day or twice a day. In some embodiments, the composition is administered once a day for at least one week.

In some embodiments, upon oral administration of the composition, $T_{max}$ of the compound is achieved between 1 hour and 3 hours after administration of the composition to a fasted subject. In some embodiments, upon administration to a subject, the compound reaches a $C_{max}$ between about 0.01 µg/ml to about 1.0 µg/ml on day 1. In some embodiments, upon administration to a subject, the compound reaches a $C_{max}$ between about 0.01 µg/ml to about 0.8 µg/ml on day 1. In some embodiments, upon administration to a subject, the compound reaches a $C_{max}$ between about 0.03 µg/ml to about 0.5 µg/ml on day 1. In some embodiments, the compound has an AUC between about 0.1 µg hr/mL to about 5.0 µg hr/ml, from 0-12 hours. In some embodiments, the compound has an AUC between about 0.1 µg hr/ml, to about 4.0 µg hr/mL. In some embodiments, the compound has an AUC between about 0.5 µg hr/ml, to about 3.0 µg hr/mL. In some embodiments, the compound has a $T_{max}$ between 0.5 and 5.0 hours. In some embodiments, the compound has a $T_{max}$ between 1.0 and 3.0 hours. In some embodiments, the compound has a $T_{max}$ between 1.0 and 2.5 hours. In some embodiments, the compound has a plasma concentration greater than about 0.01 mg/mL after 5 hours after a single dose. In some embodiments, the compound has a plasma concentration greater than about 0.01 mg/mL after 10 hours after a single dose. In some embodiments, the compound has a plasma concentration greater than about 0.01 mg/mL, after 15 hours after a single dose.

In some embodiments, upon administration to a group of 10 subjects, the compound reaches a mean $C_{max}$ between about 0.01 µg/ml to about 1.0 µg/ml on day 1. In some embodiments, upon administration to a group of 10 subjects, the compound reaches a mean $C_{max}$ between about 0.01 µg/ml to about 0.8 µg/ml on day 1. In some embodiments, upon administration to a group of 10 subjects, the compound reaches a mean $C_{max}$ between about 0.03 µg/ml to about 0.5 µg/ml on day 1. In some embodiments, the compound has a mean AUC between about 0.1 µg hr/mL, to about 5.0 µg hr/mL. In some embodiments, the compound has a mean AUC between about 0.1 µg hr/mL to about 4.0 µg hr/mL. In some embodiments, the compound has a mean AUC between about 0.5 µg hr/mL, to about 3.0 µg hr/mL. In some embodiments, the compound has a mean $T_{max}$ between 0.5 and 5.0 hours. In some embodiments, the compound has a mean $T_{max}$ between 1.0 and 3.0 hours. In some embodiments, the compound has a mean $T_{max}$ between 1.0 and 2.5 hours.

Also provided herein are methods for decreasing tumor volume by administering the compounds and compositions described herein. In some embodiments, after daily administration of the drug for 5 days, the tumor decreases in volume by at least about 25%. In some embodiments, after daily administration of the drug for 5 days, the tumor decreases in volume by at least about 50%. In some embodiments, after daily administration of the drug for 5 days, the tumor decreases in volume by at least about 20-70%. In some embodiments, after daily administration of the drug for 15 days, the tumor decreases in volume by at least about 25%. In some embodiments, after daily administration of the drug for 15 days, the tumor decreases in volume by at least about 50%. In some embodiments, after daily administration of the drug for 15 days, the tumor decreases in volume by at least about 20-70%. In some embodiments, after daily administration of the drug for 30 days, the tumor decreases in volume by at least about 25%. In some embodiments, after daily administration of the drug for 30 days, the tumor decreases in volume by at least about 50%. In some embodiments, after daily administration of the drug for 30 days, the tumor decreases in volume by at least about 20-70%.

Also provided herein are methods for inhibiting tumor growth by administering the compounds and compounds described herein. In some embodiments, after administration of the drug, the tumor growth is inhibited by at least about 20%. In some embodiments, after administration of the drug, the tumor growth is inhibited by at least about 40%. In some embodiments, after administration of the drug, the tumor growth is inhibited by at least about 60%. In some embodiments, after administration of the drug, the tumor growth is inhibited by at least about 80%. In some embodiments, after administration of the drug, the tumor growth is inhibited by between about 20% to about 100%. In some embodiments, after administration of the drug, the tumor growth is substantially inhibited.

In some embodiments, the composition is administered twice a day. In some embodiments, the composition is administered once a day.

In some embodiments, the MEK inhibitor does not interfere with the coadministration of a second tumor suprressing agent.

In some embodiments, the composition is in the form of a tablet, a capsule, a gel cap, a caplet, a pellet, or a bead. In some embodiments, the composition is in the form of a capsule or tablet dosage form has a total weight of about 50 mg to about 1000 mg. In some embodiments, the composition is in the form of a capsule or tablet has a total weight selected from the group consisting of 50 mg, 75 mg, 100 mg, 150 mg, 200 mg, 250 mg, 300 mg, 350 mg, 400 mg, 450 mg, and 500 mg. In some embodiments, the composition is in the form of a capsule or tablet has a total weight of about 240 mg.

In some embodiments, the composition further comprises at least one filler selected from microcrystalline cellulose, silicified microcrystalline cellulose, lactose, a compressible sugar, xylitol, sorbitol, mannitol, pregelatinized starch, maltodextrin, calcium phosphate, calcium carbonate, starch and a calcium silicate.

In some embodiments, the composition further comprises at least one disintegrant selected from croscarmellose sodium, sodium starch glycolate, crospovidone, methylcellulose, alginic acid, sodium alginate, starch derivatives, betonite and veegum.

In some embodiments, the composition further comprises at least one lubricant selected from magnesium stearate, metallic stearates, talc, sodium stearyl fumarate and stearic acid.

In some embodiments, the composition further comprises at least one wetting agent or surfactant selected from sodium lauryl sulfate, glycerol, sorbitan oleates, sorbitan stearates, polyoxyethylenated sorbitan laurate, palmitate, stearate, oleate or hexaolate, polyoxyethylene stearyl alcohol and sorbitan monolaurate.

Provided herein are compositions in the form of a capsule or tablet and the capsule or tablet releases at least 60 percent of the drug within 30 minutes using U.S. Pharmacopeia (USP) Apparatus II at 50 rpm with 1% sodium lauryl sulfate in water as the dissolution medium. In some embodiments, the composition is in the form of a capsule or tablet and the capsule or tablet releases about 60-100 percent of the drug within 30 minutes using U.S. Pharmacopeia (USP) Apparatus II at 50 rpm with 1% sodium lauryl sulfate in water as the dissolution medium. In some embodiments, the composition is in the form of a capsule or tablet and the capsule or tablet releases about 60-90 percent of the drug within 30 minutes using U.S. Pharmacopeia (USP) Apparatus II at 50 rpm with 1% sodium lauryl sulfate in water as the dissolution medium. In some embodiments, the composition is in the form of a capsule or tablet and the capsule or tablet releases about 60-80 percent of the drug within 30 minutes using U.S. Pharmacopeia (USP) Apparatus II at 50 rpm with 1% sodium lauryl sulfate in water as the dissolution medium.

Provided herein are also batches of capsules or tablets, each comprising from about 1 to about 50 mg of a compound described herein and having a USP acceptance value for content uniformity of less than about 15.

Methods of Treatment

The invention relates to methods for treating or preventing cancer, comprising administering to a subject in need an effective amount of a pharmaceutical composition comprising a compound of formula (I), as described herein. In various embodiments, the compounds and compositions useful in these methods are as described by the genus of formula (I) or any sub-genus or species exemplified throughout the present application falling within formula (I).

The invention relates to methods for treating or preventing an inflammation disease, comprising administering to a subject in need an effective amount of a pharmaceutical composition comprising a compound of formula (I), as described herein. In various embodiments, the compounds and compositions useful in these methods are as described by the genus of formula (I) or any sub-genus or species exemplified throughout the present application falling within formula (I).

In some embodiments, the invention relates to methods for treating or preventing ankylosing spondylitis, gout, tendonitis, bursitis or sciatica, comprising administering to a subject in need thereof an effective amount of a pharmaceutical composition comprising a compound of formula (I), as described herein. In various embodiments, the compounds and compositions useful in these methods are as described by the genus of formula (I) or any sub-genus or species exemplified throughout the present application falling within formula (I).

In some aspects, the present invention is also directed to a method of treating a disease in an individual suffering from said disease comprising administering to said individual an effective amount of a composition comprising a compound of formula I or a pharmaceutically acceptable salt, solvate, polymorph, ester, tautomer or prodrug thereof.

In other aspects, the present invention is directed to a method of treating a disorder in a mammal, comprising administering to said mammal a therapeutically effective amount of the compound of formula I or a pharmaceutically acceptable salt, solvate, polymorph, ester, tautomer or prodrug thereof.

In other aspects, the present invention is directed to a method of treating a disorder in a human, comprising administering to said mammal a therapeutically effective amount of the compound of formula I or a pharmaceutically acceptable salt, solvate, polymorph, ester, tautomer or prodrug thereof.

In other aspects, the present invention is directed to a method of treating a hyperproliferative disorder in a mammal, including a human, comprising administering to said mammal a therapeutically effective amount of the compound of formula I or a pharmaceutically acceptable salt, solvate, polymorph, ester, tautomer or prodrug thereof.

In other aspects, the present invention is directed to a method of treating an inflammatory disease, condition, or disorder in a mammal, including a human, comprising administering to said mammal a therapeutically effective amount of the compound of formula I, or a pharmaceutically acceptable salt, ester, prodrug, solvate, hydrate or derivative thereof.

In other aspects, the present invention is directed to a method of treating a disorder or condition which is modulated by the MEK cascade in a mammal, including a human, comprising administering to said mammal an amount of the compound of formula I, or a pharmaceutically acceptable salt, ester, prodrug, solvate, hydrate or derivative thereof, effective to modulate said cascade. The appropriate dosage for a particular patient can be determined, according to known methods, by those skilled in the art.

Inhibition of MEK Enzyme

In other aspects, the present invention is directed to a method for inhibiting a MEK enzyme. In some embodiments, the method comprises contacting said MEK enzyme with an amount of a composition comprising a compound of formula I or a pharmaceutically acceptable salt, solvate, polymorph, ester, tautomer or prodrug thereof, sufficient to inhibit said enzyme, wherein said enzyme is inhibited. In further or additional embodiments the enzyme is at least about 1% inhibited. In further or additional embodiments the enzyme is at least about 2% inhibited. In further or additional embodiments the enzyme is at least about 3% inhibited. In further or additional embodiments the enzyme is at least about 4% inhibited. In further or additional embodiments the enzyme is at least about 5% inhibited. In further or additional embodiments the enzyme is at least about 10% inhibited. In further or additional embodiments the enzyme is at least about 20% inhibited. In further or additional embodiments the enzyme is at least about 25% inhibited. In further or additional embodiments the enzyme is at least about 30% inhibited. In further or additional embodiments the enzyme is at least about 40% inhibited. In further or additional embodiments the enzyme is at least about 50% inhibited. In further or additional embodiments the enzyme is at least about 60% inhibited. In further or additional embodiments the enzyme is at least about 70% inhibited. In further or additional embodiments the enzyme is at least about 75% inhibited. In further or additional embodiments the enzyme is at least about 80% inhibited. In further or additional embodiments the enzyme is at least about 90% inhibited. In further or additional embodiments the enzyme is essentially completely inhibited. In further or additional embodiments the MEK enzyme is MEK kinase. In further or additional embodiments the MEK enzyme is MEK1. In further or additional embodiments the MEK enzyme is MEK2. In further or additional embodiments the contacting occurs within a cell. In further or additional embodiments the cell is a mammalian cell. In further or additional embodiments the mammalian cell is a human cell. In further or additional embodiments, the MEK enzyme is inhibited with a composition comprising a pharmaceutically acceptable salt of a compound of formula I.

MEK Mediated Disorder

In other aspects, the present invention is directed to a method of treatment of a MEK mediated disorder in an individual suffering from said disorder comprising administering to said individual an effective amount of a composition comprising a compound of formula I or a pharmaceutically acceptable salt, solvate, polymorph, ester, tautomer or prodrug thereof. In some embodiments, the composition comprising a compound of formula I is administered orally, intraduodenally, parenterally (including intravenous, subcutaneous, intramuscular, intravascular or by infusion), topically or rectally. In some embodiments, the pharmaceutical composition is in a form suitable for oral administration. In further or additional embodiments, the pharmaceutical composition is in the form of a tablet, capsule, pill, powder, sustained release formulations, solution, suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments, the pharmaceutical composition further comprises a pharmaceutical carrier, excipient and/or adjuvant.

In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the MEK mediated disorder is a mammal. In further or additional embodiments, the individual is a human.

In some embodiments, the composition comprising a compound of formula I is administered in combination with an additional therapy. In further or additional embodiments, the additional therapy is radiation therapy, chemotherapy, surgery or any combination thereof. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both.

In some embodiments, the MEK mediated disorder is selected from the group consisting of inflammatory diseases, infections, autoimmune disorders, stroke, ischemia, cardiac disorder, neurological disorders, fibrogenetic disorders, proliferative disorders, hyperproliferative disorders, non-cancer hyperproliferative disorders, tumors, leukemias, neoplasms, cancers, carcinomas, metabolic diseases, malignant disease, vascular restenosis, psoriasis, atherosclerosis, rheumatoid arthritis, osteoarthritis, heart failure, chronic pain, neuropathic pain, dry eye, closed angle glaucoma and wide angle glaucoma. In further or additional embodiments, the MEK mediated disorder is an inflammatory disease. In further or additional embodiments, the MEK mediated disorder is a hyperproliferative disease. In further or additional embodiments, the MEK mediated disorder is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, stomach cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, an effective amount of a composition comprising a pharmaceutically acceptable salt of a compound of formula I is administered.

Achieving Effects

In other aspects, the present invention is directed to a method for achieving an effect in a patient comprising the administration of an effective amount of a composition comprising a compound of formula I or a pharmaceutically acceptable salt, solvate, polymorph, ester, tautomer or prodrug thereof, to a patient, wherein the effect is selected from the group consisting of inhibition of various cancers, immunological diseases, and inflammatory diseases. In some embodiments, the effect is inhibition of various cancers. In further or additional embodiments, the effect is inhibition of immunological diseases. In further or additional embodiments, the effect is inhibition inflammatory diseases.

In some embodiments, the composition comprising a compound of formula I is administered in combination with an additional therapy. In further or additional embodiments, the additional therapy is radiation therapy, chemotherapy, surgery or any combination thereof. In further or additional embodiments, the composition comprising a compound of formula I is administered in combination with at least one therapeutic agent.

In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

In other aspects, the present invention is directed to a method for degrading, inhibiting the growth of or killing a cancer cell comprising contacting said cell with an amount of a composition effective to degrade, inhibit the growth of or to kill said cell, the composition comprising a compound of formula I or a pharmaceutically acceptable salt, solvate, polymorph, ester, tautomer or prodrug thereof. In some embodiments, the cancer cells comprise brain, breast, lung, ovarian, pancreatic, prostate, renal, or colorectal cancer cells. In further or additional embodiments, the composition is administered with at least one therapeutic agent. In further or additional embodiments, the therapeutic agent is taxol, bortezomib or both. In further or additional embodiments, the therapeutic agent is selected from the group consisting of cytotoxic agents, anti-angiogenesis agents and anti-neoplastic agents. In further or additional embodiments, the anti-neoplastic agents selected from the group of consisting of alkylating agents, anti-metabolites, epidophyllotoxins; anti-neoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In some embodiments, the cancer cells are degraded. In further or additional embodiments, 1% of the cancer cells are degraded. In further or additional embodiments, 2% of the cancer cells are degraded. In further or additional embodiments, 3% of the cancer cells are degraded. In further or additional embodiments, 4% of the cancer cells are degraded. In further or additional embodiments, 5% of the cancer cells are degraded. In further or additional embodiments, 10% of the cancer cells are degraded. In further or additional embodiments, 20% of the cancer cells are degraded. In further or additional embodiments, 25% of the cancer cells are degraded. In further or additional embodiments, 30% of the cancer cells are degraded. In further or additional embodiments, 40% of the cancer cells are degraded. In further or additional embodiments, 50% of the cancer cells are degraded. In further or additional embodiments, 60% of the cancer cells are degraded. In further or additional embodiments, 70% of the cancer cells are degraded. In further or additional embodiments, 75% of the cancer cells are degraded. In further or additional embodiments, 80% of the cancer cells are degraded. In further or additional embodiments, 90% of the cancer cells are degraded. In further or additional embodiments, 100% of the cancer cells are degraded. In further or additional embodiments, essentially all of the cancer cells are degraded. In various embodiments, the aforementioned degradation occurs in one day, five days, ten days, one month, two months, six months or one year.

In some embodiments, the cancer cells are killed. In further or additional embodiments, 1% of the cancer cells are killed. In further or additional embodiments, 2% of the cancer cells are killed. In further or additional embodiments, 3% of the cancer cells are killed. In further or additional embodiments, 4% of the cancer cells are killed. In further or additional embodiments, 5% of the cancer cells are killed. In further or additional embodiments, 10% of the cancer cells are killed. In further or additional embodiments, 20% of the cancer cells are killed. In further or additional embodiments, 25% of the cancer cells are killed. In further or additional embodiments, 30% of the cancer cells are killed. In further or additional embodiments, 40% of the cancer cells are killed. In further or additional embodiments, 50% of the cancer cells are killed. In further or additional embodiments, 60% of the cancer cells are killed. In further or additional embodiments, 70% of the cancer cells are killed. In further or additional embodiments, 75% of the cancer cells are killed. In further or additional embodiments, 80% of the cancer cells are killed. In further or additional embodiments, 90% of the cancer cells are killed. In further or additional embodiments, 100% of the cancer cells are killed. In further or additional embodiments, essentially all of the cancer cells are killed. In various embodiments, the aforementioned cancer cell killing occurs in one day, five days, ten days, one month, two months, six months or one year.

In further or additional embodiments, the growth of the cancer cells is inhibited. In further or additional embodiments, the growth of the cancer cells is about 1% inhibited. In further or additional embodiments, the growth of the cancer cells is about 2% inhibited. In further or additional embodiments, the growth of the cancer cells is about 3% inhibited. In further or additional embodiments, the growth of the cancer cells is about 4% inhibited. In further or additional embodiments, the growth of the cancer cells is about 5% inhibited. In further or additional embodiments, the growth of the cancer cells is about 10% inhibited. In further or additional embodiments, the growth of the cancer cells is about 20% inhibited. In further or additional embodiments, the growth of the cancer cells is about 25% inhibited. In further or additional embodiments, the growth of the cancer cells is about 30% inhibited. In further or additional embodiments, the growth of the cancer cells is about 40% inhibited. In further or additional embodiments, the growth of the cancer cells is about 50% inhibited. In further or additional embodiments, the growth of the cancer cells is about 60% inhibited. In further or additional embodiments, the growth of the cancer cells is about 70% inhibited. In further or additional embodiments, the growth of the cancer cells is about 75% inhibited. In further or additional embodiments, the growth of the cancer cells is about 80% inhibited. In further or additional embodiments, the growth of the cancer cells is about 90% inhibited. In further or additional embodiments, the growth of the cancer cells is about 100% inhibited. In various embodiments, the aforementioned inhibition occurs in one day, five days, ten days, one month, two months, six months or one year.

In other aspects, the present invention is directed to a method of reducing the size of a tumor, inhibiting tumor size increase, reducing tumor proliferation or preventing tumor proliferation in an individual, comprising administering to said individual an effective amount of a composition comprising a compound of formula I or a pharmaceutically acceptable salt, solvate, polymorph, ester, tautomer or prodrug thereof. In some embodiments, the size of a tumor is reduced. In further or additional embodiments, the size of a tumor is reduced by at least 1%. In further or additional embodiments, the size of a tumor is reduced by at least 2%. In further or additional embodiments, the size of a tumor is reduced by at least 3%. In further or additional embodiments, the size of a tumor is reduced by at least 4%. In further or additional embodiments, the size of a tumor is reduced by at least 5%. In further or additional embodiments, the size of a tumor is reduced by at least 10%. In further or additional embodiments, the size of a tumor is reduced by at least 20%. In further or additional embodiments, the size of a tumor is reduced by at least 25%. In further or additional embodiments, the size of a tumor is reduced by at least 30%. In further or additional embodiments, the size of a tumor is reduced by at least 40%. In further or additional embodiments, the size of a tumor is reduced by at least 50%. In further or additional embodiments, the size of a tumor is reduced by at least 60%. In further or additional embodiments, the size of a tumor is reduced by at least 70%. In further or additional embodiments, the size of a tumor is reduced by at least 75%. In further or additional embodiments, the size of a tumor is reduced by at least 80%. In further or additional embodiments, the size of a tumor is reduced by at least 85%. In further or additional embodiments, the size of a tumor is reduced by at least 90%. In further or additional embodiments, the size of a tumor is reduced by at least 95%. In further or additional embodiments, the tumor is eradicated. In some embodiments, the size of a tumor does not increase. In various embodiments, the aforementioned effects on tumor size occurs in one day, five days, ten days, one month, two months, six months or one year.

In some embodiments, tumor proliferation is reduced. In some embodiments, tumor proliferation is reduced by at least 1%. In some embodiments, tumor proliferation is reduced by at least 2%. In some embodiments, tumor proliferation is reduced by at least 3%. In some embodiments, tumor proliferation is reduced by at least 4%. In some embodiments, tumor proliferation is reduced by at least 5%. In some embodiments, tumor proliferation is reduced by at least 10%. In some embodiments, tumor proliferation is reduced by at least 20%. In some embodiments, tumor proliferation is reduced by at least 25%. In some embodiments, tumor proliferation is reduced by at least 30%. In some embodiments, tumor proliferation is reduced by at least 40%. In some embodiments, tumor proliferation is reduced by at least 50%. In some embodiments, tumor proliferation is reduced by at least 60%. In some embodiments, tumor proliferation is reduced by at least 70%. In some embodiments, tumor proliferation is reduced by at least 75%. In some embodiments, tumor proliferation is reduced by at least 75%. In some embodiments, tumor proliferation is reduced by at least 80%. In some embodiments, tumor proliferation is reduced by at least 90%. In some embodiments, tumor proliferation is reduced by at least 95%. In some embodiments, tumor proliferation is prevented. In various embodiments, the aforementioned effects on cell proliferation occurs in one day, five days, ten days, one month, two months, six months or one year.

In some embodiments, the composition comprising a compound of formula I is administered in combination with an additional therapy. In further or additional embodiments, the additional therapy is radiation therapy, chemotherapy, surgery or any combination thereto. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyliotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both.

In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

Proliferative Diseases

In other aspects, the present invention is directed to a method for the treatment or prophylaxis of a proliferative disease in an individual comprising administering to said individual an effective amount of a composition comprising a compound of formula I or a pharmaceutically acceptable salt, solvate, polymorph, ester, tautomer or prodrug thereof. In some embodiments, the proliferative disease is cancer, psoriasis, restenosis, autoimmune disease, or atherosclerosis. In further or additional embodiments, the proliferative disease is a hyperproliferative disease. In further or additional embodiments, the proliferative disease is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, colorectal cancer, stomach cancer, head and neck cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, stomach cancer, brain cancer, breast cancer, lung cancer, non small cell lung cancer, ovarian cancer, pancreatic cancer, liver cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphona. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell lung cancer. In further embodiments, the cancer is stomach cancer.

In some embodiments, the composition comprising a compound of formula I is administered in combination with an additional therapy. In further or additional embodiments, the additional therapy is radiation therapy, chemotherapy, surgery, or any combination thereof. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors.

In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally.

In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the proliferative disease is a mammal. In further or additional embodiments, the individual is a human. In further or additional embodiments, an effective amount of a composition comprising a pharmaceutically acceptable salt of a compound of formula I is administered.

Inflammatory Diseases

In other aspects, the present invention is directed to a method for the treatment or prophylaxis of an inflammatory disease in an individual comprising administering to said individual an effective amount of a composition comprising a compound of formula I or a pharmaceutically acceptable salt, solvate, polymorph, ester, tautomer or prodrug thereof. In further or additional embodiments, the inflammatory disease is selected from chronic inflammatory diseases, rheumatoid arthritis, rheumatoid arthritis, spondyloarthropathies, gouty arthritis, osteoarthritis, juvenile arthritis, acute rheumatic arthritis, enteropathic arthritis, neuropathic arthritis, psoriatic arthritis, pyogenic arthritis, atherosclerosis, systemic lupus erythematosus, inflammatory bowel disease, irritable bowel syndrome, ulcerative colitis, reflux esophagitis, Crohn's disease, gastritis, asthma, allergies, respiratory distress syndrome, pancreatitis, chronic obstructive pulmonary disease, pulmonary fibrosis, psoriasis, eczema or scleroderma.

In some embodiments, the composition comprising a compound of formula I is administered in combination with an additional therapy. In further or additional embodiments, the composition comprising a compound of formula I is administered in combination with at least one therapeutic agent.

In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the inflammatory disease is a mammal. In further or additional embodiments, the individual is a human. In further or additional embodiments, an effective amount of a composition comprising a pharmaceutically acceptable salt of a compound of formula I is administered.

Cancer

In other aspects, the present invention is directed to a method for the treatment or prophylaxis of cancer in an individual comprising administering to said individual an effective amount of a composition comprising a compound of formula I or a pharmaceutically acceptable salt, solvate, polymorph, ester, tautomer or prodrug thereof. In further or additional embodiments, the cancer is brain cancer, breast cancer, stomach cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, stomach cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphona. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell lung cancer. In some embodiments, the cancer is stomach cancer.

In some embodiments, the composition comprising a compound of formula I is administered in combination with an additional therapy. In further or additional embodiments, the additional therapy is radiation therapy, chemotherapy, surgery, or any combination thereof. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both.

In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate.

In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims, A better understanding of the features and advantages of the present invention will be obtained by reference to the following detailed description that sets forth illustrative embodiments, in which the principles of the invention are utilized, and the accompanying drawings of which:

FIGS. 12A-12C show N—(S)-(3,4-difluoro-2-(2-fluoro-4-iodophenylamino)-6-methoxyphenyl)-1-(2,3-dihydroxypropyl)cyclopropane-1-sulfonamide growth inhibition of (A) human colorectal carcinoma Colo205 cells ($GI_{50}$=11 nM); (B) A375 cells ($GI_{50}$=22 nM) and (C) inhibition of MDA-MB231 cells which do not show N—(S)-(3,4-difluoro-2-(2-fluoro-4-iodophenylamino)-6-methoxyphenyl)-1-(2,3-dihydroxypropyl)cyclopropane-1-sulfonamide-induced growth arrest in 2-dimensional anchorage dependent assays.

FIG. 13A shows inhibition of growth of human colorectal carcinoma Colo205 cells, with $GI_{50}$ values at 6 nM and 11 nM respectively.

FIG. 13B shows inhibition of growth of A375 cells with $GI_{50}$ values at 5 nM and 22 nM.

FIG. 20A depicts a graph comparing the respective apoptosis levels at increasing concentrations of N—(S)-(3,4-difluoro-2-(2-fluoro-4-iodophenylamino)-6-methoxyphenyl)-1-(2,3-dihydroxypropyl)cyclopropane-1-sulfonamide at day 5 of treatment of non-small cell lung cancer (NSCLC) MV522 cells.

FIG. 20B is a graph demonstrating the respective apoptosis levels at increasing concentrations N—(S)-(3,4-difluoro-2-(2-fluoro-4-iodophenylamino)-6-methoxyphenyl)-1-(2,3-dihydroxypropyl)cyclopropane-1-sulfonamide at day 5 of treatment of non-small cell lung cancer (NSCLC) H358 cells.

FIG. 20C is a graph demonstrating the respective apoptosis levels at increasing concentrations of N—(S)-(3,4-difluoro-2-(2-fluoro-4-iodophenylamino)-6-methoxyphenyl)-1-(2,3-dihydroxypropyl)cyclopropane-1-sulfonamide at day 6 of treatment of non-small cell lung cancer (NSCLC) A549 cells.

FIG. 20D is a graph demonstrating the respective apoptosis levels at increasing concentrations of N—(S)-(3,4-di fluoro-2-(2-fluoro-4-iodophenylamino)-6-methoxyphenyl)-1-(2,3- dihydroxypropyl)cyclopropane-1-sulfonamide at day 5 of treatment of non-small cell lung cancer (NSCLC) 1-1727 cells.

Figure 1:
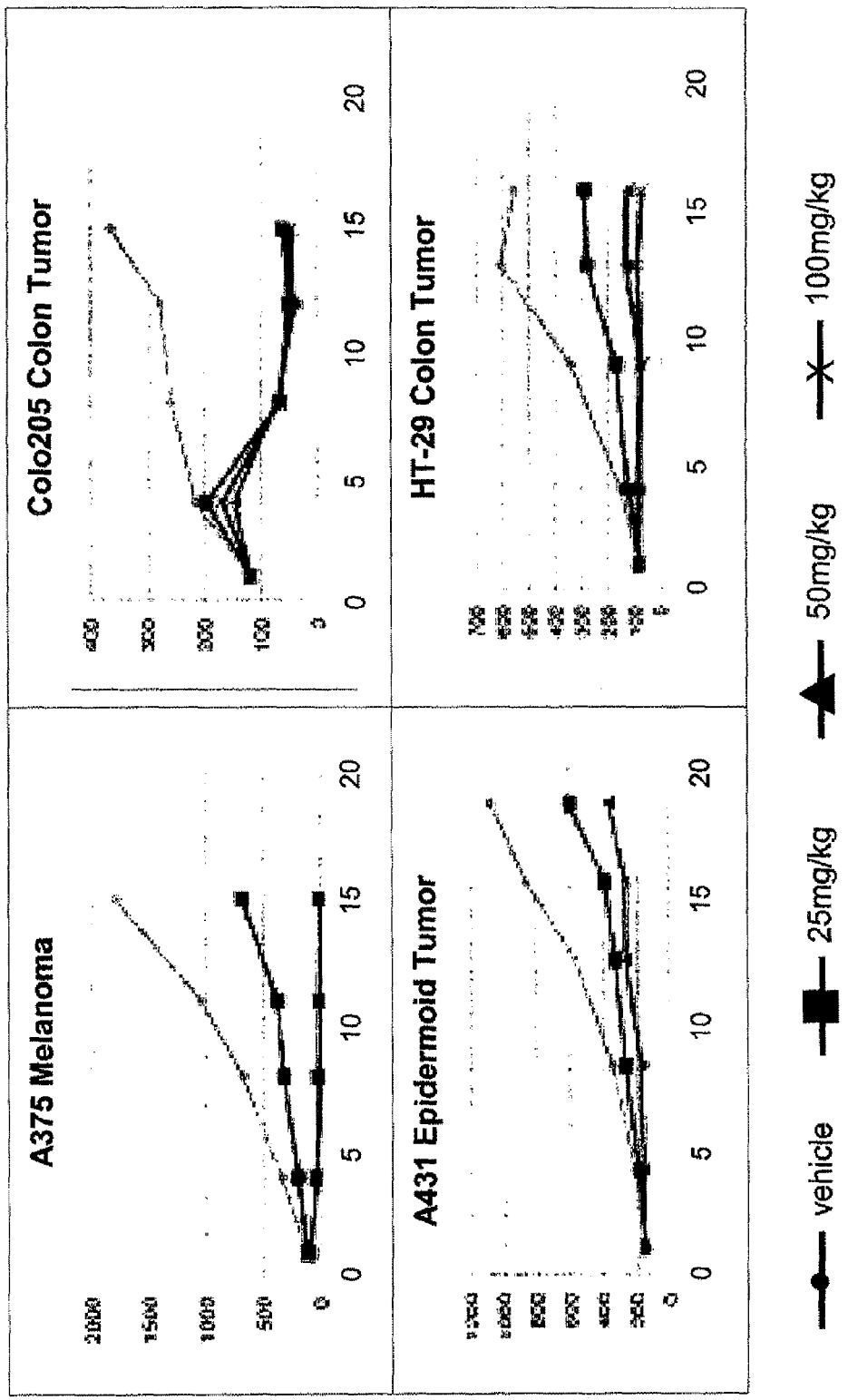
FIG. 1 shows graphs of average tumor volume against time (days) in mice implanted with A375 Melanoma, Colo205 Colon Tumor, A431 Epidermoid Tumor or HT-29 Colon Tumor cells. Mice were dosed orally (25 mg/kg, 50 mg/kg or 100 mg/kg), once a day, for 14 days.

FIG. 20E is a graph demonstrating the respective apoptosis levels at increasing concentrations of N—(S)-(3,4-difluoro-2-(2-fluoro-4-Iodophenylamino)-6-methoxyphenyl)-1-(2,3-dihydroxypropyl)cyclopropane-1-sulfonamide at day 5 of treatment of colon HT29 cells.

FIG. 20F is a graph demonstrating the respective apoptosis levels at increasing concentrations of N—(S)-(3,4-difluoro-2-(2-fluoro-4-iodophenylamino)-6-methoxyphenyl)-1-(2,3-dihydroxypropyl)cyclopropane-1-sulfonamide at day 6 of treatment of colon HCT116 cells.

FIG. 20G is a graph demonstrating the respective apoptosis levels at increasing concentrations of N—(S)-(3,4-difluoro-2-(2-fluoro-4-iodophenylamino)-6-methoxyphenyl)-1-(2,3-dihydroxypropyl)cyclopropane-1-sulfonamide at day 5 of treatment of colon HUH7 Hepatoma cells.

FIG. 20H is a graph depicting the respective apoptosis levels at increasing concentrations of N—(S)-(3,4-difluoro-2-(2-fluoro-4-iodophenylamino)-6-methoxyphenyl)-1-(2,3-dihydroxypropyl)cyclopropane-1-sulfonamide at day 5 of treatment of Sarcoma U2-OS cells.

FIG. 20I is a graph demonstrating the respective apoptosis levels at increasing concentrations of N—(S)-(3,4-difluoro-2-(2-fluoro-4-iodophenylamino)-6-methoxyphenyl)-1-(2,3-dihydroxypropyl)cyclopropane-1-sulfonamide at day 5 of treatment of Glioma D37 cells.

DETAILED DESCRIPTION OF THE INVENTION

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

Definition of standard chemistry terms may be found in reference works, including Carey and Sundberg "ADVANCED ORGANIC CHEMISTRY 4$^{TH}$ ED." Vols. A (2000) and 13 (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, —CH$_2$O— is equivalent to —OCH$_2$—.

Unless otherwise noted, the use of general chemical terms, such as though not limited to "alkyl," "amine," "aryl," are equivalent to their optionally substituted forms. For example, "alkyl," as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomerie, enantiomeric, and epimeric forms as well as the corresponding mixtures thereof. Presentation of one particular chemical structure or chemical name for a compound which contains one or more chiral centers, but which does not designate a particular stereochemistry, should be understood to include all possible stereoisomers, including mixtures of all possible stereoisomers, pure forms or substantially pure forms of one particular stereoisomer and pure forms or substantially pure forms of the alternate stereoisomer. Techniques for inverting or leaving unchanged a particular stereocenter, and those for resolving mixtures of stereoisomers are well known in the art and it is well within the ability of one of skill in the art to choose an appropriate method for a particular situation. See, for example, Furniss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, *Acc. Chem. Res.* 1990, 23, 128.

The terms "moiety", "chemical moiety", "group" and "chemical group", as used herein refer to a specific segment or functional group of a molecule. Chemical moieties are often recognized chemical entities embedded in or appended to a molecule.

The term "bond" or "single bond" refers to a chemical bond between two atoms, or two moieties when the atoms joined by the bond are considered to be part of larger substructure.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

Unless otherwise noted, the use of general chemical terms, such as though not limited to "alkyl," "amine," "aryl," are unsubstituted.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The term "A and A', together with the carbon atom to which they are attached, form a 3- to 6-member saturated ring", as used herein, refers to the following structures for compounds of formula I:

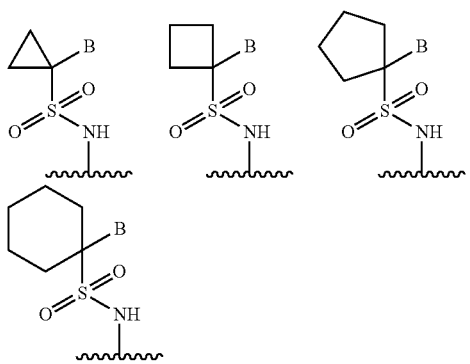

The terms "heteroatom" or "hetero" as used herein, alone or in combination, refer to an atom other than carbon or hydrogen. Heteroatoms are may be independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to a straight-chain or branched-chain saturated hydrocarbon monoradical having from one to about ten carbon atoms, or one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms. In one embodiment, the "alkyl" is substituted. Unless otherwise indicated, the "alkyl" is unsubstituted.

The term "alkenyl" as used herein, alone or in combination, refers to a straight-chain or branched-chain hydrocarbon monoradical having one or more carbon-carbon double-bonds and having from two to about ten carbon atoms, or two to about six carbon atoms. The group may be in either the cis or trans conformation about the double bond(s), and should be understood to include both isomers. Examples include, but are not limited to ethenyl (—CH═CH$_2$), 1-propenyl (—CH$_2$CH═CH$_2$), isopropenyl [—C(CH$_3$)═CH$_2$], butenyl, 1,3-butadienyl and the like. Whenever it appears herein, a numerical range such as "$C_2$-$C_5$ alkenyl" or "$C_{2-6}$ alkenyl", means that the alkenyl group may consist of 2 carbon atoms, 3 carbon atoms, 4 carbon atoms, 5 carbon atoms or 6 carbon atoms. In one embodiment, the "alkenyl" is substituted. Unless otherwise indicated, the "alkenyl" is unsubstituted.

The term "alkynyl" as used herein, alone or in combination, refers to a straight-chain or branched-chain hydrocarbon monoradical having one or more carbon-carbon triple-bonds and having from two to about ten carbon atoms, or from two to about six carbon atoms. Examples include, but are not limited to ethynyl, 2-propynyl, 2-butynyl, 1,3-butadiynyl and the like. Whenever it appears herein, a numerical range such as "$C_2$-$C_5$ alkynyl" or "$C_{2-6}$ alkynyl", means that the alkynyl group may consist of 2 carbon atoms, 3 carbon atoms, 4 carbon atoms, 5 carbon atoms or 6 carbon atoms. In one embodiment, the "alkynyl" is substituted. Unless otherwise indicated, the "alkynyl" is unsubstituted.

The terms "heteroalkyl", "heteroalkenyl" and "heteroalkynyl" as used herein, alone or in combination, refer to alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof), or heteroatomic group such as though not limited to —O—O—, —S—S—, —O—S—, —S—O—, ═N—N═, —N═N—, —N═N—NH—, —P(O)$_2$—, —O—P(O)$_2$—, —P(O)$_2$—O—, —S(O)—, —S(O)$_2$—, —SnH$_2$— and the like.

The terms "haloalkyl", "haloalkenyl" and "haloalkynyl" as used herein, alone or in combination, refer to alkyl, alkenyl and alkynyl groups respectively, as defined above, in which one or more hydrogen atoms is replaced by fluorine, chlorine, bromine or iodine atoms, or combinations thereof. In some embodiments two or more hydrogen atoms may be replaced with halogen atoms that are the same as each another (e.g. difluoromethyl); in other embodiments two or more hydrogen atoms may be replaced with halogen atoms that are not all the same as each other (e.g. 1-chloro-1-fluoro-1-iodoethyl). Non-limiting examples of haloalkyl groups are fluoromethyl, chloromethyl and bromoethyl. A non-limiting example of a haloalkenyl group is bromoethenyl. A non-limiting example of a haloalkynyl group is chloroethynyl.

The term "carbon chain" as used herein, alone or in combination, refers to any alkyl, alkenyl, alkynyl, heteroalkyl, heteroalkenyl or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "cycloalkyl" as used herein, alone or in combination, refers to a saturated, hydrocarbon monoradical ring, containing from three to about fifteen ring carbon atoms or from three to about ten ring carbon atoms, though may include additional, non-ring carbon atoms as substituents (e.g. methylcyclopropyl). Whenever it appears herein, a numerical range such as "$C_3$-$C_6$ cycloalkyl" or "$C_{3-6}$ cycloalkyl", means that the cycloalkyl group may consist of 3 carbon atoms, 4 carbon atoms, 5 carbon atoms or 6 carbon atoms, i.e., is cyclopropyl, cyclobutyl, cyclopentyl or cyclohepty, although the present definition also covers the occurrence of the term "cycloalkyl" where no numerical range is designated. The term includes fused, non-fused, bridged and spiro radicals. A fused cycloalkyl may contain from two to four fused rings where the ring of attachment is a cycloalkyl ring, and the other individual rings may be alicyclic, heterocyclic, aromatic, heteroaromatic or any combination thereof. Examples include, but are not limited to cyclopropyl, cyclopentyl, cyclohexyl, decalinyl, and bicyclo[2.2.1]heptyl and adamantyl ring systems. Illustrative examples include, but are not limited to the following moieties:

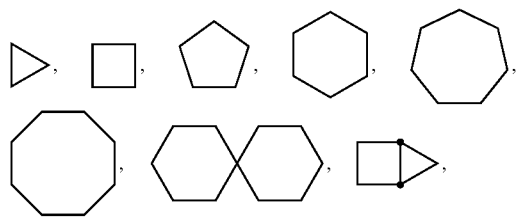

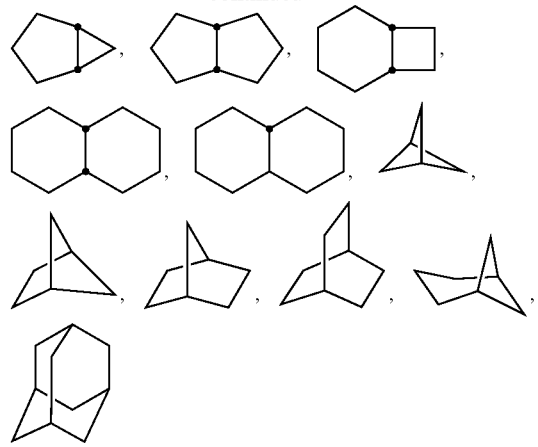

and the like.

In one embodiment, the "cycloalkyl" is substituted. Unless otherwise indicated, the "cycloalkyl" is unsubstituted.

The terms "non-aromatic heterocyclyl" and "heteroalicyclyl" as used herein, alone or in combination, refer to a saturated, partially unsaturated, or fully unsaturated nonaromatic ring monoradicals containing from three to about twenty ring atoms, where one or more of the ring atoms are an atom other than carbon, independently selected from among oxygen, nitrogen, sulfur, phosphorous, silicon, selenium and tin but are not limited to these atoms. In embodiments in which two or more heteroatoms are present in the ring, the two or more heteroatoms can be the same as each another, or some or all of the two or more heteroatoms can each be different from the others. The terms include fused, non-fused, bridged and spiro radicals. A fused non-aromatic heterocyclic radical may contain from two to four fused rings where the attaching ring is a non-aromatic heterocycle, and the other individual rings may be alicyclic, heterocyclic, aromatic, heteroaromatic or any combination thereof. Fused ring systems may be fused across a single bond or a double bond, as well as across bonds that are carbon-carbon, carbon-hetero atom or hetero atom-hetero atom. The terms also include radicals having from three to about twelve skeletal ring atoms, as well as those having from three to about ten skeletal ring atoms. Attachment of a non-aromatic heterocyclic subunit to its parent molecule can be via a heteroatom or a carbon atom. Likewise, additional substitution can be via a heteroatom or a carbon atom. As a non-limiting example, an imidazolidine non-aromatic heterocycle may be attached to a parent molecule via either of its N atoms (imidazolidin-1-yl or imidazolidin-3-yl) or any of its carbon atoms (imidazolidin-2-yl, imidazolidin-4-yl or imidazolidin-5-yl). In certain embodiments, non-aromatic heterocycles contain one or more carbonyl or thiocarbonyl groups such as, for example, oxo- and thio-containing groups. Examples include, but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxepanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Illustrative examples of heterocycloalkyl groups, also referred to as non-aromatic heterocycles, include:

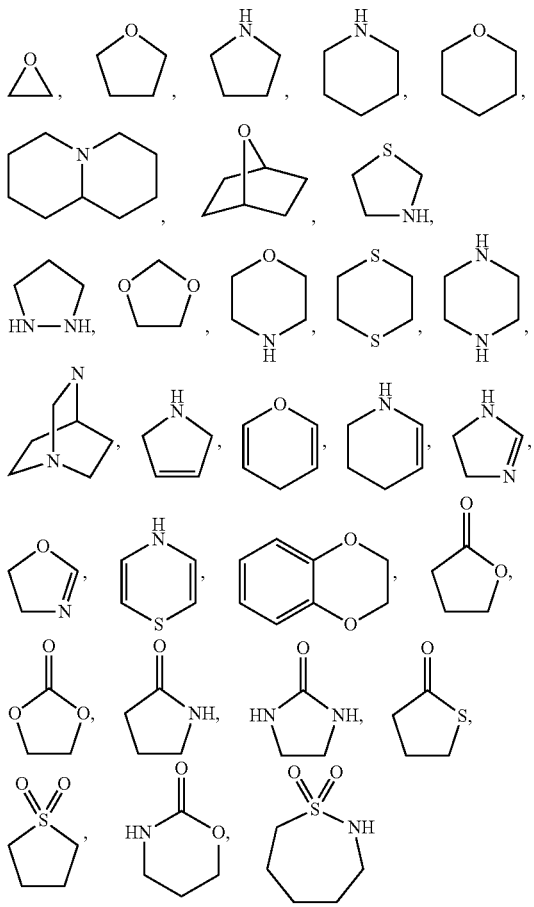

and the like.

The terms also include all ring forms of the carbohydrates, including but not limited to the monosaccharides, the disaccharides and the oligosaccharides. In one embodiment, the "non-aromatic heterocyclyl" or "heteroalicyclyl" is substituted. Unless otherwise indicated, the "non-aromatic heterocyclyl" or "heteroalicyclyl" is unsubstituted.

The term "aryl" as used herein, alone or in combination, refers to an aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl. In one embodiment, the "aryl" is substituted. Unless otherwise indicated, the "aryl" is unsubstituted.

The term "heteroaryl" as used herein, alone or in combination, refers to an aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide. Illustrative examples of heteroaryl groups include the following moieties:

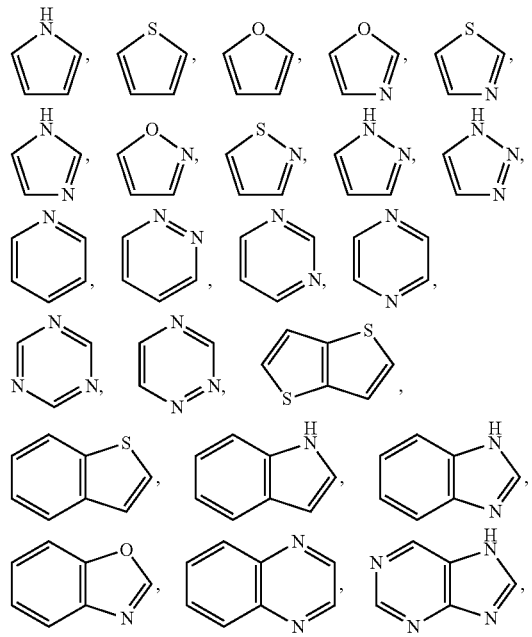

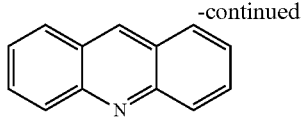

and the like.

In one embodiment, the "heteroaryl" is substituted. Unless otherwise indicated, the "heteroaryl" is unsubstituted.

The term "heterocyclyl" as used herein, alone or in combination, refers collectively to heteroalicyclyl and heteroaryl groups. Herein, whenever the number of carbon atoms in a heterocycle is indicated (e.g., $C_1$-$C_6$ heterocycle), at least one non-carbon atom (the heteroatom) must be present in the ring. Designations such as "$C_1$-$C_6$ heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, those two or more heteroatoms can be the same or different from one another. Non-aromatic heterocyclic groups include groups having only three atoms in the ring, while aromatic heterocyclic groups must have at least five atoms in the ring. Bonding (i.e. attachment to a parent molecule or further substitution) to a heterocycle can be via a heteroatom or a carbon atom. In one embodiment, the "heterocyclyl" is substituted. Unless otherwise indicated, the "heterocycyl" is unsubstituted.

The terms "halogen", "halo" or "halide" as used herein, alone or in combination refer to fluoro, chloro, bromo and/or iodo.

The term "amino" as used herein, alone or in combination, refers to the monoradical The term "alkylamino" as used herein, alone or in combination, refers to the monoradical —NH(alkyl) where alkyl is as defined herein.

The term "dialkylamino" as used herein, alone or in combination, refers to the monoradical —N(alkyl)(alkyl) where each alkyl may be identical or non-identical and is as defined herein.

The term "diamino alkyl" as used herein, alone or in combination, refers to an alkyl group containing two amine groups, wherein said amine groups may be substituents on the alkyl group which may be amino, alkylamino, or dialkylamino groups, or wherein one or both of said amine groups may form part of an alkyl chain to form -alkylene-N(H or alkyl)-alkylene-N(H or alkyl or alkylene-)(H or alkyl or alkylene-).

The term "hydroxy" as used herein, alone or in combination, refers to the monoradical —OH.

The term "cyano" as used herein, alone or in combination, refers to the monoradical —CN.

The term "cyanomethyl" as used herein, alone or in combination, refers to the monoradical —CH$_2$CN.

The term "nitro" as used herein, alone or in combination, refers to the monoradical —NO$_2$.

The term "oxy" as used herein, alone or in combination, refers to the diradical —O—.

The term "oxo" as used herein, alone or in combination, refers to the diradical. =O.

The term "carbonyl" as used herein, alone or in combination, refers to the diradical which may also be written as —C(O)—.

The terms "carboxy" or "carboxyl" as used herein, alone or in combination, refer to the moiety —C(O)OH, which may also be written as —COOH.

The term "alkoxy" as used herein, alone or in combination, refers to an alkyl ether radical, —O-alkyl, including the groups —O-aliphatic and —O-carbocyclyl, wherein the alkyl, aliphatic and carbocyclyl groups may be optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tert-butoxy and the like.

The term "sulfinyl" as used herein, alone or in combination, refers to the diradical —S(=O)—.

The term "sulfonyl" as used herein, alone or in combination, refers to the diradical —S(=O)$_2$—.

The terms "sulfonamide", "sulfonamido" and "sulfonamidyl" as used herein, alone or in combination, refer to the diradical groups —S(=O)$_2$—NH— and —NH—S(=O)$_2$—.

The terms "sulfamide", "sulfamido" and "sulfamidyl" as used herein, alone or in combination, refer to the diradical group —NH—S(=O)$_2$—NH—.

The term "reactant," as used herein, refers to a nucleophile or electrophile used to create covalent linkages.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

Certain Pharmaceutical Terminology

The term "MEK inhibitor" as used herein refers to a compound that exhibits an IC$_{50}$ with respect to MEK activity, of no more than about 100 µM or not more than about 50 µM, as measured in the Mek1 kinase assay described generally herein. "IC$_{50}$" is that concentration of inhibitor which reduces the activity of an enzyme (e.g., MEK) to half-maximal level. Compounds described herein have been discovered to exhibit inhibition against MEK. Compounds of the present invention preferably exhibit an IC$_{50}$ with respect to MEK of no more than about 10 µM, more preferably, no more than about 5 µM, even more preferably not more than about 1 µM, and most preferably, not more than about 200 nM, as measured in the Mek1 kinase assay described herein.

The term "subject", "patient" or "individual" as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to an amount of at least one agent or compound being administered that is sufficient to treat or prevent the particular disease or condition. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "substantially free of water" and "substantially free of solvent" as used herein, refer to crystalline polymorph forms comprising less than 0.01, 0.1, 0.2, 0.3, 0.4, 0.5, 1 or 2% by weight of water or solvent respectively.

The term "substantially the same as" as used herein, refers to a powder x-ray diffraction pattern or differential scanning calorimetry pattern that may be non-identical to those depicted herein, but that falls within the limits of experimental error, when considered by one of ordinary skill in the art.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical *Sciences* (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "pharmaceutically acceptable derivative or prodrug" as used herein, refers to any pharmaceutically acceptable salt, ester, salt of an ester or other derivative of a compound of formula I, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

As used herein, a "prodrug" is a compound that may be converted under physiological conditions or by solvolysis to the specified compound or to a pharmaceutically acceptable salt of such compound. Prodrugs include compounds wherein an amino acid residue, or a polypeptide chain of two or more amino acid residues, is covalently joined through an amide or ester bond to a free amino, hydroxy, or carboxylic acid group of compounds of Formulas I. The amino acid residues contemplated include but are not limited to the 20 naturally-occurring amino acids. Other suitable amino acids include 4-hydroxyproline, hydroxylysine, demosine, isodemosine, 3-methyl histidine, norvaline, β-alanine, γ-aminobutyric acid, cirtulline, homocysteine, homoserine, ornithine and methionine sulfone. Additional types of prodrugs are well known in the art.

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example *Design of Prodrugs*, Bundgaard, A. Ed., Elseview, 1985 and *Method in Enzymology*, Widder, K. et al., Ed.; Academic, 1985, vol. 42, p. 309-396; Bundgaard, H. "Design and Application of Prodrugs" in *A Textbook of Drug Design and Development*, Krosgaard-Larsen and H. Bundgaard, Ed., 1991, Chapter 5, p. 113-191; and Bundgaard, H., *Advanced Drug Delivery Review*, 1992, 8, 1-38, each of which is incorporated herein by reference. The prodrugs described herein include, but are not limited to, the following groups and combinations of these groups; amine derived prodrugs:

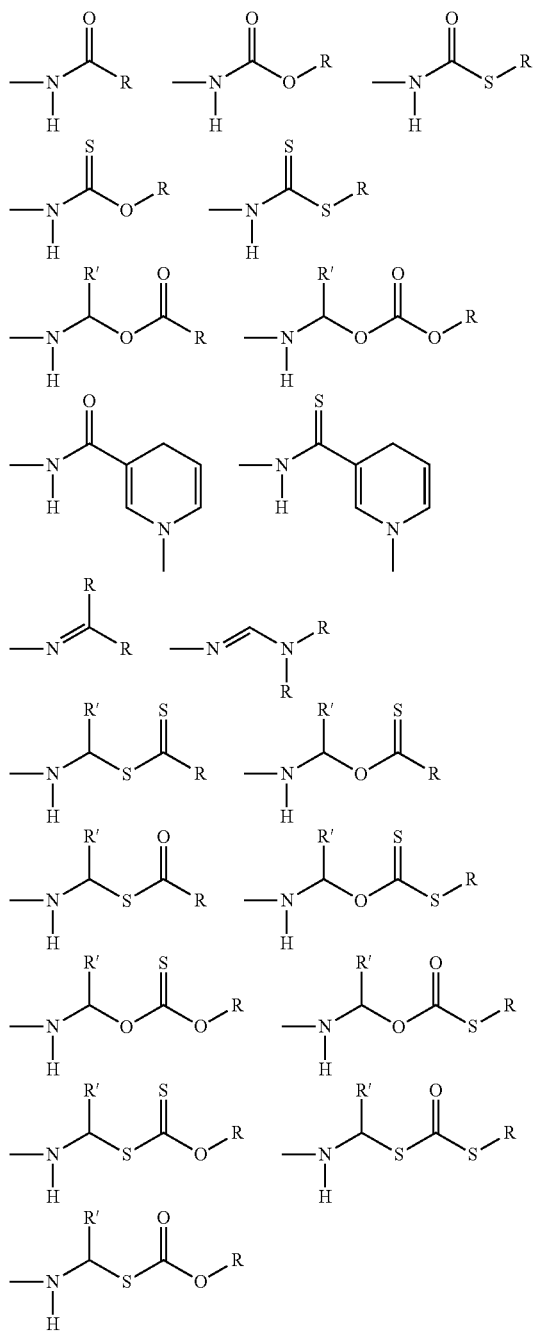

Hydroxy prodrugs include, but are not limited to acyloxyalkyl esters, alkoxycarbonyloxyalkyl esters, alkyl esters, aryl esters and disulfide containing esters.

The term "pharmaceutically acceptable salt" as used herein, includes salts that retain the biological effectiveness of the free acids and bases of the specified compound and that are not biologically or otherwise undesirable. Compounds described may possess acidic or basic groups and therefore may react with any of a number of inorganic or organic bases, and inorganic and organic acids, to form a pharmaceutically acceptable salt. Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorides, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate, metaphosphate, methanesulfonate, methoxybenzoate, methylbenzoate, monohydrogenphosphate, 1-napthalenesulfonate, 2-napthalenesulfonate, nicotinate, nitrate, oxalates, palmoate, pectinate, persulfate, phenylacetates, phenylpropionates, 3-phenylpropionate, phosphate, picrate, pivalate, propionate, pyrosulfate, pyrophosphate, propiolate, propionates, phthalate, phenylbutyrate, propanesulfonate, pyrophosphates, salicylate, succinate, sulfate, sulfite, succinate, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts. (See for example Berge at al., *J. Pharm. Sci.* 1977, 66, 1-19.) Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine, Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, $N^+(C_{1-4}\text{ alkyl})_4$, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge at al., supra. These salts can be prepared in situ during the final isolation and purification of the compounds of the invention, or by separately reacting a purified compound in its free base form with a suitable organic or inorganic acid, and isolating the salt thus formed.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from the mixing or combining of more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent(s) are administered in a single composition. In some embodiments, compounds of the invention and the other agent(s) are admixed in the composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996).

Compounds

Described herein are compounds of formula I, and pharmaceutically acceptable salts, solvates, polymorphs, esters, amides, tautomers or prodrugs thereof:

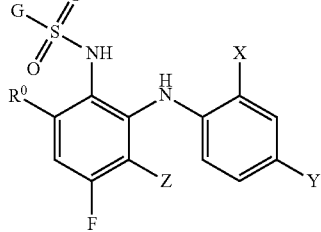

formula I wherein
Z is H or F;
X is F, Cl, $CH_3$, $CH_2OH$, $CH_2F$, $CHF_2$, or $CF_3$;

Y is I, Br, $C_1$, $CF_3$, $C_1$-$C_3$ alkyl, $C_2$-$C_3$ alkenyl, $C_2$-$C_3$ alkynyl, cyclopropyl, OMe, OEt, SMe, phenyl or Het, where Het is a 5- to 10-membered mono- or bicyclic heterocyclic group, which group is saturated, olefinic, or aromatic, containing 1-5 ring heteroatoms selected independently from N, O, and S; where all said phenyl or Het groups are optionally substituted with F, Cl, Br, I, acetyl, methyl, CN, $NO_2$, $CO_2H$, $C_1$-$C_3$ alkyl, $C_1$-$C_3$ alkoxy, O—$C_3$ alkyl-C(=O)—, $C_1$-$C_3$ alkyl-C(=S)—, $C_1$-$C_3$ alkoxy-C(=S)—, $C_1$-$C_3$ alkyl-C(=O)O—, $C_1$-$C_3$ alkyl-O—(C=O)—, $C_1$-$C_3$ alkyl-C(=O)NH—, $C_1$-$C_3$ alkyl-C(=NH)NH—, $C_1$-$C_3$ alkyl-NH—(C=O)—, di-$C_1$-$C_3$ alkyl-N—(C=O)—, $C_1$-$C_3$ alkyl-C(=O)N($C_1$-$C_3$ alkyl)-, $C_1$-$C_3$ alkyl-S(=O)$_2$NH— or trifluoromethyl;

all said methyl, ethyl, $C_1$-$C_3$ alkyl, and cyclopropyl groups are optionally substituted with OH;

all said methyl groups are optionally substituted with one, two, or three F atoms;

$R^0$ is H, F, Cl, Br, I, $CH_3NH$—, $(CH_3)_2N$—, $C_1$-$C_6$ alkyl, $C_1$-$C_4$ alkoxy, $C_3$-$C_6$ cycloalkyl, $C_2$-$C_6$ alkenyl, $C_2$-$C_6$ alkynyl, phenyl, monosubstituted phenyl, $O(C_1$-$C_4$ alkyl), O—C(=O)($C_1$-$C_4$ alkyl) or C(=O)O($C_1$-$C_4$ alkyl); where said alkyl, alkoxy, cycloalkyl, alkenyl, alkynyl and phenyl groups are optionally substituted with 1-3 substituents selected independently from F, Cl, Br, I, OH, CN, cyanomethyl, nitro, phenyl and trifluoromethyl; said $C_1$-$C_6$ alkyl and $C_1$-$C_4$ alkoxy groups also optionally substituted with $OCH_3$ or $OCH_2CH_3$;

G is $G_1$, $G_2$, $R_{1a}$, $R_{1b}$, $R_{1c}$, $R_{1d}$, $R_{1e}$, $Ar_1$, $Ar_2$ or $Ar_3$; where
$G_1$ is $C_1$-$C_6$ alkyl optionally substituted with one amino, $C_1$-$C_3$ alkylamino, or dialkylamino group, said dialkylamino group comprising two $C_1$-$C_4$ alkyl groups which may be identical or non-identical; or
$G_1$ is a $C_3$-$C_8$ diamino alkyl group;
$G_2$ is a 5- or 6-membered ring, which is saturated, unsaturated, or aromatic, containing 1-3 ring heteroatoms selected independently from N, O, and S, optionally substituted with 1-3 substituents selected independently from F, Cl, OH, O($C_1$-$C_3$ alkyl), $OCH_3$, $OCH_2CH_3$, $CH_3C$(=O)NH, $CH_3C$(=O)O, CN, $CF_3$, and a 5-membered aromatic heterocyclic group containing 1-4 ring heteroatoms selected independently from N, O, and S;

$R_{1a}$ is methyl, optionally substituted with 1-3 fluorine atoms or 1-3 chlorine atoms, or with OH, cyclopropoxy, or $C_1$-$C_3$ alkoxy, where said cyclopropoxy group or the $C_1$-$C_3$ alkyl moieties of said $C_1$-$C_3$ alkoxy groups are optionally substituted with one hydroxy or methoxy group, and where all $C_3$— alkyl groups within said $C_1$-$C_4$ alkoxy are optionally further substituted with a second OH group;

$R_{1b}$ is $CH(CH_3)$—$C_{1-3}$ alkyl or $C_3$-$C_6$ cycloalkyl, said alkyl and cycloalkyl groups optionally substituted with 1-3 substituents selected independently from F, Cl, Br, I, OH, $OCH_3$, and ON;

$R_{1c}$ is $(CH_2)_nO_mR'$; where
m is 0 or 1; and where
when m is 0, n is 1 or 2;
when m is 1, n is 2 or 3;
R' is $C_1$-$C_6$ alkyl, optionally substituted with 1-3 substituents selected independently from F, Cl, OH, $OCH_3$, $OCH_2CH_3$, and $C_3$-$C_6$ cycloalkyl;

$R_{1d}$ is C(A)(A')(B)—; where
B is H or $C_{1-4}$ alkyl, optionally substituted with one or two OH groups;

A and A' are independently H or $C_{1-4}$ alkyl, optionally substituted with one or two OH groups; or A and A', together with the carbon atom to which they are attached, form a 3- to 6-member saturated ring;

$R_{1c}$ is

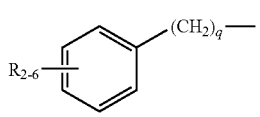

where
q is 1 or 2;
$R_2$ and $R_3$ are each independently, H, F, Cl, Br, $CH_3$, $CH_2F$, $CHF_2$, $CF_3OCH_3$, $OCH_2F$, $OCHF_2$, $OCF_3$, ethyl, n-propyl, isopropyl, cyclopropyl, isobutyl, sec-butyl, text-butyl or methylsulfonyl;
$R_4$ is H, F, Cl, Br, $CH_3$, $CH_2F$, $CHF_2$, $CF_3OCH_3$, $OCH_2F$, $OCHF_2$, $OCF_3$, ethyl, n-propyl, isopropyl, cyclopropyl, isobutyl, sec-butyl, tert-butyl, methylsulfonyl, nitro, acetamido, amidinyl, cyano, carbamoyl, methylcarbamoyl, dimethylcarbamoyl, 1,3,4-oxadiazol-2-yl, 5-methyl-1,3,4-oxadiazol, 1,3,4-thiadiazol, 5-methyl-1,3,4-thiadiazol 1H-tetrazolyl, N-morpholyl carbonyl amino, N-morpholylsulfonyl and N-pyrrolidinylcarbonylamino;
$R_5$ is H, F, Cl or methyl;
$R_6$ is H, F, Cl or methyl;
$Ar_1$ is

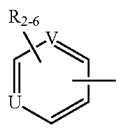

where
U and V are, independently, N, $CR_2$ or $CR_3$;
$R_2$, $R_3$ and $R_4$ are, independently, H, F, Cl, Br, $CH_3$, $CH_2F$, $CHF_2$, $CF_3OCH_3$, $OCH_2F$, $OCHF_2$, $OCF_3$, ethyl, n-propyl, isopropyl, cyclopropyl, isobutyl, sec-butyl, tert-butyl, acetamido, amidinyl, cyano, carbamoyl, methylcarbamoyl, dimethylcarbamoyl, 1,3,4-oxadiazol-2-yl, 5-methyl-1,3,4-oxadiazolyl, 1,3,4-thiadiazolyl, 5-methyl-1,3,4-thiadiazolyl, 1H-tetrazolyl, N-morpholylcarbonylamino, N-morpholylsulfonyl, N-pyrrolidinylcarbonylamino, and methylsulfonyl;
$R_5$ and $R_6$ are, independently, H, F, Cl or methyl;
$Ar_2$ is

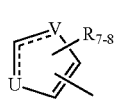

where
the dashed line represents alternative formal locations for the second ring double bond;
U is —S—, —O— or —N and where when U is —O— or —S—, V is —CH=, —CCl= or —N=;
when U is —N=, V is —CH=, —CCl=, or —N=;
$R_7$ is H or methyl;
$R_8$ is H, acetamido, methyl, F or Cl;
$Ar_3$ is

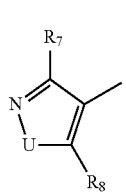

where
U is —NH—, —$NCH_3$— or —O—;
$R_7$ and $R_8$ are, independently, H, F, Cl, or methyl.

In addition to the definitions given herein for the groups G, $R^0$, X, Y and Z, additional substitutions which could be contemplated by those of skill in the chemical and pharmaceutical arts are included.

In some embodiments, the invention provides a compound of formula I, where G is $G_1$ or $G_2$. In other embodiments, G is $G_1$. In further or additional embodiments, G is $G_3$.

In some embodiments, the invention provides a compound of formula I, where G is $R_{1a}$, $R_{1b}$, $R_{1c}$, $R_{1d}$, $R_{1e}$, $Ar_1$, $Ar_2$ or $Ar_3$. In further or additional embodiments, G is $R_{1a}$, $R_{1b}$, $R_{1c}$, $R_{1d}$ or $R_{1e}$. In further or additional embodiments, G is $R_{1a}$. In further or additional embodiments, G is $R_{1b}$. In further or additional embodiments, G is $R_{1c}$. In further or additional embodiments, G is $R_{1d}$. In further or additional embodiments, G is $R_{1e}$. In further or additional embodiments, G is $Ar_1$, $Ar_2$ or $Ar_3$. In further or additional embodiments, G is $Ar_1$. In further or additional embodiments, G is $Ar_2$. In further or additional embodiments, G is $Ar_3$ In some embodiments provided are compounds of formula I, or their pharmaceutically acceptable salts. In further or additional embodiments, provided herein are compounds of formula I, or their solvates. In further or additional embodiments, provided herein are compounds of formula I or their polymorphs. In further or additional embodiments, provided herein are compounds of formula I, or their esters. In further or additional embodiments, provided herein are compounds of formula I, or their amides. In further or additional embodiments, provided herein are compounds of formula I or their tautomers. In further or additional embodiments, provided herein are compounds of formula I or their prodrugs.

In some embodiments, Z is H. In some embodiments, Z is F. In some embodiments, X is F. In some embodiments, X is Cl. In some embodiments, X is $CH_3$. In some embodiments, X is $CH_2OH$. In some embodiments, X is $CH_2F$. In some embodiments, X is $CHF_2$. In some embodiments, X is $CF_3$. In some embodiments, X is F, Cl, or $CH_3$.

In some embodiments, G is $G_1$ or $G_2$, X is F, Cl, or $CH_3$; Y is I, Br, $C_1$, $CF_3$, $C_1$-$C_3$ alkyl, phenyl, pyridyl, pyrrolyl, pyrazolyl, said phenyl, pyridyl, pyrrolyl, and pyrazolyl groups optionally substituted with F, Cl, Br, I, acetyl, methyl, CN, $NO_2$, $CO_2H$, $C_1$-$C_3$ alkyl, $C_1$-$C_3$ alkoxy, $C_1$-$C_3$ alkyl-C(=O)—, $C_1$-$C_3$ alkyl-C(=S)—, $C_1$-$C_3$ alkoxy-C(=S)—, $C_1$-$C_3$ alkyl-C(=O)O—, $C_1$-$C_3$ alkyl-O—(C=O)—, $C_1$-$C_3$ alkyl-C(=O)NH—, $C_1$-$C_3$ alkyl-C(=NH)NH—, $C_1$-$C_3$ alkyl-NH—(C=O)—, di-$C_1$-$C_3$ alkyl-N—(C=O)—, $C_1$-$C_3$ alkyl-C(=O)N($C_1$-$C_3$ alkyl)-, $C_1$-$C_3$ alkyl-S(=O)$_2$NH— or trifluoromethyl; and Z is H or F. In further or additional embodiments, G is $G_1$ or $G_2$, and $R^o$ is F, Cl, $C_1$-$C_4$ alkyl or $C_1$-$C_4$ alkoxy, said $C_1$-$C_4$ alkyl group and the $C_1$-$C_4$ alkyl moiety of said $C_1$-$C_4$ alkoxy group optionally substituted with F, Cl, $OCH_3$, or $OCH_2CH_3$. In further or additional embodiments, G is $G_1$ or $G_2$, and R is H, F, Cl, $C_1$-$C_4$ alkyl, methoxy, ethoxy, or 2-methoxy-ethoxy.

In some embodiments, $G_1$ is N-methyl-2-aminoethyl. In further or additional embodiments, $G_1$ is $(CH_3)_2N$—$CH_2CH_2$—NH—$(CH_2)_n$—, where n is 1, 2, or 3. In further or additional embodiments, $G_1$ is $(CH_3)_2N$—$CH_2CH_2$—NH—$(CH_2)_n$—, where n is 1, 2, or 3, and X is F. In further or additional embodiments, $G_1$ is $(CH_3)_2N$—$CH_2CH_2$—NH—$(CH_2)_n$—, where n is 1, 2, or 3, X is F and Z is F.

In some embodiments, $G_2$ is 1-piperidyl, 2-piperidyl, 3-piperidyl, or 4-piperidyl. In further or additional embodiments, $G_2$ is morpholyl, 1-piperazyl, or 2-piperazyl.

In some embodiments, G is $R_{1a}$, $R_{1b}$, $R_{1c}$, $R_{1d}$, $R_{1e}$, $Ar_1$, $Ar_2$ or $Ar_3$ and X is F, Cl, or $CH_3$. In further or additional embodiments, G is $R_{1a}$, $R_{1b}$, $R_{1c}$, $R_{1d}$, $R_{1e}$, $Ar_1$, $Ar_2$ or $Ar_3$, X is F, Cl, or $CH_3$ and Y is I, Br, $C_1$, $CF_3$, or $C_1$-$C_3$ alkyl In further or additional embodiments, G is $R_{1a}$, $R_{1b}$, $R_{1c}$, $R_{1d}$, $R_{1e}$, $Ar_1$, $Ar_2$ or $Ar_3$, X is F, Cl, or $CH_3$, Y is I, Br, $C_1$, $CF_3$, or $C_1$-$C_3$ alkyl and Z is H or F In further or additional embodiments, G is $R_{1a}$, $R_{1b}$, $R_{1c}$, $R_{1d}$, $R_{1e}$, $Ar_1$, $Ar_2$ or $Ar_3$ and $R^o$ is F, Cl, $C_1$-$C_4$ alkyl or $C_1$-$C_4$ alkoxy, said $C_1$-$C_4$ alkyl group and the $C_1$-$C_4$ alkyl moiety of said $C_1$-$C_4$ alkoxy group optionally substituted with F, Cl, $OCH_3$, or $OCH_2CH_3$. In further or additional embodiments, G is $R_{1a}$, $R_{1b}$, $R_{1c}$, $R_{1d}$, $R_{1e}$, $Ar_1$, $Ar_2$ or $Ar_3$ and $R^o$ is H, F, Cl, $C_1$-$C_4$ alkyl, methoxy, ethoxy, or 2-methoxy-ethoxy.

In some embodiments, G is $R_{1a}$; and Z is F. In further or additional embodiments, G is $R_{1a}$ where $R_{1a}$ is $CH_3$, $R^o$ is H; and Y is Br, I, $CF_3$, or $CH_3$. In some embodiments, G is $R_{1b}$ and Z is F. In further or additional embodiments, G is $R_{1b}$, Z is F, and $R^o$ is H, F, or $OCH_3$. In further or additional embodiments, G is $R_{1b}$, Z is F, $R^o$ is H, F, or $OCH_3$, and X is F or $CH_3$. In further or additional embodiments, G is $R_{1b}$, Z is F, $R^o$ is H, F, or $OCH_3$, X is F or $CH_3$ and Y is Br, I or $CH_3$. In further or additional embodiments, G is $R_{1b}$ where $R_{1b}$ is $C_3$-$C_6$ cycloalkyl. In further or additional embodiments, G is $R_{1b}$ where $R_{1b}$ is substituted $C_3$-$C_6$ cycloalkyl. In further or additional embodiments, G is $R_{1b}$ where $R_{1b}$ is unsubstituted $C_3$-$C_6$ cycloalkyl. In further or additional embodiments, G is $R_{1b}$ where $R_{1b}$ is unsubstituted $C_3$-$C_6$ cycloalkyl and $R^o$ is H. In further or additional embodiments, G is $R_{1b}$ where $R_{1b}$ is isopropyl or cyclopropyl.

In some embodiments, G is $R_{1c}$, and Y is I, Br, $CH_3$, or $CF_3$. In further or additional embodiments, G is $R_{10}$, Y is I, Br, $CH_3$, or $CF_3$, and Z is F. In further or additional embodiments, G is $R_{1c}$, Y is I, Br, $CH_3$, or $CF_3$, Z is F and m is zero.

In some embodiments, G is $R_{1d}$ and $R^o$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino. In further or additional embodiments, G is $R_{1d}$, $R^o$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino and X is F, Cl, $CH_3$, or mono-, di- or tri-fluoromethyl. In further or additional embodiments, G is $R_{1d}$, $R^o$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino, X is F, Cl, $CH_3$, or mono-, di- or tri-fluoromethyl and Y is I, Br, Cl, or mono-, di- or tri-fluoromethyl. In further or additional embodiments, G is $R_{1d}$, $R^o$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino, X is F, Cl, $CH_3$, or mono-, di- or tri-fluoromethyl, Y is I, Br, Cl, or mono-, di- or tri-fluoromethyl and Z is H or F. In further or additional embodiments, G is $R_{1d}$ and $R^o$ is F, Cl, methyl, ethyl, methoxy, ethoxy, or 2-methoxy-ethoxy.

In further or additional embodiments, G is $R_{1d}$, $R^o$ is F, Cl, methyl, ethyl, methoxy, ethoxy, or 2-methoxy-ethoxy and X is F, Cl, or $CH_3$. In further or additional embodiments, G is $R_{1d}$, $R^o$ is F, Cl, methyl, ethyl, methoxy, ethoxy, or 2-methoxy-ethoxy, X is F, Cl, or $CH_3$ and Y is I, Br, Cl, or mono-, di- or tri-fluoromethyl. In further or additional embodiments, G is $R_{1d}$, $R^o$ is F, Cl, methyl, ethyl, methoxy, ethoxy, or 2-methoxy-ethoxy, X is F, Cl, or $CH_3$, Y is I, Br, Cl, or mono-, di- or tri-fluoromethyl and Z is H or F. In further or additional embodiments, G is $R_{1d}$ and $R^o$ is H; X is F, Cl, $CH_3$, or mono-, di- or tri-fluoromethyl. In further or additional embodiments, G is $R_{1d}$, $R^o$ is H; X is F, Cl, $CH_3$, or mono-, di- or tri-fluoromethyl and Y is I, Br, Cl, or mono-, di- or tri-fluoromethyl. In further or additional embodiments, G is $R_{1d}$, $R^o$ is H; X is F, Cl, $CH_3$, or mono-, di- or tri-fluoromethyl, Y is I, Br, Cl, or mono-, di- or tri-fluoromethyl and Z is H or F.

In further or additional embodiments, Cl is $R_{1d}$ where $R_{1d}$ is C(A)(A') is $C_1$-$C_6$ cycloalkyl. In further or additional embodiments, G is $R_{1d}$ where $R_{1d}$ is C(A)(A') is $C_1$-$C_6$ cycloalkyl and B is H. In further or additional embodiments, G is $R_{1d}$ where $R_{1d}$ is C(A)(A') is $C_1$-$C_6$ cycloalkyl and B is methyl, ethyl, 2-hydroxyethyl, n-propyl, 3-hydroxypropyl, 2,3-dihydroxypropyl, 3,4-dihydroxybutyl, isopropyl, 1-methyl-2-hydroxy ethyl, n-butyl, sec-butyl, isobutyl, or 2-hydroxymethyl-3-hydroxy propyl.

In further or additional embodiments, G is $R_{1d}$ where $R_{1d}$ is C(A)(A') is $C_1$-$C_6$ cycloalkyl and B is 2,3-dihydroxypropyl or 3,4-dihydroxybutyl. In further or additional embodiments, G is $R_{1d}$ where $R_{1d}$ is C(A)(A') is $C_1$-$C_6$ cycloalkyl and B is 2,3-dihydroxypropyl or 3,4-dihydroxybutyl, in which the chiral carbon in 13 is in the R configuration. In further or additional embodiments, G is $R_{1d}$ where $R_{1d}$ is C(A)(A') is $C_1$-$C_6$ cycloalkyl and B is 2,3-dihydroxypropyl or 3,4-dihydroxybutyl, in which the chiral carbon in B is in the S configuration. In further or additional embodiments, G is $R_{1d}$ where $R_{1d}$ is C(A)(A') is $C_1$-$C_6$ cycloalkyl and B is methyl, optionally substituted with one OH group, or $C_2$-$C_4$ alkyl, optionally substituted with one or two OH groups. In further or additional embodiments, G is $R_{1d}$ where $R_{1d}$ is C(A)(A') is $C_1$-$C_6$ cycloalkyl and $R^o$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino. In further or additional embodiments, G is $R_{1d}$ where $R_{1d}$ is C(A)(A') is $C_1$-$C_6$ cycloalkyl and $R^o$ is F, Cl, methyl, ethyl, methoxy, ethoxy, or 2-methoxy-ethoxy. In further or additional embodiments, G is $R_{1d}$ where $R_{1d}$ is C(A)(A') is $C_1$-$C_6$ cycloalkyl and $R^o$ is H; X is F, Cl, $CH_3$, or mono-, di- or tri-fluoromethyl.

In further or additional embodiments, the invention provides a composition comprising a compound of formula I, where G is $R_{1d}$ where $R_{1d}$ is C(A)(A') is $C_1$-$C_6$ cycloalkyl and B is 2,3-dihydroxypropyl or 3,4-dihydroxybutyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is $C_1$-$C_6$ cycloalkyl and B is 2,3-dihydroxypropyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is $C_1$-$C_6$ cycloalkyl and B is 3,4-dihydroxybutyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is $C_1$-$C_6$ cycloalkyl and B is 2,3-dihydroxypropyl or 3,4-dihydroxybutyl, in which the chiral carbon in B is in the S configuration, which is substantially free of the R isomer. In further or additional embodiments, the invention provides a composition comprising a compound of formula I, where G is $R_{1d}$ where $R_{1d}$ is C(A)(A') is $C_1$-$C_6$ cycloalkyl and B is 2,3-dihydroxypropyl, in which the chiral carbon in B is in the S configuration, which is substantially free of the R isomer. In further or additional embodiments, the invention provides a composition comprising a compound of formula I, where G is $R_{1d}$ where $R_{1d}$ is C(A)(A') is $C_1$-$C_6$ cycloalkyl and B is 3,4-dihydroxybutyl, in which the chiral carbon in B is in the S configuration, which is substantially free of the R isomer.

In further or additional embodiments, G is $R_{1d}$ where $R_{1d}$ is C(A)(A') is cyclopropyl. In further or additional embodiments, G is $R_{1d}$ where $R_{1d}$ is C(A)(A') is cyclopropyl and B is H. In further or additional embodiments, G is $R_{1d}$ where $R_{1d}$ is C(A)(A') is cyclopropyl and B is methyl, ethyl, 2-hydroxyethyl, n-propyl, 3-hydroxypropyl, 2,3-dihydroxypropyl, 3,4-dihydroxybutyl, isopropyl, 1-methyl-2-hydroxy ethyl, n-butyl, sec-butyl, isobutyl, or 2-hydroxymethyl-3-hydroxy propyl. In further or additional embodiments, G is $R_{1d}$ where $R_{1d}$ is C(A)(A') is cyclopropyl and B is 2,3-dihydroxypropyl or 3,4-dihydroxybutyl. In further or additional embodiments, G is $R_{1d}$ where $R_{1d}$ is C(A)(A') is cyclopropyl and B is 2,3-dihydroxypropyl or 3,4-dihydroxybutyl, in which the chiral carbon in B is in the R configuration. In further or additional embodiments, G is $R_{1d}$ where $R_{1d}$ is C(A)(A') is cyclopropyl and B is 2,3-dihydroxypropyl or 3,4-dihydroxybutyl, in which the chiral carbon in B is in the S configuration. In further or additional embodiments, G is $R_{1d}$ where $R_{1d}$ is C(A)(A') is cyclopropyl and B is methyl, optionally substituted with one OH group, or $C_2$-$C_4$ alkyl, optionally substituted with one or two OH groups. In further or additional embodiments, G is $R_{1d}$ where $R_{1d}$ is C(A)(A') is cyclopropyl and $R^0$ is fluoro, chloro, methyl, ethyl, propyl, isopropyl, sec-butyl, iso-butyl, tort-butyl, cyclopropyl, cyclobutyl, fluoromethyl, methoxy, fluoromethoxy, methylamino or dimethylamino. In further or additional embodiments, G is $R_{1d}$ where $R_{1d}$ is C(A)(A') is cyclopropyl and $R^0$ is F, Cl, methyl, ethyl, methoxy, ethoxy, or 2-methoxy-ethoxy. In further or additional embodiments, G is $R_{1d}$ where $R_{1d}$ is C(A)(A') is cyclopropyl and $R^0$ is H; X is F, Cl, $CH_3$, or mono-, di- or tri-fluoromethyl.

In further or additional embodiments, the invention provides a composition comprising a compound of formula I, where G is $R_{1d}$ where $R_{1d}$ is C(A)(A') is cyclopropyl and B is 2,3-dihydroxypropyl or 3,4-dihydroxybutyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is cyclopropyl and B is 2,3-dihydroxypropyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is cyclopropyl and B is 3,4-dihydroxybutyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is cyclopropyl and B is 2,3-dihydroxypropyl or 3,4-dihydroxybutyl, in which the chiral carbon in B is in the S configuration, which is substantially free of the R isomer. In further or additional embodiments, the invention provides a composition comprising a compound of formula I, where G is $R_{1d}$ where $R_{1d}$ is C(A)(A') is cyclopropyl and B is 2,3-dihydroxypropyl, in which the chiral carbon in B is in the S configuration, which is substantially free of the R isomer. In further or additional embodiments, the invention provides a composition comprising a compound of formula I, where G is $R_{1d}$ where $R_{1d}$ is C(A)(A) is cyclopropyl and B is 3,4-dihydroxybutyl, in which the chiral carbon in 13 is in the S configuration, which is substantially free of the R isomer.

In some embodiments, G is $R_{1c}$ and n is 1. In further or additional embodiments, G is $R_{1c}$, $R^0$ is H, $R_{4-6}$ are H, $R_2$ and $R_3$ are, independently, H, F, Cl, Br, $CH_3$, $CH_2F$, $CHF_2$, $CF_3$, $OCH_3$, $OCH_2F$, $OCHF_2$, $OCF_3$, ethyl, n-propyl, isopropyl, cyclopropyl, isobutyl, sec-butyl, tert-butyl, and methylsulfonyl, X is F and Y is I.

In some embodiments, G is $Ar_1$ where $Ar_1$ is phenyl optionally substituted with one group selected from acetamido, amidinyl, cyano, carbamoyl, methylcarbamoyl, dimethylcarbamoyl, 1,3,4-oxadiazol-2-yl, 5-methyl-1,3,4-oxadiazolyl, 1,3,4-thiadiazolyl, 5-methyl-1,3,4-thiadiazolyl, 1H-tetrazolyl, N-morpholylcarbonylamino, N-morpholylsulfonyl, N-pyrrolidinylcarbonylamino, and methylsulfonyl, optionally substituted with 1-3 substituents selected independently from F, Cl, and $CH_3$. In further or additional embodiments, G is $Ar_1$ where $Ar_1$ is phenyl optionally substituted with one group selected from acetamido, amidinyl, cyano, carbamoyl, methylcarbamoyl, dimethylcarbamoyl, 1,3,4-oxadiazol-2-yl, 5-methyl-1,3,4-oxadiazolyl, 1,3,4-thiadiazolyl, 5-methyl-1,3,4-thiadiazolyl, 1H-tetrazolyl, N-morpholylcarbonylamino, N-morpholylsulfonyl, N-pyrrolidinylcarbonylamino, and methylsulfonyl, optionally substituted with 1-3 substituents selected independently from F, Cl, and $CH_3$, $R^0$ is H, X is F, Cl, or methyl and Y is Br, I, $CF_3$, $C_1$-$C_3$ alkyl, $C_2$-$C_3$ alkenyl, $C_2$-$C_3$ alkynyl, cyclopropyl, $OCH_3$, $OCH_2CH_3$ or $SCH_3$. In some embodiments, G is $Ar_1$ where $Ar_1$ is

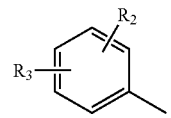

and where $R_2$ and $R_3$ are, independently, H, F, Cl, $CH_3$, $CF_3$, $OCH_3$. In further or additional embodiments, G is $Ar_1$ where $Ar_1$ is

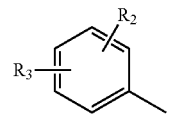

and where $R_2$ and $R_3$ are, independently, H, F, Cl, $CH_3$, $CF_3$, $OCH_3$, X is F or $CH_3$, Y is I, Br, or Cl; and Z is F. In further or additional embodiments, G is $Ar_1$ where $Ar_1$ is phenyl or mono-substituted phenyl. In further or additional embodiments, G is $Ar_1$ where $Ar_1$ is phenyl or mono-substituted phenyl, X is F or $CH_3$, Y is I, Br, or Cl, Z is F; and $R^0$ is F, methyl, ethyl, methoxy, or 2-methoxy-ethoxy. In further or additional embodiments, G is $Ar_1$ where U is N or $CR_2$ and V is N. In further or additional embodiments, G is $Ar_1$ where U is N or $CR_2$ and V is CR. In further or additional embodiments, G is $Ar_1$ where U is N or $CR_2$, V is CR, $R^0$ is H, X is F, Cl, or methyl and Y is Br, I, $CF_3$, $C_1$-$C_3$ alkyl, $C_2$-$C_3$ alkenyl, $C_2$-$C_3$ alkynyl, cyclopropyl, $OCH_3$, $OCH_2CH_3$ or $SCH_3$.

In some embodiments, G is $Ar_2$ where $Ar_2$ is

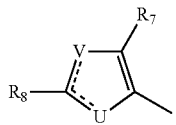

where $R_7$ is H or methyl and $R_8$ is H, acetamido, methyl, F or Cl. In further or additional embodiments, G is $Ar_2$ where $Ar_2$ is

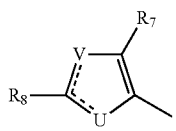

where $R_7$ is H or methyl, $R_8$ is H, acetamido, methyl, F or Cl, $R^0$ is H, X is F, Cl, or methyl, Y is Br, I, $CF_3$, $C_1$-$C_3$ alkyl, $C_2$-$C_3$ alkenyl, $C_2$-$C_3$ alkynyl, cyclopropyl, $OCH_3$, $OCH_2CH_3$ or $SCH_3$, and Z is F. In further or additional embodiments, G is $Ar_2$ where $Ar_2$ is

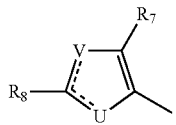

where U is S or O, V is CH=, and $R_8$ is H or $CH_3$, $R_7$ is H or methyl, $R_8$ is H, acetamido, methyl, F or Cl, $R^0$ is H, X is F, Cl, or methyl, Y is Br, I, $CF_3$, $C_1$-$C_3$ alkyl, $C_2$-$C_3$ alkenyl, $C_2$-$C_3$ alkynyl, cyclopropyl, $OCH_3$, $OCH_2CH_3$ or $SCH_3$ and Z is F. In further or additional embodiments, $R^0$ is H. In further or additional embodiments, $R^0$ is H, X is F or Cl and Y is Br, I, $CH_2CH_3$ or $SCH_3$ In some embodiments, G is $Ar_3$ where U is —O—.

In further or additional embodiments, G is $R_{1a}$, where $R_{1a}$ is defined as above. In further or additional embodiments, G is $R_{1a}$, and $R^0$ is H, where $R_{1a}$ is defined as above. In further or additional embodiments, G is $R_{1a}$ and $R^0$ is as defined above, other than H, and $R_{1a}$ is defined as above. In further or additional embodiments, G is $R_{1a}$, where $R_{1a}$ is methyl, monohalomethyl, $C_1$-$C_3$ alkoxymethyl, or cyclopropoxymethyl. In further or additional embodiments, G is $R_{1a}$, where $R_{1a}$ is methyl, monohalomethyl, $C_1$-$C_3$ alkoxymethyl, or cyclopropoxy methyl and where $R^0$ is F, Cl, $C_1$-$C_3$ alkyl, monochloro $C_1$-$C_3$ alkyl, $C_1$-$C_3$ alkoxy, trifluoro methoxy, or 2-methoxy-ethoxy.

In further or additional embodiments, G is $R_{1b}$, where $R_{1b}$ is defined as above. In further or additional embodiments, G is $R_{1b}$, and $R^0$ is H, where $R_{1b}$ is defined as above. In further or additional embodiments, G is $R_{1b}$, $R^0$ is H and Z is F, where $R_{1b}$ is defined as above. In further or additional embodiments, G is $R_{1b}$ and $R^0$ is as defined above, other than H, and $R_{1b}$ is defined as above. In further or additional embodiments, G is $R_{1b}$, where $R_{1b}$ is isopropyl, 2-butyl, 2-pentyl, cyclopropyl, cyclobutyl, cyclopentyl, or cyclohexyl, all optionally substituted with 1 or 2 substituents selected independently from F, Cl, OH, and $OCH_3$; Y is Br, I, methyl, or trifluoromethyl. In further or additional embodiments, G is $R_{1b}$, where $R_{1b}$ is isopropyl, 2-butyl, 2-pentyl, cyclopropyl, cyclobutyl, cyclopentyl, or cyclohexyl, optionally substituted with 1 or 2 substituents selected independently from F, Cl, OH, and $OCH_3$; Y is Br, I, methyl, or trifluoromethyl; and $R^0$ is F, Cl, $C_1$-$C_3$ alkyl, monochloro $C_1$-$C_3$ alkyl, $C_1$-$C_3$ alkoxy, trifluoromethoxy, or 2-methoxy-ethoxy. In further or additional embodiments, G is $R_{1b}$, where $R_{1b}$ is isopropyl, 2-butyl, 2-pentyl, cyclopropyl, cyclobutyl, cyclopentyl, or cyclohexyl, all optionally substituted with one Cl or with 1 or 2OH groups; and Y is Br, I, methyl, or trifluoromethyl. In further or additional embodiments, G is $R_{1b}$, where $R_{1b}$ is isopropyl, 2-butyl, 2-pentyl, cyclopropyl, cyclobutyl, cyclopentyl, or cyclohexyl, all optionally substituted with one Cl or with 1 or 2OH groups; Y is Br, I, methyl, or trifluoromethyl; and $R^0$ is F, Cl, $C_1$-$C_3$ alkyl, monochloro $C_1$-$C_3$ alkyl, $C_1$-$C_3$ alkoxy, trifluoromethoxy, or 2-methoxy-ethoxy.

In further or additional embodiments, G is $R_{1c}$, where $R_{1c}$ is defined as above. In further or additional embodiments, G is $R_{1c}$, and $R^0$ is H, where $R_{1c}$ is defined as above. In further or additional embodiments, G is $R_{1c}$, and $R^0$ is as defined above, other than H, and $R_{1c}$ is defined as above. In further or additional embodiments, G is $R_{1c}$, and $R^0$ is H, where $R_{1c}$ is $(CH_2)_nO_mR'$, where m is 0 or 1, n is 2 or 3 when m is 1, and n is 1 or 2 when m is 0, and R' is $C_1$-$C_6$ alkyl, optionally substituted with 1-3 substituents selected independently from F, Cl, OH, $OCH_3$, $OCH_2CH_3$, and $C_3$-$C_6$ cycloalkyl. In another more specific subgeneric embodiment, m is zero, n is 1 or 2, and R' is $C_1$-$C_4$ alkyl, optionally substituted as described above. In another more specific subgeneric embodiment, m is 1, n is 2 or 3, and R' is $C_1$-$C_4$ alkyl, optionally substituted as described above. In a still more specific subgeneric embodiment, m is zero, n is 1 or 2, and R' is $C_1$-$C_4$ alkyl, optionally substituted with 1-3 groups selected from OH, $OCH_3$, Cl, and cyclopropyl.

In further or additional embodiments, G is $R_{1d}$, where $R_{1d}$ is defined as above. In further or additional embodiments, G is $R_{1d}$, and $R^0$ is H, where $R_{1d}$ is defined as above. In further or additional embodiments, G is $R_{1d}$ and $R^0$ is as defined above, other than H, and $R_{1d}$ is defined as above. In further or additional embodiments, G is $R_{1d}$, and $R^0$ is H, where $R_{1d}$ is C(A)(A')(B)— where B, A, and A' are, independently, H or $C_{1-4}$ alkyl, optionally substituted with one or two OH groups or halogen atoms, or A and $A^1$, together with the carbon atom to which they are attached, form a 3- to 6-member saturated ring, said ring optionally containing one or two heteroatoms selected, independently, from O, N, and S and optionally substituted with one or two groups selected independently from methyl, ethyl, fluoro, chloro, bromo and judo.

In further or additional embodiments, G is $R_{1e}$, where $R_{1e}$ is defined as above. In further or additional embodiments, G is $R_{1e}$, and $R^0$ is H, where $R_{1e}$ is defined as above. In further or additional embodiments, G is $R_{1e}$ and $R^0$ is as defined above, other than H, and $R_{1e}$ is defined as above.

In further or additional embodiments, G is $Ar_1$, where $Ar_1$ is defined as above. In further or additional embodiments, G is $Ar_1$, and $R^0$ is H, where $Ar_1$ is defined as above. In further or additional embodiments, G is $Ar_1$ and $R^0$ is as defined above, other than H, and $Ar_1$ is defined as above.

In further or additional embodiments, G is $Ar_2$, where $Ar_2$ is defined as above. In further or additional embodiments, G is $Ar_2$, and $R^0$ is H, where $Ar_2$ defined as above. In further or additional embodiments, G is $Ar_2$ and $R^0$ is as defined above, other than H, and $Ar_2$ is defined as above.

In further or additional embodiments, X is F, Cl, or $CH_3$; Y is I, Br, $C_1$, $CF_3$ or $C_1$-$C_3$ alkyl, and Z is H or F. In further or additional embodiments, X is F, Cl, or $CH_3$: Y is I, Br, $C_1$, $CF_3$, or $C_1$-$C_3$ alkyl, Z is H or F, and $R^0$ is halogen, $C_1$-$C_6$ alkyl, monohalo $C_1$-$C_6$ alkyl, $C_3$-$C_6$ cycloalkyl, $C_2$-$C_6$ alkenyl, $C_2$-$C_6$ alkynyl, phenyl, monosubstituted phenyl, $OR_3$, O—C(=O)$R_4$, or C(=O)$OR_5$. In further or additional embodiments, X is F, Cl, or $CH_3$: Y is I, Br, $C_1$, $CF_3$, or $C_1$-$C_3$ alkyl, Z is H or F, and $R^0$ is furyl, thienyl, thiazolyl, isothiazolyl, oxazolyl, isoxazolyl, pyrrolyl, or pyrazolyl. In further or additional embodiments, X is F, Cl, or $CH_3$: Y is I, Br, $C_1$, $CF_3$, or $C_1$-$C_3$ alkyl, Z is H or F, and $R^0$ is F, Cl, $C_1$-$C_4$ alkyl, $C_1$-$C_3$ alkoxy, trifluoromethoxy, or 2-methoxy-ethoxy.

In another more specific subgeneric embodiment, $R_{1d}$ is cycloalkyl or 1-alkyl-cycloalkyl, in which the 1-alkyl group is optionally substituted with one or two OH groups or with one or two halogen atoms.

In another more specific subgeneric embodiment, $R^0$ is halogen, $C_1$-$C_6$ alkyl, monohalo $C_1$-$C_6$ alkyl, $C_3$-$C_6$ cycloalkyl, $C_2$-$C_5$ alkenyl, $C_2$-$C_6$ alkynyl, phenyl, monosubstituted phenyl, $OR_3$, O—C(=O)$R_4$, or C(=O)$OR_5$; and $R_{1d}$ is cycloalkyl or 1-alkyl-cycloalkyl, in which the 1-alkyl group is optionally substituted with one or two OH groups or with one or two halogen atoms.

In another more specific subgeneric embodiment, $R^0$ is furyl, thienyl, thiazolyl, isothiazolyl, oxazolyl, isoxazolyl, pyrrolyl, or pyrazolyl; and $R_{1d}$ is cycloalkyl or 1-alkyl-cycloalkyl, in which the 1-alkyl group is optionally substituted with one or two OH groups or one or two halogen atoms.

In another more specific subgeneric embodiment, $R_{1d}$ is cycloalkyl or 1-alkyl-cycloalkyl, in which the 1-alkyl group is optionally substituted with one or two OH groups, and where Y is Br, I, methyl, or trifluoromethyl. In another more specific subgeneric embodiment, $R_{1d}$ is cycloalkyl or 1-alkyl-cycloalkyl, in which the 1-alkyl group is optionally substituted with one or two fluorine or chlorine atoms, and where Y is Br, I, methyl, or trifluoromethyl. In another more specific subgeneric embodiment, $R_{1d}$ is cycloalkyl or (1-alley 1)-cycloalkyl, in which the 1-alkyl group is optionally substituted with one or two OH groups, and where $R^{0'}$ is F, Cl, $C_1$-$C_3$ alkyl, monochloro $C_1$-$C_3$ alkyl, $C_1$-$C_3$ alkoxy, trifluoromethoxy, or 2-methoxy-ethoxy. In another more specific subgeneric embodiment, $R_{1d}$ is tetrahydrofuryl, tetrahydrothienyl, pyrrolidyl, piperidyl, piperazinyl, or morpholyl, each optionally substituted as described above, and where Y is Br, I, methyl, or trifluoromethyl. In another more specific subgeneric embodiment, $R_{1d}$ is oxazolidinyl, thiazolidinyl, isoxazolidinyl, isothiazolidinyl, tetrahydrofuryl, tetrahydrothienyl, pyrrolidyl, piperidyl, piperazinyl, or morpholyl, each optionally substituted as described above, and where Y is Br, I, methyl, or trifluoromethyl. In another more specific subgeneric embodiment, $R_{1d}$ is cyclopropyl or 1-alkyl-cyclopropyl, in which the 1-alkyl group is optionally substituted with one or two OH groups, and where $R^{0'}$ is F, Cl, methyl, ethyl, chloromethyl, $C_1$-$C_2$ alkoxy, trifluoromethoxy, or 2-methoxy-ethoxy. In an even more specific embodiment, $R_{1d}$ is 1-(monohydroxyalkyl)cycloalkyl. In another more specific embodiment, $R_{1d}$ is 1-(monohydroxyalkyl)cycloalkyl, where $R^{0'}$ is F, Cl, methyl, ethyl, chloromethyl, $C_1$-$C_2$ alkoxy, trifluoromethoxy, or 2-methoxy-ethoxy. In an even more specific embodiment, $R_{1d}$ is 1-(dihydroxyalkyl)cycloalkyl. In another more specific embodiment, $R_{1d}$ is 1-(dihydroxyalkyl)cycloalkyl, where $R^{0'}$ is F, Cl, methyl, ethyl, chloromethyl, $C_1$-$C_2$ alkoxy, trifluoromethoxy, or 2-methoxy-ethoxy.

In a more specific subgeneric embodiment U is $CR_2$ and V is N. In another more specific, subgeneric embodiment, U and V are both N. In a more specific, subgeneric embodiment, U is $CR_2$ and V is $CR_3$.

In a still more specific subgeneric embodiment, this invention provides a compound of formula I, where G is $Ar_1$ and $Ar_1$ is phenyl or monosubstituted phenyl, $R^0$ is F, methyl, ethyl, $C_1$-$C_3$ alkoxy, trifluoromethoxy, or 2-methoxy-ethoxy; X is F, Cl, or $CH_3$; Y is I; and Z is F. In another subgeneric embodiment, this invention provides a compound of formula I, where G is $Ar_1$, where $Ar_1$ is phenyl or monosubstituted phenyl, $R^0$ is halogen, $C_1$-$C_6$ alkyl, $C_3$-$C_6$ cycloalkyl, $C_2$-$C_6$ alkenyl, $C_2$-$C_6$ alkynyl, all such alkyl, cycloalkyl, alkenyl, and alkynyl groups optionally substituted with 1-3 substituents selected independently from halogen, OH, CN, cyanomethyl, nitro, phenyl, and trifluoromethyl; or $R^0$ is phenyl, $OR_3$, furyl, thienyl, thiazolyl, isothiazolyl, oxazolyl, isoxazolyl, pyrrolyl, or pyrazolyl. In a more specific subgeneric embodiment, this invention provides a compound of formula I, where A is $Ar_1$, where $Ar_1$ is phenyl or monosubstituted phenyl, $R^0$ is F, Cl, $C_1$-$C_3$ alkyl, $C_1$-$C_3$ alkoxy, 2-methoxyethoxy, $C_2$-$C_3$ alkenyl, $C_2$-$C_3$ alkynyl, trifluoromethyl, phenyl, furyl, or thienyl, thiazolyl, isothiazolyl, oxazolyl, isoxazolyl, pyrrolyl, or pyrazolyl; X is F, Cl, or methyl; Y is I, Br, $C_1$, $CF_3$, or $C_1$-$C_3$ alkyl; and Z is F.

In another still more specific subgeneric embodiment, this invention provides a compound of formula I, where G is $Ar_1$, where $Ar_1$ is phenyl or monosubstituted phenyl, $R^0$ is H; X is F, Cl, or $CH_3$; Y is Br or I; and Z is F.

In another subgeneric embodiment his invention provides a compound of formula I, where G is $Ar_2$, where $Ar_2$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen. In a more specific subgeneric embodiment his invention provides a compound of formula I, where G is $Ar_2$, where $Ar_2$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen; $R^0$ is other than H; X is F, Cl, or $CH_3$: Y is I, Br, $C_1$, $CF_3$, or $C_1$-$C_3$ alkyl, and Z is H or F. In another subgeneric embodiment this invention provides a compound of formula I, where G is $Ar_2$, where $Ar_2$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen; $R^0$ is F, Cl, $C_1$-$C_3$ alkyl, monochloro $C_3$ alkyl, $C_1$-$C_3$ alkoxy, trifluoromethoxy, methyloxy-methoxy, or 2-methoxy-ethoxy; X is F, Cl, or $CH_3$: Y is I, Br, $C_1$, $CF_3$, or $C_1$-$C_3$ alkyl, and Z is H or F. In another subgeneric embodiment his invention provides a compound of formula I, where G is $Ar_2$, where $Ar_2$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen; $R^0$ is H; X is F, Cl, or $CH_3$: Y is I, Br, $C_1$, $CF_3$, or $C_1$-$C_3$ alkyl, and Z is H or F. In another subgeneric embodiment his invention provides a compound of formula I, where G is $Ar_2$, where $Ar_2$ is thiazolyl, isothiazolyl, oxazolyl, isoxazolyl, pyrrolyl, or pyrazolyl, all optionally substituted with methoxycarbonyl, methylcarbamoyl, acetamido, acetyl, methyl, ethyl, trifluoromethyl, or halogen; $R^0$ is H or methoxy; X is F, Cl, or $CH_3$; Y is I, Br, $C_1$, $CF_3$, or $C_1$-$C_3$ alkyl, and Z is H or F.

In some embodiments, the compound of formula (I), or a pharmaceutical salt thereof, is selected from

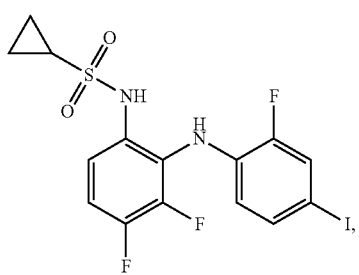
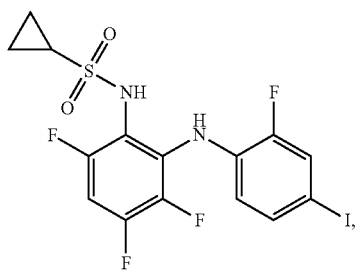
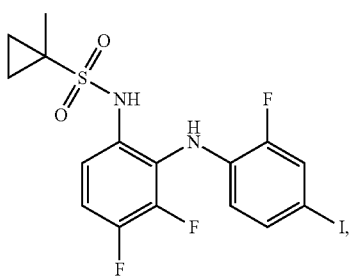
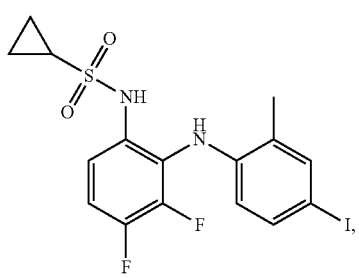
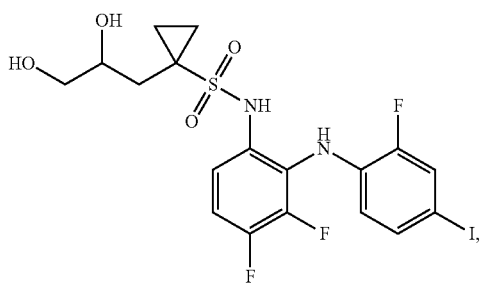
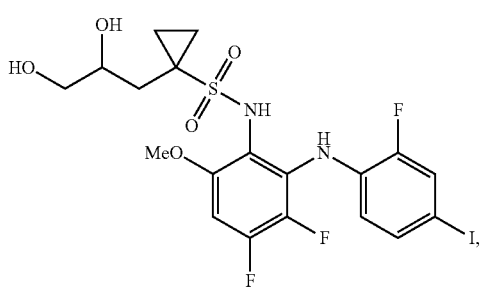
-continued
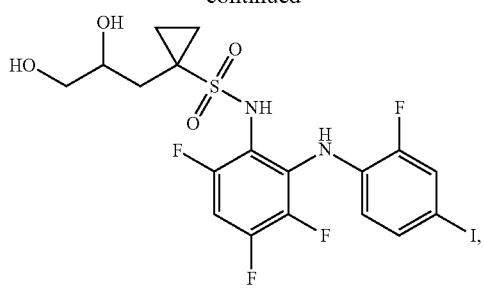
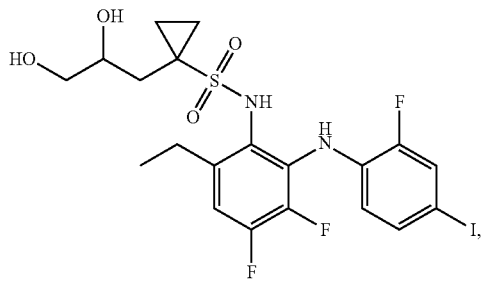
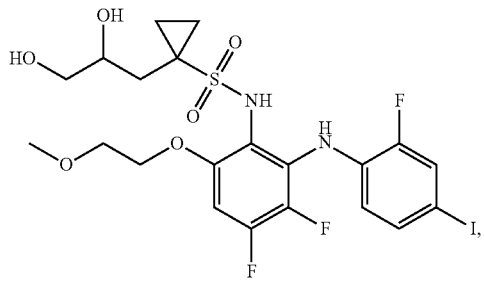
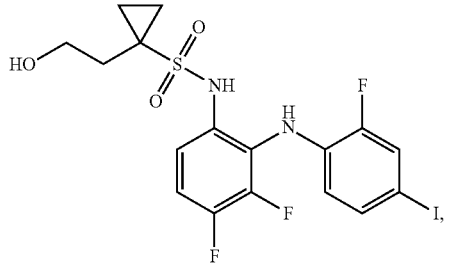
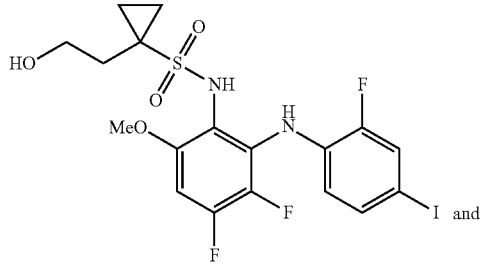 and
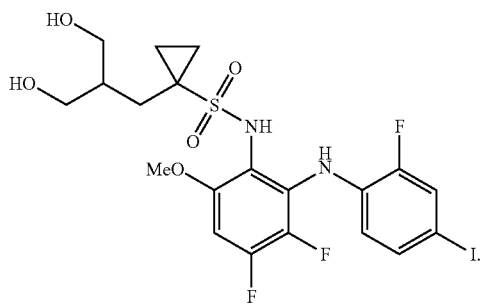

In some embodiments, the invention provides a compound of formula I, or a pharmaceutical salt thereof, selected from:

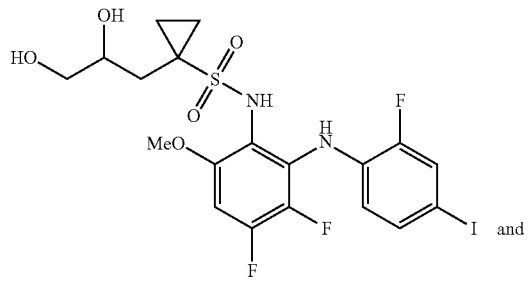

and

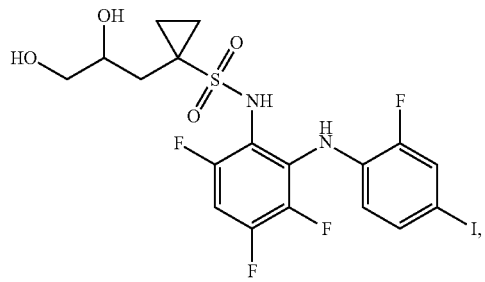

where the 2-OH carbon is in the R configuration.

In some embodiments, the invention provides a compound of formula I, or a pharmaceutical salt thereof, selected from:

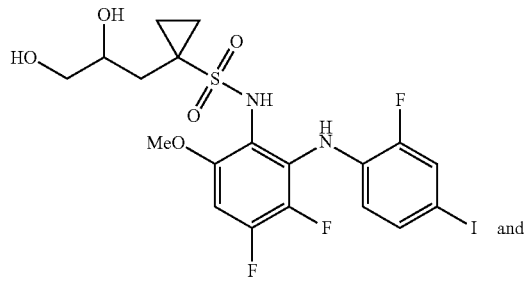

and

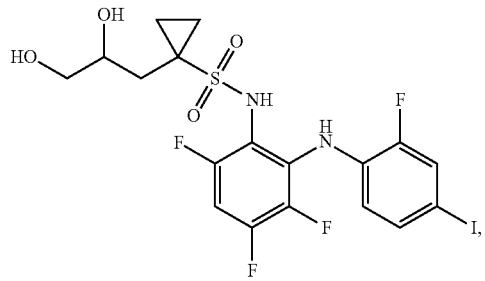

where the 2-OH carbon is in the S configuration.

In further or additional embodiments, the compound of formula (I), or a pharmaceutical salt thereof, is

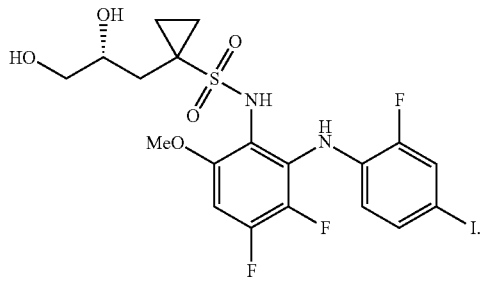

In further or additional embodiments, the compound of formula (I), or a pharmaceutical salt thereof, is

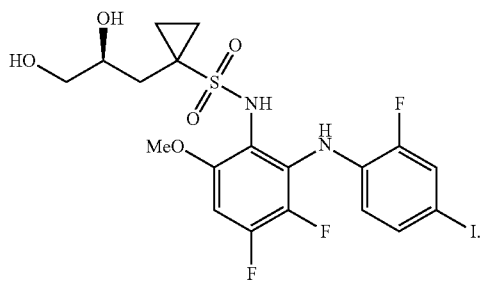 [SMILES: COc1cc(F)c(F)c(Nc2ccc(I)cc2F)c1NS(=O)(=O)C1(C[C@H](O)CO)CC1]

In some embodiments, the invention provides a composition comprising a compound of formula I, selected from those shown below, where the 2-OH carbon is in the R configuration, substantially free of the S-isomer.

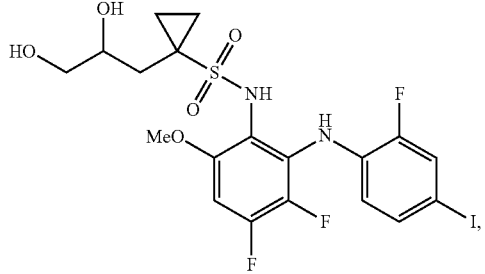 [SMILES: COc1cc(F)c(F)c(Nc2ccc(I)cc2F)c1NS(=O)(=O)C1(C[C@@H](O)CO)CC1]

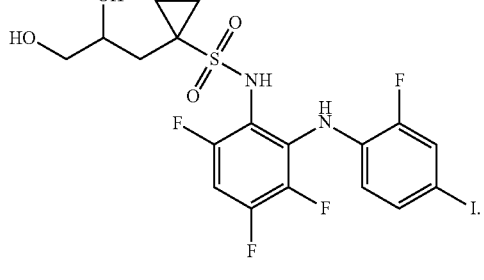

In some embodiments, the invention provides a composition comprising a compound of formula I, selected from those shown below, where the 2-OH carbon is in the S configuration, substantially free of the R-isomer.

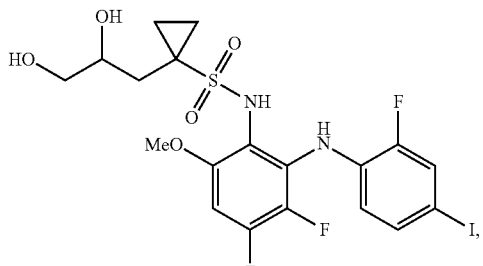

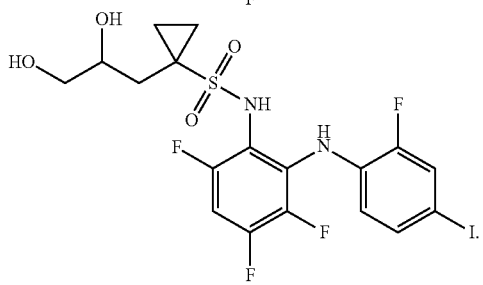

In some embodiments, this invention provides a compound of formula I, where Y is phenyl, pyridyl, or pyrazolyl. In another subgeneric embodiment, this invention provides a compound of formula I, where Y is substituted phenyl, pyridyl, or pyrazolyl. In yet another subgeneric embodiment, this invention provides a compound of formula I, where Y is Br or I. In one subgeneric embodiment, this invention provides a compound of formula I, where G is 1-piperidyl, 2-piperidyl, 3-piperidyl, or 4-piperidyl. In another subgeneric embodiment, this invention provides a compound of formula I, where G is I-piperazyl or 2-piperazyl. In another subgeneric embodiment, this invention provides a compound of formula I, where G is morpholyl. In another subgeneric embodiment, this invention provides a compound of formula I, where G is N-methyl-2-aminoethyl. In one subgeneric embodiment, this invention provides a compound of formula I, where G is N-methyl-3-amino-n-propyl. In another subgeneric embodiment, this invention provides a compound of formula I, where G is $(CH_3)_2N—CH_2CH_2—NH—(CH_2)_n—$, where n is 1, 2, or 3. In another subgeneric embodiment, this invention provides a compound of formula I, where G is $(CH_3CH_2)_2N—CH_2CH_2—NH—(CH_2)_n—$, where n is 1 or 2. In a more specific subgeneric embodiment, this invention provides a compound of formula I, where G is 1-piperidyl, 2-piperidyl, 3-piperidyl, or 4-piperidyl; $R^o$ is H, halo, or methoxy; X is F; and Y is I. In another more specific subgeneric embodiment, this invention provides a compound of formula I, where G is 1-piperazyl or 2-piperazyl; $R^o$ is H, halo, or methoxy; X is F; and Y is I In another more specific subgeneric embodiment, this invention provides a compound of formula I, where G is morpholyl; $R^o$ is H, halo, or methoxy; X is F; and Y is I. In another more specific subgeneric embodiment, this invention provides a compound of formula I, where G is N-methyl-2-aminoethyl; $R^o$ is H, halo, or methoxy; X is F; and Y is I In another more specific subgeneric embodiment, this invention provides a compound of formula I, where G is N-methyl-3-amino-n-propyl; $R^o$ is H, halo, or methoxy; X is F; and Y is I. In another more specific subgeneric embodiment, this invention provides a compound of formula I, where G is $(CH_3)_2N—CH_2CH_2—NH—(CH_2)_n—$, where n is 1, 2, or 3; $R^o$ is H, halo, or methoxy; X is F; and Y is 1. In another more specific subgeneric embodiment, this invention provides a compound of formula I, where G is $(CH_3CH_2)_2N—CH_2CH_2—NH—(CH_2)_n—$, where n is 1 or 2; $R^o$ is H, halo, or methoxy; X is F; and Y is I.

In some embodiments, the invention provides a pharmaceutical composition comprising a compound of formula I or a pharmaceutically acceptable salt, solvate, polymorph, ester, amide, tautomer or prodrug thereof. In some embodiments the pharmaceutical composition further comprises at least one pharmaceutically acceptable carrier.

In some embodiments, the invention provides a pharmaceutical composition comprising a compound selected from:

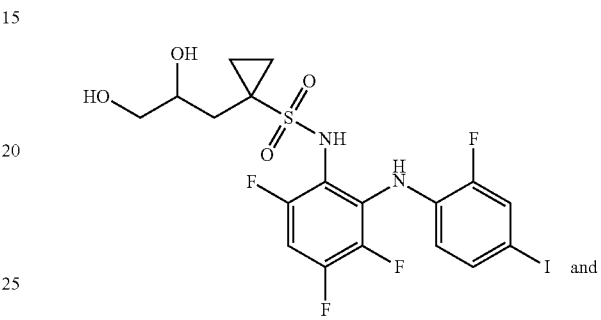

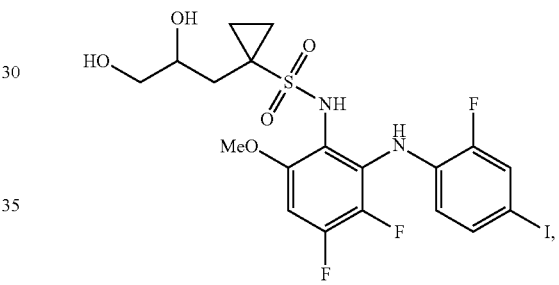

or a pharmaceutically acceptable salt, solvate, polymorph, ester, amide, tautomer or prodrug thereof. In some embodiments, the pharmaceutical composition further comprises at least one pharmaceutically acceptable carrier. In some embodiments, the compound is in the R configuration. In some embodiments, the compound is in the R configuration, substantially free of the S-isomer. In some embodiments, the compound is in the S configuration. In some embodiments, the compound is in the S configuration, substantially free of the R-isomer. In some embodiments, the compound is:

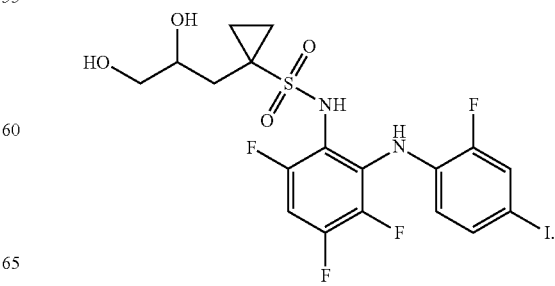

In some embodiments, the compound is:

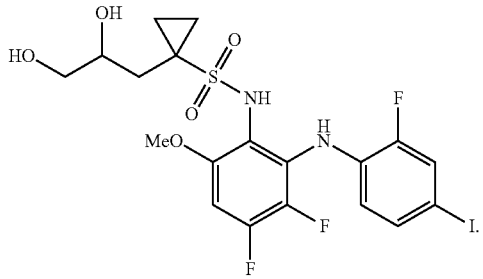

In some embodiments, the compound is:

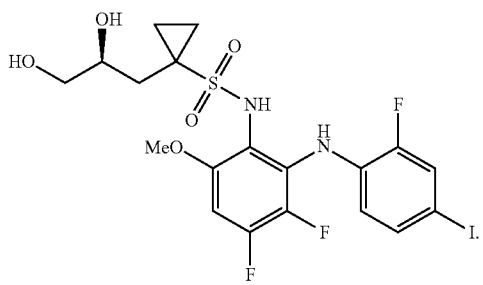 [SMILES: COc1cc(F)c(F)c(Nc2ccc(I)cc2F)c1NS(=O)(=O)C1(C[C@H](O)CO)CC1]

In some embodiments, the compound is:

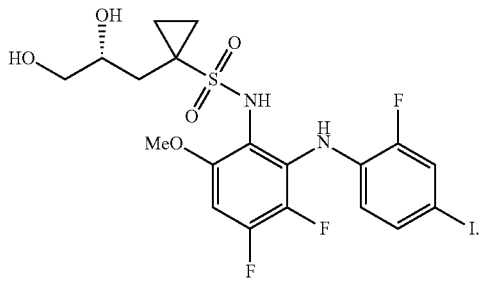 [SMILES: COc1cc(F)c(F)c(Nc2ccc(I)cc2F)c1NS(=O)(=O)C1(C[C@@H](O)CO)CC1]

Tables with Non-Limiting Examples of Compounds of Formula I

The tables below show examples of individual compounds provided or contemplated by this invention. These examples should in no way be construed as limiting.

Table 1 shows embodiments of this invention which are compounds of formula I, wherein $R^0$ is as defined herein, G is $R_{1a}$ where $R_{1a}$ is as defined in the table and X, Y and Z are defined in the table.

TABLE 1

| $R_{1a}$ | X | Y |
|---|---|---|
| $CH_3$ | F | I |
| $CH_3$ | Cl | I |
| $CH_3$ | F | Br |
| $CH_3$ | Cl | Br |
| $CH_3$ | F | $CH_3$ |
| $CH_3$ | Cl | $CH_3$ |
| $CH_3$ | F | $CF_3$ |
| $CH_3$ | Cl | $CF_3$ |
| $CH_3$ | F | C≡CH |
| $CH_3$ | Cl | C≡CH |
| $CH_3$ | F | $SCH_3$ |
| $CH_3$ | Cl | $SCH_3$ |
| $CH_3$ | F | $(CH_2)_2CH_3$ |
| $CH_3$ | Cl | $(CH_2)_2CH_3$ |
| $CH_3$ | F | $CH_2CH_3$ |
| $CH_3$ | Cl | $CH_2CH_3$ |
| $CH_3$ | F | $CH_2OH$ |
| $CH_3$ | Cl | $CH_2OH$ |
| $CH_3$ | F | ▷ |
| $CH_3$ | Cl | ▷ |
| $CH_3$ | $CH_3$ | CH=CH2 |
| $CH_3$ | $CH_3$ | C≡CH |
| $CH_3$ | $CH_3$ | $SCH_3$ |
| $CH_2F$ | F | I |
| $CH_2F$ | Cl | I |
| $CH_2F$ | F | Br |
| $CH_2F$ | Cl | Br |
| $CH_2F$ | F | $CH_3$ |
| $CH_2F$ | Cl | $CH_3$ |
| $CH_2F$ | F | $CF_3$ |
| $CH_2F$ | Cl | $CF_3$ |
| $CF_3$ | F | I |
| $CF_3$ | Cl | I |
| $CF_3$ | F | Br |
| $CF_3$ | Cl | Br |
| $CF_3$ | F | $CH_3$ |
| $CF_3$ | Cl | $CH_3$ |
| $CF_3$ | F | $CF_3$ |
| $CF_3$ | Cl | $CF_3$ |
| $CH_2Cl$ | F | I |
| $CH_2Cl$ | Cl | I |
| $CH_2Cl$ | F | Br |
| $CH_2Cl$ | Cl | Br |
| $CH_2Cl$ | F | $CH_3$ |
| $CH_2Cl$ | Cl | $CH_3$ |
| $CH_2Cl$ | F | $CF_3$ |
| $CH_2Cl$ | Cl | $CF_3$ |
| $CHCl_2$ | F | I |
| $CHCl_2$ | Cl | I |
| $CHCl_2$ | F | Br |
| $CHCl_2$ | Cl | Br |
| $CHCl_2$ | F | $CH_3$ |
| $CHCl_2$ | Cl | $CH_3$ |
| $CHCl_2$ | F | $CF_3$ |
| $CHCl_2$ | Cl | $CF_3$ |
| $CCl_3$ | F | I |
| $CCl_3$ | Cl | I |
| $CCl_3$ | F | Br |
| $CCl_3$ | Cl | Br |
| $CCl_3$ | F | $CH_3$ |
| $CCl_3$ | Cl | $CH_3$ |
| $CCl_3$ | F | $CF_3$ |
| $CCl_3$ | Cl | $CF_3$ |
| $CH_2OH$ | F | I |
| $CH_2OH$ | Cl | I |
| $CH_2OH$ | F | Br |
| $CH_2OH$ | Cl | Br |
| $CH_2OH$ | F | $CH_3$ |
| $CH_2OH$ | Cl | $CH_3$ |
| $CH_2OH$ | F | $CF_3$ |
| $CH_2OH$ | Cl | $CF_3$ |
| $CH_2OMe$ | F | I |
| $CH_2OMe$ | Cl | I |
| $CH_2OMe$ | F | Br |
| $CH_2OMe$ | Cl | Br |
| $CH_2OMe$ | F | $CH_3$ |
| $CH_2OMe$ | Cl | $CH_3$ |
| $CH_2OMe$ | F | $CF_3$ |
| $CH_2OMe$ | Cl | $CF_3$ |
| $CH_2OMe$ | F | C≡CH |
| $CH_2OMe$ | Cl | $SCH_3$ |

TABLE 1-continued

| R$_{1a}$ | X | Y |
|---|---|---|
| CH$_2$OMe | CH$_3$ | CF$_3$ |
| CH$_2$OMe | CH$_3$ | C≡CH |
| CH$_2$OEt | F | I |
| CH$_2$OEt | Cl | I |
| CH$_2$OEt | F | Br |
| CH$_2$OEt | Cl | Br |
| CH$_2$OEt | F | CH$_3$ |
| CH$_2$OEt | Cl | CH$_3$ |
| CH$_2$OEt | F | CF$_3$ |
| CH$_2$OEt | Cl | CF$_3$ |
| CH$_2$O-cyclopropyl | F | I |
| CH$_2$O-cyclopropyl | Cl | I |
| CH$_2$O-cyclopropyl | F | Br |
| CH$_2$O-cyclopropyl | Cl | Br |
| CH$_2$O-cyclopropyl | F | CH$_3$ |
| CH$_2$O-cyclopropyl | Cl | CH$_3$ |
| CH$_2$O-cyclopropyl | F | CF$_3$ |
| CH$_2$O-cyclopropyl | Cl | CF$_3$ |
| CH$_2$O-iPr | F | I |
| CH$_2$O-iPr | Cl | I |
| CH$_2$O-iPr | F | Br |
| CH$_2$O-iPr | Cl | Br |
| CH$_2$O-iPr | F | CH$_3$ |
| CH$_2$O-iPr | Cl | CH$_3$ |
| CH$_2$O-iPr | F | CF$_3$ |
| CH$_2$O-iPr | Cl | CF$_3$ |
| CH$_2$OCH$_2$CH$_2$OH | F | I |
| CH$_2$OCH$_2$CH$_2$OH | Cl | I |
| CH$_2$OCH$_2$CH$_2$OH | F | Br |
| CH$_2$OCH$_2$CH$_2$OH | Cl | Br |
| CH$_2$OCH$_2$CH$_2$OH | F | CH$_3$ |
| CH$_2$OCH$_2$CH$_2$OH | Cl | CH$_3$ |
| CH$_2$OCH$_2$CH$_2$OH | F | CF$_3$ |
| CH$_2$OCH$_2$CH$_2$OH | Cl | CF$_3$ |
| CH$_2$OCH$_2$CH$_2$OMe | F | I |
| CH$_2$OCH$_2$CH$_2$OMe | Cl | I |
| CH$_2$OCH$_2$CH$_2$OMe | F | Br |
| CH$_2$OCH$_2$CH$_2$OMe | Cl | Br |
| CH$_2$OCH$_2$CH$_2$OMe | F | CH$_3$ |
| CH$_2$OCH$_2$CH$_2$OMe | Cl | CH$_3$ |
| CH$_2$OCH$_2$CH$_2$OMe | F | CF$_3$ |
| CH$_2$OCH$_2$CH$_2$OMe | Cl | CF$_3$ |
| CH$_2$OCH(CH$_2$OH)$_2$ | F | I |
| CH$_2$OCH(CH$_2$OH)$_2$ | Cl | I |
| CH$_2$OCH(CH$_2$OH)$_2$ | F | Br |
| CH$_2$OCH(CH$_2$OH)$_2$ | Cl | Br |
| CH$_2$OCH(CH$_2$OH)$_2$ | F | CH$_3$ |

TABLE 1-continued

| R$_{1a}$ | X | Y |
|---|---|---|
| CH$_2$O—CH(OH)—CH$_2$OH (i.e. CH$_2$O-branched with two OH) | Cl | CH$_3$ |
| CH$_2$O—CH(OH)—CH$_2$OH | F | CF$_3$ |
| CH$_2$O—CH(OH)—CH$_2$OH | Cl | CF$_3$ |
| CH$_3$ | F | phenyl |
| CH$_3$ | Cl | phenyl |
| CH$_3$ | CH$_3$ | phenyl |
| CH$_3$ | F | 3-pyridyl |
| CH$_3$ | Cl | 3-pyridyl |
| CH$_3$ | CH$_3$ | 4-pyridyl |
| CH$_3$ | F | pyrazolyl |
| CH$_3$ | Cl | pyrazolyl |
| CH$_3$ | F | 4-pyridyl |
| CH$_3$ | Cl | 4-pyridyl |
| CH$_3$ | CH$_3$ | 2-(CH$_3$—SO$_2$—NH)-phenyl |
| CH$_3$ | CH$_3$ | 3-(CH$_3$—SO$_2$—NH)-phenyl |
| CH$_3$ | Cl | 3-(CH$_3$—SO$_2$—NH)-phenyl |
| CH$_3$ | F | 3-(CH$_3$—SO$_2$—NH)-phenyl |

Table 2 shows embodiments of this invention which are compounds of formula I, wherein R$^0$ is as defined herein, G is R$_{1b}$ where R$_{1b}$ is as defined in the table and X, Y and Z are defined in the table.

TABLE 2

| R$_{1b}$ | X | Y | Z |
|---|---|---|---|
| cyclopropyl | F | I | F |
| cyclopropyl | Cl | I | F |
| cyclopropyl | F | Br | F |
| cyclopropyl | Cl | Br | F |
| cyclopropyl | F | CH$_3$ | F |
| cyclopropyl | Cl | CH$_3$ | F |
| cyclopropyl | F | CF$_3$ | F |
| cyclopropyl | Cl | CF$_3$ | F |
| cyclopropyl | F | C≡CH | F |
| cyclopropyl | Cl | C≡CH | F |
| cyclopropyl | F | SCH$_3$ | F |
| cyclopropyl | Cl | SCH$_3$ | F |
| cyclopropyl | F | CH$_2$OH | F |
| cyclopropyl | Cl | CH$_2$OH | F |
| cyclopropyl | F | (CH$_2$)$_3$OH | F |
| cyclopropyl | Cl | (CH$_2$)$_3$OH | F |
| cyclopropyl | F | (CH$_2$)$_2$CH$_3$ | F |
| cyclopropyl | Cl | (CH$_2$)$_2$CH$_3$ | F |
| cyclopropyl | F | CH$_2$CH$_3$ | F |
| cyclopropyl | Cl | CH$_2$CH$_3$ | F |
| cyclopropyl | F | (CH$_2$)$_2$CH$_3$ | F |
| cyclopropyl | Cl | (CH$_2$)$_2$CH$_3$ | F |
| cyclopropyl | CH$_3$ | I | F |
| cyclopropyl | CH$_3$ | Br | F |
| cyclopropyl | CH$_3$ | CH$_3$ | F |
| cyclopropyl | CH$_3$ | CF$_3$ | F |
| cyclopropyl | CH$_3$ | CH$_2$CH$_3$ | F |
| cyclopropyl | CH$_3$ | (CH$_2$)$_2$CH$_3$ | F |
| cyclopropyl | CH$_3$ | C≡CH | F |
| cyclopropyl | CH$_3$ | SCH$_3$ | F |
| Cl-cyclopropyl (trans-substituted) | CH$_3$ | (CH$_2$)$_2$CH$_3$ | F |

TABLE 2-continued

| $R_{1b}$ | X | Y | Z |
|---|---|---|---|
| NC-cyclopropyl | CH$_3$ | I | F |
| cyclopropyl | F | CH=CH$_2$ | F |
| cyclopropyl | Cl | CH=CH$_2$ | F |
| cyclopropyl | CH$_3$ | CH=CH$_2$ | F |
| cyclopropyl | F | cyclopropyl | F |
| cyclopropyl | F | OCH$_3$ | F |
| cyclopropyl | Cl | (CH$_2$)$_2$CH$_2$OH | F |
| cyclobutyl | F | I | F |
| cyclobutyl | Cl | I | F |
| cyclobutyl | F | Br | F |
| cyclobutyl | Cl | Br | F |
| cyclobutyl | F | CH$_3$ | F |
| cyclobutyl | Cl | CH$_3$ | F |
| cyclobutyl | F | CF$_3$ | F |
| cyclobutyl | Cl | CF$_3$ | F |
| cyclopentyl | F | I | F |
| cyclopentyl | Cl | I | F |
| cyclopentyl | F | Br | F |
| cyclopentyl | Cl | Br | F |

TABLE 2-continued

| $R_{1b}$ | X | Y | Z |
|---|---|---|---|
| cyclopentyl | F | CH$_3$ | F |
| cyclopentyl | Cl | CH$_3$ | F |
| cyclopentyl | F | CF$_3$ | F |
| cyclopentyl | Cl | CF$_3$ | F |
| cyclopentyl | Cl | cyclopropyl | F |
| OCH$_3$-cyclopentyl | F | (CH$_2$)$_2$CH$_3$ | F |
| OH-cyclopentyl | Cl | C≡CH | F |
| Cl-cyclopentyl | CH$_3$ | SCH$_3$ | F |
| OCH$_3$-cyclopentyl | Cl | CF$_3$ | F |
| OH-cyclopentyl | CH$_3$ | CH$_3$ | F |
| OCH$_3$-cyclopentyl | F | CH$_2$OH | F |
| OH-cyclopentyl | Cl | (CH$_2$)$_3$OH | F |
| OCH$_3$-cyclopentyl | F | OCH$_2$CH$_3$ | F |
| cyclohexyl | F | I | F |
| cyclohexyl | Cl | I | F |

TABLE 2-continued

| R$_{1b}$ | X | Y | Z |
|---|---|---|---|
|  | F | Br | F |
|  | Cl | Br | F |
|  | F | CH$_3$ | F |
|  | Cl | CH$_3$ | F |
|  | F | CF$_3$ | F |
|  | Cl | CF$_3$ | F |
|  | F | phenyl | F |
|  | Cl | phenyl | F |
|  | F | 3-pyridyl | F |
|  | Cl | 3-pyridyl | F |
|  | F | pyrazol-4-yl | F |
|  | Cl | pyrazol-4-yl | F |
|  | F | 4-pyridyl | F |
|  | Cl | 4-pyridyl | F |
|  | F | 1-methyl-pyrazol-4-yl | F |
|  | Cl | 1-methyl-pyrazol-4-yl | F |
|  | F | pyrazol-3-yl | F |
|  | Cl | pyrazol-3-yl | F |
|  | F | 2-(CH$_3$—SO$_2$—NH)-phenyl | F |
|  | Cl | 2-(CH$_3$—SO$_2$—NH)-phenyl | F |

TABLE 2-continued

| R$_{1b}$ | X | Y | Z |
|---|---|---|---|
|  | F | 3-(CH$_3$—SO$_2$—NH)-phenyl | F |
|  | Cl | 3-(CH$_3$—SO$_2$—NH)-phenyl | F |
|  | CH$_3$ | 2-(CH$_3$—SO$_2$—NH)-phenyl | F |
|  | CH$_3$ | 3-(CH$_3$—SO$_2$—NH)-phenyl | F |
|  | F | 4-CF$_3$O-phenyl | F |
|  | Cl | 4-CF$_3$O-phenyl | F |
|  | CH$_3$ | 4-CF$_3$O-phenyl | F |
|  | Cl | 2-(CH$_3$—SO$_2$—NH)-phenyl | F |
|  | F | phenyl | F |
|  | | phenyl | |
|  | Cl | 3-pyridyl | F |
|  | F | 3-pyridyl | F |
|  | Cl | pyrazol-4-yl | F |
|  | F | pyrazol-4-yl | F |
|  | Cl | 4-pyridyl | F |
|  | F | 4-pyridyl | F |
|  | Cl | 1-methyl-pyrazol-4-yl | F |
|  | CH$_3$ | 1-methyl-pyrazol-4-yl | F |
|  | F | pyrazol-3-yl | F |

TABLE 2-continued

| R$_{1b}$ | X | Y | Z |
|---|---|---|---|
| cyclopentyl | Cl | pyrazol-3-yl | F |
| cyclopentyl | F | 2-(CH$_3$—SO$_2$—NH)-phenyl | F |
| cyclopentyl | Cl | 2-(CH$_3$—SO$_2$—NH)-phenyl | F |
| cyclopentyl | F | phenyl | F |
| cyclopentyl | Cl | phenyl | F |
| cyclopentyl | F | 3-pyridyl | F |
| cyclopentyl | Cl | 3-pyridyl | F |
| cyclopentyl | Cl | pyrazol-3-yl | F |

Table 3 shows embodiments of this invention which are compounds of formula I, wherein R$^0$ is as defined herein, G is R$_1$, where R$_{1c}$ is as defined in the table and X, Y and Z are defined in the table.

TABLE 3

| R$_{1c}$ | X | Y | Z |
|---|---|---|---|
| CH$_2$CH$_3$ | F | I | F |
| CH$_2$CH$_3$ | Cl | I | F |
| CH$_2$CH$_3$ | F | Br | F |
| CH$_2$CH$_3$ | Cl | Br | F |
| CH$_2$CH$_3$ | F | CH$_3$ | F |
| CH$_2$CH$_3$ | Cl | CH$_3$ | F |
| CH$_2$CH$_3$ | F | CF$_3$ | F |
| CH$_2$CH$_3$ | Cl | CF$_3$ | F |
| CH$_2$CH$_3$ | CH$_3$ | CH$_3$ | F |
| CH$_2$CH$_3$ | CH$_3$ | CH$_3$ | F |
| CH$_2$CH$_3$ | CH$_3$ | C≡CH | F |
| CH$_2$CH$_3$ | CH$_3$ | SCH$_3$ | F |
| CH$_2$CH$_3$ | F | C≡CH | F |
| CH$_2$CH$_3$ | Cl | SCH$_3$ | F |
| CH$_2$CH$_3$ | F | cyclopropyl | F |
| CH$_2$CH$_3$ | Cl | cyclopropyl | F |
| CH$_2$CH$_3$ | CH$_3$ | cyclopropyl | F |
| CH(CH$_3$)$_2$ | F | OCH$_3$ | F |
| CH(CH$_3$)$_2$ | Cl | OCH$_3$ | F |
| CH(CH$_3$)$_2$ | F | I | F |
| CH(CH$_3$)$_2$ | Cl | I | F |
| CH(CH$_3$)$_2$ | F | Br | F |
| CH(CH$_3$)$_2$ | Cl | Br | F |
| CH(CH$_3$)$_2$ | F | CH$_3$ | F |
| CH(CH$_3$)$_2$ | Cl | CH$_3$ | F |
| CH(CH$_3$)$_2$ | F | CH$_2$CH$_3$ | F |
| CH(CH$_3$)$_2$ | Cl | CH$_2$CH$_3$ | F |
| CH(CH$_3$)$_2$ | CH$_3$ | CH$_2$CH$_3$ | F |
| CH(CH$_3$)$_2$ | Cl | CH$_2$CH$_3$ | F |
| CH(CH$_3$)$_2$ | Fl | CH(CH$_3$)$_2$ | F |
| CH(CH$_3$)$_2$ | Cl | CH(CH$_3$)$_2$ | F |
| CH(CH$_3$)$_2$ | F | CF$_3$ | F |
| CH(CH$_3$)$_2$ | Cl | CH$_3$ | F |
| CH(CH$_3$)$_2$ | CH$_3$ | Br | F |
| CH(CH$_3$)$_2$ | CH$_3$ | C≡CH | F |
| CH(CH$_3$)$_2$ | CH$_3$ | SCH$_3$ | F |
| CH(CH$_3$)$_2$ | CH$_3$ | cyclopropyl | F |
| CH(CH$_3$)$_2$ | F | CH$_2$OH | F |
| CH(CH$_3$)$_2$ | Cl | (OH)-cyclopropyl | F |
| n-butyl | F | I | F |
| n-butyl | Cl | I | F |
| n-butyl | F | Br | F |
| n-butyl | Cl | Br | F |
| n-butyl | F | CH$_3$ | F |
| n-butyl | Cl | CH$_3$ | F |
| n-butyl | F | OCH$_3$ | F |
| n-butyl | Cl | OCH$_3$ | F |
| n-butyl | CH$_3$ | OCH$_3$ | F |
| n-butyl | Cl | OCH$_2$CH$_3$ | F |
| n-butyl | F | OCH$_2$CH$_3$ | F |
| n-butyl | CH$_3$ | OCH$_2$CH$_3$ | F |
| n-butyl | F | OCH$_2$CH$_2$OH | F |
| n-butyl | F | CF$_3$ | F |
| n-butyl | Cl | CF$_3$ | F |
| sec-butyl | F | I | F |
| sec-butyl | Cl | I | F |
| sec-butyl | F | Br | F |
| sec-butyl | Cl | Br | F |
| sec-butyl | F | CH$_3$ | F |
| sec-butyl | Cl | CH$_3$ | F |
| sec-butyl | F | CF$_3$ | F |
| sec-butyl | Cl | CF$_3$ | F |
| CH$_2$CF$_3$ | F | I | F |
| CH$_2$CF$_3$ | Cl | I | F |
| CH$_2$CF$_3$ | F | Br | F |
| CH$_2$CF$_3$ | Cl | Br | F |
| CH$_2$CF$_3$ | F | CH$_3$ | F |
| CH$_2$CF$_3$ | Cl | CH$_3$ | F |
| CH$_2$CF$_3$ | F | CF$_3$ | F |
| CH$_2$CF$_3$ | Cl | CF$_3$ | F |
| CH$_2$CCl$_3$ | F | I | F |
| CH$_2$CCl$_3$ | Cl | I | F |
| CH$_2$CCl$_3$ | F | Br | F |
| CH$_2$CCl$_3$ | Cl | Br | F |
| CH$_2$CCl$_3$ | F | CH$_3$ | F |
| CH$_2$CCl$_3$ | Cl | CH$_3$ | F |
| CH$_2$CCl$_3$ | F | CF$_3$ | F |
| CH$_2$CCl$_3$ | Cl | CF$_3$ | F |
| CH$_2$-cyclopropyl | F | I | F |
| CH$_2$-cyclopropyl | Cl | I | F |
| CH$_2$-cyclopropyl | F | Br | F |

TABLE 3-continued

| R$_{1c}$ | X | Y | Z |
|---|---|---|---|
| CH$_2$— | Cl | Br | F |
| CH$_2$— | F | CH$_3$ | F |
| CH$_2$— | Cl | CH$_3$ | F |
| CH$_2$— | F | CF$_3$ | F |
| CH$_2$— | Cl | CF$_3$ | F |
| CH$_2$CH$_2$F | F | I | F |
| CH$_2$CH$_2$F | Cl | I | F |
| CH$_2$CH$_2$F | F | Br | F |
| CH$_2$CH$_2$F | Cl | Br | F |
| CH$_2$CH$_2$F | F | CH$_3$ | F |
| CH$_2$CH$_2$F | Cl | CH$_3$ | F |
| CH$_2$CH$_2$F | F | CF$_3$ | F |
| CH$_2$CH$_2$F | Cl | CF$_3$ | F |
| CH$_2$CH$_2$Cl | F | I | F |
| CH$_2$CH$_2$Cl | Cl | I | F |
| CH$_2$CH$_2$Cl | F | Br | F |
| CH$_2$CH$_2$Cl | Cl | Br | F |
| CH$_2$CH$_2$Cl | F | CH$_3$ | F |
| CH$_2$CH$_2$Cl | Cl | CH$_3$ | F |
| CH$_2$CH$_2$Cl | F | CF$_3$ | F |
| CH$_2$CH$_2$Cl | Cl | CF$_3$ | F |
| CH$_2$CH$_2$CH$_2$Cl | F | I | F |
| CH$_2$CH$_2$CH$_2$Cl | Cl | I | F |
| CH$_2$CH$_2$CH$_2$Cl | F | Br | F |
| CH$_2$CH$_2$CH$_2$Cl | Cl | Br | F |
| CH$_2$CH$_2$CH$_2$Cl | F | CH$_3$ | F |
| CH$_2$CH$_2$CH$_2$Cl | Cl | CH$_3$ | F |
| CH$_2$CH$_2$CH$_2$Cl | F | CF$_3$ | F |
| CH$_2$CH$_2$CH$_2$Cl | Cl | CF$_3$ | F |
| CH$_2$CH$_2$OH | F | I | F |
| CH$_2$CH$_2$OH | Cl | I | F |
| CH$_2$CH$_2$OH | F | Br | F |
| CH$_2$CH$_2$OH | Cl | Br | F |
| CH$_2$CH$_2$OH | F | CH$_3$ | F |
| CH$_2$CH$_2$OH | Cl | CH$_3$ | F |
| CH$_2$CH$_2$OH | F | CF$_3$ | F |
| CH$_2$CH$_2$OH | Cl | CF$_3$ | F |
| CH$_2$CH$_2$CH$_2$OH | F | I | F |
| CH$_2$CH$_2$CH$_2$OH | Cl | I | F |
| CH$_2$CH$_2$CH$_2$OH | F | Br | F |
| CH$_2$CH$_2$CH$_2$OH | Cl | Br | F |
| CH$_2$CH$_2$CH$_2$OH | F | CH$_3$ | F |
| CH$_2$CH$_2$CH$_2$OH | Cl | CH$_3$ | F |
| CH$_2$CH$_2$CH$_2$OH | F | CF$_3$ | F |
| CH$_2$CH$_2$CH$_2$OH | Cl | CF$_3$ | F |
| (CH$_2$)$_4$OH | F | I | F |
| (CH$_2$)$_4$OH | Cl | I | F |
| (CH$_2$)$_4$OH | F | Br | F |
| (CH$_2$)$_4$OH | Cl | Br | F |
| (CH$_2$)$_4$OH | F | CH$_3$ | F |
| (CH$_2$)$_4$OH | Cl | CH$_3$ | F |
| (CH$_2$)$_4$OH | F | CF$_3$ | F |
| (CH$_2$)$_4$OH | Cl | CF$_3$ | F |
| CH$_2$CH$_2$OCH$_3$ | F | I | F |
| CH$_2$CH$_2$OCH$_3$ | Cl | I | F |
| CH$_2$CH$_2$OCH$_3$ | F | Br | F |
| CH$_2$CH$_2$OCH$_3$ | Cl | Br | F |
| CH$_2$CH$_2$OCH$_3$ | F | CH$_3$ | F |
| CH$_2$CH$_2$OCH$_3$ | Cl | CH$_3$ | F |
| CH$_2$CH$_2$OCH$_3$ | F | CF$_3$ | F |
| CH$_2$CH$_2$OCH$_3$ | Cl | CF$_3$ | F |
| (CH$_2$)$_3$OCH$_3$ | F | I | F |
| (CH$_2$)$_3$OCH$_3$ | Cl | I | F |
| (CH$_2$)$_3$OCH$_3$ | F | Br | F |
| (CH$_2$)$_3$OCH$_3$ | Cl | Br | F |
| (CH$_2$)$_3$OCH$_3$ | F | CH$_3$ | F |
| (CH$_2$)$_3$OCH$_3$ | Cl | CH$_3$ | F |
| (CH$_2$)$_3$OCH$_3$ | F | CF$_3$ | F |
| (CH$_2$)$_3$OCH$_3$ | Cl | CF$_3$ | F |
| CH$_2$CH$_2$OEt | F | I | F |
| CH$_2$CH$_2$OEt | Cl | I | F |
| CH$_2$CH$_2$OEt | F | Br | F |
| CH$_2$CH$_2$OEt | Cl | Br | F |
| CH$_2$CH$_2$OEt | F | CH$_3$ | F |
| CH$_2$CH$_2$OEt | Cl | CH$_3$ | F |
| CH$_2$CH$_2$OEt | F | CF$_3$ | F |
| CH$_2$CH$_2$OEt | Cl | CF$_3$ | F |
| CH$_2$CH$_2$O— | F | I | F |
| CH$_2$CH$_2$O— | Cl | I | F |
| CH$_2$CH$_2$O— | F | Br | F |
| CH$_2$CH$_2$O— | Cl | Br | F |
| CH$_2$CH$_2$O— | F | CH$_3$ | F |
| CH$_2$CH$_2$O— | Cl | CH$_3$ | F |
| CH$_2$CH$_2$O— | F | CF$_3$ | F |
| CH$_2$CH$_2$O— | Cl | CF$_3$ | F |
| CH$_2$CH$_2$O— | F | I | F |
| CH$_2$CH$_2$O— | Cl | I | F |
| CH$_2$CH$_2$O— | F | Br | F |
| CH$_2$CH$_2$O— | Cl | Br | F |
| CH$_2$CH$_2$O— | F | CH$_3$ | F |
| CH$_2$CH$_2$O— | Cl | CH$_3$ | F |
| CH$_2$CH$_2$O— | F | CF$_3$ | F |
| CH$_2$CH$_2$O— | Cl | CF$_3$ | F |

TABLE 3-continued

| $R_{1c}$ | X | Y | Z |
|---|---|---|---|
| CH₂CH₂CH₂OEt | F | I | F |
| CH₂CH₂CH₂OEt | Cl | I | F |
| CH₂CH₂CH₂OEt | F | Br | F |
| CH₂CH₂CH₂OEt | Cl | Br | F |
| CH₂CH₂CH₂OEt | F | CH₃ | F |
| CH₂CH₂CH₂OEt | Cl | CH₃ | F |
| CH₂CH₂CH₂OEt | F | CF₃ | F |
| CH₂CH₂CH₂OEt | Cl | CF₃ | F |
|  | F | I | F |
|  | Cl | I | F |
|  | F | Br | F |
|  | Cl | Br | F |
|  | F | CH₃ | F |
|  | Cl | CH₃ | F |
|  | F | CF₃ | F |
|  | Cl | CF₃ | F |
|  | F | I | F |
|  | Cl | I | F |
|  | F | Br | F |
|  | Cl | Br | F |
|  | F | CH₃ | F |
| 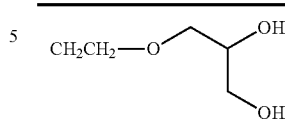 | Cl | CH₃ | F |
| 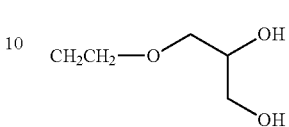 | F | CF₃ | F |
| 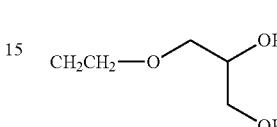 | Cl | CF₃ | F |

TABLE 3-continued

| $R_{1c}$ | X | Y | Z |
|---|---|---|---|
| 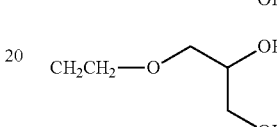 | F | I | F |
| 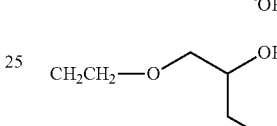 | Cl | I | F |
| 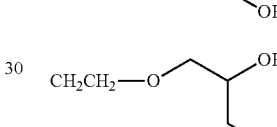 | F | Br | F |
| 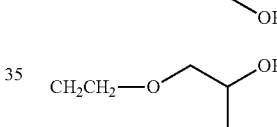 | Cl | Br | F |
| 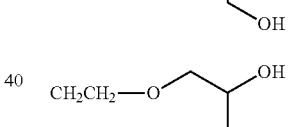 | F | CH₃ | F |
| 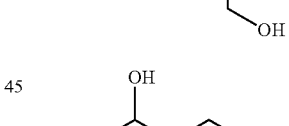 | Cl | CH₃ | F |
| 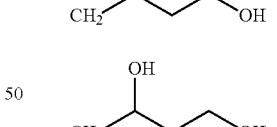 | F | CF₃ | F |
| 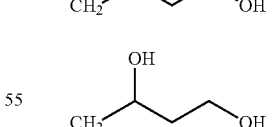 | Cl | CF₃ | F |
| 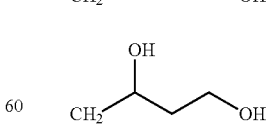 | F | I | F |
| 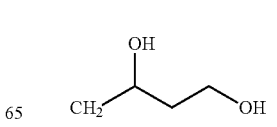 | Cl | I | F |
|  | F | Br | F |
|  | Cl | Br | F |
|  | F | CH₃ | F |

TABLE 3-continued

| R1c | X | Y | Z |
|---|---|---|---|
| 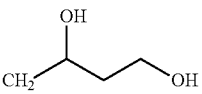 | Cl | CH3 | F |
| 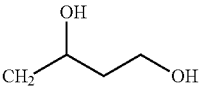 | F | CF3 | F |
| 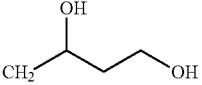 | Cl | CF3 | F |
| 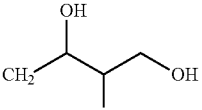 | F | I | F |
| 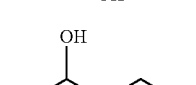 | Cl | I | F |
| 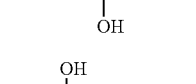 | CH3 | I | F |
| 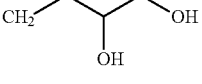 | F | Br | F |
| 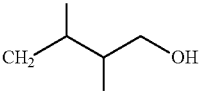 | Cl | Br | F |
| 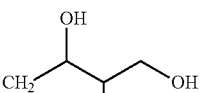 | CH3 | Br | F |
| 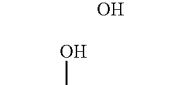 | F | CH3 | F |
| 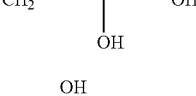 | Cl | CH3 | F |
| 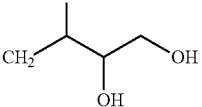 | CH3 | CH3 | F |

TABLE 3-continued

| R1c | X | Y | Z |
|---|---|---|---|
| 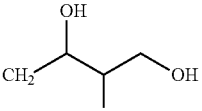 | F | C≡CH | F |
| 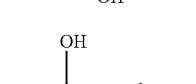 | F | SCH3 | F |
| 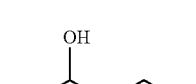 | F | CH2CH2CH3 | F |
| 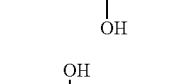 | Cl | CH2CH(OH)CH3 | F |
| 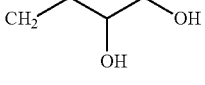 | F | CH(CH3)2 | F |
| 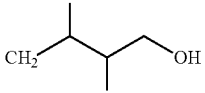 | Cl | CF3 | F |
| CH2CH3 | F | phenyl | F |
| CH2CH3 | Cl | phenyl | F |
| CH2CH3 | F | phenyl | F |
| CH2CH3 | Cl | 3-pyridyl | F |
| CH2CH3 | F | 3-pyridyl | F |
| CH2CH3 | Cl | 4-pyridyl | F |
| CH2CH3 | F | pyrazolyl | F |
| CH2CH3 | Cl | pyrazolyl | F |
| CH2CH3 | CH3 | 4-pyridyl | F |
| CH2CH3 | CH3 | 4-pyridyl | Z |
| CH2CH3 | CH3 | 2-(CH3—SO2—NH)-phenyl | F |
| CH2CH3 | CH3 | 3-(CH3—SO2—NH)-phenyl | F |
| CH2CH3 | F | 3-(CH3—SO2—NH)-phenyl | F |
| CH2CH3 | Cl | 3-(CH3—SO2—NH)-phenyl | F |
| CH2CH3 | F | phenyl | F |
| CH2CH3 | Cl | phenyl | F |
| CH2CH3 | CH3 | phenyl | F |
| | | 3-pyridyl | |
| CH(CH3)2 | F | 3-pyridyl | F |
| CH(CH3)2 | Cl | 4-pyridyl | F |
| CH(CH3)2 | F | pyrazolyl | F |
| CH(CH3)2 | Cl | pyrazolyl | F |
| CH(CH3)2 | F | 4-pyridyl | F |
| CH(CH3)2 | Cl | 4-pyridyl | F |
| CH(CH3)2 | F | 2-(CH3—SO2—NH)-phenyl | F |
| CH(CH3)2 | Cl | 3-(CH3—SO2—NH)-phenyl | F |
| CH(CH3)2 | F | 3-(CH3—SO2—NH)-phenyl | F |
| CH(CH3)2 | Cl | 3-(CH3—SO2—NH)-phenyl | F |
| CH(CH3)2 | CH3 | phenyl | F |
| CH(CH3)2 | Cl | phenyl | F |
| CH(CH3)2 | Fl | phenyl | F |
| CH(CH3)2 | Cl | 3-pyridyl | F |
| CH(CH3)2 | F | 4-pyridyl | F |
| CH(CH3)2 | Cl | pyrazolyl | F |
| CH(CH3)2 | CH3 | pyrazolyl | F |

TABLE 3-continued

| R$_{1c}$ | X | Y | Z |
|---|---|---|---|
| CH(CH$_3$)$_2$ | CH$_3$ | 4-pyridyl | F |
| CH(CH$_3$)$_2$ | CH$_3$ | 4-pyridyl | F |
| CH(CH$_3$)$_2$ | CH$_3$ | 2-(CH$_3$—SO$_2$—NH)-phenyl | F |
| CH(CH$_3$)$_2$ | F | 3-(CH$_3$—SO$_2$—NH)-phenyl | F |
| CH(CH$_3$)$_2$ | Cl | 3-(CH$_3$—SO$_2$—NH)-phenyl | F |
| | | 3-(CH$_3$—SO$_2$—NH)-phenyl | |
| n-butyl | F | phenyl | F |
| n-butyl | Cl | phenyl | F |
| n-butyl | F | phenyl | F |
| n-butyl | Cl | 3-pyridyl | F |
| n-butyl | F | 3-pyridyl | F |
| n-butyl | Cl | 4-pyridyl | F |
| n-butyl | F | pyrazolyl | F |
| n-butyl | Cl | pyrazolyl | F |
| n-butyl | CH$_3$ | 4-pyridyl | F |
| n-butyl | Cl | 4-pyridyl | F |
| n-butyl | F | 2-(CH$_3$—SO$_2$—NH)-phenyl | F |
| n-butyl | CH$_3$ | 3-(CH$_3$—SO$_2$—NH)-phenyl | F |
| n-butyl | F | 3-(CH$_3$—SO$_2$—NH)-phenyl | F |
| | | 3-(CH$_3$—SO$_2$—NH)-phenyl | |
| n-butyl | F | phenyl | F |
| n-butyl | Cl | phenyl | F |
| | | phenyl | |
| sec-butyl | F | 3-pyridyl | F |
| sec-butyl | Cl | 3-pyridyl | F |
| sec-butyl | F | 4-pyridyl | F |
| sec-butyl | Cl | pyrazolyl | F |
| sec-butyl | F | pyrazolyl | F |
| sec-butyl | Cl | 4-pyridyl | F |
| sec-butyl | F | 4-pyridyl | F |
| sec-butyl | Cl | CF$_3$ | F |
| CH$_2$CF$_3$ | F | phenyl | F |
| CH$_2$CF$_3$ | Cl | phenyl | F |
| CH$_2$CF$_3$ | F | phenyl | F |
| CH$_2$CF$_3$ | Cl | 3-pyridyl | F |
| CH$_2$CF$_3$ | F | 3-pyridyl | F |
| CH$_2$CF$_3$ | Cl | 4-pyridyl | F |
| CH$_2$CF$_3$ | F | pyrazolyl | F |
| CH$_2$CF$_3$ | Cl | pyrazolyl | F |
| | | 4-pyridyl | |
| CH$_2$CCl$_3$ | F | 4-pyridyl | F |
| CH$_2$CCl$_3$ | Cl | 2-(CH$_3$—SO$_2$—NH)-phenyl | F |
| CH$_2$CCl$_3$ | F | 3-(CH$_3$—SO$_2$—NH)-phenyl | F |
| CH$_2$CCl$_3$ | Cl | 3-(CH$_3$—SO$_2$—NH)-phenyl | F |
| CH$_2$CCl$_3$ | F | 3-(CH$_3$—SO$_2$—NH)-phenyl | F |
| CH$_2$CCl$_3$ | Cl | phenyl | F |
| CH$_2$CCl$_3$ | F | phenyl | F |
| CH$_2$CCl$_3$ | Cl | phenyl | F |
| | | 3-pyridyl | |
| 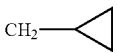 | F | 3-pyridyl | F |
| 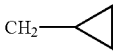 | Cl | 4-pyridyl | F |
| 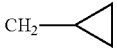 | F | pyrazolyl | F |
| 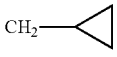 | Cl | pyrazolyl | F |
| 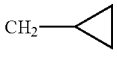 | F | 4-pyridyl | F |
| 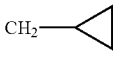 | Cl | 4-pyridyl | F |
| 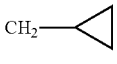 | F | 2-(CH$_3$—SO$_2$—NH)-phenyl | F |
| 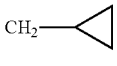 | Cl | 3-(CH$_3$—SO$_2$—NH)-phenyl | F |
| | | 3-(CH$_3$—SO$_2$—NH)-phenyl | |
| CH$_2$CH$_2$F | F | 3-(CH$_3$—SO$_2$—NH)-phenyl | F |
| CH$_2$CH$_2$F | Cl | phenyl | F |
| CH$_2$CH$_2$F | F | phenyl | F |
| CH$_2$CH$_2$F | Cl | phenyl | F |
| CH$_2$CH$_2$F | F | 3-pyridyl | F |
| CH$_2$CH$_2$F | Cl | 3-pyridyl | F |
| CH$_2$CH$_2$F | F | 4-pyridyl | F |
| CH$_2$CH$_2$F | Cl | pyrazolyl | F |
| | | pyrazolyl | |
| CH$_2$CH$_2$Cl | F | 4-pyridyl | F |
| CH$_2$CH$_2$Cl | Cl | 4-pyridyl | F |
| CH$_2$CH$_2$Cl | F | 2-(CH$_3$—SO$_2$—NH)-phenyl | F |
| CH$_2$CH$_2$Cl | Cl | 3-(CH$_3$—SO$_2$—NH)-phenyl | F |
| CH$_2$CH$_2$Cl | F | 3-(CH$_3$—SO$_2$—NH)-phenyl | F |
| CH$_2$CH$_2$Cl | Cl | 3-(CH$_3$—SO$_2$—NH)-phenyl | F |
| CH$_2$CH$_2$Cl | F | phenyl | F |
| CH$_2$CH$_2$Cl | Cl | phenyl | F |
| CH$_2$CH$_2$CH$_2$Cl | F | 3-pyridyl | F |
| CH$_2$CH$_2$CH$_2$Cl | Cl | 3-pyridyl | F |
| CH$_2$CH$_2$CH$_2$Cl | F | 4-pyridyl | F |
| CH$_2$CH$_2$CH$_2$Cl | Cl | pyrazolyl | F |
| CH$_2$CH$_2$CH$_2$Cl | F | pyrazolyl | F |
| CH$_2$CH$_2$CH$_2$Cl | Cl | 4-pyridyl | F |
| CH$_2$CH$_2$CH$_2$Cl | F | 4-pyridyl | F |
| CH$_2$CH$_2$CH$_2$Cl | Cl | 2-(CH$_3$—SO$_2$—NH)-phenyl | F |
| | | 3-(CH$_3$—SO$_2$—NH)-phenyl | |
| CH$_2$CH$_2$OH | F | 3-(CH$_3$—SO$_2$—NH)-phenyl | F |
| CH$_2$CH$_2$OH | Cl | 3-(CH$_3$—SO$_2$—NH)-phenyl | F |
| CH$_2$CH$_2$OH | F | phenyl | F |
| CH$_2$CH$_2$OH | Cl | phenyl | F |
| CH$_2$CH$_2$OH | F | phenyl | F |
| CH$_2$CH$_2$OH | Cl | 3-pyridyl | F |
| CH$_2$CH$_2$OH | F | 3-pyridyl | F |
| CH$_2$CH$_2$OH | Cl | 4-pyridyl | F |
| | | pyrazolyl | |
| CH$_2$CH$_2$CH$_2$OH | F | pyrazolyl | F |
| CH$_2$CH$_2$CH$_2$OH | Cl | 4-pyridyl | F |
| CH$_2$CH$_2$CH$_2$OH | F | 4-pyridyl | F |
| CH$_2$CH$_2$CH$_2$OH | Cl | 2-(CH$_3$—SO$_2$—NH)-phenyl | F |
| CH$_2$CH$_2$CH$_2$OH | F | 3-(CH$_3$—SO$_2$—NH)-phenyl | F |
| CH$_2$CH$_2$CH$_2$OH | Cl | 3-(CH$_3$—SO$_2$—NH)-phenyl | F |
| CH$_2$CH$_2$CH$_2$OH | F | 3-(CH$_3$—SO$_2$—NH)-phenyl | F |
| CH$_2$CH$_2$CH$_2$OH | Cl | phenyl | F |
| | | phenyl | |
| (CH$_2$)$_4$OH | F | phenyl | F |
| (CH$_2$)$_4$OH | Cl | 3-pyridyl | F |
| (CH$_2$)$_4$OH | F | 3-pyridyl | F |
| (CH$_2$)$_4$OH | Cl | 4-pyridyl | F |
| (CH$_2$)$_4$OH | F | pyrazolyl | F |
| (CH$_2$)$_4$OH | Cl | pyrazolyl | F |
| (CH$_2$)$_4$OH | F | 4-pyridyl | F |
| (CH$_2$)$_4$OH | Cl | 4-pyridyl | F |
| | | 2-(CH$_3$—SO$_2$—NH)-phenyl | |
| CH$_2$CH$_2$OCH$_3$ | F | 3-(CH$_3$—SO$_2$—NH)-phenyl | F |
| CH$_2$CH$_2$OCH$_3$ | Cl | 3-(CH$_3$—SO$_2$—NH)-phenyl | F |
| CH$_2$CH$_2$OCH$_3$ | F | 3-(CH$_3$—SO$_2$—NH)-phenyl | F |
| CH$_2$CH$_2$OCH$_3$ | Cl | phenyl | F |
| CH$_2$CH$_2$OCH$_3$ | F | phenyl | F |
| CH$_2$CH$_2$OCH$_3$ | Cl | phenyl | F |
| CH$_2$CH$_2$OCH$_3$ | F | 3-pyridyl | F |
| CH$_2$CH$_2$OCH$_3$ | Cl | 3-pyridyl | F |
| | | 4-pyridyl | |
| (CH$_2$)$_3$OCH$_3$ | F | pyrazolyl | F |
| (CH$_2$)$_3$OCH$_3$ | Cl | pyrazolyl | F |
| (CH$_2$)$_3$OCH$_3$ | F | 4-pyridyl | F |
| (CH$_2$)$_3$OCH$_3$ | Cl | 4-pyridyl | F |
| (CH$_2$)$_3$OCH$_3$ | F | 2-(CH$_3$—SO$_2$—NH)-phenyl | F |
| (CH$_2$)$_3$OCH$_3$ | Cl | 3-(CH$_3$—SO$_2$—NH)-phenyl | F |
| (CH$_2$)$_3$OCH$_3$ | F | 3-(CH$_3$—SO$_2$—NH)-phenyl | F |
| (CH$_2$)$_3$OCH$_3$ | Cl | 3-(CH$_3$—SO$_2$—NH)-phenyl | F |
| | | phenyl | |
| CH$_2$CH$_2$OEt | F | phenyl | F |
| CH$_2$CH$_2$OEt | Cl | phenyl | F |
| CH$_2$CH$_2$OEt | F | 3-pyridyl | F |
| CH$_2$CH$_2$OEt | Cl | 3-pyridyl | F |
| CH$_2$CH$_2$OEt | F | 4-pyridyl | F |
| CH$_2$CH$_2$OEt | Cl | pyrazolyl | F |

TABLE 3-continued

| $R_{1c}$ | X | Y | Z |
|---|---|---|---|
| $CH_2CH_2OEt$ | F | pyrazolyl | F |
| $CH_2CH_2OEt$ | Cl | 4-pyridyl | F |

Tables 4a and 4b show embodiments of this invention which are compounds of formula I, where $G=R_{1d}$, Z is F, X is F and $R_{1d}$ and $R^O$ are defined in the table. Each line in the table corresponds to five species which differ only at position Y.

TABLE 4a

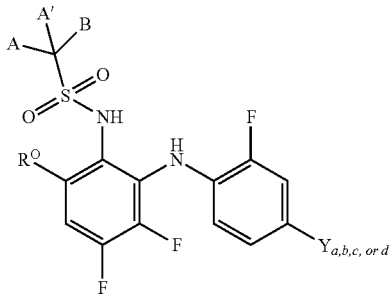

$Y_a = CH_3$; $Y_b = Br$; $Y_c = I$; $Y_d = Cl$;

| CMPD # | A, A' | B | $R^O$ |
|---|---|---|---|
| 1(a-d) | H, H | H | $OCH_3$ |
| 2(a-d) | H, H | H | $NHCH_3$ |
| 3(a-d) | H, H | H | $CH_2CH_3$ |
| 4(a-d) | H, H | H | $CH_2CH=CH_2$ |
| 5(a-d) | H, H | H | CN |
| 6(a-d) | H, H | H | $CF_3$ |
| 7(a-d) | H, H | H | F |
| 8(a-d) | H, H | H | $C_6H_6$ |
| 9(a-d) | H, H | —$CH_2CH(OH)CH_2OH$ | $OCH_3$ |
| 10(a-d) | H, H | —$CH_2CH(OH)CH_2OH$ | $NHCH_3$ |
| 11(a-d) | H, H | —$CH_2CH(OH)CH_2OH$ | $CH_2CH_3$ |
| 12(a-d) | —$(CH_2)_2$— | —$CH_2(C_3H_5)$ | $OCH_3$ |
| 13(a-d) | —$(CH_2)_2$— | —$CH_2(C_3H_5)$ | $NHCH_3$ |
| 14(a-d) | —$(CH_2)_2$— | —$CH_2(C_3H_5)$ | $CH_2CH_3$ |
| 15(a-d) | —$(CH_2)_2$— | $CH_3$ | F |
| 16(a-d) | —$(CH_2)_2$— | —$CH_2CH_2OH$ | F |
| 17(a-d) | —$(CH_2)_2$— | —$(CH_2)_2CH(OH)CH_2OH$ | F |
| 18(a-d) | $CH_3$, H | —$(CH_2)_2CH(OH)CH_2OH$ | F |
| 19(a-d) | —$(CH_2)_2$— | $CH_3$ | $OCH_3$ |
| 20(a-d) | —$(CH_2)_2$— | —$CH_2CH_2OH$ | $OCH_3$ |
| 21(a-d) | —$(CH_2)_2$— | —$(CH_2)_2CH(OH)CH_2OH$ | $OCH_3$ |
| 22(a-d) | $CH_3$, H | —$(CH_2)_2CH(OH)CH_2OH$ | $OCH_3$ |
| 23(a-d) | —$(CH_2)_2$— | $CH_3$ | H |
| 24(a-d) | —$(CH_2)_2$— | —$CH_2CH_2OH$ | H |
| 25(a-d) | —$(CH_2)_2$— | —$(CH_2)_2CH(OH)CH_2OH$ | H |
| 26(a-d) | $CH_3$, H | —$(CH_2)_2CH(OH)CH_2OH$ | H |
| 27(a-d) | H, H | H | $OCH_3$ |
| 28(a-d) | H, H | H | $NHCH_3$ |
| 29(a-d) | H, H | H | $CH_2CH_3$ |
| 30(a-d) | H, H | H | $CH_2CH=CH_2$ |
| 31(a-d) | H, H | H | CN |
| 32(a-d) | H, H | H | $CF_3$ |
| 33(a-d) | H, H | H | F |
| 34(a-d) | H, H | H | $C_6H_6$ |
| 35(a-d) | H, H | —$CH_2CH(OH)CH_2OH$ | $OCH_3$ |
| 36(a-d) | H, H | —$CH_2CH(OH)CH_2OH$ | $NHCH_3$ |
| 37(a-d) | H, H | —$CH_2CH(OH)CH_2OH$ | $CH_2CH_3$ |
| 38(a-d) | —$(CH_2)_2$— | —$CH_2(C_3H_5)$ | $OCH_3$ |
| 39(a-d) | —$(CH_2)_2$— | —$CH_2(C_3H_5)$ | $NHCH_3$ |
| 40(a-d) | —$(CH_2)_2$— | —$CH_2(C_3H_5)$ | $CH_2CH_3$ |
| 41(a-d) | —$(CH_2)_2$— | $CH_3$ | F |
| 42(a-d) | —$(CH_2)_2$— | —$CH_2CH_2OH$ | F |
| 43(a-d) | —$(CH_2)_2$— | —$(CH_2)_2CH(OH)CH_2OH$ | F |
| 44(a-d) | $CH_3$, H | —$(CH_2)_2CH(OH)CH_2OH$ | F |
| 45(a-d) | —$(CH_2)_2$— | $CH_3$ | $OCH_3$ |
| 46(a-d) | —$(CH_2)_2$— | —$CH_2CH_2OH$ | $OCH_3$ |
| 47(a-d) | —$(CH_2)_2$— | —$(CH_2)_2CH(OH)CH_2OH$ | $OCH_3$ |

TABLE 4a-continued $Y_a = CH_3$; $Y_b = Br$; $Y_c = I$; $Y_d = Cl$;

| CMPD # | A, A' | B | $R^O$ |
|---|---|---|---|
| 48(a-d) | $CH_3$, H | —$(CH_2)_2CH(OH)CH_2OH$ | $OCH_3$ |
| 49(a-d) | —$(CH_2)_2$— | $CH_3$ | H |
| 50(a-d) | —$(CH_2)_2$— | —$CH_2CH_2OH$ | H |
| 51(a-d) | —$(CH_2)_2$— | —$(CH_2)_2CH(OH)CH_2OH$ | H |
| 52(a-d) | $CH_3$, H | —$(CH_2)_2CH(OH)CH_2OH$ | H |

TABLE 4b

| CMPD # | A, A' | B | $R^O$ |
|---|---|---|---|
| 1(a-d) | H, H | H | 2-furanyl |
| 2(a-d) | H, H | H | 1,2,3 triazolyl-4-yl |
| 3(a-d) | H, H | H | 4-imidazolyl |
| 4(a-d) | H, H | H | 2-furanyl |
| 5(a-d) | H, H | H | 1,2,3 triazolyl-4-yl |
| 6(a-d) | H, H | H | 4-imidazolyl |
| 7(a-d) | H, H | —$(CH_2)_2CH(OH)CH_2OH$ | 2-furanyl |
| 8(a-d) | H, H | —$(CH_2)_2CH(OH)CH_2OH$ | 1,2,3 triazolyl-4-yl |
| 9(a-d) | H, H | —$(CH_2)_2CH(OH)CH_2OH$ | 4-imidazolyl |
| 10(a-d) | —$(CH_2)_2$— | —$CH_2(C_3H_5)$ | 2-furanyl |
| 11(a-d) | —$(CH_2)_2$— | —$CH_2(C_3H_5)$ | 1,2,3 triazolyl-4-yl |
| 12(a-d) | —$(CH_2)_2$— | —$CH_2(C_3H_5)$ | 4-imidazolyl |
| 13(a-d) | —$(CH_2)_2$— | $CH_3$ | 4-thiazolyl |
| 14(a-d) | —$(CH_2)_2$— | —$CH_2CH_2OH$ | 4-thiazolyl |
| 15(a-d) | —$(CH_2)_2$— | —$(CH_2)_2CH(OH)CH_2OH$ | 4-thiazolyl |
| 16(a-d) | $CH_3$, H | —$(CH_2)_2CH(OH)CH_2OH$ | 4-thiazolyl |
| 17(a-d) | —$(CH_2)_2$— | $CH_3$ | 2-oxazolyl |
| 18(a-d) | —$(CH_2)_2$— | —$CH_2CH_2OH$ | 2-oxazolyl |
| 19(a-d) | —$(CH_2)_2$— | —$(CH_2)_2CH(OH)CH_2OH$ | 2-oxazolyl |
| 20(a-d) | $CH_3$, H | —$(CH_2)_2CH(OH)CH_2OH$ | 2-oxazolyl |
| 21(a-d) | H, H | H | 2-furanyl |
| 22(a-d) | H, H | H | 1,2,3 triazolyl-4-yl |
| 23(a-d) | H, H | H | 4-imidazolyl |
| 24(a-d) | H, H | H | 2-furanyl |
| 25(a-d) | H, H | H | 1,2,3 triazolyl-4-yl |
| 26(a-d) | H, H | H | 4-imidazolyl |
| 27(a-d) | H, H | —$CH_2CH(OH)CH_2OH$ | 2-furanyl |
| 28(a-d) | H, H | —$CH_2CH(OH)CH_2OH$ | 1,2,3 triazolyl-4-yl |
| 29(a-d) | H, H | —$CH_2CH(OH)CH_2OH$ | 4-imidazolyl |
| 30(a-d) | —$(CH_2)_2$— | —$CH_2(C_3H_5)$ | 2-furanyl |
| 31(a-d) | —$(CH_2)_2$— | —$CH_2(C_3H_5)$ | 1,2,3 triazolyl-4-yl |
| 32(a-d) | —$(CH_2)_2$— | —$CH_2(C_3H_5)$ | 4-imidazolyl |
| 33(a-d) | —$(CH_2)_2$— | $CH_3$ | 4-thiazolyl |
| 34(a-d) | —$(CH_2)_2$— | —$CH_2CH_2OH$ | 4-thiazolyl |
| 35(a-d) | —$(CH_2)_2$— | —$(CH_2)_2CH(OH)CH_2OH$ | 4-thiazolyl |
| 36(a-d) | $CH_3$, H | —$(CH_2)_2CH(OH)CH_2OH$ | 4-thiazolyl |
| 37(a-d) | —$(CH_2)_2$— | $CH_3$ | 2-oxazolyl |
| 38(a-d) | —$(CH_2)_2$— | —$CH_2CH_2OH$ | 2-oxazolyl |
| 39(a-d) | —$(CH_2)_2$— | —$(CH_2)_2CH(OH)CH_2OH$ | 2-oxazolyl |
| 40(a-d) | $CH_3$, H | —$(CH_2)_2CH(OH)CH_2OH$ | 2-oxazolyl |

Table 5a shows embodiments of this invention which are compounds of formula I, where G is $Ar_1$, $Ar_2$ or $R_{1d}$, and where $R^O$ is H, Z is F and G and X are defined in the table. Each line in the table corresponds to five species ($Y_a$, $Y_b$, $Y_c$, $Y_d$ and $Y_e$) which differ only at position Y, where $Y_n$=$SCH_3$; $Y_b$=Br; Y, I; $Y_d$=Cl; $Y_e$=$CH_3$.

TABLE 5a

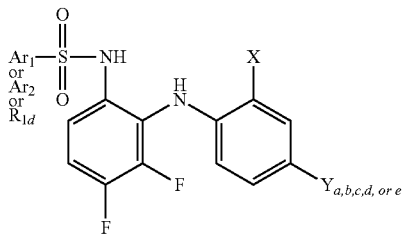

$Y_a = SCH_3$; $Y_b = Br$; $Y_c = I$; $Y_d = Cl$; $Y_e = CH_3$

TABLE 5a-continued

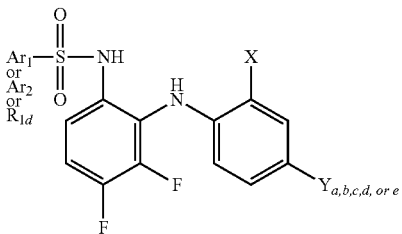

$Y_a = SCH_3$; $Y_b = Br$; $Y_c = I$; $Y_d = Cl$; $Y_e = CH_3$

| Compound # | G = $R_{1d}$, $Ar_1$, or $Ar_2$ | X |
|---|---|---|
| 1 (a-e) | phenyl | Cl |
| 2 (a-e) | phenyl | F |
| 3 (a-e) | 2-F-phenyl | Cl |
| 4 (a-e) | 2-F-phenyl | F |
| 5 (a-e) | 3-F-phenyl | Cl |
| 6 (a-e) | 3-F-phenyl | F |
| 7 (a-e) | 4-F-phenyl | Cl |
| 8 (a-e) | 4-F-phenyl | F |
| 9 (a-e) | 2,4-di-F-phenyl | Cl |
| 10 (a-e) | 2,4-di-F-phenyl | F |
| 11 (a-e) | 2,5-di-F-phenyl | Cl |
| 12 (a-e) | 2,5-di-F-phenyl | F |
| 13 (a-e) | 2,6-di-F-phenyl | Cl |
| 14 (a-e) | 2,6-di-F-phenyl | F |
| 15 (a-e) | 3,4-di-F-phenyl | Cl |
| 16 (a-e) | 3,4-di-F-phenyl | F |
| 17 (a-e) | 3,5-di-F-phenyl | Cl |
| 18 (a-e) | 3,5-di-F-phenyl | F |
| 19 (a-e) | 2,6-di-F-phenyl | Cl |
| 20 (a-e) | 2,6-di-F-phenyl | F |
| 21 (a-e) | 2,3,4-tri-F-phenyl | Cl |
| 22 (a-e) | 2,3,4-tri-F-phenyl | F |
| 23 (a-e) | 3,4,5-tri-F-phenyl | Cl |
| 24 (a-e) | 3,4,5-tri-F-phenyl | F |
| 25 (a-e) | penta-F-phenyl | Cl |
| 26 (a-e) | penta-F-phenyl | F |
| 27 (a-e) | 3-Cl-4-F-phenyl | Cl |
| 28 (a-e) | 3-Cl-4-F-phenyl | F |
| 29 (a-e) | 2-Cl-4-F-phenyl | Cl |
| 30 (a-e) | 2-Cl-4-F-phenyl | F |
| 31 (a-e) | 2-F-3-Cl-phenyl | Cl |
| 32 (a-e) | 2-F-3-Cl-phenyl | F |
| 33 (a-e) | 2-F-4-Cl-phenyl | Cl |
| 34 (a-e) | 2-F-4-Cl-phenyl | F |
| 35 (a-e) | 2-F-5-Cl-phenyl | Cl |
| 36 (a-e) | 2-F-5-Cl-phenyl | F |
| 37 (a-e) | 3-cyano-4-F-phenyl | Cl |
| 38 (a-e) | 3-cyano-4-F-phenyl | F |
| 39 (a-e) | 2-Cl-phenyl | Cl |
| 40 (a-e) | 2-Cl-phenyl | F |
| 41 (a-e) | 3-Cl-phenyl | Cl |
| 42 (a-e) | 3-Cl-phenyl | F |
| 43 (a-e) | 4-Cl-phenyl | Cl |
| 44 (a-e) | 4-Cl-phenyl | F |
| 45 (a-e) | 2,3-di-Cl-phenyl | Cl |
| 46 (a-e) | 2,3-di-Cl-phenyl | F |
| 47 (a-e) | 2,5-di-Cl-phenyl | Cl |
| 48 (a-e) | 2,5-di-Cl-phenyl | F |
| 49 (a-e) | 2,6-di-Cl-phenyl | Cl |
| 50 (a-e) | 2,6-di-Cl-phenyl | F |
| 51 (a-e) | 3,5-di-Cl-phenyl | Cl |
| 52 (a-e) | 3,5-di-Cl-phenyl | F |
| 53 (a-e) | 2,4-di-Cl-phenyl | Cl |
| 54 (a-e) | 2,4-di-Cl-phenyl | F |
| 55 (a-e) | 3,4-di-Cl-phenyl | Cl |
| 56 (a-e) | 3,4-di-Cl-phenyl | F |
| 57 (a-e) | 2,4,6-tri-Cl-phenyl | Cl |
| 58 (a-e) | 2,4,6-tri-Cl-phenyl | F |
| 59 (a-e) | 2-Cl-4-CF$_3$-phenyl | Cl |
| 60 (a-e) | 2-Cl-4-CF$_3$-phenyl | F |
| 61 (a-e) | 2-CF$_3$-phenyl | Cl |
| 62 (a-e) | 2-CF$_3$-phenyl | F |
| 63 (a-e) | 3-CF$_3$-phenyl | Cl |
| 64 (a-e) | 3-CF$_3$-phenyl | F |
| 65 (a-e) | 4-CF$_3$-phenyl | Cl |
| 66 (a-e) | 4-CF$_3$-phenyl | F |
| 67 (a-e) | 2-CF$_3$O phenyl | Cl |
| 68 (a-e) | 2-CF$_3$O phenyl | F |
| 69 (a-e) | 3-CF$_3$O phenyl | Cl |
| 70 (a-e) | 3-CF$_3$O phenyl | F |
| 71 (a-e) | 4-CF$_3$O phenyl | Cl |
| 72 (a-e) | 4-CF$_3$O phenyl | F |
| 73 (a-e) | 2-CHF$_2$O phenyl | Cl |
| 74 (a-e) | 2-CHF$_2$O phenyl | F |
| 75 (a-e) | 2-methyl-5-nitro-phenyl | Cl |
| 76 (a-e) | 2-methyl-5-nitro-phenyl | F |
| 77 (a-e) | 2-cyano-phenyl | Cl |
| 78 (a-e) | 2-cyano-phenyl | F |
| 79 (a-e) | 3-cyano-phenyl | Cl |
| 80 (a-e) | 3-cyano-phenyl | F |
| 81 (a-e) | 4-cyano-phenyl | Cl |
| 82 (a-e) | 4-cyano-phenyl | F |
| 83 (a-e) | 4-methoxy-phenyl | Cl |
| 84 (a-e) | 4-methoxy-phenyl | F |
| 85 (a-e) | 3,4-dimethoxy-phenyl | Cl |
| 86 (a-e) | 3,4-dimethoxy-phenyl | F |
| 87 (a-e) | 3-carbamyl-phenyl | Cl |
| 88 (a-e) | 3-carbamyl-phenyl | F |
| 89 (a-e) | 3-carboxyl-phenyl | Cl |
| 90 (a-e) | 3-carboxyl-phenyl | F |
| 91 (a-e) | 3-(N,N-dimethylcarbamoyl)phenyl | Cl |
| 92 (a-e) | 3-(N,N-dimethylcarbamoyl)phenyl | F |
| 93 (a-e) | 4-methylsulfonyl-phenyl | Cl |
| 94 (a-e) | 4-methylsulfonyl-phenyl | F |
| 95 (a-e) | 3-(1,3,4 oxadiazol-2-yl)phenyl | Cl |
| 96 (a-e) | 3-(1,3,4 oxadiazol-2-yl)phenyl | F |
| 97 (a-e) | 3-(1,3,4 thiadiazol-2-yl)phenyl | Cl |
| 98 (a-e) | 3-(1,3,4 thiadiazol-2-yl)phenyl | F |
| 99 (a-e) | 3-(5-methyl-1-1,3,4-oxadiazol)phenyl | Cl |
| 100 (a-e) | 3-(5-methyl-1-1,3,4-oxadiazol)phenyl | F |
| 101 (a-e) | 3-(5-methyl-1-1,3,4-thiadiazol)phenyl | Cl |
| 102 (a-e) | 3-(5-methyl-1-1,3,4-thiadiazol)phenyl | F |
| 103 (a-e) | 3-amidinyl-phenyl | Cl |
| 104 (a-e) | 3-amidinyl-phenyl | F |
| 105 (a-e) | 3-(1H-tetrazolyl)phenyl | Cl |
| 106 (a-e) | 3-(1H-tetrazolyl)phenyl | F |
| 107 (a-e) | 4-acetamido-phenyl | Cl |
| 108 (a-e) | 4-acetamido-phenyl | F |
| 109 (a-e) | 3-Cl-4-[(N-morpholinylcarbonyl)amino]phenyl | Cl |
| 110 (a-e) | 3-Cl-4-[(N-morpholinylcarbonyl)amino]phenyl | F |
| 111 (a-e) | 3-Cl-4-[(N-pyrrolidinylcarbonyl)amino]phenyl | Cl |
| 112 (a-e) | 3-Cl-4-[(N-pyrrolidinylcarbonyl)amino]phenyl | F |
| 113 (a-e) | 3,5-dimethylisoxazolyl | Cl |
| 114 (a-e) | 3,5-dimethylisoxazolyl | F |
| 115 (a-e) | 4-(N-morpholinylsulfonyl)phenyl | Cl |
| 116 (a-e) | 4-(N-morpholinylsulfonyl)phenyl | F |
| 117 (a-e) | 3-F-benzyl | Cl |
| 118 (a-e) | 3-F-benzyl | F |

TABLE 5a-continued

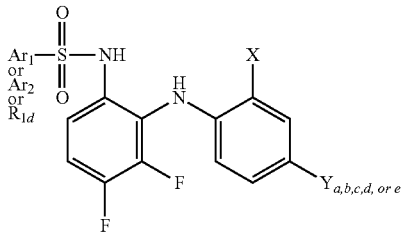

$Y_a$ = SCH$_3$; $Y_b$ = Br; $Y_c$ = I; $Y_d$ = Cl; $Y_e$ = CH$_3$

| Compound # | G = R$_{1d}$, Ar$_1$, or Ar$_2$ | X |
|---|---|---|
| 119 (a-e) | 4-F-benzyl | Cl |
| 120 (a-e) | 4-F-benzyl | F |
| 121 (a-e) | 3-F-phenyl-ethyl | Cl |
| 122 (a-e) | 3-F-phenyl-ethyl | F |
| 123 (a-e) | 4-F-phenyl-ethyl | Cl |
| 124 (a-e) | 4-F-phenyl-ethyl | F |
| 125 (a-e) | 8-quinolinyl | Cl |
| 126 (a-e) | 8-quinolinyl | F |
| 127 (a-e) | 2-thienyl | Cl |
| 128 (a-e) | 2-thienyl | F |
| 129 (a-e) | 2,3-di-Cl-thien-5-yl | Cl |
| 130 (a-e) | 2,3-di-Cl-thien-5-yl | F |
| 131 (a-e) | 1,3,5 trimethyl-1H-pyrazolyl | Cl |
| 132 (a-e) | 1,3,5 trimethyl-1H-pyrazolyl | F |
| 133 (a-e) | 1,3-dimethyl-5-Cl-1H-pyrazolyl | Cl |
| 134 (a-e) | 1,3-dimethyl-5-Cl-1H-pyrazolyl | F |
| 135 (a-e) | 1-methyl-3CF$_3$-1H-pyrazol-4-yl | Cl |
| 136 (a-e) | 1-methyl-3CF$_3$-1H-pyrazol-4-yl | F |
| 137 (a-e) | 2-acetamido-4-methyl-thiazol-5-yl | Cl |
| 138 (a-e) | 2-acetamido-4-methyl-thiazol-5-yl | F |
| 139 (a-e) | 2,4-dimethyl-thiazol-5-yl | Cl |
| 140 (a-e) | 2,4-dimethyl-thiazol-5-yl | F |
| 141 (a-e) | 1,2-dimethyl-1H-imidazol-4-yl | Cl |
| 142 (a-e) | 1,2-dimethyl-1H-imidazol-4-yl | F |

Table 5b shows embodiments of this invention which are compounds of formula I, where G is Ar$_1$, Ar$_2$ or R$_{1d}$, and where R$^0$ is H, Z is F and G and X are defined in the table. Each line in the table corresponds to five species ($Y_a$, $Y_b$, $Y_c$, $Y_d$ and $Y_e$) which differ only at position Y, where $Y_a$=phenyl; $Y_b$=3-substituted phenyl; $Y_c$=3-pyridyl; $Y_d$=4-pyridyl; $Y_e$=3-pyrazolyl.

TABLE 5b

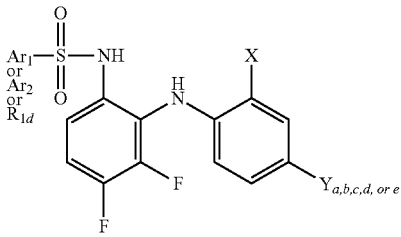

$Y_a$ = phenyl; $Y_b$ = 3-substituted phenyl; $Y_c$ = 3-pyridyl; $Y_d$ = 4-pyridyl; $Y_e$ = 3-pyrazolyl

| Compound # | G = R$_{1d}$, Ar$_1$, or Ar$_2$ | X |
|---|---|---|
| 1 (a-e) | phenyl | Cl |
| 2 (a-e) | phenyl | F |
| 3 (a-e) | 2-F-phenyl | Cl |
| 4 (a-e) | 2-F-phenyl | F |
| 5 (a-e) | 3-F-phenyl | Cl |
| 6 (a-e) | 3-F-phenyl | F |
| 7 (a-e) | 4-F-phenyl | Cl |
| 8 (a-e) | 4-F-phenyl | F |

TABLE 5b-continued

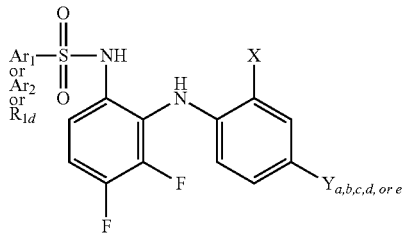

$Y_a$ = phenyl; $Y_b$ = 3-substituted phenyl; $Y_c$ = 3-pyridyl; $Y_d$ = 4-pyridyl; $Y_e$ = 3-pyrazolyl

| Compound # | G = R$_{1d}$, Ar$_1$, or Ar$_2$ | X |
|---|---|---|
| 9 (a-e) | 2,4-di-F-phenyl | Cl |
| 10 (a-e) | 2,4-di-F-phenyl | F |
| 11 (a-e) | 2,5-di-F-phenyl | Cl |
| 12 (a-e) | 2,5-di-F-phenyl | F |
| 13 (a-e) | 2,6-di-F-phenyl | Cl |
| 14 (a-e) | 2,6-di-F-phenyl | F |
| 15 (a-e) | 3,4-di-F-phenyl | Cl |
| 16 (a-e) | 3,4-di-F-phenyl | F |
| 17 (a-e) | 3,5-di-F-phenyl | Cl |
| 18 (a-e) | 3,5-di-F-phenyl | F |
| 19 (a-e) | 2,6-di-F-phenyl | Cl |
| 20 (a-e) | 2,6-di-F-phenyl | F |
| 21 (a-e) | 2,3,4-tri-F-phenyl | Cl |
| 22 (a-e) | 2,3,4-tri-F-phenyl | F |
| 23 (a-e) | 3,4,5-tri-F-phenyl | Cl |
| 24 (a-e) | 3,4,5-tri-F-phenyl | F |
| 25 (a-e) | penta-F-phenyl | Cl |
| 26 (a-e) | penta-F-phenyl | F |
| 27 (a-e) | 3-Cl-4-F-phenyl | Cl |
| 28 (a-e) | 3-Cl-4-F-phenyl | F |
| 29 (a-e) | 2-Cl-4-F-phenyl | Cl |
| 30 (a-e) | 2-Cl-4-F-phenyl | F |
| 31 (a-e) | 2-F-3-Cl-phenyl | Cl |
| 32 (a-e) | 2-F-3-Cl-phenyl | F |
| 33 (a-e) | 2-F-4-Cl-phenyl | Cl |
| 34 (a-e) | 2-F-4-Cl-phenyl | F |
| 35 (a-e) | 2-F-5-Cl-phenyl | Cl |
| 36 (a-e) | 2-F-5-Cl-phenyl | F |
| 37 (a-e) | 3-cyano-4-F-phenyl | Cl |
| 38 (a-e) | 3-cyano-4-F-phenyl | F |
| 39 (a-e) | 2-Cl-phenyl | Cl |
| 40 (a-e) | 2-Cl-phenyl | F |
| 41 (a-e) | 3-Cl-phenyl | Cl |
| 42 (a-e) | 3-Cl-phenyl | F |
| 43 (a-e) | 4-Cl-phenyl | Cl |
| 44 (a-e) | 4-Cl-phenyl | F |
| 45 (a-e) | 2,3-di-Cl-phenyl | Cl |
| 46 (a-e) | 2,3-di-Cl-phenyl | F |
| 47 (a-e) | 2,5-di-Cl-phenyl | Cl |
| 48 (a-e) | 2,5-di-Cl-phenyl | F |
| 49 (a-e) | 2,6-di-Cl-phenyl | Cl |
| 50 (a-e) | 2,6-di-Cl-phenyl | F |
| 51 (a-e) | 3,5-di-Cl-phenyl | Cl |
| 52 (a-e) | 3,5-di-Cl-phenyl | F |
| 53 (a-e) | 2,4-di-Cl-phenyl | Cl |
| 54 (a-e) | 2,4-di-Cl-phenyl | F |
| 55 (a-e) | 3,4-di-Cl-phenyl | Cl |
| 56 (a-e) | 3,4-di-Cl-phenyl | F |
| 57 (a-e) | 2,4,6-tri-Cl-phenyl | Cl |
| 58 (a-e) | 2,4,6-tri-Cl-phenyl | F |
| 59 (a-e) | 2-Cl-4-CF$_3$-phenyl | Cl |
| 60 (a-e) | 2-Cl-4-CF$_3$-phenyl | F |
| 61 (a-e) | 2-CF$_3$-phenyl | Cl |
| 62 (a-e) | 2-CF$_3$-phenyl | F |
| 63 (a-e) | 3-CF$_3$-phenyl | Cl |
| 64 (a-e) | 3-CF$_3$-phenyl | F |
| 65 (a-e) | 4-CF$_3$-phenyl | Cl |
| 66 (a-e) | 4-CF$_3$-phenyl | F |
| 67 (a-e) | 2-CF$_3$O phenyl | Cl |
| 68 (a-e) | 2-CF$_3$O phenyl | F |
| 69 (a-e) | 3-CF$_3$O phenyl | Cl |
| 70 (a-e) | 3-CF$_3$O phenyl | F |

TABLE 5b-continued

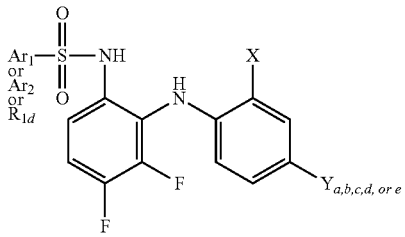

$Y_a$ = phenyl; $Y_b$ = 3-substituted phenyl; $Y_c$ = 3-pyridyl;
$Y_d$ = 4-pyridyl; $Y_e$ = 3-pyrazolyl

| Compound # | G = $R_{1d}$, $Ar_1$, or $Ar_2$ | X |
|---|---|---|
| 71 (a-e) | 4-CF$_3$O phenyl | Cl |
| 72 (a-e) | 4-CF$_3$O phenyl | F |
| 73 (a-e) | 4-CHF$_2$O-phenyl | Cl |
| 74 (a-e) | 4-CHF$_2$O-phenyl | F |
| 75 (a-e) | 2-methyl-5-nitro-phenyl | Cl |
| 76 (a-e) | 2-methyl-5-nitro-phenyl | F |
| 77 (a-e) | 2-cyano-phenyl | Cl |
| 78 (a-e) | 2-cyano-phenyl | F |
| 79 (a-e) | 3-cyano-phenyl | Cl |
| 80 (a-e) | 3-cyano-phenyl | F |
| 81 (a-e) | 4-cyano-phenyl | Cl |
| 82 (a-e) | 4-cyano-phenyl | F |
| 83 (a-e) | 4-methoxy-phenyl | Cl |
| 84 (a-e) | 4-methoxy-phenyl | F |
| 85 (a-e) | 3,4-dimethoxy-phenyl | Cl |
| 86 (a-e) | 3,4-dimethoxy-phenyl | F |
| 87 (a-e) | 3-carbamyl-phenyl | Cl |
| 88 (a-e) | 3-carbamyl-phenyl | F |
| 89 (a-e) | 3-carboxyl-phenyl | Cl |
| 90 (a-e) | 3-carboxyl-phenyl | F |
| 91 (a-e) | 3-(N,N-dimethylcarbamoyl)phenyl | Cl |
| 92 (a-e) | 3-(N,N-dimethylcarbamoyl)phenyl | F |
| 93 (a-e) | 4-methylsulfonyl-phenyl | Cl |
| 94 (a-e) | 4-methylsulfonyl-phenyl | F |
| 95 (a-e) | 3-(1,3,4 oxadiazol-2-yl)phenyl | Cl |
| 96 (a-e) | 3-(1,3,4 oxadiazol-2-yl)phenyl | F |
| 97 (a-e) | 3-(1,3,4 thiadiazol-2-yl)phenyl | Cl |
| 98 (a-e) | 3-(1,3,4 thiadiazol-2-yl)phenyl | F |
| 99 (a-e) | 3-(5-methyl-1,3,4-oxadiazol)phenyl | Cl |
| 100 (a-e) | 3-(5-methyl-1,3,4-oxadiazol)phenyl | F |
| 101 (a-e) | 3-(5-methyl-1,3,4-thiadiazol)phenyl | Cl |
| 102 (a-e) | 3-(5-methyl-1,3,4-thiadiazol)phenyl | F |
| 103 (a-e) | 3-amidinyl-phenyl | Cl |
| 104 (a-e) | 3-amidinyl-phenyl | F |
| 105 (a-e) | 3-(1H-tetrazolyl)phenyl | Cl |
| 106 (a-e) | 3-(lH-tetrazolyl)phenyl | F |
| 107 (a-e) | 4-acetamido-phenyl | Cl |
| 108 (a-e) | 4-acetamido-phenyl | F |
| 109 (a-e) | 3-Cl-4-[(N-morpholinylcarbonyl)amino]phenyl | Cl |
| 110 (a-e) | 3-Cl-4-[(N-morpholinylcarbonyl)amino]phenyl | F |
| 111 (a-e) | 3-Cl-4-[(N-pyrrolidinylcarbonyl)amino]phenyl | Cl |
| 112 (a-e) | 3-Cl-4-[(N-pyrrolidinylcarbonyl)amino]phenyl | F |
| 113 (a-e) | 3,5-dimethylisoxazolyl | Cl |
| 114 (a-e) | 3,5-dimethylisoxazolyl | F |

TABLE 5b-continued

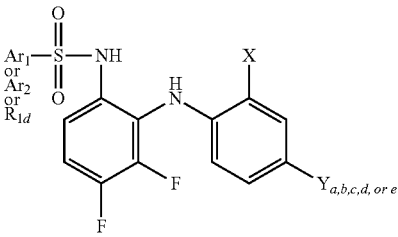

$Y_a$ = phenyl; $Y_b$ = 3-substituted phenyl; $Y_c$ = 3-pyridyl;
$Y_d$ = 4-pyridyl; $Y_e$ = 3-pyrazolyl

| Compound # | G = $R_{1d}$, $Ar_1$, or $Ar_2$ | X |
|---|---|---|
| 115 (a-e) | 4-(N-morpholinylsulfonyl)phenyl | Cl |
| 116 (a-e) | 4-(N-morpholinylsulfonyl)phenyl | F |
| 117 (a-e) | 3-F-benzyl | Cl |
| 118 (a-e) | 3-F-benzyl | F |
| 119 (a-e) | 4-F-benzyl | Cl |
| 120 (a-e) | 4-F-benzyl | F |
| 121 (a-e) | 3-F-phenyl-ethyl | Cl |
| 122 (a-e) | 3-F-phenyl-ethyl | F |
| 123 (a-e) | 4-F-phenyl-ethyl | Cl |
| 124 (a-e) | 4-F-phenyl-ethyl | F |
| 125 (a-e) | 8-quinolinyl | Cl |
| 126 (a-e) | 8-quinolinyl | F |
| 127 (a-e) | 2-thienyl | Cl |
| 128 (a-e) | 2-thienyl | F |
| 129 (a-e) | 2,3-di-Cl-thien-5-yl | Cl |
| 130 (a-e) | 2,3-di-Cl-thien-5-yl | F |
| 131 (a-e) | 1,3,5 trimethyl-1H-pyrazolyl | Cl |
| 132 (a-e) | 1,3,5 trimethyl-1H-pyrazolyl | F |
| 133 (a-e) | 1,3-dimethyl-5-Cl-1H-pyrazolyl | Cl |
| 134 (a-e) | 1,3-dimethyl-5-Cl-1H-pyrazolyl | F |
| 135 (a-e) | 1-methyl-3-CF$_3$-1H-pyrazolyl-4-yl | Cl |
| 136 (a-e) | 1-methyl-3-CF$_3$-1H-pyrazolyl-4-yl | F |
| 137 (a-e) | 2-acetamido-4-methyl-thiazol-5-yl | Cl |
| 138 (a-e) | 2-acetamido-4-methyl-thiazol-5-yl | F |
| 139 (a-e) | 2,4-dimethyl-thiazolyl-5-yl | Cl |
| 140 (a-e) | 2,4-dimethyl-thiazolyl-5-yl | F |
| 141 (a-e) | 1,2-dimethyl-1H-imidazol-4-yl | Cl |
| 142 (a-e) | 1,2-dimethyl-1H-imidazol-4-yl | F |
| 143 (a-e) | 1-(2-hydroxyethyl)cyclopropyl | F |
| 144 (a-e) | 1-(3-hydroxypropyl)cyclopropyl | F |
| 145 (a-e) | 1-(2,3-dihydroxypropyl)cyclopropyl | F |
| 146 (a-e) | 1-(3,4-dihydroxybutyl)cyclopropyl | F |
| 147 (a-e) | 1-(2,3-dihydroxypropyl)cyclobutyl | F |

Synthetic Procedures

In another aspect, methods for synthesizing the compounds described herein are provided. In some embodiments, the compounds described herein can be made by the methods described below. The procedures and examples below are intended to illustrate those methods. Neither the procedures nor the examples should be construed as limiting the invention in any way. Compounds described herein may also be synthesized using standard synthetic techniques known to those of skill in the art or using methods known in the art in combination with methods described herein. In additions, solvents, temperatures and other reaction conditions presented herein may vary according to the practice and knowledge of those of skill in the art.

The starting materials for the synthesis of the compounds as described herein may be obtained from commercial sources, such as Aldrich Chemical Co. (Milwaukee, Wis.), Sigma Chemical Co. (St, Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999) (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. As a guide the following synthetic methods may be utilized.

Formation of Covalent Linkages by Reaction of an Electrophile with a Nucleophile The compounds described herein can be modified using various electrophiles or nucleophiles to form new functional groups or substituents. The table below entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

Examples of Covalent Linkages and Precursors Thereof

| Covalent Linkage Product | Electrophile | Nucleophile |
|---|---|---|
| Carboxamides | Activated esters | Amines/anilines |
| Carboxamides | Acyl azides | Amines/anilines |
| Carboxamides | Acyl halides | Amines/anilines |
| Esters | Acyl halides | Alcohols/phenols |
| Esters | Acyl nitriles | Alcohols/phenols |
| Carboxamides | Acyl nitriles | Amines/anilines |
| Imines | Aldehydes | Amines/anilines |
| Hydrazones | Aldehydes or ketones | Hydrazines |
| Oximes | Aldehydes or ketones | Hydroxylamines |
| Alkyl amines | Alkyl halides | Amines/anilines |
| Esters | Alkyl halides | Carboxylic acids |
| Thioethers | Alkyl halides | Thiols |
| Ethers | Alkyl halides | Alcohols/phenols |
| Thioethers | Alkyl sulfonates | Thiols |
| Esters | Alkyl sulfonates | Carboxylic acids |
| Ethers | Alkyl sulfonates | Alcohols/phenols |
| Esters | Anhydrides | Alcohols/phenols |
| Carboxamides | Anhydrides | Amines/anilines |
| Thiophenols | Aryl halides | Thiols |
| Aryl amines | Aryl halides | Amines |
| Thioethers | Aziridines | Thiols |
| Boronate esters | Boronates | Glycols |
| Carboxamides | Carboxylic acids | Amines/anilines |
| Esters | Carboxylic acids | Alcohols |
| Hydrazines | Hydrazides | Carboxylic acids |
| N-acylureas or Anhydrides | Carbodiimides | Carboxylic acids |
| Esters | Diazoalkanes | Carboxylic acids |

Examples of Covalent Linkages and Precursors Thereof

| Covalent Linkage Product | Electrophile | Nucleophile |
|---|---|---|
| Thioethers | Epoxides | Thiols |
| Thioethers | Haloacetamides | Thiols |
| Ammotriazines | Halotriazines | Amines/anilines |
| Triazinyl ethers | Halotriazines | Alcohols/phenols |
| Amidines | Imido esters | Amines/anilines |
| Ureas | Isocyanates | Amines/anilines |
| Urethanes | Isocyanates | Alcohols/phenols |
| Thioureas | Isothiocyanates | Amines/anilines |
| Thioethers | Maleimides | Thiols |
| Phosphite esters | Phosphoramidites | Alcohols |
| Silyl ethers | Silyl halides | Alcohols |
| Alkyl amines | Sulfonate esters | Amines/anilines |
| Thioethers | Sulfonate esters | Thiols |
| Esters | Sulfonate esters | Carboxylic acids |
| Ethers | Sulfonate esters | Alcohols |
| Sulfonamides | Sulfonyl halides | Amines/anilines |
| Sulfonate esters | Sulfonyl halides | Phenols/alcohols |

Use of Protecting Groups

In the reactions described, it may be necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. In some embodiments, each protective group is removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

109

Protecting or blocking groups may be selected from:

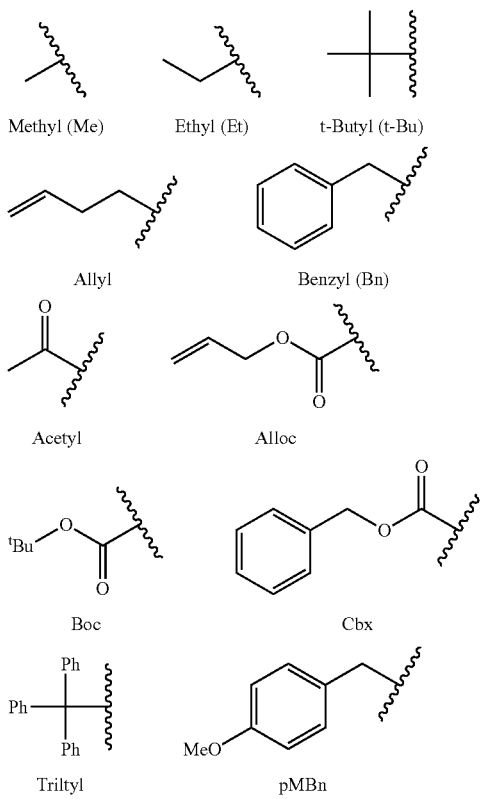

110

-continued

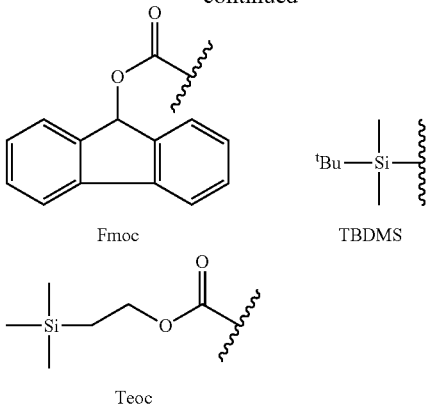

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference in their entirety.

Making Compounds of Formula I

Compounds of this invention can be made by a variety of methods. The procedures below are intended to illustrate those methods, and the examples given are intended to illustrate the scope of this invention. Neither the methods not the examples should be construed as limiting the invention in any way.

I. The Preparation of Compound of Formula VI is Outlined Below

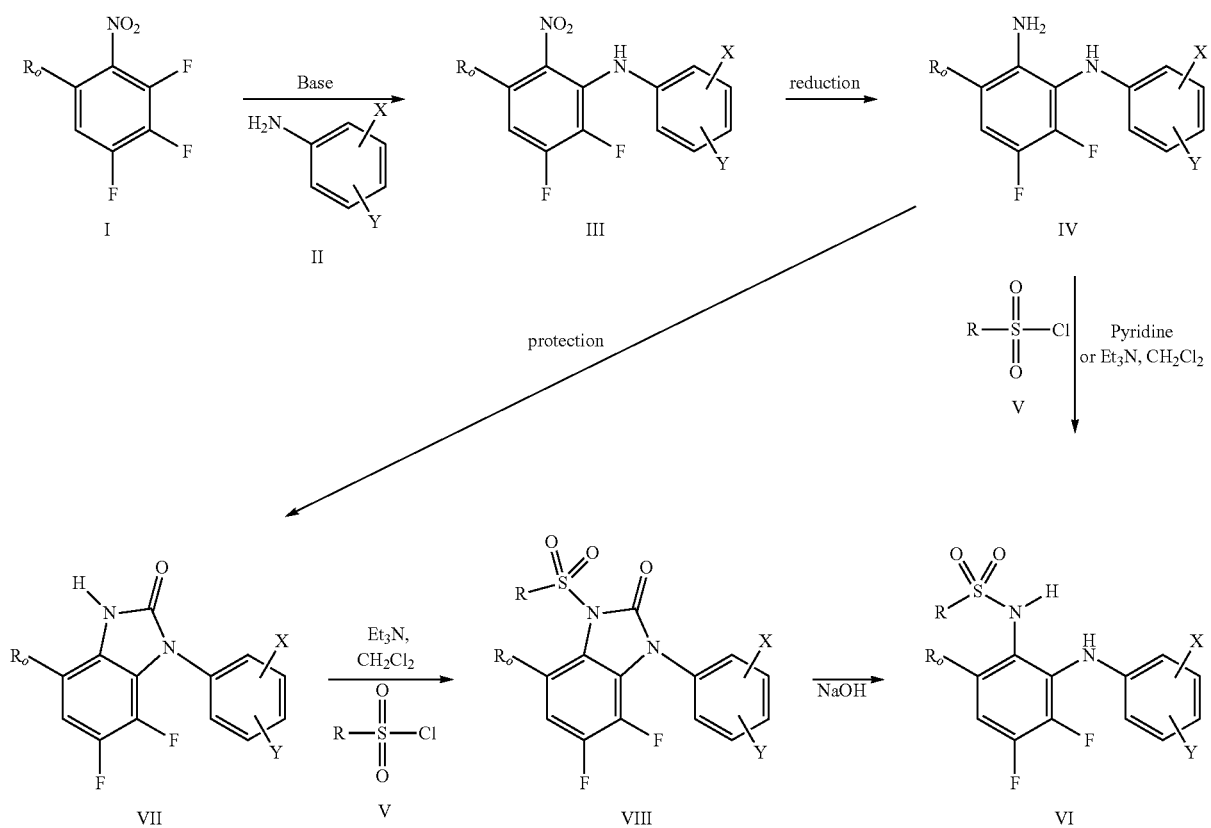

Scheme I above illustrates a method for making the sulfonamide derivatives of formula VI. 1,2 Diamine derivative (formula IV) can be easily prepared in two steps from the desired nitro derivatives (formula I). Compounds of formula IV can be reacted with the sulfonyl chloride derivatives (formula V, see next scheme) to form the desired sulfonamide. Alternatively, the 1,2 diamine derivatives IV can be protected to for an imidazolidone (formula VII), before being reacted with the corresponding sulfonyl chloride. Deprotection of the 1,2 diamine VIII under basic conditions provided the desired material VI.

II. The General Route to Synthesis Compound of General Formula V is Outlined Below

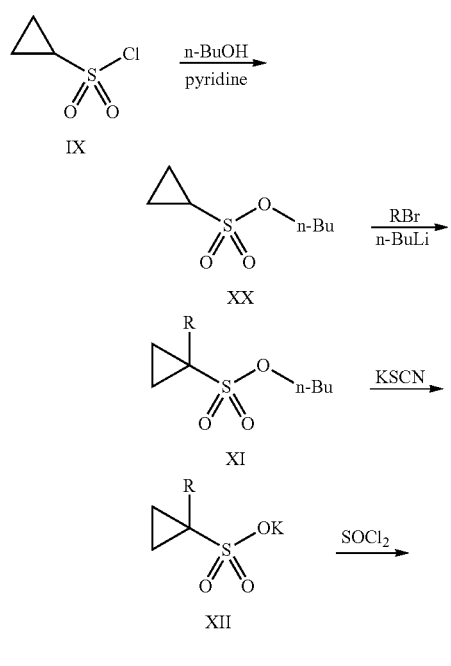

Scheme II above shows one example of the preparation of complex sulfonyl chloride. Compound XX can be synthesized from IX, alkylated, and converted to the potassium salt XII. Treatment of the salt with $SOCl_2$ or $POCl_3$ affords the desired compounds. Other more specific procedures to prepare unique sulfonyl chloride derivatives are reported in the experimental section.

III. The General Route to Synthesis Compound of General Formula XIII is Outlines Scheme 3.

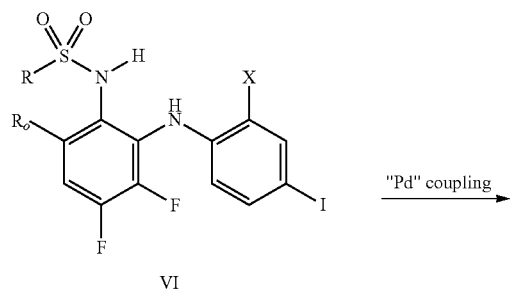

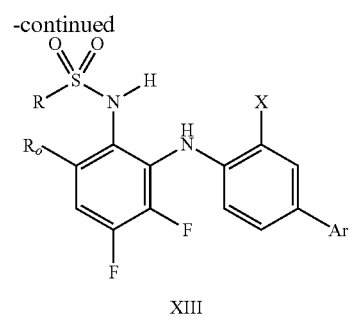

Scheme III above illustrates the preparation of sulfonamide derivatives of general formula XIII. For example, these compounds can be easily obtained by reacting the compound VI with a boronic acid using a palladium catalyst under Suzuki conditions.

IV. The General Route to Synthesis Compound of General Formula XIII is Outlines Scheme 4.

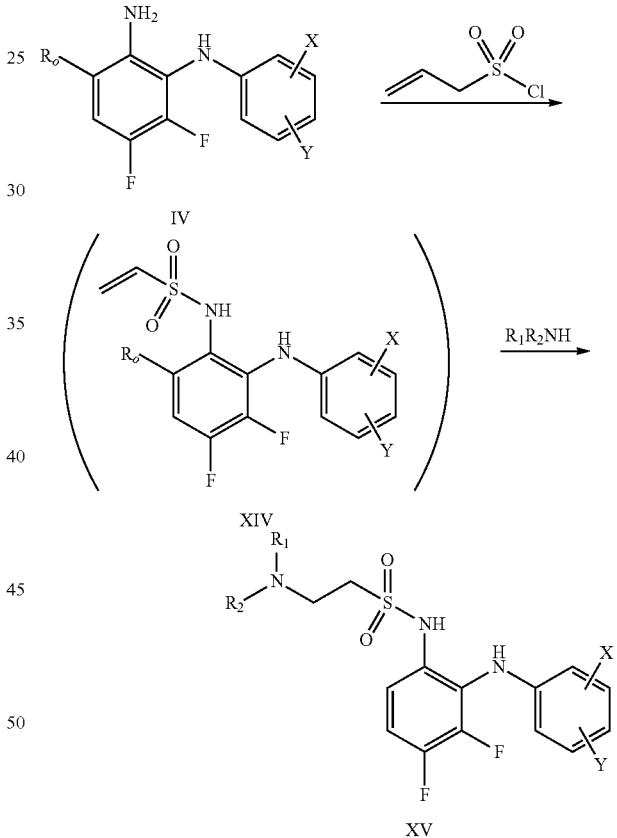

Scheme IV above illustrates the preparation of sulfonamide derivatives of general formula XV. The vinyl sulfonamide (XIV) is reacted with amines to form derivatives of general formulas XV.

Further Forms of Compounds of Formula I

Isomers of Compounds of Formula I

The compounds described herein may exist as geometric isomers. The compounds described herein may possess one or more double bonds. The compounds presented herein include all cis, trans, syn, anti, entgegen (E), and zusammen (Z) isomers as well as the corresponding mixtures thereof. In some situations, compounds may exist as tautomers. The compounds described herein include all possible tautomers within the formulas described herein. The compounds described herein may possess one or more chiral centers and each center may exist in the R or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion may also be useful for the applications described herein. The compounds described herein can be prepared as their individual stereoisomers by reacting a racemic mixture of the compound with an optically active resolving agent to form a pair of diastereoisomeric compounds, separating the diastercomers and recovering the optically pure enantiomers. Resolution of enantiomers can be carried out using covalent diastereomeric derivatives of the compounds described herein, or dissociable complexes may be used (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chiral chromatography, or separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981, herein incorporated by reference in its entirety.

Labeled Compounds of Formula I

Also described herein are isotopically-labeled compounds of formula I and methods of treating disorders. For example, the invention provides for methods of treating diseases, by administering isotopically-labeled compounds of formula I. The isotopically-labeled compounds of formula I can be administered as pharmaceutical compositions. Thus, compounds of formula I also include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, pharmaceutically acceptable salts, thereof which contain the aforementioned isotopes and/or other isotopes of other atoms are within the scope of this invention. Certain isotopically-labeled compounds of formula I, for example those into which radioactive isotopes such as $^3$H and $^{14}$C are incorporated, are useful in drug and/or substrate tissue distribution assays. Tritiated, i.e., $^3$H and carbon-14, i.e., $^{14}$C, isotopes are often easily prepared and detectabilited. Further, substitution with heavier isotopes such as deuterium, i.e., $^2$H, can afford certain therapeutic advantages resulting from greater metabolic stability, for example increased in vivo half-life or reduced dosage requirements and, hence, may be desirable in some circumstances. Isotopically labeled compounds and pharmaceutically acceptable salts thereof can generally be prepared by carrying out procedures described herein, by substituting a readily available isotopically labeled reagent for a non-isotopically labeled reagent.

The compounds described herein may be labeled by other means, including, but not limited to, the use of chromophores or fluorescent moieties, bioluminescent labels, or chemiluminescent labels.

Pharmaceutically Acceptable Salts of Compounds of Formula.

Also described herein are pharmaceutically acceptable salts of compounds of formula I and methods of treating disorders. For example, the invention provides for methods of treating diseases, by administering pharmaceutically acceptable salts of compounds of formula I. The pharmaceutically acceptable salts of compounds of formula I can be administered as pharmaceutical compositions.

Thus, the compounds described herein can be prepared as pharmaceutically acceptable salts formed when an acidic proton present in the parent compound either is replaced by a metal ion, for example an alkali metal ion, an alkaline earth ion, or an aluminum ion; or coordinates with an organic base. Base addition salts can also be prepared by reacting the free acid form of the compounds described herein with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like. In addition, the salt forms of the disclosed compounds can be prepared using salts of the starting materials or intermediates.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Solvates of Compounds of Formula I

Also described herein are solvates of compounds of formula I and methods of treating disorders. For example, the invention provides for methods of treating diseases, by administering solvates of compounds of formula I. The solvates of compounds of formula I can be administered as pharmaceutical compositions.

Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs of Compounds of Formula I

Also described herein are polymorphs of compounds of formula I and methods of treating disorders. For example, the invention provides for methods of treating diseases, by administering polymorphs of compounds of formula I. The polymorphs of compounds of formula I can be administered as pharmaceutical compositions.

Thus, the compounds described herein include all their crystalline forms, known as polymorphs. Polymorphs include the different crystal packing arrangements of the same elemental composition of a compound. Polymorphs may have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Crystalline Polymorph Form of N—(S)-(3,4-difluoro-2-(2-fluoro-4-iodophenylamino)-6-methoxyphenyl)-1-(2,3-dihydroxypropyl)cyclopropane-1-sulfonamide The invention also relates to a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide:

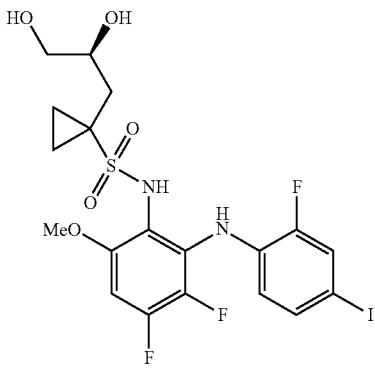 [SMILES: COc1cc(F)c(F)c(Nc2ccc(I)cc2F)c1NS(=O)(=O)C1(C[C@H](O)CO)CC1]

that exhibits a specific powder x-ray diffraction pattern. In some embodiments, the powder x-ray diffraction pattern contains at least about 50% of the peaks shown in FIG. 5. In some embodiments, the powder x-ray diffraction pattern contains at least about 70% of the peaks shown in FIG. 5. In some embodiments, the powder x-ray diffraction pattern contains at least about 90% of the peaks shown in FIG. 5. In some embodiments, the powder x-ray diffraction pattern is substantially the same the powder x-ray diffraction pattern shown in FIG. 5.

The invention also relates to a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide that exhibits a specific differential scanning calorimetry pattern. In some embodiments, the specific differential scanning calorimetry patern is substantially the same as the differential scanning calorimetry pattern shown in FIG. 6. In some embodiments the crystalline polymorph form A has a melting point onset as determined by differential scanning calorimetry at about 143° C.

The invention also relates to a polymorphic form of N—(S)-(3,4-difluoro-2-(2-fluoro-4-iodophenylamino)-6-methoxyphenyl)-1-(2,3-dihydroxypropyl)cyclopropane-1-sulfonamide made by a method comprising the step of crystallizing amorphous N—(S)-(3,4-difluoro-2-(2-fluoro-4-iodophenylamino)-6-methoxyphenyl)-1-(2,3-dihydroxypropyl) cyclopropane-1-sulfonamide from a solvent. The invention also relates to a polymorphic form of N—(S)-(3,4-difluoro-2-(2-fluoro-4-iodophenylamino)-6-methoxyphenyl)-1-(2,3-dihydroxypropyl)cyclopropane-1-sulfonamide made by a method comprising the step of crystallizing amorphous N—(S)-(3,4-difluoro-2-(2-fluoro-4-iodophenylamino)-6-methoxyphenyl)-1-(2,3-dihydroxypropyl)cyclopropane-1-sulfonamide from a mixture of hexane and ethyl acetate.

The invention also relates to pharmaceutical compositions comprising an effective amount of crystalline polymorph form A of N—(S)-(3,4-difluoro-2-(2-fluoro-4-iodophenylamino)-6-methoxyphenyl)-1-(2,3-dihydroxypropyl) cyclopropane-1-sulfonamide and a pharmaceutically acceptable carrier or vehicle. Other aspects of the invention relate to a pharmaceutical composition comprising the crystalline polymorph form A and at least one excipient or carrier.

The crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide is useful for treating or preventing cancer or an inflammatory disease. The invention further relates to methods for treating or preventing cancer or an inflammatory disease, comprising administering an effective amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide to a subject in need thereof. Yet other aspects of the invention relate to methods for the treatment or prophylaxis of an inflammatory disease comprising administering to a subject in need thereof an effective amount of the crystalline polymorph. Further aspects of the invention relate to methods for the treatment or prophylaxis of a proliferative disease comprising administering to a subject in need thereof an effective amount of the crystalline polymorph.

Prodrugs of Compounds of Formula I

Also described herein are prodrugs of compounds of formula I and methods of treating disorders. For example, the invention provides for methods of treating diseases, by administering prodrugs of compounds of formula I. The prodrugs of compounds of formula I can be administered as pharmaceutical compositions.

Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyamino acid) bonded to an acid group where the peptide is metabolized to reveal the active moiety.

Prodrugs may be designed as reversible drug derivatives, for use as modifiers to enhance drug transport to site-specific tissues. The design of prodrugs to date has been to increase the effective water solubility of the therapeutic compound for targeting to regions where water is the principal solvent. See, e.g., Fedorak et al., *Am. J. Physiol.*, 269:0210-218 (1995); McLoed et al., *Gastroenterol*, 106:405-413 (1994); Hochhaus et al., *Biomed. Chrom.*, 6:283-286 (1992); 3. Larsen and H. Bundgaard, *Int. J. Pharmaceutics*, 37, 87 (1987); 3. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein in their entirety.

Additionally, prodrug derivatives of compounds described herein can be prepared by methods known to those of ordinary skill in the art (e.g., for further details see Saulnier et al., (1994), Bioorganic and Medicinal Chemistry Letters, Vol. 4, p. 1985). By way of example only, appropriate prodrugs can be prepared by reacting a non-derivatized compound of formula I with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds may be a prodrug for another derivative or active compound.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. Additional types of prodrugs are also encompassed.

Compounds of formula I having free amino, amido, hydroxy or carboxylic groups can be converted into prodrugs. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews* 1996, 19, 115. Carbamate prodrugs of hydroxy and amino groups are also included, as are carbonate prodrugs, sulfonate esters and sulfate esters of hydroxy groups.

Derivatization of hydroxy groups as (acyloxy) methyl and (acyloxy) ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides.

All of these prodrug moieties may incorporate groups including but not limited to ether, amine and carboxylic acid functionalities.

Sites on the aromatic ring portions of compounds of formula I may be susceptible to various metabolic reactions, therefore incorporation of appropriate substituents on the aromatic ring structures, can reduce, minimize or eliminate this metabolic pathway.

Pharmaceutical Compositions

Described herein are pharmaceutical compositions. In some embodiments, the pharmaceutical compositions comprise an effective amount of a compound formula I, or a pharmaceutically acceptable salt, thereof. In some embodiments, the pharmaceutical compositions comprise an effective amount of a compound formula I, or a pharmaceutically acceptable salt, solvate, polymorph, ester, amide, tautomer, prodrug, hydrate, or derivative thereof and at least one pharmaceutically acceptable carrier. In some embodiments the pharmaceutical compositions are for the treatment of disorders. In some embodiments the pharmaceutical compositions are for the treatment of disorders in a mammal. In some embodiments the pharmaceutical compositions are for the treatment of disorders in a human.

In further aspects, the present invention is directed to a pharmaceutical composition comprising a compound of formula I or a pharmaceutically acceptable salt, solvate, polymorph, ester, amide, tautomer or prodrug thereof. In some embodiments, the pharmaceutical compositions further comprise a pharmaceutically acceptable carrier. Such compositions may contain adjuvants, excipients, and preservatives, agents for delaying absorption, fillers, binders, adsorbents, buffers, disintegrating agents, solubilizing agents, other carriers, and other inert ingredients. Methods of formulation of such compositions are well-known in the art.

In some embodiments, the pharmaceutical composition is in a form suitable for oral administration. In further or additional embodiments, the pharmaceutical composition is in the form of a tablet, capsule, pill, powder, sustained release formulation, solution, suspension, for parenteral injection as a sterile solution, suspension or emulsion, for topical administration as an ointment or cream or for rectal administration as a suppository.

In further or additional embodiments, the pharmaceutical composition is in unit dosage forms suitable for single administration of precise dosages. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.002 to about 6 g/day. In further or additional embodiments the amount of compound of formula I is about 0.005 to about 5 g/day. In further or additional embodiments the amount of compound of formula I is about 0.01 to about 5 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the pharmaceutical composition is for administration to a mammal. In further or additional embodiments, the mammal is human.

In further or additional embodiments, the pharmaceutical composition further comprises a pharmaceutical carrier, excipient and/or adjuvant. In further or additional embodiments, the pharmaceutical composition further comprises at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; anti-neoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is taxol, bortezomib or both. In further or additional embodiments, the pharmaceutical composition is administered in combination with an additional therapy. In further or additional embodiments, the additional therapy is radiation therapy, chemotherapy, surgery, or any combination thereof. In further or additional embodiments, the pharmaceutical composition comprises a pharmaceutically acceptable salt of a compound of formula I.

The invention also relates to a composition comprising

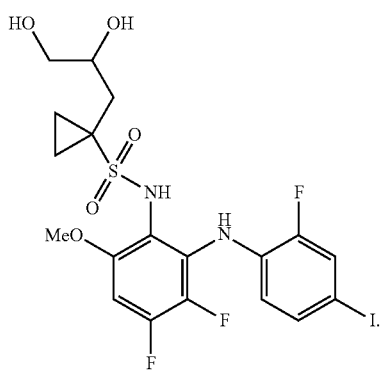

In some embodiments, the 2-OH carbon on the compound is in the R configuration. In some embodiments, composition is substantially free of the S-isomer of the compound. In some embodiments, the compound contains less than 10% of the S-isomer of the compound. In some embodiments, the compound contains less than 5% of the S-isomer of the compound. In some embodiments, the compound contains less than 1% of the S-isomer of the compound. In some embodiments, the compound is in the R configuration.

In some embodiments, the 2-OH carbon on the compound is in the S configuration. In some embodiments, composition is substantially free of the R-isomer of the compound. In some embodiments, the compound contains less than 10% of the R-isomer of the compound. In some embodiments, the compound contains less than 5% of the R-isomer of the compound. In some embodiments, the compound contains less than 1% of the R-isomer of the compound. In some embodiments, the compound is in the S configuration.

Figure 5:
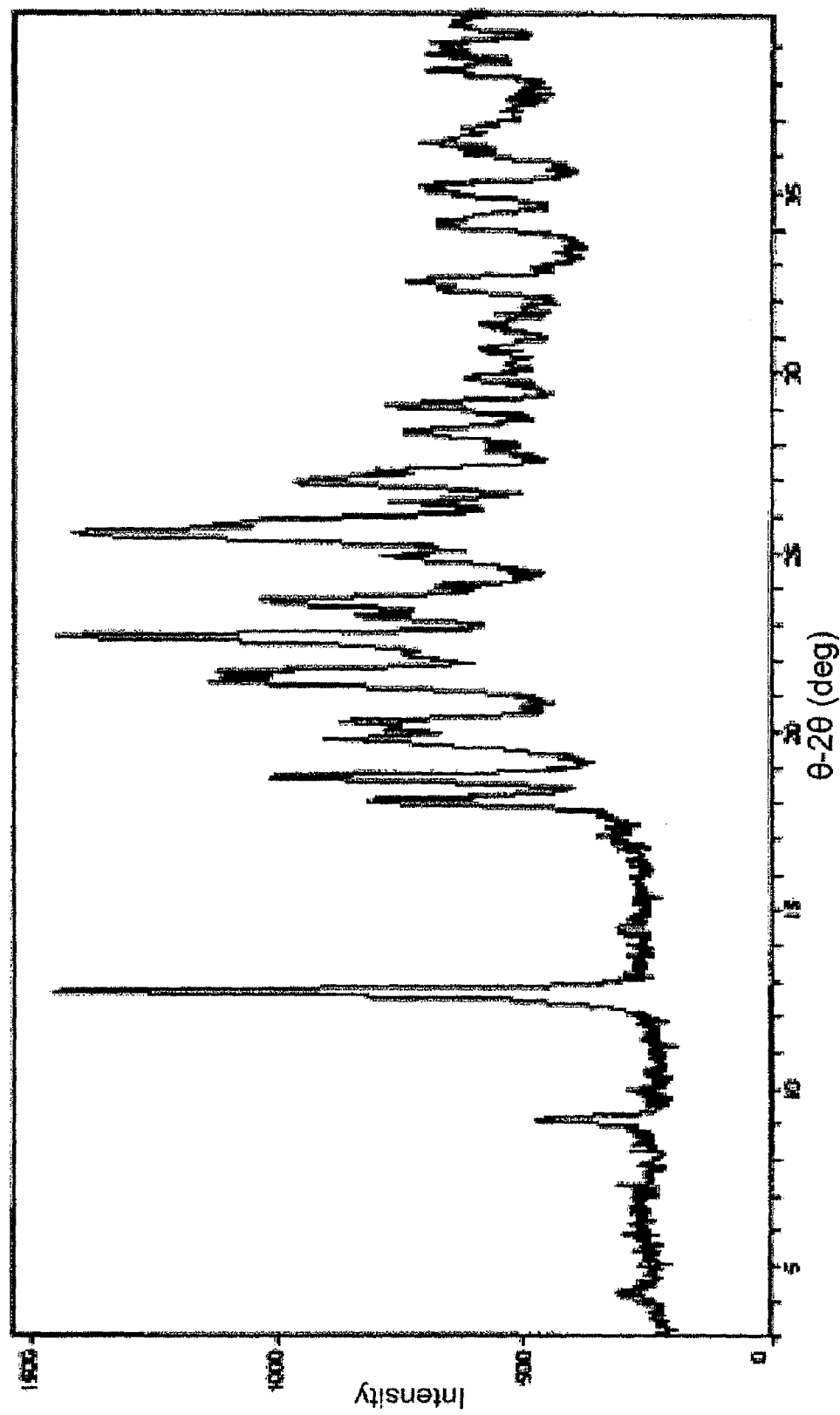
FIG. 5 is a graph of a powder x-ray diffraction (PXRD) pattern of N—(S)-(3,4-difluoro-2-(2-fluoro-4-iodophenylamino)-6-methoxyphenyl)-1-(2,3-dihydroxypropyl)cyclopropane-1-sulfonamide Form A, generated using a Inel XRG-3000 diffractometer. The graph plots the intensity of the peaks as defined by counts per second versus the diffraction angle 2θ in degrees.

In some embodiments, the composition contains at least about 50% of a compound which exhibits a powder x-ray diffraction pattern comprising at least 50% of the peaks identified in the powder x-ray diffraction pattern shown in FIG. 5. In some embodiments, the powder x-ray diffraction pattern comprises at least 70% of the peaks identified in the powder x-ray diffraction pattern shown in FIG. 5. In some embodiments, the powder x-ray diffraction pattern comprises at least 90% of the peaks identified in the In some embodiments, the powder x-ray diffraction pattern substantially the same as the powder x-ray diffraction pattern shown in FIG. 5.

In some embodiments, the composition contains at least about 75% of a compound which exhibits a powder x-ray diffraction pattern comprising at least 50% of the peaks identified in the powder x-ray diffraction pattern shown in FIG. 5. In some embodiments, the powder x-ray diffraction pattern comprises at least 70% of the peaks identified in the powder x-ray diffraction pattern shown in FIG. 5. In some embodiments, the powder x-ray diffraction pattern comprises at least 90% of the peaks identified in the In some embodiments, the powder x-ray diffraction pattern substantially the same as the powder x-ray diffraction pattern shown in FIG. 5.

In some embodiments, the composition contains at least about 90% of a compound which exhibits a powder x-ray diffraction pattern comprising at least 50% of the peaks identified in the powder x-ray diffraction pattern shown in FIG. 5. In some embodiments, the powder x-ray diffraction pattern comprises at least 70% of the peaks identified in the powder x-ray diffraction pattern shown in FIG. 5. In some embodiments, the powder x-ray diffraction pattern comprises at least 90% of the peaks identified in the In some embodiments, the powder x-ray diffraction pattern substantially the same as the powder x-ray diffraction pattern shown in FIG. 5.

In some embodiments, substantially all of the compound in the composition exhibits a powder x-ray diffraction pattern comprising at least 50% of the peaks identified in the powder x-ray diffraction pattern shown in FIG. 5. In some embodiments, the powder x-ray diffraction pattern comprises at least 70% of the peaks identified in the powder x-ray diffraction pattern shown in FIG. 5. In some embodiments, the powder x-ray diffraction pattern comprises at least 90% of the peaks identified in the In some embodiments, the powder x-ray diffraction pattern substantially the same as the powder x-ray diffraction pattern shown in FIG. 5.

In some embodiments, the crystalline polymorph present in the composition has a melting point onset as determined by differential scanning calorimetry at about 143° C. In some embodiments, the crystalline polymorph is substantially free of water. In some embodiments, the crystalline polymorph is substantially free of solvent.

Figure 6:
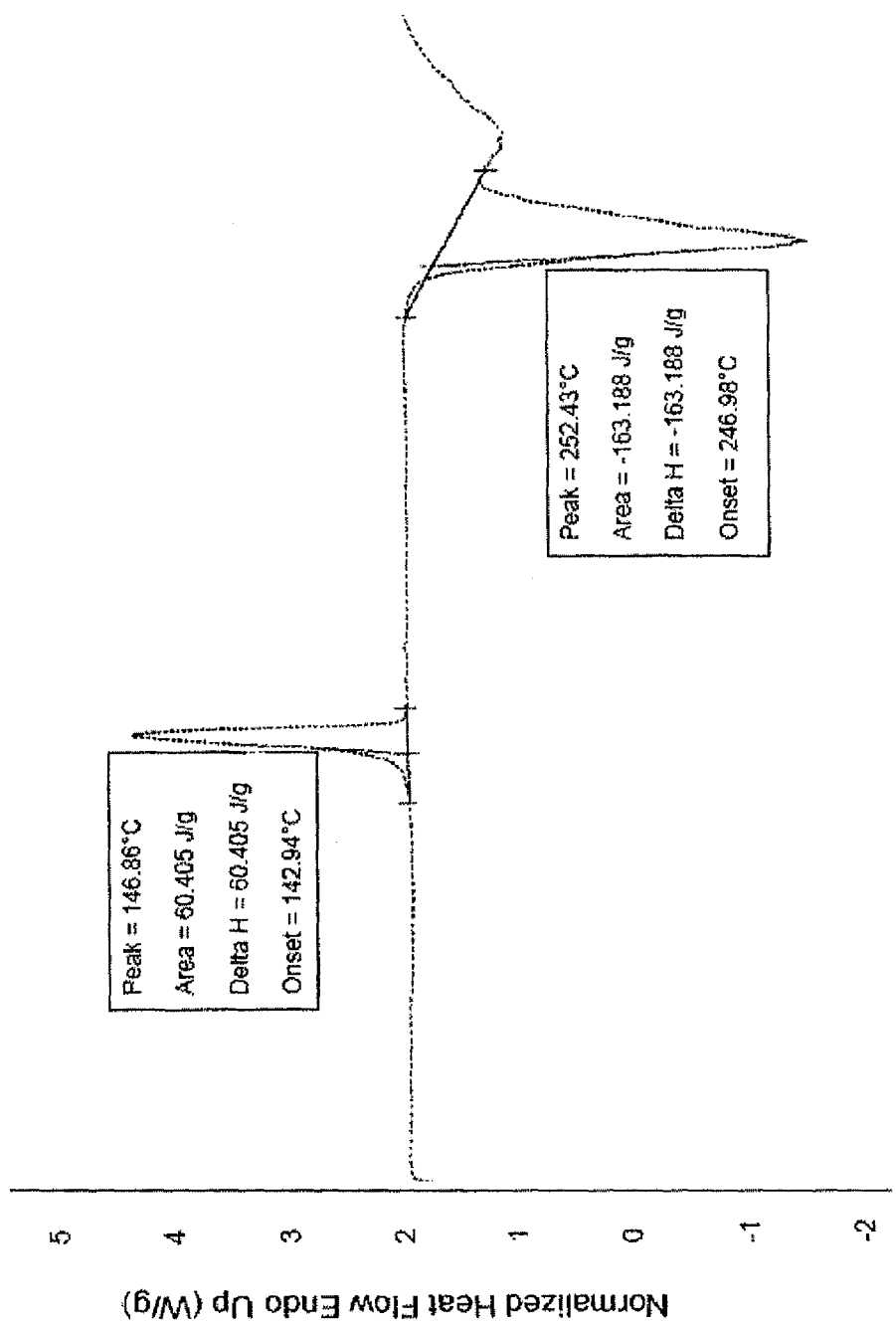
FIG. 6 is a graph of a modulated Differential Scanning calorimetry (DSC) thermogram of N—(S)-(3,4-difluoro-2-(2-fluoro-4-iodophenylamino)-6-methoxyphenyl)-1-(2,3-dihydroxypropyl)cyclopropane-1-sulfonamide Form A generated using a TA Instruments differential scanning calorimeter Q1000. The graph plots the normalized heat flow in units of Watts/gram (W/g) versus the measured sample temperature in °C.

In some embodiments, the composition contains at least about 50% of a compound which exhibits a differential scanning calorimetry pattern substantially the same as the differential scanning calorimetry pattern shown in FIG. 6. In some embodiments, the crystalline polymorph has a melting point onset as determined by differential scanning calorimetry at about 143° C. In some embodiments, the crystalline polymorph is substantially free of water. In some embodiments, the crystalline polymorph is substantially free of solvent.

In some embodiments, the composition contains at least about 75% of a compound which exhibits a differential scanning calorimetry pattern substantially the same as the differential scanning calorimetry pattern shown in FIG. 6. In some embodiments, the crystalline polymorph has a melting point onset as determined by differential scanning calorimetry at about 143° C. In some embodiments, the crystalline polymorph is substantially free of water. In some embodiments, the crystalline polymorph is substantially free of solvent.

In some embodiments, the composition contains at least about 90% of a compound which exhibits a differential scanning calorimetry pattern substantially the same as the differential scanning calorimetry pattern shown in FIG. 6. In some embodiments, the crystalline polymorph has a melting point onset as determined by differential scanning calorimetry at about 143° C. In some embodiments, the crystalline polymorph is substantially free of water. In some embodiments, the crystalline polymorph is substantially free of solvent.

In some embodiments, substantially all the compound in the composition exhibits a differential scanning calorimetry pattern substantially the same as the differential scanning calorimetry pattern shown in FIG. 6. In some embodiments, the crystalline polymorph has a melting point onset as determined by differential scanning calorimetry at about 143° C. In some embodiments, the crystalline polymorph is substantially free of water. In some embodiments, the crystalline polymorph is substantially free of solvent.

In some embodiments, the polymorphic form of N-(3,4-difluoro-2-(2-fluoro-4-iodophenylamino)-6-methoxyphenyl)-1-(2,3-dihydroxypropyl)cyclopropane-1-sulfonamide made by a method comprising the step of crystallizing amorphous N-(3,4-difluoro-2-(2-fluoro-4-iodophenylamino)-6-methoxyphenyl)-1-(2,3-dihydroxypropyl) cyclopropane-1-sulfonamide. In some embodiments, the crystallization step comprises crystallizing from a mixture of ethyl acetate and heptane, for example, a mixture of ethyl acetate and heptane is in a ratio of from about 1-4 parts ethyl acetate to about 2-10 parts heptane or more specifically, a ratio of from about 2 parts ethyl acetate to about 5 parts heptane.

In some embodiments, the compound is formulated for the immediate release of the compound. In some embodiments, the compound is formulated for the sustained release of the compound. In other embodiments, the compound is formulated for the extended release of the compound.

In some embodiments, the composition is in a tablet dosage form. In other embodiments, the composition is in a capsule dosage form. The composition can be made into a capsule or tablet dosage form and a wide range of alternative compositions and manufacturing approaches can be used, References: (1) Remington, The Science and Practice of Pharmacy, 20$^{th}$ Edition, 2000, (2) Pharmaceutical Dosage Forms Tablets Volumes 1-3, 1989 and (3) Modern Pharmaceuticals 4$^{th}$ Edition, 2002. A range of manufacturing approaches can be employed including dry blending, wet granulation, roller compaction, extrusion, spheronization, coating, and spray drying processes. Soft gel formulation and manufacturing approaches are also possible.

In some embodiments, the composition includes a filler or diluent. In various embodiments, the filler or diluent is selected from microcrystalline cellulose, silicified microcrystalline cellulose, lactose, mannitol, compressible sugar, calcium phosphate, calcium sulfate, calcium carbonate, calcium silicate and starch. In other embodiments, the filler or diluent is microcrystalline cellulose.

In some embodiments, the composition includes a disintegrant. In various embodiments, the disintegrant is selected from croscarmellose sodium, sodium starch glycolate, crospovidone, methylcellulose, alginic acid, sodium alginate, starch derivatives, betonite and veegum. In some embodiment, the disintegrant is croscarmellose sodium.

In some embodiments, the composition includes a lubricant. In various embodiments, the lubricant is selected from magnesium stearate, metallic stearates, talc, sodium stearyl fumarate and stearic acid. In some embodiments, the lubricant is magnesium stearate.

In some embodiments, the composition includes a wetting agent or surfactant. In various embodiments, the wetting agent or surfactant is selected from sodium lauryl sulfate, glycerol, sorbitan oleates, sorbitan stearates, polyoxyethylenated sorbitan laurate, palmitate, stearate, oleate or hexaolate, polyoxyethylene stearyl alcohol and sorbitan monolaurate. In some embodiments, the wetting agent or surfactant is sodium lauryl sulfate.

Additional excipients such as glidants, flavors, and colorants can also be added. Additional alternative excipients can be found in The Handbook of Pharmaceutical Excipients, 5$^{th}$ Edition, 2005 and the FDA Inactive Ingredient database.

The invention also relates to a composition comprising:
about 1 mg of a compound of structure:

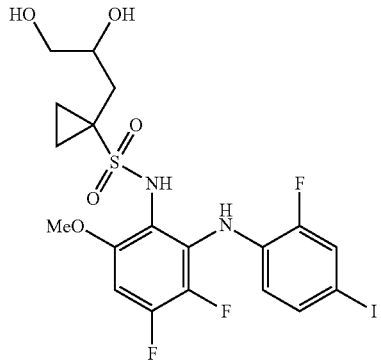 [SMILES: COc1cc(F)c(F)c(Nc2ccc(I)cc2F)c1NS(=O)(=O)C1(CC(O)CO)CC1]

(as defined in any of the above embodiments);
about 222.2 mg of microcrystalline cellulose;
about 12.0 mg of croscarmellose sodium;
about 2.4 mg of sodium lauryl sulfate; and
about 2.4 mg of magnesium stearate.
The invention also relates to a composition comprising:
about 10 mg of a compound of structure:

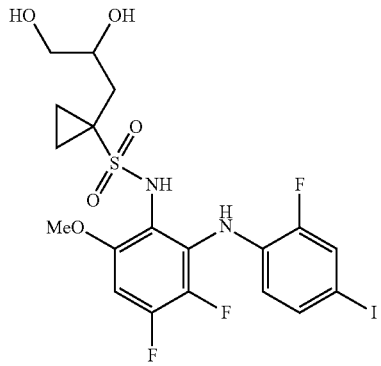 [SMILES: COc1cc(F)c(F)c(Nc2ccc(I)cc2F)c1NS(=O)(=O)C1(CC(O)CO)CC1]

(as defined in any of the above embodiments);
about 213.2 mg of microcrystalline cellulose;
about 12.0 mg of croscarmellose sodium;
about 2.4 mg of sodium lauryl sulfate; and
about 2.4 mg of magnesium stearate.

The invention also relates to a composition comprising: about 20 mg of a compound of structure:

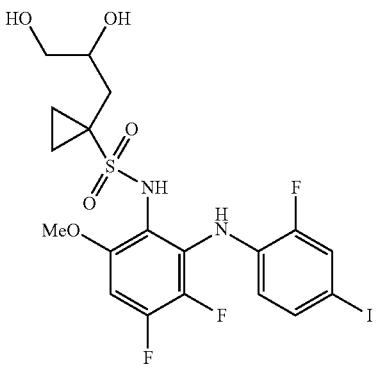 [SMILES: COc1cc(F)c(F)c(Nc2ccc(I)cc2F)c1NS(=O)(=O)C1(CC(O)CO)CC1]

(as defined in any of the above embodiments);
about 203.2 mg of microcrystalline cellulose;
about 12.0 mg of croscarmellose sodium;
about 2.4 mg of sodium lauryl sulfate; and
about 2.4 mg of magnesium stearate.

The invention also relates to a composition comprising: about 40 mg of a compound of structure:

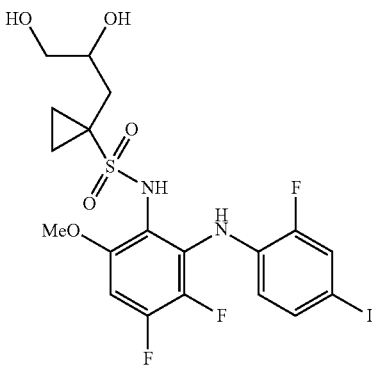 [SMILES: COc1cc(F)c(F)c(Nc2ccc(I)cc2F)c1NS(=O)(=O)C1(CC(O)CO)CC1]

(as defined in any of the above embodiments);
about 183.2 mg of microcrystalline cellulose;
about 12.0 mg of croscarmellose sodium;
about 2.4 mg of sodium lauryl sulfate; and
about 2.4 mg of magnesium stearate.

The invention also relates to a composition comprising: about 0.4% by weight of a compound of structure:

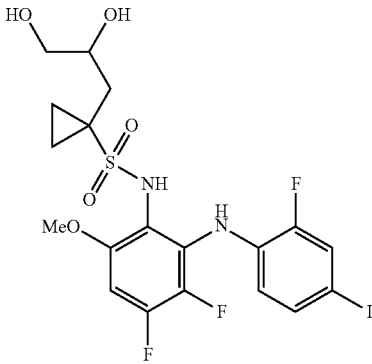 [SMILES: COc1cc(F)c(F)c(Nc2ccc(I)cc2F)c1NS(=O)(=O)C1(CC(O)CO)CC1]

(as defined in any of the above embodiments), and about 99.6% by weight of a pharmaceutically acceptable carrier or vehicle. In some embodiments, the pharmaceutically acceptable carrier or vehicle comprises microcrystalline cellulose. In further or additional embodiments, the microcrystalline cellulose is about 92.6% by weight of the composition. In further or additional embodiments, the composition further comprises: about 5% by weight croscarmellose sodium; about 1% by weight sodium lauryl sulfate; and about 1% by weight magnesium stearate.

The invention also relates to a composition comprising: about 4.2% by weight of a compound of structure:

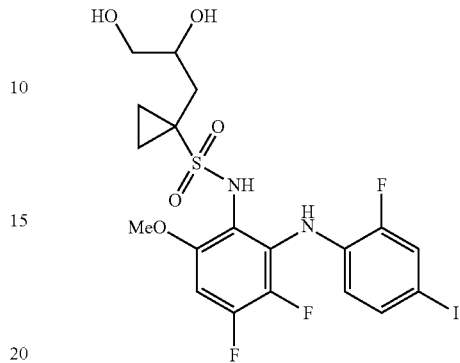

(as defined in any of the above embodiments); and about 95.8% by weight of a pharmaceutically acceptable carrier or vehicle. In some embodiments, the pharmaceutically acceptable carrier or vehicle comprises microcrystalline cellulose. In further or additional embodiments, the microcrystalline cellulose is about 88.8% by weight of the composition. In further or additional embodiments, the composition further comprises: about 5% by weight croscarmellose sodium; about 1% by weight sodium lauryl sulfate; and about 1% by weight magnesium stearate.

The invention also relates to a composition comprising: from about 2% to about 10% by weight of a compound of structure:

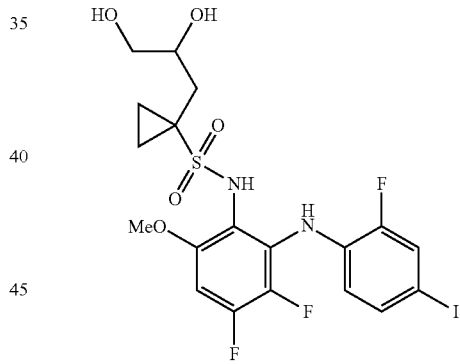

(as defined in any of the above embodiments); and from about 98% to about 90% by weight of a pharmaceutically acceptable carrier or vehicle. In some embodiments, the pharmaceutically acceptable carrier or vehicle comprises microcrystalline cellulose. In further or additional embodiments, the microcrystalline cellulose is from about 85% to about 95% by weight of the composition. In further or additional embodiments, the composition further comprises: from about 1% to about 6% by weight croscarmellose sodium; from about 0.1% to about 2% by weight sodium lauryl sulfate; and from about 0.25% to about 1.5% by weight magnesium stearate. In some embodiments, the pharmaceutically acceptable carrier or vehicle comprises microcrystalline cellulose. In further or additional embodiments, the microcrystalline cellulose is from about 85% to about 95% by weight of the composition. In further or additional embodiments, the composition further comprises: from about 1% to about 6% by weight croscarmellose sodium; and from about 0.25% to about 1.5% by weight magnesium stearate.

The invention also relates to a composition comprising:
about 1 mg of a compound of structure:

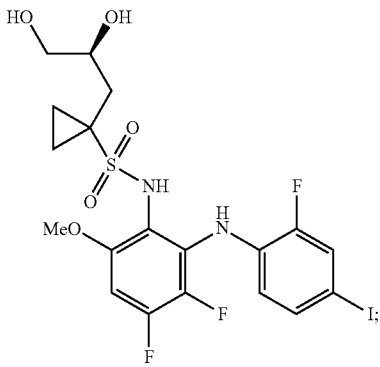 [SMILES: COc1cc(F)c(F)c(Nc2ccc(I)cc2F)c1NS(=O)(=O)C1(C[C@H](O)CO)CC1]

about 222.2 mg of microcrystalline cellulose;
about 12.0 mg of croscarmellose sodium;
about 2.4 mg of sodium lauryl sulfate; and
about 2.4 mg of magnesium stearate.
The invention also relates to a composition comprising:
about 10 mg of a compound of structure:

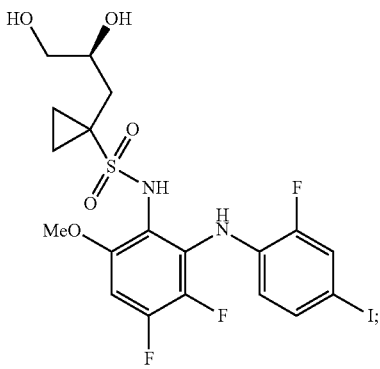 [SMILES: COc1cc(F)c(F)c(Nc2ccc(I)cc2F)c1NS(=O)(=O)C1(C[C@H](O)CO)CC1]

about 213.2 mg of microcrystalline cellulose;
about 12.0 mg of croscarmellose sodium;
about 2.4 mg of sodium lauryl sulfate; and
about 2.4 mg of magnesium stearate.
The invention also relates to a composition comprising:
about 20 mg of a compound of structure:

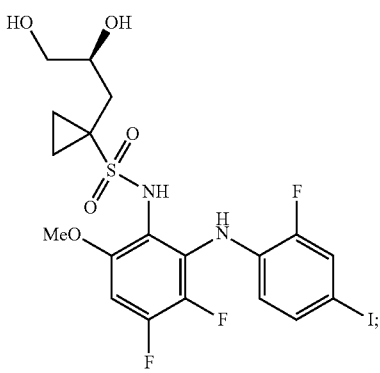 [SMILES: COc1cc(F)c(F)c(Nc2ccc(I)cc2F)c1NS(=O)(=O)C1(C[C@H](O)CO)CC1]

about 203.2 mg of microcrystalline cellulose;
about 12.0 mg of croscarmellose sodium;
about 2.4 mg of sodium lauryl sulfate; and
about 2.4 mg of magnesium stearate.

The invention also relates to a composition comprising:
about 40 mg of a compound of structure:

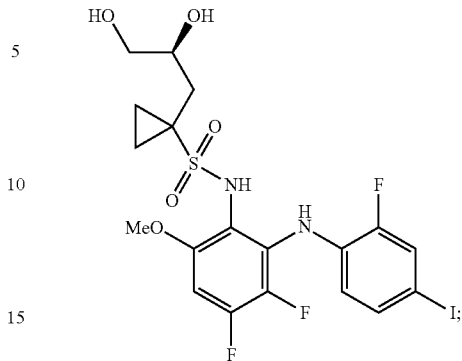

about 183.2 mg of microcrystalline cellulose;
about 12.0 mg of croscarmellose sodium;
about 2.4 mg of sodium lauryl sulfate; and
about 2.4 mg of magnesium stearate.
The invention also relates to a composition comprising:
about 0.4% by weight of a compound of structure:

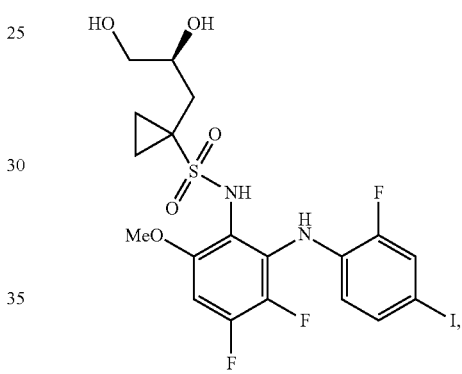

and about 99.6% by weight of a pharmaceutically acceptable carrier or vehicle. In some embodiments, the pharmaceutically acceptable carrier or vehicle comprises microcrystalline cellulose. In further or additional embodiments, the microcrystalline cellulose is about 92.6% by weight of the composition. In further or additional embodiments, the composition further comprises: about 5% by weight croscarmellose sodium; about 1% by weight sodium lauryl sulfate; and about 1% by weight magnesium stearate.

The invention also relates to a composition comprising:
about 4.2% by weight of a compound of structure:

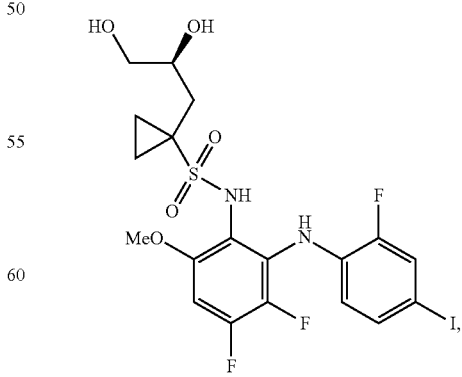

and about 95.8% by weight of a pharmaceutically acceptable carrier or vehicle. In some embodiments, the pharmaceutically acceptable carrier or vehicle comprises microcrystalline cellulose. In further or additional embodiments, the microcrystalline cellulose is about 88.8% by weight of the composition. In further or additional embodiments, the composition further comprises: about 5% by weight croscarmellose sodium; about 1% by weight sodium lauryl sulfate; and about 1% by weight magnesium stearate.

The invention also relates to a composition comprising: from about 2% to about 10% by weight of a compound of structure:

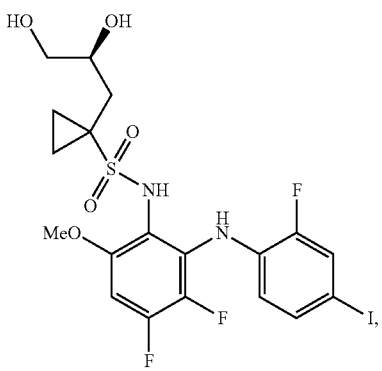 [SMILES: COc1cc(F)c(F)c(Nc2ccc(I)cc2F)c1NS(=O)(=O)C1(C[C@H](O)CO)CC1]

and from about 98% to about 90% by weight of a pharmaceutically acceptable carrier or vehicle. In some embodiments, the pharmaceutically acceptable carrier or vehicle comprises microcrystalline cellulose. In further or additional embodiments, the microcrystalline cellulose is from about 85% to about 95% by weight of the composition. In further or additional embodiments, the composition further comprises: from about 1% to about 6% by weight croscarmellose sodium; from about 0.1% to about 2% by weight sodium lauryl sulfate; and from about 0.25% to about 1.5% by weight magnesium stearate. In some embodiments, the pharmaceutically acceptable carrier or vehicle comprises microcrystalline cellulose. In further or additional embodiments, the microcrystalline cellulose is from about 85% to about 95% by weight of the composition. In further or additional embodiments, the composition further comprises: from about 1% to about 6% by weight croscarmellose sodium; and from about 0.25% to about 1.5% by weight magnesium stearate.

The invention also relates to a composition comprising: about 1 mg of a compound of structure:

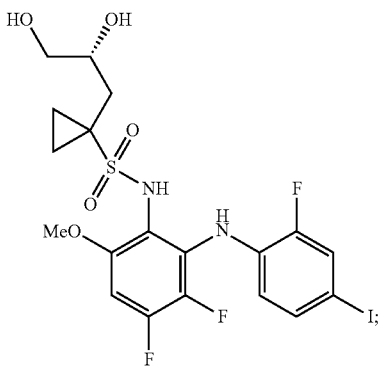 [SMILES: COc1cc(F)c(F)c(Nc2ccc(I)cc2F)c1NS(=O)(=O)C1(C[C@@H](O)CO)CC1]

about 222.2 mg of microcrystalline cellulose;
about 12.0 mg of croscarmellose sodium;
about 2.4 mg of sodium lauryl sulfate; and
about 2.4 mg of magnesium stearate.

The invention also relates to a composition comprising: about 10 mg of a compound of structure:

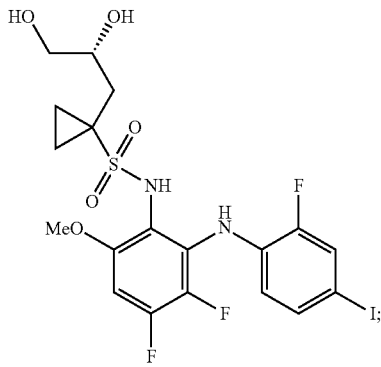 [SMILES: COc1cc(F)c(F)c(Nc2ccc(I)cc2F)c1NS(=O)(=O)C1(C[C@@H](O)CO)CC1]

about 213.2 mg of microcrystalline cellulose;
about 12.0 mg of croscarmellose sodium;
about 2.4 mg of sodium lauryl sulfate; and
about 2.4 mg of magnesium stearate.

The invention also relates to a composition comprising: about 20 mg of a compound of structure:

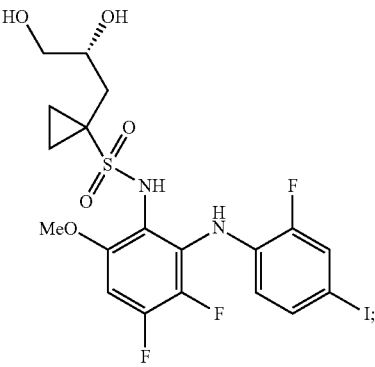 [SMILES: COc1cc(F)c(F)c(Nc2ccc(I)cc2F)c1NS(=O)(=O)C1(C[C@@H](O)CO)CC1]

about 203.2 mg of microcrystalline cellulose;
about 12.0 mg of croscarmellose sodium;
about 2.4 mg of sodium lauryl sulfate; and
about 2.4 mg of magnesium stearate.

The invention also relates to a composition comprising: about 40 mg of a compound of structure:

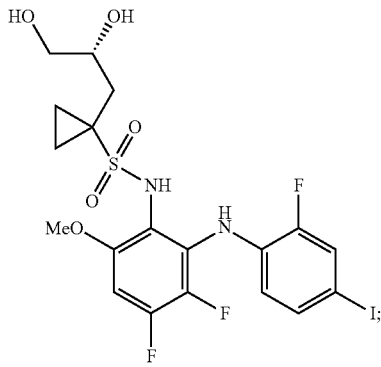 [SMILES: COc1cc(F)c(F)c(Nc2ccc(I)cc2F)c1NS(=O)(=O)C1(C[C@@H](O)CO)CC1]

about 183.2 mg of microcrystalline cellulose;
about 12.0 mg of croscarmellose sodium;
about 2.4 mg of sodium lauryl sulfate; and
about 2.4 mg of magnesium stearate.

The invention also relates to a composition comprising: about 0.4% by weight of a compound of structure:

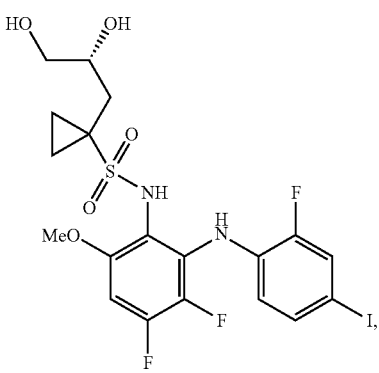 [SMILES: COc1cc(F)c(F)c(Nc2ccc(I)cc2F)c1NS(=O)(=O)C1(C[C@@H](O)CO)CC1]

and about 99.6% by weight of a pharmaceutically acceptable carrier or vehicle. In some embodiments, the pharmaceutically acceptable carrier or vehicle comprises microcrystalline cellulose. In further or additional embodiments, the microcrystalline cellulose is about 92.6% by weight of the composition. In further or additional embodiments, the composition further comprises: about 5% by weight croscarmellose sodium; about 1% by weight sodium lauryl sulfate; and about 1% by weight magnesium stearate.

The invention also relates to a composition comprising: about 4.2% by weight of a compound of structure:

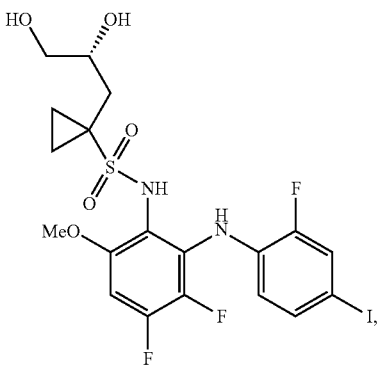 [SMILES: COc1cc(F)c(F)c(Nc2ccc(I)cc2F)c1NS(=O)(=O)C1(C[C@@H](O)CO)CC1]

and about 95.8% by weight of a pharmaceutically acceptable carrier or vehicle. In some embodiments, the pharmaceutically acceptable carrier or vehicle comprises microcrystalline cellulose. In further or additional embodiments, the microcrystalline cellulose is about 88.8% by weight of the composition. In further or additional embodiments, the composition further comprises: about 5% by weight croscarmellose sodium; about 1% by weight sodium lauryl sulfate; and about 1% by weight magnesium stearate.

The invention also relates to a composition comprising: from about 2% to about 10% by weight of a compound of structure:

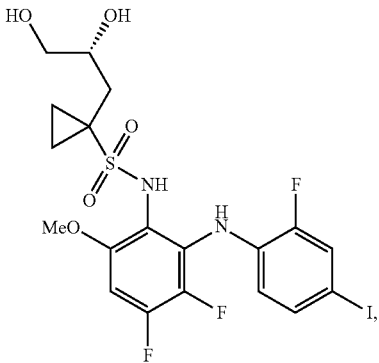 [SMILES: COc1cc(F)c(F)c(Nc2ccc(I)cc2F)c1NS(=O)(=O)C1(C[C@@H](O)CO)CC1]

and from about 98% to about 90% by weight of a pharmaceutically acceptable carrier or vehicle. In some embodiments, the pharmaceutically acceptable carrier or vehicle comprises microcrystalline cellulose. In further or additional embodiments, the microcrystalline cellulose is from about 85% to about 95% by weight of the composition. In further or additional embodiments, the composition further comprises: from about 1% to about 6% by weight croscarmellose sodium; from about 0.1% to about 2% by weight sodium lauryl sulfate; and from about 0.25% to about 1.5% by weight magnesium stearate. In some embodiments, the pharmaceutically acceptable carrier or vehicle comprises microcrystalline cellulose. In further or additional embodiments, the microcrystalline cellulose is from about 85% to about 95% by weight of the composition. In further or additional embodiments, the composition further comprises: from about 1% to about 6% by weight croscarmellose sodium; and from about 0.25% to about 1.5% by weight magnesium stearate.

Also described herein are pharmaceutical compositions comprising an effective amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide. In some embodiments, the pharmaceutical compositions comprise an effective amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide, and at least one pharmaceutically acceptable carrier. In some embodiments the pharmaceutical compositions are for the treatment of disorders. In some embodiments the pharmaceutical compositions are for the treatment of disorders in a mammal. In some embodiments the pharmaceutical compositions are for the treatment of disorders in a human. In some embodiments the pharmaceutical compositions are for the treatment or prophylaxis of inflammatory diseases. In some embodiments the pharmaceutical compositions are for the treatment or prophylaxis of proliferative diseases.

Methods of Use of the Compounds, Including Polymorph Forms, and the Compositions In other aspects, the present invention is directed to a method for achieving an effect in a patient comprising the administration of an effective amount of a compound of formula I or a pharmaceutically acceptable salt, solvate, polymorph, ester, amide, tautomer or prodrug thereof, to a patient, wherein the effect is selected from the group consisting of inhibition of various cancers, immunological diseases, and inflammatory diseases. In some embodiments, the compound or pharmaceutically acceptable salt, solvate, polymorph, ester, amide, tautomer or prodrug thereof is administered as a component of a composition that further comprises a pharmaceutically acceptable carrier or vehicle. In some embodiments, the effect is inhibition of various cancers. In further or additional embodiments, the effect is inhibition of immunological diseases. In further or additional embodiments, the effect is inhibition inflammatory diseases.

Any of the compositions described and claimed herein may be used in the methods provided in this section.

In some embodiments, the composition comprising a compound of formula I is administered in combination with an additional therapy. In further or additional embodiments, the additional therapy is radiation therapy, chemotherapy, or surgery or any combination thereof. In further or additional embodiments, the composition comprising a compound of formula I is administered in combination with at least one therapeutic agent.

In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In some embodiments of the compositions and methods provided herein, provided are MEK protein kinase inhibitors further comprising a compound of formula I, wherein the compound of formula I is present in an amount of about 0.1 mg to about 200 mg. In other embodiments, the MEK protein kinase inhibitor comprises a compound of formula I and is present in an amount of about 0.2 mg to about 100 mg. In other embodiments, the MEK protein kinase inhibitor comprises a compound of formula I and is present in an amount of about 0.3 mg to about 90 mg. In other embodiments, the MEK protein kinase inhibitor comprises a compound of formula I and is present in an amount of about 0.4 mg to about 80 mg. In other embodiments, the MEK protein kinase inhibitor comprises a compound of formula I and is present in an amount of about 0.5 mg to about 70 mg. In other embodiments, the MEK protein kinase inhibitor comprises a compound of formula I and is present in an amount of about 0.4 mg to about 80 mg. In other embodiments, the MEK protein kinase inhibitor comprises a compound of formula I and is present in an amount of about 0.5 mg to about 70 mg. In other embodiments, the MEK protein kinase inhibitor comprises a compound of formula I and is present in an amount of about 1 mg to about 60 mg. In other embodiments, the MEK protein kinase inhibitor comprises a compound of formula I and is present in an amount of about 1.5 mg to about 50 mg. In other embodiments, the MEK protein kinase inhibitor comprises a compound of formula I and is present in an amount of about 2 mg to about 45 mg. In other embodiments, the MEK protein kinase inhibitor comprises a compound of formula I and is present in an amount of about 2.5 mg to about 40 mg. In further embodiments, MEK protein kinase inhibitor further comprising the compound of formula I present in the dosage amounts provided herein is selected from the group consisting of:

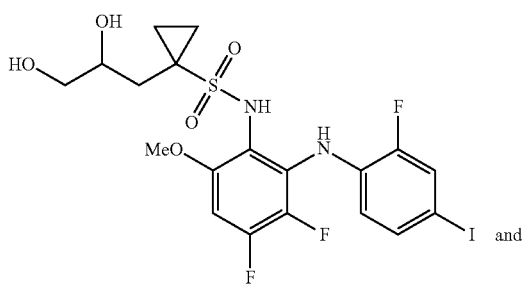

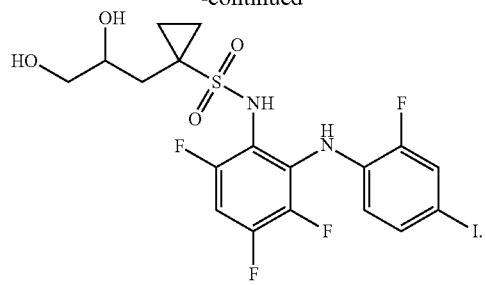

In some embodiments of the compositions and methods provided herein, provided are MEK protein kinase inhibitors further comprising a compound of formula I, wherein the compound of formula I is present in an amount of about 0.1 mg, about 0.2 mg, about 0.25 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, about 2.5 mg, about 3 mg, about 3.5 mg, about 4.0 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, and/or about 13 mg, about 14 mg, or about 15 mg. In further embodiments, the compound of formula I present in the dosage amounts provided herein is selected from the group consisting of:

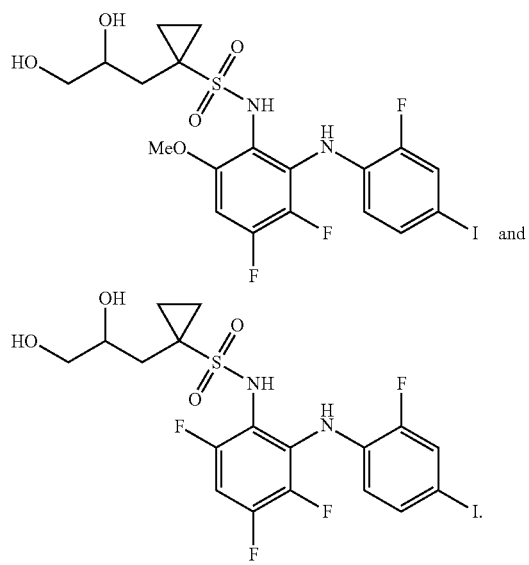

In some embodiments of the compositions and methods provided herein, provided are MEK protein kinase inhibitors further comprising a compound of formula I, wherein the compound of formula I is present in an amount of about 15 mg, about 20 mg, about 25 mg, about 30 mg, about 35 mg, about 40 mg, about 45 mg, about 50 mg, about 55 mg, about 60 mg, about 65 mg, about 75 mg, about 80 mg, about 85 mg, about 90 mg, about 95 mg, about 100 mg, about 110 mg, about 120 mg, about 125 mg, about 130 mg, about 140 mg, about 150 mg, about 160 mg, about 170 mg, about 175 mg, about 180 mg, about 190 mg, or about 200 mg. In further embodiments, the compound of formula I present in the dosage amounts provided herein is selected from the group consisting of:

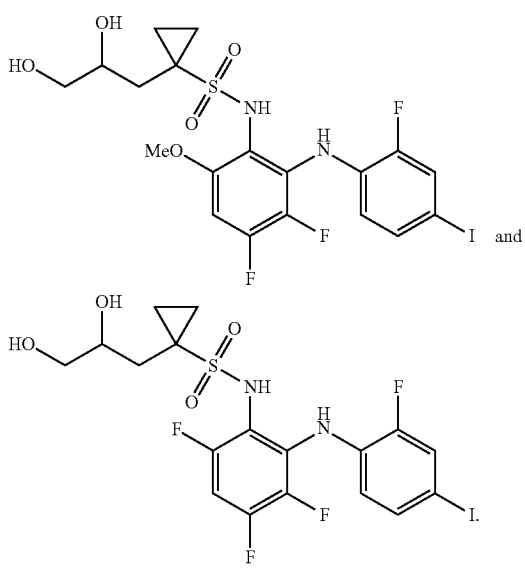

In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

In some aspects, the present invention is directed to a method of treating a disease in an individual suffering from said disease comprising administering to said individual an effective amount of a composition comprising a compound of formula I or a pharmaceutically acceptable salt, solvate, polymorph, ester, tautomer or prodrug thereof.

In other aspects, the present invention is directed to a method of treating a disorder in a mammal, comprising administering to said mammal a therapeutically effective amount of the compound of formula I or a pharmaceutically acceptable salt, solvate, polymorph, ester, tautomer or prodrug thereof.

In other aspects, the present invention is directed to a method of treating a disorder in a human, comprising administering to said mammal a therapeutically effective amount of the compound of formula I or a pharmaceutically acceptable salt, solvate, polymorph, ester, tautomer or prodrug thereof.

MEK Modulated Disease and Disorders

Also described herein are methods of modulating MEK activity by contacting MEK with an amount of a compound of formula I sufficient to modulate the activity of MEK. Modulate can be inhibiting or activating MEK activity. In some embodiments, the invention provides methods of inhibiting MEK activity by contacting MEK with an amount of a compound of formula I sufficient to inhibit the activity of MEK. In some embodiments, the invention provides methods of inhibiting MEK activity in a solution by contacting said solution with an amount of a compound of formula I sufficient to inhibit the activity of MEK in said solution. In some embodiments, the invention provides methods of inhibiting MEK activity in a cell by contacting said cell with an amount of a compound described herein sufficient to inhibit the activity of MEK in said cell. In some embodiments, the invention provides methods of inhibiting MEK activity in a tissue by contacting said tissue with an amount of a compound described herein sufficient to inhibit the activity of MEK in said tissue. In some embodiments, the invention provides methods of inhibiting MEK activity in an organism by contacting said organism with an amount of a compound described herein sufficient to inhibit the activity of MEK in said organism. In some embodiments, the invention provides methods of inhibiting MEK activity in an animal by contacting said animal with an amount of a compound described herein sufficient to inhibit the activity of MEK in said animal. In some embodiments, the invention provides methods of inhibiting MEK activity in a mammal by contacting said mammal with an amount of a compound described herein sufficient to inhibit the activity of MEK in said mammal. In some embodiments, the invention provides methods of inhibiting MEK activity in a human by contacting said human with an amount of a compound described herein sufficient to inhibit the activity of MEK in said human.

Compounds of formula I, and compositions containing a compound of formula I, and pharmaceutically acceptable salts, solvates, polymorphs, esters, amides, tautomers or prodrugs thereof, may modulate the activity of MEK enzymes; and, as such, are useful for treating diseases or conditions in which aberrant MEK enzyme activity contributes to the pathology and/or symptoms of a disease or condition.

In some aspects, the present invention is directed to a method of treating a disorder or condition which is modulated by the MEK cascade in a mammal, including a human, comprising administering to said mammal an amount of the compound of formula I, or a pharmaceutically acceptable salt, ester, prodrug, solvate, hydrate or derivative thereof, effective to modulate said cascade. The appropriate dosage for a particular patient can be determined, according to known methods, by those skilled in the art.

In other aspects, the present invention is directed to a method for inhibiting a MEK enzyme. In some embodiments, the method comprises contacting said MEK enzyme with an amount of a composition comprising a compound of formula I or a pharmaceutically acceptable salt, solvate, polymorph, ester, amide, tautomer or prodrug thereof, sufficient to inhibit said enzyme, wherein said enzyme is inhibited. In further or additional embodiments the enzyme is at least about 1% inhibited. In further or additional embodiments the enzyme is at least about 2% inhibited. In further or additional embodiments the enzyme is at least about 3% inhibited. In further or additional embodiments the enzyme is at least about 4% inhibited. In further or additional embodiments the enzyme is at least about 5% inhibited. In further or additional embodiments the enzyme is at least about 10% inhibited. In further or additional embodiments the enzyme is at least about 20% inhibited. In further or additional embodiments the enzyme is at least about 25% inhibited. In further or additional embodiments the enzyme is at least about 30% inhibited. In further or additional embodiments the enzyme is at least about 40% inhibited. In further or additional embodiments the enzyme is at least about 50% inhibited. In further or additional embodiments the enzyme is at least about 60% inhibited. In further or additional embodiments the enzyme is at least about 70% inhibited. In further or additional embodiments the enzyme is at least about 75% inhibited. In further or additional embodiments the enzyme is at least about 80% inhibited. In further or additional embodiments the enzyme is at least about 90% inhibited. In further or additional embodiments the enzyme is essentially completely inhibited. In further or additional embodiments the MEK enzyme is MEK kinase. In further or additional embodiments the MEK enzyme is MEK1. In further or additional embodiments the MEK enzyme is MEK2. In further or additional embodiments the contacting occurs within a cell. In further or additional embodiments the cell is a mammalian cell. In further or additional embodiments the mammalian cell is a human cell. In further or additional embodiments, the MEK enzyme is inhibited with a composition comprising a pharmaceutically acceptable salt of a compound of formula I.

In further or additional aspects, the present invention is directed to a method of treatment of a MEK mediated disorder in an individual suffering from said disorder comprising administering to said individual an effective amount of a composition comprising a compound of formula I or a pharmaceutically acceptable salt, solvate, polymorph, ester, amide, tautomer or prodrug thereof. In some embodiments, the composition comprising a compound of formula I is administered orally, intraduodenally, parenterally (including intravenous, subcutaneous, intramuscular, intravascular or by infusion), topically or rectally. In some embodiments, the pharmaceutical composition is in a form suitable for oral administration. In further or additional embodiments, the pharmaceutical composition is in the form of a tablet, capsule, pill, powder, sustained release formulations, solution, suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments, the pharmaceutical composition further comprises a pharmaceutical carrier, excipient and/or adjuvant.

In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the MEK mediated disorder is a mammal. In further or additional embodiments, the individual is a human.

In some embodiments, the composition comprising a compound of formula I is administered in combination with an additional therapy. In further or additional embodiments, the additional therapy is radiation therapy, chemotherapy, surgery or any combination thereof. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both.

In some embodiments, the MEK mediated disorder is selected from the group consisting of inflammatory diseases, infections, autoimmune disorders, stroke, ischemia, cardiac disorder, neurological disorders, fibrogenetic disorders, proliferative disorders, hyperproliferative disorders, non-cancer hyperproliferative disorders, tumors, leukemias, neoplasms, cancers, carcinomas, metabolic diseases, malignant disease, vascular restenosis, psoriasis, atherosclerosis, rheumatoid arthritis, osteoarthritis, heart failure, chronic pain, neuropathic pain, dry eye, closed angle glaucoma and wide angle glaucoma. In further or additional embodiments, the MEK mediated disorder is an inflammatory disease. In further or additional embodiments, the MEK mediated disorder is a hyperproliferative disease. In further or additional embodiments, the MEK mediated disorder is selected from the group consisting of tumors, leukemias, neoplasms, cancers, carcinomas and malignant disease. In further or additional embodiments, stomach cancer, brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, an effective amount of a composition comprising a pharmaceutically acceptable salt of a compound of formula I is administered.

The invention also relates to methods of modulating MEK activity by contacting MEK with an amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide sufficient to modulate the activity of MEK. Modulate can be inhibiting or activating MEK activity. In some embodiments, the invention provides methods of inhibiting MEK activity by contacting MEK with an amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide sufficient to inhibit the activity of MEK. In some embodiments, the invention provides methods of inhibiting MEK activity in a solution by contacting said solution with an amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide sufficient to inhibit the activity of MEK in said solution. In some embodiments, the invention provides methods of inhibiting MEK activity in a cell by contacting said cell with an amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide sufficient to inhibit the activity of MEK in said cell. In some embodiments, the invention provides methods of inhibiting MEK activity in a tissue by contacting said tissue with an amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide sufficient to inhibit the activity of MEK in said tissue. In some embodiments, the invention provides methods of inhibiting MEK activity in an organism by contacting said organism with an amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide sufficient to inhibit the activity of MEK in said organism. In some embodiments, the invention provides methods of inhibiting MEK activity in an animal by contacting said animal with an of amount a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide sufficient to inhibit the activity of MEK in said animal. In some embodiments, the invention provides methods of inhibiting MEK activity in a mammal by contacting said mammal with an amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide sufficient to inhibit the activity of MEK in said mammal. In some embodiments, the invention provides methods of inhibiting MEK activity in a human by contacting said human with an amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide sufficient to inhibit the activity of MEK in said human.

Cancer

In other aspects, the present invention is directed to a method for the treatment, prevention or prophylaxis of cancer in an individual comprising administering to said individual an effective amount of a compound of formula I or a pharmaceutically acceptable salt, solvate, polymorph, ester, amide, tautomer or prodrug thereof. In some embodiments, the compound or pharmaceutically acceptable salt, solvate, polymorph, ester, amide, tautomer or prodrug thereof is administered as a component of a composition that further comprises a pharmaceutically acceptable carrier or vehicle. In further or additional embodiments, the cancer is brain cancer, breast cancer, lung cancer, ovarian cancer, pancreatic cancer, prostate cancer, renal cancer, colorectal cancer, stomach cancer, or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, colorectal cancer, leukemia, melanoma, thyroid cancer, or basal cell carcinoma. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphona. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell lung cancer. In some embodiments, the cancer is stomach cancer.

In some embodiments, the composition comprising a compound of formula I is administered in combination with an additional therapy. In further or additional embodiments, the additional therapy is radiation therapy, chemotherapy, surgery or any combination thereof. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both.

In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In some embodiments, the composition is administered orally, intraduodenally, parenterally (including intravenous, subcutaneous, intramuscular, intravascular or by infusion), topically or rectally. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

Abnormal Cell Growth

Also described herein are compounds, pharmaceutical compositions and methods for inhibiting abnormal cell growth. In some embodiments, the abnormal cell growth occurs in a mammal. Methods for inhibiting abnormal cell growth comprise administering an effective amount of a compound of formula I, or a pharmaceutically acceptable salt, solvate, polymorph, ester, amide, tautomer, prodrug, hydrate, or derivative thereof, wherein abnormal cell growth is inhibited. Methods for inhibiting abnormal cell growth in a mammal comprise administering to the mammal an amount of a compound of formula I, or a pharmaceutically acceptable salt, solvate, polymorph, ester, amide, tautomer, prodrug, hydrate, or derivative thereof, wherein the amounts of the compound, or salt, is effective in inhibiting abnormal cell growth in the mammal.

In some embodiments, the methods comprise administering an effective amount of a compound of formula I, or a pharmaceutically acceptable salt, solvate, polymorph, ester, amide, tautomer, prodrug, hydrate, or derivative thereof, in combination with an amount of a chemotherapeutic, wherein the amounts of the compound, or its salt, solvate, polymorph, ester, amide, tautomer, prodrug, hydrate, or derivative thereof and the chemotherapeutic are together effective in inhibiting abnormal cell growth. Many chemotherapeutics are presently known in the art and can be used in combination with the compounds of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Also described are methods for inhibiting abnormal cell growth in a mammal comprising administering to the mammal an amount of a compound of formula I, or a pharmaceutically acceptable salt, solvate, polymorph, ester, amide, tautomer, prodrug, hydrate, or derivative thereof, in combination with radiation therapy, wherein the amounts of the compound, or its salt, solvate, polymorph, ester, amide, tautomer, prodrug, hydrate, or a derivative thereof is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of formula I in this combination therapy can be determined as described herein.

The invention also relates to a method of and to a pharmaceutical composition of inhibiting abnormal cell growth in a mammal which comprises an amount of a compound of formula I, or a pharmaceutically acceptable salt, solvate, polymorph, ester, amide, tautomer, prodrug, hydrate, or derivative thereof, or an isotopically-labeled derivative thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997), all of which are incorporated herein in their entireties by reference. Some MMP-2 and MMP-9 inhibitors have little or no activity inhibiting MMP-1, while some selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

In other aspects, the present invention is directed to a method for degrading, inhibiting the growth of or killing a cancer cell comprising contacting said cell with an amount of a composition effective to degrade, inhibit the growth of or to kill said cell, the composition comprising a compound of formula I or a pharmaceutically acceptable salt, solvate, polymorph, ester, amide, tautomer or prodrug thereof. In some embodiments, the cancer cells comprise brain, breast, lung, ovarian, pancreatic, prostate, renal, or colorectal cancer cells.

In further or additional embodiments, the composition is administered with at least one therapeutic agent. In further or additional embodiments, the therapeutic agent is taxol, bortezomib or both. In further or additional embodiments, the therapeutic agent is selected from the group consisting of cytotoxic agents, anti-angiogenesis agents and anti-neoplastic agents. In further or additional embodiments, the anti-neoplastic agents selected from the group of consisting of alkylating agents, anti-metabolites, epidophyllotoxins; anti-neoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors.

In some embodiments, the cancer cells are degraded. In further or additional embodiments, 1% of the cancer cells are degraded. In further or additional embodiments, 2% of the cancer cells are degraded. In further or additional embodiments, 3% of the cancer cells are degraded. In further or additional embodiments, 4% of the cancer cells are degraded. In further or additional embodiments, 5% of the cancer cells are degraded. In further or additional embodiments, 10% of the cancer cells are degraded. In further or additional embodiments, 20% of the cancer cells are degraded. In further or additional embodiments, 25% of the cancer cells are degraded. In further or additional embodiments, 30% of the cancer cells are degraded. In further or additional embodiments, 40% of the cancer cells are degraded. In further or additional embodiments, 50% of the cancer cells are degraded. In further or additional embodiments, 60% of the cancer cells are degraded. In further or additional embodiments, 70% of the cancer cells are degraded. In further or additional embodiments, 75% of the cancer cells are degraded. In further or additional embodiments, 80% of the cancer cells are degraded. In further or additional embodiments, 90% of the cancer cells are degraded. In further or additional embodiments, 100% of the cancer cells are degraded. In further or additional embodiments, essentially all of the cancer cells are degraded.

In some embodiments, the cancer cells are killed. In further or additional embodiments, 1% of the cancer cells are killed. In further or additional embodiments, 2% of the cancer cells are killed. In further or additional embodiments, 3% of the cancer cells are killed. In further or additional embodiments, 4% of the cancer cells are killed. In further or additional embodiments, 5% of the cancer cells are killed. In further or additional embodiments, 10% of the cancer cells are killed. In further or additional embodiments, 20% of the cancer cells are killed. In further or additional embodiments, 25% of the cancer cells are killed. In further or additional embodiments, 30% of the cancer cells are killed. In further or additional embodiments, 40% of the cancer cells are killed. In further or additional embodiments, 50% of the cancer cells are killed. In further or additional embodiments, 60% of the cancer cells are killed. In further or additional embodiments, 70% of the cancer cells are killed. In further or additional embodiments, 75% of the cancer cells are killed. In further or additional embodiments, 80% of the cancer cells are killed. In further or additional embodiments, 90% of the cancer cells are killed. In further or additional embodiments, 100% of the cancer cells are killed. In further or additional embodiments, essentially all of the cancer cells are killed.

In further or additional embodiments, the growth of the cancer cells is inhibited. In further or additional embodiments, the growth of the cancer cells is about 1% inhibited. In further or additional embodiments, the growth of the cancer cells is about 2% inhibited. In further or additional embodiments, the growth of the cancer cells is about 3% inhibited. In further or additional embodiments, the growth of the cancer cells is about 4% inhibited. In further or additional embodiments, the growth of the cancer cells is about 5% inhibited. In further or additional embodiments, the growth of the cancer cells is about 10% inhibited. In further or additional embodiments, the growth of the cancer cells is about 20% inhibited. In further or additional embodiments, the growth of the cancer cells is about 25% inhibited. In further or additional embodiments, the growth of the cancer cells is about 30% inhibited. In further or additional embodiments, the growth of the cancer cells is about 40% inhibited. In further or additional embodiments, the growth of the cancer cells is about 50% inhibited. In further or additional embodiments, the growth of the cancer cells is about 60% inhibited. In further or additional embodiments, the growth of the cancer cells is about 70% inhibited. In further or additional embodiments, the growth of the cancer cells is about 75% inhibited. In further or additional embodiments, the growth of the cancer cells is about 80% inhibited. In further or additional embodiments, the growth of the cancer cells is about 90% inhibited. In further or additional embodiments, the growth of the cancer cells is about 100% inhibited. In further or additional embodiments, a composition comprising a pharmaceutically acceptable salt of a compound of formula I is used.

Also described herein are methods for inhibiting abnormal cell growth. In some embodiments, the abnormal cell growth occurs in a mammal. Methods for inhibiting abnormal cell growth comprise administering an effective amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide, wherein abnormal cell growth is inhibited. Methods for inhibiting abnormal cell growth in a mammal comprise administering to the mammal an amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide, wherein the amount of a crystalline polymorph form A of N—(S)-(3,4-difluoro-2-(2-fluoro-4-iodophenylamino)-6-methoxyphenyl)-1-(2,3-dihyclroxypropyl)cyclopropane-1-sulfonamide is effective in inhibiting abnormal cell growth in the mammal.

In some embodiments, the methods comprise administering an effective amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide in combination with an amount of a chemotherapeutic, wherein the amounts of the crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide and of the chemotherapeutic are together effective in inhibiting abnormal cell growth.

Many chemotherapeutics are presently known in the art and can be used in combination with the compounds and compositions of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

In some embodiments, the methods for inhibiting abnormal cell growth in a mammal comprise administering to the mammal an amount of a crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide in combination with radiation therapy, wherein the amount of crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide in combination with the radiation therapy is effective in inhibiting abnormal cell growth. Techniques for administering radiation therapy are known in the art, and these techniques can be used in the combination therapy described herein.

Treatment of a Hyperproliferative Disorder

In other aspects, the present invention is directed to a method of treating a hyperproliferative disorder in a mammal, including a human, comprising administering to said mammal a therapeutically effective amount of the compound of formula I or a pharmaceutically acceptable salt, solvate, polymorph, ester, tautomer or prodrug thereof.

In other aspects, the present invention is directed to a method for the treatment, prevention or prophylaxis of a proliferative disease in an individual comprising administering to said individual an effective amount of a compound of formula I, or a pharmaceutically acceptable salt, solvate, polymorph, ester, amide, tautomer or prodrug thereof. In some embodiments, the compound or pharmaceutically acceptable salt, solvate, polymorph, ester, amide, tautomer or prodrug thereof is administered as a component of a composition that further comprises a pharmaceutically acceptable carrier or vehicle. In some embodiments, the proliferative disease is cancer, psoriasis, restenosis, autoimmune disease, or atherosclerosis. In further or additional embodiments, the proliferative disease is a hyperproliferative disease. In further or additional embodiments, the proliferative disease is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, stomach cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, stomach cancer, pancreatic cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphona. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell lung cancer. In some embodiments, the cancer is stomach cancer.

In some embodiments, the composition comprising a compound of formula I is administered in combination with an additional therapy. In further or additional embodiments, the additional therapy is radiation therapy, chemotherapy, surgery or a combination thereof. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both.

In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the proliferative disease is a mammal. In further or additional embodiments, the individual is a human. In further or additional embodiments, an effective amount of a composition comprising a pharmaceutically acceptable salt of a compound of formula I is administered.

Tumor Size

In other aspects, the present invention is directed to a method of reducing the size of a tumor, inhibiting tumor size increase, reducing tumor proliferation or preventing tumor proliferation in an individual, comprising administering to said individual an effective amount of a compound of formula I or a pharmaceutically acceptable salt, solvate, polymorph, ester, amide, tautomer or prodrug thereof. In some embodiments, the compound or pharmaceutically acceptable salt, solvate, polymorph, ester, amide, tautomer or prodrug thereof is administered as a component of a composition that further comprises a pharmaceutically acceptable carrier or vehicle. In some embodiments, the size of a tumor is reduced. In further or additional embodiments, the size of a tumor is reduced by at least 1%. In further or additional embodiments, the size of a tumor is reduced by at least 2%. In further or additional embodiments, the size of a tumor is reduced by at least 3%. In further or additional embodiments, the size of a tumor is reduced by at least 4%. In further or additional embodiments, the size of a tumor is reduced by at least 5%. In further or additional embodiments, the size of a tumor is reduced by at least 10%. In further or additional embodiments, the size of a tumor is reduced by at least 20%. In further or additional embodiments, the size of a tumor is reduced by at least 25%. In further or additional embodiments, the size of a tumor is reduced by at least 30%. In further or additional embodiments, the size of a tumor is reduced by at least 40%. In further or additional embodiments, the size of a tumor is reduced by at least 50%. In further or additional embodiments, the size of a tumor is reduced by at least 60%. In further or additional embodiments, the size of a tumor is reduced by at least 70%. In further or additional embodiments, the size of a tumor is reduced by at least 75%. In further or additional embodiments, the size of a tumor is reduced by at least 80%. In further or additional embodiments, the size of a tumor is reduced by at least 85%. In further or additional embodiments, the size of a tumor is reduced by at least 90%. In further or additional embodiments, the size of a tumor is reduced by at least 95%. In further or additional embodiments, the tumor is eradicated. In some embodiments, the size of a tumor does not increase.

In some embodiments, tumor proliferation is reduced. In some embodiments, tumor proliferation is reduced by at least 1%. In some embodiments, tumor proliferation is reduced by at least 2%. In some embodiments, tumor proliferation is reduced by at least 3%. In some embodiments, tumor proliferation is reduced by at least 4%. In some embodiments, tumor proliferation is reduced by at least 5%. In some embodiments, tumor proliferation is reduced by at least 10%. In some embodiments, tumor proliferation is reduced by at least 20%. In some embodiments, tumor proliferation is reduced by at least 25%. In some embodiments, tumor proliferation is reduced by at least 30%. In some embodiments, tumor proliferation is reduced by at least 40%. In some embodiments, tumor proliferation is reduced by at least 50%. In some embodiments, tumor proliferation is reduced by at least 60%. In some embodiments, tumor proliferation is reduced by at least 70%. In some embodiments, tumor proliferation is reduced by at least 75%. In some embodiments, tumor proliferation is reduced by at least 75%. In some embodiments, tumor proliferation is reduced by at least 80%. In some embodiments, tumor proliferation is reduced by at least 90%. In some embodiments, tumor proliferation is reduced by at least 95%. In some embodiments, tumor proliferation is prevented.

In some embodiments, the composition comprising a compound of formula I is administered in combination with an additional therapy. In further or additional embodiments, the additional therapy is radiation therapy, chemotherapy, surgery or any combination thereof. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both.

In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

Inflammatory Disease

In other aspects, the present invention is directed to a method for the treatment, prevention or prohylaxis of an inflammatory disease in an individual comprising administering to said individual an effective amount of compound of formula I or a pharmaceutically acceptable salt, solvate, polymorph, ester, amide, tautomer or prodrug thereof. In some embodiments, the compound or pharmaceutically acceptable salt, solvate, polymorph, ester, amide, tautomer or prodrug thereof is administered as a component of a composition that further comprises a pharmaceutically acceptable carrier or vehicle. In further or additional embodiments, the inflammatory disease is selected from chronic inflammatory diseases, rheumatoid arthritis, rheumatoid arthritis, spondyloarthropathies, ankylosing spondylitis, gout, tendonitis, bursitis, sciatica, gouty arthritis, osteoarthritis, juvenile arthritis, acute rheumatic arthritis, enteropathic arthritis, neuropathic arthritis, psoriatic arthritis, pyogenic arthritis, atherosclerosis, systemic lupus erythematosus, inflammatory bowel disease, irritable bowel syndrome, ulcerative colitis, reflux esophagitis, Crohn's disease, gastritis, asthma, allergies, respiratory distress syndrome, pancreatitis, chronic obstructive pulmonary disease, pulmonary fibrosis, psoriasis, eczema or scleroderma.

In some embodiments, the composition comprising a compound of formula I is administered in combination with an additional therapy. In further or additional embodiments, the composition comprising a compound of formula I is administered in combination with at least one therapeutic agent. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required.

In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the inflammatory disease is a mammal. In further or additional embodiments, the individual is a human. In further or additional embodiments, an effective amount of a composition comprising a pharmaceutically acceptable salt of a compound of formula I is administered.

Modes of Administration

Described herein are compounds of formula I or a pharmaceutically acceptable salt solvate, polymorph, ester, amide, tautomer, prodrug, hydrate, or derivative thereof. Also described, are pharmaceutical compositions comprising a compound of formula I or a pharmaceutically acceptable salt, solvate, polymorph, ester, amide, tautomer, prodrug, hydrate, or derivative thereof. The compounds and compositions described herein may be administered either alone or in combination with pharmaceutically acceptable carriers, excipients or diluents, in a pharmaceutical composition, according to standard pharmaceutical practice.

Also described herein are pharmaceutical compositions comprising crystalline polymorph N—(S)-(3,4-difluoro-2-(2-fluoro-4-iodophenylamino)-6-methoxyphenyl)-1-(2,3-dihydroxypropyl)cyclopropane-1-sulfonamide (Form A). The compounds and compositions described herein may be administered either alone or in combination with pharmaceutically acceptable carriers, excipients or diluents, in a pharmaceutical composition, according to standard pharmaceutical practice. Administration can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. Those of skill in the art will be familiar with administration techniques that can be employed with the compounds and methods of the invention. By way of example only, compounds described herein can be administered locally to the area in need of treatment, by for example, local infusion during surgery, topical application such as creams or ointments, injection, catheter, or implant, said implant made for example, out of a porous, non-porous, or gelatinous material, including membranes, such as sialastic membranes, or fibers. The administration can also be by direct injection at the site of a diseased tissue or organ.

Administration of the compounds and compositions described herein can be effected by any method that enables delivery of the compounds to the site of action. These methods include oral routes, intraduodenal routes, parenteral injection (including intravenous, subcutaneous, intraperitoneal, intramuscular, intravascular or infusion), topical, and rectal administration. For example, compounds described herein can be administered locally to the area in need of treatment. This may be achieved by, for example, but not limited to, local infusion during surgery, topical application, e.g., cream, ointment, injection, catheter, or implant, said implant made, e.g., out of a porous, non-porous, or gelatinous material, including membranes, such as sialastic membranes, or fibers. The administration can also be by direct injection at the site (or former site) of a tumor or neoplastic or pre-neoplastic tissue. Those of ordinary skill in the art are familiar with formulation and administration techniques that can be employed with the compounds and methods of the invention, e.g., as discussed in Goodman and Gilman, The Pharmacological Basis of Therapeutics, current ed.; Pergamon; and Remington's, Pharmaceutical *Sciences* (current edition), Mack Publishing Co., Easton, Pa.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject invention or a pharmaceutically acceptable salt, solvate, polymorph, ester, amide, tautomer, prodrug, hydrate, or derivative thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which are useful for oral administration include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules or tablets can contain the active ingredient; in admixture with a filler such as microcrystalline cellulose, silicified microcrystalline cellulose, pregelatinized starch, lactose, dicalcium phosphate, or compressible sugar; a binder such as hypromellose, povidone or starch paste; a disintegrant such as croscarmellose sodium, crospovidone or sodium starch glycolate; a surfactant such as sodium lauryl sulfate and/or lubricants and processing aides such as talc, magnesium stearate, stearic acid or colloidal silicon dioxide and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions are useful, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

Pharmaceutical preparations may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical preparations may also be formulated in rectal compositions such as suppositories or retention enemas, e.g., containing conventional suppository bases such as cocoa butter, polyethylene glycol, or other glycerides.

Pharmaceutical preparations may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical preparations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w or may comprise less than 5% w/w, or from 0.1% to 1% w/w of the formulation.

Pharmaceutical preparations for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Formulations

It should be noted that any of the compositions and compounds described herein may be used in any of the formulations discussed in this section, which is not intended to be limiting and should not be so construed.

The compounds or compositions described herein can be delivered in a vesicle, e.g., a liposome (see, for example, Langer, *Science* 1990, 249, 1527-1533; Treat et al., *Liposomes in the Therapy of Infectious Disease and Cancer*, Lopez-Bernstein and Fidler, Ed., Liss, N.Y., pp. 353-365, 1989). The compounds and pharmaceutical compositions described herein can also be delivered in a controlled release system. In one embodiment, a pump may be used (see, Sefton, 1987, CRC Crit. Ref. Biomed. Eng. 14:201; Buchwald et al. Surgery, 1980 88, 507; Saudek et al. *N. Engl. J. Med,* 1989, 321, (574). Additionally, a controlled release system can be placed in proximity of the therapeutic target. (See, Goodson, *Medical Applications of Controlled Release,* 1984, Vol. 2, pp. 115-138). The pharmaceutical compositions described herein can also contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents; fillers such as microcrystalline cellulose, silicified microcrystalline cellulose, pregelatinized starch, lactose, dicalcium phosphate, or compressible sugar; binders such as hypromellose, povidone or starch paste; disintegrants such as croscarmellose sodium, crospovidone or sodium starch glycolate; a surfactant such as sodium lauryl sulfate and/or lubricants and processing aides such as talc, sodium croscarmellose, corn starch, or alginic acid; binding agents, for example starch, gelatin, polyvinyl-pyrrolidone or acacia, and lubricating agents, for example magnesium stearate, stearic acid or colloidal silicion dioxide and, optionally, talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil. The capsule and tablet dosage forms may be prepared by various processing techniques including dry blending and wet granulation techniques. In the dry blending method of manufacture the drug substance may be incorporated into the dosage form by dry blending with the excipients followed by encapsulation into a capsule shell or compression into a tablet form. The dry blending operation may be approached in a stepwise manner and include screening steps between the blending steps to facilitate formation of a uniform blend. In the wet granulation method of manufacture the drug substance may be added to the dry excipients and mixed prior to the addition of the binder solution or the drug substance may be dissolved and added as a solution as part of granulation. In the wet granulation technique the surfactant, if used, may be added to the dry excipients or added to the binder solution and incorporated in a solution form. Capsule dosage forms may also be manufactured by dissolving the drug substance in a material that can be filled into and is compatible with hard gelatin capsule shells that can be subsequently banded and sealed. Capsule and tablet dosage forms may also be produced by dissolving the drug substance in a material such a molten form of a high molecular weight polyethylene glycol and cooling to a solid form, milling and incorporating this material into conventional capsule and tablet manufacturing processes.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

Pharmaceutical compositions may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening agents, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

Pharmaceutical compositions may be in the form of a sterile injectable aqueous solution. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion. The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutical compositions may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing a compound or composition of the invention are useful for topical administration. As used herein, topical application can include mouth washes and gargles.

Pharmaceutical compositions may be administered in intranasal form via topical use of suitable intranasal vehicles and delivery devices, or via transdermal routes, using those forms of transdermal skin patches well known to those of ordinary skill in the art.

The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Methods of preparing various pharmaceutical compositions with a specific amount of active compound are known, or will be apparent, to those skilled in this art. To be administered in the form of transdermal delivery, the dosage form will, of course, be continuous rather than intermittent throughout the dosage regimen.

Doses

The amount of pharmaceutical compositions administered will firstly be dependent on the mammal being treated. In the instances where pharmaceutical compositions are administered to a human subject, the daily dosage will normally be determined by the prescribing physician with the dosage generally varying according to the age, sex, diet, weight, general health and response of the individual patient, the severity of the patient's symptoms, the precise indication or condition being treated, the severity of the indication or condition being treated, time of administration, route of administration, the disposition of the composition, rate of excretion, drug combination, and the discretion of the prescribing physician. Also, the route of administration may vary depending on the condition and its severity. The pharmaceutical composition may be in unit dosage form. In such form, the preparation is subdivided into unit doses containing appropriate quantities of the active component, e.g., an effective amount to achieve the desired purpose. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. The amount and frequency of administration of the compounds described herein, and if applicable other therapeutic agents and/or therapies, will be regulated according to the judgment of the attending clinician (physician) considering such factors as described above. Thus the amount of pharmaceutical composition to be administered may vary widely. Administration may occur in an amount of between about 0.001 mg/kg of body weight to about 100 mg/kg of body weight per day (administered in single or divided doses), or at least about 0.1 mg/kg of body weight per day. A particular therapeutic dosage can include, e.g., from about 0.01 mg to about 7000 mg of compound, or, e.g., from about 0.05 mg to about 2500 mg. The quantity of active compound in a unit dose of preparation may be varied or adjusted from about 0.1 mg to 1000 mg, from about 1 mg to 300 mg, or 10 mg to 200 mg, according to the particular application. In some instances, dosage levels below the lower limit of the aforesaid range may be more than adequate, while in other cases still larger doses may be employed without causing any harmful side effect, e.g. by dividing such larger doses into several small doses for administration throughout the day. The amount administered will vary depending on the particular $IC_{50}$ value of the compound used. In combinational applications in which the compound is not the sole therapy, it may be possible to administer lesser amounts of compound and still have therapeutic or prophylactic effect.

Additional dosing is provided throughout the specification and claims.

Dosage Forms

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules, including lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 18th Edition (1990).

Combination Therapies

The compounds described herein or a pharmaceutically acceptable salt, solvate, polymorph, ester, amide, tautomer, prodrug, hydrate, or derivative thereof may be administered as a sole therapy. The compounds described herein or a pharmaceutically acceptable salt, solvate, polymorph, ester, amide, tautomer, prodrug, hydrate, or derivative thereof may also be administered in combination with another therapy or therapies.

Also described herein is N—(S)-(3,4-difluoro-2-(2-fluoro-4-iodophenylamino)-6-methoxyphenyl)-1-(2,3-dihydroxypropyl)cyclopropane-1-sulfonamide (Form A) which may be administered as a sole therapy. Crystalline polymorph form A of N—(S)-(3,4-difluoro-2-(2-fluoro-4-iodophenylamino)-6-methoxyphenyl)-1-(2,3-dihydroxypropyl)cyclopropane-1-sulfonamide may also be administered in combination with another therapy or therapies.

By way of example only, if one of the side effects experienced by a patient upon receiving one of the compounds described herein is hypertension, then it may be appropriate to administer an anti-hypertensive agent in combination with the compound. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Other therapies include, but are not limited to administration of other therapeutic agents, radiation therapy or both. In the instances where the compounds described herein are administered with other therapeutic agents, the compounds described herein need not be administered in the same pharmaceutical composition as other therapeutic agents, and may, because of different physical and chemical characteristics, be administered by a different route. For example, the compounds/compositions may be administered orally to generate and maintain good blood levels thereof, while the other therapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician. The particular choice of compound (and where appropriate, other therapeutic agent and/or radiation) will depend upon the diagnosis of the attending physicians and their judgment of the condition of the patient and the appropriate treatment protocol. Other therapeutic agents may include chemotherapeutic agents, such as anti-tumor substances, for example those selected from, mitotic inhibitors, for example vinblastine; alkylating agents, for example cis-platin, carboplatin and cyclophosphamide; anti-metabolites, for example 5-fluorouracil, cytosine arabinside and hydroxyurea, or, for example, an anti-metabolite disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example, interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl) propionanilide). Such conjoint treatment may be achieved by way of the simultaneous, sequential or separate dosing of the individual components of treatment.

The compounds and compositions described herein (and where appropriate chemotherapeutic agent and/or radiation) may be administered concurrently (e.g., simultaneously, essentially simultaneously or within the same treatment protocol) or sequentially, depending upon the nature of the disease, the condition of the patient, and the actual choice of chemotherapeutic agent and/or radiation to be administered in conjunction (i.e., within a single treatment protocol) with the compound/composition.

In combinational applications and uses, the compound/composition and the chemotherapeutic agent and/or radiation need not be administered simultaneously or essentially simultaneously, and the initial order of administration of the compound/composition, and the chemotherapeutic agent and/or radiation, may not be important. Thus, the compounds/compositions of the invention may be administered first followed by the administration of the chemotherapeutic agent and/or radiation; or the chemotherapeutic agent and/or radiation may be administered first followed by the administration of the compounds/compositions of the invention. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of the compounds/compositions of the invention followed, where determined advantageous, by the administration of the chemotherapeutic agent and/or radiation, and so on until the treatment protocol is complete. Thus, in accordance with experience and knowledge, the practicing physician can modify each protocol for the administration of a compound/composition for treatment according to the individual patient's needs, as the treatment proceeds. The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Specific, non-limiting examples of possible combination therapies include use of the compounds of the invention with agents found in the following pharmacotherapeutic classifications as indicated below. These lists should not be construed to be closed, but should instead serve as illustrative examples common to the relevant therapeutic area at present. Moreover, combination regimens may include a variety of routes of administration and should include oral, intravenous, intraocular, subcutaneous, dermal, and inhaled topical.

For the treatment of oncologic diseases, proliferative disorders, and cancers, compounds according to the present invention may be administered with an agent selected from the group comprising: aromatase inhibitors, antiestrogen, anti-androgen, corticosteroids, gonadorelin agonists, topoisomerase 1 and 2 inhibitors, microtubule active agents, alkylating agents, nitrosoureas, antineoplastic antimetabolites, platinum containing compounds, lipid or protein kinase targeting agents, IMiDs, protein or lipid phosphatase targeting agents, anti-angiogenic agents, Akt inhibitors, IGF-I inhibitors, FGF3 modulators, mTOR inhibitors, Smac mimetics, HDAC inhibitors, agents that induce cell differentiation, bradykinin 1 receptor antagonists, angiotensin II antagonists, cyclooxygenase inhibitors, heparanase inhibitors, lymphokine inhibitors, cytokine inhibitors, IKK inhibitors, P38MAPK inhibitors, ARRY-797, HSP90 inhibitors, multikinase inhibitors, bisphosphanates, rapamycin derivatives, anti-apoptotic pathway inhibitors, apoptotic pathway agonists, PPAR agonists, RAR agonists, inhibitors of Ras isoforms, telomerase inhibitors, protease inhibitors, metalloproteinase inhibitors, aminopeptidase inhibitors, SHIP activators—AQX-MN100, Humax-CD20 (ofatumumab), CD20 antagonists, IL2-diptheria toxin fusions.

For the treatment of oncologic diseases, proliferative disorders, and cancers, compounds according to the present invention may be administered with an agent selected from the group comprising: dacarbazine (DTIC), actinomycins $C_2$, $C_3$, D, and $F_1$, cyclophosphamide, melphalan, estramustine, maytansinol, rifamycin, streptovaricin, doxorubicin, daunorubicin, epirubicin, idarubicin, detorubicin, caminomycin, idarubicin, epirubicin, esorubicin, mitoxantrone, bleomycins A, $A_2$, and B, camptothecin, Irinotecan®, Topotecan®, 9-aminocamptothecin, 10,11-methylenedioxycamptothecin, 9-nitrocamptothecin, bortezomib, temozolomide, TAS103, NPI0052, combretastatin, combretastatin A-2, combretastatin A-4, calicheamicins, neocarcinostatins, epothilones A B, C, and semi-synthetic variants, Herceptin®, Rituxan®, CD40 antibodies, asparaginase, interleukins, interferons, leuprolide, and pegaspargase, 5-fluorouracil, fluorodeoxyuridine, ptorafur, 5'-deoxyfluorouridine, UFT, MITC, S-1 capecitabine, diethylstilbestrol, tamoxifen, toremefine, tolmudex, thymitaq, flutamide, fluoxymesterone, bicalutamide, finasteride, estradiol, trioxifene, dexamethasone, leuproelin acetate, estramustine, droloxifene, medroxyprogesterone, megesterol acetate, aminoglutethimide, testolactone, testosterone, diethylstilbestrol, hydroxyprogesterone, mitomycins A, B and C, porfiromycin, cisplatin, carboplatin, oxaliplatin, tetraplatin, platinum-DACH, ormaplatin, thalidomide, lenalidomide, CI-973, telomestatin, CHIR258, Rad 001, SAHA, Tubacin, 17-AAG, sorafenib, JM-216, podophyllotoxin, epipodophyllotoxin, etoposide, teniposide, Tarceva®, Iressa®, Imatinib®, Miltefosine®, Perifosine®, aminopterin, methotrexate, methopterin, dichloro-methotrexate, 6-mercaptopurine, thioguanine, azattuoprine, allopurinol, cladribine, fludarabine, pentostatin, 2-chloroadenosine, deoxycytidine, cytosine arabinoside, cytarabine, azacitidine, 5-azacytosine, gencitabine, 5-azacytosine-arabinoside, vincristine, vinblastine, vinorelbine, leurosine, leurosidine and vindesine, paclitaxel, taxotere and docetaxel.

For the treatment of inflammatory diseases or pain, compounds and pharmaceutically acceptable salts of the compounds according to the present invention may be administered with an agent selected from the group comprising: corticosteroids, non-steroidal anti-inflammatories, muscle relaxants and combinations thereof with other agents, anaesthetics and combinations thereof with other agents, expectorants and combinations thereof with other agents, antidepressants, anticonvulsants and combinations thereof; antihypertensives, opioids, topical cannabinoids, capsaicin, betamethasone dipropionate (augmented and nonatigeranted), betamethasone valerate, clobetasol propionate, prednisone, methyl prednisolone, diflorasone diacetate, halobetasol propionate, amcinonide, dexamethasone, dexosimethasone, fluocinolone acetononide, fluocinonide, halocinonide, clocortalone pivalate, dexosimetasone, flurandrenalide, salicylates, ibuprofen, ketoprofen, etodolac, diclofenac, meclofenamate sodium, naproxen, piroxicam, celecoxib, cyclobenzaprine, baclofen, cyclobenzaprine/ lidocaine, baclofen/cyclobenzaprine, cyclobenzaprine/ lidocaine/ketoprofen, lidocaine, lidocaine/deoxy-D-glucose, prilocalne, EMLA Cream (Eutectic Mixture of Local Anesthetics (lidocaine 2.5% and prilocalne 2.5%), guaifenesin, guaifenesin/ketoprofen/cyclobenzaprine, amitryptiline, doxepin, desipramine, imipramine, amoxapine, clomipramine, nortriptyline, protriptyline, duloxetine, mirtazepine, nisoxetine, maprotiline, reboxetine, fluoxetine, fluvoxamine, carbamazepine, felbamate, lamotrigine, topiramate, tiagabine, oxcarbazepine, carbamezipine, zonisamide, mexiletine, gabapentin/clonidine, gabapentin/carbamazepine, carbamazepine/cyclobenzaprine, antihypertensives including clonidine, codeine, loperamide, tramadol, morphine, fentanyl, oxycodone, hydrocodone, levorphanol, butorphanol, menthol, oil of wintergreen, camphor, eucalyptus oil, turpentine oil; CB1/CB2 ligands, acetaminophen, infliximab, nitric oxide synthase inhibitors, particularly inhibitors of inducible nitric oxide synthase, PDE4 inhibitors—similar mechanism to Ibudilast (AV-411), CDC-801, JNK inhibitors—CC-401, Combination TNF/PDE4 inhibitors—CDC-998, IL1 antagonists e.g. Anakinra Kineret, AMG 108, (mAb) that targets IL-1, SHIP activators—AQX-MN100, CS antagonists, C5a inhibitors, Pexelizumab, Pyrimidine synthesis inhibitors, lymphokine inhibitors, cytokine inhibitors, IKK inhibitors, P38MAPK inhibitors, ARRY-797, HSP90 inhibitors, multlikinase inhibitors, bisphosphanates, PPAR agonists, Cox1 and cox 2 inhibitors, Anti-CD4 therapy, B-cell inhibitors, COX/LOX dual inhibitors, Immunosuppressive agents, iNOS inhibitors, NSAIDs, sPLA2 inhibitors, Colchicine, allopurinol, oxypurinol, Gold, Ridaura Auranofin, febuxostat, Puricase, PEG-uricase formulations, Benzbromarone, Long-acting beta-2 agonists (LABAs), salmeterol (Serevent Diskus) and formoterol (Foradil), Leukotriene modifiers include montelukast (Singulair) and zafirlukast (Accolate). Inhaled cromolyn (Intal) or nedocromil (Tilade), Theophylline. Short-acting beta-2 agonists, Ipratropium (Atrovent), Immunotherapy-(Allergy-desensitization shots), Anti-IgE monoclonal antibodies—Xolair, Common DMARDs include hydroxychloroquine (Plaquenil), the gold compound auranofin (Ridaura), sulfasalazine (Azulfidine), minocycline (Dynacin, Minocin) and methotrexate (Rheumatrex), leflunomide (Arava), azathioprine (Imuran), cyclosporine (Neoral, Sandimmune) and cyclophosphamide (Cytoxan), Antibiotics, CD80 antagonists, costimulatory factor antagonists, Humax-CD20 (ofatumumab); CD20 antagonists, MEK inhibitors, NF kappa B inhibitors, anti B-cell antibodies, denosumab, mAb that specifically targets the receptor activator of nuclear factor kappa B ligand (RANKL). IL17 inactivating anti-bodies, IL-17 receptor antagonists/inhibitors, CTLA inhibitors, CD20 inhibitors, soluble VEGFR-1 receptors, anti-VEGFR-1 receptor antibodies, anti-VEGF antibodies, integrin receptor antagonist, Selectin inhibitors, P-selectin and E-selectin inhibitors, Phospholipase A2 Inhibitors, Lipoxygenase Inhibitors, RANKL and RANK antagonists/antibodies, Osteoprotegerin antagonists, Lymphotoxin inhibitors, B-lymphocyte stimulator, MCP-1 inhibitors, MIF inhibitors, inhibitors of: CD2, CD3, CD4 CD25, CD40 and CD40 Ligand CD152 (CTLA4), Macrolide immunosuppressants, Selective inhibitors of nucleotide metabolism, Inhibitors of chemotaxis, CXC receptor and CXC ligand inhibitors, Chemokine Antagonists, leukocyte chemotaxis inhibitors Adhesion Molecule blockers, Selecting Lymphocyte Function Antigen-1 (LFA-1, CD11a) antagonists, Very Late Antigen-4 (VLA-4) antagonists, Matrix Metalloprotease Inhibitors, Elastase Inhibitors, Cathepsin Inhibitors.

For the treatment of ophthalmologic disorders and diseases of the eye, compounds and pharmaceutically acceptable salts of the compounds according to the present invention may be administered with an agent selected from the group comprising: beta-blockers, carbonic anhydrase inhibitors, .alpha.- and .beta.-adrenergic antagonists including al-adrenergic antagonists, .alpha.2 agonists, miotics, prostaglandin analogs, corticosteroids, and immunosuppressant agents.

For the treatment of ophthalmologic disorders and diseases of the eye, compounds pharmaceutically acceptable salts of the compounds according to the present invention may be administered with an agent selected from the group comprising: timolol, betaxolol, levobetaxolol, carteolol, levobunolol, propranolol, brinzolamide, dorzolamide, nipradilol, iopidine, brimonidine, pilocarpine, epinephrine, latanoprost, travoprost, bimatoprost, unoprostone, dexamethasone, prednisone, methylprednisolone, azathioprine, cyclosporine, and immunoglobulins.

For the treatment of autoimmune disorders, compounds pharmaceutically acceptable salts of the compounds according to the present invention may be administered with an agent selected from the group comprising: corticosteroids, immunosuppressants, prostaglandin analogs and antimetabolites.

For the treatment of autoimmune disorders, compounds according to the present invention may be administered with an agent selected from the group comprising: dexamethasome, prednisone, methylprednisolone, azathioprine, cyclosporine, immunoglobulins, latanoprost, travoprost, bimatoprost, unoprostone, infliximab, rutuximab, methotrexate, non-steroidal anti-inflammatories, muscle relaxants and combinations thereof with other agents, anaesthetics and combinations thereof with other agents, expectorants and combinations thereof with other agents, antidepressants, anticonvulsants and combinations thereof; antihypertensives, opioids, topical cannabinoids, and other agents, such as capsaicin, betamethasone dipropionate (augmented and non-augemnted), betamethasone valerate, clobetasol propionate, prednisone, methyl prednisolone, diflorasone diacetate, halobetasol propionate, ameinonide, dexamethasone, dexosimethasone, fluocinolone acetononide, fluocinonide, halocinonide, clocortalone pivalate, dexosimetasone, flurandrenalide, salicylates, ibuprofen, ketoprofen, etodolac, diclofenac, meclofenamate sodium, naproxen, piroxicam, celecoxib, cyclobenzaprine, baclofen, cyclobenzaprine/lidocaine, baclofen/cyclobenzaprine, cyclobenzaprine/lidocaine/ketoprofen, lidocaine, lidocaine/deoxy-D-glucose, prilocalne, EMLA Cream (Eutectic Mixture of Local. Anesthetics (lidocaine 2.5% and prilocalne 2.5%), guaifenesin, guaifenesin/ketoprofen/cyclobenzaprine, amitryptiline, doxepin, desipramine, imipramine, amoxapine, clomipramine, nortriptyline, protriptyline, duloxetine, mirtazepine, nisoxetine, maprotiline, reboxetine, fluoxetine, fluvoxamine, carbamazepine, felbamate, lamotrigine, topiramate, tiagabine, oxcarbazepine, carbamezipine, zonisamide, mexiletine, gabapentin/clonidine, gabapentin/carbamazepine, carbamazepine/cyclobenzaprine, antihypertensives including clonidine, codeine, loperamide, tramadol, morphine, fentanyl, oxycodone, hydrocodone, levorphanol, butorphanol, menthol, oil of wintergreen, camphor, eucalyptus oil, turpentine oil; CB1/CB2 ligands, acetaminophen, infliximab; nitric oxide synthase inhibitors, particularly inhibitors of inducible nitric oxide synthase; and other agents, such as capsaicin. PDE4 inhibitors—similar mechanism to Ibudilast (AV-411), CDC-801, INK inhibitors—CC-401, Combination TNF/PDE4 inhibitors—CDC-998, IL1 antagonists e.g. Anakinra Kineret, AMG 108, (mAb) that targets IL-1, SHIP activators—AQX-MN100, CS antagonists, C5a inhibitors, Pexelizumab, Pyrimidine synthesis inhibitors, lymphokine inhibitors, cytokine inhibitors, IKK inhibitors, P38MAPK inhibitors, ARRY-797, HSP90 inhibitors, multlikinase inhibitors, bisphosphanates, PPAR agonists, Cox1 and cox 2 inhibitors, Anti-CD4 therapy, B-cell inhibitors, COX/LOX dual inhibitors, Immunosuppressive agents, iNOS inhibitors, NSAIDs, sPLA2 inhibitors, Colchicine, allopurinol, oxypurinol, Gold, Ridaura Auranofin, febuxostat, Puricase, PEG-uricase formulations, Benzbromarone, Long-acting beta-2 agonists (LABAs), salmeterol (Serevent Diskus) and formoterol (Foradil), Leukotriene modifiers include montelukast (Singulair) and zafirlukast (Accolate). Inhaled cromolyn (Intal) or nedocromil (Tilade), Theophylline. Short-acting beta-2 agonists, Ipratropium (Atrovent), Immunotherapy-(Allergy-desensitization shots), Anti-IgE monoclonal antibodies—Xolair, Common DMARDs include hydroxychloroquine (Plaquenil), the gold compound auranofin (Ridaura), sulfasalazine (Azulfidine), minocycline (Dynacin, Minocin) and methotrexate (Rheumatrex), leflunomide (Arava), azathioprine (Imuran), cyclosporine (Neoral, Sandimmune) and cyclophosphamide (Cytoxan), Antibiotics, CD80 antagonists, costimulatory factor antagonists, Humax-CD20 (ofatumumab); CD20 antagonists, MEK inhibitors, NF kappa B inhibitors, anti B-cell antibodies, denosumab, mAb that specifically targets the receptor activator of nuclear factor kappa B ligand (RANKL). IL17 inactivating anti-bodies, IL-17 receptor antagonists/inhibitors, CTLA inhibitors, CD20 inhibitors, soluble VEGFR-1 receptors, anti-VEGFR-1 receptor antibodies, anti-VEGF antibodies, integrin receptor antagonist, Selectin inhibitors, P-selectin and E-selectin inhibitors, Phospholipase A2 Inhibitors, Lipoxygenase Inhibitors, RANKL and RANK antagonists/antibodies, Osteoprotegerin antagonists, Lymphotoxin inhibitors, B-lymphocyte stimulator, MCP-1 inhibitors, MIF inhibitors, inhibitors of: CD2, CD3, CD4 CD25, CD40 and CD40 Ligand CD252 (CTLA4), Macrolide immunosuppressants, Selective inhibitors of nucleotide metabolism, Inhibitors of chemotaxis, CXC receptor and CXC ligand inhibitors, Chemokine Antagonists, leukocyte chemotaxis inhibitors Adhesion Molecule blockers, Selectins Lymphocyte Function Antigen-1 (LFA-1, CD11a) antagonists, Very Late Antigen-4 (VLA-4) antagonists, Matrix Metalloprotease Inhibitors, Elastase Inhibitors, Cathepsin Inhibitors.

For the treatment of metabolic disorders, compounds and pharmaceutically acceptable salts of the compounds according to the present invention may be administered with an agent selected from the group comprising: insulin, insulin derivatives and mimetics, insulin secretagogues, insulin sensitizers, biguanide agents, alpha-glucosidase inhibitors, insulinotropic sulfonylurea receptor ligands, protein tyrosine phosphatase-IB (PTP-1B) inhibitors, GSK3 (glycogen synthase kinase-3) inhibitors, GLP-1 (glucagon like peptide-1), GLP-1 analogs, DPPIV (dipeptidyl peptidase IV) inhibitors, RXR ligands sodium-dependent glucose co-transporter inhibitors, glycogen phosphorylase A inhibitors, an AGE breaker, PPAR modulators, LXR and FXR modulators, non-glitazone type PPARS agonist, selective glucocorticoid antagonists, metformin, Glipizide, glyburide, Amaryl, meglitinides, nateglinide, repaglinide, PT-112, SB-517955, SB4195052, SB-216763, NN-57-05441, NN-57-05445, GW-0791, AGN-.sup.194.sup.204, T-1095, BAY 83401, acarbose Exendin-4, DPP728, LAF237, vildagliptin, MK-0431, saxagliptin, GSK23A, pioglitazone, rosiglitazone, (R)-1-{4-[5-methyl-2-(4-trifluoromethyl-phenyl)-oxazol-4-ylmethoxyl]-benzenesulfonyl}2,3-dihydro-1H-indole-2-carboxylic acid described in the patent application WO 03/043985, as compound 19 of Example 4, and G1-262570.

Diseases

Described herein are methods of treating a disease in an individual suffering from said disease comprising administering to said individual an effective amount of a compound of formula I or a pharmaceutically acceptable salt, solvate, polymorph, ester, amide, tautomer, prodrug, hydrate, or derivative thereof.

Also described herein are methods of treating a disease or disorder in an individual suffering from said disease or disorder comprising administering to said individual an effective amount of N—(S)-(3,4-difluoro-2-(2-fluoro-4-iodophenylamino)-6-methoxyphenyl)-1-(2,3-dihydroxypropyl)cyclopropane-1-sulfonamide (Form A). The invention extends to the use of N—(S)-(3,4-difluoro-2-(2-fluoro-4-iodophenylamino)-6-methoxyphenyl)-1-(2,3-dihydroxypropyl)cyclopropane-1-sulfonamide (Form A) in the manufacture of a medicament for treating a disease or disorder.

In some embodiments, the invention relates to the prophylaxis or treatment of any disease or disorder in which MEK kinase plays a role including, without limitation: oncologic, hematologic, inflammatory, ophthalmologic, neurological, immunologic, cardiovascular, and dermatologic diseases as well as diseases caused by excessive or unregulated pro-inflammatory cytokine production including for example excessive or unregulated TNF, IL-1, IL-6 and IL-8 production in a human, or other mammal. The invention extends to such a use and to the use of the compounds for the manufacture of a medicament for treating such cytokine-mediated diseases or disorders. Further, the invention extends to the administration to a human an effective amount of a MEK inhibitor for treating any such disease or disorder.

Diseases or disorders in which MEK kinase plays a role, either directly or via pro-inflammatory cytokines including the cytokines TNF, IL-1, IL-6 and IL-8, include, without limitation: dry eye, glaucoma, autoimmune diseases, inflammatory diseases, destructive-bone disorders, proliferative disorders, neurodegenerative disorders, viral diseases, allergies, infectious diseases, heart attacks, angiogenic disorders, reperfusion/ischemia in stroke, vascular hyperplasia, organ hypoxia, cardiac hypertrophy, thrombin-induced platelet aggregation, and conditions associated with prostaglandin endoperoxidase synthetase-2 (COX-2).

In certain aspects of the invention, the disease is a hyperproliferative condition of the human or animal body, including, but not limited to cancer, hyperplasias, restenosis, inflammation, immune disorders, cardiac hypertrophy, atherosclerosis, pain, migraine, angiogenesis-related conditions or disorders, proliferation induced after medical conditions, including but not limited to surgery, angioplasty, or other conditions.

In further embodiments, said hyperproliferative condition is selected from the group consisting of hematologic and nonhematologic cancers. In yet further embodiments, said hematologic cancer is selected from the group consisting of multiple myeloma, leukemias, and lymphomas. In yet further embodiments, said leukemia is selected from the group consisting of acute and chronic leukemias. In yet further embodiments, said acute leukemia is selected from the group consisting of acute lymphocytic leukemia (ALL) and acute nonlymphocytic leukemia (ANLL). In yet further embodiments, said chronic leukemia is selected from the group consisting of chronic lymphocytic leukemia (CLL) and chronic myelogenous leukemia (CML). In further embodiments, said lymphoma is selected from the group consisting of Hodgkin's lymphoma and non-Hodgkin's lymphoma. In further embodiments, said hematologic cancer is multiple myeloma. In other embodiments, said hematologic cancer is of low, intermediate, or high grade. In other embodiments, said nonhematologic cancer is selected from the group consisting of: brain cancer, cancers of the head and neck, lung cancer, breast cancer, cancers of the reproductive system, cancers of the digestive system, pancreatic cancer, and cancers of the urinary system. In further embodiments, said cancer of the digestive system is a cancer of the upper digestive tract or colorectal cancer. In further embodiments, said cancer of the urinary system is bladder cancer or renal cell carcinoma. In further embodiments, said cancer of the reproductive system is prostate cancer.

Additional types of cancers which may be treated using the compounds and methods described herein include: cancers of oral cavity and pharynx, cancers of the respiratory system, cancers of bones and joints, cancers of soft tissue, skin cancers, cancers of the genital system, cancers of the eye and orbit, cancers of the nervous system, cancers of the lymphatic system, and cancers of the endocrine system. In certain embodiments, these cancer s may be selected from the group consisting of: cancer of the tongue, mouth, pharynx, or other oral cavity; esophageal cancer, stomach cancer, or cancer of the small intestine; colon cancer or rectal, anal, or anorectal cancer; cancer of the liver, intrahepatic bile duct, gallbladder, pancreas, or other biliary or digestive organs; laryngeal, bronchial, and other cancers of the respiratory organs; heart cancer, melanoma, basal cell carcinoma, squamous cell carcinoma, other non-epithelial skin cancer; uterine or cervical cancer; uterine corpus cancer; ovarian, vulvar, vaginal, or other female genital cancer; prostate, testicular, penile or other male genital cancer; urinary bladder cancer; cancer of the kidney; renal, pelvic, or urethral cancer or other cancer of the genito-urinary organs; thyroid cancer or other endocrine cancer; chronic lymphocytic leukemia; and cutaneous T-cell lymphoma, both granulocytic and monocytic.

Yet other types of cancers which may be treated using the compounds and methods described herein include: adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, hemangioblastoma, hepatocellular carcinoma, hepatoma, Kaposi's sarcoma, large cell carcinoma, leiomyosarcoma, liposarcoma, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, parathyroid tumors, pheochromocytoma, pinealoma, plasmacytomas, retinoblastoma, rhabdomyosarcoma, sebaceous gland carcinoma, seminoma, skin cancers, melanoma, small cell lung carcinoma, squamous cell carcinoma, sweat gland carcinoma, synovioma, thyroid cancer, uveal melanoma, and Wilm's tumor.

Also described are methods for the treatment of a hyperproliferative disorder in a mammal that comprise administering to said mammal a therapeutically effective amount of a compound of formula I, or a pharmaceutically acceptable salt, solvate, polymorph, ester, amide, tautomer, prodrug, hydrate, or derivative thereof, in combination with an anti-tumor agent. In some embodiments, the anti-tumor agent is selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, anti-androgens, SHIP activators—AQX-MN100, Humax-CD20 (ofatumumab), CD20 antagonists, IL2-diptheria toxin fusions.

The disease to be treated using the compounds, compositions and methods described herein may be a hematologic disorder. In certain embodiments, said hematologic disorder is selected from the group consisting of sickle cell anemia, myelodysplastic disorders (MDS), and myeloproliferative disorders. In further embodiments, said myeloproliferative disorder is selected from the group consisting of polycythemia vera, myelofibrosis and essential thrombocythemia.

The compounds, compositions and methods described herein may be useful as anti-inflammatory agents with the additional benefit of having significantly less harmful side effects. The compounds, compositions and methods described herein are useful to treat arthritis, including but not limited to rheumatoid arthritis, spondyloarthropathies, ankylosing spondylitis, gout, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis. The compounds, compositions and methods described herein are also useful in treating osteoporosis and other related bone disorders. These compounds, compositions and methods described herein are also useful to treat gastrointestinal conditions such as reflux esophagitis, diarrhea, inflammatory bowel disease, Crohn's disease, gastritis, irritable bowel syndrome and ulcerative colitis. The compounds, compositions and methods described herein may also be used in the treatment of pulmonary inflammation, such as that associated with viral infections and cystic fibrosis. In addition, the compounds, compositions and methods described herein are also useful in organ transplant patients either alone or in combination with conventional immunomodulators. Yet further, the compounds, compositions and methods described herein are useful in the treatment of pruritis and vitaligo. In particular, compounds, compositions and methods described herein are useful in treating the particular inflammatory disease rheumatoid arthritis.

Further inflammatory diseases which may be prevented or treated include, without limitation: asthma, allergies, respiratory distress syndrome or acute or chronic pancreatitis. Furthermore, respiratory system diseases may be prevented or treated including but not limited to chronic obstructive pulmonary disease, and pulmonary fibrosis. In addition, MEK kinase inhibitors described herein are also associated with prostaglandin endoperoxidase synthetase-2 (COX-2) production. Pro-inflammatory mediators of the cyclooxygenase pathway derived from arachidonic acid, such as prostaglandins, are produced by inducible COX-2 enzyme. Regulation of COX-2 would regulate these pro-inflammatory mediators, which affect a wide variety of cells and are important and critical inflammatory mediators of a wide variety of disease states and conditions. In particular, these inflammatory mediators have been implicated in pain, such as in the sensitization of pain receptors, and edema. Accordingly, additional MEK kinase-mediated conditions which may be prevented or treated include edema, analgesia, fever and pain such as neuromuscular pain, headache, dental pain, arthritis pain and pain caused by cancer.

Further, the disease to be treated by the compounds, compositions and methods described herein may be an ophthalmologic disorder. Ophthalmologic diseases and other diseases in which angiogenesis plays a role in pathogenesis, may be treated or prevented and include, without limitation, dry eye (including Sjogren's syndrome), macular degeneration, closed and wide angle glaucoma, retinal ganglion degeneration, occular ischemia, retinitis, retinopathies, uveitis, ocular photophobia, and of inflammation and pain associated with acute injury to the eye tissue. The compounds, compositions and methods described herein are useful to treat glaucomatous retinopathy and/or diabetic retinopathy. The compounds, compositions and methods described herein are also useful to treat post-operative inflammation or pain as from ophthalmic surgery such as cataract surgery and refractive surgery. In further embodiments, said ophthalmologic disorder is selected from the group consisting of dry eye, closed angle glaucoma and wide angle glaucoma.

Further, the disease to be treated by the compounds, compositions and methods described herein may be an autoimmune disease. Autoimmune diseases which may be prevented or treated include, but are not limited to: rheumatoid arthritis, inflammatory bowel disease, inflammatory pain, ulcerative colitis, Crohn's disease, periodontal disease, temporomandibular joint disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, chronic active hepatitis, myasthenia gravis, atopic dermatitis, graft vs. host disease, and psoriasis. Inflammatory diseases which may be prevented or treated include, but are not limited to: asthma, allergies, respiratory distress syndrome or acute or chronic pancreatitis. In particular, compounds, compositions and methods described herein are useful in treating the particular autoimmune diseases rheumatoid arthritis and multiple sclerosis.

Further, the disease to be treated by the compounds, compositions and methods described herein may be a dermatologic disorder. In certain embodiments, said dermatologic disorder is selected from the group including, without limitation, melanoma, basel cell carcinoma, squamous cell carcinoma, and other non-epithelial skin cancer as well as psoriasis and persistent itch, and other diseases related to skin and skin structure, may be treated or prevented with MEK kinase inhibitors of this invention.

Metabolic diseases which may be treated or prevented include, without limitation, metabolic syndrome, insulin resistance, and Type 1 and Type 2 diabetes. In addition, the compositions described herein may be useful to treat insulin resistance and other metabolic disorders such as atherosclerosis that are typically associated with an exaggerated inflammatory signaling.

The compounds, compositions and methods described herein are also useful in treating tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephritis, nephrotic syndrome, Behcet's syndrome, polymyositis, gingivitis, periodontis, hypersensitivity, swelling occurring after injury, ischemias including myocardial ischemia, cardiovascular ischemia, and ischemia secondary to cardiac arrest, and the like. The compounds, compositions and methods described herein may also be useful to treat allergic rhinitis, respiratory distress syndrome, endotoxin shock syndrome, and atherosclerosis.

Further, the disease to be treated by the compounds, compositions and methods described herein may be a cardiovascular condition. In certain embodiments, said cardiovascular condition is selected from the group consisting of atherosclerosis, cardiac hypertrophy, idiopathic cardiomyopathies, heart failure, angiogenesis-related conditions or disorders, and proliferation induced after medical conditions, including, but not limited to restenosis resulting from surgery and angioplasty.

Further, the disease to be treated by the compounds, compositions and methods described herein may be a neurological disorder. In certain embodiments, said neurologic disorder is selected from the group consisting of Parkinson's disease, Alzheimer's disease, Alzheimer's dementia, and central nervous system damage resulting from stroke, ischemia and trauma. In other embodiments, said neurological disorder is selected from the group consisting of epilepsy, neuropathic pain, depression and bipolar disorders.

Further, the disease to be treated by the compounds, compositions and methods described herein may cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, the compounds and compositions are for the treatment of a non-cancerous hyperproliferative disorder such as benign hyperplasia of the skin (e.g., psoriasis), restenosis, or prostate (e.g., benign prostatic hypertrophy (BPH)).

Further, the disease to be treated by the compounds, compositions and methods described herein may pancreatitis, kidney disease (including proliferative glomerulonephritis and diabetes-induced renal disease), pain, a disease related to vasculogenesis or angiogenesis, tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, tendonitis, bursitis, sciatica, glioma, melanoma, Kaposi's sarcoma and ovarian, breast, lung, pancreatic, prostate, colon and epidermoid cancer in a mammal.

Further, the disease to be treated by the compounds, compositions and methods described herein may the prevention of blastocyte implantation in a mammal.

Patients that can be treated with the compounds described herein, or their pharmaceutically acceptable salts, solvate, polymorphs, esters, amides, tautomers, prodrugs, hydrates, or derivatives according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, and myeloproliferative disorders; bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type I (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

Kits

The compounds, compositions and methods described herein provide kits for the treatment of disorders, such as the ones described herein. These kits comprise a compound, compounds or compositions described herein in a container and, optionally, instructions teaching the use of the kit according to the various methods and approaches described herein. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

The compounds described herein can be utilized for diagnostics and as research reagents. For example, the compounds described herein, either alone or in combination with other compounds, can be used as tools in differential and/or combinatorial analyses to elucidate expression patterns of genes expressed within cells and tissues. As one non-limiting example, expression patterns within cells or tissues treated with one or more compounds are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Besides being useful for human treatment, the compounds and formulations of the present invention are also useful for veterinary treatment of companion animals (eg dogs, cats), exotic animals and farm animals (eg horses), including mammals, rodents, and the like.

The examples and preparations provided below further illustrate and exemplify the compounds of the present invention and methods of preparing such compounds. It is to be understood that the scope of the present invention is not limited in any way by the scope of the following examples and preparations.

EXAMPLES

General Exemplary Procedures for the Synthesis of Sulfonamides

Procedure A

To a solution of the amine (1 eq) in anhydrous dichloromethane (3 mL/mmole) was added anhydrous triethylamine (5 eq). To this solution was added the sulfonyl chloride (1 eq) and the solution was stirred at room temperature for 16 h. The solvent was evaporated and the residue was purified by flash column chromatography on silica.

Procedure B

To a stirred solution of the amine (1 eq) in anhydrous pyridine (5 ml/mmole) was added the sulfonyl chloride (1-5 eq). The reaction mixture was stirred at 40° C. for 48 hours. The reaction mixture was partitioned with water and EtOAc. The organic layer was washed with brine, dried (MGSO$_4$) and concentrated under reduced pressure. The residue was purified by flash column chromatography on silica.

Procedure C: Substitution of the Iodo-Atom

A suspension containing 1 eq. aryl iodide, 1.5 equiv. of the boronic acid or boronic ester, 0.25 eq. PdCl$_2$(dppf) x DCM and 10 eq. anhydrous K$_2$CO$_3$ powder in a deoxygenated mixture of dioxane and water (3:1) was heated in a microwave reactor for 60 min at 115° C. It was extracted using aq. NH$_4$Cl/THF, and the organic fraction was dried using Na$_2$SO$_4$. The crude reaction products were purified using flash-column chromatography (Si, EtOAc/Hexanes, or CHCl$_3$/MeOH). Yields: 20-40%.

Procedure D: Synthesis of N-(3,4-difluoro-2-(2-fluoro-4-iodophenylamino)phenyl)-2-(alkylamino)ethanesulfonamide 2-Chloro-ethanesulfonyl chloride (0.1 ml, 1 mmol) was added to a solution of 5,6-difluoro-N$^1$-(2-fluoro-4-iodophenyl)benzene-1,2-diamine (0.364 g, 1 mmol) and triethylamine (0.28 ml, 2 mmol) in CH$_2$Cl$_2$ (5 ml) and the reaction mixture was stirred at room temperature for 16 h. Then it's treated with an excess amine (10 eq) either in solution or as a neat liquid. The reaction mixture stirred at room temperature for additional 6 h. The reaction mixture diluted with CH$_2$Cl$_2$ (10 ml) and water (10 ml). The organic layer was sequentially washed with dil. HCl (2×20 ml, 2N) and saturated NaHCO$_3$ (2×10 ml) solution. Then the CH$_2$Cl$_2$ layer dried (MgSO$_4$) and evaporated to obtain the crude product. The impure product was purified under preparative HPLC conditions to obtain the pure products in 50-60% yield.

Example 1

N-(3,4-difluoro-2-(2-fluoro-4-iodophenylamino)phenyl)methanesulfonamide

Step A: 2,3-Difluoro-N-(2-fluoro-4-iodophenyl)-6-nitroaniline

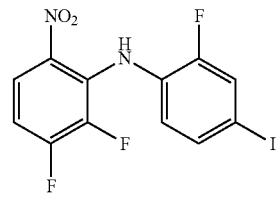 [SMILES: O=[N+]([O-])c1ccc(F)c(F)c1Nc1ccc(I)cc1F]

To a solution of 2-fluoro-4-iodoaniline (11.40 g, 47 mmol) in 100 ml anhydrous THF at 0° C., 47 ml of a 1M solution of LHMDS in THF (47 mmol) was added dropwise. The color of the solution turned dark purple. The solution was transferred via cannula to a dropping funnel, and the solution (containing the amine free base) was added in small portions to a solution of 2,3,4-trifluoronitrobenzene (8.321 g, 47.0 mmol) in anhydrous THF (50 ml) at 0° C. After completion of addition the mixture was stirred under argon at room temperature for 15 hours. The volume of the solvent was reduced, followed by extraction using ethyl acetate and brine. The organic layer was dried over sodium sulfate, the solvent was removed, and the obtained dark oil was purified by flash chromatography (EtOAc/hexane 1:5, R$_f$=0.58) yielding the crude product, which became a brown solid upon drying in vacuo (yield: 6.23 g, 33.6%): In/z=393 [M−1]$^-$.

Step B: 5,6-Difluoro-N1-(2-fluoro-4-iodophenyl)benzene-1,2-diamine

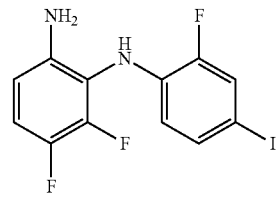

To a solution of nitro-diarylamine (6.23 g, 15.8 mmol) in 300 ml ethanol was added iron powder (13.74 g, 246 mmol) and ammonium chloride (13.59 g, 254 mmol) and the mixture was heated with stirring at 100° C. oil bath temperature for 14 hours. It was filtered and the residue washed two times with ethanol. The ethanol was removed in vacuo, and the residue was extracted using ethyl acetate/1M NaOH solution. During the extraction, more precipitate was formed which was filtered and discarded. The combined organic layers were washed with brine and dried over sodium sulfate. The solvent was removed, and the crude product was recrystallized from CHCl$_3$/hexane (1:50). The product was obtained as brown needles (2.094 g, 66%,), R$_f$=0.44 (EtOAc/Hex 1:3), $^1$H-NMR (500 MHz, CDCl$_3$), δ=7.40-7.38 (dd, 1H, J=11.3 Hz, J=1.5 Hz), 7.25-7.23 (d, 1H, J=8.5 Hz), 6.97-6.92 (q, 1H, J=9 Hz), 6.51-6.48 (m, 1H), 6.24-6.21 (t, 1H, J=9 Hz), 5.3 (s, 1H, NH, br), 3.80 (s, 2H, NH$_2$, br), LRMS (ESI): m/z=365 [M+H]$^-$.

Step C: N-(3,4-difluoro-2-(2-fluoro-4-iodophenylamino)phenyl)methanesulfonamide

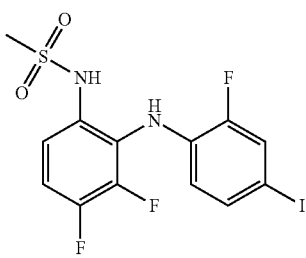 [SMILES: CS(=O)(=O)Nc1ccc(F)c(F)c1Nc1ccc(I)cc1F]

According to the general procedure A, 5,6-difluoro-N1-(2-fluoro-4-iodophenyl)benzene-1,2-diamine was reacted with methanesulfonyl chloride to obtain the desired product. $^1$H NMR: (500 MHz, CDCl$_3$): δ=7.38-7.37 (d, 1H), 7.35-7.34 (m, 1H), 7.27-7.26 (m, 1H), 7.20-7.0 (q, 1H), 6.68 (s, 1H, br), 6.15-6.12 (q, 1H), 5.65 (s, 1H, br), 2.95 (s, 3H); m/z=441 [M−1]$^-$.

Example 2

2N-(3,4-difluoro-2-(2-fluoro-4-iodophenylamino)phenyl)cyclopropanesulfonamide

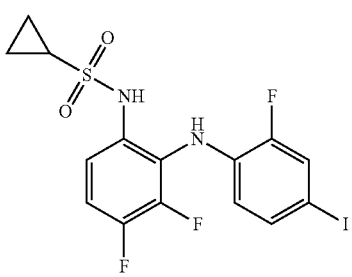 [SMILES: O=S(=O)(Nc1ccc(F)c(F)c1Nc1ccc(I)cc1F)C1CC1]

According to the general procedure A, 5,6-difluoro-N1-(2-fluoro-4-iodophenyl)benzene-1,2-diamine was reacted with cyclopropanesulfonyl chloride to obtain the desired product. $^1$H NMR: (500 MHz, CDCl$_3$): δ=7.38-7.37 (d, 1H), 7.35-7.34 (m, 1H), 121-1 Id (m, 1H), 7.20-7.0 (q, 1H), 6.68 (s, 1H, br), 6.15-6.12 (q, 1H), 5.65 (s, 1H, br), 3.25-3.20 (m, 1H), 2.4-2.3 (m, 2H), 2.0-1.8 (m, 2H); m/z=467 [M−1]$^-$.

Example 3

N-(3,4-difluoro-2-(2-fluoro-4-iodophenylamino)phenyl)propane-2-sulfonamide

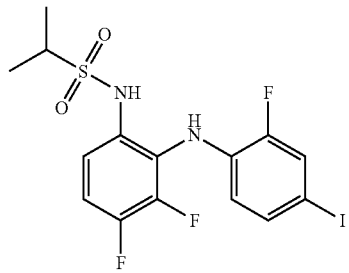 [SMILES: CC(C)S(=O)(=O)Nc1ccc(F)c(F)c1Nc1ccc(I)cc1F]

According to the general procedure A, 5,6-difluoro-N1-(2-fluoro-4-iodophenyl)benzene-1,2-diamine was reacted with isopropylsulfonyl chloride to obtain the desired product. Yield: 39%. $^1$H-NMR (500 MHz, CDCl$_3$): δ=7.50-7.43 (m, 1H), 7.35-7.34 (m, 1H), 7.27-7.26 (m, 1H), 7.15-7.09 (q, 1H, J=1.6 Hz), 6.62 (s, 1H, br), 6.22-6.18 (q, 1H, J=1.5 Hz), 5.65 (s, 1H, br), 3.30-3.28 (m, 1H), 1.38-1.37 (d, 6H, J=1.2 Hz); m/z=469 [M−1]$^-$.

Example 4

N-(3,4-difluoro-2-(2-fluoro-4-iodophenylamino)phenyl)butane-1-sulfonamide

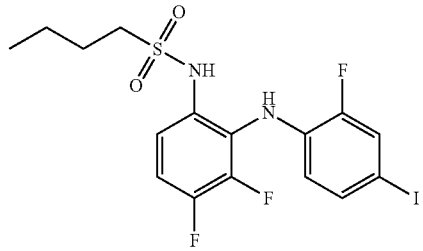 [SMILES: CCCCS(=O)(=O)Nc1ccc(F)c(F)c1Nc1ccc(I)cc1F]

According to the general procedure A, 5,6-difluoro-N1-(2-fluoro-4-iodophenyl)benzene-1,2-diamine was reacted with n-butylsulfonyl chloride to obtain the desired product. Yield: 55%. $^1$H-NMR (500 MHz, CDCl$_3$): δ=7.50-7.43 (m, 1H), 7.35-7.34 (m, 1H), 7.27-7.26 (m, 1H), 7.15-7.09 (q, 1H, J=1.6 Hz), 6.62 (s, 1H, br), 6.22-6.18 (q, 1H, J=1.5 Hz)$_5$ 5.65 (s, 1H, br), 3.06-3.031 (t, 2H, J=1.4 Hz), 1.75-1.71 (m, 2H), 1.38-1.36 (m, 2H), 0.87-0.86 (t, 3H, J=1.3 Hz); m/z 483 [M−1]$^-$.

Example 5

N-(3,4-difluoro-2-(2-fluoro-4-iodophenylamino)phenyl)-2,2,2-trifluoro ethane sulfonamide

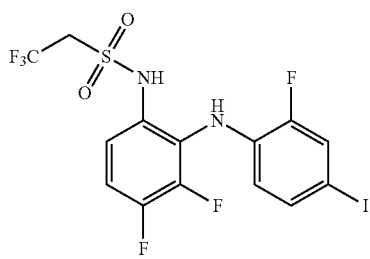 [SMILES: O=S(=O)(CC(F)(F)F)Nc1ccc(F)c(F)c1Nc1ccc(I)cc1F]

According to the general procedure A, 5,6-difluoro-N1-(2-fluoro-4-iodophenyl)benzene-1,2-diamine was reacted with 1,1,1-trifluoroethylsulfonyl chloride to obtain the desired product. Yield: 28%. m/z=509 [M−1]⁻.

Example 6

N-(3,4-difluoro-2-(2-fluoro-4-iodophenylamino)phenyl)butane-2-sulfonamide

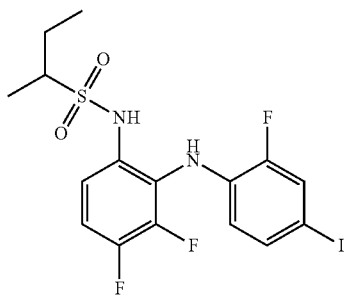 [SMILES: CCC(C)S(=O)(=O)Nc1ccc(F)c(F)c1Nc1ccc(I)cc1F]

According to the general procedure A, 5,6-difluoro-N1-(2-fluoro-4-iodophenyl)benzene-1,2-diamine was reacted with sec-butylsulfonyl chloride to obtain the desired product. Yield: 22%. ¹H-NMR (500 MHz, MeOH[d4]): δ=7.60-7.40 (m, 3H), 7.18-7.00 (q, 1H), 6.55-6.45 (m, 1H), 3.55-3.50 (m, 1H), 2.20-2.00 (m, 1H), 1.80-1.60 (m, 1H), 1.43-1.40 (d, 3H), 1.06-1.04 (t, 3H); m/z=483 [M−1]⁻.

Example 7

N-(3,4-difluoro-2-(2-fluoro-4-iodophenylamino)phenyl)-N-methyl cyclopropane sulfonamide

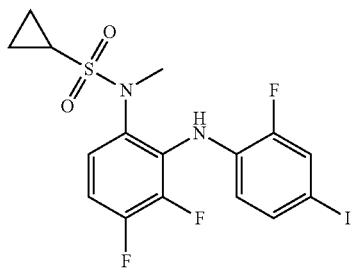

To a solution of N-(3,4-difluoro-2-(2-fluoro-4-iodophenylamino)phenyl)cyclopropane-sulfonamide (see Example 2) (283.9 mg, 0.61 mmol) in 3 ml anhydrous TI-IF was added at −78° C. a IM solution of LHMDS (0.6 ml, 0.6 mol) and the solution was stirred for 10 min at this temperature. Then, methyl iodide (0.8 ml, 1.824 g, 12.9 mmol) was added and the mixture was warmed to room temperature and stirred for 7 h. The solvent was removed and the residue extracted using EtOAc and brine. The organic fractions were dried using Na₂SO₄ and the solvent was removed. The obtained crude product was purified using flash-column chromatography (Si, EtOAc/Hexanes 1:2, R$_f$=0.45). Yield: 205 mg, 70%). ¹H-NMR (500 MHz, CDCl₃): δ=7.41-7.39 (d, 1H, J=10 Hz), 7.30-7.29 (d, 1H, J=8.0 Hz), 7.23-7.20 (m, 1H), 6.98-6.93 (q, 1H, J=8.5 Hz), 6.60 (s, 1H, br), 6.51-6.47 (m, 1H), 3.23 (s, 3H), 2.46-2.42 (m, 1H), 1.19-1.16 (m, 2H), 1.04-1.02 (m, 2H); m/z=481 [M−1]⁻.

Example 8

1-Chloro-N-(3,4-difluoro-2-(2-fluoro-4-iodophenylamino)phenyl)methane sulfonamide

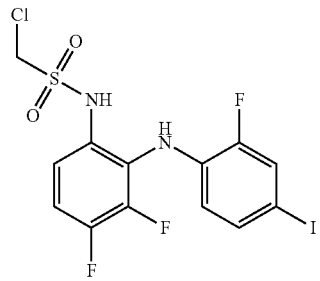 [SMILES: O=S(=O)(CCl)Nc1ccc(F)c(F)c1Nc1ccc(I)cc1F]

According to the general procedure A, 5,6-difluoro-N1-(2-fluoro-4-iodophenyl)benzene-1,2-diamine was reacted with chloromethanesulfonyl chloride to obtain the desired product, m/z=475 [M−1]⁻.

Example 9

N-(3,4-difluoro-2-(2-fluoro-4-iodophenylamino)phenyl)-2-methylpropane-2-sulfonamide

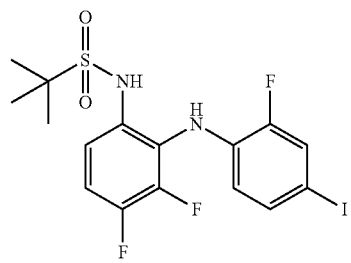 [SMILES: CC(C)(C)S(=O)(=O)Nc1ccc(F)c(F)c1Nc1ccc(I)cc1F]

According to the general procedure B, 5,6-difluoro-N1-(2-fluoro-4-iodophenyl)benzene-1,2-diamine was reacted with 2-methylpropane-2-sulfonyl chloride (synthesized according to the literature procedure) to obtain the desired product. ¹H NMR (300 MHz, CDCl₃): δ 7.50 (m, 1H), 7.43 (dd, J=1.8 & 10.5 Hz, 1H), 7.28 (br s, 1H), 7.10 (dd, J=9.0 & 17.7 Hz, 1H), 6.48 (br s, D₂O exchangeable, 1H), 6.19 (t, J=7.8 & 9.6 Hz, 1H), 5.58 (br s, D₂O exchangeable, 1H), 1.39 (s, 9H); m/z=383 [M−1]⁻.

Example 10

N-(3,4-difluoro-2-(2-fluoro-4-iodophenylamino)phenyl)cyclopentanesulfonamide

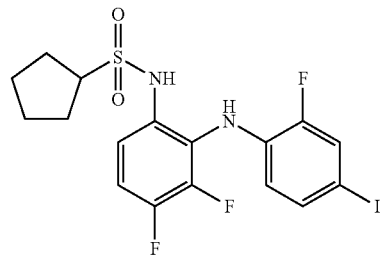 [SMILES: O=S(=O)(Nc1ccc(F)c(F)c1Nc1ccc(I)cc1F)C1CCCC1]

According to the general procedure B, 5,6-difluoro-N1-(2-fluoro-4-iodophenyl)benzene-1,2-diamine was reacted with cyclopentanesulfonyl chloride to obtain the desired product $^1$H NMR (300 MHz, CDCl$_3$): δ 7.42 (dd, J=2.1 & 10.5 Hz, 1H), 7.36 (ddd, J=2.4, 4.8, & 9.3 Hz, 1H), 7.25 (m, 2H), 7.10 (dd, J=9.6 & 17.7 Hz, 1H), 6.67 (br s, D$_2$O exchangeable, 1H), 6.20 (dt, J=1.5, 8.4 & 17.4 Hz, 1H), 3.53 (p, 1H), 1.80 (m, 8H); m/z=495 [M–1]$^-$.

Example 11

N-(3,4-difluoro-2-(2-fluoro-4-Iodophenylamino) phenyl)cyclohexanesulfonamide

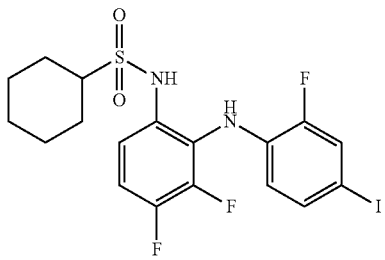 [SMILES: O=S(=O)(Nc1ccc(F)c(F)c1Nc1ccc(I)cc1F)C1CCCCC1]

According to the general procedure B, 5,6-difluoro-N1-(2-fluoro-4-iodophenyl)benzene-1,2-diamine was reacted with cyclohexanesulfonyl chloride to obtain the desired product. $^1$H NMR (300 MHz, CDCl$_3$): δ 7.43 (dd, J=1.5 & 10.2 Hz, 1H), 7.37 (ddd, J=2.4, 4.8 & 9.6 Hz, 1H), 7.27 (m, 1H), 7.11 (dd, J=9.3 & 18.0 Hz, 1H), 6.64 (br s, 1H), 6.18 (dt, J=1.5, 9.0 & 17.4 Hz, 1H), 5.63 (br s, 1H), 2.95 (triplet of triplet, 2.10-1.16 (m, 10H); m/z=509 [M–1]$^-$.

Example 12

N-(3,4-difluoro-2-(2-fluoro-4-iodophenylamino) phenyl)-1-methylcyclopropane-1-sulfonamide Step A: n-Butyl 3-chloro-1-propanesulfonate

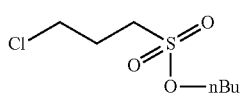

Triethylamine (28 ml, 200 mmol) in CH$_2$Cl$_2$ (50 ml) was slowly added to an ice-cooled solution of 3-chloro-1-propanesulfonyl chloride (36.6 g, 200 mmol) and 1-butanol (18.4 g, 240 m mol) in CH$_2$Cl$_2$ (250 ml) and stirring was continued for 16 h. The mixture was diluted with CH$_2$Cl$_2$ (200 ml), washed (aqueous HCl) and dried (MgSO$_4$) and the solvent was evaporated to obtain the titled product 1 (40.85 g, 95%) in crude form as slightly yellow oil which was used for the next reaction without further purification. $^1$H NMR (CDCl$_3$)) δ 0.94 (1, J=7.5 Hz, 3H), 1.44 (sextet, 2H), 1.72 (quintet, 2H), 2.31 (quintet, 2H), 3.27 (t, J=6.9 Hz, 2H), 3.68 (t, J=6.3 Hz), 4.23 (t, J=6.6 Hz, 2H).

Step B: 1-Butyl cyclopropanesulfonate

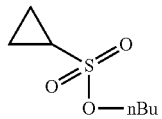

Solutions of 1-butyl 3-chloro-1-propanesulfonate (4.6 g, 21.39 mmol in 25 ml THF) and of butyllithium (14.7 ml, 23.53 mmol, 1.6M, THF) were simultaneously added to THF (150 ml) at –78° C. under nitrogen atmosphere. The solution was allowed to warm to 0° C. and then quenched with water (2 ml). The volatiles evaporated under reduced pressure and the residue extracted with CH$_2$Cl$_2$ (150 ml). The extract was washed with water and dried (MgSO$_4$) and evaporated to give crude desired product (3.23 g, 78.22%) in almost pure form as pale yellow oil which was used for next step without further purification. $^1$H NMR (300 MHz, CDCl$_3$) δ 0.94 (t, J=7.5 Hz, 3H), 1.07 (m, 2H), 1.25 (m, 2H), 1.45 (sextet, 2H), 1.74 (quintet, 2H), 2.45 (heptet, 1H), 4.23 (t, J=6.6 Hz, 2H).

Step C: Butyl 1-Methyl-cyclopropanesulfonate

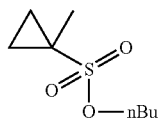

To a solution of 1-Butyl cyclopropanesulfonate (1 g, 5.58 mmol) in THF (15 ml) butyllithium solution (3.84 ml, 6.14 mmol, 1.6M, THF) was slowly added at –78° C. under nitrogen atmosphere. After 15 minutes MeI (0.72 ml, 11.16 mmol) was added and the solution was allowed to warm to 0° C. and quenched with water (1 ml). The volatiles evaporated under reduced pressure and the residue extracted with CH$_2$Cl$_2$ (100 ml). The extract was washed with water, dried (MgSO$_4$) and evaporated. The residue was purified over silica gel chromatography (eluants: hexane/CH$_2$Cl$_2$) to obtain the titled product (0.59 g, 55.0%) as a colorless oil. $^1$H NMR (300 MHz, CDCl$_3$)) δ 0.84 (m, 2H), 0.95 (t, J=7.2 Hz, 3H), 1.43 (m, 4H), 1.53 (s, 3H), 1.74 (m, 2H), 4.21 ((t, J=6.6 Hz, 2H).

Step D: 1-Potassium 1-Meth 1-cyclopropanesulfonate

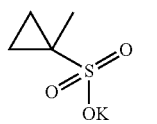

A mixture of 1-Butyl 1-Methyl-cyclopropanesulfonate (0.386 g, 2 mmol) and potassium thiocyanate (0.194 g, 2 mmol) in DME (5 ml) and water (5 ml) was refluxed for 16 h. The volatiles were evaporated to obtain the crude sulfonate (0.348 g, quantitative) which was dried under vacuum at 50° C. for 16 h. The crude product was used in the next reaction without further purification. ¹H NMR (300 MHz, D₂O) δ 0.56 (t, J=6.3 Hz, 2H), 0.96 (t, J=6.3 Hz, 2H), 1.26 (s, 3H).

Step E: 1-Methyl-cyclopropanesulfonylchloride

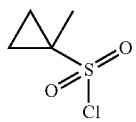

A solution of 1-potassium 1-methyl-cyclopropanesulfonate (0.348 g, 2 mmol), thionyl chloride (5 ml) and DMF (5 drops) was refluxed at 60° C. for 16 h. The volatiles evaporated under reduced pressure and the residue extracted with CH₂Cl₂ (50 ml). The extract was washed with water, dried (MgSO₄) and evaporated to obtain the crude product as yellow gummy oil which was used in the next reaction without further purification.

Step F: N-(3,4-difluoro-2-(2-fluoro-4-iodophenylamino)phenyl)-1-methylcyclopropane-1-sulfonamide

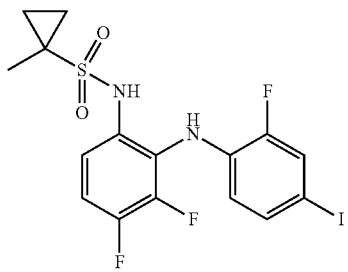 [SMILES: CC1(S(=O)(=O)Nc2ccc(F)c(F)c2Nc2ccc(I)cc2F)CC1]

According to the general procedure B, 5,6-difluoro-N1-(2-fluoro-4-iodophenyl)benzene-1,2-diamine was reacted with 1-methyl-cyclopropanesulfonylchloride to obtain the desired product. ¹H NMR (300 MHz, CDCl₃): δ 7.42 (dd, J=1.8 & 10.5 Hz, 1H), 7.36 (ddd, J=2.4, 4.5 & 9.0 Hz, 1H), 7.27 (d, J=6.0 Hz, 1H), 7.07 (dd, J=9.3 & 17.7 Hz, 1H), 6.24 (dt, J=2.1, 8.7 & 17.4 Hz, 1H), 5.86 (br s, 1H), 1.43 (s, 3H), 1.33 (t, J=5.4 Hz, 2H), 0.75 (dd, J=5.1 & 6.3 Hz, 2H); m/z=481 [M−1]⁻.

Example 13

N-(3,4-difluoro-2-(2-fluoro-4-iodophenylamino)phenyl)-1-(2,3-dihydroxypropyl)cyclopropane-1-sulfonamide Step A: Butyl cyclopropanesulfonate

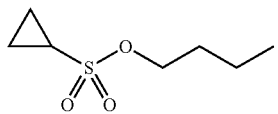

Cyclopropanesulfonyl chloride (5 g, 35 mmol, 1 eq) was dissolved in an excess BuOH (20 ml), the reaction mixture was cooled at −10° C. and pyridine (5.8 mL, 70 mmol, 2 eq) was slowly added dropwise. The mixture was slowly warmed at room temperature and stirred overnight. The solvent was removed under reduced pressure and the resulting white solid was dissolved in CHCl₃. The organic phase was washed with water, brine and dried (MgSO4) and concentrated to give an oil (4.8 g, 24.9 mmol, 71%). ¹H NMR (300 MHz, CDCl₃): δ 4.25 (t, 2H), 2.46 (m, 1H), 1.74 (m, 2H), 1.45 (m, 2H), 1.25 (dd, 2H), 1.09 (dd, 2H), 0.93 (t, 3H).

Step B: Butyl 1-allylcyclopropane-1-sulfonate

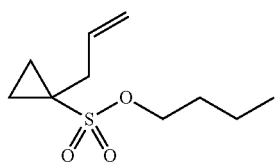

To a solution of 1-butyl cyclopropanesulfonate (4.8 g, 24.9 mmol) in THF at −78° C. was added simultaneously butyllithium solution (15.6 ml, 24.9 mmol, 1.6M, THF) and allyl iodide (24.9 mmol) under nitrogen atmosphere. The reaction mixture was stirred 2 hours at −78° C. and 3 hours at room temperature. The volatiles were evaporated under reduced pressure and the residue extracted with CH₂Cl₂ (100 ml). The extract was washed with water, dried (MgSO₄) and evaporated. The residue was purified over silica gel chromatography (eluants: hexane/CH₂Cl₂) to obtain the titled product (3.75 g, 69.0%) as a colorless oil. ¹H NMR (300 MHz, CDCl₃): δ 5.6 (m, 1H), 5.13-5.08 (t, 2H), 4.21 (t, 2H), 2.65 (d, 2H), 1.7 (m, 2H), 1.4 (m, 4H), 0.93 (m, 5H).

Step C: Potassium 1-allylcyclopropane-1-sulfonate

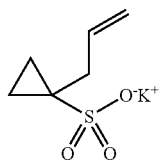

A mixture of 1-butyl 1-methyl-cyclopropanesulfonate (3.75 g, 17.2 mmol) and potassium thiocyanate (1.7 g, 17.2 mmol) in DME (20 ml) and water (20 ml) was refluxed for 16 h. The volatiles were evaporated to obtain the crude sulfonate (3.44 g, quantitative) which was dried under vacuum at 50° C. for 16 h. The crude product was used in the next reaction without further purification. ¹H NMR (CDCl₃): δ 5.6 (m, 1H), 4.91-4.85 (dd, 2H), 2.471-2.397 (d, 2H), 0.756 (m, 2H), 0.322 (m, 2H).

Step D: 1-allylcyclopropane-1-sulfonyl chloride

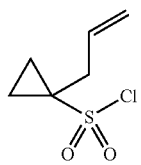

A solution of potassium 1-allylcyclopropane-1-sulfonate (3.44 g, 17.2 mmol), thionyl chloride (10 ml) and DMF (5 drops) was refluxed at 60° C. for 16 h. The volatiles evaporated under reduced pressure and the residue extracted with CH₂Cl₂ (50 ml). The extract was washed with water, dried (MgSO₄) and evaporated to obtain the crude product as yellow gummy oil which was washed with hexane and used in the next reaction without further purification (2.7 g, 15 mmol, 87%). ¹HNMR (300 MHz, CDCl₃): δ 5.728 (m, 1H), 5.191 (t, 2H), 2.9 (d, 2H), 0.756 (m, 2H), 0.322 (m, 2H).

Step E: 1-allyl-N-(3,4-difluoro-2-(2-fluoro-4-iodophenylamino)phenyl)cyclopropane-1-sulfonamide

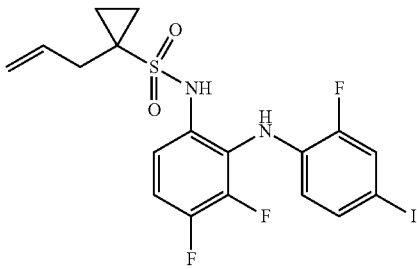 [SMILES: C=CCC1(S(=O)(=O)Nc2ccc(F)c(F)c2Nc2ccc(I)cc2F)CC1]

According to the general procedure B, 5,6-difluoro-N1-(2-fluoro-4-iodophenyl)benzene-1,2-diamine was reacted with 1-allylcyclopropane-1-sulfonyl chloride to obtain the desired product. m/z=507 [M−1]⁻.

Step F: N-(3,4-difluoro-2-(2-fluoro-4-iodophenylamino)phenyl)-1-(2,3-dihydroxypropyl)cyclopropane-1-sulfonamide

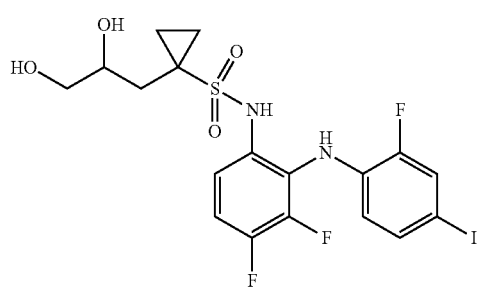 [SMILES: O=S(=O)(Nc1ccc(F)c(F)c1Nc1ccc(I)cc1F)C1(CC(O)CO)CC1]

1-Allyl-N-(3,4-difluoro-2-(2-fluoro-4-iodophenylamino)phenyl)cyclopropane-1-sulfonamide (0.77 g, 1.52 mmol) and 4-methylmorpholine N-oxide (0.18 g, 1.52 mmol) were dissolved in THF (50 mL). Osmium tetroxide was added at room temperature (0.152 mmol, 0.965 mL, 4% in H₂O) and the reaction mixture was stirred at room temperature for 16 hours. EtOAc was added, the organic phase was washed with water, dried (MgSO₄) and concentrated under reduced pressure. The residue was purified over silica gel chromatography (eluants: EtOAc/MeOH) to obtain the titled product (0.65 g, 79%). ¹H NMR (300 MHz, CDCl₃+D₂O): δ 7.38 (dd, J=1.8 & 10.5 Hz, 1H), 7.36 (ddd, J=2.4, 5.1 & 9.3 Hz, 1H), 7.25 (d, J=8.7 Hz, 1H), 7.02 (dd, J=9.0 & 17.7 Hz, 1H), 6.27 (dt, J=3.0, 8.7 & 17.4 Hz, 1H), 3.92 (m, 1H), 3.54 (dd, J=3.9 & 11.1 Hz, 1H), 3.39 (dd, J=6.6 & 11.1 Hz, 1H), 2.16 (dd, J=9.6 & 15.9 Hz, 1H), 1.59 (d, J=14.1 Hz, 1H), 1.41 (m, 1H), 1.26 (m, 1H), 0.83 (m, 2H); m/z=542 [M−1]⁻.

Example 14

(S)—N-(3,4-difluoro-2-(2-fluoro-4-iodophenylamino)phenyl)-1-(2,3-dihydroxypropyl)cyclopropane-1-sulfonamide

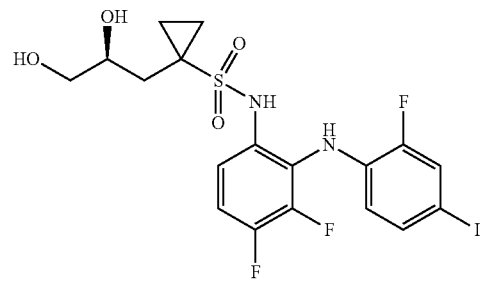 [SMILES: O=S(=O)(Nc1ccc(F)c(F)c1Nc1ccc(I)cc1F)C1(C[C@H](O)CO)CC1]

The pure S isomer was obtained by chiral. HPLC separation of the racemic mixture (example 13). ¹H NMR (300 MHz, CDCl₃+D₂O): δ 7.38 (dd, J=1.8 & 10.5 Hz, 1H), 736 (ddd, J=2.4, 5.1 & 9.3 Hz, 1H), 7.25 (d, J=8.7 Hz, 1H), 7.02 (dd, J=9.0 & 17.7 Hz, 1H), 6.27 (dt, J=3.0, 8.7 & 17.4 Hz, 1H), 3.92 (m, 1H), 3.54 (dd, J=3.9 & 11.1 Hz, 1H), 3.39 (dd, J=6.6 & 11.1 Hz, 1H), 2.16 (dd, J=9.6 & 15.9 Hz, 1H), 1.59 (d, J=14.1 Hz, 1H), 1.41 (m, 1H), 1.26 (m, 1H), 0.83 (m, 2H); m/z=542 [M−1]⁻.

Example 15

(R)—N-(3,4-difluoro-2-(2-fluoro-4-iodophenylamino)phenyl)-1-(2,3-dihydroxypropyl)cyclopropane-1-sulfonamide

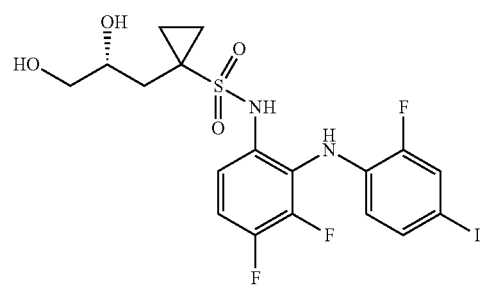 [SMILES: O=S(=O)(Nc1ccc(F)c(F)c1Nc1ccc(I)cc1F)C1(C[C@@H](O)CO)CC1]

The pure R isomer was obtained by chiral HPLC separation of the racemic mixture (example 13). ¹H NMR (300 MHz, CDCl₃+D₂O): δ 7.38 (dd, J=1.8 & 10.5 Hz, 1H), 7.36 (ddd, j=2.4, 5.1 & 9.3 Hz, 1H), 7.25 (d, J=8.7 Hz, 1H), 7.02 (dd, J=9.0 & 17.7 Hz, 1H), 6.27 (dt, J=3.0, 8.7 & 17.4 Hz, 1H), 3.92 (m, 1H), 3.54 (dd, J=3.9 & 11.1 Hz, 1H), 3.39 (dd, J=6.6 & 11.1 Hz, 1H), 2.16 (dd, J=9.6 & 15.9 Hz, 1H), 1.59 (d, J=14.1 Hz, 1H), 1.41 (m, 1H), 1.26 (m, 1H), 0.83 (m, 2H); m/z=542 [M−1]⁻.

Example 16

N-(3,4-difluoro-2-(2-fluoro-4-iodophenylamino)phenyl)-1-(2-hydroxyethyl)cyclopropane-1-sulfonamide Step A: 2-d-bromocyclopropyl)ethanol

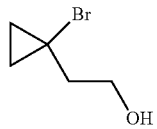

To a solution of neat diethyl zinc (3.3 ml, 3.977 g, 30 mmol) in 100 ml anhydrous DCM was added very slowly trifluoroacetic acid (2.31 ml, 3.4188 g, 30 mmol) dropwise at 0° C. (Caution: Violent gas evolution, exothermic!). After completed addition of the TEA, the suspension was stirred for 20 min at the same temperature, followed by the addition of diiodo methane (2.45 ml, 8.134 g, 30.4 mmol). It was further stirred at 0° C. for 20 min, and then a solution of 3-bromobut-3-en-1-ol (1 ml, 1.523 g, 10.1 mmol) in 10 ml DCM was added at the same temperature. After complete addition, the mixture was warmed to room temperature and stirred for 4 hours. The mixture was quenched with 100 ml MeOH and 40 ml brine, and it was further stirred for 30 min. The solvents were reduced, and the residue extracted using $CHCl_3$/aq. $NH_4Cl$. The organic layers were collected, washed with brine and water, and the solvent was removed to give 2-(1-bromocyclopropyl)-ethanol in sufficient purity (1.6564 g, 100%). $^1$H-NMR (500 MHz, $CDCl_3$); δ=3.90-3.83 (t, 2H), 1.91-1.87 (t, 2H), 1.71 (s, 1H, br), 1.14-1.09 (m, 2H), 0.83-0.79 (m, 2H).

Step B: TBS protected 2-(1-bromocyclopropyl)ethanol

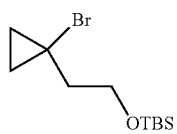

To a solution of the cyclopropyl alcohol (Step A) (1.303 g, 7.95 mmol) in 30 ml anhydrous DCM was added anhydrous pyridine (1.2 ml, 1.1736 g, 14.8 mmol) and TBSOTf (2.7 ml, 3.1077 g, 11.76 mol) and the solution was stirred at room temperature for 16 h. It was extracted with $CHCl_3$/brine and the organic fraction was dried with $MgSO_4$. The solvent was reduced and the crude product purified using flash-column chromatography (Si, $CHCl_3$/hexanes 1:10, $R_f$=0.4). Yield: 0.796 g, 36%. $^1$H-NMR (500 MHz, $CDCl_3$): δ=3.95-3.75 (t, 2H), 1.95-1.85 (t, 2H), 1.15-1.05 (m, 2H), 0.95-0.80 (m, HH), 0.15-0.05 (s, 6H).

Step C: TBS protected 2-(1-chlorosulfonylcyclopropyl)ethanol

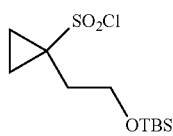 [SMILES: CC(C)(C)[Si](C)(C)OCCC1(S(=O)(=O)Cl)CC1]

To a solution of the cyclopropyl bromide prepared in step B (1.1227 g, 4.04 mmol) in 15 ml anhydrous diethyl ether was added a 1.7 M solution of t-BuLi in pentane (4.8 ml, 8.16 mmol) at −78° C. The solution was stirred for 30 min at this temperature, and was then transferred via a transfer canola into a solution of freshly distilled sulfuryl chloride (0.65 ml, 1.029 g, 8.1 mmol) in 8 ml diethyl ether at −78° C. The yellow suspension was warmed to room temperature. The solvent was removed, and the residue was dried in vacuo to remove excessive sulfuryl chloride. Then, the residue was extracted two times with hexane, and after filtration the solvent was evaporated in vacuo to give the sulfonyl chloride in sufficient purity as a colorless oil. Yield: 870 mg (72%). $^1$H-NMR (300 MHz, $CDCl_3$): δ=3.95-3.85 (t, 2H), 2.35-2.25 (t, 2H), 1.80-1.70 (m, 2H), 1.45-1.38 (m, 2H), 0.90 (s, 9H), 0.10 (s, 6H).

Step D: TBS-protected N-(3,4-difluoro-2-(2-fluoro-4-iodophenylamino)phenyl)-1-(2-hydroxyethyl)cyclopropane-1-sulfonamide

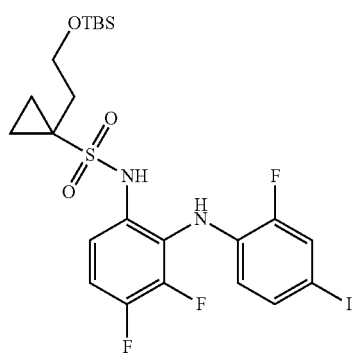 [SMILES: CC(C)(C)[Si](C)(C)OCCC1(S(=O)(=O)Nc2ccc(F)c(F)c2Nc2ccc(I)cc2F)CC1]

According to the general procedure B, 5,6-difluoro-N1-(2-fluoro-4-iodophenyl)benzene-1,2-diamine was reacted with the cyclpropylsulfonyl chloride prepared in step C to obtain the desired product. $^1$H-NMR (300 MHz, $CDCl_3$): δ=7.44-7.39 (dd, 1H), 7.32-7.24 (m, 2H), 7.1-6.98 (q, 1H), 6.34-6.24 (m, 1H), 6.16 (s, 1H, br), 3.85-3.75 (t, 2H), 2.15-2.00 (t, 2H), 1.35-1.20 (m, 2H), 0.95-0.75 (m, 11H), 0.10 (s, 6H); m/z=625 [M−1]⁻.

Step E: N-(3,4-difluoro-2-(2-fluoro-4-iodophenylamino)phenyl)-1-(2-hydroxyethyl)cyclopropane-1-sulfonamide

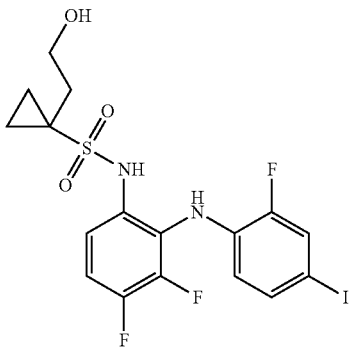 [SMILES: O=S(=O)(Nc1ccc(F)c(F)c1Nc1ccc(I)cc1F)C1(CCO)CC1]

To a solution of the TBS-protected sulfonamide prepared in step D (21 mg, 0.033 mmol) in 1 ml THF was added 0.1 ml aq. 1.2N HCl solution at 0° C. and the solution was stirred for 2 h. The solvents were reduced and the residue was extracted using aq. NaHCO$_3$ solution and EtOAc. The organic fractions were dried with MgSO$_4$ and the volatiles were removed. The crude product was purified using flash-column chromatography (Si, CHCl$_3$/MeOH 10:1, R$_f$=0.45) to give the pure product. Yield: 16.9 mg (100%). $^1$H-NMR (300 MHz, CDCl$_3$): δ=7.44-7.39 (dd, 1H), 7.32-7.24 (m, 2H), 7.1-6.98 (q, 1H), 6.34-6.24 (m, 1H), 6.16 (s, 1H, br), 3.85-3.75 (t, 2H), 2.15-2.00 (t, 2H), 1.35-1.20 (m, 2H), 0.95-0.85 (m, 2H); m/z=511 [M−1]$^-$.

Example 17

N-(3,4-difluoro-2-(2-fluoro-4-iodophenylamino)phenyl)-3-hydroxypropane-1-sulfonamide

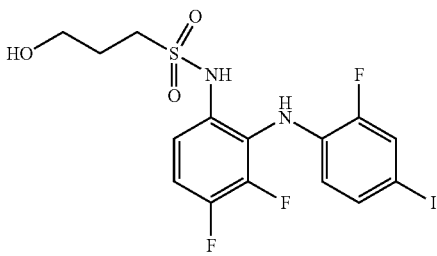 [SMILES: O=S(=O)(CCCO)Nc1ccc(F)c(F)c1Nc1ccc(I)cc1F]

To a solution of 3-chloro-N-(3,4-difluoro-2-(2-fluoro-4-iodophenylamino)phenyl)-propane-1-sulfonamide (69.4 mg, 0.138 mmol) in a mixture of 8 ml 1,4-dioxane and 2 ml H$_2$O was added KOH powder (0.674 g, 12.0 mmol) and the mixture was heated to the reflux temperature for 3 days. It was extracted using EtOAc/brine, the organic fraction was dried with Na$_2$SO$_4$ and the volatiles were removed. The residue was purified using flash-column chromatography (Si, DCM/MeOH 5:1, R$_f$=0.3). Yield: 41 mg (62%). $^1$H-NMR (500 MHz, MeOH [d4]): δ=7.38-7.21 (d, 1H), 7.23-7.21 (d, 1H), 7.06-7.00 (q, 1H), 6.52-6.50 (m, 1H), 6.17-6.13 (t, 1H), 3.30-3.27 (t, 2H), 2.86-2.83 (t, 2H), 2.05-2.00 (m, 2H); m/z=485 [M−1]$^-$.

Example 18

N-(3,4-difluoro-2-(2-fluoro-4-iodophenylamino)phenyl)-2-methyl-5-(trifluoromethyl)furan-3-sulfonamide

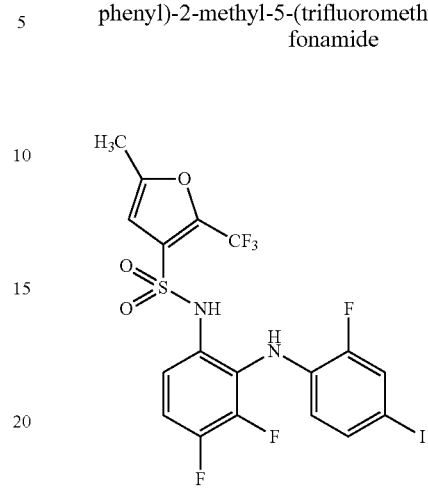

According to the general procedure B, 5,6-difluoro-N1-(2-fluoro-4-iodophenyl)benzene-1,2-diamine (0.182 mmol) was reacted with 2-methyl-5-(trifluoromethyl)furan-3-sulfonyl chloride (0.5 mmol) to form N-(3,4-difluoro-2-(2-fluoro-4-iodophenylamino)phenyl)-2-methyl-5-(trifluoromethyl)furan-3-sulfonamide. $^1$H NMR (CDCl$_3$) δ 2.2 (s, 3H), 5.3 (s, 1H), 6.0 (dt, 1H), 6.8 (s, 1H), 6.95 (s, 1H), 7.0-7.3 (m, 3H), 7.4 (dd, 1H).

Example 19

N-(5-(N-(3,4-difluoro-2-(2-fluoro-4-iodophenylamino)phenyl)sulfamoyl)-methylthiazol-2-yl)acetamide

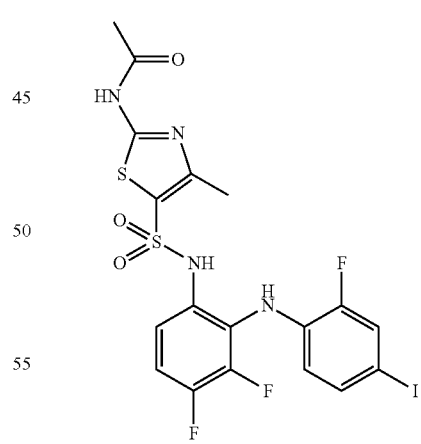

According to the general procedure B, 5,6-difluoro-N1-(2-fluoro-4-iodophenyl)benzene-1,2-diamine (0.182 mmol) was reacted with 2-acetamido-4-methylthiazole-5-sulfonyl chloride (0.5 mmol) to obtain N-(5-(N-(3,4-difluoro-2-(2-fluoro-4-iodophenylamino)phenyl)sulfamoyl)-4-methylthiazol-2-yl)acetamide. $^1$H NMR (CDCl$_3$)) δ 2.1 (s, 3H), 2.2 (s, 3H), 5.9 (dt, 1H), 6.05 (s, 1H), 7.0-7.6 (m, 3H), 7.4 (dd, 1H), 8.0 (s, 1H).

Example 20

5-(5-Chloro-1,2,4-thiadiazol-3-yl)-N-(3,4-difluoro-2-(2-fluoro-4-iodophenylamino)phenyl)thiophene-2-sulfonamide

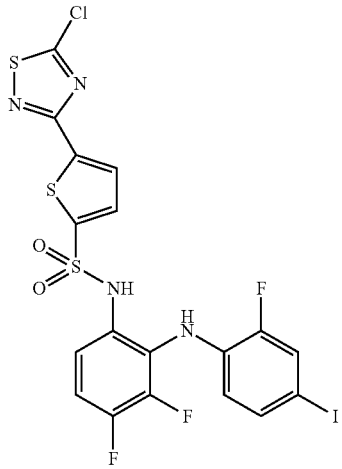 [SMILES: O=S(=O)(Nc1ccc(F)c(F)c1Nc1ccc(I)cc1F)c1ccc(-c2nsc(Cl)n2)s1]

According to the general procedure B, 5,6-difluoro-N1-(2-fluoro-4-iodophenyl)benzene-1,2-diamine (0.182 mural) was reacted with 5-(5-chloro-1,2,4-thiadiazol-3-yl)thiophene-2-sulfonyl chloride (0.5 mmol) to obtain 5-(5-chloro-1,2,4-thiadiazol-3-yl)-N-(3,4-difluoro-2-(2-fluoro-4-iodophenylamino)phenyl)thiophene-2-sulfonamide. ¹H NMR (300 MHz, CDCl₃)) δ 5.8 (dt, 1H), 5.95 (s, 1H), 6.95 (d, 1H), 7.4 (m, 2H), 7.6 (d, 1H), 7.8 (s, 1H).

Example 21

N-(3,4-difluoro-2-(2-fluoro-4-iodophenylamino)phenyl)-3,5-dimethylisoxazole-4-sulfonamide

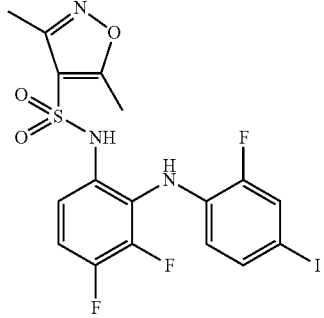 [SMILES: Cc1noc(C)c1S(=O)(=O)Nc1ccc(F)c(F)c1Nc1ccc(I)cc1F]

According to the general procedure B, 5,6-difluoro-N1-(2-fluoro-4-iodophenyl)benzene-1,2-diamine (0.182 mmol) was reacted with 3,5-dimethylisoxazole-4-sulfonyl chloride (0.5 mmol) to obtain N-(3,4-difluoro-2-(2-fluoro-4-iodophenyl amino)phenyl)-3,5-dimethylisoxazole-4-sulfonamide. ¹H NMR (300 MHz, CDCl₃)) δ 2.2 (s, 3H), 2.4 (s, 3H), 5.8 (s, 1H), 6.0 (dt, 1H), 5.95 (s, 1H), 6.9 (s, 1H), 7.0 (q, 1H), 7.2 (m, 3H), 7.4 (dd, 1H).

Example 22

5-Chloro-N-(3,4-difluoro-2-(2-fluoro-4-iodophenylamino)phenyl)-1,3-dimethyl-1H-pyrazole-4-sulfonamide

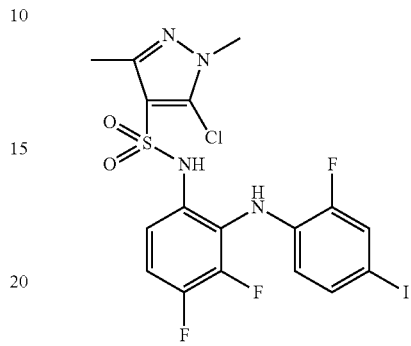

According to the general procedure B, 5,6-difluoro-N1-(2-fluoro-4-iodophenyl)benzene-1,2-diamine (0.182 mmol) was reacted with 5-chloro-1,3-dimethyl-1H-1-pyrazole-4-sulfonyl chloride (0.5 mmol) to obtain 5-chloro-N-(3,4-difluoro-2-(2-fluoro-4-iodophenylamino) phenyl)-1,3-dimethyl-1H-pyrazole-4-sulfonamide. ¹H NMR (300 MHz, CDCl₃)) δ 2.1 (s, 3H), 3.6 (s, 3H), 5.8 (s, 1H), 5.95 (dt, 1H), 7.0 (q, 1H), 7.2 (d, 1H), 7.3 (m, 2H), 7.4 (dd, 1H).

Example 23

N-(3,4-difluoro-2-(2-fluoro-4-iodophenylamino)phenyl)-2,5-dimethylfuran-3-sulfonamide

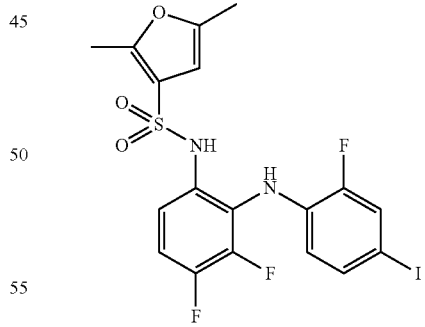

According to the general procedure B, 5,6-difluoro-N1-(2-fluoro-4-iodophenyl)benzene-1,2-diamine (0.182 mmol) was reacted with 2,5-dimethylfuran-3-sulfonyl chloride (0.5 mmol) to obtain N-(3,4-difluoro-2-(2-fluoro-4-iodophenylamino) phenyl)-2,5-dimethylfuran-3-sulfonamide. ¹H NMR (300 MHz, CDCl₃)) δ 2.2 (s, 3H), 2.3 (s, 3H), 5.8 (s, 1H), 6.0 (dt, 1H), 6.8 (s, 1H), 7.0 (q, 1H), 7.2 (d, 1H), 7.3 (m, 2H), 7.4 (dd, 1H).

Example 24

N-(3,4-difluoro-2-(2-fluoro-4-indophenylamino)phenyl)-1-methyl-3-(trifluoromethyl)-1,1-pyrazole-4-sulfonamide

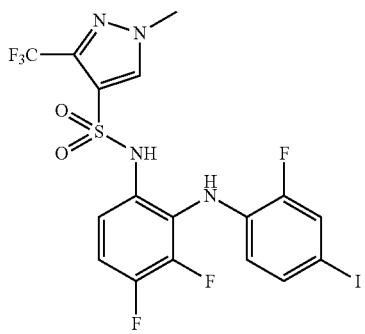 [SMILES: Cn1cc(S(=O)(=O)Nc2ccc(F)c(F)c2Nc2ccc(I)cc2F)c(C(F)(F)F)n1]

According to the general procedure B, 5,6-difluoro-N1-(2-fluoro-4-iodophenyl)benzene-1,2-diamine (0.182 mmol) was reacted with 1-methyl-3-(trifluoromethyl)-1H-pyrazole-4-sulfonyl chloride (0.5 mmol) to obtain N-(3,4-difluoro-2-(2-fluoro-4-iodophenylamino)phenyl)-1-methyl-3-(trifluoromethyl)-1H-pyrazole-4-sulfonamide. $^1$H NMR (300 MHz, CDCl$_3$)) δ 3.8 (s, 3H), 5.7 (s, 1H), 6.0 (dt, 1H), 7.0 (q, 1H), 7.2 (m, 2H), 7.4 (dd, 1H), 7.8 (s, 1H).

Example 25

N-(3,4-difluoro-2-(2-fluoro-4-iodophenylamino)phenyl)-2,4-dimethylthiazole-5-sulfonamide

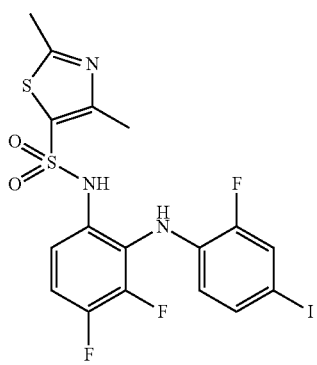 [SMILES: Cc1nc(C)c(S(=O)(=O)Nc2ccc(F)c(F)c2Nc2ccc(I)cc2F)s1]

According to the general procedure B, 5,6-difluoro-N1-(2-fluoro-4-iodophenyl)benzene-1,2-diamine (0.182 mmol) was reacted with 2,4-dimethylthiazole-5-sulfonyl chloride (0.5 mmol) to obtain N-(3,4-difluoro-2-(2-fluoro-4-iodophenylamino)phenyl)-2,4-dimethylthiazole-5-sulfonamide. $^1$H NMR (300 MHz, CDCl$_3$)) δ 23 (s, 3H), 2.6 (s, 3H), 5.7 (s, 1H), 5.9 (dt, 1H), 7.1 (q, 1H), 7.2 (d, 1H), 7.3 (m, 1H), 7.4 (d, 1H), 7.4 (s, 1H).

Example 26

N-(3,4-difluoro-2-(2-fluoro-4-iodophenylamino)phenyl)-1,2-dimethyl-1H-imidazole-4-sulfonamide

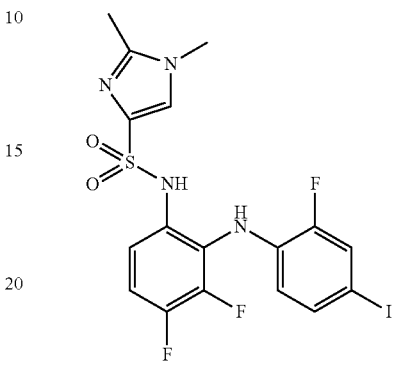

According to the general procedure B, 5,6-difluoro-N1-(2-fluoro-4-iodophenyl)benzene-1,2-diamine was reacted with 1,2-dimethyl-1H-imidazole-4-sulfonyl chloride to obtain the title compound. $^1$H NMR (300 MHz, CDCl$_3$): δ 7.95 (br s, 1H), 7.37 (dd, J=1.8 & 10.8 Hz, 1H), 7.32-7.14 (m, 3H), 6.98 (dd, J=9.6 & 17.7 Hz, 1H), 5.87 (dt, J=4.2, 9.0 & 17.4 Hz, 1H), 5.55 (br s, 1H), 3.49 (s, 3H), 2.31 (s, 3H).

Example 27

N-(3,4-difluoro-2-(2-fluoro-4-iodophenylamino)phenyl)thiophene-3-sulfonamide

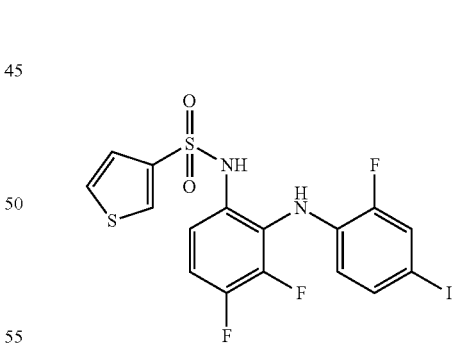

According to the general procedure B, 5,6-difluoro-N1-(2-fluoro-4-iodophenyl)benzene-1,2-diamine was reacted with thiophene-3-sulfonyl chloride to obtain the title compound. $^1$H NMR (300 MHz, CDCl$_3$): δ 8.00 (dd, J=1.2 & 3.3 Hz, 1H), 7.45 (dd, J=0.9 & 5.1 Hz, 1H), 7.35 (m, 2H), 7.27 (m, 2H), 6.91 (dd, J=9.3 & 17.1 Hz, 1H), 6.64 (ddd, 2.1, 4.8 & 8.7 Hz, 1H), 6.34 (dt, J=5.4, 8.7 & 14.1 Hz, 1H), 5.98 d, J=2.1 Hz, D$_2$O exchangeable, 1H).

Example 28

N-(3,4-difluoro-2-(2-fluoro-4-iodophenylamino)phenyl)furan-2-sulfonamide

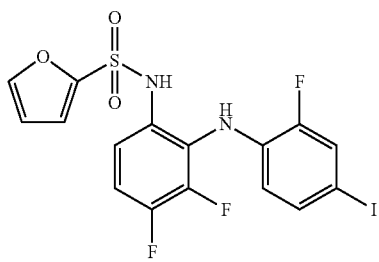 [SMILES: O=S(=O)(Nc1ccc(F)c(F)c1Nc1ccc(I)cc1F)c1ccco1]

According to the general procedure B, 5,6-difluoro-N1-(2-fluoro-4-iodophenyl)benzene-1,2-diamine was reacted with furan-2-sulfonyl chloride to obtain the title compound. $^1$H NMR (300 MHz, CDCl$_3$): δ 7.53 (br s, D$_2$O exchangeable, 1H), 7.38 (dd, J=1.8 & 10.5 Hz, 1H), 7.30 (d, J=8.4 Hz, 1H), 7.21 (d, J=3.0 Hz, 1H), 6.96 (dd, J=8.7 & 16.5 Hz, 1H), 6.87 (ddd, J=1.8, 5.1 & 9.0 Hz, 1H), 6.53 (dd, J=1.8 & 3.6 Hz, 1H), 6.44 (dt, J=5.1, 8.7 & 13.8 Hz, 1H), 6.22 (br s, D$_2$O exchangeable, 1H).

Example 29

N-(3,4-difluoro-2-(2-fluoro-4-iodophenylamino)phenyl)-5-methylthiophene-2-sulfonamide

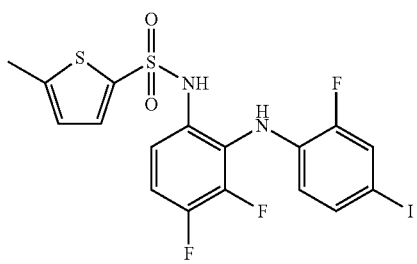 [SMILES: Cc1ccc(S(=O)(=O)Nc2ccc(F)c(F)c2Nc2ccc(I)cc2F)s1]

According to the general procedure B, 5,6-difluoro-N1-(2-fluoro-4-iodophenyl)benzene-1,2-diamine was reacted with 5-methylthiophene-2-sulfonyl chloride to obtain the title compound. $^1$H NMR (300 MHz, CDCl$_3$): δ 7.34 (dd, J=0.9 & 10.2 Hz, 1H), 7.30 (ddd, J=2.1, 4.8 & 9.0 Hz, 1H), 7.25 (d, J=3.9 Hz, 1H), 7.07 (m, 2H), 6.65 (dd, J=1.2 & 3.9 Hz, 1H), 5.89 (dt, J=2.4, 8.7 & 17.4 Hz, 1H), 5.54 (br s, D$_2$O exchangeable, 1H), 2.46 (s, 3H).

Example 30

5-Chloro-N-(3,4-difluoro-2-(2-fluoro-4-iodophenylamino)phenyl)thiophene-2-sulfonamide

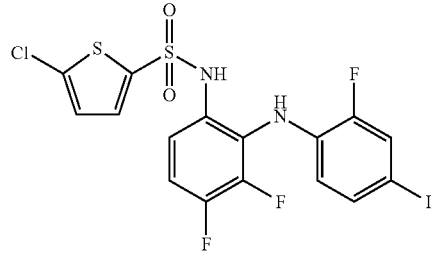

According to the genera/procedure B, 5,6-difluoro-NI-(2-fluoro-4-iodophenyl)benzene-1,2-diamine was reacted with 5-chlorothiophene-2-sulfonyl chloride to obtain the title compound. $^1$H NMR (300 MHz, CDCl$_3$): δ 7.38 (dd, J=1.5 & 10.2 Hz, 1H), 7.32 (ddd, J=2.1, 5.1 & 9.3 Hz, 1H), 7.25 (d, J=3.9 Hz, 1H), 7.10 (dd, J=9.0 & 18.6 Hz, 3H), 6.84 (d, J=4.2 Hz, 1H), 5.86 (dt, J=1.8, 8.7 & 17.4 Hz, 1H), 5.49 (br s, D$_2$O exchangeable, 1H).

Example 31

5-Bromo-N-(3,4-difluoro-2-(2-fluoro-4-iodophenylamino)phenyl)thiophene-2-sulfonamide

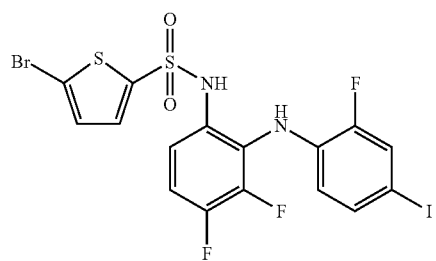 [SMILES: O=S(=O)(Nc1ccc(F)c(F)c1Nc1ccc(I)cc1F)c1ccc(Cl)s1]

According to the general procedure B, 5,6-difluoro-N1-(2-fluoro-4-iodophenyl)benzene 1,2-diamine was reacted with 5-bromothiophene-2-sulfonyl chloride to obtain the title compound. $^1$H NMR (300 MHz, CDCl$_3$): δ 7.39-7.29 (m, 2H), 7.20-7.05 (m, 3H), 6.96 (d, J=3.6 Hz, 1H), 5.85 (dt, J=2.1, 9.0 & 17.4 Hz, 1H), 5.54 (br s, 1H).

Example 32

4-Bromo-N-(3,4-difluoro-2-(2-fluoro-4-iodophenylamino)phenyl)thiophene-3-sulfonamide

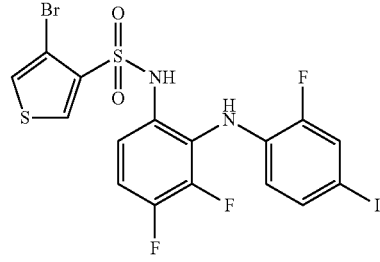 [SMILES: O=S(=O)(Nc1ccc(F)c(F)c1Nc1ccc(I)cc1F)c1cscc1Br]

According to the general procedure B, 5,6-difluoro-N1-(2-fluoro-4-iodophenyl)benzene 1,2-diamine was reacted with 4-bromothiophene-3-sulfonyl chloride to obtain the title compound. ¹H NMR (300 MHz, CDCl₃): δ 7.48 (br m, 2H), 7.39 (dd, J=1.8 & 10.5 Hz, 1H), 7.28 (ddd, J=2.4, 4.8 & 9.0 Hz, 1H), 7.17 (d, J=8.4 Hz, 1H), 7.02 (m, 1H), 6.02 (dt, J=2.4, 8.7 & 17.4 Hz, 1H), 5.68 (br s, 1H).

Example 33

4-Bromo-5-chloro-N-(3,4-difluoro-2-(2-fluoro-4-iodophenylamino)phenyl)thiophene-2-sulfonamide

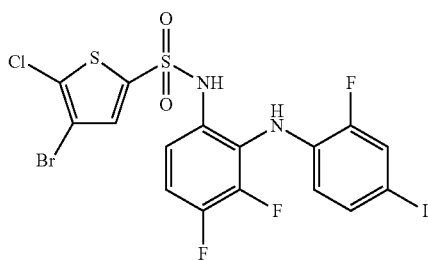 [SMILES: O=S(=O)(Nc1ccc(F)c(F)c1Nc1ccc(I)cc1F)c1cc(Br)c(Cl)s1]

According to the general procedure B, 5,6-difluoro-N1-(2-fluoro-4-iodophenyl)benzene 1,2-diamine was reacted with 4-bromo-5-chlorothiophene-2-sulfonyl chloride to obtain the title compound. ¹H NMR (300 MHz, CDCl₃): δ 7.42-7.34 (m, 2H), 7.25 (br m, 3H), 7.13 (dd, J=9.0 & 17.1 Hz, 1H), 6.02 (dt, J=2.4, 6.6 & 17.4 Hz, 1H), 5.52 (br s, 1H).

Example 34

3-Bromo-5-chloro-N-(3,4-difluoro-2-(2-fluoro-4-iodophenylamino) phenyl)thiophene-2-sulfonamide

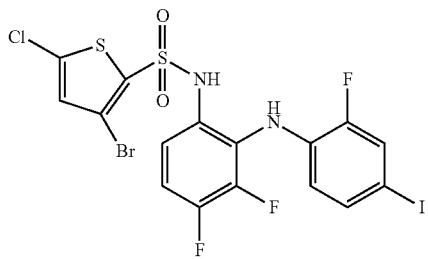 [SMILES: O=S(=O)(Nc1ccc(F)c(F)c1Nc1ccc(I)cc1F)c1sc(Cl)cc1Br]

According to the general procedure B, 5,6-difluoro-N1-(2-fluoro-4-iodophenyl)benzene 1,2-diamine was reacted with 3-bromo-5-chlorothiophene-2-sulfonyl chloride to obtain the title compound. ¹H NMR (300 MHz, CDCl₃): δ 7.41 (dd, J=2.1 & 10.5 Hz, 1H), 7.35 (br m, 2H), 7.31 (dd, J=2.1 & 4.2 Hz, 1H), 7.19 (d, J=8.7 Hz, 1H), 7.08 (dd, J=9.0 & 17.4 Hz, 1H), 6.02 (dt, J=2.1, 8.4 & 17.1 Hz, 1H), 5.59 (br s, 1H).

Example 35

N-(3,4-difluoro-2-(2-fluoro-4-iodophenylamino)phenyl)-2,5-dimethylthiophene-3-sulfonamide

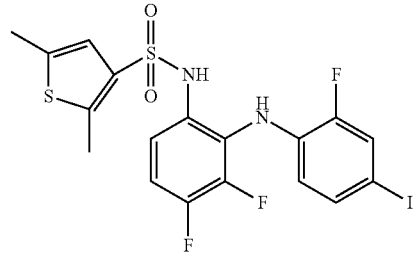 [SMILES: Cc1cc(S(=O)(=O)Nc2ccc(F)c(F)c2Nc2ccc(I)cc2F)c(C)s1]

According to the general procedure B, 5,6-difluoro-N1-(2-fluoro-4-iodophenyl)benzene 1,2-diamine was reacted with 2,5-dimethylthiophene-3-sulfonyl chloride to obtain the title compound. ¹H NMR (300 MHz, CDCl₃): δ 7.39 (dd, J=1.8 & 10.2 Hz, 1H), 7.24-7.16 (br m, 2H), 7.13 (dd, J=9.0 & 17.4 Hz, 1H), 6.77 (d, J=9.6 Hz, 1H), 5.98 (dt, J=2.4, 8.7 & 17.4 Hz, 1H), 5.55 (br s, 1H), 2.33 (s, 6H).

Example 36

2,5-Dichloro-N-(3,4-difluoro-2-(2-fluoro-4-iodophenylamino)phenyl)thiophene-3-sulfonamide

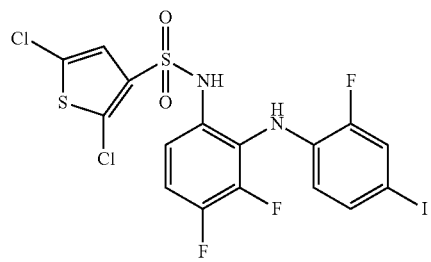 [SMILES: O=S(=O)(Nc1ccc(F)c(F)c1Nc1ccc(I)cc1F)c1cc(Cl)sc1Cl]

According to the general procedure B, 5,6-difluoro-N1-(2-fluoro-4-iodophenyl)benzene 1,2-diamine was reacted with 2,5-dichlorothiophene-3-sulfonyl chloride to obtain the title compound. ¹H NMR (300 MHz, CDCl₃): δ 7.41 (dd, J=1.5 & 10.5 Hz, 1H), 7.28-7.20 (m, 2H), 7.08 (dd, J=9.0 & 17.4 Hz, 2H), 6.99 (s, 1H), 6.03 (dt, J=2.1, 8.7 & 17.4 Hz, 1H), 5.56 (br s, 1H).

Example 37

Methyl 3-(N-(3,4-difluoro-2-(2-fluoro-4-iodophenylamino)phenyl)sulfamoyl)thiophene-2-carboxylate

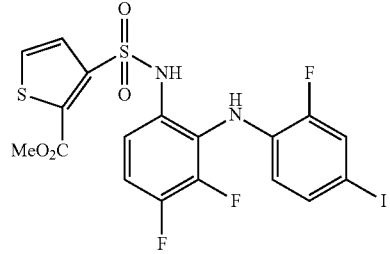 [SMILES: COC(=O)c1sccc1S(=O)(=O)Nc1ccc(F)c(F)c1Nc1ccc(I)cc1F]

According to the general procedure B, 5,6-difluoro-N1-(2-fluoro-4-iodophenyl)benzene 1,2-diamine was reacted with methyl 3-(chlorosulfonyl)thiophene-2-carboxylate to obtain the title compound. ¹H NMR (300 MHz, CDCl₃): δ 8.58 (s, 1H), 7.43 (dd, J=5.1 & 10.8 Hz, 2H), 7.35 (dd, J=1.8 & 10.2 Hz, 1H), 7.31 (ddd, J=2.1, 4.2 & 9.3 Hz, 1H), 7.04 (m, 2H), 5.88 (dt, J=2.7, 8.7 & 17.4 Hz, 1H), 5.65 (br s, 1H), 3.85 (s, 3H).

Example 38

Methyl 5-(N-(3,4-difluoro-2-(2-fluoro-4-iodophenylamino)phenyl)sulfamoyl)-1-methyl-1H-pyrrole-2-carboxylate

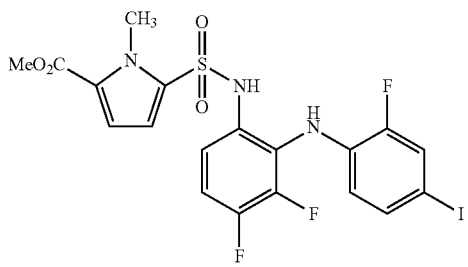 [SMILES: COC(=O)c1ccc(S(=O)(=O)Nc2ccc(F)c(F)c2Nc2ccc(I)cc2F)n1C]

According to the general procedure B, 5,6-difluoro-N1-(2-fluoro-4-iodophenyl)benzene-1,2-diamine was reacted with methyl 5-(chlorosulfonyl)-1-methyl-1H-pyrrole-2-carboxylate to obtain the title compound. $^1$H NMR (300 MHz, CDCl$_3$): δ 7.37 (dd, J=1.8 & 10.5 Hz, 1H), 7.29 (m, 2H), 7.12-6.94 (m, 4H), 5.87 (dt, J=1.8, 8.4 & 17.4 Hz, 1H), 5.56 (br s, 1H), 3.65 (s, 3H), 3.75 (s, 3H).

Example 39

N-(3,4-difluoro-2-(2-fluoro-4-iodophenylamino)phenyl)-5-methylisoxazole-4-sulfonamide

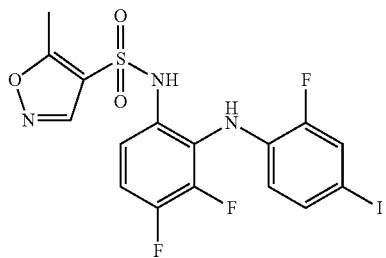 [SMILES: Cc1oncc1S(=O)(=O)Nc1ccc(F)c(F)c1Nc1ccc(I)cc1F]

According to the general procedure A, 5,6-difluoro-N1-(2-fluoro-4-iodophenyl)benzene 1,2-diamine was reacted with the corresponding sulfonyl chloride to obtain the title compound. Yield: 22%. m/z=508 [M−1]$^−$.

Example 40

3-Chloro-N-(3,4-difluoro-2-(2-fluoro-4-iodophenylamino)phenyl)propane-1-sulfonamide

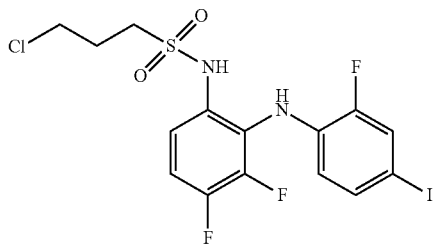 [SMILES: O=S(=O)(CCCCl)Nc1ccc(F)c(F)c1Nc1ccc(I)cc1F]

According to the general procedure A, 5,6-difluoro-N1-(2-fluoro-4-iodophenyl)benzene-1,2-diamine was reacted with 3-chloropropane-1-sulfonyl chloride to obtain the desired product. $^1$H NMR (500 MHz, CDCl$_3$): 7.39-7.38 (d, 1H), 7.35-7.34 (m, 1H), 7.27-7.26 (m, 1H), 7.10-7.0 (q, 1H), 6.63 (s, 1H, br), 6.15-6.11 (q, 1H), 5.60 (s, 1H, br), 3.60-3.56 (t, 2H), 3.22-3.20 (m, 2H), 2.22-2.16 (m, 2H).

Example 41

N-(2-(4-chloro-2-fluorophenylamino)-3,4-difluorophenyl)cyclopropanesulfonamide

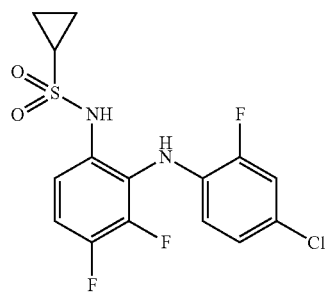 [SMILES: O=S(=O)(Nc1ccc(F)c(F)c1Nc1ccc(Cl)cc1F)C1CC1]

See example 1. $^1$H NMR (300 MHz, CDCl$_3$) δ 0.85-0.95 (m, 2H), 1.05-1.15 (m, 2H), 2.2-2.4 (m, 1H), 5.8 (s, 1H), 6.3 (t, 1H), 6.6-7.4 (m, 5H); m/z=375 [M−1]$^−$.

Example 42

N-(3,4-difluoro-2-(4-iodo-2-methylphenylamino)phenyl)cyclopropanesulfonamide

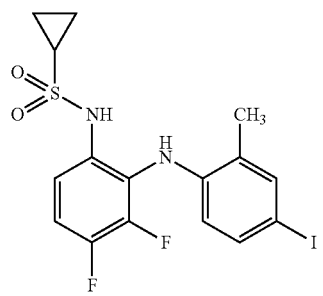 [SMILES: Cc1cc(I)ccc1Nc1c(NS(=O)(=O)C2CC2)ccc(F)c1F]

See example 1. $^1$H NMR (CDCl$_3$) δ 0.80-1.0 (m, 2H), 1.05-1.20 (m, 2H), 1.55 (s, 3H), 2.4-2.5 (m, 1H), 5.6 (s, 1H), 6.2 (dd, 1H), 6.4 (s, 1H), 7.1 (q, 1H), 7.3-7.4 (m, 2H), 7.5 (s, 1H); m/z=463 [M−1]$^−$.

Example 43

N-(2-(4-tert-butyl-2-chlorophenylamino)-3,4-difluorophenyl)cyclopropanesulfonamide

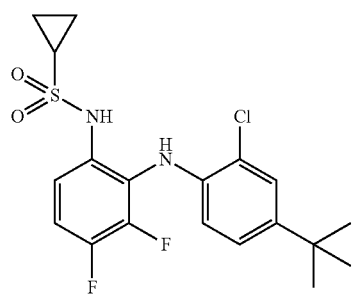 [SMILES: CC(C)(C)c1ccc(Nc2c(NS(=O)(=O)C3CC3)ccc(F)c2F)c(Cl)c1]

See example 1. ¹H NMR (300 MHz, CDCl₃) δ 0.9-1.0 (m, 2H), 1.05-1.20 (m, 2H), 1.3 (s, 9H), 2.4-2.5 (m, 1H), 5.8 (s, 1H), 6.3 (dd, 1H), 6.6 (s, 1H), 7.0-7.2 (m, 2H), 7.3-7.4 (m, 2H); m/z=413 [M−1]⁻.

Example 44

N-(2-(2,4-dichlorophenylamino)-3,4-difluorophenyl) cyclopropanesulfonamide

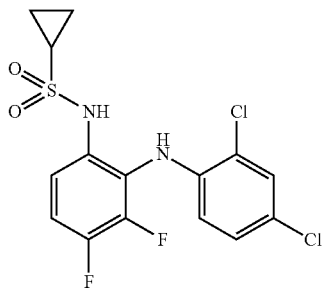 [SMILES: O=S(=O)(Nc1ccc(F)c(F)c1Nc1ccc(Cl)cc1Cl)C1CC1]

See example 1. ¹H NMR (300 MHz, CDCl₃) δ 0.9-1.0 (m, 2H), 1.05-1.20 (m, 2H), 2.4-2.5 (m, 1H), 6.0 (s, 1H), 6.3 (dd, 1H), 6.6 (s, 1H), 7.0-7.2 (m, 2H), 7.3-7.4 (m, 2H); m/z=392 [M−1]⁻.

Example 45

3-Chloro-N-(3,4-difluoro-2-(2-fluoro-4-trifluoromethyl)phenylamino)phenyl)propane-1-sulfonamide

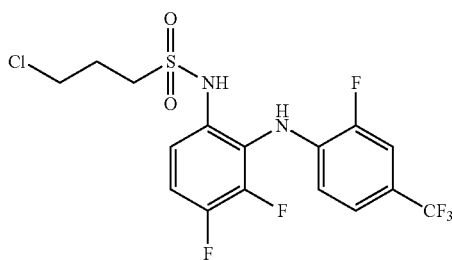 [SMILES: O=S(=O)(CCCCl)Nc1ccc(F)c(F)c1Nc1ccc(C(F)(F)F)cc1F]

See example 1. ¹H NMR (300 MHz, CDCl₃): δ 7.39-7.26 (m, 2H), 7.25 (m, 1H), 7.18 (dd, J=9.0 & 17.7 Hz, 1H), 6.78 (br s, D₂O exchangeable, 1H), 6.50 (t, J=8.1 Hz, 1H), 6.00 (br d, D₂O exchangeable, J=1.5 Hz, 1H), 3.63 (t, J=6.0 & 6.3 Hz, 2H), 3.29 (t, J=7.2 & 7.8 Hz, 2H), 2.26 (quintet, 2H); m/z=445 [M−1]⁻.

Example 46

N-(3,4-difluoro-2-(2-chloro-4-trifluoromethyl)phenylamino)methanesulfonamide

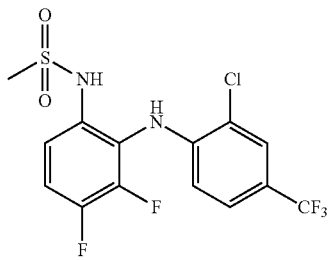 [SMILES: CS(=O)(=O)Nc1ccc(F)c(F)c1Nc1ccc(C(F)(F)F)cc1Cl]

See example 1. ¹H NMR (300 MHz, CDCl₃): δ 7.65 (d, J=7.8 Hz, 1H), 7.33 (m, 2H), 7.19 (dd, J=9.3 & 17.4 Hz, 1H), 6.90 (br s, D₂O exchangeable, 1H), 6.45 (dd, J=1.5 & 8.4 Hz, 1H), 6.39 (br s, D₂O exchangeable, 1H), 3.02 (s, 3H); m/z=399 [M−1]⁻.

Example 47

3-Chloro-N-(3,4-difluoro-2-(2-chloro-4-trifluoromethyl)phenylamino)phenyl)propane-1-sulfonamide

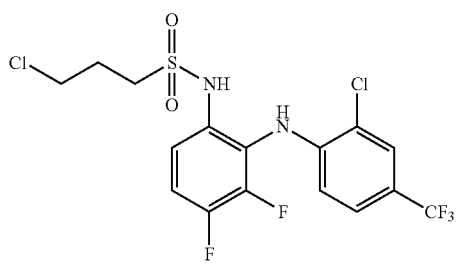

See example 1. ¹H NMR (300 MHz, CDCl₃): δ 7.66 (d, J=1.5 Hz, 1H), 7.36 (m, 2H), 7.19 (dd, J=9.0 & 17.4 Hz, 1H), 6.91 (br s, D₂O exchangeable, 1H), 6.50 (dd, J=8.4 & 1.5 Hz, 1H), 6.37 (s, D₂O exchangeable, 1H), 3.62 (t, J=6.0 Hz, 2H), 3.29 (t, J=7.5 & 7.8 Hz, 2H), 2.27 (quintet, 2H); m/z=462 [M−1]⁻.

Example 48

3-Chloro-N-(3,4-difluoro-2-(2-bromo-4-trifluoromethyl)phenylamino)phenyl)propane-1-sulfonamide

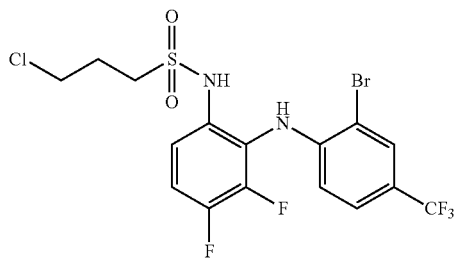 [SMILES: O=S(=O)(CCCCl)Nc1ccc(F)c(F)c1Nc1ccc(C(F)(F)F)cc1Br]

See example 1. ¹H NMR (300 MHz, CDCl₃): δ 7.82 (s, 1H), 7.38 (m, 2H), 7.20 (dd, J=9.0 & 17.7 Hz, 1H), 6.62 (br s, D₂O exchangeable, 1H), 6.43 (d, J=8.4 Hz, 1H), 6.23 (s, D₂O exchangeable, 1H), 3.65 (t, J=6.0 Hz, 2H), 3.30 (t, J=7.5 Hz, 2H), 2.28 (quintet, 2H); m/z=506 [M−1]⁻.

Example 49

Cyclopropanesulfonic acid (3,4,6-trifluoro-2-(2-fluoro-4-iodo-phenylamino)-phenyl)-amide Step A: (2-Fluoro-4-iodo-phenyl)-(2,3,5-trifluoro-6-nitro-phenyl)-amine

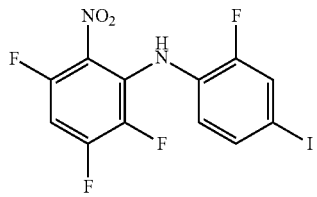 [SMILES: O=[N+]([O-])c1c(F)cc(F)c(F)c1Nc1ccc(I)cc1F]

A stirred solution of 2-fluoro-4-iodoaniline (3.64 gm, 15.37 mmol) in dry THF (100 ml) under nitrogen was cooled to −78° C. and a solution of 1.0 M lithium hexa methyl disilazide (LiN(SiMe₃)₂) "LHMDS" (15.37 ml, 15.37 mmol) was added slowly. This reaction mixture was kept stirring at −78° C. for another hour and then 2,3,4,6-tetrafluoronitrobenzene was added. The reaction mixture was allowed to warm to room temperature and stirring continued for another 16 hours. Ethyl acetate (200 ml) was added to the reaction mixture and was washed with water. Organic layer was dried over sodium sulfate and further purified by column chromatography to provide yellow solid (3.75 gm, yield: 59.24%). M−H⁺: 410.9. ¹H NMR (DMSO, 300 MHz): 6.85 (t, 1H); 7.38 (d, 1H); 7.62 (m, 2H); 8.78 (s, 1H).

Step B: 3,4,6-Tri fluoro-N²-(2-Fluoro-4-iodo-phenyl)-benzene-1,2-diamine

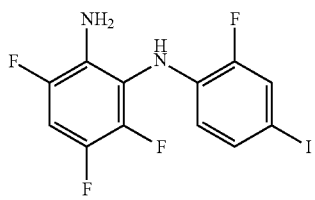

To the stirred solution of (2-fluoro-4-iodo-phenyl)-(2,3,5-trifluoro-6-nitro-phenyl)-amine 3 (5.2 gm, 12.62 mmol) in EtOH (200 ml), ammonium chloride (10.12 gm, 189.3 mmol) and iron powder (10.57 gm, 189.3 mmol) was added. This reaction mixture was kept stirring at reflux for 16 hours. Reaction mixture was allowed to cool and was filtered over celite and concentrated to dryness. The residue obtained was taken into EtOAc and was washed with water. The EtOAc layer was dried over sodium sulfate and further purified by crystallization from EtOH to provide off-white solid (3.2 gm, yield: 66.39%). M−H⁺: 381.1. ¹H NMR (DMSO, 300 MHz): 5.0 (s, 2H); 6.2 (t, 1H); 7.2-7.3 (m, 2H); 7.45 (s, 1H); 7.5 (d, 1H).

Step C: 4,6,7-Trifluoro-1-(2-Fluoro-4-iodo-phenyl)-1,3,-dihydrobenzoimidazole-2-one

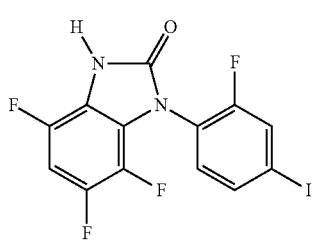 [SMILES: O=c1[nH]c2c(F)cc(F)c(F)c2n1-c1ccc(I)cc1F]

To the stirred solution of 3,4,6-trifluoro-N2-(2-Fluoro-4-iodo-phenyl)-benzene-1,2-diamine 3 (0.285 gm, 0.74 mmol) in CH₂Cl₂ (2 ml), 1,1'-carbonyldiimidazole (0.125 gm, 0.75 mmol) was added. This reaction mixture was kept stirring at room temperature for 16 hours when product precipitated out. The white solid was filtered and used further without any purification. (0.2 gm, yield: 65.85%): m/z=407 [M−1]⁻.

Step D/E: Cyclopropanesulfonic acid (3,4,6-trifluoro-2-(2-fluoro-4-iodo-phenylamino)-phenyl)-amide

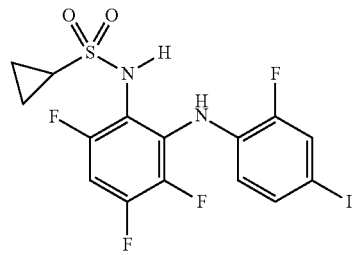 [SMILES: O=S(=O)(Nc1c(F)cc(F)c(F)c1Nc1ccc(I)cc1F)C1CC1]

A stirred solution of 4,6,7-trifluoro-1-(2-fluoro-4-iodo-phenyl)-1,3,-dihydrobenzimidazol-2-one (0.2 gm, 0.41 mmol) in dry THF (4 ml) under nitrogen was cooled to −78° C. and a solution of 1.0 M LiHMDS (0.41 ml, 0.41 mmol) was added slowly, (2 ml) followed by addition of cyclopropanesulfonyl chloride (0.050 ml, 0.49 mmol). This reaction mixture was kept stirring at room temperature for 16 hours, concentrated to dryness and was taken into EtOAc. The EtOAc was washed with water, dried over sodium sulfate and concentrated to dryness. The residue obtained 1-cyclopropanesulfonyl-4,5,7-trifluoro-3-(2-fluoro-4-iodo-phenyl)-1,3-dihydro-benzimidazol-2-one 5 was taken into dioxane (2 ml) and to this 1.0 N NaOH (0.5 ml) was added and kept stirring at room 50° C. for 16 hours. TLC indicated incomplete reaction, the product was purified by HPLC to provide off-white solid (4.4 mg) M+H⁺: 484.7, M−H⁺: 486.7. ¹H NMR (CDCl₃, 300 MHZ): 0.9-1.1-(m, 2H); 1.1-1.2 (m, 2H); 2.45-2.55 (m, 1H); 6.05 (s, 1H); 6.44-6.54 (m, 1H); 7.1 (s, 1H); 7.4-7.7 (d, 1H); 7.38-7.44 (dd, 1H); m/z=485 [M−1]⁻.

Example 50

N-(3,4-difluoro-2-(4-fluoro-2-iodophenylamino)-6-ethoxyphenyl)cyclopropane sulfonamide Step A: (2J-Difluoro-5-methoxy-6-nitro-phenyl)-(2-fluoro-4-iodo-phenyl)-amine

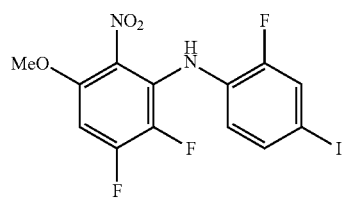 [SMILES: COc1cc(F)c(F)c(Nc2ccc(I)cc2F)c1[N+](=O)[O-]]

A stirred solution of (2-fluoro-4-iodo-phenyl)-(2,3,5-trifluoro-6-nitro-phenyl)-amine (1.23 gm, 3 mmol) in dry THF (25 ml) under nitrogen was cooled to −78° C. and a solution of 25% NaOMe (0.68 ml, 0.3 mmol) was added slowly. Reaction mixture was allowed to warm to room temperature and stirring continued for another 16 hours. TLC indicated incomplete reaction. Ethyl acetate (100 ml) was added to the reaction mixture and was washed with water. Organic layer was dried over sodium sulfate and further purified by column chromatography to provide yellow solid (0.6 gm, yield: 47.6%). m/z=424 [M=H]⁺.

Step B: 5,6-Difluoro-N1-(4-fluoro-2-iodophenyl)-3-methoxybenzene-1,2-diamine

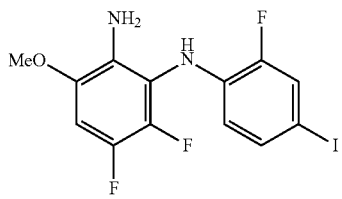 [SMILES: COc1cc(F)c(F)c(Nc2ccc(I)cc2F)c1N]

To the stirred solution of (2,3-difluoro-5-methoxy-6-nitrophenyl)-(2-fluoro-4-iodo-phenyl)-amine (0.57 gm, 1.34 mmol) in EtOH (20 ml), ammonium chloride (1.18 gm, 20.16 mmol) and iron powder (1.15 gm, 21.44 mmol) was added. This reaction mixture was kept stirring at reflux for 16 hours. Reaction mixture was allowed to cool and was filtered over celite and concentrated to dryness. The residue obtained was taken into EtOAc and was washed with water. The EtOAc layer was dried over sodium sulfate and further purified by crystallization from EtOH to provide off-white solid (0.47 gm, yield: 90.3%). M-Fr: 393.2, $^1$H NMR (DMSO, 300 MHz): 3.76 (s, 3H); 6.1 (t, 1H); 6.8-7.0 (m, 1H); 7.2 (d, 1H); 7.35 (s, 1H); 7.42 (d, 1H).

Step C: 6,7-Difluoro-1-(4-fluoro-2-iodophenyl)-4-methoxy-1H-benzo[d]imidazol-2(3H)-one

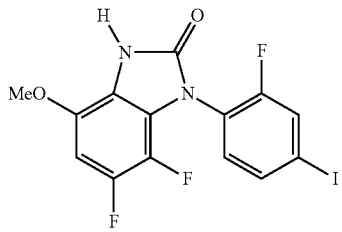 [SMILES: COc1cc(F)c(F)c2c1[nH]c(=O)n2-c1ccc(I)cc1F]

To the stirred solution of 5,6-difluoro-N1-(4-fluoro-2-iodophenyl)-3-methoxybenzene-1,2-diamine (0.17 gm, 0.43 mmol) in CH$_2$Cl$_2$ (2 ml), 1,1'-Carbonyldiimidazole (0.085 gm, 0.53 mmol) was added. This reaction mixture was kept stirring at room temperature for 16 hours when product precipitated out. The white solid was filtered and used further without any purification. (0.089 gm); m/z=419 [M−1]$^-$.

Step D/F: N-(3,4-difluoro-2-(4-fluoro-2-iodophenylamino)-6-methoxyphenyl)cyclopropanesulfonamide

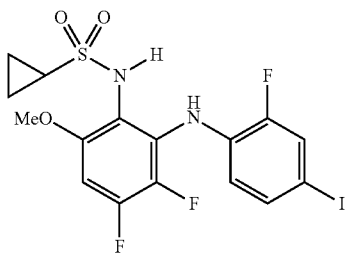 [SMILES: COc1cc(F)c(F)c(Nc2ccc(I)cc2F)c1NS(=O)(=O)C1CC1]

A stirred solution of 1-(cyclopropylsulfonyl)-4,5-difluoro-3-(2-fluoro-4-iodophenyl)-7-methoxy-1H-benzo[d]imidazol-2(3H)-one (0.89 gm, 0.17 mmol) in dry THF (4 ml) under nitrogen was cooled to −78° C. and a solution of 1.0 M LiHMDS (0.17 ml, 0.17 mmol) was added slowly. (2 ml) followed by addition of cyclopropanesulfonyl chloride (0.021 ml, 0.21 mmol). This reaction mixture was kept stirring at room temperature for 16 hours, concentrated to dryness and was taken into EtOAc. The EtOAc was washed with water, dried over sodium sulfate and concentrated to dryness. The resulting 1-(cyclopropylsulfonyl)-4,5-difluoro-3-(2-fluoro-4-iodophenyl)-7-methoxy-1H-benzo[d]imidazol-2 (3H)-one was taken into dioxane (2 ml) and to this 1.0 N NaOH (0.5 ml) was added and kept stirring at room 50° C. for 16 hours. TLC indicated incomplete reaction, the product was purified by HPLC to provide off-white solid (2.5 mg) M+H$^+$: 484.7, M−H$^+$: 497.3. $^1$H NMR (CDCl$_3$, 300 MHz): 0.85-0.95 (m, 2H); 1.05-1.15 (m, 2H); 2.4-2.5 (m, 1H); 3.9 (s, 3H); 6.1 (s, 1H); 6.4-6.6 (m, 2H); 7.3 (m, 1H); 7.35-7.4 (dd, 1H); m/z=497 [M−1]$^-$.

Example 51

Methylsulfonic acid (3,4-difluoro-2-(2-fluoro-4-iodo-phenylamino)-6-methoxy-phenyl)-amide

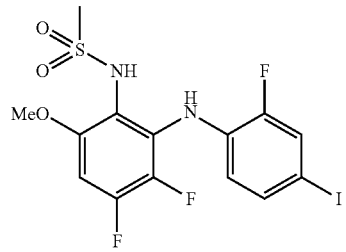 [SMILES: COc1cc(F)c(F)c(Nc2ccc(I)cc2F)c1NS(C)(=O)=O]

A stirred solution of 5,6-difluoro-N1-(4-fluoro-2-iodophenyl)-3-methoxybenzene-1,2-diamine (0.150 gm, 0.38 mmol) in dry CH$_2$Cl$_2$ (4 ml), TEA (0.264 ml, 1.9 mmol) and methanesulfonyl chloride was added slowly. This reaction mixture was kept stirring at room temperature for 16 hours, TLC indicated incomplete reaction along with starting material two products were observed. The reaction mixture was washed with water, organic layer was dried over sodium sulfate and concentrated to dryness, the product was purified by column chromatography. The minor product was found to be the expected compound (6.4 mg). M−H$^+$: 471.5. $^1$H NMR (CDCl$_3$, 300 MHz): 3.9 (s, 3H); 6.05 (s, 1H); 6.4-6.5 (m, 1H); 6.5-6.6 (m, 1H); 7.2 (s, 1H); 7.28 (d, 1H); 7.35-7.4 (d, 1H); m/z=471 [M−1]$^-$.

Example 52

1-(2,3-Dihydroxy-propyl)-cyclopropanesulfonic acid [3,4,6-trifluoro-2-(4-fluoro-2-iodo-phenylamino)-phenyl]-amide Step A: 1-Allyl-cyclopropanesulfonic acid [3,4,6-trifluoro-2-(2-fluoro-4-iodo-phenylamino)phenyl]-amide

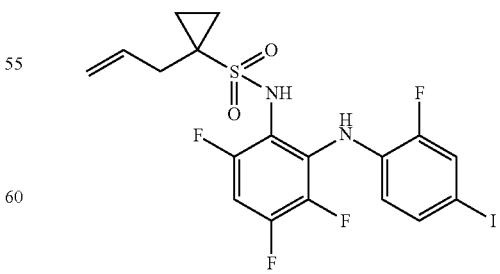

According to the general procedure B, 1-allyl-cyclopropanesulfonyl chloride was reacted with 3,5,6-trifluoro-N$^1$-(2-fluoro-4-iodophenyl)benzene-1,2-diamine to obtain the title product. $^1$H NMR (CDCl$_3$, 300 MHz): δ 7.41 (dd, 1H), 7.38

(dd, 1H), 7.09 (s, 1H), 6.78 (m, 1H), 6.49 (m, 1H), 5.96 (s, 1H), 5.86 (m, 1H), 5.18 (d, 2H), 2.76 (d, 2H), 1.23 (m, 2H), 0.872 (m, 2H).

Step B: 1-(2,3-Dihydroxypropyl)-N-(3,4,6-trifluoro-2-(2-fluoro-4-iodophenylamino)phenyl)cyclopropane-1-sulfonamide

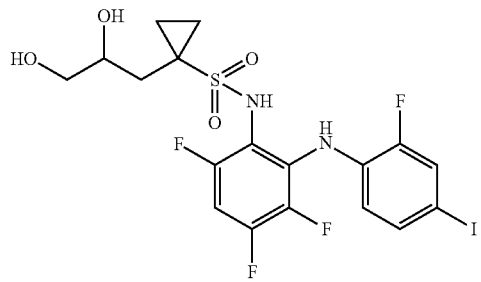 [SMILES: O=S(=O)(Nc1c(F)cc(F)c(F)c1Nc1ccc(I)cc1F)C1(CC(O)CO)CC1]

1-Allyl-cyclopropanesulfonic acid [3,4,6-trifluoro-2-(2-fluoro-4-iodo-phenyl amino)-phenyl]-amide (110 mg, 0.21 mmol) and 4-methylmorpholine N-oxide (24.6 mg, 0.21 mmol) was dissolved in THF (8 mL). Osmium tetroxide was added at room temperature (0.021 mmol, 0.153 mL, 4% in $H_2O$) and the reaction mixture was stirred at room temperature for 16 hours. EtOAc was added, the organic phase was washed with water, dried ($MgSO_4$) and concentrated under reduced pressure. The residue was purified over silica gel chromatography (eluants: EtOAc/MeOH) to obtain the titled product (0.89 g, 75%). $^1$H NMR ($CDCl_3$, 300 MHz): δ 7.39 (dd, J=1.5 & 10.6 Hz, 1H), 7.29 (d, J=8.8 Hz, 1H), 7.28 (s, 1H), 6.97 (s, 1H), 6.76 (m, 1H), 6.49 (m, 1H), 4.13 (m, 1H), 3.66 (dd, J=3.7 & 11.4 Hz, 1H), 3.53 (dd, J=6.7 & 11.2 Hz, 1H), 2.50 (dd, J=10.0 & 16.1 Hz, 1H), 1.6 (m, 1H), 1.46 (m, 1H), 1.28 (m, 1H), 1.20 (m, 2H), 0.92 (m, 2H); m/z=559 [M−1]⁻.

Example 53

(S)-1-(2,3-dihydroxypropyl)-N-(3,4,6-trifluoro-2-(2-fluoro-4-iodophenylamino)phenyl)cyclopropane-1-sulfonamide

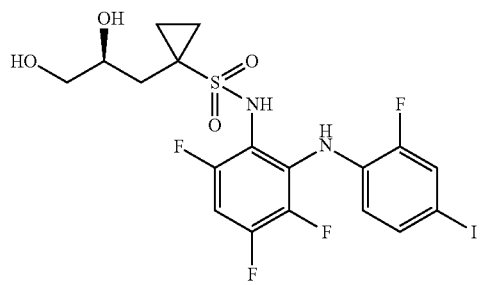 [SMILES: O=S(=O)(Nc1c(F)cc(F)c(F)c1Nc1ccc(I)cc1F)C1(C[C@H](O)CO)CC1]

The pure S isomer was obtained by chiral HPLC separation of the racemic mixture (example 52). $^1$H NMR ($CDCl_3$, 300 MHz): δ 7.39 (dd, J=1.5 & 10.6 Hz₅ 1H), 7.29 (d, J=8.8 Hz, 1H), 728 (s, 1H), 6.97 (s, 1H), 6.76 (m, 1H), 6.49 (m, 1H), 4.13 (m, 1H), 3.66 (dd, J=3.7 & 11.4 Hz₅ 1H), 3.53 (dd, J=6.7 & 11.2 Hz, 1H), 2.50 (dd, J=10.0 & 16.1 Hz, 1H), 1.6 (m, 1H), 1.46 (m, 1H), 1.28 (m, 1H), 1.20 (m, 2H), 0.92 (m, 2H); m/z=559 [M−1]⁻.

Example 54

(R)-1-(2,3-dihydroxypropyl)-N-(3,4,6-trifluoro-2-(2-fluoro-4-iodophenylamino)phenyl)cyclopropane-1-sulfonamide

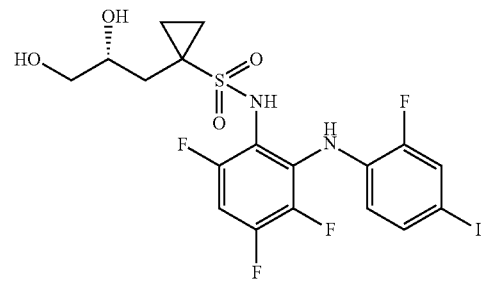 [SMILES: O=S(=O)(Nc1c(F)cc(F)c(F)c1Nc1ccc(I)cc1F)C1(C[C@@H](O)CO)CC1]

The pure R isomer was obtained by chiral HPLC separation of the racemic mixture (example 52). $^1$H NMR ($CDCl_3$, 300 MHz): δ 7.39 (dd, J=1.5 & 10.6 Hz, 1H), 7.29 (d, J=8.8 Hz, 1H), 7.28 (s, 1H), 6.97 (s, 1H), 6.76 (m, 1H), 6.49 (m, 1H), 4.13 (m, 1H), 3.66 (dd, J=3.7 & 11.4 Hz, 1H), 3.53 (dd, J=6.7 & 11.2 Hz, 1H), 2.50 (dd, J=10.0 & 16.1 Hz, 1H), 1.6 (m, 1H), 1.46 (m, 1H), 1.28 (m, 1H), 1.20 (m, 2H), 0.92 (m, 2H); m/z=559 [M−1]⁻.

Example 55

N-(3,4-difluoro-2-(2-fluoro-4-iodophenylamino)phenyl)-1-(2,3-dihydroxypropyl)cyclopropane-1-sulfonamide Step A: 1-Allyl-N-3,4-difluoro-2-(2-fluoro-4-iodophenylamino)-6-methoxyphenyl)cyclopropane-1-sulfonamide

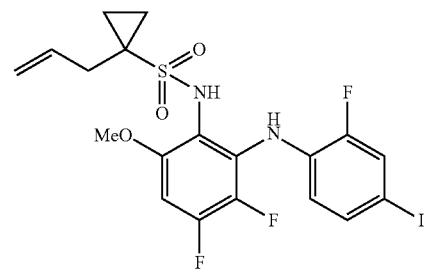 [SMILES: C=CCC1(S(=O)(=O)Nc2c(OC)cc(F)c(F)c2Nc2ccc(I)cc2F)CC1]

According to the general procedure B, 1-allyl-cyclopropanesulfonyl chloride was reacted with 5,6-difluoro-N1-(2-fluoro-4-iodophenyl)-3-methoxybenzene-1,2-diamine to obtain the title product. $^1$H NMR ($CDCl_3$, 300 MHz): δ 7.417 (dd, 1H), 7.309 (s, 1H), 7.25 (m, 1H), 6.89 (m, 1H), 6.52 (m, 1H), 6.427 (m, 1H), 6.03 (s, 1H), 5.668 (m, 1H), 5.11 (t, 1H), 3.9 (s, 3H), 2.75 (d, 2H), 1.21 (m, 2H), 0.767 (m, 2H).

Step B: N-(3,4-difluoro-2-(2-fluoro-4-iodophenylamino)phenyl)-1-(2,3-dihydroxypropyl)cyclopropane-1-sulfonamide

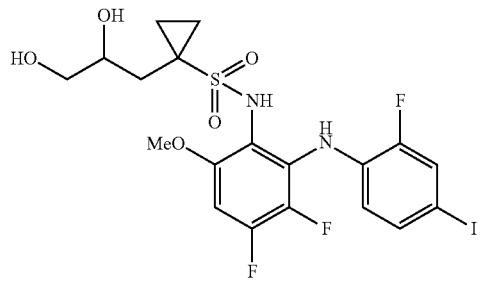 [SMILES: COc1cc(F)c(F)c(Nc2ccc(I)cc2F)c1NS(=O)(=O)C1(CC(O)CO)CC1]

1-Allyl-N-(3,4-difluoro-2-(2-fluoro-4-iodophenylamino)-6-methoxyphenyl)cyclopropane-1-sulfonamide (97 mg, 0.18 mmol) and 4-methylmorpholine N-oxide (21 mg, 0.18 mmol) were dissolved in THF (8 mL). Osmium tetroxide was added at room temperature (0.018 mmol, 0.13 mL, 4% in H$_2$O) and the reaction mixture was stirred at room temperature for 16 hours. EtOAc was added, the organic phase was washed with water, dried (MgSO$_4$) and concentrated under reduced pressure. The residue was purified over silica gel chromatography (eluants: EtOAc/MeOH) to obtain the titled product (0.80 g, 78%). $^1$H NMR (CDCl$_3$, 300 MHz): δ 7.38 (dd, J=1.7 & 10.3 Hz, 1H), 7.26 (m, 1H), 7.14 (s, 1H), 6.87 (s, 1H), 6.53 (dd, J=6.8 & 11.4 Hz, 1H), 6.43 (m, 1H), 4.06 (m, 1H), 3.89 (s, 3H), 3.63 (dd, J=3.7 & 11.1 Hz, 1H), 3.49 (dd, J=6.4 & 11.1 Hz, 1H), 2.3 (dd, J=9.7 & 16.1 Hz, 1H), 1.77 (dd, J=1.9 & 16.0 Hz, 1H), 1.37 (m, 1H), 1.25 (m, 1H), 1.21 (m, 2H), 0.86 (m, 2H); m/z=571 [M−1]$^-$.

Example 56

(S)—N-(3,4-difluoro-2-(2-fluoro-4-iodophenylamino)-6-methoxyphenyl)-1-(2,3-dihydroxypropyl)cyclopropane-1-sulfonamide

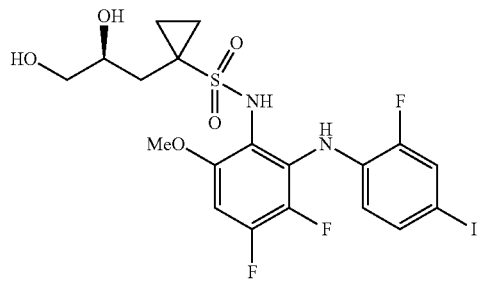 [SMILES: COc1cc(F)c(F)c(Nc2ccc(I)cc2F)c1NS(=O)(=O)C1(C[C@H](O)CO)CC1]

The pure S isomer was obtained by chiral HPLC separation of the racemic mixture (example 55). $^1$H NMR (CDCl$_3$, 300 MHz): δ 7.38 (dd, J=1.7 & 10.3 Hz, 1H), 7.26 (m, 1H), 7.14 (s, 1H), 6.87 (s, 1H), 6.53 (dd, J=6.8 & 11.4 Hz, 1H), 6.43 (m, 1H), 4.06 (m, 1H), 3.89 (s, 3H), 3.63 (dd, J=3.7 & 11.1 Hz, 1H), 3.49 (dd, J=6.4 & 11.1 Hz, 1H), 2.3 (dd, J=9.7 & 16.1 Hz, 1H), 1.77 (dd, J=1.9 & 16.0 Hz, 1H), 1.37 (m, 1H), 1.25 (m, 1H), 1.21 (m, 2H), 0.86 (m, 2H); m/z=571 [M−1]$^-$.

Example 57

(R)—N-(3,4-difluoro-2-(2-fluoro-4-iodophenylamino)-6-methoxyphenyl)-1-(2,3-dihydroxypropyl)cyclopropane-1-sulfonamide

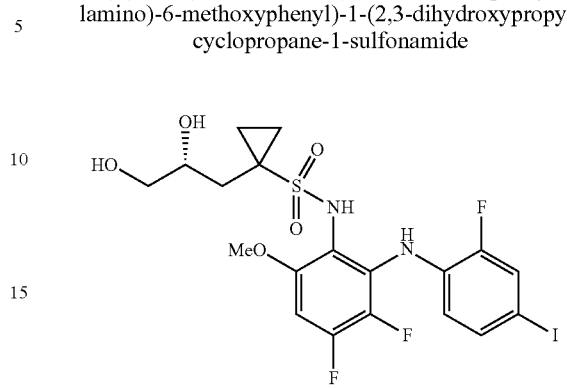

The pure R isomer was obtained by chiral HPLC separation of the racemic mixture (example 55). $^1$H NMR (CDCl$_3$, 300 MHz): δ 7.38 (dd, J=1.7 & 10.3 Hz, 1H), 7.26 (m, 1H), 7.14 (s, 1H), 6.87 (s, 1H), 6.53 (dd, J=6.8 & 11.4 Hz, 1H), 6.43 (m, 1H), 4.06 (m, 1H), 189 (s, 3H), 3.63 (dd, J=3.7 & 11.1 Hz, 1H), 3.49 (dd, J=6.4 & 11.1 Hz, 1H), 2.3 (did, J=9.7 & 16.1 Hz, 1H), 1.77 (dd, J=1.9 & 16.0 Hz, 1H), 1.37 (m, 1H), 1.25 (m, 1H), 1.21 (m, 2H), 0.86 (m, 2H); m/z=571 [M−1]$^-$.

Example 58

1-(2-hydroxyethyl)-N-(3,4,6-trifluoro-2-(2-fluoro-4-iodophenylamino)phenyl)cyclopropane-1-sulfonamide Step A: TBS-protected 1-(2-hydroxyethyl)-N-(3,4,6-trifluoro-2-(2-fluoro-4-iodophenylamino)phenyl)cyclopropane-1-sulfonamide

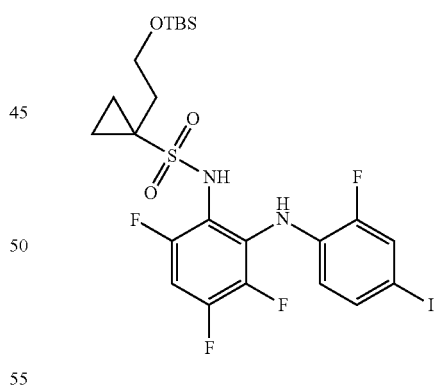

According to the general procedure B, the sulfonyl chloride prepared in step C of example 16 was reacted with 5,6-difluoro-N1-(2-fluoro-4-iodophenyl)-3-fluorobenzene-1,2-diamine to obtain the title product. Yield: 13%. $^1$H-NMR (300 MHz, CDCl$_3$): δ=7.51 (s, 1H, br), 7.37-7.35 (d, 1H), 7.27-7.25 (d, 1H), 6.94 (s, 1H, br), 6.78-6.68 (m, 1H), 6.46-6.44 (m, 1H), 3.90-3.88 (t, 2H), 2.12-2.10 (t, 2H), 1.31-1.28 (m, 2H), 0.91-0.89 (m, 2H), 0.86 (s, 9H), 0.05 (s, 6H); m/z=643 [M−1]$^-$.

Step B: 1-(2-hydroxyethyl)-N-(3,4,6-trifluoro-2-(2-fluoro-4-iodophenylamino)-phenyl)cyclopropane-1-sulfonamide

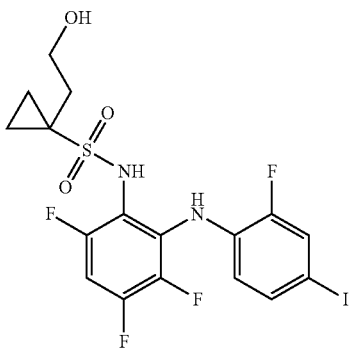 [SMILES: O=S(=O)(Nc1c(F)cc(F)c(F)c1Nc1ccc(I)cc1F)C1(CCO)CC1]

Same procedure as in step E, example 16. Yield: 100%. ¹H-NMR (300 MHz, CDCl₃): δ=7.51 (s, 1H, br), 7.37-7.35 (d, 1H), 7.27-7.25 (d, 1H), 6.94 (s, 1H, br), 6.78-6.68 (m, 1H), 6.46-6.44 (m, 1H), 3.90-3.88 (t, 2H), 2.12-2.10 (t, 2H), 1.31-1.28 (m, 2H), 0.91-0.89 (m, 2H); m/z=529 [M−1]⁻.

Example 59

N-(3,4-difluoro-2-(2-fluoro-4-iodophenylamino)-6-methoxyphenyl)-1-(2-hydroxyethyl)cyclopropane-1-sulfonamide

Step A: TBS-protected N-(3,4-difluoro-2-(2-fluoro-4-iodophenylamino)-6-methoxyphenyl)-1-(2-hydroxyethyl)cyclopropane-1-sulfonamide

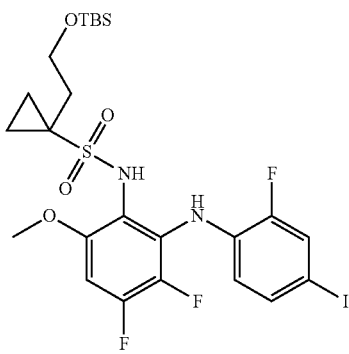 [SMILES: COc1cc(F)c(F)c(Nc2ccc(I)cc2F)c1NS(=O)(=O)C1(CCO[Si](C)(C)C(C)(C)C)CC1]

According to the general procedure B, the sulfonyl chloride prepared in step C of example 16 was reacted with 5,6-difluoro-N¹-(2-fluoro-4-iodophenyl)-3-methoxy-benzene-1,2-diamine to obtain the title product. Yield: 37%. ¹H-NMR (300 MHz, CDCl₃): δ=7.40-7.34 (dd, 1H), 7.23-7.21 (m, 1H), 6.61 (s, 1H, br), 6.57-6.49 (dd, 1H), 6.48-6.39 (m, 1H), 3.9-3.7 (m, 5H), 2.15-2.05 (t, 2H), 1.30-1.20 (m, 2H), 0.95-0.80 (m, 11H), 0.05 (s, 6H); m/z=655 [M−1]⁻.

Step B: N-(3,4-difluoro-2-(2-fluoro-4-iodophenylamino)-6-methoxyphenyl)-1-(2-hydroxyethyl)cyclopropane-1-sulfonamide

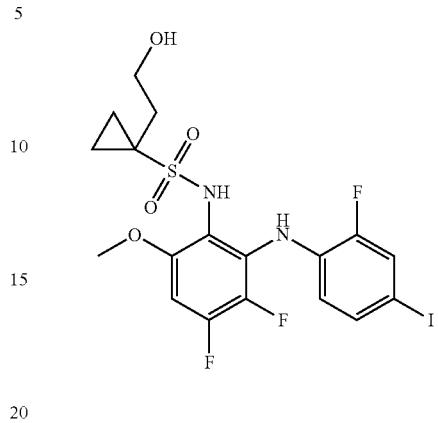

Same procedure as in step E, example 16. Yield: 100%. ¹H-NMR (300 MHz, CDCl₃): δ=7.40-7.34 (dd, 1H), 7.23-7.21 (m, 1H), 6.61 (s, 1H, br), 6.57-6.49 (dd, 1H), 6.48-6.39 (m, 1H), 3.9-3.7 (m, 5H), 2.15-2.05 (t, 2H), 1.30-1.20 (m, 2H), 0.95-0.80 (m, 2H); m/z=541 [M−1]⁻.

Example 60

N-(3,4-difluoro-2-(2-fluoro-4-iodophenylamino)-6-methoxyphenyl)-1-(3-hydroxy-2-(hydroxymethyl)propyl)cyclopropane-1-sulfonamide

Step A: Dimethyl 2-(2-bromoallyl)malonate

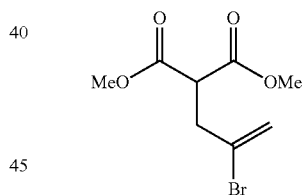

To a suspension of sodium hydride (5.0 g, 125 mmol) in HMPA (50 ml, distilled from calcium hydride) was added a solution of dimethyl malonate (11.7 ml, 100 mmol) in HMPA (5 ml) at 0° C. under argon. The mixture was heated to 50° C. and stirred 1 hour. Following this the solution was again cooled to 0° C., and a solution of 2,3-dibromopropene (12.2 ml, 100 mmol) in HMPA (5 ml) was added to the reaction mixture. Next, the solution was warmed to 40° C. and stirred for 1 hour. The reaction mixture was quenched with aq. HCl (10%, 88 ml) and extracted with ether (3×45 ml). The organic fractions were collected, dried over MgSO—₄, and the solvent was removed in vacuo. The crude oil was purified via silica gel chromatography (eluants: chloroform/hexane) to obtain the titled product as a colorless oil (16.3 g, 65%). ¹H-NMR (300 MHz, CDCl₃) δ 5.70 (d, J=1.8 Hz, 1H), 5.48 (d, J=1.8 Hz, 1H), 3.63 (t, J=7.5 Hz, 1H), 3.76 (s, 6H), 3.04 (d, J=7.5 Hz, 2H).

Step B: 2-(2-Bromoallyl)propane-1,3-diol

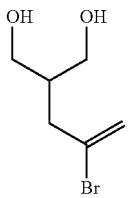

Lithium aluminum hydride (1.9 g, 7.65 mmol) was slurried in anhydrous diethyl ether (50 ml) and cooled to −78° C. in a dry ice/acetone bath. A solution of the product from step A (0.639 g, 16.84 mmol) in dry ether (26 ml) was then added dropwise. After the malonate was added, the solution was allowed warm to room temperature and stirring was continued for 3 hours. The reaction was quenched with brine (50 ml), extracted with ethyl acetate (3×25 ml) and dried over MgSO$_4$. The solvent was removed in vacuo to give the desired product (1.3 g, 86%) which was used for the next step without further purification. $^1$H-NMR (300 MHz, CDCl$_3$) δ 5.66 (d, J=1.2 Hz, 1H), 5.48 (d, J=1.5 Hz, 1H), 3.86 (m, 2H), 3.73 (m, 2H), 2.51 (d, J=7.5 Hz, 2H), 2.40 (br s, 2H), 2.15 (m, 1H).

Step C: Di-tert-butyldimethylsilyl protected 2-(2-bromoallyl)propane-1,3-diol

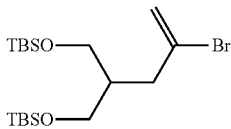 [SMILES: C=C(Br)CC(CO[Si](C)(C)C(C)(C)C)CO[Si](C)(C)C(C)(C)C]

The product from step B (2.8 g, 14.20 mmol) was dissolved in anhydrous THF (140 ml). Anhydrous pyridine (2.5 ml, 31.24 mmol) was added, and the solution was cooled to 0° C. tert-Butyldimethylsilyltriflate (7.2 ml, 31.24 mmol) was added dropwise, and upon completion, the reaction solution was heated to 35° C. After stirring for 6 days, the reaction was quenched with 100 ml brine, extracted with ethyl acetate (3×50 ml) and dried over MgSO$_4$. The combined organic phases were evaporated to obtain the crude product (5.5 g, 91%) as a yellow oil which was used in the next step without further purification. $^1$H-NMR (300 MHz, CDCl$_3$) δ 5.54 (d, J=0.9 Hz, 1H), 5.40 (d, J=1.2 Hz, 1H), 3.55 (d, J=5.4, 4H), 2.40 (d, J=6.9 Hz, 2H), 1.97 (m, 1H), 0.85 (s, 18H), 0.02 (s, 9H).

Step D: Di-tert-butyldimethylsilyl protected 2-((1-bromocyclopropyl)methyl)propane-1,3-diol

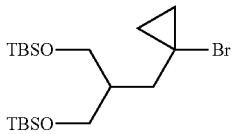

A reaction flask was charged with anhydrous CH$_2$Cl$_2$ (10 ml) and diethyl zinc (1.0 M in hexanes, 4.65 ml, 4.65 mmol) at 0° C. Trifluoroacetic acid (0.358 ml, 4.65 mmol) was added dropwise and the solution was allowed to stir for 20 minutes. Diiodomethane (0.375 ml, 4.65 mmol) was then added and the solution was stirred for another 20 minutes. Finally, the product from step C (0.492 g, 1.16 mmol) was added and the solution was allowed to warm to ambient temperature, stirring for 16 hours. The reaction was quenched with saturated aqueous NH$_4$Cl. The layers were partitioned and the aqueous phase was extracted with chloroform (3×5 ml). The combined organic phases were washed with brine (10 ml), dried over MgSO$_4$, and the volatiles were removed in vacuo. The resulting crude was purified via silica gel chromatography (eluants: chloroform/hexanes) to provide the product as a clear oil (0.280 g, 64%). $^1$H-NMR (300 MHz, CDCl$_3$) δ 3.66 (d, J=5.4, 4H), 2.08 (m, 1H), 1.64 (d, J=6.9, 2H), 1.13 (m, 2H), 0.88 (s, 18H), 0.81 (m, 2H), 0.04 (s, 9H).

Step E: Di-tert-butyldimethylsilyl protected 1-(3-hydroxy-2-(hydroxymethyl)-propyl)cyclopropane-1-sulfonyl chloride

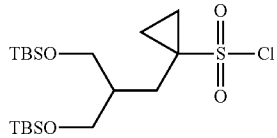

The product from step D (0.507 g, 1.16 mmol) was dissolved in anhydrous ether (6 ml) and the reaction solution was cooled to −78° C. Following this, tert-butyllithium (1.7 M in pentane, 1.50 ml, 2.55 mmol) was added dropwise over 5 minutes. After stirring for 0.5 hours, the lithiated product was transferred via cannula to a stirred solution of sulfuryl chloride (0.206 ml, 2.55 mmol) in dry ether (6 ml) at −78° C. Once the transfer is complete, the solution was allowed to warm to room temperature, the solvent was evaporated and the resulting white solid was slurried in dry hexanes. This slurry was immediately filtered through celite, and all volatiles were removed in vacuo. The resulting crude product (0.376 g, 71%) was isolated as a yellow oil and was used in the following step without further purification. $^1$H-NMR (300 MHz, CDCl$_3$) δ 3.60 (m, 4H), 2.16 (m, 1H), 2.03 (d, 2H), 0.88 (s, 18H), 0.04 (s, 9H).

Step F: Di-tert-butyldimethylsilyl protected N-(3,4-difluoro-2-(2-fluoro-4-iodophenylamino)-6-methoxyphenyl)-1-(3-hydroxy-2-(hydroxymethyl)propyl)cyclopropane-1-sulfonamide

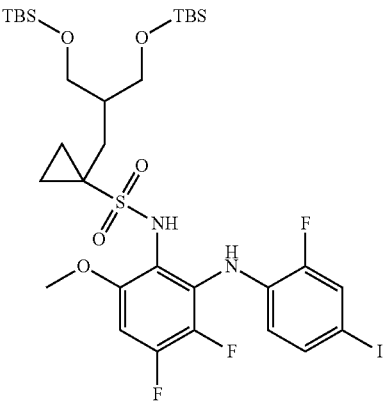

5,6-difluoro-N1-(2-fluoro-4-iodophenyl)-3-methoxybenzene-1,2-diamine (8.8 mg, 0.022 mmol) was dissolved in anhydrous pyridine (0.5 ml) under an argon atmosphere. The product from step E (20.5 mg, 0.045 mmol), dissolved in dry pyridine (0.5 ml), was added to the reaction flask and the mixture was heated at 80° C. for 21 hours. The solvent was removed in vacuo and the resulting crude was purified via silica gel chromatography (eluents: ethyl acetate/hexanes) to provide the title compound (2.75 mg, 15%). m/z 813.5 (M−1).

Step G: N-(3,4-difluoro-2-(2-fluoro-4-iodophenylamino)-6-methoxyphenyl)-1-(3-hydroxy-2-(hydroxymethyl)propyl)cyclopropane-1-sulfonamide

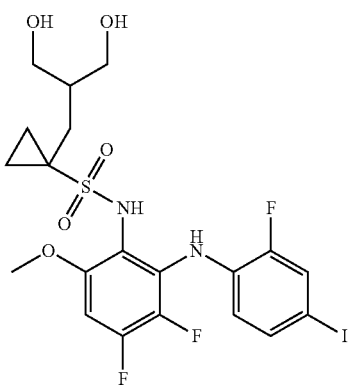 [SMILES: COc1cc(F)c(F)c(Nc2ccc(I)cc2F)c1NS(=O)(=O)C1(CC(CO)CO)CC1]

The product from step F (27.9 mg, 0.0342 mmol) was dissolved in THF (1 ml) and treated with aqueous HCl (1.2 N, 0.2 ml) at 0° C. The resulting solution was stirred for 4 hours. Following this, the reaction was quenched with saturated aqueous NaHCO$_3$, extracted with ethyl acetate, dried over MgSO$_4$ and the volatiles were removed in vacuo. The resulting crude was purified via silica gel chromatography (eluents: methanol/chloroform) followed by LC-MS purification to provide the title compound (11.8 mg, 59%). $^1$H-NMR (300 MHz, CD$_3$OD) δ 7.32 (dd, 1H), 7.21 (d, 1H), 6.76 (dd, 1H), 6.33 (m, 1H), 3.82 (s, 3H), 3.52 (d, 4H), 2.01 (m, 1H), 1.88 (d, 2H), 1.07 (m, 2H), 0.75 (m, 2H), m/z 585.3 (M−1)$^-$.

Example 61

N-(3,4-difluoro-2-(2-fluoro-4-iodophenylamino)-6-methoxyphenyl)cyclobutane sulfonamide Step A: Cyclobutanesulfonyl chloride

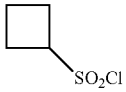

To a suspension of Mg turnings (0.790 g, 32.5 mmol) in 20 ml anhydrous diethyl ether was added a solution of cyclobutylbromide (1.8 ml, 2.5722 g, 19.1 mmol) in 20 ml diethyl ether in small portions with strong stirring. After the initial exothermic reaction had ceased, the mixture was further heated to the reflux temperature for 30 min. The suspension was cooled down to room temperature and the supernatant was added in small portions to an ice-cold solution of sulfuryl chloride (4.6 ml, 7.728 g, 57.2 mmol) in 30 ml anhydrous DCM. After complete addition, the suspension was warmed to room temperature and the volatiles were removed in vacuo. The residue was dried in oil-pump vacuo for 15 min, then it was extracted with hexane (150 ml). The hexane suspension was filtered and the hexane was removed in vacuo to give the crude product as dark purple oil which was used for the next step without further purification. There is still some unreacted cyclopropylbromide present. Crude yield: 1.1 g (38%).

Step B: N-(3,4-difluoro-2-(2-fluoro-4-iodophenylamino)-6-methoxyphenyl)cyclobutanesulfonamide

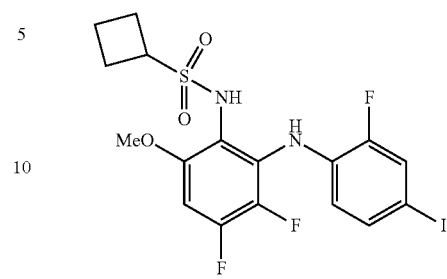

According to the general procedure B, the cyclobutylsulfonyl chloride prepared in the step above was reacted with 5,6-difluoro-N1-(2-fluoro-4-iodophenyl)-3-methoxy-benzene-1,2-diamine to obtain the title product. Yield: 75%. $^1$H-NMR (300 MHz, CDCl$_3$): δ=7.44 (s, 1H, br), 7.41-7.36 (dd, 1H), 7.24-7.23 (m, 1H), 6.54-6.38 (m, 2H), 5.90 (s, 1H, br), 3.85-3.75 (m, 5H), 2.60-2.40 (m, 2H), 2.25-2.15 (m, 1H), 2.15-1.95 (m, 2H); m/z=511 [M−1]$^-$.

Example 62

N-(3,4-difluoro-2-(2-fluoro-4-iodophenylamino)-6-methylphenyl)-1-(2,3-dihydroxypropyl)cyclopropane-1-sulfonamide Step A: (3,4,5-Trifluorophenyl)methanol

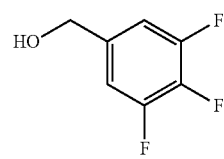

To a cooled (−5° C.) solution of 3,4,5-trifluorobenzaldehyde (7.0 g, 43.75 mmol) in a mixture (50 ml, 9:1) of THF and water NaBH$_4$ (1.662 g, 43.75 mmol) was slowly added in portions over a period of 30 min. The reaction mixture was allowed to attain room temperature over a period of 2 h and carefully poured into ice-cold dil HCl (200 ml, 1N). The oily layer was extracted into CH$_2$Cl$_2$ (250 ml) and the organic layer washed with water (200 ml), dried (MgSO$_4$) and evaporated. The crude product (7.08 g, quantitative) obtained was taken forward without further purification.

Step B: 5-(Bromomethyl)-1,2,3-trifluorobenzene

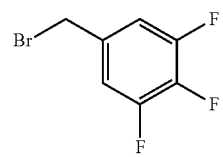 [SMILES: Fc1cc(CBr)cc(F)c1F]

To a solution of the (3,4,5-Trifluorophenyl)methanol (40 mmol) in CH$_2$Cl$_2$ (150 ml), a solution of thionyl bromide (6.16 ml, 80 mmol) in CH$_2$Cl$_2$ (50 ml) was added slowly. The reaction mixture stirred at room temperature for 16 h and poured into ice-water (200 ml). The organic layer was separated and washed with saturated NaHCO$_3$ (2×200 ml), water (200 ml), dried (MgSO$_4$) and evaporated to obtain the corresponding bromo compound as a pale yellow oil in quantitative yield. The crude product was carried forward for the next reaction without further purification.

Step C: 1,2,3-Trifluoro-5-methylbenzene

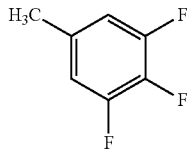

The above bromo compound (40 mmol) was mixed with triethylsilane (48 mmol) and the reaction mixture was treated with solid PdCl₂ (4 mmol) in small portions. After a few minutes a vigorous exothermic reaction was ensued and care was taken to reflux the contents of the flask by placing a reflux condenser. The reaction mixture was stirred at room temperature for additional 6 h and the contents were allowed to settle over 16 h. Then the crude liquid product was decanted carefully and carried forward for the next reaction without further purification. It was assumed that the reaction proceeds in quantitative yield.

Step D: 1,2,3-Trifluoro-5-methyl-4-nitrobenzene

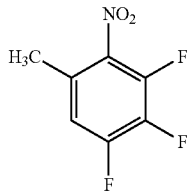

1,2,3-Trifluoro-5-methylbenzene (40 mmol) was added to conc. $H_2SO_4$ (50 ml) at 0-5° C. Then the reaction mixture was slowly treated with conc. $HNO_3$ (3.39 ml, 48.44 mmol, 90%) while maintaining the internal temperature below 20° C. The reaction mixture was stirred at room temperature for 16 h and poured onto ice (300 g) and the oily layer was extracted with $CH_2Cl_2$ (2×125 ml). The organic layer was washed with water (2×200 ml), brine (200 ml) and dried ($MgSO_4$) and evaporated to obtain the crude product which was purified over flash silica gel chromatography to obtain the title product (6.5 g, 85%). $^1$H-NMR (300 MHz, CDCl₃): δ 6.96 (septet, 1H), 2.39 (s, 3H). $^{19}$FNMR (CDCl₃): δ −128.18, −141.50, −159.05.

Step E: 2,3-Difluoro-N-(2-fluoro-4-iodophenyl)-5-methyl-6-nitroaniline

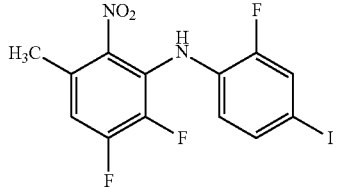

2-Fluoro-4-iodoaniline and 1,2,3-trifluoro-5-methyl-4-nitrobenzene were reacted using the condition described in Example 1 (Step A) to form the title compound. M−H⁺: 407.9

Step F: 5,6-Difluoro-N1-(2-fluoro-4-iodophenyl)-3-methylbenzene-1,2-diamine

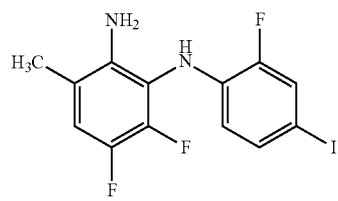 [SMILES: Cc1cc(F)c(F)c(Nc2ccc(I)cc2F)c1[N+](=O)[O-]]

2,3-Difluoro-N-(2-fluoro-4-iodophenyl)-5-methyl-6-nitroaniline was reduced using the condition described in Example 1 (step B) to form the title compound. M−H⁺: 377.4

Step G: 1-Allyl-N-(3,4-difluoro-2-(2-fluoro-4-iodophenylamino)-6-methylphenyl)cyclopropane-1-sulfonamide

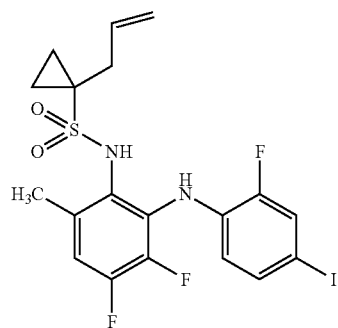 [SMILES: C=CCC1(S(=O)(=O)Nc2c(C)cc(F)c(F)c2Nc2ccc(I)cc2F)CC1]

According to the general procedure B, 1-allyl-cyclopropanesulfonyl chloride (142 mg, 142 mg) was reacted with 5,6-difluoro-N1-(2-fluoro-4-iodophenyl)-3-methylbenzene-1,2-diamine (150 mg, 0.4 mmol) to obtain the title product (100 mg, 47%); m/z=521 [M−1]⁻.

Step H: N-(3,4-difluoro-2-(2-fluoro-4-iodophenylamino)-6-methylphenyl)-1-(2,3-dihydroxypropyl)cyclopropane-1-sulfonamide

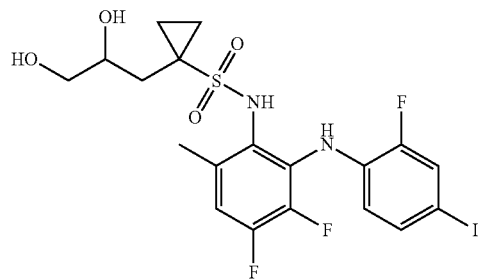 [SMILES: Cc1cc(F)c(F)c(Nc2ccc(I)cc2F)c1NS(=O)(=O)C1(CC(O)CO)CC1]

1-Allyl-N-(3,4-difluoro-2-(2-fluoro-4-iodophenylamino)-6-methylphenyl)cyclopropane-1-sulfonamide (150 mg, 0.29 mmol) and 4-methylmorpholine N-oxide (33 mg, 0.29 mmol) was dissolved in THF (5 mL). Osmium tetroxide was added at room temperature (0.029 mmol, 0.18 mL, 4% in $H_2O$) and the reaction mixture was stirred at room temperature for 16 hours. EtOAc was added, the organic phase was washed with water, dried ($MgSO_4$) and concentrated under reduced pressure. The residue was purified over silica gel chromatography (eluants: EtOAc/MeOH) to obtain the titled product (0.110 g, 68%). $^1$H-NMR (300 MHz, CDCl₃): δ 7.07 (m, 1H), 6.97 (br m, 2H), 6.84 (m, 2H), 6.60 (br m, 2H), 3.98 (br m, 1H), 3.58 (m, 1H), 3.43 (m, 1H), 3.20 (d, J=3.9 Hz, 1H), 2.42 (s, 3H), 2.31 (dd, J=9.9 & 15.6 Hz, 1H), 2.01 (br t, 1H), 2.31 (dd, J=9.9 & 15.6 Hz, 1H), 1.66 (dd, J=2.1 & 15.9 Hz, 1H), 1.52 (m, 1H), 1.40 (m, 1H), 0.91 (m, 2H).

Example 63

1-(2,3-Dihydroxypropyl)-N-(6-ethyl-3,4-difluoro-2-(2-fluoro-4-iodophenylamino) phenyl)cyclopropane-1-sulfonamide Step A: 1-(3,4,5-Trifluorophenyl)ethanol

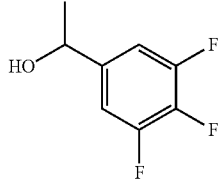

An ethereal solution (17.41 ml, 52.24 mmol, 3M) of MeMgBr was slowly added at −78° C. to a solution of 3,4,5-trifluorobenzaldehyde (6.96 g, 43.53 mmol) in THF (125 ml). The reaction mixture was stirred at room temperature for 16 h and was cooled (0° C.) and was quenched, sequentially, with excess ethyl acetate (10 ml) and water (5 ml). Excess anhydrous MgSO$_4$ (5 g) was added and stirred for 30 minutes at room temperature. The suspension was filtered over celite and the solids were washed with ethyl acetate (2×25 ml). The combined filtrate was evaporated to obtain the product in quantitative yield (7.65 g).

Step B: 5-(1-Bromoethyl)-1,2,3-trifluorobenzene

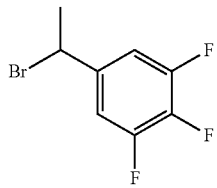

To a solution of the 1-(3,4,5-Trifluorophenyl)ethanol: (7.65 g, 43.5 mmol) in CH$_2$Cl$_2$ (250 ml), a solution of thionyl bromide (18.1 g, 87 mmol) in CH$_2$Cl$_2$ (50 ml) was added slowly. The reaction mixture stirred at room temperature for 16 h and poured into ice-water (200 ml). The organic layer was separated and washed with saturated NaHCO$_3$ (2×200 ml), water (200 ml), dried (MgSO$_4$) and evaporated to obtain the corresponding bromo compound as a pale yellow oil in quantitative yield (10.4 g). The crude product was carried forward for the next reaction without further purification.

Step C: 5-Ethyl-1,2,3-trifluorobenzene

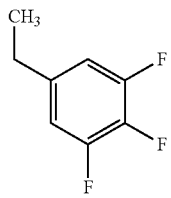

The above bromo compound (9.65 g, 40.4 mmol) was mixed with triethylsilane (41 mmol) and the reaction mixture was treated with solid PdCl$_2$ (177 mg, 4 mmol) in small portions. After a few minutes a vigorous exothermic reaction was ensued and care was taken to reflux the contents of the flask by placing a reflux condenser. The reaction mixture was stirred at room temperature for additional 6 h and the contents were allowed to settle over 16 h. Then the crude liquid product was decanted carefully and carried forward for the next reaction without further purification. It was assumed that the reaction proceeds in quantitative yield.

Step D: 1-Ethyl-3,4,5-trifluoro-2-nitrobenzene

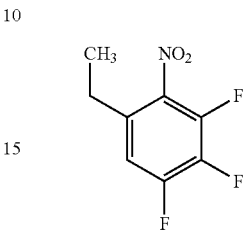

1,2,3-Trifluoro-5-methylbenzene (6.46 g, 40.4 mmol) was added to conc. H$_2$SO$_4$ (50 ml) at 0-5° C. Then the reaction mixture was slowly treated with conc. HNO$_3$ (3.39 ml, 48.44 mmol, 90%) while maintaining the internal temperature below 20° C. The reaction mixture was stirred at room temperature for 16 h and poured onto ice (300 g) and the oily layer was extracted with CH$_2$Cl$_2$ (2×125 ml). The organic layer was washed with water (2×200 ml), brine (200 ml) and dried (MgSO$_4$) and evaporated to obtain the crude product which was purified over flash silica gel chromatography to obtain the title product (6.6 g, 79%). $^1$H NMR (CDCl$_3$): δ 6.98 (septet, 1H), 2.68 (q, 2H), 1.26 (t, J=7.8 & 7.2 Hz, 3H).

Step E: 3-Ethyl-5,6-difluoro-N-(2-fluoro-4-iodophenyl)-2 nitroaniline

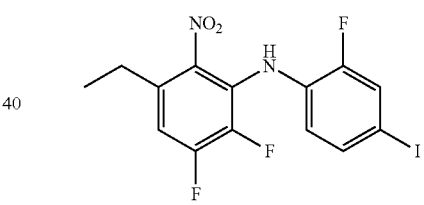

2-Fluoro-4-iodoaniline (2.05 g, 10 mmol) and 1-ethyl-3,4,5-trifluoro-2-nitrobenzene (2.37 g, 10 mmol) were reacted using the condition described in example 1 (Step A) to form the title compound (2.47 g, 60%); m/z=407 [M−1]$^−$.

Step F: 3-Ethyl-5,6-difluoro-N1-(2-fluoro-4-iodophenyl)benzene-1,2-diamine

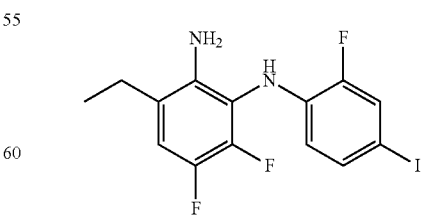

1,2,3-Trifluoro-5-methyl-4-nitrobenzene (2.47 g, 5.85 mmol) was reduced using the condition described in example 1 (Step B) to form the title compound. M−H$^+$: 393

213

Step G: 1-Allyl-N-(6-ethyl-3,4-difluoro-2-(2-fluoro-4-iodophenylamino)phenyl)cyclopropane-1-sulfonamide

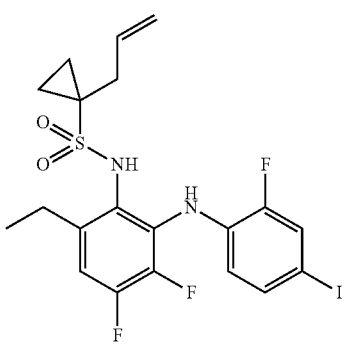 [SMILES: C=CCC1(S(=O)(=O)Nc2c(CC)cc(F)c(F)c2Nc2ccc(I)cc2F)CC1]

According to the general procedure B, 1-allyl-cyclopropanesulfonyl chloride (230 mg, 1.27 mmol) was reacted with 5,6-difluoro-N1-(2-fluoro-4-iodophenyl)-3-methylbenzene-1,2-diamine (100 mg, 0.255 mmol) to obtain the title product (72 mg, 53%); m/z=535 [M−1]⁻.

Step H: 1-(2,3-Dihydroxypropyl)-N-(6-ethyl-3,4-difluoro-2-(2-fluoro-4-iodophenylamino)phenyl)cyclopropane-1-sulfonamide

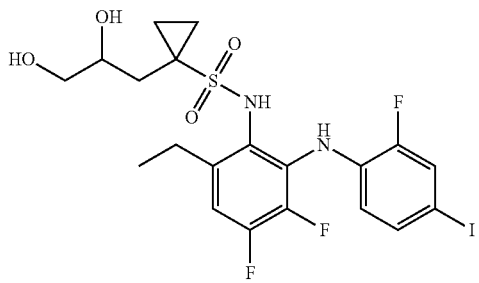 [SMILES: CCc1cc(F)c(F)c(Nc2ccc(I)cc2F)c1NS(=O)(=O)C1(CC(O)CO)CC1]

1-Allyl-N-(3,4-difluoro-2-(2-fluoro-4-iodophenylamino)-6-methylphenyl)cyclopropane-1-sulfonamide (70 mg, 0.13 mmol) and 4-methylmorpholine N-oxide (15 mg, 0.13 mmol) was dissolved in THF (2 Osmium tetroxide was added at room temperature (0.013 mmol) 0.075 mL, 4% in H₂O) and the reaction mixture was stirred at room temperature for 16 hours. EtOAc was added, the organic phase was washed with water, dried (MgSO₄) and concentrated under reduced pressure. The residue was purified over silica gel chromatography (eluants: EtOAc/MeOH) to obtain the titled product. $^1$H NMR (300 MHz, CDCl₃): δ 7.38 (dd, J=2.1 & 10.8 Hz, 1H), 7.27 (m, 2H), 7.12 (br s, 1H), 6.91 (dd, J=8.1 & 10.8 Hz, 1H), 6.69 (br s, 1H), 6.36 (dt, J=4.8, 8.7 & 13.5 Hz, 1H), 4.00 (m, 1H), 3.62 (dd, J=3.6 & 10.5 Hz, 1H), 3.47 (br m, 2H), 2.81 (q, 2H), 2.40 (dd, J=10.2 & 15.9 Hz, 1H), 1.73 (br m, 2H), 1.58 (m, 1H), 1.43 (m, 1H), 0.94 (m, 2H).

214

Example 64

N-(3,4-difluoro-2-(2-fluoro-4-iodophenylamino)-6-(2-methoxyethoxy)phenyl)-1-(2,3-dihydroxypropyl)cyclopropane-1-sulfonamide Step A: 1,2,3-Trifluoro-5-(2-methoxyethoxy)-4-nitrobenzene

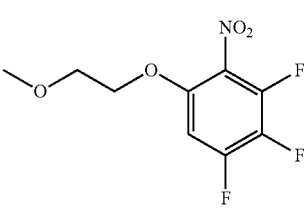 [SMILES: COCCOc1cc(F)c(F)c(F)c1[N+](=O)[O-]]

To a mixture of 3,4,5-trifluoro-2-nitrophenol (1.93, 10 mmol), Ph₃P (3.93 g, 15 mmol), and 2-methoxy-ethanol (1.18 ml, 15 mmol) in anhydrous THF (25 ml) a solution of diisopropyl azodicarboxylate (2.91 ml, 15 mmol) in THF (5 ml) was added at 0° C. and the reaction mixture was stirred at room temperature for 16 h. The volatiles were evaporated and the residue was dissolved in CH₂Cl₂ (100 ml) and the organic layer was washed with water (100 ml), brine (100 ml) dried (MgSO₄) and evaporated. The residue obtained was purified over flash silica gel chromatography to obtain the titled product in 68% (1.70 g) yield. $^1$H NMR (300 MHz, CDCl₃): δ 6.78 (ddd, J=2.4, 6.0, 11.7 Hz, 1H), 4.19 (t, J=4.5 Hz, 2H), 3.72 (t, J=4.5 Hz, 2H), 3.39 (s, 3H).

Step B: 2,3-Difluoro-N-(2-fluoro-4-iodophenyl)-5-(2-methoxyethoxy)-6-nitroaniline

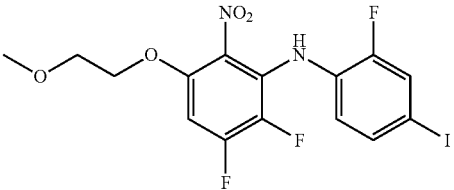 [SMILES: COCCOc1cc(F)c(F)c(Nc2ccc(I)cc2F)c1[N+](=O)[O-]]

2-Fluoro-4-iodoaniline (1.6 g, 6.8 mmol) and 1,2,3-trifluoro-5-(2-methoxyethoxy)-4-nitrobenzene (1.7 g, 6.8 mmol) were reacted using the condition described in Example 1 (Step A) to form the title compound (1.02 g, 32%); m/z=467 [M−1].

Step C: 5,6-Difluoro-N1-(2-fluoro-4-iodophenyl)-3-(2-methoxyethoxy)benzene-1,2-diamine

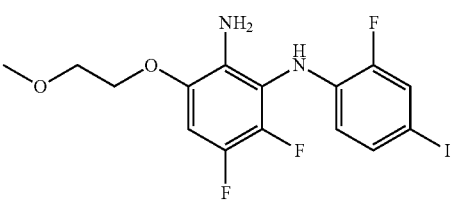 [SMILES: COCCOc1cc(F)c(F)c(Nc2ccc(I)cc2F)c1N]

2,3-Difluoro-N-(2-fluoro-4-iodophenyl)-5-(2-methoxyethoxy)-6-nitroaniline (1.017 g, 2.17 mmol) was reduced Step D: 1-Allyl-N-(3,4-difluoro-2-(2-fluoro-4-iodophenylamino)-6-(2-methoxyethoxy)phenyl)cyclopropane-1-sulfonamide

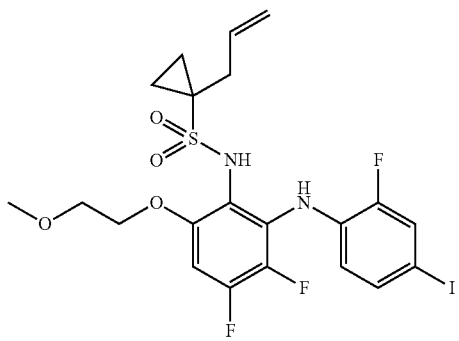 [SMILES: C=CCC1(S(=O)(=O)Nc2c(OCCOC)cc(F)c(F)c2Nc2ccc(I)cc2F)CC1]

According to the general procedure B, 1-allyl-cyclopropanesulfonyl chloride (450 mg, 2.5 mmol) was reacted with 5,6-difluoro-N1-(2-fluoro-4-iodophenyl)-3-(2-methoxyethoxy)benzene-1,2-diamine (219 mg, 2.5 mmol) to obtain the title product (230 mg, 78%); m/z=581 [M−1].

Step E: N-(3,4-difluoro-2-(2-fluoro-4-iodophenylamino)-6-(2-methoxyethoxy)phenyl)-1-(2,3-dihydroxypropyl)cyclopropane-1-sulfonamide

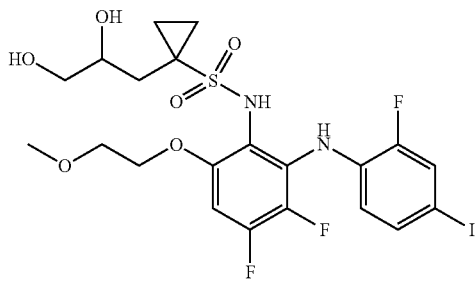 [SMILES: COCCOc1cc(F)c(F)c(Nc2ccc(I)cc2F)c1NS(=O)(=O)C1(CC(O)CO)CC1]

1-allyl-N-(3,4-difluoro-2-(2-fluoro-4-iodophenylamino)-6-(2-methoxyethoxy)phenyl)cyclopropane-1-sulfonamide (230 mg, 0.395 mmol) and 4-methylmorpholine N-oxide (46 mg, 0.395 mmol) was dissolved in THF (2 mL). Osmium tetroxide was added at room temperature (0.039 mmol, 0.25 mL, 4% in $H_2O$) and the reaction mixture was stirred at room temperature for 16 hours. EtOAc was added, the organic phase was washed with water, dried ($MgSO_4$) and concentrated under reduced pressure. The residue was purified over silica gel chromatography (eluants: EtOAc/MeOH) to obtain the titled product. $^1H$ NMR (300 MHz, $CDCl_3$): δ 7.36 (dd, J=1.8 & 10.5 Hz, 1H), 7.27 (m, 2H), 6.56 (dd, J=6.9 & 11.4 Hz, 1H), 6.40 (dt, J=5.7, 7.5 & 12.9 Hz, 1H), 4.17 (m, 2H), 4.01 (m, 1H), 3.78 (m, 2H), 3.60 (dd, J=3.6 & 11.1 Hz, 1H), 3.47 (m, 1H), 3.45 (s, 3H), 2.36 (dd, J=9.6 & 15.9 Hz, 1H), 1.78 (dd, J=2.4 & 15.6 Hz, 1H), 1.45-1.25 (m, 2H), 0.89 (m, 2H).

Example 65

2,4-dichloro-N-(3,4-difluoro-2-(2-fluoro-4-Iodophenylamino)phenyl)benzene sulfonamide

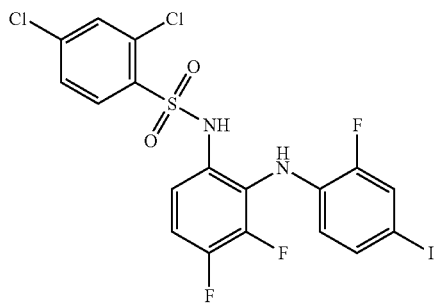 [SMILES: O=S(=O)(Nc1ccc(F)c(F)c1Nc1ccc(I)cc1F)c1ccc(Cl)cc1Cl]

Synthesized by method A using the appropriate sulfonyl chloride, m/z=571 [M−1].

Example 66

2-chloro-N-(3,4-difluoro-2-(2-fluoro-4-Iodophenylamino)phenyl)-4-(trifluoromethyl)benzenesulfonamide

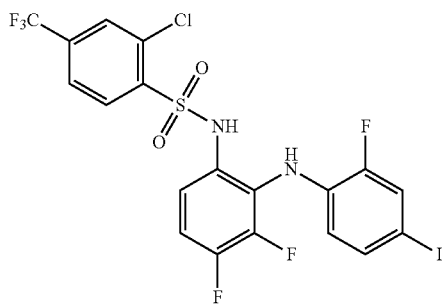 [SMILES: O=S(=O)(Nc1ccc(F)c(F)c1Nc1ccc(I)cc1F)c1ccc(C(F)(F)F)cc1Cl]

Synthesized by method A using the appropriate sulfonyl chloride, m/z=605 [M−1].

Example 67

N-(3,4-difluoro-2-(2-fluoro-4-iodophenylamino)phenyl)-2-(trifluoromethoxy)benzene sulfonamide

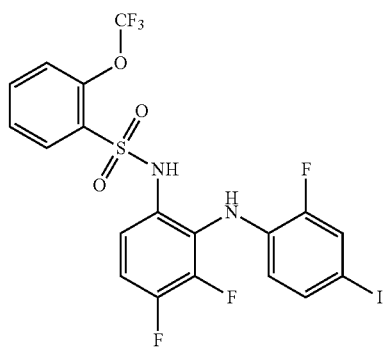 [SMILES: O=S(=O)(Nc1ccc(F)c(F)c1Nc1ccc(I)cc1F)c1ccccc1OC(F)(F)F]

Synthesized by method A using the appropriate sulfonyl chloride, m/z=587 [M−1].

Example 68

4-(N-(3,4-difluoro-2-(2-fluoro-4-iodophenylamino)phenyl)sulfamoyl)benzoic acid

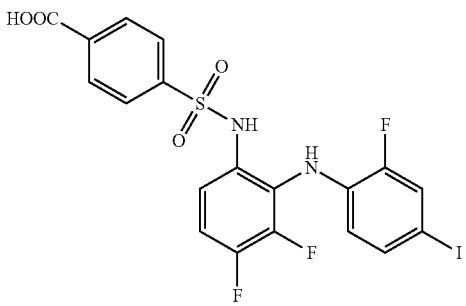 [SMILES: O=C(O)c1ccc(S(=O)(=O)Nc2ccc(F)c(F)c2Nc2ccc(I)cc2F)cc1]

Synthesized by method A using the appropriate sulfonyl chloride, m/z=584 [M−1].

Example 69

N-(3,4-difluoro-2-(2-fluoro-4-iodophenylamino)phenyl)benzenesulfonamide

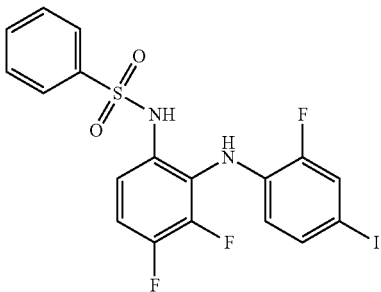 [SMILES: O=S(=O)(Nc1ccc(F)c(F)c1Nc1ccc(I)cc1F)c1ccccc1]

Synthesized by method A using the appropriate sulfonyl chloride, m/z=503 [M−1].

Example 70

N-(3,4-difluoro-2-(2-fluoro-4-iodophenylamino)phenyl)-2-fluorobenzene sulfonamide

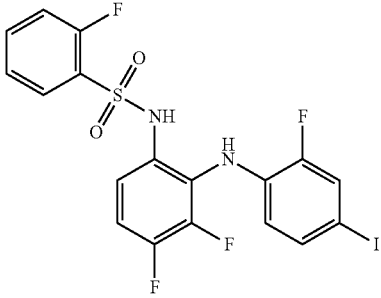 [SMILES: O=S(=O)(Nc1ccc(F)c(F)c1Nc1ccc(I)cc1F)c1ccccc1F]

Synthesized by method A using the appropriate sulfonyl chloride, m/z=521 [M−1].

General Procedure D: Substitution of the Iodine Atom

A suspension containing 1 eq. aryl iodide, 1.5 equiv. of the boronic acid or boronic ester, 0.25 eq. PdCl$_2$(dppf)×DCM and 10 eq. anhydrous K$_2$CO$_3$ powder in a deoxygenated mixture of dioxane and water (3:1) was heated in a microwave reactor for 60 min at 115° C. It was extracted using aq. NH$_4$Cl/THF, and the organic fraction was dried using Na$_2$SO$_4$. The crude reaction products were purified using flash-column chromatography (Si, EtOAc/Hexanes, or CHCl$_3$/MeOH). Yields: 20-40%.

Example 71

N-(3,4-difluoro-2-(2-fluoro-4-methylphenylamino)phenyl)cyclopropanesulfonamide

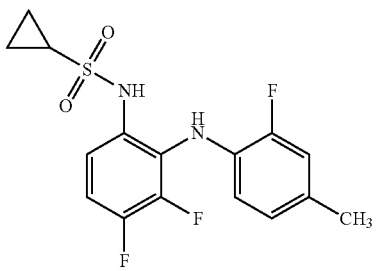 [SMILES: Cc1ccc(Nc2c(NS(=O)(=O)C3CC3)ccc(F)c2F)c(F)c1]

General procedure D: $^1$H-NMR (500 MHz, CDCl$_3$): δ=738-7.36 (m, 1H), 7.06-7.03 (q, 1H), 6.92-6.90 (1H), 6.73-6.72 (d, 1H), 6.63 (s, 1H, br), 6.37-6.33 (t, 1H), 5.54 (s, 1H, br), 2.42-2.39 (m, 1H), 2.25 (s, 3H), 1.14-1.11 (m, 2H), 0.94-0.90 (m, 2H); m/z=355 [M−1].

Where racemic mixtures of chiral compounds have been resolved into separate enantiomers, the phrase "substantially free" of the epimer, as used herein, means an enantiomeric excess of at least 90%.

Example 72

N-(3,4-difluoro-2-(2-fluoro-4-(1H-pyrazol-4-yl)phenylamino)phenyl)cyclopropane sulfonamide Step A: 2,3-Difluoro-N-(2-fluoro-4-iodophenyl)-6-nitroaniline

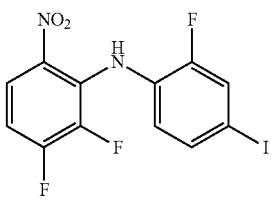 [SMILES: O=[N+]([O-])c1ccc(F)c(F)c1Nc1ccc(I)cc1F]

To a solution of 2-fluoro-4-iodoaniline (11.40 g, 47 mmol) in 100 ml anhydrous THF at 0° C., 47 ml of a 1M solution of LHMDS in THF (47 mmol) was added dropwise. The color of the solution turned dark purple. The solution was transferred via cannula to a dropping funnel, and the solution (containing the amine free base) was added in small portions to a solution of 2,3,4-trifluoronitrobenzene (8.321 g, 47.0 mmol) in anhydrous THF (50 ml) at 0° C. After completion of addition the mixture was stirred under argon at room temperature for 15 hours. The volume of the solvent was reduced, followed by extraction using ethyl acetate and brine. The organic layer was dried over sodium sulfate, the solvent was removed, and the obtained dark oil was purified by flash chromatography (EtOAc/hexane 1:5, R$_f$=0.58) yielding the crude product, which became a brown solid upon drying in vacuo (yield: 6.23 g, 33.6%). m/z=393 [M−1]$^−$.

Step B: 5,6-Difluoro-N1-(2-fluoro-4-iodophenyl)benzene-1,2-diamine

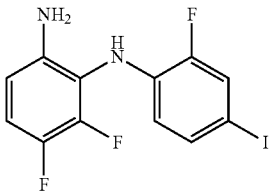

To a solution of nitro-diarylamine (6.23 g, 15.8 mmol) in 300 ml ethanol was added iron powder (13.74 g, 246 mmol) and ammonium chloride (13.59 g, 254 mmol) and the mixture was heated with stirring at 100° C. oil bath temperature for 14 hours. It was filtered and the residue washed two times with ethanol. The ethanol was removed in vacuo, and the residue was extracted using ethyl acetate/1M NaOH solution. During the extraction, more precipitate was formed which was filtered and discarded. The combined organic layers were washed with brine and dried over sodium sulfate. The solvent was removed, and the crude product was recrystallized from CHCl$_3$/hexane (1:50). The product was obtained as brown needles (2.094 g, 66%,). R$_f$=0.44 (EtOAc/Hex 1:3). $^1$H-NMR (500 MHz, CDCl$_3$): δ=7.40-7.38 (dd, 1H, J=11.3 Hz, J=1.5 Hz), 7.25-7.23 (d, 1H, J=8.5 Hz), 6.97-6.92 (q, 1H, J=9 Hz), 6.51-6.48 (m, 1H), 6.24-6.21 (t, 1H, J=9 Hz), 5.3 (s, 1H, NH, br), 3.80 (s, 2H, NH$_2$, br); LRMS (ESI): m/z=365 [M+H]$^+$.

Step C: N-(3,4-difluoro-2-(2-fluoro-4-iodophenylamino)phenyl)cyclopropane sulfonamide

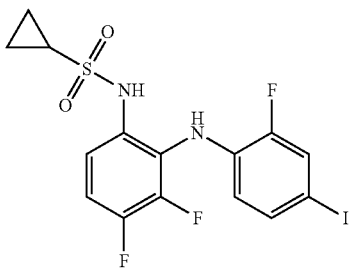 [SMILES: O=S(=O)(Nc1ccc(F)c(F)c1Nc1ccc(I)cc1F)C1CC1]

According to the general procedure A, 5,6-difluoro-N1-(2-fluoro-4-iodophenyl)benzene-1,2-diamine was reacted with cyclopropanesulfonyl chloride to obtain the desired product. (500 MHz, CDCl$_3$): δ=7.38-7.37 (d, 1H), 7.35-7.34 (m, 1H), 7.27-7.26 (m, 1H), 7.20-7.0 (q, 1H), 6.68 (s, 1H, br), 6.15-6.12 (q, 1H), 5.65 (s, 1H, br), 3.25-3.20 (m, 1H), 2.4-2.3 (m, 2H), 2.0-1.8 (m, 2H); m/z=467 [M−1]$^-$.

Step D: N-(3,4-difluoro-2-(2-fluoro-4-(1H-pyrazol-4-yl)phenylamino)phenyl)cyclopronanesulfonamide

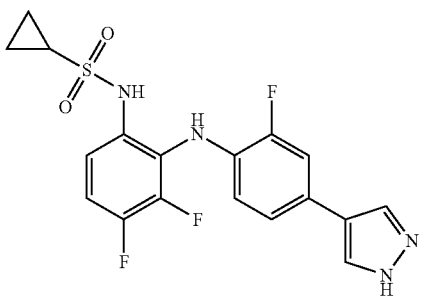 [SMILES: O=S(=O)(Nc1ccc(F)c(F)c1Nc1ccc(-c2cn[nH]c2)cc1F)C1CC1]

General procedure C: $^1$H-NMR (500 MHz, CDCl$_3$): δ=8.00-7.90 (m, 2H), 7.30-7.20 (m, 2H), 7.15-7.10 (m, 1H), 7.05-7.00 (m, 1H), 6.70-6.60 (m, 1H), 2.40-2.35 (m, 1H), 1.05-1.0 (m, 2H), 0.95-0.85 (m, 2H); m/z=407 [M−1]$^-$.

Example 73

N-(3,4-difluoro-2-(2-fluoro-4-(1-methyl-1H-pyrazol-4-yl)phenylamino)phenyl)cyclopropanesulfonamide

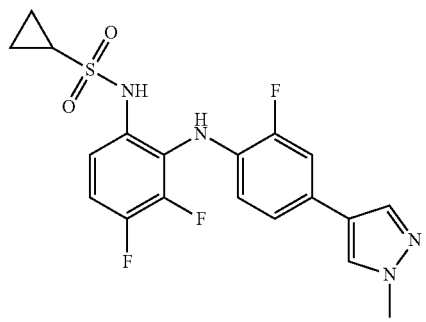 [SMILES: Cn1cc(-c2ccc(Nc3c(NS(=O)(=O)C4CC4)ccc(F)c3F)c(F)c2)cn1]

General procedure C: $^1$H-NMR (500 MHz, CDCl$_3$): δ=7.95 (s, 1H), 7.75 (s, 1H), 7.30-7.20 (m, 2H), 7.15-7.10 (m, 1H), 7.05-7.00 (m, 1H), 6.70-6.60 (m, 1H), 3.95 (s, 3H), 2.40-2.35 (m, 1.05-1.0 (m, 2H), 0.95-0.85 (m, 2H); m/z=421 [M−1]$^-$.

Example 74

N-(3,4-difluoro-2-(2-fluoro-4-(1H-pyrazol-3-yl)phenylamino)phenyl)cyclopropanesulfonamide

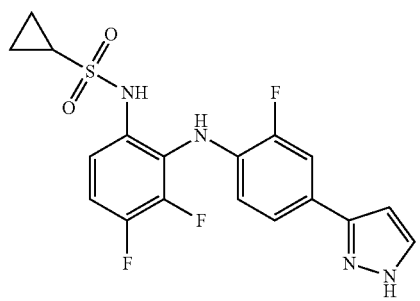 [SMILES: O=S(=O)(Nc1ccc(F)c(F)c1Nc1ccc(-c2cc[nH]n2)cc1F)C1CC1]

General procedure C: $^1$H-NMR (500 MHz, CDCl$_3$): δ=7.90 (s, 1H), 7.80 (s, 1H), 7.30-7.20 (m, 2H), 7.15-7.10 (m, 1H), 7.05-7.00 (m, 1H), 6.70-6.60 (m, 1H), 3.95 (s, 3H), 2.40-2.35 (m, 1H), 1.05-1.0 (m, 2H), 0.95-0.85 (m, 2H); m/z=407 [M−1]$^-$

Example 75

N-(3,4-difluoro-2-(2-fluoro-4-(pyridin-4-yl)phenylamino)phenyl)cyclopropanesulfonamide

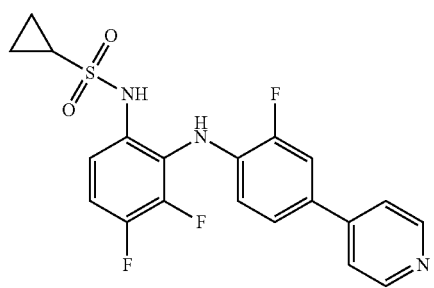 [SMILES: O=S(=O)(Nc1ccc(F)c(F)c1Nc1ccc(-c2ccncc2)cc1F)C1CC1]

General procedure C: $^1$H-NMR (500 MHz, CDCl$_3$): δ=8.62-8.61 (d, 2H), 7.43-7.41 (m, 4H), 7.23-7.22 (m, 1H), 7.16-7.11 (q, 1H), 6.61-6.58 (t, 1H), 6.11 (s, 1H, br), 2.53-2.50 (m, 1H), 1.21-1.10 (m, 2H), 1.02-0.99 (m, 2H); m/z=418 [M−1]$^-$.

Example 76

N-(3,4-difluoro-2-(2-fluoro-4-(pyridin-3-yl)phenylamino)phenyl)cyclopropanesulfonamide

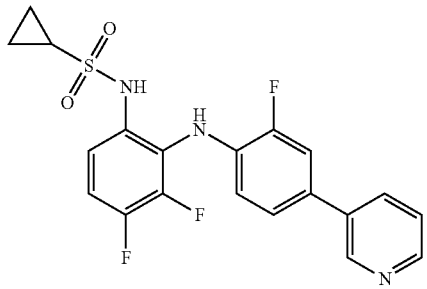 [SMILES: O=S(=O)(Nc1ccc(F)c(F)c1Nc1ccc(-c2cccnc2)cc1F)C1CC1]

General procedure C: $^1$H-NMR (500 MHz, [D6]-DMSO): δ=9.45 (s, 1H), 8.91 (s, 1H), 8.54 (s, 1H), 8.07-8.06 (d, 1H), 7.76-7.70 (m, 2H), 7.46-7.34 (m, 2H), 7.34-7.33 (d, 2H), 6.80-6.78 (m, 1H), 0.86-0.79 (m, 4H); m/z=418 [M−1]$^-$

Example 77

N-(2-(4-cyano-2-fluorophenylamino)-3,4-difluorophenyl)cyclopropanesulfonamide

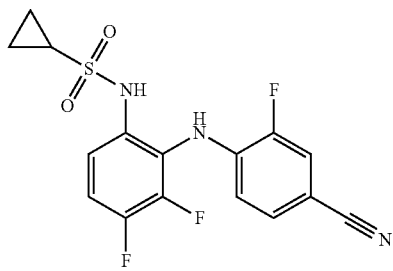 [SMILES: N#Cc1ccc(Nc2c(NS(=O)(=O)C3CC3)ccc(F)c2F)c(F)c1]

A suspension containing the aryl iodide (75.5 mg, 0.161 mmol), CuCN (46.6 mg, 0.520 mmol and Pd(OAc)$_2$ (0.47 mg) in 1 ml anhydrous DMF was heated to 130° C. for 60 min. in a microwave reactor. The mixture was extracted using brine/THF, and the organic fractions were dried using Na$_2$SO$_4$. Subsequent flash-column chromatography gave the product as a dark red semi-solid (R$_f$=0A2 (EtOAc/Hexanes 1:1). Yield: 15%.
m/z=366 [M−1]$^-$.

Example 78

N-(3,4-difluoro-2-(3-fluorobiphenyl-4-ylamino)phenyl)cyclopropanesulfonamide

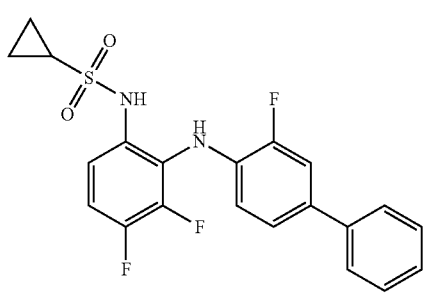 [SMILES: O=S(=O)(Nc1ccc(F)c(F)c1Nc1ccc(-c2ccccc2)cc1F)C1CC1]

General procedure C: $^1$H-NMR (500 MHz, CDCl$_3$): δ=7.55-7.53 (m, 2H), 7.45-7.3 (m, 5H), 7.20-7.15 (d, 1H), 7.13-7.10 (q, 1H), 6.70 (s, 1H, br), 6.60-6.55 (t, 1H), 5.75 (s, 1H, br), 2.53-2.50 (m, 1H), 1.21-1.10 (m, 2H), 1.02-0.99 (m, 2H); m/z=417 [M−1]$^-$.

Example 79

N-(2-(3'-acetyl-3-fluorobiphenyl-4-ylamino)-3,4-difluorophenyl)cyclopropanesulfonamide

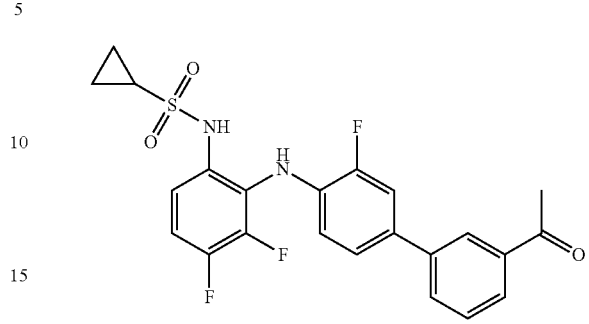

General procedure C: $^1$H-NMR (500 MHz, CDCl$_3$): δ=8.6 (s, 1H), 7.86-7.85 (d, 1H), 7.68-7.66 (d, 1H), 7.49-7.46 (t, 1H), 7.38-7.33 (m, 2H), 7.20-7.18 (d, 1H), 7.09-7.03 (q, 1H), 6.90 (s, 1H, br), 6.57-6.54 (t, 1H), 5.90 (s, 1H), br), 2.61 (s, 3H), 2.46-2.43 (m, 1H), 1.15-1.13 (m, 2H), 0.94-0.91 (m, 2H); m/z=459 [M−1]$^-$.

Example 80

N-(2-(4'-cyano-3-fluorobiphenyl-4-ylamino)-3,4-difluorophenyl)cyclopropanesulfonamide

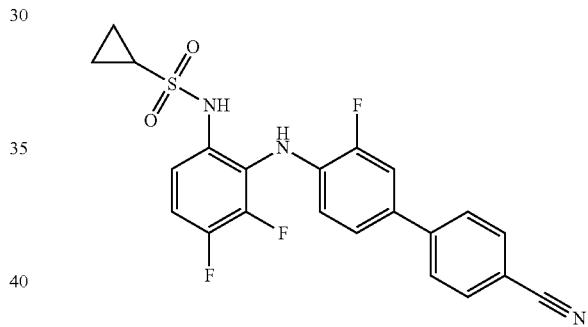

General procedure C: $^1$H-NMR (500 MHz, CDCl$_3$): δ=7.68-7.66 (m, 2H), 7.58-7.57 (m, 2H), 7.38-7.35 (m, 2H), 7.20-7.18 (d, 1H), 7.18-7.02 (q, 1H), 6.67 (s, 1H, br), 6.58-6.54 (t, 1H), 5.99 (s, 1H, br), 2.47-2.44 (m, 1H), 1.15-1.13 (m, 2H), 0.94-0.91 (m, 2H); m/z=442 [M−1]$^-$.

Example 81

N-(2-(3,4'-difluorobiphenyl-4-ylamino)-3,4-difluorophenyl)cyclopropanesulfonamide

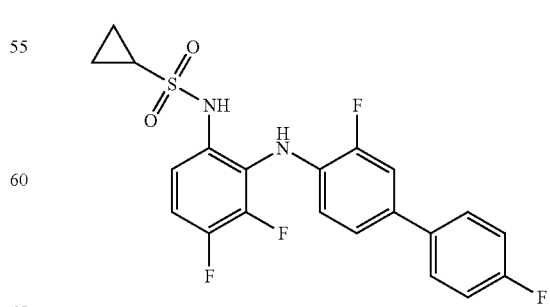

General procedure C: $^1$H-NMR (500 MHz, CDCl$_3$): δ=7.44-7.37 (m, 3H), 7.29-7.27 (d, 1H), 7.11-7.05 (m, 4H), 6.70 (s, 1H, br), 6.53-6.50 (t, 1H), 5.81 (s, 1H, br), 2.47-2.44 (m, 1H), 1.15-1.13 (m, 2H), 0.94-0.91 (m, 2H); m/z=435 [M−1]⁻.

Example 82

N-(3,4-difluoro-2-(3-fluoro-4'-(methylsulfonamido) biphenyl-4-ylamino)phenyl)cyclopropanesulfonamide

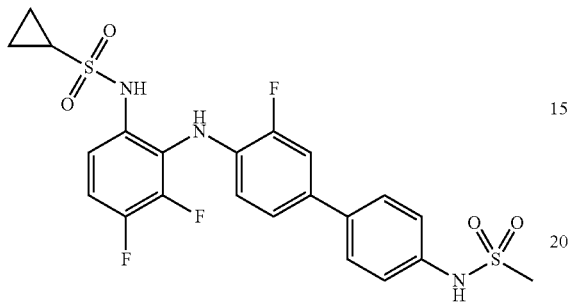

General procedure C: ¹H-NMR (500 MHz, [D6]-DMSO): δ=9.39 (s, 1H, br), 7.63-7.60 (m, 3H), 7.53-7.50 (d, 1H), 7.30-7.23 (m, 4H), 7.74-7.65 (m, 1H), 2.99 (s, 3H), 0.80-0.73 (m, 4H); m/z=510 [M−1]⁻.

Example 83

N-(3,4-difluoro-2-(2-fluoro-4-methylphenylamino) phenyl)cyclopropanesulfonamide

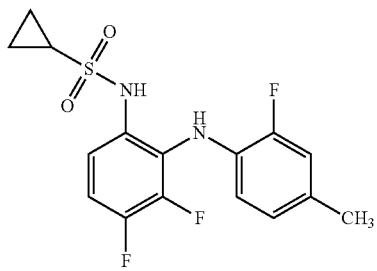 [SMILES: Cc1ccc(Nc2c(NS(=O)(=O)C3CC3)ccc(F)c2F)c(F)c1]

General procedure C: ¹H-NMR (500 MHz, CDCl₃): δ=7.38-7.36 (m, 1H), 7.06-7.03 (q, 1H), 6.92-6.90 (1H), 6.73-6.72 (d, 1H), 6.63 (s, 1H, br), 6.37-6.33 (t, 1H), 5.54 (s, 1H, br), 2.42-2.39 (m, 1H), 2.25 (s, 3H), 1.14-1.11 (m, 2H), 0.94-0.90 (m, 2H); m/z=355 [M−1]⁻.

Example 84

4'-(6-(cyclopropanesulfonamido)-2,3-difluorophenylamino)-3'-fluorobiphenyl-3-carboxylic acid

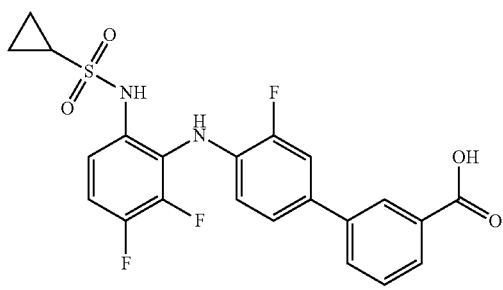 [SMILES: O=C(O)c1cccc(-c2ccc(Nc3c(NS(=O)(=O)C4CC4)ccc(F)c3F)c(F)c2)c1]

General procedure C: ¹H-NMR (500 MHz, [D4]-MeOH): δ=8.21 (s, 1H), 7.93-7.91 (d, 1H), 7.73-7.72 (d, 1H), 7.47-7.43 (m, 2H), 7.33-7.31 (d, 2H), 7.15-7.12 (q, 1H), 6.71-6.68 (m, 1H), 2.51-2.46 (m, 1H), 0.94-0.93 (m, 2H), 0.88-0.87 (m, 2H); m/z=499 [M−1]⁻.

Example 85

N-(3,4-difluoro-2-(3-fluoro-3'-(methylsulfonamido) biphenyl-4-ylamino)phenyl)cyclopropanesulfonamide

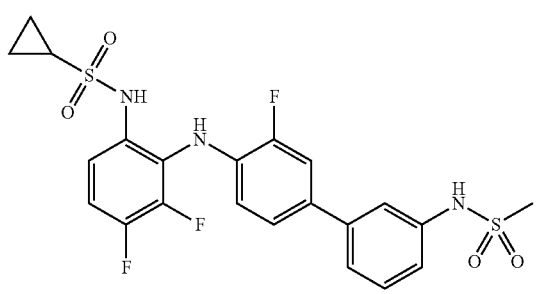 [SMILES: CS(=O)(=O)Nc1cccc(-c2ccc(Nc3c(NS(=O)(=O)C4CC4)ccc(F)c3F)c(F)c2)c1]

General procedure C: ¹H-NMR (500 MHz, [D4]-MeOH): δ=7.92 (s, 1H), 7.46-7.34 (m, 5H), 7.34-7.31 (d, 1H), 7.29-7.22 (m, 1H), 7.16-7.15 (q, 1H), 6.74-6.71 (m, 1H), 2.80 (s, 3H), 2.54-2.51 (m, 1H), 0.94-0.92 (m, 2H), 0.91-0.90 (m, 2H); m/z=510 [M−1]⁻.

Example 86

N-(3,4-difluoro-2-(3-fluoro-2'-(methylsulfonamido) biphenyl-4-ylamino)phenyl)cyclopropanesulfonamide

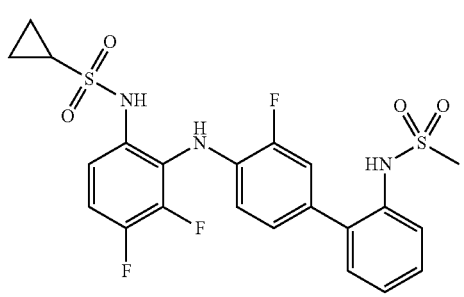 [SMILES: CS(=O)(=O)Nc1ccccc1-c1ccc(Nc2c(NS(=O)(=O)C3CC3)ccc(F)c2F)c(F)c1]

General procedure C: ¹H-NMR (500 MHz, (D41-MeOH): δ=7.50-7.49 (d, 1H), 7.40-7.32 (m, 4H), 7.29-7.28 (d, 1H), 7.26-7.10 (m, 2H), 6.73-6.71 (m, 1H), 2.80 (s, 3H), 2.51-2.49 (m, 1H), 0.94-0.92 (m, 2H), 0.91-0.90 (m, 2H); m/z=510 [M−1]⁻.

Example 87

N-(3,4-difluoro-2-(3-fluoro-4'-(trifluoromethoxy)biphenyl-4-ylamino)phenyl)cyclopropanesulfonamide

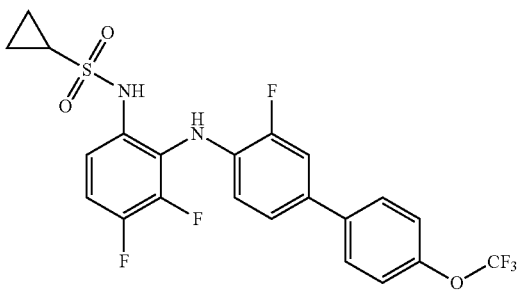 [SMILES: O=S(=O)(Nc1ccc(F)c(F)c1Nc1ccc(-c2ccc(OC(F)(F)F)cc2)cc1F)C1CC1]

General procedure C: ¹H-NMR (500 MHz, [D4]-MeOH): δ=7.69-7.67 (d, 2H), 7.46-7.43 (d, 1H), 7.36-7.33 (m, 4H), 7.30-7.29 (q, 1H), 6.73-6.72 (m, 1H), 2.51-2.49 (m, 1H), 0.94-0.92 (m, 2H), 0.91-0.90 (m, 2H); m/z=501 [M−1]⁻.

Example 88

N-(3,4-Difluoro-2-(2-fluoro-4-iodophenylamino)phenyl)-2-(methylamino)ethanesulfonamide

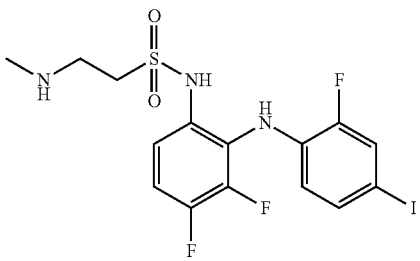 [SMILES: CNCCS(=O)(=O)Nc1ccc(F)c(F)c1Nc1ccc(I)cc1F]

General procedure D. ¹H NMR (300 MHz, CDCl₃): δ 9.01 (br s, D₂O exchangeable, 1H), 7.36 (dd, J=2.1 & 10.5 Hz, 1H), 7.27 (m, 1H), 7.17 (m, 1H), 7.03 (dd, J=9.0 & 16.8 Hz, 1H), 6.48 (s, D₂O exchangeable, 1H), 6.31 (dt, J=3.0, 8.7 & 17.4 Hz, 1H), 3.45 (br t, 2H), 3.31 (br s, 2H), 2.65 (s, 3H), 1.80 (br s, D₂O exchangeable, 1H).

Example 89

N-(3,4-difluoro-2-(2-fluoro-4-iodophenylamino)phenyl)-2-(2-(dimethylamino)ethylamino) ethanesulfonamide

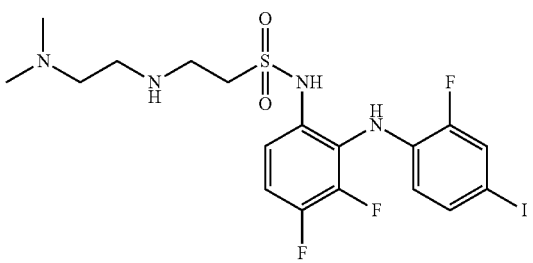 [SMILES: CN(C)CCNCCS(=O)(=O)Nc1ccc(F)c(F)c1Nc1ccc(I)cc1F]

General procedure D. ¹H NMR (300 MHz, CDCl₃): δ 7.35 (m, 1H), 7.25 (m, 1H), 7.18 (d, J=8.7 Hz, 1H), 7.02 (dd, J=8.7 & 18.0 Hz, 1H), 6.38 (m, 1H), 6.18 (dd, J=8.7 & 17.1 Hz, 1H), 3.62 (t, J=5.7 & 6.3 Hz, 2H), 3.35 (m, 2H), 3.26 (m, 2H), 3.26 (t, J=5.7 & 6.6 Hz, 2H), 3.11 (t, J=5.1 & 6.0 Hz, 2H), 2.85 (s, 6H).

Example 90

N-(3,4-difluoro-2-(2-fluoro-4-iodophenylamino)phenyl)-2-(ethyl(methyl)amino)ethanesulfonamide

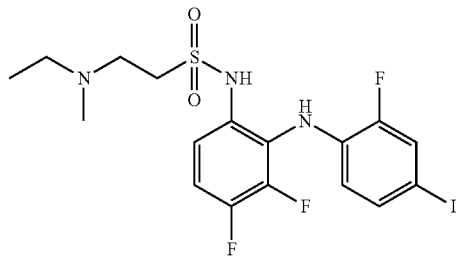 [SMILES: CCN(C)CCS(=O)(=O)Nc1ccc(F)c(F)c1Nc1ccc(I)cc1F]

General procedure D. ¹H NMR (300 MHz, (CDCl₃+D₂O)): δ 7.39 (dd, J=1.5 & 10.5 Hz, 1H), 7.31 (m, 2H), 7.07 (dd, J=9.0 & 17.4 Hz, 1H), 6.30 (dt, J=2.4, 9.0 & 17.4 Hz, 1H), 3.55 (t, J=6.9 & 7.8 Hz, 2H), 3.38 (br t, J=6.0 & 8.7 Hz, 2H), 3.05 (q, 2H), 2.69 (s, 3H), 1.31 (t, J=7.2 Hz, 3H).

Example 91

N-(3,4-difluoro-2-(2-fluoro-4-iodophenylamino)phenyl)-2-(4-methylpiperazin-1-yl)ethanesulfonamide

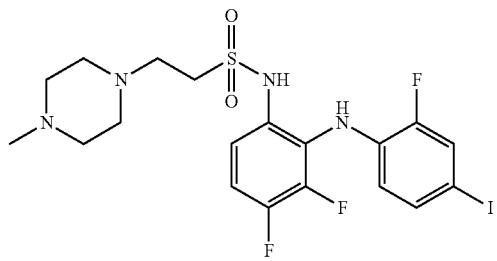 [SMILES: CN1CCN(CCS(=O)(=O)Nc2ccc(F)c(F)c2Nc2ccc(I)cc2F)CC1]

General procedure D. ¹H NMR (300 MHz, CD₃OD): δ 7.45 (dd, J=2.1 & 10.8 Hz, 1H), 7.30 (m, 2H), 7.16 (dd, J=9.6 & 17.7 Hz, 1H), 6.39 (dt, J=33, 9.3 & 17.7 Hz, 1H), 3.26 (m, J=7.5 Hz, 2H), 3.10 (br m, 6H), 2.87 (s, 3H), 2.82 (t, J=7.5 Hz, 2H), 2.48 (br m, 4H).

In Vitro Biological Activity

Example 92

Generation of IC50 Data

Materials and preparation of reagents: Human GST-MEK1 and the constitutively active allele GST-MEK1$^{CA}$ (harboring the mutations Ser218Asp and Ser222Asp) were subcloned into the yeast expression vector pGEM4Z (Promega, Madison, Wis.) from the wild type human MEK1 cDNA. GST-MEK1$^{CA}$ was expressed in *Escherichia coli* and partially purified using Glutathione Sepharose 4B affinity resin (Amersham Pharmacia Biotech, Piscataway, N.J.). The ERK2 allele was subcloned from MAPK2/Erk2 cDNA (wild type) in pUSEamp (Upstate Biotechnology, Inc., Waltham, Mass.) into the vector pBT21a (Novagen, Madison, Wis.) resulting in an N-terminal histidine-tagged mouse ERK2 allele. ERK2 was expressed and purified to homogeneity [Zhang, 1993 #33]. Myelin basic protein (MBP) was purchased from Gibco BRL (Rockville, Md.). EasyTides adenosine 5'-triphosphate (ATP) ([γ-$^{33}$P]) (NEN Perkin Elmer, Wellesley, Mass.) was the source of radiolabel for all kinase reactions. Activated Raf-1 (truncated) and activated MAPKinase 2/ERK2 were purchased from Upstate, Inc. (Lake Placid, N.Y.). 4-20% Criterion Precast gels were purchased from Bio-Rad (Hercules, Calif.).

Determination of enzymatic activity: Compounds were diluted from dimethylsulfoxide (DMSO) stocks into 1×HMNDE (20 mM HEPES pH 7.2, 1 mM $MgCl_2$, 100 mM NaCl, 1.25 mM DTT, 0.2 mM EDTA). A typical 25-microliter assay contained 0.002 nanomoles $MEK1^{CA}$, 0.02 nanomoles ERK2, 0.25 nanomoles MBP, 0.25 nanomoles unlabeled ATP, and 0.1 µCi [γ$^{33}$P] ATP. The screening assay essentially comprised four additions. Five µl of diluted compound were dispensed to 96-well assay plates. Ten µl of 2.5× enzyme cocktail ($MEK1^{CA}$ and ERK2 only) were then added to each well followed by a pre-incubation for 30 minutes at ambient temperature. Ten µl of 2.5× substrate cocktail (labeled and unlabeled ATP plus MBP) were then added, followed by incubation for 60 minutes at ambient temperature. Finally, 100 µl of 10% trichloroacetic acid (TCA) were added and incubated for 30 minutes at room temperature to halt the reaction and precipitate radiolabeled protein products. Reaction products were harvested on glass fiber 96 well filter plates prewetted with water and 1% pyrophosphate. The filter plate was then washed 5 times with water. Water was displaced by absolute ethanol and the plate was allowed to air dry for 30 minutes at room temperature. A back seal was applied manually and 40 µl of scintillation cocktail were dispensed to each well. A top seal was applied and the plate was counted in the TopCount for two seconds per well.

For certain experiments a truncated version of MEK that requires activation by Raf kinase were used.

Example 93

Generation of EC50 Data

Effects of compounds in the cell were determined by Western blotting for phosphorylated ERK. MDA-MB-231 breast cancer cells were plated in a 48 well plate at 20,000 cells per well and grown in a 37° humidified $CO_2$ incubator. The following day, the growth media (DMEM+10% fetal bovine serum) was removed and replaced with starve media (DMEM+0.1% fetal bovine serum). Cells were incubated in the starve media for sixteen hours and then treated with a range of compound concentrations for thirty minutes. After incubation with compound, cells were stimulated with 100 ng/ml EGF for five minutes. The cells were then lysed and analyzed by Western blot using a monoclonal antibody raised to phosphorylated ERK. The signal was amplified using a secondary antibody conjugated to a near-IR dye and detected on a Licor Odyssey scanner. The intensity of signal was quantitated and this data was used to generate dose response curves and EC50 calculations.

| Compound Number | Structure | Activity µM |
|---|---|---|
| 1000 | 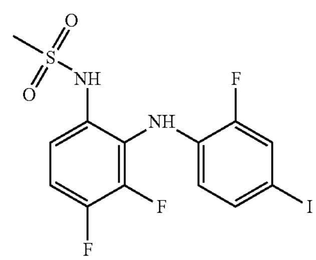 [SMILES: CS(=O)(=O)Nc1ccc(F)c(F)c1Nc1ccc(I)cc1F] | A |
| 1001 | 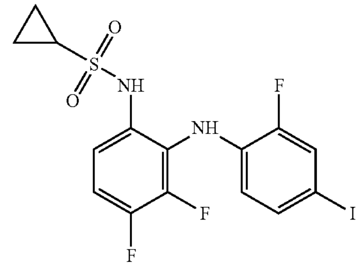 [SMILES: O=S(=O)(Nc1ccc(F)c(F)c1Nc1ccc(I)cc1F)C1CC1] | A |
| 1002 | 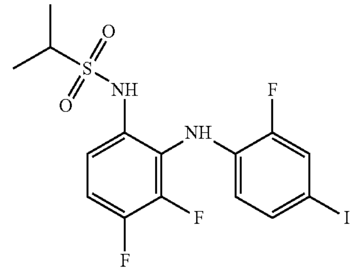 [SMILES: CC(C)S(=O)(=O)Nc1ccc(F)c(F)c1Nc1ccc(I)cc1F] | B |

-continued

| Compound Number | Structure | Activity μM |
|---|---|---|
| 1003 | 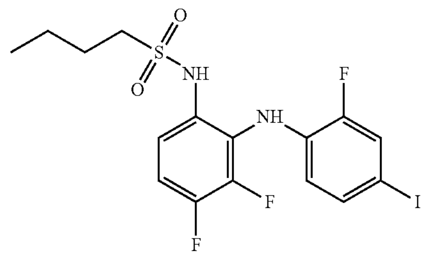 [SMILES: CCCCS(=O)(=O)Nc1ccc(F)c(F)c1Nc1ccc(I)cc1F] | C |
| 1004 | 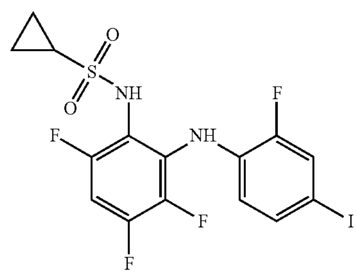 [SMILES: O=S(=O)(Nc1c(F)cc(F)c(F)c1Nc1ccc(I)cc1F)C1CC1] | C |
| 1005 | 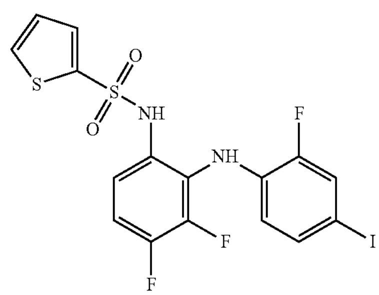 | C |
| 1006 | 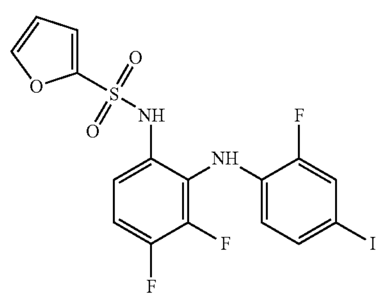 [SMILES: O=S(=O)(Nc1ccc(F)c(F)c1Nc1ccc(I)cc1F)c1ccco1] | C |
| 1007 | 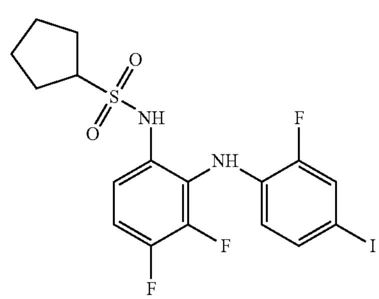 [SMILES: O=S(=O)(Nc1ccc(F)c(F)c1Nc1ccc(I)cc1F)C1CCCC1] | C |

-continued

| Compound Number | Structure | Activity μM |
|---|---|---|
| 1008 | 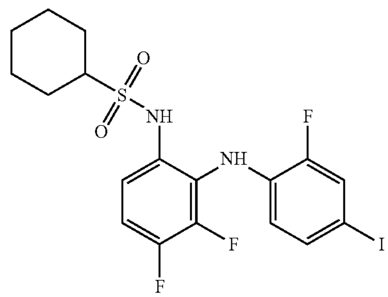 [SMILES: O=S(=O)(Nc1ccc(F)c(F)c1Nc1ccc(I)cc1F)C1CCCCC1] | C |
| 1009 | 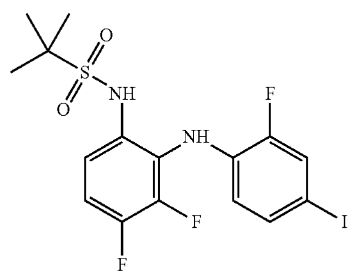 [SMILES: CC(C)(C)S(=O)(=O)Nc1ccc(F)c(F)c1Nc1ccc(I)cc1F] | C |
| 1010 | 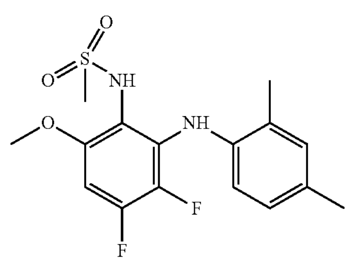 | A |
| 1011 | 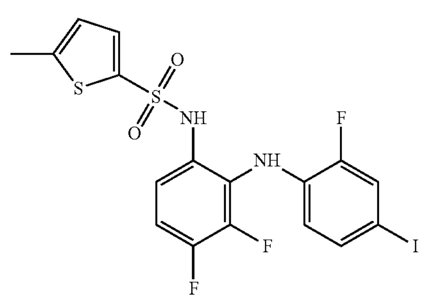 [SMILES: Cc1ccc(S(=O)(=O)Nc2ccc(F)c(F)c2Nc2ccc(I)cc2F)s1] | C |
| 1012 | 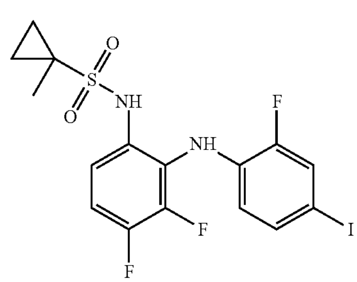 [SMILES: CC1(S(=O)(=O)Nc2ccc(F)c(F)c2Nc2ccc(I)cc2F)CC1] | B |

-continued
| Compound Number | Structure | Activity μM |
|---|---|---|
| 1013 | 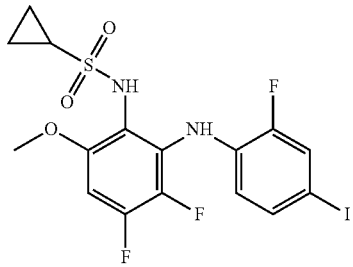 [SMILES: COc1cc(F)c(F)c(Nc2ccc(I)cc2F)c1NS(=O)(=O)C1CC1] | B |
| 1014 | 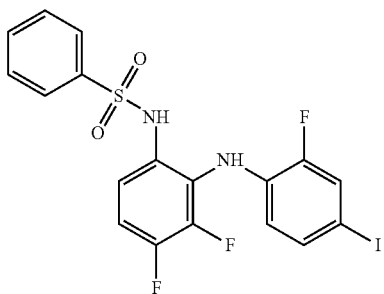 [SMILES: O=S(=O)(Nc1ccc(F)c(F)c1Nc1ccc(I)cc1F)c1ccccc1] | C |
| 1015 | 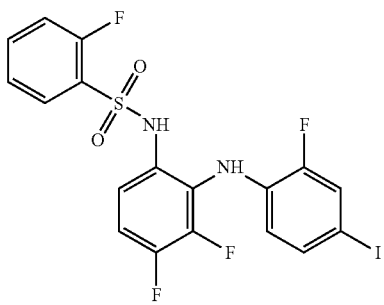 [SMILES: O=S(=O)(Nc1ccc(F)c(F)c1Nc1ccc(I)cc1F)c1ccccc1F] | D |
| 1016 | 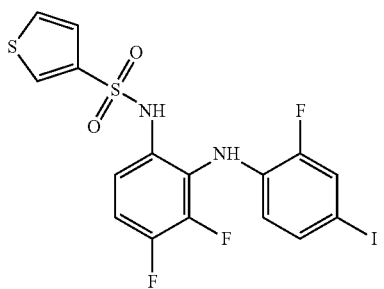 [SMILES: O=S(=O)(Nc1ccc(F)c(F)c1Nc1ccc(I)cc1F)c1ccsc1] | C |
| 1017 | 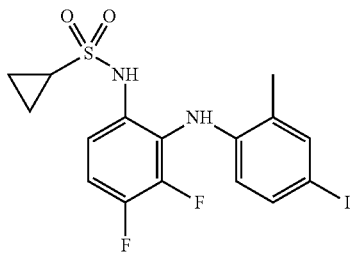 [SMILES: Cc1cc(I)ccc1Nc1c(NS(=O)(=O)C2CC2)ccc(F)c1F] | B |

-continued

| Compound Number | Structure | Activity μM |
|---|---|---|
| 1018 (Racemic) | 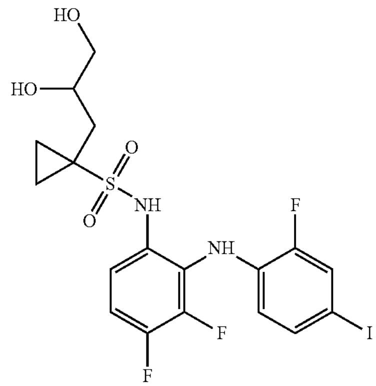 [SMILES: O=S(=O)(Nc1ccc(F)c(F)c1Nc1ccc(I)cc1F)C1(CC(O)CO)CC1] | A |
| 1019 (Racemic) | 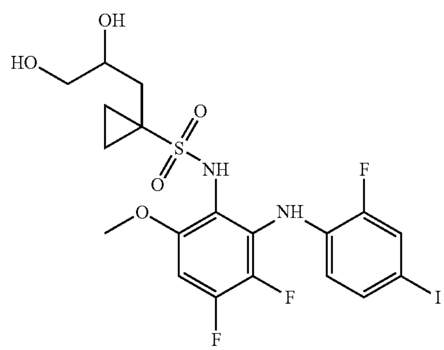 [SMILES: COc1cc(F)c(F)c(Nc2ccc(I)cc2F)c1NS(=O)(=O)C1(CC(O)CO)CC1] | A |
| 1020 (Racemic) | 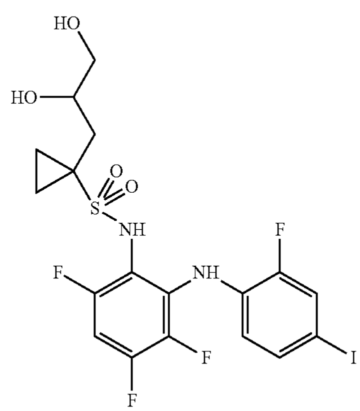 [SMILES: O=S(=O)(Nc1c(F)cc(F)c(F)c1Nc1ccc(I)cc1F)C1(CC(O)CO)CC1] | A |
| 1021 (S isomer) Compound A | 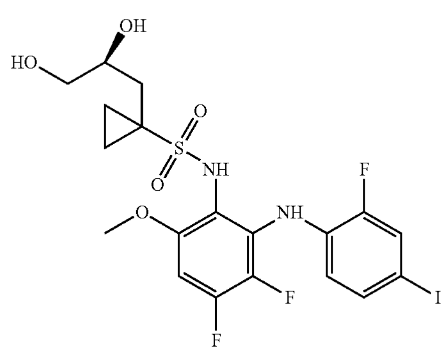 [SMILES: COc1cc(F)c(F)c(Nc2ccc(I)cc2F)c1NS(=O)(=O)C1(C[C@H](O)CO)CC1] | A |

| Compound Number | Structure | Activity µM |
|---|---|---|
| 1022 (R isomer) Compound B | *(structure)* | B |
| 1023 (R isomer) | *(structure)* | B |
| 1024 (S isomer) | *(structure)* | B |
| 1025 | *(structure)* | B |

-continued

| Compound Number | Structure | Activity μM |
|---|---|---|
| 1026 | 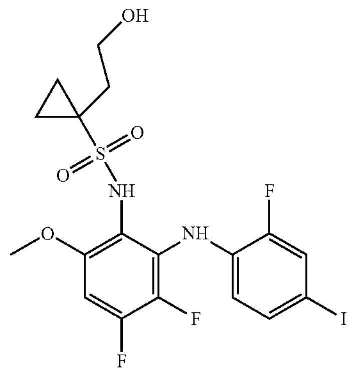 [SMILES: COc1cc(F)c(F)c(Nc2ccc(I)cc2F)c1NS(=O)(=O)C1(CCO)CC1] | A |
| 1027 | 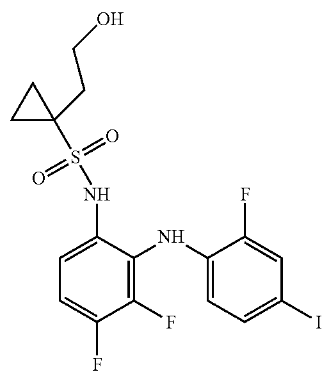 [SMILES: O=S(=O)(Nc1ccc(F)c(F)c1Nc1ccc(I)cc1F)C1(CCO)CC1] | A |
| 1028 | 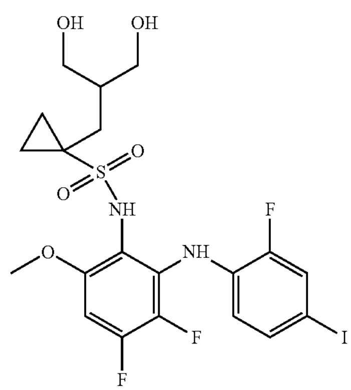 [SMILES: COc1cc(F)c(F)c(Nc2ccc(I)cc2F)c1NS(=O)(=O)C1(CC(CO)CO)CC1] | A |
| 1029 | 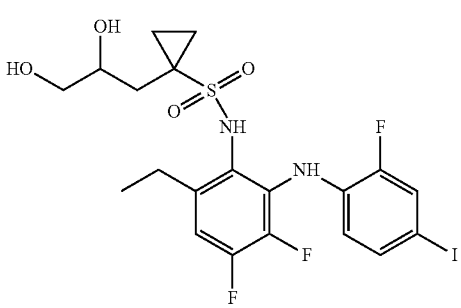 [SMILES: CCc1cc(F)c(F)c(Nc2ccc(I)cc2F)c1NS(=O)(=O)C1(CC(O)CO)CC1] | C |

-continued
| Compound Number | Structure | Activity µM |
|---|---|---|
| 1030 | 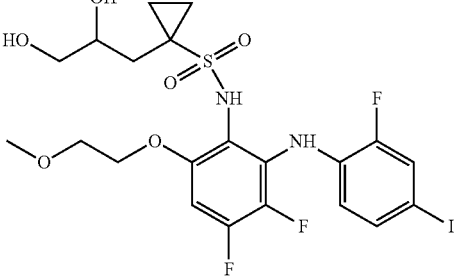 | C |
| 1031 | 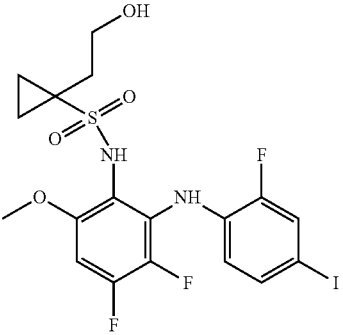 [SMILES: COc1cc(F)c(F)c(Nc2ccc(I)cc2F)c1NS(=O)(=O)C1(CCO)CC1] | A |
Legend:
A, $EC_{50}$ = <2.0 nM;
B, $EC_{50}$ = 2.0-15 nM;
C, $EC_{50}$ = 15 nM-100 nM;
D, $EC_{50}$ > 100 nM, $IC_{50}$ < 20 µM;
F, $EC_{50}$ > 100 nM, $IC_{50}$ > 20 µM
| CPD # | Structure | MDA pERK ELISA $EC_{50}$ |
|---|---|---|
| 0497618 | 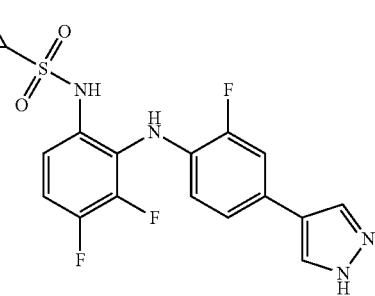 | E |

-continued
| CPD # | Structure | MDA pERK ELISA EC$_{50}$ |
|---|---|---|
| 0497620 | 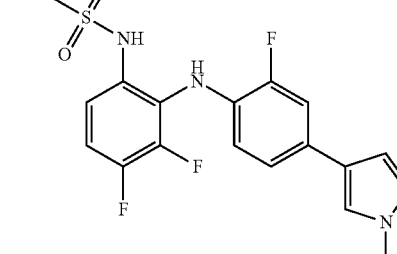 | E |
| 0497654 | 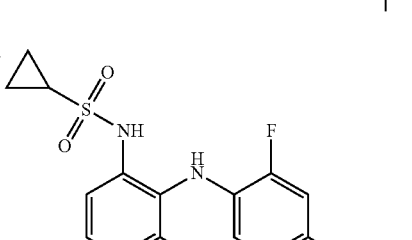 | D |
| 0497688 | 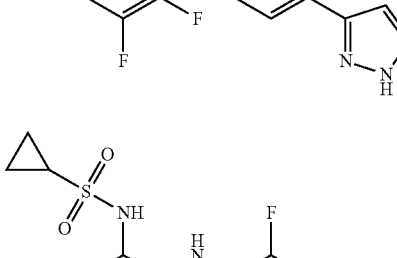 | E |
| 0497689 | 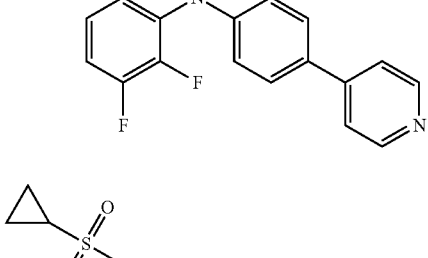 | E |
| 0497692 | 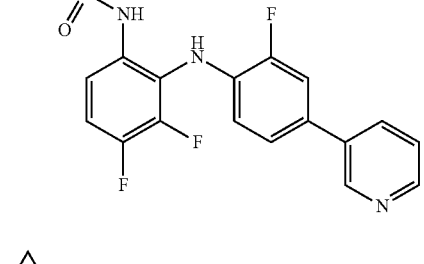 | E |

-continued

| CPD # | Structure | MDA pERK ELISA EC$_{50}$ |
|---|---|---|
| 0499266 | 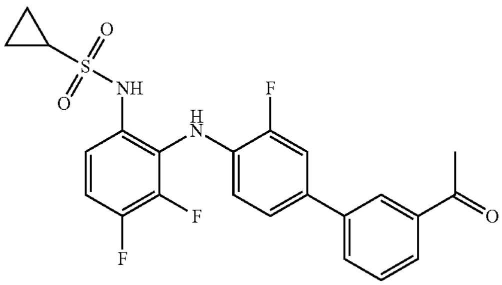 [SMILES: CC(=O)c1cccc(-c2ccc(Nc3c(NS(=O)(=O)C4CC4)ccc(F)c3F)c(F)c2)c1] | E |
| 0499267 | 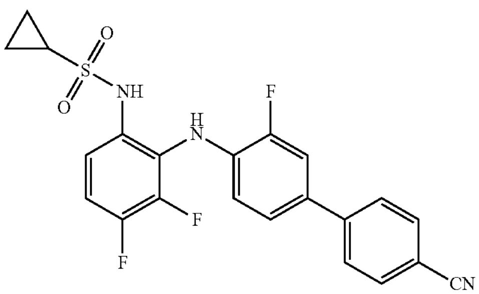 [SMILES: N#Cc1ccc(-c2ccc(Nc3c(NS(=O)(=O)C4CC4)ccc(F)c3F)c(F)c2)cc1] | ND |
| 0499268 | 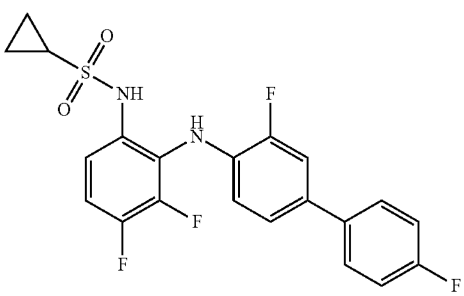 [SMILES: O=S(=O)(Nc1ccc(F)c(F)c1Nc1ccc(-c2ccc(F)cc2)cc1F)C1CC1] | ND |
| 0499271 | 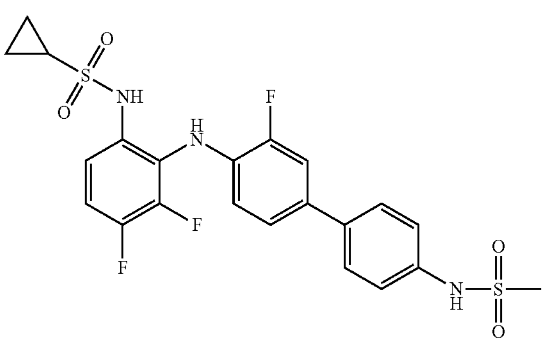 [SMILES: CS(=O)(=O)Nc1ccc(-c2ccc(Nc3c(NS(=O)(=O)C4CC4)ccc(F)c3F)c(F)c2)cc1] | E |
| 0530701 | 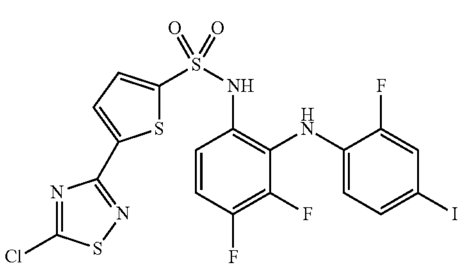 [SMILES: O=S(=O)(Nc1ccc(F)c(F)c1Nc1ccc(I)cc1F)c1ccc(-c2nsc(Cl)n2)s1] | D |

-continued
| CPD # | Structure | MDA pERK ELISA EC$_{50}$ |
|---|---|---|
| 0530716 | 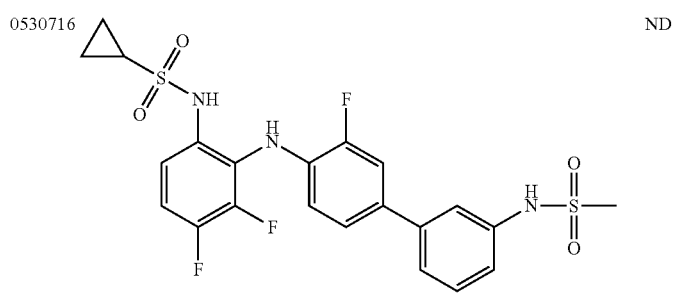 | ND |
| 0530717 | 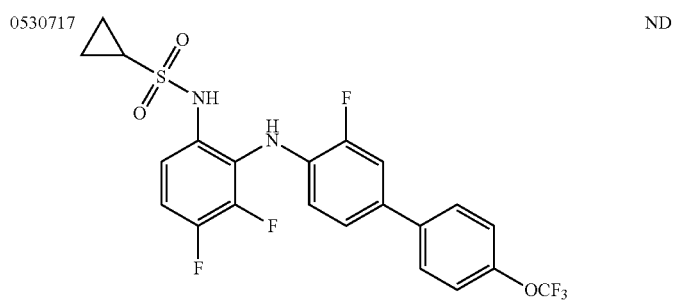 | ND |
| 0561599 | 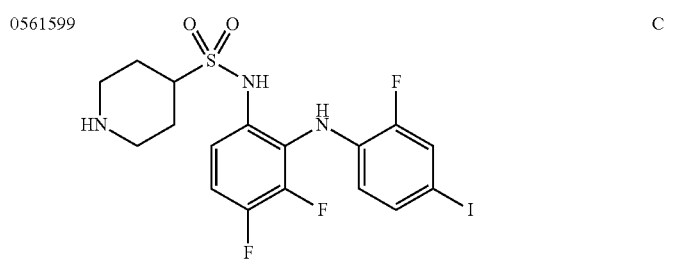 | C |
| 0561608 | 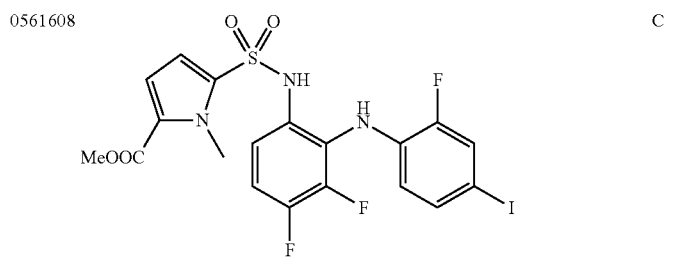 | C |
| 0620926 | 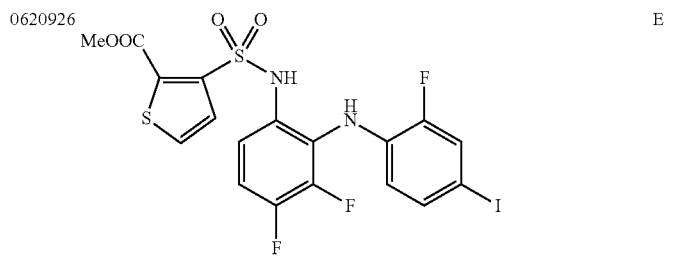 | E |

-continued
| CPD # | Structure | MDA pERK ELISA EC$_{50}$ |
|---|---|---|
| 0620927 | 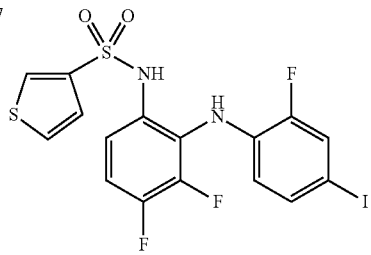 | C |
| 0621002 | 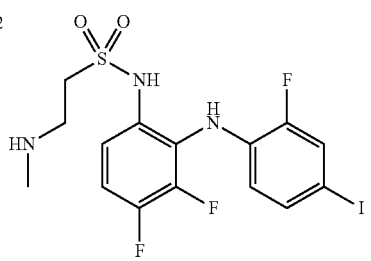 | C |
| 0621016 | 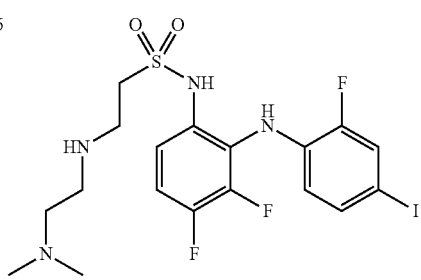 | C |
| 0621026 | 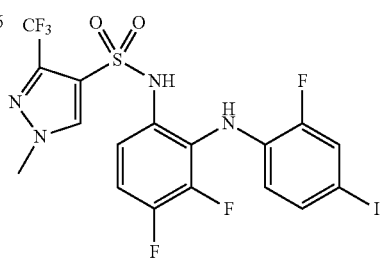 | D |
| 0621029 | 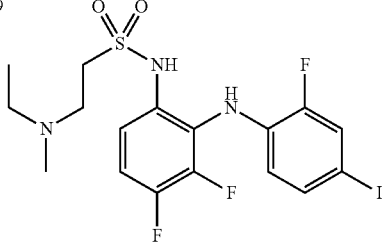 | D |

-continued

| CPD # | Structure | MDA pERK ELISA EC$_{50}$ |
|---|---|---|
| 0621030 | [structure] | ND |

Legend:
A, EC$_{50}$ = <2.0 nM;
B, EC$_{50}$ = 2.0-15 nM;
C, EC$_{50}$ = 15 nM-100 nM;
D, EC$_{50}$ = 100 nM-200 nM;
E, EC$_{50}$ > 200 nM;
ND = not yet determined In Vivo Biological Activity Example 94

The compounds and compositions described herein are useful for the treatment or prophylaxis of one or more diseases including but not limited to cancer, inflammatory bowel disease (IBD), psoriasis and rheumatoid arthritis (RA). The compounds and compositions described herein are also useful for the once- or twice-daily oral treatment or prophylaxis of one or more diseases including but not limited to cancer, IBD, psoriasis and RA.

In vivo tests of the compound of the structure below (Compound A, prepared as described herein), are described in this example:

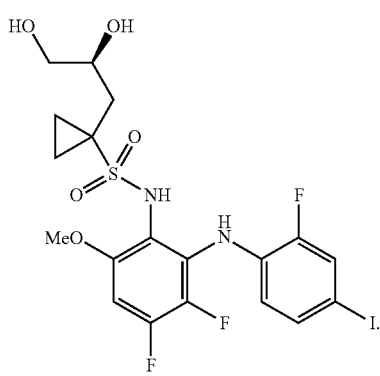 [SMILES: COc1cc(F)c(F)c(Nc2ccc(I)cc2F)c1NS(=O)(=O)C1(C[C@H](O)CO)CC1]

Human tumors were implanted in nu/nu mice. Compound A was administered orally for 14 days once tumors were approximately 100 mm$^3$ in size. Tumor growth inhibition (TGI) was determined after 14 days of treatment as the reduction in the size of tumors in treated groups versus vehicle controls. The time to endpoint (TTE) was calculated as the time for the tumor to reach the specified endpoint volume or the last day of the study, whichever came first. Treatment outcome was determined from percent tumor growth delay (% TGD), defined as the percent increase in median TTE of treated versus vehicle-treated control mice. Animals were also monitored for regression responses. Levels of pERK in tumors and brain were determined by Western blots and correlated with plasma levels of Compound A for the pharmacodynamic/pharmacokinetic study. A number of tumor models were evaluated with different doses and dosing regimens. Treatment with 25 or 50 mg/kg once daily (QD) showed statistically significant % TGD in A375 melanoma tumors, Colo205 colon cancer tumors, and A431 epidermoid tumors. Statistically significant TGI was observed for oral dosing at 25 mg/kg QD for these tumor models as well as in HT29 colon cancer tumors. The effect of different dosing regimens was evaluated in A375 xenografts. Although 100 mg/kg Compound A given orally once every two days showed statistically significant % TGD (91%), it was not as effective as QD treatments at 25 mg/kg (143% TGD) or 50 mg/kg (233% TGD). Twice daily (BID) dosing was also more effective than QD dosing as measured by % TGI. Dosing at 12.5 mg/kg BID resulted in 79.5% TGI compared to 51.7% for 25 mg/kg QD of Compound A. Dosing at 25 mg/kg BID resulted in 110.1% TGI compared to 69.9% TGI for 50 mg/kg QD. A pharmacodynamic/pharmacokinetic study in Colo205 xenografts show inhibition of pERK formation in tumors while minimal inhibition was observed in brain suggesting potent anti-tumor activity with limited CNS penetration.

Compound A is a potent inhibitor of MEK1/2 that suppresses tumor cell growth in vitro and in vivo. BRAE status determines sensitivity to growth inhibition by the compound in anchorage-dependent growth but not anchorage-independent growth or in xenografts. Maintaining adequate MEK inhibition throughout the dosing interval appears to be more important than peak levels due to the greater efficacy with more frequent dosing. Compound A has a favorable pk profile in humans, with the projected therapeutic dose, based on xenograft results, of 20-40 mg/day in humans.

Example 94A

Inhibition of Cancer Cell Growth (GI$_{50}$)

Anchorage-dependent growth inhibition was measured using CellTiterGlo reagent after 48 hr treatment with Compound A of cells grown in 384-well plates. Anchorage-independent growth assays used MTS (methanethiosulfonate) reagent after 7 days treatment of cells grown in media containing 0.15% agarose or on non-binding plates (A431). Growth inhibition values (GI$_{50}$) are shown in the table below.

| Tumor Cell Line | BRAF status | Anchorage-Dependent GI$_{50}$ (nM ± sd) | Anchorage-Independent GI$_{50}$ (nM ± sd) |
|---|---|---|---|
| A375 Melanoma | V600E | 67 ± 12 | 68 ± 34 |
| Colo205 Colon | V600E | 74 ± 45 | 33 ± 16 |
| HT29 Colon | V600E | 70 ± 12 | Not determined |
| A431 Epidermoid | Normal | >10,000 | 65 ± 19 |

Example 94B

Anti-Tumor Xenograft Activity

Female nu/nu mice were implanted with A375 Melanoma, Colo205 Colon Tumor, A431 Epidermoid Tumor or HT-29 Colon Tumor cells, which were allowed to grow to 100-200 mm$^3$. Compound A or vehicle was administered orally (25 mg/kg, 50 mg/kg or 100 mg/kg), once a day, for 14 days. Average tumor volumes were graphed for vehicle and treated groups and are shown in FIG. 1.

Example 94C

Tumor Growth Inhibition (TGI) 25 mg/kg QD

Tumor Growth Inhibition for the groups treated with 25 mg/kg Compound A were calculated for the indicated tumor xenografts. Tumor Growth Inhibition was measured at the end of once daily dosing for 14 days and calculated according to:

$$\%TGI = 100 \times 1 - \frac{\left(\text{treated tumor } volume_{final} - \text{tumor } volume_{initial}\right)}{\left(\text{vehicle treated tumor } volume_{fianl} - \text{tumor } volume_{initial}\right)}$$

The range for A375 and Colo205 represent values from 2 separate studies.

| Tumor Xenograft | % TGI | P value |
|---|---|---|
| A375 Melanoma | 52-72** | <0.001 |
| Colo205 Colon | 70-123** | <0.001 |
| HT29 Colon | 56 | <0.001 |
| A431 Epidermoid | 67 | <0.001 |

**Regressions noted during course of experiment

Example 94D

ED$_{50}$ in Colo205 Xenografts

Male nu/nu mice were implanted with Colo205 tumor cells. After 10 days animals were randomized by tumor size (range 126-256 mm$^3$) and treated with paclitaxel (IV, QODx5), vehicle or Compound A (PO, QDx14).

Pharmacokinetic parameters were obtained from dosing Balb/c mice with 25 mg/kg Compound A and extrapolating values for the lower dose groups and shown in the table below.

| Group | n | Treatment Regimen Agent | mg/kg | Initial Tumor Volume (mm$^3$) | Day 15 Tumor Volume (mm$^3$) | % TGI | C$_{max}$ (µg/mL) | C$_{min}$ (µg/mL) | AUC (µg-hr/mL) |
|---|---|---|---|---|---|---|---|---|---|
| 1 | 10 | Vehicle | — | 185 ± 11.1 | 2093 ± 174 | — | — | — | — |
| 2 | 10 | Paclitaxel | 30 | 184 ± 9.8 | 113 ± 9.6 | 104* | — | — | — |
| 3 | 10 | Compound A | 2.5 | 184 ± 9.8 | 1187 ± 127 | 47* | 0.99 | 0.003 | 5.5 |
| 4 | 10 | | 5 | 183.8 ± 9.8 | 1175 ± 104 | 48* | 1.97 | 0.006 | 11.0 |
| 5 | 10 | | 10 | 185.1 ± 11.7 | 1045 ± 160 | 55* | 3.94 | 0.012 | 22.0 |
| 6 | 10 | | 25 | 185.1 ± 11.7 | 762 ± 81 | 70* | 9.85 | 0.029 | 55.0 |

*P < 0.001

Example 94E

Tumor Growth Inhibition with A375 Xenografts

Figure 2:
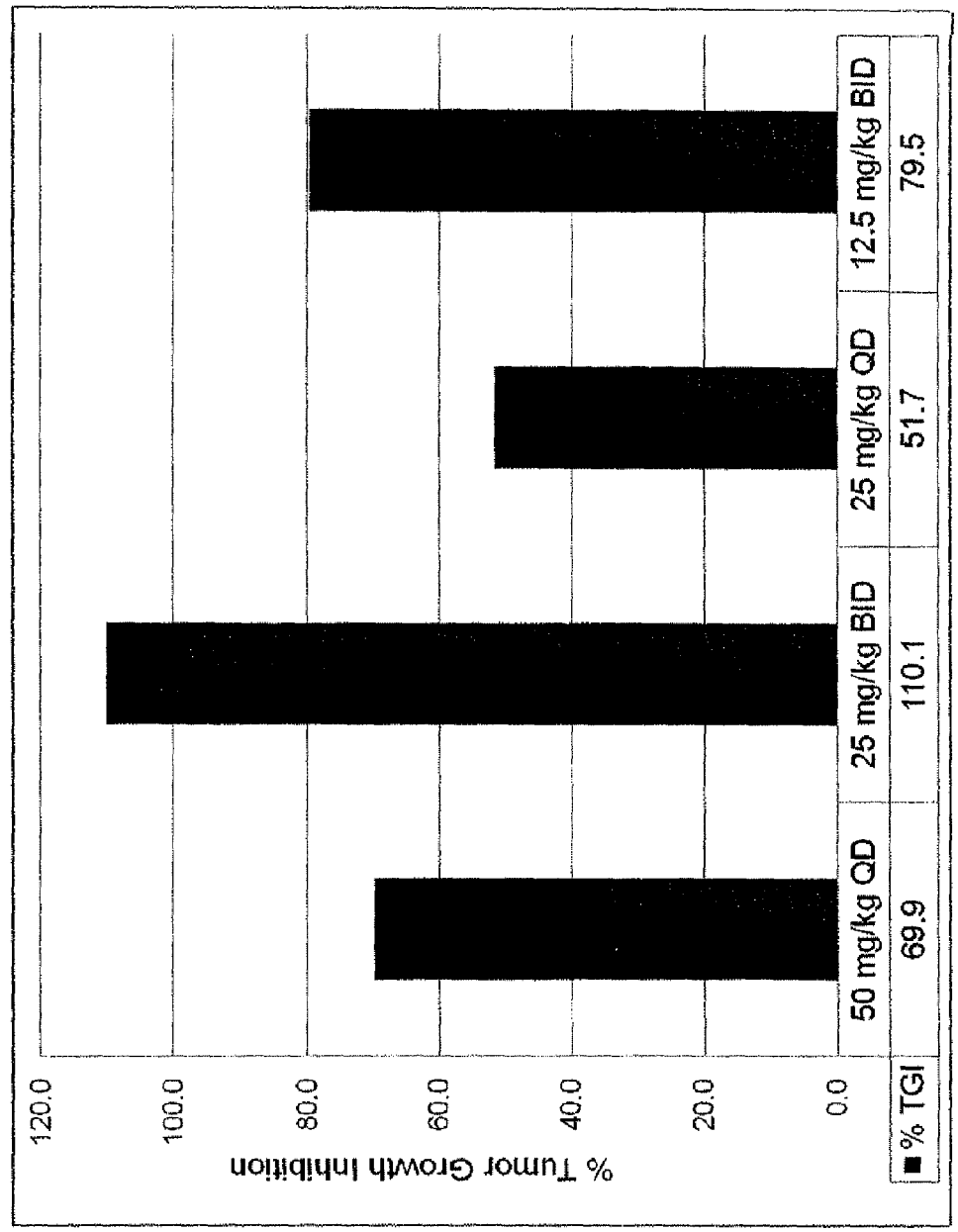
FIG. 2 shows a graph of % Tumor growth inhibition (% TGI) in A375 Xenograft mice dosed 50 mg/kg QD, 25 mg/kg BID, 50 mg/kg QD and 12.5 mg/kg BID.

A375 Xenograft mice were administered Compound A 50 mg/kg QD, 25 mg/kg BID, 50 mg/kg QD and 12.5 mg/kg BID. The % TGI was calculated and graphed and is shown in FIG. 2.

Example 94F

Plasma Concentrations in Mice

Female nu/nu mice were implanted with A375 tumor cells, which were allowed to grow to 100-200 mm$^3$. Compound. A or vehicle was administered orally once a day (QD) or twice a day (BID) (50 mg/kg QD, 25 mg/kg BID, 50 mg/kg QD and 12.5 mg/kg BID). Tumor Growth Inhibition was measured at the end of once daily dosing for 14 days and calculated according to:

$$\%TGI = 100 \times 1 - \frac{\left(\text{treated tumor } volume_{final} - \text{tumor } volume_{initial}\right)}{\left(\text{vehicle treated tumor } volume_{fianl} - \text{tumor } volume_{initial}\right)}$$

| | | | | |
|---|---|---|---|---|
| AUC (µg · hr/ml) | 132.5 | 117.0 | 66.5 | 78.0 |
| C$_{max}$ (µg/ml) | 23.8 | 10.2 | 11.9 | 7.8 |
| C$_{min}$ (µg/ml) | 0.06 | 1.24 | 0.03 | 0.49 |
| C$_{min}$ Free Fraction (ng/ml) | 0.117 | 2.48 | 0.059 | 0.986 |

Statistical Significance = Logrank test

Example 94G

Mouse Xenograft Tumors and Inhibition of Brain MEK Activity

Female nu/nu mice implanted with Colo205 tumor cells were given a single dose of vehicle or Compound A at 2.5, 5, 10, or 25 mg/kg. Compound levels were determined in plasma samples and pERK levels were determined in tumor and brain samples collected at 2, 6, 12, and 24 hr post-dose. The pERK levels from Western blots were quantified using the LI-COR Odyssey, normalized to total ERK levels and compared to vehicle-treated levels to determine % MEK inhibition. MEK inhibition in tumor or brain for each mouse was graphed with the corresponding plasma concentration of Compound A in the animal. Non-linear regression gave an $EC_{50}$ of 73 nM for MEK inhibition in tumors. The brain $EC_{50}$ was >5000 nM.

Figure 3:
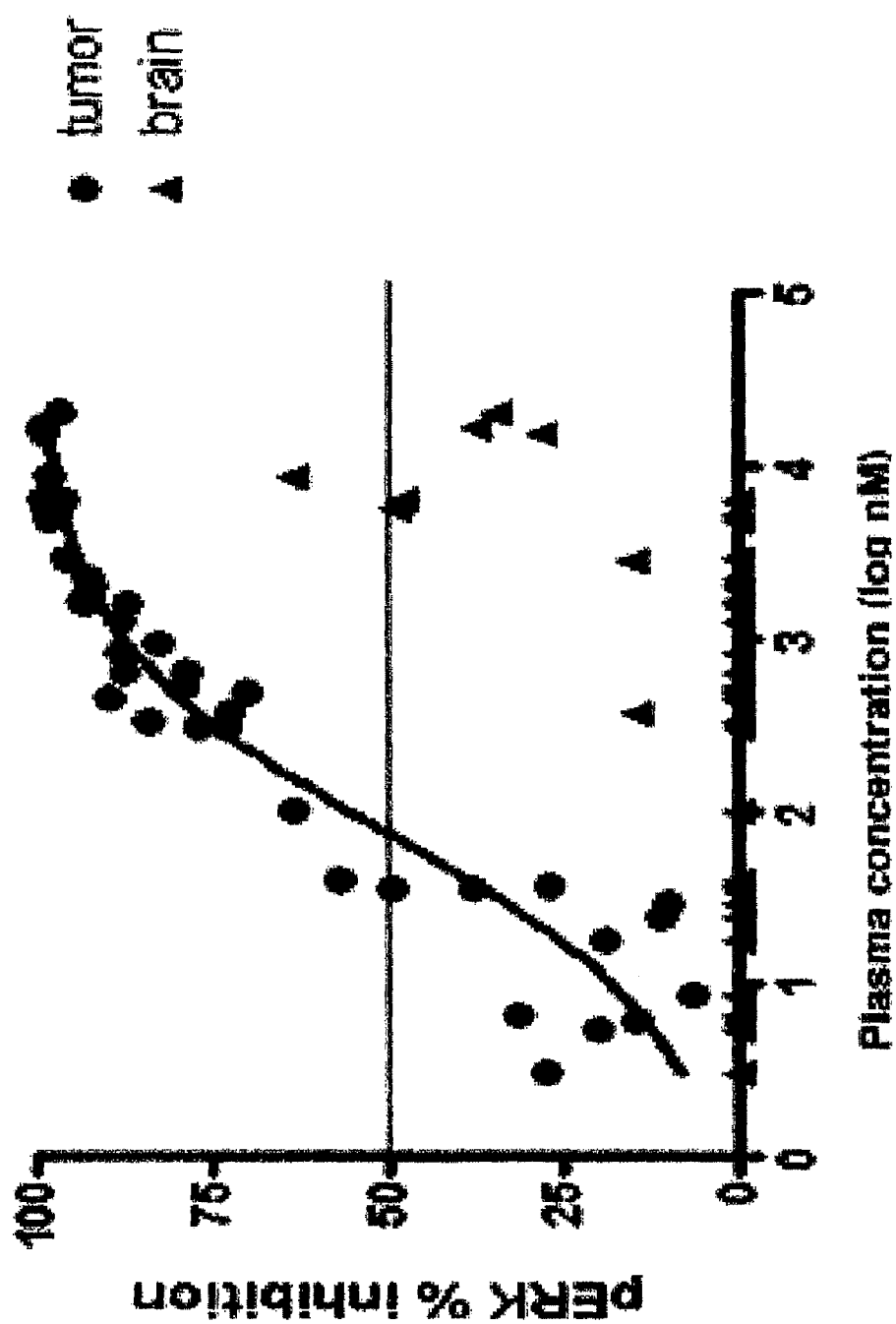
FIG. 3 shows a graph of plasma concentration (log nM) against pERK % inhibition in female nu/nu mice implanted with Colo205 tumor cells. Mice were given a single dose of 2.5, 5, 10, or 25 mg/kg.

A graph of plasma concentration (log nM) against pERK % inhibition is shown in FIG. 3.

Preparation of Capsules

Example 95A

Blue size 1 hard gelatin capsules were prepared containing a dry powder blend composition in 1 mg and 10 mg strengths of Compound A (see table shown in example 93 above) of structure:

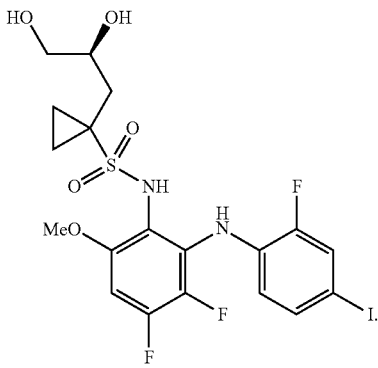 [SMILES: COc1cc(F)c(F)c(Nc2ccc(I)cc2F)c1NS(=O)(=O)C1(C[C@H](O)CO)CC1]

Compound A was prepared as described herein, and then micronized using a fluid energy mill (Spiral Jet Mill, electronically grounded, with a grinding chamber diameter of 50 mm; a 50°. 4×0.8 mm nozzle ring; an injector nozzle diameter of 0.8 mm and injector nozzle distance of 3 mm). Compound A and a portion of the microcrystalline cellulose were mixed and screened through a #20 mesh screen and added to a diffusion-tumble blender (V-blender). The remaining Microcrystalline Cellulose was screened through a #20 mesh screen, added to the materials in the blender and blended. The Croscarmellose Sodium and Sodium Lauryl Sulfate were screened through a #20 mesh screen, added to the materials in the blender and blended. The powder blend was passed through a rotating impeller mill (Quadro CoMil) and added back to the blender and blending continued. The Magnesium Stearate was screened through a #20 mesh screen and blended with the milled powder blend. The powder blend was filled into size 1 capsules. The 10 mg capsules were banded for identification.

The composition of the capsules is shown in the table below:

| Component | 1 mg capsule mg/unit | % | 10 mg capsule mg/unit | % |
|---|---|---|---|---|
| Compound A | 1.0 | 0.4 | 10.0 | 4.2 |
| Microcrystalline Cellulose, NF (Avicel PH302) | 222.2 | 92.6 | 213.2 | 88.8 |
| Croscarmellose Sodium, NF (Ac-Di-Sol) | 12.0 | 5.0 | 12.0 | 5.0 |
| Sodium Lauryl Sulfate, NF | 2.4 | 1.0 | 2.4 | 1.0 |
| Magnesium Stearate, NF | 2.4 | 1.0 | 2.4 | 1.0 |
| Total[a] | 240.0 | 100.0 | 240.0 | 100.0 |
| Blue Size 1 Hard Gelatin Capsule Shell | 1 | | 1 | |

[a]Target fill weight adjusted based on actual potency of blend.

Typical batch formula for a 10,000 batch of 1 mg capsules were as follows:

| Batch Formula Components | Quantity per batch (g) (for 10,000 units) |
|---|---|
| Compound A | 10.0 |
| Microcrystalline Cellulose, NF (Avicel PH302) | 2222 |
| Croscarmellose Sodium, NF (Ac-Di-Sol) | 120.0 |
| Sodium Lauryl Sulfate, NF | 24.0 |
| Magnesium Stearate, NF | 24.0 |
| Total Fill Weight[a] | 2400 |
| Blue Size 1 Hard Gelatin Capsule Shell | 10,000 |

[a]Target fill weight adjusted based on actual potency of blend.

Typical batch formula for a 10,000 batch of 10 mg capsules were as follows:

| Batch Formula Components | Quantity per batch (g) (for 10,000 units) |
|---|---|
| Compound A | 100.0 |
| Microcrystalline Cellulose, NF (Avicel PH302) | 2132 |
| Croscarmellose Sodium, NF (Ac-Di-Sol) | 120.0 |
| Sodium Lauryl Sulfate, NF | 24.0 |
| Magnesium Stearate, NF | 24.0 |
| Total Fill Weight[a] | 2400 |
| Blue Size 1 Hard Gelatin Capsule Shell[b] | 10,000 |

[a]Target fill weight adjusted based on actual potency of blend.

Example 95B

Blue size 1 hard gelatin capsules are prepared containing a dry powder blend composition in 1 mg and 10 mg strengths of Compound B (see table shown in example 93 above) of structure:

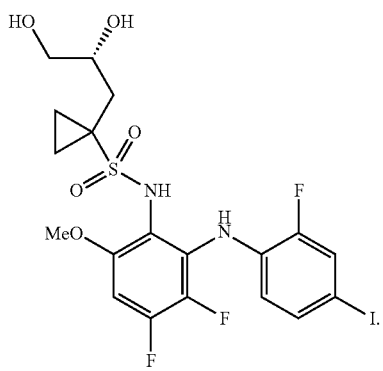 [SMILES: COc1cc(F)c(F)c(Nc2ccc(I)cc2F)c1NS(=O)(=O)C1(C[C@@H](O)CO)CC1]

Compound B is prepared as described herein, and micronized using a fluid energy mill (Spiral Jet Mill, electronically grounded, with a grinding chamber diameter of 50 mm; a 50°. 4×0.8 mm nozzle ring; an injector nozzle diameter of 0.8 mm and injector nozzle distance of 3 mm). Compound B and a portion of the microcrystalline cellulose are mixed, screened through a #20 mesh screen and added to a diffusion-tumble blender (V-blender). The remaining Microcrystalline Cellulose is screened through a #20 mesh screen, added to the materials in the blender and blended. The Croscarmellose Sodium and Sodium Lauryl Sulfate are screened through a #20 mesh screen, added to the materials in the blender and blended. The powder blend is passed through a rotating impeller mill (Quadra CoMil), added back to the blender and blending continued. The Magnesium Stearate is screened through a #20 mesh screen and blended with the milled powder blend. The powder blend is filled into size 1 capsules. The 10 mg capsules are banded for identification.

The composition of the capsules is shown in the table below:

| Component | 1 mg capsule | | 10 mg capsule | |
|---|---|---|---|---|
| | mg/unit | % | mg/unit | % |
| Compound B | 1.0 | 0.4 | 10.0 | 4.2 |
| Microcrystalline Cellulose, NF (Avicel PH302) | 222.2 | 92.6 | 213.2 | 88.8 |
| Croscarmellose Sodium, NF (Ac-Di-Sol) | 12.0 | 5.0 | 12.0 | 5.0 |
| Sodium Lauryl Sulfate, NF | 2.4 | 1.0 | 2.4 | 1.0 |
| Magnesium Stearate, NF | 2.4 | 1.0 | 2.4 | 1.0 |
| Total[a] | 240.0 | 100.0 | 240.0 | 100.0 |
| Blue Size 1 Hard Gelatin Capsule Shell | 1 | | 1 | |

In Vivo Activity in Humans

Example 96

Administration of the capsules described in example 95A in Human Cancer Patients Human cancer patients were administered a single dose of the 1 mg or 10 mg capsule composition described above in example 95A. For a 2 mg dose, patients were given 2×1 mg capsules; for a 4 mg dose, patients were given 4×1 mg capsules; for a 6 mg dose, patients were given 6×1 mg capsules; for a 10 mg dose, patients were given 1×10 mg capsule; for a 20 mg dose, patients were given 2×10 mg capsules.

Figure 4:
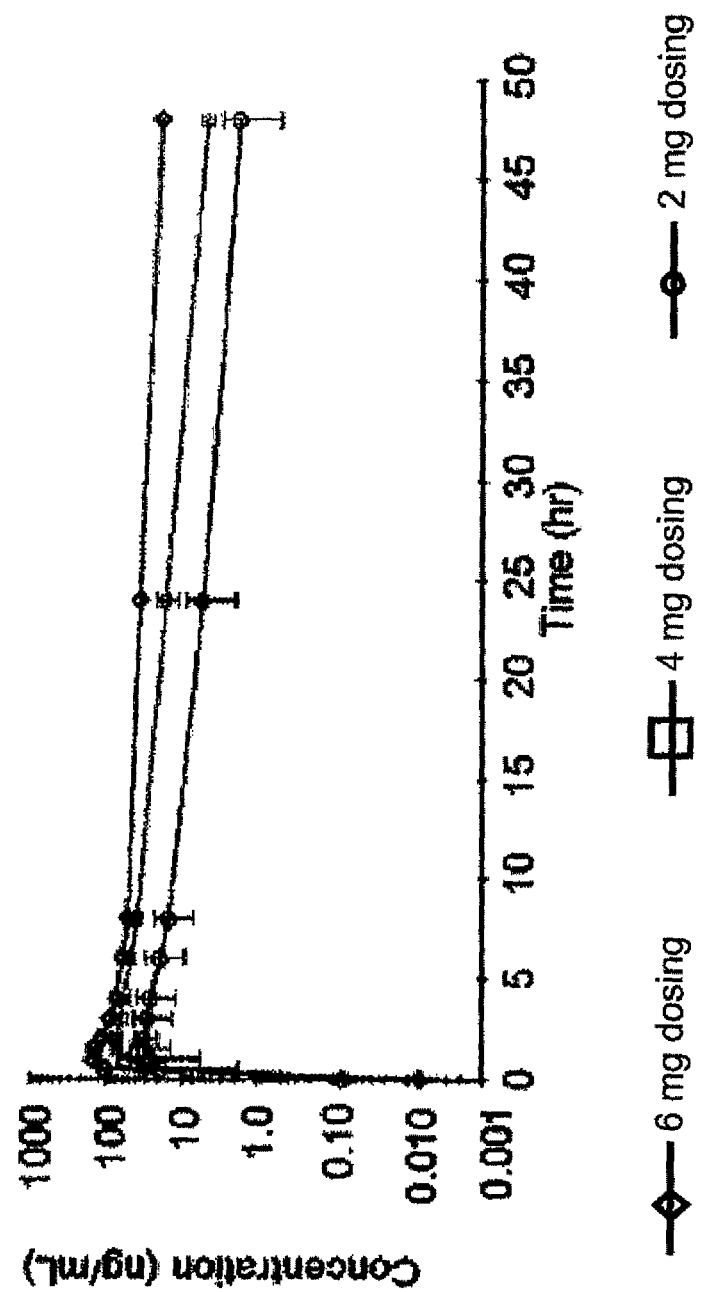
FIG. 4 shows a graph of plasma concentration (ng/mL) against time (hours) in humans after administration of a single dose 2 mg (2×1 mg capsules), 4 mg (4×1 mg capsules) or 6 mg (6×1 mg capsules).

The concentration-time profiles were monitored and are shown in FIG. 4 and in the table below:

| Dose (mg) | Day | $T_{max}$ (hr) | $C_{max}$ (ng/mL) | $C_{12hr}$ (ng/mL) | $AUC_{0-12hr}$ (ng·hr/mL) | $AUC\tau$ (ng·hr/mL) |
|---|---|---|---|---|---|---|
| 2 | 1 | 2.0 | 0.111 | 0.0378 | 0.700 | NA |
|  | 35 | 2.0 | 0.202 | 0.0756 | NA | 2.07 |
| 4 | 1 | 1.5 | 0.292 | 0.134 | 2.26 | NA |
|  | 35 | 1.0 | 0.544 | 0.310 | NA | 5.12 |
| 10 | 35 | NA | 1.57 | 1.01 | NA | 14.3 |
| 20 | 35 | NA | 3.28 | 2.19 | NA | 29.5 |

Crystalline Polymorph Forms

Example 97

Preparation of N-(3,4-difluoro-2-(2-fluoro-4-iodophenylamino)phenyl)-1-(2,3-dihydroxypropyl) cyclopropane-1-sulfonamide N-(3,4-difluoro-2-(2-fluoro-4-iodophenylamino)phenyl)-1-(2,3-dihydroxypropyl)cyclopropane-1-sulfonamide was prepared according to previously described procedures (see published international patent application WO 2007/014011) and as outlined below.

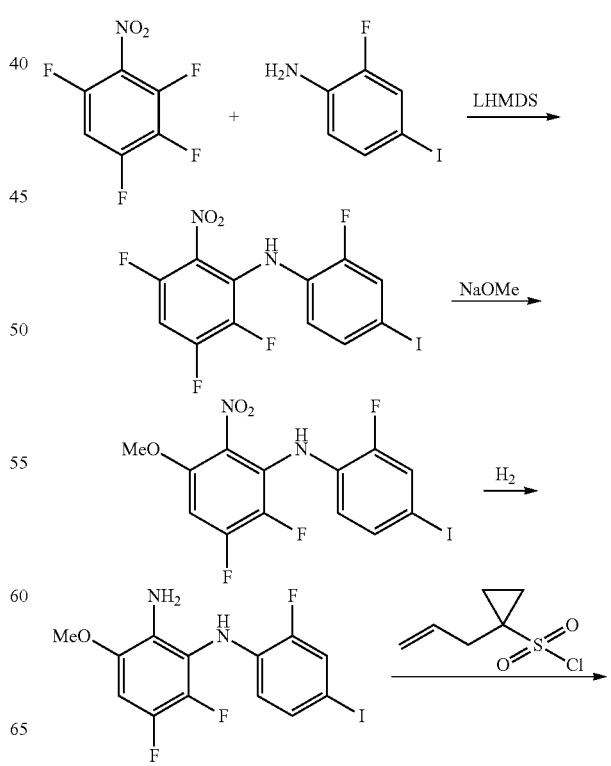

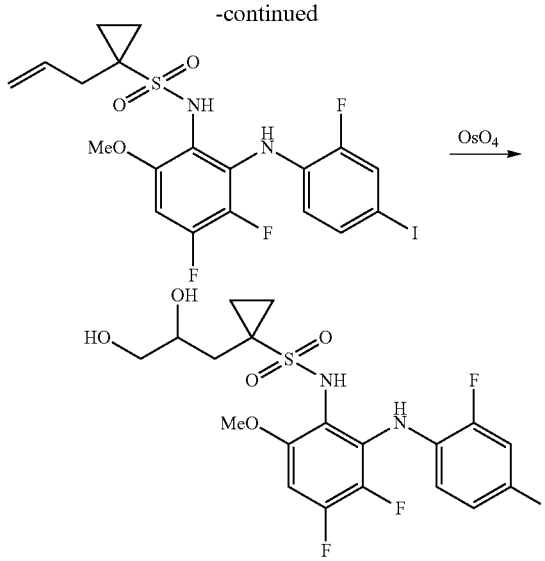

Step A: 2-Fluoro-N-(2,3,5-trifluoro-6-nitrophenyl)-4-iodobenzenamine

A solution of 1.0 M lithium hexa methyl disilazide (LiN(SiMe$_3$)$_2$) "LHMDS" (15.37 mL, 15.37 mmol) was slowly added to a stirred solution of 2-fluoro-4-iodoaniline (3.64 g, 15.37 mmol) in dry THF (100 mL) under nitrogen at −78° C. and stirring continued at −78° C. for another hour. 2,3,4,6-Tetrafluoronitrobenzene was added, and the reaction mixture was allowed to warm to room temperature and stirring continued for another 16 hours. Ethyl acetate (200 mL) was added and the organic phase was washed with water, dried over sodium sulfate and further purified by column chromatography to provide the product as a yellow solid (3.75 g, 59.24%). M−H$^+$: 410.9. $^1$H NMR (DMSO, 300 MHz): 6.85 (t, 1H); 7.38 (d, 1H); 7.62 (m, 2H); 8.78 (s, 1H).

Step B: 2-Fluoro-N-(2,3-difluoro-5-methoxy-6-nitrophenyl)-4-iodobenzenamine

A stirred solution of (2-fluoro-4-iodo-phenyl)-(2,3,5-trifluoro-6-nitro-phenyl)-amine (1.23 g, 3 mmol) in dry THF (25 ml) under nitrogen was cooled to −78° C. and a solution of 25% sodium methoxide (0.68 ml, 0.3 mmol) was added slowly. The reaction mixture was allowed to warm to room temperature and stirring continued for another 16 hours. TLC indicated incomplete reaction. Ethyl acetate (100 mL) was added to the reaction mixture and the organic layer was washed with water, dried over sodium sulfate and further purified by column chromatography to provide the desired compound as a yellow solid (0.6 g, 47.6%). m/z=424 [M+H]$^+$.

Step C: 5,6-Difluoro-N$^1$-(2-fluoro-4-iodophenyl)-3-methoxybenzene-1,2-diamine

Ammonium chloride (1.18 g, 20.16 mmol) and iron powder (1.15 g, 21.44 mmol) were added to a stirred solution of (2,3-difluoro-5-methoxy-6-nitro-phenyl)-(2-fluoro-4-iodo-phenyl)-amine (0.57 g, 1.34 mmol) in ethanol (20 mL). The mixture was stirred at reflux for 16 hours, cooled to room temperature, filtered over celite and the filtrate concentrated to dryness. The resulting residue was taken into ethyl acetate, washed with water, dried over sodium sulfate and further purified by crystallization from ethanol to provide the product as an off-white solid (0.47 g, 90.3%). M+H$^+$: 393.2. $^1$H NMR (DMSO, 300 MHz): 3.76 (s, 3H); 6.1 (t, 1H); 6.8-7.0 (m, 1H); 7.2 (d, 1H); 7.35 (s, 1H); 7.42 (d, 1H).

Step D: 1-Allyl-N-(3,4-difluoro-2-(2-fluoro-4-iodophenylamino)-6-methoxyphenyl)cyclopropane-1-sulfonamide To a stirred solution of 5,6-difluoro-N$^1$-(2-fluoro-4-iodophenyl)-3-methoxybenzene-1,2-diamine (1 eq) in anhydrous pyridine (5 ml/mmole) was added 1-allyl-cyclopropanesulfonyl chloride (1-5 eq). The reaction mixture was stirred at 40° C. for 48 hours. The reaction mixture was partitioned with water and ethyl acetate. The organic layer was washed with brine, dried (MgSO$_4$) and concentrated under reduced pressure. The residue was purified by flash column chromatography on silica to obtain the title product. $^1$H NMR (CDCl$_3$, 300 MHz): δ 7.417 (dd, 1H), 7.309 (s, 1H), 7.25 (m, 1H), 6.89 (m, 1H), 6.52 (m, 1H), 6.427 (m, 1H), 6.03 (s, 1H), 5.668 (m, 1H), 5.11 (t, 1H), 3.9 (s, 3H), 2.75 (d, 2H), 1.21 (m, 2H), 0.767 (m, 2H).

Step E: N-(3,4-difluoro-2-(2-fluoro-4-iodophenylamino)-6-methoxyphenyl)-1-(2,3-dihydroxypropyl)cyclopropane-1-sulfonamide 1-Allyl-N-(3,4-difluoro-2-(2-fluoro-4-iodophenylamino)-6-methoxyphenyl)cyclopropane-1-sulfonamide (97 mg, 0.18 mmol) and 4-methylmorpholine N-oxide (21 mg, 0.18 mmol) were dissolved in THF (8 mL). Osmium tetroxide was added at room temperature (0.018 mmol, 0.13 mL, 4% in H$_2$O) and the reaction mixture was stirred at room temperature for 16 hours. Ethyl acetate was added, and the organic phase was washed with water, dried (MgSO$_4$) and concentrated under reduced pressure. The residue was purified over silica gel chromatography (eluants: EtOAc/MeOH) to obtain the titled product (0.80 g, 78%). $^1$H NMR (CDCl$_3$, 300 MHz): δ 7.38 (dd, J=1.7 & 10.3 Hz, 1H), 7.26 (m, 1H), 7.14 (s, 1H), 6.87 (s, 1H), 6.53 (dd, J=6.8 & 11.4 Hz, 1H), 6.43 (m, 1H), 4.06 (m, 1H), 3.89 (s, 3H), 3.63 (dd, J=3.7 & 11.1 Hz, 1H), 3.49 (dd, J=6.4 & 11.1 Hz, 1H), 2.3 (dd, J=9.7 & 16.1 Hz, 1H), 1.77 (dd, J=1.9 & 16.0 Hz, 1H), 1.37 (m, 1H), 1.25 (m, 1H), 1.21 (m, 2H), 0.86 (m, 2H); m/z=571 [M−1]$^−$.

Example 98

Preparation of N—(S)-(3,4-difluoro-2-(2-fluoro-4-iodophenylamino)-6-methoxyphenyl)-1-(2,3-dihydroxypropyl)cyclopropane-1-sulfonamide

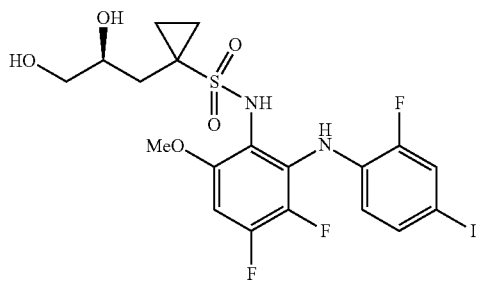 [SMILES: COc1cc(F)c(F)c(Nc2ccc(I)cc2F)c1NS(=O)(=O)C1(C[C@H](O)CO)CC1]

The pure S isomer was obtained by chiral HPLC separation of the racemic mixture. $^1$H NMR (CDCl$_3$, 300 MHz): δ 7.38 (dd, J=1.7 & 10.3 Hz, 1H), 7.26 (m, 1H), 7.14 (s, 1H), 6.87 (s, 1H), 6.53 (dd, J=6.8 & 11.4 Hz, 1H), 6.43 (m, 1H), 4.06 (m, 1H), 3.89 (s, 3H), 3.63 (dd, J=3.7 & 11.1 Hz, 1H), 3.49 (dd, J=6.4 & 11.1 Hz, 1H), 2.3 (dd, J=9.7 & 16.1 Hz, 1H), 1.77 (dd, J=1.9 & 16.0 Hz, 1H), 1.37 (m, 1H), 1.25 (m, 1H), 1.21 (m, 2H), 0.86 (m, 2H); m/z=571 [M−1]⁻.

Example 99

Preparation of N—(R)-(3,4-difluoro-2-(2-fluoro-4-iodophenylamino)-6-methoxyphenyl)-1-(2,3-dihydroxypropyl)cyclopropane-1-sulfonamide

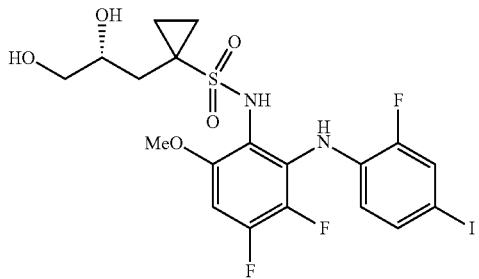 [SMILES: COc1cc(F)c(F)c(Nc2ccc(I)cc2F)c1NS(=O)(=O)C1(C[C@@H](O)CO)CC1]

The pure R isomer was obtained by chiral HPLC separation of the racemic mixture. ¹H NMR (CDCl₃, 300 MHz): δ 7.38 (dd, J=1.7 & 10.3 Hz, 1H), 7.26 (m, 1H), 7.14 (s, 1H), 6.87 (s, 1H), 6.53 (dd, J=6.8 & 11.4 Hz, 1H), 6.43 (m, 1H), 4.06 (m, 1H), 3.89 (s, 3H), 3.63 (dd, J=3.7 & 11.1 Hz, 1H), 3.49 (dd, J=6.4 & 11.1 Hz, 1H), 2.3 (dd, J=9.7 & 16.1 Hz, 1H), 1.77 (dd, J=1.9 & 16.0 Hz, 1H), 1.37 (m, 1H), 1.25 (m, 1H), 1.21 (m, 2H), 0.86 (m, 2H); m/z=571 [M−1]⁻.

Example 100

Preparation of crystalline polymorph Form A of N—(S)-(3,4-difluoro-2-(2-fluoro-4-iodophenylamino)-6-methoxyphenyl)-1-(2,3-dihydroxypropyl)cyclopropane-1-sulfonamide Preparation i)
N—(S)-(3,4-difluoro-2-(2-fluoro-4-iodophenylamino)-6-methoxyphenyl)-1-(2,3-dihydroxypropyl)cyclopropane-1-sulfonamide (216.10 g) was charged to a 4 L Erlenmeyer flask equipped with a large magnetic stir bar and a magnetic stirrer/hot plate. Ethyl Acetate (ca. 600 mL, purchased from Fisher) was added. Heating and stirring were initiated to form a brown suspension. The mixture was brought to a low reflux and additional ethyl acetate (ca. 200 mL) was added to effect complete dissolution giving a dark brown solution. Heptane (purchased from Acros) was slowly added portionwise to the refluxing solution at a rate that all precipitates that formed on each addition were quickly dissolved and reflux maintained. Upon the addition of 2 L of heptanes to the solution the solids formed dissolved very slowly at reflux. Heating was stopped and the crystallization mixture allowed to equilibrate to room temperature with stirring over 16 h. A thick layer of crystalline material developed around the surface of the glass over the aging period. The resulting suspension was equilibrated in an ice/water bath with stirring. The suspension was filtered on a 25 cm Buchner funnel dressed with Whatman #1 filter media. The collected crystals were washed with heptanes (1 L) and allowed to air dry under vacuum. The crystals were further dried at 40° C./<1 torr over 20 h to yield the product as a pink crystalline solid (160.99 g, 77.2%).

Preparation ii)
N—(S)-(3,4-difluoro-2-(2-fluoro-4-iodophenylamino)-6-methoxyphenyl)-1-(2,3-dihydroxypropyl)cyclopropane-1-sulfonamide (13.2 g) and ethyl acetate (30 mL) were charged to an Erlenmeyer flask equipped with a large magnetic stir bar and a magnetic stirrer/hot plate, Stirring and heating to low reflux were initiated to effect complete dissolution giving a dark brown solution. Heptanes were slowly added portionwise to the refluxing solution at a rate that all precipitates that formed on each addition were quickly dissolved and reflux maintained, until the addition of heptanes to the solution caused the solids formed to dissolve very slowly at reflux (~90 mL heptanes). Heating was stopped and the crystallization mixture allowed to equilibrate to room temperature with stirring over 16 h. A thick layer of crystalline material developed around the surface of the glass over the aging period. The resulting suspension was equilibrated in an ice/water bath with stirring. The suspension was filtered on Buchner funnel dressed with Whatman #1 filter media. The collected crystals were washed with heptanes, and allowed to air dry under vacuum. The crystals were further dried at 40° C./<1 torr over 20 h to yield the product as a pink crystalline solid.

Preparation iii)
N—(S)-(3,4-difluoro-2-(2-fluoro-4-iodophenylamino)-6-methoxyphenyl)-1-(2,3-dihydroxypropyl)cyclopropane-1-sulfonamide (44.8 g) and ethyl acetate (750 mL) were charged to an Erlenmeyer flask equipped with a large magnetic stir bar and a magnetic stirrer/hot plate. Stirring and heating to low reflux were initiated to effect complete dissolution giving a dark brown solution. Hexanes were slowly added portionwise to the refluxing solution at a rate that all precipitates that formed on each addition were quickly dissolved and reflux maintained, until the addition of hexanes to the solution caused the solids formed to dissolve very slowly at reflux (~2 L hexanes). Heating was stopped and the crystallization mixture allowed to equilibrate to room temperature with stirring over 16 h. A thick layer of crystalline material developed around the surface of the glass over the aging period. The resulting suspension was equilibrated in an ice/water bath with stirring. The suspension was filtered on Buchner funnel dressed with Whatman #1 filter media. The collected crystals were washed, and allowed to air dry under vacuum. The crystals were further dried at 40° C./<1 torr over 20 h to yield the product as a pink crystalline solid.

Example 101

Preparation of crystalline polymorph of N—(R)-(3,4-difluoro-2-(2-fluoro-4-iodophenylamino)-6-methoxyphenyl)-1-(2,3-dihydroxypropyl)cyclopropane-1-sulfonamide N—(R)-(3,4-difluoro-2-(2-fluoro-4-iodophenylamino)-6-methoxyphenyl)-1-(2,3-dihydroxypropyl)cyclopropane-1-sulfonamide (216.10 g) is charged to a 4 L Erlenmeyer flask equipped with a large magnetic stir bar and a magnetic stirrer/hot plate. Ethyl Acetate (ca. 600 mL) is added. Heating and stirring are initiated to form a brown suspension. The mixture is brought to a low reflux and additional ethyl acetate (ca. 200 mL) is added to effect complete dissolution giving a dark brown solution. Heptane is charged to the solution slowly portionwise to the refluxing solution at a rate that all precipitates that form on each addition are quickly dissolved and reflux is maintained. Upon the addition of 2 L of heptanes to the solution the solids formed dissolve very slowly at reflux. Heating is stopped and the crystallization mixture is allowed to equilibrate to room temperature with stirring over 16 h. A

Example 102

Generation of IC50 Data

Materials and preparation of reagents: Human GST-MEK1 and the constitutively active allele GST-MEK1$^{CA}$ (harboring the mutations Ser218Asp and Ser222Asp) were subcloned into the yeast expression vector pGEM4Z (Promega, Madison, Wis.) from the wild type human MEK1 cDNA. GST-MEK1$^{CA}$ was expressed in *Escherichia coli* and partially purified using Glutathione Sepharose 4B affinity resin (Amersham Pharmacia Biotech, Piscataway, N.J.). The ERK2 allele was subcloned from MAPK2/Erk2 cDNA (wild type) in pUSEamp (Upstate Biotechnology, Inc., Waltham, Mass.) into the vector pET21a (Novagen, Madison, Wis.) resulting in an N-terminal histidine-tagged mouse ERK2 allele. ERK2 was expressed and purified to homogeneity [Zhang, 1993 #33]. Myelin basic protein (MBP) was purchased from Gibco BRL (Rockville, Md.). EasyTides adenosine 5'-triphosphate (ATP) ([γ-$^{33}$P]) (NEN Perkin Elmer, Wellesley, Mass.) was the source of radiolabel for all kinase reactions. Activated Raf-1 (truncated) and activated MAPKinase 2/ERK2 were purchased from Upstate, Inc. (Lake Placid, N.Y.). 4-20% Criterion Precast gels were purchased from Bio-Rad (Hercules, Calif.).

Determination of enzymatic activity: Compounds were diluted from dimethylsulfoxide (DMSO) stocks into 1×HMNDE (20 mM HEPES pH 7.2, 1 mM MgCl$_2$, 100 mM. NaCl, 1.25 mM DTT, 0.2 mM EDTA). A typical 25-microliter assay contained 0.002 nanomoles MEK1$^{CA}$, 0.02 nanomoles ERK2, 0.25 nanomoles MBP, 0.25 nanomoles unlabeled ATP, and 0.1 μCi [γ$^{33}$P] ATP. The screening assay essentially comprised four additions. Five pd of diluted compound were dispensed to 96-well assay plates. Ten μl of 2.5× enzyme cocktail (MEK1$^{CA}$ and ERK2 only) were then added to each well followed by a pre-incubation for 30 minutes at ambient temperature. Ten μl of 2.5× substrate cocktail (labeled and unlabeled ATP plus MBP) were then added, followed by incubation for 60 minutes at ambient temperature. Finally, 100 μl of 10% trichloroacetic acid (TCA) were added and incubated for 30 minutes at room temperature to halt the reaction and precipitate radiolabeled protein products. Reaction products were harvested on glass fiber 96 well filter plates prewetted with water and 1% pyrophosphate. The filter plate was then washed 5 times with water. Water was displaced by absolute ethanol and the plate was allowed to air dry for 30 minutes at room temperature. A back seal was applied manually and 40 of scintillation cocktail were dispensed to each well. A top seal was applied and the plate was counted in the TopCount for two seconds per well. For certain experiments a truncated version of MEK that requires activation by Raf kinase were used.

Example 103

Generation of EC50 Data

Effects of compounds in the cell were determined by Western blotting for phosphorylated ERK. MDA-MB-231 breast cancer cells were plated in a 48 well plate at 20,000 cells per well and grown in a 37° humidified CO$_2$ incubator. The following day, the growth media (DMEM+10% fetal bovine serum) was removed and replaced with starve media (DMEM+0.1% fetal bovine serum). Cells were incubated in the starve media for sixteen hours and then treated with a range of compound concentrations for thirty minutes. After incubation with compound, cells were stimulated with 100 ng/ml EGF for five minutes. The cells were then lysed and analyzed by Western blot using a monoclonal antibody raised to phosphorylated ERK. The signal was amplified using a secondary antibody conjugated to a near-IR dye and detected on a Licor Odyssey scanner. The intensity of signal was quantitated and this data was used to generate dose response curves and EC50 calculations.

Example 104

Activity Data of Compounds

The compounds described in examples 1, 2 and 3 were tested in the assays described above. The results are summarized in the table below (A, EC$_{50}$=<2.0 nM; B, BC$_{50}$=2.0-15 nM):

thick layer of crystalline material develops around the surface of the glass over the aging period. The resulting suspension is equilibrated in an ice/water bath with stirring. The suspension is filtered on a 25 cm Buchner funnel dressed with Whatman #1 filter media. The collected crystals are washed with heptanes (1 L) and allowed to air dry under vacuum. The crystals are further dried at 40° C./<1 torr over 20 h.

| Compound Number | Structure | Activity |
|---|---|---|
| Eg. 97 (Racemic) | 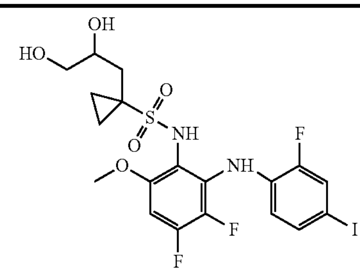 | A |
| Eg. 98 (S isomer) | 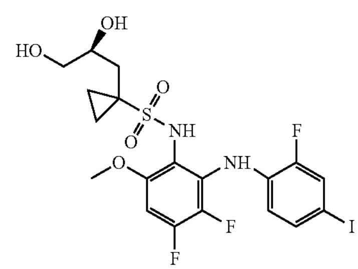 [SMILES: COc1cc(F)c(F)c(Nc2ccc(I)cc2F)c1NS(=O)(=O)C1(C[C@H](O)CO)CC1] | A |
| Eg. 99 (R isomer) | 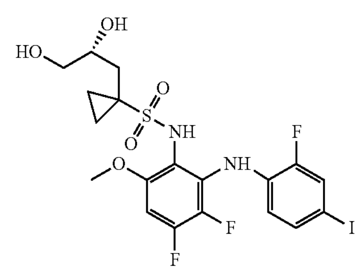 [SMILES: COc1cc(F)c(F)c(Nc2ccc(I)cc2F)c1NS(=O)(=O)C1(C[C@@H](O)CO)CC1] | B |

Example 105

XRPD Data

Figure 7:
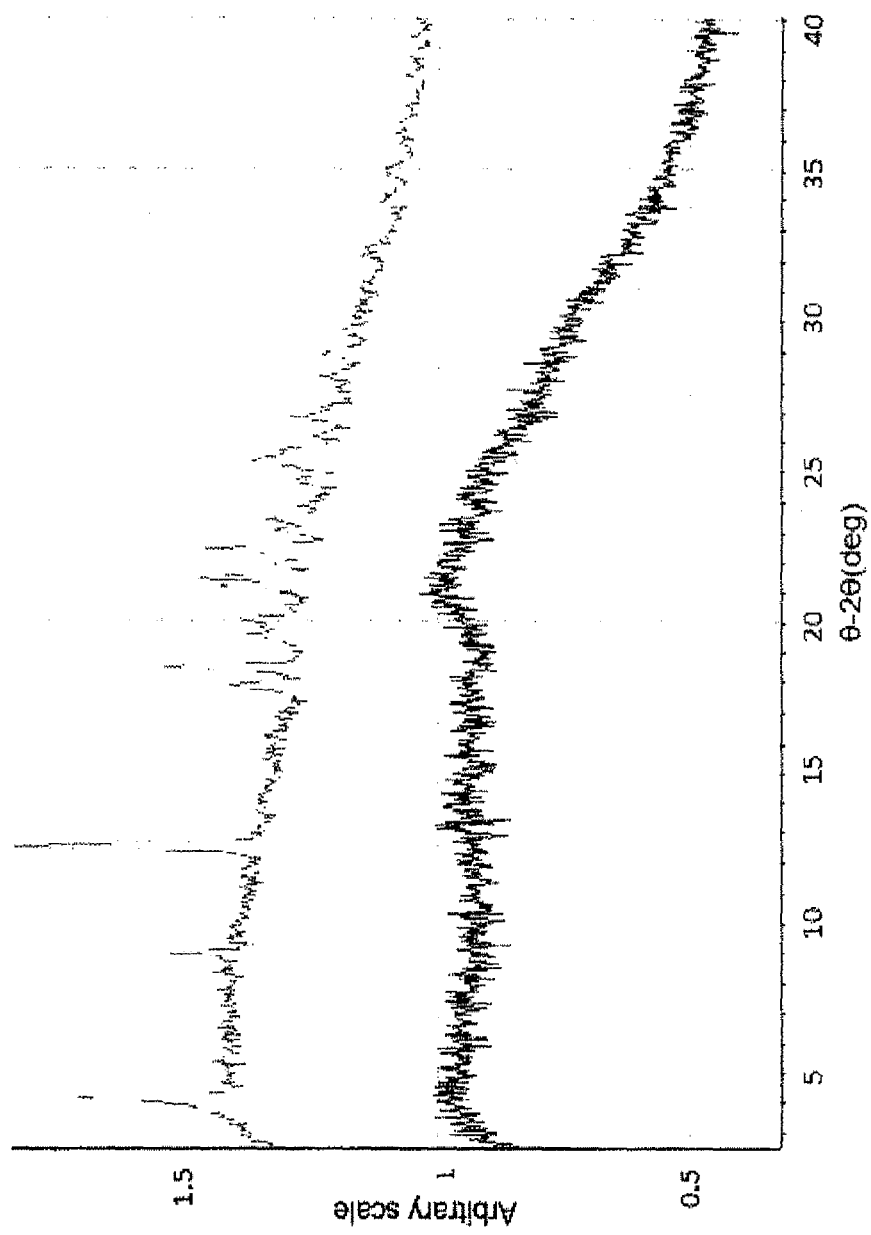
FIG. 7 is a graph of the PXRD patterns of N—(S)-(3,4-difluoro-2-(2-fluoro-4-iodophenylamino)-6-triethoxyphenyl)-1-(2,3-dihydroxypropyl)cyclopropane-1-sulfonamide Form A (top) and N—(S)-(3,4-difluoro-2-(2-fluoro-4-iodophenylamino)-6-methoxyphenyl)-1-(2,3-dihydroxypropyl)cyclopropane-1-sulfonamide amorphous (bottom), generated using a Inel XRG-3000 diffractometer. The graph plots the intensity of the peaks as defined by counts per second versus the diffraction angle 2θ in degrees.

XPRD was performed on a Inel XRG-3000 diffractometer, equipped with a curved position-sensitive detector with a 2θ range of 120°. Real time data was collected using Cu Kα radiation at a resolution of 0.03°2θ. The tube voltage and amperage were set to 40 kV and 30 mA, respectively. Patterns are displayed from 2.5 to 40°2θ to facilitate direct pattern comparisons. Samples of (S)—N-(3,4-difluoro-2-(2-fluoro-4-iodophenylamino)-6-methoxyphenyl)-1-(2,3-dihydroxypropyl)cyclopropane-1-sulfonamide (synthesized as described herein) were prepared for analysis by packing them into thin-walled glass capillaries. Each capillary was moved onto a goniometer head that is motorized to permit spinning of the capillary during data acquisition. The samples were analyzed for 5 minutes. Instrument calibration was preformed daily using a silicon reference standard. FIG. 5 is a graph of a powder x-ray diffraction (PXRD) pattern of N—(S)-(3,4-difluoro-2-(2-fluoro-4-iodophenylamino)-6-methoxyphenyl)-1-(2,3-dihydroxypropyl)cyclopropane-1-sulfonamide Form A. FIG. 7 is a graph of the powder x-ray diffraction (PXRD) patterns of N—(S)-(3,4-difluoro-2-(2-fluoro-4-iodophenylamino)-6-methoxyphenyl)-1-(2,3-dihydroxypropyl)cyclopropane-1-sulfonamide Form A (top) and Amorphous (bottom).

Example 106

Differential Scanning Calorimetry (DSC)

Analyses were carried out on a TA Instruments differential scanning calorimeter Q1000. The instrument was calibrated using indium as the reference material. The sample was placed into a standard aluminum DSC pan with a non-crimped lid configuration, and the weight accurately recorded. To determine the glass transition temperature ($T_g$) of amorphous material, the sample cell was cycled several times between −40° C. and 140° C. The final temperature was ramped to 150° C. The $T_g$ is reported from the inflection point of the last cycle transition. FIG. 6 is a graph of a modulated DSC thermogram of N—(S)-(3,4-difluoro-2-(2-fluoro-4-iodophenylamino)-6-methoxyphenyl)-1-(2,3-dihydroxypropyl)cyclopropane-1-sulfonamide (Form A). The graph plots the normalized heat flow in Watts/gram (W/g) versus the measured sample temperature in ° C.

Example 107

Dynamic Vapor Sorption/Desorption (DVS)

Figure 8:
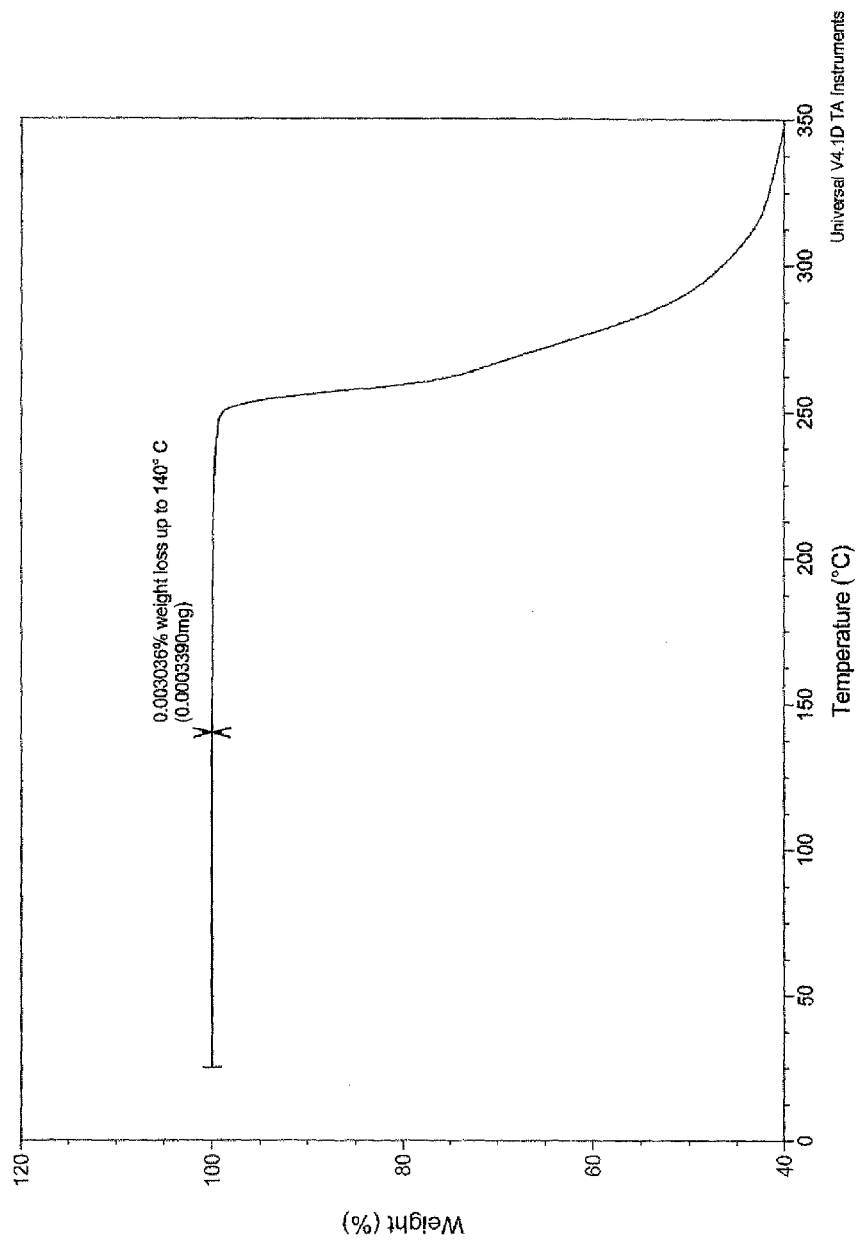
FIG. 8 shows a Dynamic Vapor Sorption/Desorption (DVS) isotherm of N—(S)-(3,4-difluoro-2-(2-fluoro-4-iodophenylamino)-6-methoxyphenyl)-1-(2,3-dihydroxypropyl)cyclopropane-1-sulfonamide Form A generated using a VTI SGA-100 Vapor Sorption Analyzer.

Moisture sorption/desorption data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. Sodium chloride and polyvinypyrrolidine were used as calibration standards. FIG. 8 shows a DVS isotherm of N—(S)-(3,4-difluoro-2-(2-fluoro-4-iodophenylamino)-6-methoxyphenyl)-1-(2,3-dihydroxypropyl)cyclopropane-1-sulfonamide (Form A). The material exhibits a negligible weight change during the experiment.

Example 108

Thermogravimetry (TG)

Figure 9:
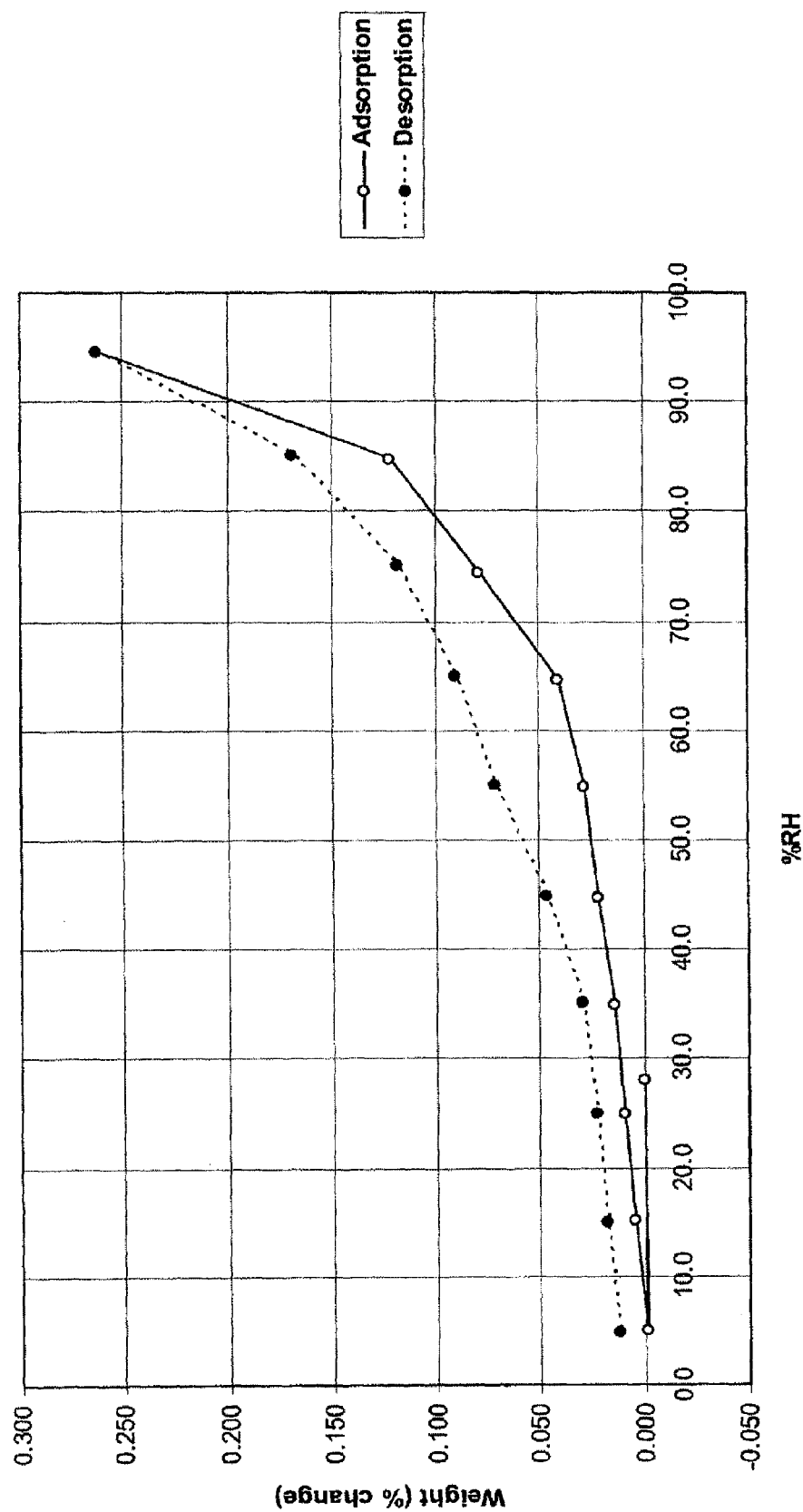
FIG. 9 shows a Thermogravimetry (TG) thermogram of N—(S)-(3,4-difluoro-2-(2-fluoro-4-iodophenylamino)-6-methoxyphenyl)-1-(2,3-dihydroxypropyl)cyclopropane-1-sulfonamide Form A) generated using a TA Instrument 2950 thermogravimetric analyzer.

Analyses were carried out on a TA Instrument 2950 thermogravimetric analyzer. The calibration standards were nickel and Alumel™. Each sample was placed in an aluminum sample pan and inserted into the TG furnace. Samples were equilibrated at 25° C., and then heated under a stream of nitrogen at a heating rate of 10° C./min, up to a final temperature of 350° C. FIG. 9 shows a TG thermogram of N—(S)-(3,4-difluoro-2-(2-fluoro-4-iodophenylamino)-6-methoxyphenyl)-1-(2,3-dihydroxypropyl)cyclopropane-1-sulfonamide (Form A) demonstrating negligible weight loss up to 140° C., indicating polymorph, form A is unsolvated.

Example 109

In Vitro Cancer Screen

The human tumor cell lines were grown in RPMI 1640 medium containing 5% fetal bovine serum and 2 mM L-glutamine. Cells are inoculated into 96 well microtiter plates in 100 µL at plating densities ranging from 5,000 to 40,000 cells/well depending on the doubling time of individual cell lines. After cell inoculation, the microtiter plates are incubated at 37° C., 5% $CO_2$, 95% air and 100% relative humidity for 24 h prior to addition of N—(S)-(3,4-difluoro-2-(2-fluoro-4-iodophenylamino)-6-methoxyphenyl)-1-(2,3-dihydroxypropyl)cyclopropane-1-sulfonamide.

After 24 h, two plates of each cell line were fixed in situ with TCA, to represent a measurement of the cell population for each cell line at the time of N—(S)-(3,4-difluoro-2-(2-fluoro-4-iodophenylamino)-6-methoxyphenyl)-1-(2,3-dihydroxypropyl)cyclopropane-1-sulfonamide addition (Tz). N—(S)-(3,4-difluoro-2-(2-fluoro-4-iodophenylamino)-6-methoxyphenyl)-1-(2,3-dihydroxypropyl)cyclopropane-1-sulfonamide was solubilized in dimethyl sulfoxide at 400-fold the desired final maximum test concentration and stored frozen prior to use. At the time of addition, an aliquot of frozen concentrate is thawed and diluted to twice the desired final maximum test concentration with complete medium containing 50 µg/ml gentamicin. Additional four, 10-fold or ½ log serial dilutions are made to provide a total of five concentrations plus control. Aliquots of 100 µl of these different dilutions are added to the appropriate microtiter wells already containing 100 µl of medium, resulting in the required final concentrations.

Following addition of N—(S)-(3,4-difluoro-2-(2-fluoro-4-iodophenylamino)-6-methoxyphenyl)-1-(2,3-dihydroxypropyl)cyclopropane-1-sulfonamide, the plates were incubated for an additional 48 h at 37° C., 5% $CO_2$, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements [time zero, (Tz), control growth, (C), and test growth in the presence of N—(S)-(3,4-difluoro-2-(2-fluoro-4-iodophenylamino)-6-methoxyphenyl)-1-(2,3-dihydroxypropyl)cyclopropane-1-sulfonamide at the five concentration levels (Ti)], the percentage growth was calculated at each of the drug concentrations levels. Percentage growth inhibition is calculated as:

$$\text{Percentage growth inhibition (concentrations for which } Ti >/= Tz) = \frac{(Ti - Tz)}{(C - Tz)} \times 100$$

$$\text{Percentage growth inhibition (concentrations for which } Ti < Tz) = \frac{(Ti - Tz)}{Tz} \times 100$$

Three dose response parameters were calculated. Growth inhibition of 50% (GI50) was calculated from [(Ti−Tz)/(C−Tz)]×100=50, which is the concentration resulting in a 50% reduction in the net protein increase (as measured by SRB staining) in control cells during the drug incubation. The N—(S)-(3,4-difluoro-2-(2-fluoro-4-iodophenylamino)-6-methoxyphenyl)-1-(2,3-dihydroxypropyl)cyclopropane-1-sulfonamide concentration resulting in total growth inhibition (TGI) was calculated from Ti=Tz. The LC50 (concentration of drug resulting in a 50% reduction in the measured protein at the end of the drug treatment as compared to that at the beginning) indicating a net loss of cells following treatment is calculated from [(Ti−Tz)/Tz]×100=−50. Values were calculated for each of these three parameters if the level of activity was reached; however, if the effect was not reached or was exceeded, the value for that parameter is expressed as greater or less than the maximum or minimum concentration tested.

Panels corresponding to Leukemia, Non-Small Cell Lung Cancer, Colon Cancer, CNS Cancer, melanoma, ovarian cancer, renal cancer, prostate cancer and breast cancer, for the cell lines indicated were examined and the results are shown below.

| Panel | Cell Line | GI50 (µM) | LC50 (µM) | TGI (µM) |
|---|---|---|---|---|
| Leukemia | CCRF-CEM | 17.378 | 100.000 | 60.256 |
| Leukemia | HL-60(TB) | 0.010 | 100.000 | 100.000 |
| Leukemia | K-562 | 6.607 | 100.000 | 100.000 |
| Leukemia | MOLT-4 | 10.965 | 100.000 | 69.183 |
| Leukemia | RPMI-8226 | 26.915 | 100.000 | 100.000 |
| Leukemia | SR | 38.019 | 100.000 | 100.000 |
| Non-Small Cell Lung Cancer | A549/ATCC | 0.589 | 100.000 | 64.565 |
| Non-Small Cell Lung Cancer | EKVX | 0.214 | 61.660 | 13.804 |
| Non-Small Cell Lung Cancer | HOP-62 | 0.069 | 42.658 | 12.589 |
| Non-Small Cell Lung Cancer | HOP-92 | 0.047 | 58.884 | 0.324 |
| Non-Small Cell Lung Cancer | NCI-H226 | 3.311 | 74.131 | 24.547 |
| Non-Small Cell Lung Cancer | NCI-H23 | 0.056 | 74.131 | 2.884 |
| Non-Small Cell Lung Cancer | NCI-H322M | 0.162 | 46.774 | 15.488 |
| Non-Small Cell Lung Cancer | NCI-H460 | 3.631 | 52.481 | 19.498 |
| Non-Small Cell Lung Cancer | NCI-H522 | 5.248 | 100.000 | 29.512 |
| Colon Cancer | HCC-2998 | 0.010 | 0.457 | 0.035 |
| Colon Cancer | HCT-116 | 0.195 | 67.608 | 12.589 |
| Colon Cancer | HCT-15 | 0.603 | 60.256 | 16.982 |
| Colon Cancer | HT29 | 0.026 | 29.512 | 3.090 |
| Colon Cancer | KM12 | 0.229 | 48.978 | 13.490 |
| Colon Cancer | SW-620 | 0.039 | 66.069 | 12.589 |
| CNS Cancer | SF-268 | 2.570 | 100.000 | 25.704 |
| CNS Cancer | SF-295 | 9.333 | 53.703 | 23.442 |
| CNS Cancer | SF-539 | 1.514 | 60.256 | 20.417 |
| CNS Cancer | SNB-19 | 0.251 | 75.858 | 24.547 |
| CNS Cancer | SNB-75 | 0.302 | 34.674 | 4.467 |
| CNS Cancer | U251 | 0.891 | 44.668 | 17.378 |
| Melanoma | LOX IMVI | 0.195 | 38.905 | 10.715 |
| Melanoma | MALME-3M | 0.010 | 19.953 | 0.014 |
| Melanoma | M14 | 0.015 | 29.512 | 0.166 |
| Melanoma | SK-MEL-28 | 0.028 | 22.387 | 0.214 |
| Melanoma | SK-MEL-5 | 0.062 | 38.905 | 13.804 |
| Melanoma | UACC-257 | 0.020 | 66.069 | 10.233 |
| Melanoma | UACC-62 | 0.014 | 20.893 | 0.170 |
| Ovarian Cancer | IGROV1 | 0.018 | 19.055 | 0.295 |
| Ovarian Cancer | OVCAR-3 | 2.512 | 48.978 | 17.783 |
| Ovarian Cancer | OVCAR-4 | 0.562 | 72.444 | 16.218 |
| Ovarian Cancer | OVCAR-5 | 0.017 | 40.738 | 12.023 |
| Ovarian Cancer | SK-OV-3 | 12.882 | 100.000 | 41.687 |
| Renal Cancer | 786-0 | 5.129 | 63.096 | 23.442 |
| Renal Cancer | A498 | 0.191 | 44.668 | 4.169 |
| Renal Cancer | ACHN | 0.275 | 83.176 | 21.878 |
| Renal Cancer | CAKI-1 | 0.389 | 100.000 | 26.915 |
| Renal Cancer | SN12C | 0.851 | 47.863 | 18.621 |
| Renal Cancer | TK-10 | 0.224 | 100.000 | 23.442 |
| Renal Cancer | UO-31 | 0.158 | 40.738 | 11.482 |
| Prostate Cancer | PC-3 | 8.128 | 100.000 | 37.154 |
| Prostate Cancer | DU-145 | 2.138 | 95.499 | 22.387 |
| Breast Cancer | MCF7 | 10.965 | 85.114 | 30.903 |
| Breast Cancer | NCI/ADR-RES | 3.467 | 100.000 | 25.704 |
| Breast Cancer | MDA-MB-231 | 0.069 | 35.481 | 10.471 |
| Breast Cancer | HS 578T | 0.617 | 85.114 | 13.490 |
| Breast Cancer | MDA-MB-435 | 0.035 | 41.687 | 12.303 |
| Breast Cancer | BT-549 | 5.754 | 47.863 | 20.893 |
| Breast Cancer | T-47D | 4.898 | 100.000 | 38.019 |
| Breast Cancer | MDA-MB-468 | 0.019 | 54.954 | 10.233 |

Example 110

In Vitro Anti-Proliferative Activity

In the present example, the following effects of N—(S)-(3,4-difluoro-2-(2-fluoro-4-iodophenylamino)-6-methoxyphenyl)-1-(2,3-dihydroxypropyl)cyclopropane-1-sulfonamide were examined: (1) activity ($GI_{50}$) against the growth of several tumor cell lines harboring different mutations; (2) activity ($GI_{50}$) against the growth of several B-Raf mutant cell lines; (3) effects on anchorage independent cell growth; (4) effects on the cell cycle; and (5) toxic effects on primary liver and kidney cells.

Cell Culture/Growth Inhibition Assay

Human melanoma A375 cells and human colon cancer Colo205 cells were obtained from ATCC (Manassas, Va.). A375 cells were maintained in DMEM supplemented with 10% fetal bovine serum, glutamine (2 mM), penicillin (100 U/ml), and streptomycin (100 µg/ml). Cells were maintained at 37° C., 5% $CO_2$, and 100% humidity. Colo205 cells were maintained in RPMI supplemented with 10% fetal bovine serum, glutamine (2 mM), penicillin (100 U/ml), and streptomycin (100 µg/ml). For growth inhibition experiments, cells were plated in white 384-well microplates at 1000 cells/20 dwell. After 24 hr, 5 µl of a 5× drug stock solution was added. All drugs were initially prepared as 200× stocks in DMSO, such that final DMSO concentration was 0.5%. Cells were incubated for 48 hr at 37° C. and ATP levels were determined using CellTiterGlo (Promega, Madison, Wis.). Adenylate kinase (AK) release was determined using Toxilight (Cambrex, Walkersville, Md.). Non-linear curve-fitting was performed using GraphPad Prism 4 (GraphPad Software, San Diego, Calif.). 4-Amino-8-(2R,3R,4S,5R)-3,4-dihydroxy-5-(hydroxymethyl)tetrahydrofuran-2-yl)pyrido[2,3-d]pyrimidin-5(8H)-one (VRX-14686) is a cytotoxic agent used as a reference compound.

Growth inhibition (%)=(Vehicle Only control (RLU)-N—(S)-(3,4-difluoro-2-(2-fluoro-4-iodophenylamino)-6-methoxyphenyl)-1-(2,3-dihydroxypropyl)cyclopropane-1-sulfonamide RLU)/(Vehicle Only control RLU-1 µM N—(S)-(3,4-difluoro-2-(2-fluoro-4-iodophenylamino)-6-methoxyphenyl)-1-(2,3-dihydroxypropyl)cyclopropane-1-sulfonamide RLU); based on growth arrest induced by N—(S)-(3,4-difluoro-2-(2-fluoro-4-iodophenylamino)-6-methoxyphenyl)-1-(2,3-dihydroxypropyl)cyclopropane-1-sulfonamide where ATP levels are measured.

Cell Viability (%)=(N—(S)-(3,4-difluoro-2-(2-fluoro-4-iodophenylamino)-6-methoxyphenyl)-1-(2,3-dihydroxypropyl)cyclopropane-1-sulfonamide RLU-10 µM VRX-14686 RLU)/(Vehicle Only control RLU-10 µM Tamoxifen RLU); based on cell killing induced by VRX-14686 where ATP levels are measured.

Cell Killing (%) (N—(S)-(3,4-difluoro-2-(2-fluoro-4-iodophenylamino)-6-methoxyphenyl)-1-(2,3-dihydroxypropyl)cyclopropane-1-sulfonamide RLU-Vehicle Only control RLU)/(10 µM Tamoxifen RLU-Vehicle Only control RLU); based on cell killing induced by Tamoxifen where AK release is measured.

RLU=Relative Luminescence Units

Evaluation of Cell Cycle Arrest

A375 cells were plated in 96-well microplates at 10,000 cells/200 µl/well. After 24 hr cells were approximately 50% confluent and 50 µl of a 5× drug stock solution was added. After another 24 hr, cells were trypsinized, fixed in 200 µl Prefer (Anatech, Battle Creek, Mich.), and stored at 4° C. overnight. Cells were then rinsed in PBS, permeabilized and stained in 0.1% Triton X-100, 200 µg/ml DNase-free RNase, and 25 mg/ml propidium iodide (Molecular Probes, Sunnyvale, Calif.), and analyzed on the Guava PCA-96 (Guava Technologies, Foster City, Calif.). Data were analyzed using ModFit LT (version 3.0, Verity, Topsham, Me.).

(1) Evaluation of Anchorage Independent Cell Growth Inhibition

Wells of an "ultra low binding" plate (Corning, Acton Mass.) were filled with 60 µl of a 0.15% agarose solution in complete RPMI. Then, 60 µl complete RPMI containing 9000 Colo205 cells in 0.15% agarose was added per well. After 24 hr, 60 µl of a 3× drug solution in agarose free complete RPMI was added. After 7 days, 36 µl 6×MTS reagent (CellTiter 96 Aqueous, Promega, Madison, Wis.) was added per well. After 2 hr at 37° C., absorbance at 490 nm was determined on the M5 plate reader (Molecular Devices, Sunnyvale, Calif.). Non-linear curve-fitting was performed using GraphPad Prism 4.

(2) Growth Inhibition ($GI_{50}$) Against MEK-Dependent Cancer Cell Growth

Log phase dividing B-Raf mutant cells A375 (human melanoma), A431 (melanoma), Colo205 (colon carcinoma), HT29 (colorectal adenocarcinoma), MDA-MB231 (breast adenocarcinoma), and BxPC3 (pancreatic adenocarcinoma) were exposed to N—(S)-(3,4-difluoro-2-(2-fluoro-4-iodophenylamino)-6-methoxyphenyl)-1-(2,3-dihydroxypropyl)cyclopropane-1-sulfonamide for 48 hr and analyzed for ATP content. 100% growth arrest was determined using 1 µM N—(S)-(3,4-difluoro-2-(2-fluoro-4-iodophenylamino)-6-methoxyphenyl)-1-(2,3-dihydroxypropyl)cyclopropane-1-sulfonamide.

The table below shows the mean $GI_{50}$ values from at least three experiments, for each cell line and show that N—(S)-(3,4-difluoro-2-(2-fluoro-4-iodophenylamino)-6-methoxyphenyl)-1-(2,3-dihydroxypropyl)cyclopropane-1-sulfonamide caused growth inhibition in three B-Raf mutant cell lines (A375, Colo205, and HT29), as well as one ras/raf/MEK/MAPK pathway wild-type cell line (A431) with a mean potency of 79 nM (±9 nM).

| Cell Line | Mean | StDev | C.V. |
|---|---|---|---|
| A375 | 71 nM | 12.1 nM | 17% |
| A431 | 86 nM | 25.4 nM | 30% |
| Colo205 | 89 nM | 40.1 nM | 45% |
| HT29 | 70 nM | 12.2 nM | 18% |
| MDA | >1 uM | | |
| BxPC3 | >1 uM | | |

In a separate study, log phase dividing B-Raf mutant cells A375 (human melanoma), SK Mel28 (human melanoma), and Colo205 (human colon carcinoma) were exposed to N—(S)-(3,4-difluoro-2-(2-fluoro-4-iodophenylamino)-6-methoxyphenyl)-1-(2,3-dihydroxypropyl)cyclopropane-1-sulfonamide for 48 hr and analyzed for ATP content. The table below shows the $GI_{50}$ for each cell line indicating N—(S)-(3,4-difluoro-2-(2-fluoro-4-iodophenylamino)-6-methoxyphenyl)-1-(2,3-dihydroxypropyl)cyclopropane-1-sulfonamide caused growth inhibition with a potency approximating its $BC_{50}$ value for MEK inhibition.

| Cell Line | $GI_{50}$ (nM) |
|---|---|
| A375 | 56 |
| SK Mel 28 | 105 |
| Colo205 | 27 |

Figures 10, 10A, 10B:
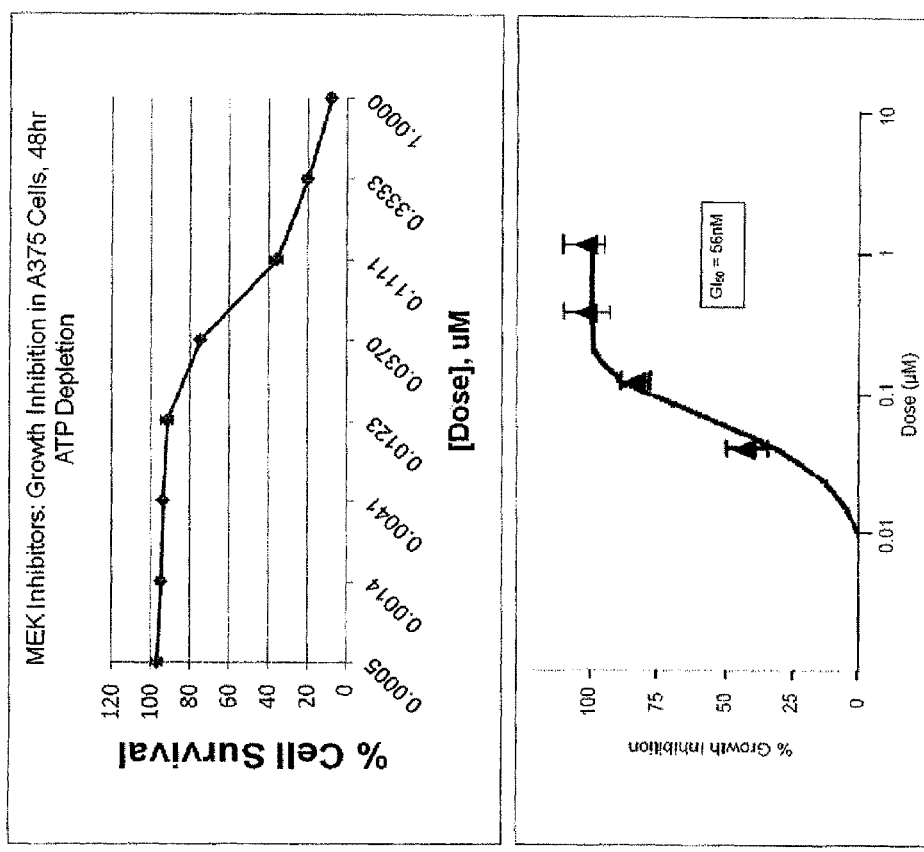
FIG. 10(a) and FIG. 10(b) show growth arrest of Log phase dividing A375 cells exposed to increasing concentrations of N—(S)-(3,4-difluoro-2-(2-fluoro-4-iodophenylamino)-6-methoxyphenyl)-1-(2,3-dihydroxypropyl)cyclopropane-1-sulfonamide. Cells were analyzed for ATP content. 100% growth arrest was determined using 1 µM N—(S)-(3,4-difluoro-2-(2-fluoro-4-iodophenylamino)-6-methoxyphenyl)-1-(2,3-dihydroxypropyl)cyclopropane-1-sulfonamide.

FIGS. 10A and 10B show growth arrest of Log phase dividing A375 cells exposed to increasing concentrations of N—(S)-(3,4-di fluoro-2-(2-fluoro-4-iodophenylamino)-6-methoxyphenyl)-1-(2,3-dihydroxypropyl)cyclopropane-1-sulfonamide. Cells were analyzed for ATP content. 100% growth arrest was determined using 1 µM N—(S)-(3,4-difluoro-2-(2-fluoro-4-iodophenylamino)-6-methoxyphenyl)-1-(2,3-dihydroxypropyl)cyclopropane-1-sulfonamide.

Figure 11:
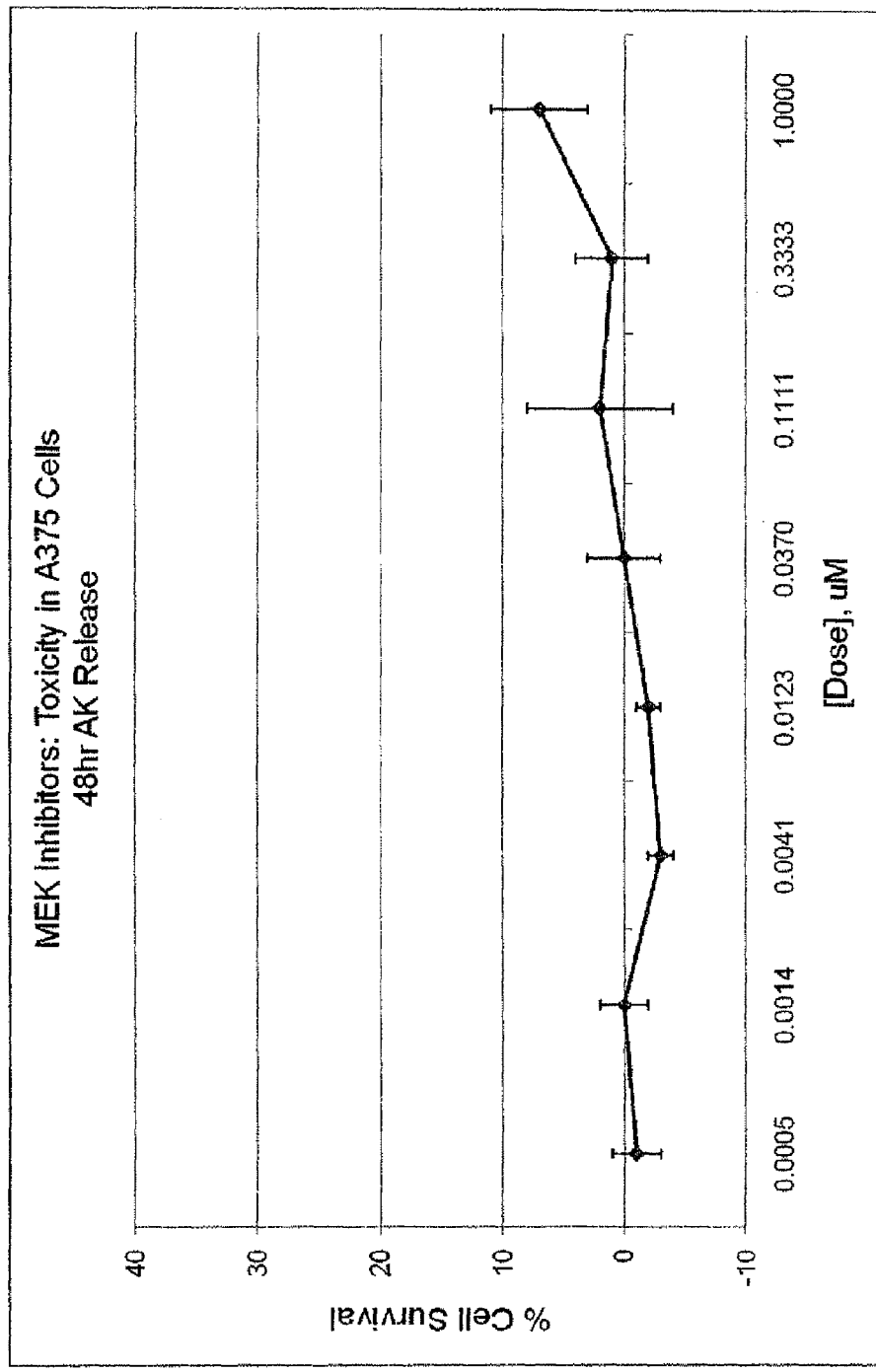
FIG. 11 shows a 48 hr AK assay in A375 cells. Log phase dividing A375 cells were exposed to N—(S)-(3,4-difluoro-2-(2-fluoro-4-iodophenylamino)-6-methoxyphenyl)-1-(2,3-dihydroxypropyl)cyclopropane-1-sulfonamide and PD-325901 for 48 hr and analyzed for AK release.

Cell supernatants were analyzed for cytotoxic lysis by measuring adenylate kinase (AK) release. Log phase dividing A375 cells were exposed to N—(S)-(3,4-difluoro-2-(2-fluoro-4-iodophenylamino)-6-methoxyphenyl)-1-(2,3-dihydroxypropyl)cyclopropane-1-sulfonamide and PD-325901 for 48 hr. (100% cell killing was determined using 20 µM tamoxifen.) The results are shown in FIG. 11. This data indicates that N—(S)-(3,4-difluoro-2-(2-fluoro-4-iodophenylamino)-6-methoxyphenyl)-1-(2,3-dihydroxypropyl)cyclopropane-1-sulfonamide causes a non-toxic growth arrest in several susceptible human cancer cell lines, demonstrated by i) growth arrest measurements (ATP quantitation); and ii) lack of cytotoxic cell lysis (AK release). The lack of AK release was confirmed for all cell lines tested.

Anchorage Independent Growth Inhibition

Anchorage independent growth of Colo205, A375, and MDA-MB231 cells exposed to N—(S)-(3,4-difluoro-2-(2-fluoro-4-iodophenylamino)-6-methoxyphenyl)-1-(2,3-dihydroxypropyl)cyclopropane-1-sulfonamide for 7 days, was quantitatively assessed in a 96-well microplate format. Viability was determined by MTS assay. $GI_{50}$ values are shown below:

| Cell Line | Mean | StDev | C.V. |
| --- | --- | --- | --- |
| Colo205 | 40 nM | 8.1 nM | 20% |
| A375 | 84 nM | 17.2 nM | 21% |
| MDA-MB231 | 81 nM | 55.6 nM | 69% |

FIGS. 12A-12C show N—(S)-(3,4-difluoro-2-(2-fluoro-4-iodophenylamino)-6-methoxyphenyl)-1-(2,3-dihydroxypropyl)cyclopropane-1-sulfonamide growth inhibition of (A) human colorectal carcinoma Colo205 cells ($GI_{50}=11$ nM); (B) A375 cells ($GI_{50}=22$ nM) and (C) inhibition of MDA-M8231 cells which do not show N—(S)-(3,4-difluoro-2-(2-fluoro-4-iodophenylamino)-6-methoxyphenyl)-1-(2,3-dihydroxypropyl)cyclopropane-1-sulfonamide-induced growth arrest in 2-dimensional anchorage dependent assays.

Log phase dividing A375 cells were exposed to N—(S)-(3,4-difluoro-2-(2-fluoro-4-iodophenylamino)-6-methoxyphenyl)-1-(2,3-dihydroxypropyl)cyclopropane-1-sulfonamide (1 uM) for 48 hr and the cell supernatants analyzed for growth inhibition (ATP content) and cytotoxic lysis (AK release). 100% viability (ATP assay) was determined in vehicle only control wells. The table below shows the results indicating N—(S)-(3,4-difluoro-2-(2-fluoro-4-iodophenylamino)-6-methoxyphenyl)-1-(2,3-dihydroxypropyl)cyclopropane-1-sulfonamide causes non-toxic growth arrest in B-Raf mutant human melanoma A375 cells.

|  | % Control |
| --- | --- |
| ATP, Cell viability | 27% |
| AK, Cell killing | 4% |

Anchorage Independent Growth Inhibition

Anchorage independent growth was quantitatively assessed in a 96-well microplate format. FIG. 13A shows inhibition of growth of human colorectal carcinoma Colo205 cells, with $GI_{50}$ values at 6 nM and 11 nM respectively. FIG. 13B shows inhibition of growth of A375 cells with $GI_{50}$ values at 5 nM and 22 nM.

Cell Cycle Analysis of N—(S)-(3,4-difluoro-2-(2-fluoro-4-iodophenylamino)-6-methoxyphenyl)-1-(2,3-dihydroxypropyl)cyclopropane-1-sulfonamide Induced Growth Arrest MEK inhibition has been shown to induce G1/S phase cell cycle arrest in A375 cells.

Log phase dividing A375 cells were exposed to N—(S)-(3,4-difluoro-2-(2-fluoro-4-iodophenylamino)-6-methoxyphenyl)-1-(2,3-dihydroxypropyl)cyclopropane-1-sulfonamide for 24 hr and the percentages of cells which stained for phase dependent amounts of intracellular DNA were determined using flow cytometry.

The table below shows percentage distribution of cells in respective growth phases in N—(S)-(3,4-difluoro-2-(2-fluoro-4-iodophenylamino)-6-methoxyphenyl)-1-(2,3-dihydroxypropyl)cyclopropane-1-sulfonamide and control (vehicle only) treated cells.

|  |  | Phase % | | |
| --- | --- | --- | --- | --- |
|  |  | G1 | S | G2 |
| Control |  | 61.8 | 27.1 | 11.1 |
| N-(S)-(3,4-difluoro-2-(2-fluoro-4-iodophenylamino)-6-methoxyphenyl)-1-(2,3-dihydroxypropyl)cyclopropane-1-sulfonamide | 111 nM | 84.7 | 11.8 | 3.5 |
|  | 37 nM | 74.3 | 18.7 | 7.0 |

Figure 14:
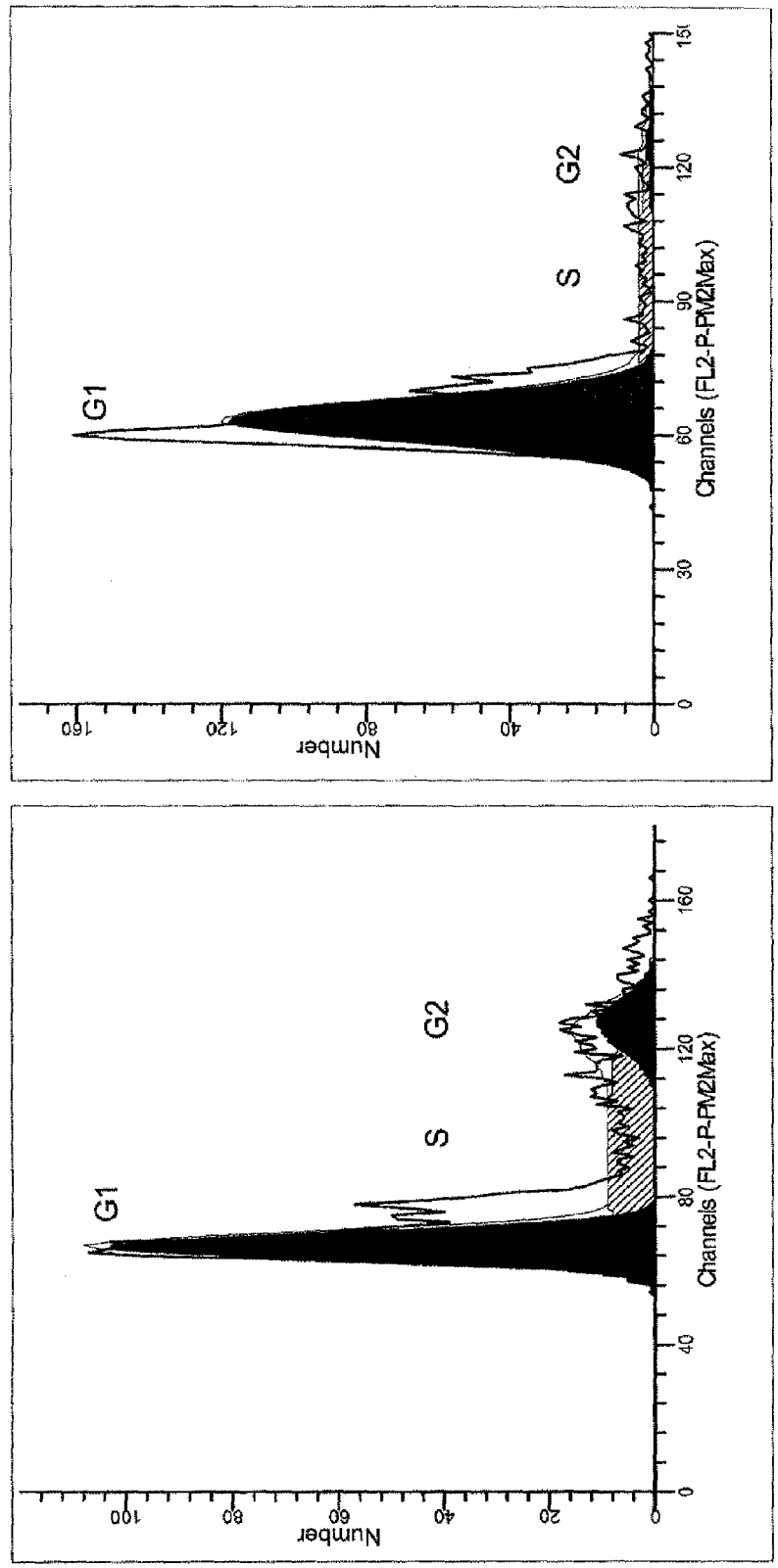
FIG. 14A and FIG. 14B show the effect of N—(S)-(3,4-difluoro-2-(2-fluoro-4-iodophenylamino)-6-methoxyphenyl)-1-(2,3-dihydroxypropyl)cyclopropane-1-sulfonamide on cell cycle progression, demonstrating that exposure of A375 cells to N—(S)-(3,4-difluoro-2-(2-fluoro-4-iodophenylamino)-6-methoxyphenyl)-1-(2,3-dihydroxypropyl)cyclopropane-1-sulfonamide causes arrest in the G1 phase of the cell cycle, indicated by the depletion of cells in both the G2 and S phases.

FIG. 14A and FIG. 14B show the effect of N—(S)-(3,4-difluoro-2-(2-fluoro-4-iodophenylamino)-6-methoxyphenyl)-1-(2,3-dihydroxypropyl)cyclopropane-1-sulfonamide on cell cycle progression, demonstrating that exposure of A375 cells to N—(S)-(3,4-difluoro-2-(2-fluoro-4-iodophenylamino)-6-methoxyphenyl)-1-(2,3-dihydroxypropyl)cyclopropane-1-sulfonamide causes arrest in the G1 phase of the cell cycle, indicated by the depletion of cells in both the G2 and S phases.

Evaluation of Primary Hepatocyte and Renal Cell Toxicity

Cryopreserved rat hepatocytes were obtained from CellzDirect (Austin, Tex.) and plated on collagen coated 96-well plates according to manufacturer's instructions. Drug was added 4 hr after plating (final DMSO concentration 0.5%).

Plated human hepatocytes were obtained from CellzDirect and processed according to manufacturer's instructions.

Cryopreserved human renal proximal tubule epithelial cells (RPTEC) were obtained from Cambrex and were processed according to manufacturer's instructions. Cells were expanded for 4 days and then plated in 96-well plates at 50,000 cells/well for drug exposure.

After 48 hr, supernatant AK levels were determined using Toxilight, and cellular ATP levels were determined using CellTiterGlo. Full kill values were determined using 15 μM VRX-14686.

The results are shown in below. Very little cell lysis was observed. Minimal toxicity (81% survival) was seen at 30 μM N—(S)-(3,4-difluoro-2-(2-fluoro-4-iodophenylamino)-6-methoxyphenyl)-1-(2,3-dihydroxypropyl)cyclopropane-1-sulfonamide in freshly plated primary human hepatocytes. RPTEC cells showed a dose dependent ATP depletion and evident cell lysis at 30 W.

|  | ATP (% Cell Survival) | | AK release (% Cell Survival) | |
| --- | --- | --- | --- | --- |
|  | Hepatocytes | RPTEC | Hepatocytes | RPTEC |
| Compound A | Rat | Human | Human | Rat | Human | Human |
| 30.0 | 57% | 81% | 34% | 91% | 109% | 41% |
| 10.0 | 72% | 107% | 85% | 93% | 112% | 99% |
| 3.3 | 87% | 104% | 91% | 97% | 102% | 95% |
| 1.1 | 114% | 108% | 94% | 96% | 92% | 96% |

The above data illustrates that (1) N—(S)-(3,4-difluoro-2-(2-fluoro-4-iodophenylamino)-6-methoxyphenyl)-1-(2,3-dihydroxypropyl)cyclopropane-1-sulfonamide inhibits cell growth and division in select human cancer cells with $GI_{50}$ values ranging from 70-89 nM in anchorage dependent proliferation assays without causing toxicity as determined by cell lysis assay; (2) N—(S)-(3,4-difluoro-2-(2-fluoro-4-iodophenylamino)-6-methoxyphenyl)-1-(2,3-dihydroxypropyl)cyclopropane-1-sulfonamide inhibits cell growth and division in select human cancer cells with $GI_{50}$ values of 51 nM and 22 nM in anchorage dependent and independent proliferation assays respectively; (3) N—(S)-(3,4-difluoro-2-(2-fluoro-4-iodophenylamino)-6-methoxyphenyl)-1-(2,3-dihydroxypropyl)cyclopropane-1-sulfonamide causes G1 arrest and inhibits anchorage independent growth in A375 cells, providing evidence of anticancer activity in a physiologically relevant in vitro model; and (4) N—(S)-(3,4-difluoro-2-(2-fluoro-4-iodophenylamino)-6-methoxyphenyl)-1-(2,3-dihydroxypropyl)cyclopropane-1-sulfonamide shows little cytotoxicity against primary normal human hepatocytes, human renal proximal tubule epithelial cells and rat hepatocytes.

Example 111

Pharmacokinetics of N—(S)-(3,4-difluoro-2-(2-fluoro-4-iodophenylamino)-6-methoxyphenyl)-1-(2,3-dihydroxypropyl)cyclopropane-1-sulfonamide in Cancer Patients following Multiple Doses

| Dose (mg) | N | $T_{max}$ (hr) | $C_{max}$ (μg/mL) | $C_{24hr}$ (μg/mL) | $AUC_\tau$ (μg · hr/mL) | $t_{1/2}$* (hr) | $R_{ac}$ $C_{max}$ | $R_{ac}$ $AUC_\tau$ |
|---|---|---|---|---|---|---|---|---|
| 2 | 3 | 1.33 (21.7) | 0.0504 (49.2) | 0.00938 (82.8) | 0.517 (61.2) | 11.4 (38.8) | 1.76 (35.6) | 1.90 (23.9) |
| 4 | 3 | 1.50 (33.3) | 0.105 (41.0) | 0.0313 (41.1) | 1.39 (42.7) | 14.9 (0.992) | 1.49 (21.6) | 1.91 (36.1) |
| 6 | 3 | 1.50 (33.3) | 0.205 (16.6) | 0.0489 (12.2) | 2.22 (5.79) | 15.6 (23.8) | 1.58 (38.5) | 2.07 (23.5) |

$R_{ac}$: accumulation index
*Inaccurate estimate due to limited sampling time

Following multiple dosing of N—(S)-(3,4-difluoro-2-(2-fluoro-4-iodophenylamino)-6-methoxyphenyl)-1-(2,3-dihydroxypropyl)cyclopropane-1-sulfonamide at 2, 4, or 6 mg/subject, N—(S)-(3,4-difluoro-2-(2-fluoro-4-iodophenylamino)-6-methoxyphenyl)-1-(2,3-dihydroxypropyl)cyclopropane-1-sulfonamide was readily absorbed with mean $T_{max}$ ranging between 1.33 to 1.50 hr. Mean $C_{max}$, $C_t$, and AUC values increased with dose in a dose-proportional manner. Accumulation indices range between 1.49 to 1.76 for $C_{max}$ and 1.90 to 2.07 for AUC, respectively, indicating moderate accumulation. Although the half-life cannot be accurately measured due to limited sampling time following multiple doses, the hale-life was expected to be longer than 22 hr following multiple doses based on the accumulation indices. These half-life values are significantly longer than observed in the mouse efficacy model which a typical range of 2-3 hr was seen. In addition, encouraging peak-to-trough ratios were seen in all doses.

Example 112

Pharmacokinetics of N—(S)-(3,4-difluoro-2-(2-fluoro-4-iodophenylamino)-6-methoxyphenyl)-1-(2,3-dihydroxypropyl)cyclopropane-1-sulfonamide in Healthy Volunteers following Multiple Doses

| Dose (mg) | N | $T_{max}$ (hr) | $C_{max}$ (μg/mL) | $C_{24hr}$ (μg/mL) | $AUC_\tau$ (μg · hr/mL) | $t_{1/2}$* (hr) | $R_{ac}$ $C_{max}$ | $R_{ac}$ $AUC_\tau$ |
|---|---|---|---|---|---|---|---|---|
| 10 | 6 | 2.00 (61.2) | 0.182 (35.5) | 0.0318 (53.0) | 1.02 (1.80) (43.7) (39.7) | 14.6 (15.2) | 1.14 (19.0) | 1.29 (13.4) |
| 20 | 6 | 2.25 (39.1) | 0.313 (17.6) | 0.0350 (36.5) | 2.60 (22.0) | 13.4 (21.9) | 1.23 (24.1) | 1.24 (6.51) |

$R_{ac}$: accumulation index
*Inaccurate estimate due to limited sampling time

Following multiple dosing of N—(S)-(3,4-difluoro-2-(2-fluoro-4-iodophenylamino)-6-methoxyphenyl)-1-(2,3-dihydroxypropyl)cyclopropane-1-sulfonamide at 10 or 20 mg/subject, N—(S)-(3,4-difluoro-2-(2-fluoro-4-iodophenylamino)-6-methoxyphenyl)-1-(2,3-dihydroxypropyl)cyclopropane-1-sulfonamide was readily absorbed with mean $T_{max}$ ranging between 2.00 to 2.25 hr. Mean $C_{max}$, $C_t$, and AUC values increased with dose. Accumulation indices range between 1.14 to 1.23 for $C_{max}$ and 1.24 to 1.29 for AUC, respectively, indicating insignificant accumulation. Half-lives were similar for two dose regimens ranging between 13 and 15 hr. These half-life values are shorter than observed in the cancer patients.

Example 113

In Vitro Anti-Proliferative Activity

The effect of N—(S)-(3,4-difluoro-2-(2-fluoro-4-iodophenylamino)-6-methoxyphenyl)-1-(2,3-dihydroxypropyl)cyclopropane-1-sulfonamide on inhibition of cell proliferation was examined in a cell line derived from a human gastric carcinoma ("stomach cancer") in a cell proliferation assay.

Cell Culture/Growth Inhibition Assay:

Human gastric carcinoma Hs746t cells were obtained from ATCC (Manassas, Va.). Hs746t cells were maintained in DMEM supplemented with 10% fetal bovine serum, penicillin (100 U/ml), and streptomycin (100 μg/ml). Cells were maintained at 37° C., 5% $CO_2$, and 100% humidity. For cell proliferation experiments, cells were plated in white 96-well plates with clear bases at 3000 cells/100 μl/well. After 24 hr, cell media was removed and replaced with media containing N—(S)-(3,4-difluoro-2-(2-fluoro-4-iodophenylamino)-6-methoxyphenyl)-1-(2,3-dihydroxypropyl)cyclopropane-1-sulfonamide at various doses. Following incubation for 48 hours at 37° C., ATP levels were determined using CellTiter-Glo (Promega, Madison, Wis.) and reading luminescence values using a LIE Biosystems Analyst HT (Sunnyvale, Calif.). The ATP level for each dose was determined in triplicate using independent wells.

Relative cell number=(mean RLU (N—(S)-(3,4-difluoro-2-(2-fluoro-4-iodophenylamino)-6-methoxyphenyl)-1-(2,3-dihydroxypropyl)cyclopropane-1-sulfonamide treated))/(mean RLU Vehicle Only control).

Figure 19:
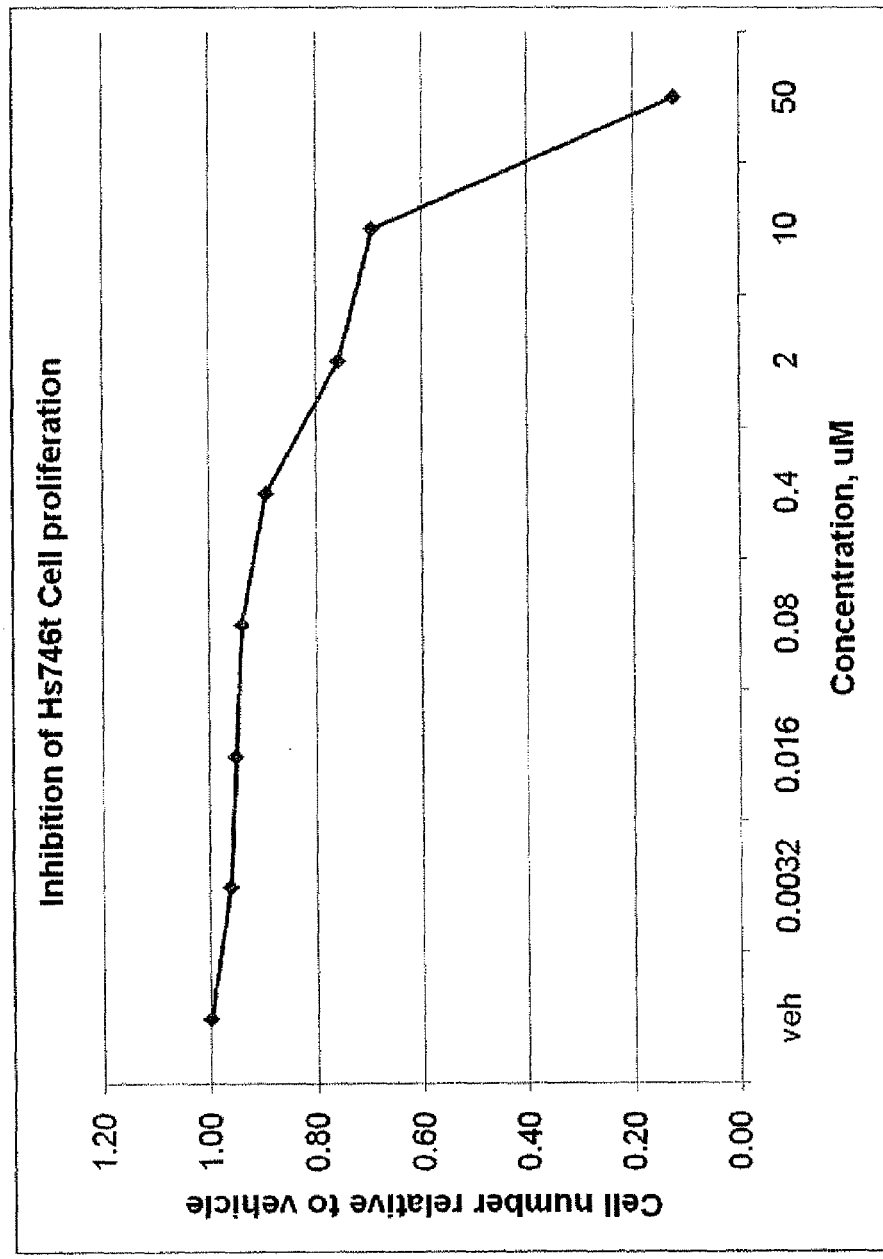
FIG. 19 shows the inhibition of Hs746t Cell proliferation in a graph of cell number (relative to vehicle) vs concentration of N—(S)-(3,4-difluoro-2-(2-fluoro-4-iodophenylamino)-6-methoxyphenyl)-1-(2,3-dihydroxypropyl)cyclopropane-1-sulfonamide.

FIG. 19 shows a graph of cell number (relative to vehicle) vs concentration of N—(S)-(3,4-difluoro-2-(2-fluoro-4-iodophenylamino)-6-methoxyphenyl)-1-(2,3-dihydroxypropyl)cyclopropane-1-sulfonamide and demonstrates that N—(S)-(3,4-difluoro-2-(2-fluoro-4-iodophenylamino)-6-methoxyphenyl)-1-(2,3-dihydroxypropyl)cyclopropane-1-sulfonamide inhibits the proliferation of human gastric carcinoma Hs746t cells after 48 hours treatment Example 114

In Vitro Anti-Proliferative Activity

The effect of N—(S)-(3,4-difluoro-2-(2-fluoro-4-iodophenylamino)-6-methoxyphenyl)-1-(2,3-dihydroxypropyl)cyclopropane-1-sulfonamide on inhibition of cell proliferation was examined in a cell line derived from a human gastric adenocarcinoma ("stomach cancer") in a cell proliferation assay.

Cell Culture/Growth Inhibition Assay

Human gastric adenocarcinoma AGS cells were obtained from ATCC (Manassas, Va.). AGS cells were maintained in DMEM/F12 supplemented with 10% fetal bovine serum, penicillin (100 U/ml), and streptomycin (100 µg/ml). Cells were maintained at 37° C., 5% $CO_2$, and 100% humidity. For cell proliferation experiments, cells were plated in white 96-well plates with clear bases at 3000 cells/100 µl/well. After 24 hr, cell media was removed and replaced with media containing N—(S)-(3,4-difluoro-2-(2-fluoro-4-iodophenylamino)-6-methoxyphenyl)-1-(2,3-dihydroxypropyl)cyclopropane-1-sulfonamide at various doses. Following incubation for 3 days at 37° C., ATP levels were determined using CellTiterGlo (Promega, Madison, Wis.) and reading luminescence values using a LJL Biosystems Analyst HT (Sunnyvale, Calif.). The ATP level for each dose was determined in triplicate using independent wells. In another experiment, 1000 cells/100 µl/well were plated and the cells were treated for 6 days and assayed as before.

Relative cell number=(mean RLU (N—(S)-(3,4-difluoro-2-(2-fluoro-4-iodophenylamino)-6-methoxyphenyl)-1-(2,3-dihydroxypropyl)cyclopropane-1-sulfonamide treated))/(mean RLU Vehicle Only control).

Figure 15:
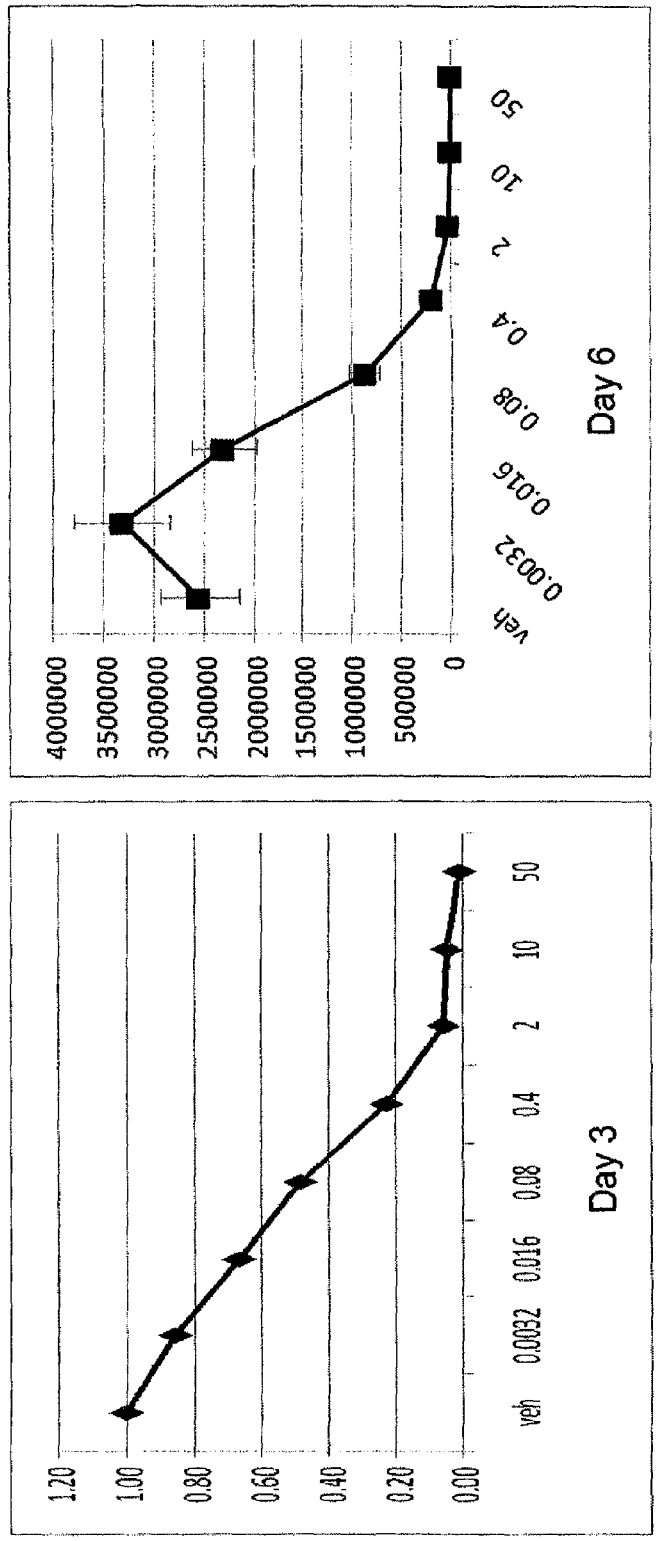
FIG. 15A and FIG. 15B show the effect of N—(S)-(3,4-difluoro-2-(2-fluoro-4-iodophenylamino)-6-methoxyphenyl)-1-(2,3-dihydroxypropyl)cyclopropane-1-sulfonamide on the stomach cancer (gastric adenocarcinoma) cell line AGS after 3 days (FIG. 15A) and 6 days (FIG. 15B). The y axis is the cell number relative to vehicle and the x axis is uM of N—(S)-(3,4-difluoro-2-(2-fluoro-4-iodophenylamino)-6-methoxyphenyl)-1-(2,3-dihydroxypropyl)cyclopropane-1-sulfonamide.

FIG. 15A and FIG. 15B shows a graphical plot of N—(S)-(3,4-difluoro-2-(2-fluoro-4-iodophenylamino)-6-methoxyphenyl)-1-(2,3-dihydroxypropyl)cyclopropane-1-sulfonamide concentration vs cell number (relative to vehicle) after (A) 3 days and (B) 6 days exposure to N—(S)-(3,4-difluoro-2-(2-fluoro-4-iodophenylamino)-6-methoxyphenyl)-1-(2,3-dihydroxypropyl)cyclopropane-1-sulfonamide, demonstrating that N—(S)-(3,4-difluoro-2-(2-fluoro-4-iodophenylamino)-6-methoxyphenyl)-1-(2,3-dihydroxypropyl)cyclopropane-1-sulfonamide inhibits the proliferation of the human gastric adenocarcinoma AGS cell line.

Example 115

Growth Response of Orthotopic Human Hep3B Tumors in Nude Mice Treated with Different Amounts of N—(S)-(3,4-difluoro-2-(2-fluoro-4-iodophenylamino)-6-methoxyphenyl)-1-(2,3-dihydroxypropyl)cyclopropane-1-sulfonamide The dose response efficacy of N—(S)-(3,4-difluoro-2-(2-fluoro-4-iodophenylamino)-6-methoxyphenyl)-1-(2,3-dihydroxypropyl)cyclopropane-1-sulfonamide ("Compound A"), in inhibiting the development of orthotopic Hep3B2.1-7 human hepatic carcinoma was assessed in BALB/c nu/nu mice, in comparison with an optimal dose of 5-Fluorouracil (75 mg/kg).

Animals:

Female BALB/c nu/nu mice (University of Adelaide, Waite Campus, SA, Australia), aged 10-14 weeks, with a body weight range: of 19.1-29.94 g (mean 22.95 g) were used for the study. The mice were divided into 6 Study groups (4 treatment groups and 2 control groups) as follows:

Number of Mice per Group: 10 in Groups 1 to 5 inclusive 15 in 'Take-Rate' Control Group (Group 6)

The mice were kept in a controlled environment (targeted ranges: temperature 21±3° C., humidity 30-70%, 10-15 air changes per hour) under barrier (quarantine) conditions with a 12 hour light/12 hour dark cycle. Temperature and relative humidity were monitored continuously. A commercial rodent diet (Rat and Mouse Cubes, Speciality Feeds Pty Ltd, Glen Forrest, Western Australia) and tap water were provided to the animals ad libitum. Both food and water supplies were sterilized by autoclaving.

Tumor Inoculation:

Hep3B human hepatic carcinoma cells (Passage 2 from working stock VP-Stock 353) were cultured in RPMI1640 cell culture medium, which was supplemented with 10% FBS and penicillin-streptomycin (501 U/mL final concentration). The cells were harvested by trypsinisation, washed twice in HBSS and counted. The cells were then resuspended in HBSS:Matrigel (1:1, v/v) and adjusted to a final volume containing $1 \times 10^8$ cells/mL. Prior to inoculation, the incision site was liberally swabbed with alcohol and an incision made through the abdominal wall to expose the liver. The needle was introduced through the surface of the liver where 10 µL of cells ($1 \times 10^6$ cells) were discharged. The needle was held in this position for approximately 30 seconds to allow the Matrigel® to polymerize in order to avoid leakage of tumor cells into the abdominal cavity.

Treatment commenced 14 days post-inoculation. On Day 7 of the study (21 days post-inoculation), all mice from the 'Take-Rate' control group were culled and the livers visually assessed for the presence of tumors.

Materials:

The following were obtained from the respective suppliers. Sterile saline solution (0.9% NaCl(aq)) was obtained from Baxter Healthcare Australia, Old Toongabbie, NSW, Australia. CremophorEL was obtained from Sigma-Aldrich Pty Ltd, Castle Hill, NSW, Australia. 5-Fluorouracil, clinical formulation, clear, colorless liquid was obtained from Mayne Pharma Pty Ltd. RPMI1640 cell culture medium, PBS and HBSS were obtained from Invitrogen Australia Pty Ltd, Mt Waverley, VIC, Australia. Penicillin-streptomycin and Trypan Blue were obtained from Sigma-Aldrich, Castle Hill, NSW, Australia. Hep3B2.1-7 human hepatic carcinoma cells were sourced from American Type Culture Collection (ATCC), Rockville, Md., USA. Matrigel® was obtained from BD Biosciences, North Ryde, NSW, Australia.

The use of Matrigel® in the inoculation suspension improves the take rate of the tumor and decrease tumor size variability, and the growth of the Hep3B2.1-7 human hepatic carcinoma is more stable when inoculated in the presence of this extracellular matrix.

Compound Preparation and Administration:

CremophorEL:Saline (1:9, v/v; vehicle control), N—(S)-(3,4-difluoro-2-(2-fluoro-4-iodophenylamino)-6-methoxyphenyl)-1-(2,3-dihydroxypropyl)cyclopropane-1-sulfonamide ("Compound A") or 5-Fluorouracil (compound control) were administered according to the schedule below:

| Group | Compound | Dose (mg/kg) | Scheduled Treatment | Treatment Administered |
|---|---|---|---|---|
| 1 | Vehicle Control | 10 mL/kg | Once daily for 21 Days (Day 0 to 20) | Once daily for 19 Days (Day 0 to 18) |
| 2 | Compound A | 0.2 mL @ 10 mL/kg = 2 mg/kg | Once daily for 21 Days (Day 0 to 20) | Once daily for 19 Days (Day 0 to 18) |
| 3 | Compound A | 1.0 mL @ 10 mL/kg = 10 mg/kg | Once daily for 21 Days (Day 0 to 20) | Once daily for 19 Days (Day 0 to 18) |
| 4 | Compound A | 5.0 mL @ 10 mL/kg = 50 mg/kg | Once daily for 21 Days (Day 0 to 20) | Once daily for 19 Days (Day 0 to 18) |
| 5 | 5-Fluorouracil | 7.5 mL @ 10 mL/kg = 75 mg/kg | Once weekly for 21 Days (Day 0, 7 and 14) | Once weekly for three weeks (Day 0, 7 and 14) |
| 6 | 'Take-Rate' Control | No treatment | — | — |

The Vehicle Control, CremophorEL:Saline (1:9, v/v), was administered p.o. in a dosing volume of 10 mL/kg, once daily for 21 consecutive days (Day 0 to 20).

N—(S)-(3,4-difluoro-2-(2-fluoro-4-iodophenylamino)-6-methoxyphenyl)-1-(2,3-dihydroxypropyl)cyclopropane-1-sulfonamide, was formulated in CremophorEL:Saline (1:9, v/v). A stock solution was prepared weekly and stored at 4° C. Dosing solutions were prepared on each day of administration. N—(S)-(3,4-difluoro-2-(2-fluoro-4-iodophenylamino)-6-methoxyphenyl)-1-(2,3-dihydroxypropyl)cyclopropane-1-sulfonamide was administered p.o. in a dosing volume of 10 mL/kg, once daily for 21 days (Day 0 to 20). The compound was administered at doses of 2, 10 and 50 mg/kg.

5-Fluorouracil clinical formulation was diluted in sterile saline and administered i.v. via the tail vein at a concentration of 75 mg/kg, in a dosing volume of 10 mL/kg, once per week for three weeks (on Day 0, 7 and 14).

No treatment was administered to the mice in Group 6 ('Take-Rate' Control). On Day 7 of the study (21 days post-inoculation), the mice were culled and the liver exposed to determine the 'Take-Rate' and the size of the tumors in the liver wall.

Each animal's body weight was measured immediately prior to dosing. The volume administered to each mouse was calculated and adjusted based on the body weight.

Tumor Measurements:

Liver and tumor wet weight were measured when each were excised post-mortem on the termination day of the study. At the termination of the study, livers were excised from all mice in each study group and weighed. The number of visible tumors, if present, was counted. These tumors were removed from the liver and weighed.

Data Acquisition and Calculation:

Each animal's transponder (Bar Code Data Systems Pty Ltd, Botany Bay, NSW) was scanned using a barcode reader (LabMax I, DataMars, Switzerland) immediately prior to acquisition of data. All measurements were acquired with the same handheld calipers (Absolute Digimatic Model CD-6" CS, Mitutoyo Corporation, Japan). The data was synchronized with vivoPharm's secure relational database using Pendragon Forms 4.0 (Pendragon® Software Corporation, Libertyville, Ill., U.S.A.) as transfer software. ADAM v2.4 was used for data reports and data calculation.

Statistical and Calculations:

All statistical calculations were performed using SigmaStat 3.0. (SPSS Australasia Pty Ltd, North Sydney, NSW, Australia).

A two-sample t-test was used to determine the significance in body weight change within a treatment group between Day 0 and the termination day of the study. Where the data failed the Normality test or the Equal Variance Test, a Mann-Whitney Rank Sum Test was performed.

A One-Way Analysis of Variance (ANOVA) (All Pairwise Multiple Comparison Procedure and Multiple Comparison versus Control Group) was performed on liver weight and tumor weight data at the end of the study. Where this test did not pass the Equal Variance test, the Kruskal-Wallis One-Way Analysis of Variance (ANOVA) on ranks was performed. The same statistical analyses were performed on the data for the tumor-bearing mice in the study.

A p value of less than 0.05 was considered significant.

| Data Measurement and Sample Collection Schedule | |
|---|---|
| | Schedule |
| Data Measurement | |
| Body weight | Day 0, then three times per week (Monday, Wednesday and Friday), and on the termination day of the study for Groups 1 to 5 inclusive. |
| Liver weight and tumor weight | Wet weight of excised liver and tumor all mice in Groups 1 to 5 inclusive, post-mortem on the termination day of the study, and from one mouse in Group 5 which died on the final treatment day. |
| Sample Collection | |
| Livers and tumors | From all mice in Group 6 ('Take-Rate' Control) on Day 7 of the study. |
| Livers and tumors | From all mice in Groups 1 to 5 inclusive, post-mortem on the termination day of the study, and from one mouse in Group 5 which died on the final treatment day. |
| Liver | From all mice in Groups 1 to 5 inclusive, post-mortem on the termination day of the study, and from one mouse in Group 5 which died on the final treatment day. |

Liver Weight and Tumor Weight Data for Tumor-Bearing Mice and Average Weight of Liver and Tumors Per Mouse Per Group for Tumor-Bearing Mice

| Group | Treatment | Average Liver Weight (g) | SEM | Average Tumor Weight (g) | SEM | No. of Mice with Tumors (out of 10) |
|---|---|---|---|---|---|---|
| 1 | Vehicle Control | 4.560 | 0.673 | 3.382 | 0.979 | 4 |
| 2 | Compound A @ 2 mg/kg | 2.775 | 0.475 | 1.776 | 0.576 | 6 |
| 3 | Compound A @ 10 mg/kg | 2.551 | 0.446 | 1.407 | 0.465 | 7 |
| 4 | Compound A @ 50 mg/kg | 1.677 | 0.161 | 0.624 | 0.257 | 4 |
| 5 | 5FU ™ @ 75 mg/kg | 1.217 | 0.051 | 0.143 | 0.078 | 4 |

Samples were not collected from the mouse in Group 5 (5-Fluorouracil at 75 mg/kg) which was culled during the study period. Due to the presence of large tumors in some of the mice, as indicated by a swollen appearance of the abdomen, the study was terminated 18 days post-initial treatment.

A dose-dependent trend in the decrease in liver and tumor weight is evident in the N—(S)-(3,4-difluoro-2-(2-fluoro-4-iodophenylamino)-6-methoxyphenyl)-1-(2,3-dihydroxypropyl)cyclopropane-1-sulfonamide-treated groups. When considering only the tumor-bearing mice, the average weight of the liver in the groups treated with N—(S)-(3,4-difluoro-2-(2-fluoro-4-iodophenylamino)-6-methoxyphenyl)-1-(2,3-dihydroxypropyl)cyclopropane-1-sulfonamide at the highest dose (Group 4 at 50 mg/kg) and 5-Fluorouracil (Group 5 at 75 mg/kg) was found to be significantly different to the Vehicle Control group (Group 1; p<0.05). Also, the average weight of the tumors in the groups treated with N—(S)-(3,4-difluoro-2-(2-fluoro-4-iodophenylamino)-6-methoxyphenyl)-1-(2,3-dihydroxypropyl)cyclopropane-1-sulfonamide (Groups 3 and 4 at 10 mg/kg and 50 mg/kg respectively) and 5-Fluorouracil (Group 5 at 75 mg/kg) was found to be significantly different to the Vehicle Control group.

Figure 16:
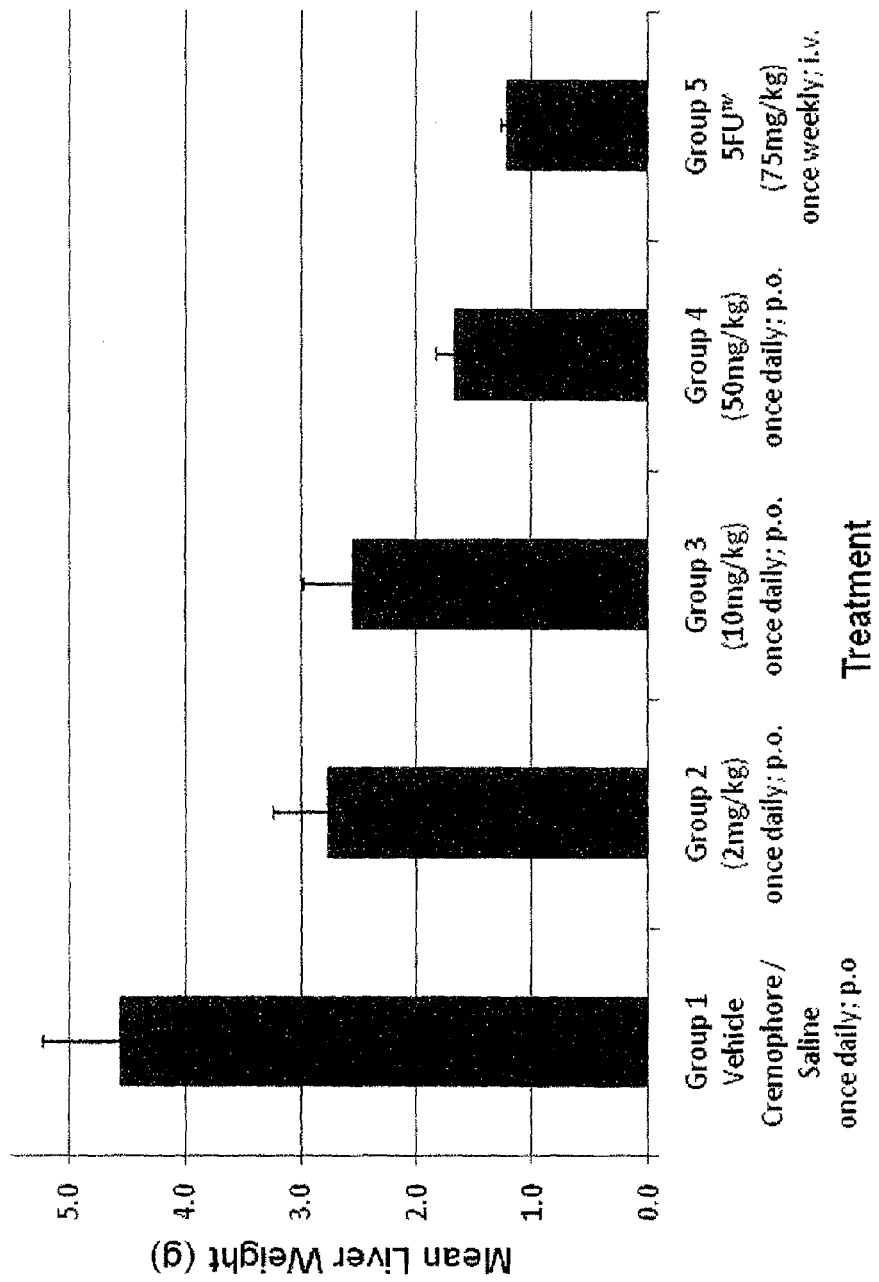
FIG. 16 shows the mean liver weights in tumor bearing mice after treatment with N—(S)-(3,4-difluoro-2-(2-fluoro-4-iodophenylamino)-6-methoxyphenyl)-1-(2,3-dihydroxypropyl)cyclopropane-1-sulfonamide (2 mg/kg, once daily, po; 10 mg/kg, once daily, po and 50 mg/kg, once daily, po).
Figure 17:
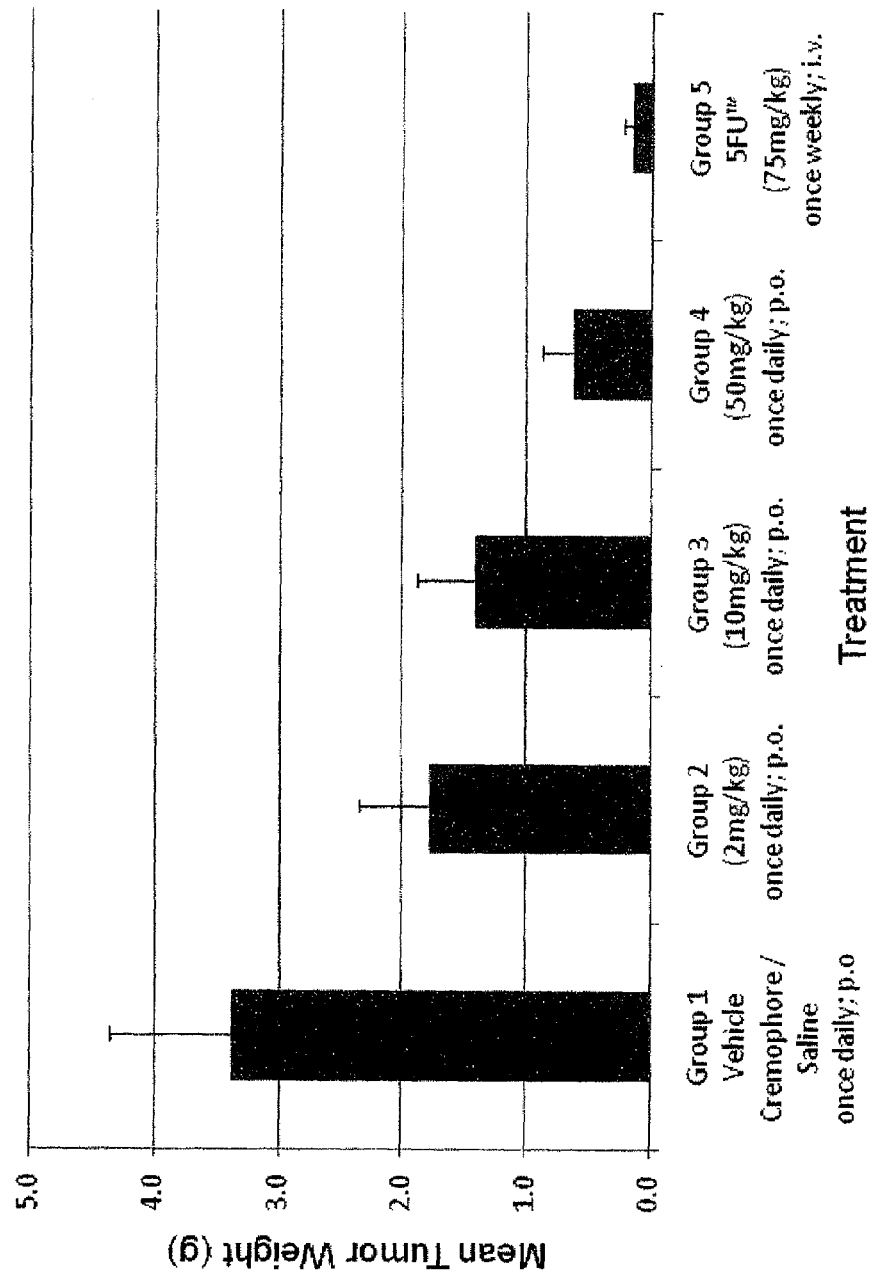
FIG. 17 shows liver tumor weights in tumor bearing mice after treatment with N—(S)-(3,4-difluoro-2-(2-fluoro-4-iodophenylamino)-6-methoxyphenyl)-1-(2,3-dihydroxypropyl)cyclopropane-1-sulfonamide (2 mg/kg, once daily, po; 10 mg/kg, once daily, po and 50 mg/kg, once daily, po).

These results are presented graphically in FIG. 16 (Mean Liver weight—tumor-bearing mice only) and FIG. 17 (liver tumor weights—tumor bearing mice only)

Example 116

Growth Response of Orthotopic Human HT-29 Colon Tumors in Nude Mice Treated with Different Amounts of N—(S)-(3,4-difluoro-2-(2-fluoro-4-iodophenylamino)-6-methoxyphenyl)-1-(2,3-dihydroxypropyl)cyclopropane-1-sulfonamide The dose response efficacy of N—(S)-(3,4-difluoro-2-(2-fluoro-4-iodophenylamino)-6-methoxyphenyl)-1-(2,3-dihydroxypropyl)cyclopropane-1-sulfonamide ("Compound A"), in inhibiting the development of the orthotopic HT-29 human colorectal adenocarcinoma was assessed in BALB/c nu/nu mice, in comparison with an optimal dose of 5-Fluorouracil (75 mg/kg).

Animals:

Female BALB/c nu/nu mice (University of Adelaide, Waite Campus, SA, Australia), aged 7-12 weeks, with a body weight range: of 16.58-25.39 g (mean 21.52 g) were used for the study. The mice were divided into 6 Study groups (4 treatment groups and 2 control groups) as follows:

Number of Mice per Group: 10 in Groups 1 to 5 inclusive 9 in 'Take-Rate' Control Group (Group 6)

The mice were kept in a controlled environment (targeted ranges: temperature 21±3° C., humidity 30-70%, 10-15 air changes per hour) under barrier (quarantine) conditions with a 12 hour light/12 hour dark cycle. Temperature and relative humidity were monitored continuously. A commercial rodent diet (Rat and Mouse Cubes, Speciality Feeds Pty Ltd, Glen Forrest, Western Australia) and tap water were provided to the animals ad libitum. Both food and water supplies were sterilized by autoclaving.

Tumor Inoculation:

HT-29 human colorectal adenocarcinoma cells (Passage 4 from working stock VP-Stock 325) were cultured in RPMI1640 cell culture medium, which was supplemented with 10% FBS and penicillin-streptomycin (501 U/mL final concentration). The cells were harvested by trypsinisation, washed twice in HBSS and counted. The cells were then resuspended in HESS and adjusted to a final volume containing $2\times10^8$ cells/mL. Prior to inoculation, the incision site was liberally swabbed with alcohol and an incision made through the abdominal wall to expose the caecum wall. The needle was introduced through the surface of the caecum wall where 5 µL of cells ($1\times10^6$ cells) were discharged.

Materials:

The following were obtained from the respective suppliers.

Sterile saline solution (0.9% NaCl(aq)) was obtained from Baxter Healthcare Australia, Old Toongabbie, NSW, Australia. CremophorEL was obtained from Sigma-Aldrich Pty Ltd, Castle Hill, NSW, Australia. 5-Fluorouracil, clinical formulation, clear, colorless liquid was obtained from Mayne Pharma Pty Ltd. RPMI1640 cell culture medium, PBS and HBSS were obtained from Invitrogen Australia Pty Ltd, Mt Waverley, VIC, Australia. Penicillin-streptomycin and Trypan Blue were obtained from Sigma-Aldrich, Castle Hill, NSW, Australia. HT-29 human colorectal adenocarcinoma cells were sourced from American Type Culture Collection (ATCC), Rockville, Md., USA.

Compound Preparation and Administration:

CremophorEL:Saline (1:9, v/v; vehicle control), N—(S)-(3,4-difluoro-2-(2-fluoro-4-iodophenylamino)-6-methoxyphenyl)-1-(2,3-dihydroxypropyl)cyclopropane-1-sulfonamide or 5-Fluorouracil (compound control) were administered according to the schedule below:

| Group | Compound | Dose (mg/kg) | Scheduled Treatment | Treatments Administered |
|---|---|---|---|---|
| 1 | Vehicle Control | 10 mL/kg | Once daily for 21 Days (Day 0 to 20) | Once daily for 21 Days (Day 0 to 20) |
| 2 | Compound A | 0.2 mL @ 10 mL/kg = 2 mg/kg | Once daily for 21 Days (Day 0 to 20) | Once daily for 10 Days (Day 0 to 9) |
| 3 | Compound A | 1.0 mL @ 10 mL/kg = 10 mg/kg | Once daily for 21 Days (Day 0 to 20) | Once daily for 21 Days (Day 0 to 20) |

| Group | Compound | Dose (mg/kg) | Scheduled Treatment | Treatments Administered |
|---|---|---|---|---|
| 4 | Compound A | 5.0 mL @ 10 mL/kg = 50 mg/kg | Once daily for 21 Days (Day 0 to 20) | Once daily for 8 Days (Day 0 to 7) | tumors intact. The tumors were then excised from the caecum and weighed.

The livers was also excised from all mice in each group at the termination of the study and fixed in 10% buffered formalin. Five liver samples from the Vehicle Control group were embedded in paraffin, sectioned and stained with haematoxylin and eosin (H&E) for histological assessment for morphological changes.

Data Measurement and Sample Collection Schedule

| | Schedule |
|---|---|
| Data Measurement | |
| Body weight | Day 0, then three times per week (Monday, Wednesday and Friday), and on the termination day of the study for Groups 1 to 5 inclusive. |
| Caecum weight and tumor weight | Excised caecum and tumor from each mouse at termination in Groups 1 to 5 inclusive |
| Sample Collection | |
| Caecum and tumors | From all mice in Group 6 ('Take-Rate' Control) post-mortem, on Day 7 of the study. |
| Caecum and tumors | From all mice in Groups 1 to 5 inclusive post-mortem, on the termination day of the study, and from mice which died during the study period. |
| Liver | From all mice in Groups 1 to 5 inclusive post-mortem, on the termination day of the study and from mice which died during the study period. |

-continued

| Group | Compound | Dose (mg/kg) | Scheduled Treatment | Treatments Administered |
|---|---|---|---|---|
| 5 | 5-Fluorouracil | 7.5 mL @ 10 mL/kg = 75 mg/kg | Once weekly for three weeks (Day 0, 7 and 14) | Once weekly for 3 weeks (Day 0, 7 and 14) |
| 6 | 'Take-Rate' Control | No treatment | — | — |

The Vehicle Control, CremophoreEL:Saline (1:9, v/v), was administered p.o. in a dosing volume of 10 mL/kg, once daily for 21 consecutive days (Day 0 to 20).

N—(S)-(3,4-difluoro-2-(2-fluoro-4-iodophenylamino)-6-methoxyphenyl)-1-(2,3-dihydroxypropyl)cyclopropane-1-sulfonamide was formulated in CremophorEL:Saline (1:9, v/v). A stock solution was prepared weekly and stored at 4° C. Dosing solutions were prepared on each day of administration. N—(S)-(3,4-difluoro-2-(2-fluoro-4-iodophenylamino)-6-methoxyphenyl)-1-(2,3-dihydroxypropyl)cyclopropane-1-sulfonamide was administered p.o. at doses of 2, 10 and 50 mg/kg, in a dosing volume of 10 mL/kg, once daily for 21 days (Day 0 to 20).

5-Fluorouracil clinical formulation was diluted in sterile saline and administered i.v. via the tail vein at a concentration of 75 mg/kg, in a dosing volume of 10 mL/kg, once per week for three weeks (on Day 0, 7 and 14).

No treatment was administered to the mice in Group 6 ('Take-Rate' Control). On Day 7 of the study (21 days post-inoculation), the mice were culled and the colon exposed to determine the take-rate and size of the tumors in the caecum wall.

Each animal's body weight was measured immediately prior to dosing. The volume administered to each mouse was calculated and adjusted based on the body weight.

Tumor Measurements:

Caecum and tumor wet weight were measured when each were excised post-mortem on the termination day of the study. At the termination of the study, the caecum was excised from all mice in each study group and weighed with the Data Acquisition and Calculation:

Each animal's transponder (Bar Code Data Systems Pty Ltd, Botany Bay, NSW) was scanned using a barcode reader (LabMax I, DataMars, Switzerland) immediately prior to acquisition of data. All measurements were acquired with the same handheld calipers (Absolute Digimatic Model CD-6" CS, Mitutoyo Corporation, Japan). The data was synchronized with vivoPharm's secure relational database using Pendragon Forms 4.0 (Pendragon® Software Corporation, Libertyville, Ill., U.S.A.) as transfer software. AIDAM v2.4 was used for data reports and data calculations.

Statistical and Calculations:

All statistical calculations were performed using SigmaStat 3.0. (SPSS Australasia Pty Ltd, North Sydney, NSW, Australia).

A two-sample t-test was used to determine the significance in body weight change within a treatment group between Day 0 and the termination day of the study. In the groups treated with N—(S)-(3,4-difluoro-2-(2-fluoro-4-iodophenylamino)-6-methoxyphenyl)-1-(2,3-dihydroxypropyl)cyclopropane-1-sulfonamide at 2 and 50 mg/kg, treatment was discontinued early due to excessive body weight loss. In these groups, a two-sample t-test was used to determine the significance in body weight change within a treatment group between Day 0 and the final treatment day of the study, and between the last treatment day and the termination day of the study. Where the data did not pass the Normality test or the Equal Variance Test, a Mann-Whitney Rank Sum Test was performed.

A One-Way Analysis of Variance (ANOVA) (All Pairwise Multiple Comparison Procedure and Multiple Comparison versus Control Group) was performed on the caecum weight and tumor weight data at the end of the study. Where the data did not pass the Normality test the values were converted to the natural logarithm prior to performing the procedure.

A p value of less than 0.05 was considered significant.

Observations:

Average body weight loss was measured in all study groups, including the Vehicle Control group. Diarrhoea and signs of dehydration (loss of skin elasticity) were observed in all of the study groups, including the Vehicle Control. Severe body weight loss early during the study period led to the cessation of treatment in the groups receiving N—(S)-(3,4-difluoro-2-(2-fluoro-4-iodophenylamino)-6-methoxyphenyl)-1-(2,3-dihydroxypropyl)cyclopropane-1-sulfonamide at the lowest (2 mg/kg) and highest dose (50 mg/kg) on Day 9 and Day 7 of the study, respectively. As body weight loss was less severe in the group receiving N—(S)-(3,4-difluoro-2-(2-fluoro-4-iodophenylamino)-6-methoxyphenyl)-1-(2,3-dihydroxypropyl)cyclopropane-1-sulfonamide at 10 mg/kg, all treatments for this group were administered as scheduled. The average body weight losses at the end of the study for this group and the 5-Fluorouracil treatment group were significant.

Although the take rate of the HT-29 tumors in the 'Take-Rate' group 21 days after inoculation was 100%, the size of these tumors was much lower than anticipated. This may have contributed to there being no significant difference in average caecum and tumor weights between N—(S)-(3,4-difluoro-2-(2-fluoro-4-iodophenylamino)-6-methoxyphenyl)-1-(2,3-dihydroxypropyl)cyclopropane-1-sulfonamide-treated Groups and the Vehicle Control Group. There was also no effect of 5-Fluorouracil on the weight of the caecum and HT-29 tumors.

(Day 21 post-inoculation) to assess visually whether the tumors were growing adequately for the purpose of the study.

Treatment was discontinued in Group 2 (N—(S)-(3,4-difluoro-2-(2-fluoro-4-iodophenylamino)-6-methoxyphenyl)-1-(2,3-dihydroxypropyl)cyclopropane-1-sulfonamide at 2 mg/kg) on Day 9 of the study and in Group 4 (N—(S)-(3,4-difluoro-2-(2-fluoro-4-iodophenylamino)-6-methoxyphenyl)-1-(2,3-dihydroxypropyl)cyclopropane-1-sulfonamide at 50 mg/kg) on Day 7 of the study, as the mice were losing excessive body weight. The remaining groups all received all of the scheduled treatments during the study period.

Figure 18:
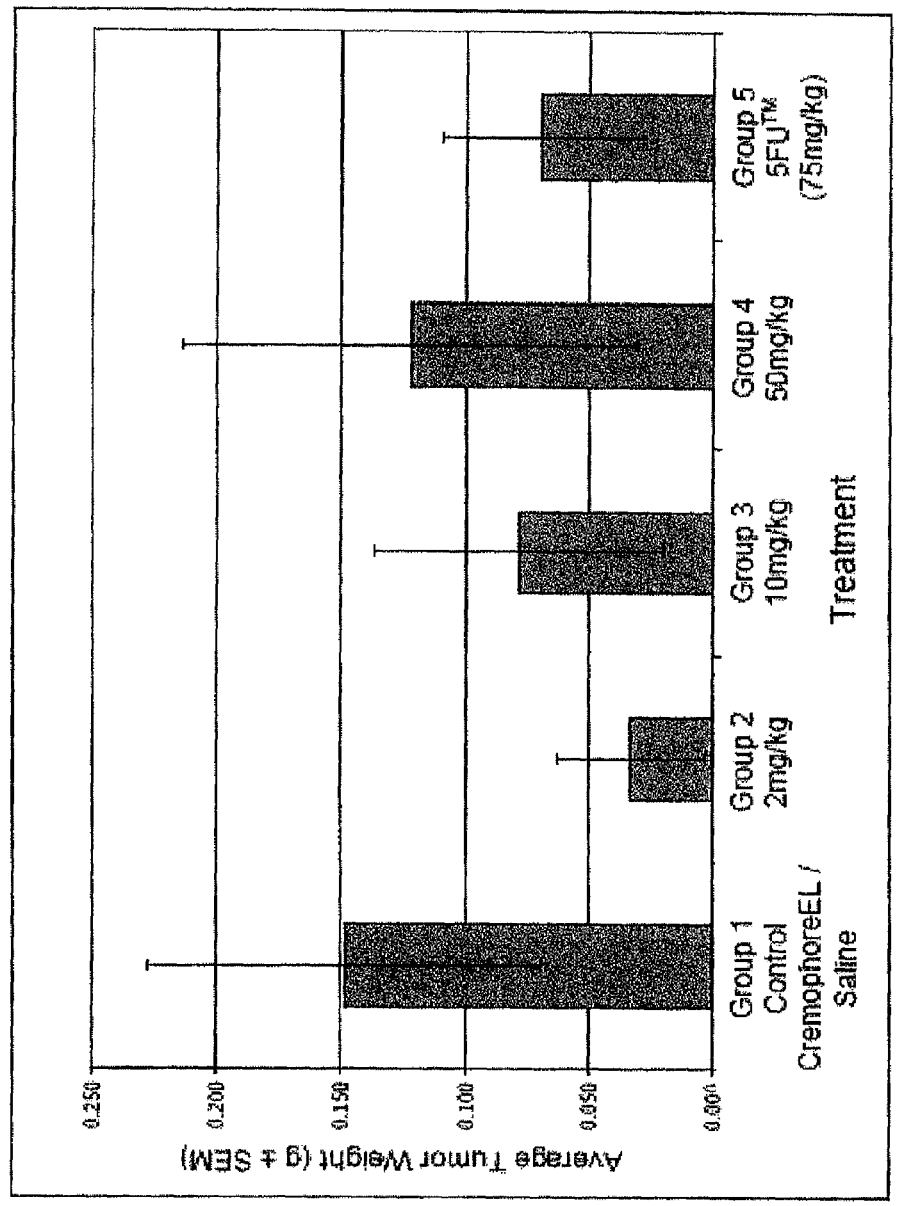
FIG. 18 shows the average tumor weights in after treatment with N—(S)-(3,4-difluoro-2-(2-fluoro-4-iodophenylamino)-6-methoxyphenyl)-1-(2,3-dihydroxypropyl)cyclopropane-1-sulfonamide (2 mg/kg; 10 mg/kg; and 50 mg/kg).

The average tumor weight in each group is shown in FIG. 18. The average weight of tumor for each group includes only those which survived until the final day of the study. Values for mice which died during the study period are not included in the calculated average values.

| | | | | | Body Weight Measurements (±SEM) (Final Treatment Days and Study End Date) | | | | |
|---|---|---|---|---|---|---|---|---|---|
| | | | | | Host Response | | | | |
| Grp | Compound | | Dose (mg/kg), Route, Schedule | | Delta Body Weight (g) (±SEM) Final Treatment Day | % Delta Body Weight Final Treatment Day | Delta Body Weight (g) (±SEM) Final Study Day | % Delta Body Weight Final Study Day | Survival Number (No. Alive/ Total) |
| 1 | Vehicle Control | — | p.o. | Once daily for 21 days (Day 0 to 20) | — | — | −0.8 ± 0.4 | −3.6 | 8/10 |
| 2 | Compound A | 2 | p.o. | Once daily for ten Days (Day 0 to 9) | −2.4 ± 1.4 (Day 9) | −11.1 | 0.1 ± 0.9 | 0.4 | 4/10 |
| 3 | Compound A | 10 | p.o. | Once daily for 21 days (Day 0 to 20) | — | — | −1.5 ± 0.3 | −6.9 | 7/10 |
| 4 | Compound A | 50 | p.o. | Once daily for eight Days (Day 0 to 7) | −3.8 ± 0.5 (Day 7) | −17.8 | −1.3 ± 0.9 | −5.9 | 7/10 |
| 5 | 5-Fluorouracil | 75 | i.v. | Once weekly for three weeks (Day 0, 7 and 14) | — | — | −3.3 ± 0.4 | −15.2 | 8/10 |

Body weight data was not collected for Group 6 ('Take-Rate' Control). The group was culled on Day 7 of the study

| | | | | | Caecum Weight and Tumor Weight Data | | | |
|---|---|---|---|---|---|---|---|---|
| Group | Treatment | Animal ID | Caecum Weight (g) | Tumour Weight (g) | Average Caecum Weight (g) | SEM | Average Tumour Weight (g) | SEM |
| 1 | Vehicle Control (CremophorEL:Saline) | 173811 | 0.290 | 0.070 | 0.413 | 0.081 | 0.149 | 0.080 |
| | | 170774 | 0.331 | 0.160 | | | | |
| | | 170729 | 0.267 | 0.017 | | | | |
| | | 173673 | 0.307 | 0.005 | | | | |
| | | 171429 | 0.311 | 0.326 | | | | |
| | | 175732 | 0.946 | 0.627 | | | | |
| | | 171539 | 0.286 | 0.038 | | | | |
| | | 173576 | 0.287 | 0.002 | | | | |
| | | 170836 | 0.397 | 0.000 | | | | |
| | | 172014 | 0.506 | 0.176 | | | | |
| 2 | Compound A @ 2 mg/kg | 175867 | 0.347 | 0.001 | 0.296 | 0.033 | 0.033 | 0.030 |
| | | 170936 | 0.170 | 0.001 | | | | |
| | | 172003 | 0.150 | 0.000 | | | | |
| | | 176472 | 0.205 | 0.005 | | | | |
| | | 171338 | 0.377 | 0.001 | | | | |
| | | 170825 | 0.233 | 0.122 | | | | |
| | | 174466 | 0.251 | 0.005 | | | | |
| | | 171587 | 0.322 | 0.003 | | | | |

Caecum Weight and Tumor Weight Data

| Group | Treatment | Animal ID | Caecum Weight (g) | Tumour Weight (g) | Average Caecum Weight (g) | SEM | Average Tumour Weight (g) | SEM |
|---|---|---|---|---|---|---|---|---|
| 3 | Compound A @ 10 mg/kg | 173623 | 0.287 | 0.000 | 0.244 | 0.025 | 0.078 | 0.059 |
| | | 170793 | 0.198 | 0.000 | | | | |
| | | 172304 | 0.258 | 0.257 | | | | |
| | | 175676 | 0.111 | 0.008 | | | | |
| | | 171003 | 0.263 | 0.422 | | | | |
| | | 171466 | 0.237 | 0.001 | | | | |
| | | 176386 | 0.234 | 0.014 | | | | |
| | | 170858 | 0.289 | 0.004 | | | | |
| | | 175862 | 0.320 | 0.100 | | | | |
| | | 171364 | 0.251 | 0.000 | | | | |
| 4 | Compound A @ 50 mg/kg | 175697 | 0.230 | 0.002 | 0.290 | 0.038 | 0.122 | 0.092 |
| | | 171349 | 0254 | 0.002 | | | | |
| | | 174272 | 0.238 | 0.000 | | | | |
| | | 176335 | 0.201 | 0.004 | | | | |
| | | 171041 | 0.337 | 0.166 | | | | |
| | | 174536 | 0.169 | 0.655 | | | | |
| | | 175656 | 0.328 | 0.001 | | | | |
| | | 173626 | 0.217 | 0.001 | | | | |
| | | 171437 | 0.312 | 0.001 | | | | |
| | | 174501 | 0.463 | 0.026 | | | | |
| 5 | 5FU ™ at 75 mg/kg | 171322 | 0.355 | 0.245 | 0.391 | 0.050 | 0.069 | 0.041 |
| | | 175559 | 0.199 | 0.001 | | | | |
| | | 176302 | 0.360 | 0.000 | | | | |
| | | 176241 | 0.284 | 0.000 | | | | |
| | | 175857 | 0.421 | 0.010 | | | | |
| | | 176242 | 0.706 | 0.329 | | | | |
| | | 174165 | 0.415 | 0.130 | | | | |
| | | 176417 | 0.327 | 0.079 | | | | |
| | | 170592 | 0.237 | 0.000 | | | | |
| | | 171501 | 0.377 | 0.003 | | | | |

The shaded boxes indicate samples collected from mice which died during the study period. Calculated average values for caecum weight and tumor weight exclude these values. Trends indicate a reduction in HT-29 tumor and caecum weight data after treatment with 10 mg/kg N—(S)-(3,4-difluoro-2-(2-fluoro-4-iodophenylamino)-6-methoxyphenyl)-1-(2,3-dihydroxypropyl)cyclopropane-1-sulfonamide.

Example 117

Tumor Growth Delay in Nude Mice Bearing Human A375 Melanoma Xenografts

Six groups (n=9) of tumored mice were used. Control groups included one receiving the 10% Cremophor EL/saline vehicle by oral gavage (po), once-daily for 14 days (qd×14), and a second given paclitaxel as a reference agent at 30 mg/kg by tail vein injection (iv), every other day for five doses (qod×5). The four experimental groups received oral N—(S)-(3,4-difluoro-2-(2-fluoro-4-iodophenylamino)-6-methoxyphenyl)-1-(2,3-dihydroxypropyl)cyclopropane-1-sulfonamide ("Compound A") at 25 mg/kg or 50 mg/kg, qd×14, or at 12.5 or 25 mg/kg, bid×14. Treatment outcome was assessed by TGD, defined as the difference in median time to endpoint tumor volume in a treatment group compared to the control group. Toxicity was assessed by body weight measurements and clinical observations.

Animals:

Female athymic nude mice (nu/nu, Harlan) were 10 to 11 weeks old and had a body weight (BW) range of 19.3 to 25.5 grams on Day 1 of the study. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated ALPHA-Dri® Bed-O'Cobs® Laboratory Animal Bedding in static microisolators on a 12-hour light cycle at 21-22° C. (70-72° F.) and 40-60% humidity. The recommendations of the *Guide for Care and Use of Laboratory Animals* with respect to restraint, husbandry, surgical procedures, feed and fluid regulation, and veterinary care were adhered to.

Tumor Implantation:

Xenografts were initiated from A375 human melanoma tumors by serial transplantation in athymic nude mice. An A375 tumor fragment (~1 mm$^3$) was implanted subcutaneously into the right flank of each test mouse, and tumor growth was monitored as the average size approached 100-150 mm$^3$. Thirteen days later, designated as Day 1 of the study, animals were placed into six groups each consisting of nine mice (reduced from ten) with individual tumor volumes ranging from 63 to 221 mm$^3$ and group mean tumor volumes of 125.3 to 125.9 mm$^3$. Tumor volume was calculated using the formula: Tumor Volume (mm$^3$)=w$^2$×l/2, where w=width and l=length in mm of an A375 tumor.

Materials:

N—(S)-(3,4-difluoro-2-(2-fluoro-4-iodophenylamino)-6-methoxyphenyl)-1-(2,3-dihydroxypropyl)cyclopropane-1-sulfonamide was dissolved at 5 mg/mL in 10% Cremophor EL in saline with sonication, shaking, and heating to 35° C. to assist in dissolution. The 5 mg/mL solution served as the dosing solution for treatment at 50 mg/kg, and dosing solutions for 25 mg/kg and 12.5 mg/kg treatment were prepared by serial dilution. Dosing solutions were stored for up to one week at room temperature protected from light.

Paclitaxel (NPI) dosing solutions were prepared from a 30 mg/mL stock for each day's use by diluting to 3 mg/mL in 5% ethanol, 5% Cremophor EL in 5% dextrose in water (D5W). Paclitaxel dosing was at 30 mg/kg.

Treatment: The table below shows the treatment regimen.

| | | Treatment Regimen | | | |
|---|---|---|---|---|---|
| Group | n | Agent | mg/kg | Route | Schedule |
| 1 | 9 | Vehicle | — | po | qd × 14 |
| 2 | 9 | Paclitaxel | 30 | iv | qod × 14 |
| 3 | 9 | Compound A | 50 | po | qd × 14 |
| 4 | 9 | Compound A | 25 | po | bid × 14 first day 1 dose |
| 5 | 9 | Compound A | 25 | po | qd × 14 |
| 6 | 9 | Compound A | 12.5 | po | bid × 14 first day 1 dose |

Mice in Group 1 received vehicle consisting of 10% Cremophor EL in saline by oral gavage (po) daily for fourteen doses (qd×4), and served as a control for tumor progression. Group 2 animals were administered intravenous (iv) paclitaxel as a reference agent at 30 mg/kg, once every other day for five doses (qod×5). Group 3-6 mice received oral N—(S)-(3,4-difluoro-2-(2-fluoro-4-iodophenylamino)-6-methoxyphenyl)-1-(2,3-dihydroxypropyl)cyclopropane-1-sulfonamide at the following respective schedules: 50 mg/kg, qd×14; 25 mg/kg, twice-daily for 14 days with a single dose given on the first and last days (bid×14); 25 mg/kg, qd×14; and 12.5 mg/kg, bid×14. All doses were given in volumes of 0.2 mL per 20 g of body weight, and were scaled to the body weight of the animal.

Endpoint:

Tumors in all groups were measured twice weekly using calipers. Each animal was euthanized when its tumor reached the endpoint size of 2000 mm$^3$ or on the final day of the study (Day 60), whichever came first. The time to endpoint (TTE) for each mouse was calculated from the following equation:

$$TTE(\text{days}) = \frac{\log_{10}(\text{endpoint volume, mm}^3) - b}{m},$$

where b is the intercept and m is the slope of the line obtained by linear regression of a log-transformed tumor growth data set.

The data set was comprised of the first observation that exceeded the study endpoint volume and the three consecutive observations that immediately preceded the attainment of the endpoint volume. Animals that do not reach the endpoint are assigned a TTE value equal to the last day of the study. Animals classified as NTR (non-treatment-related) deaths due to accident (NTRa) or due to unknown causes (NTRu) are excluded from TTE calculations (and all further analyses). Animals classified as TR (treatment-related) deaths or NTRm (non-treatment-related due to metastasis) are assigned a TTE value equal to the day of death.

Treatment outcome was determined from tumor growth delay (TGD), defined as the increase in the median time to endpoint (TTE) in a treatment group compared to the control group: TGD=T–C, expressed in days, or as a percentage of the median TTE of the control group:

$$\% \ TGD = \frac{T - C}{C} \times 100,$$

where: T=median TTE for a treatment group, C=median TTE for the control group (Group 1).

Treatment may cause partial regression (PR) or complete regression (CR) of the tumor in an animal. In a PR response, the tumor volume is 50% or less of its Day 1 volume for three consecutive measurements during the course of the study, and equal to or greater than 13.5 mm$^3$ for one or more of these three measurements. In a CR response, the tumor volume is less than 13.5 mm$^3$ for three consecutive measurements during the course of the study. An animal with a CR response at the termination of a study is additionally classified as a tumor-free survivor (TFS). Tumor regressions were monitored and recorded.

Side Effects:

Animals were weighed daily for the first five days of the study and then twice weekly. The mice were observed frequently for overt signs of any adverse, treatment-related side effects, and clinical signs were recorded when observed. Acceptable tolerability is defined as a group mean body-weight loss of less than 20% during the test and not more than one treatment-related death in a group of animals. Any dosing regimen that does not meet these criteria is considered above the maximum tolerated dose (MTD). A death is classified as TR if attributable to treatment side effects as evidenced by clinical signs and/or necropsy, or may be classified as TR if due to unknown causes during the dosing period or within 10 days of the last dose. A death is classified as NTR if there is no evidence that death was related to treatment side effects.

Statistical and Graphical Analyses:

The logrank test was used to analyze the significance of the differences between the TTE values of treated and control groups. Two-tailed statistical analyses were conducted at significance level P=0.05.

Median tumor growth curves show group median tumor volumes as a function of time. When an animal exited the study due to tumor size or TR death, the final tumor volume recorded for the animal was included with the data used to calculate the group median tumor volume at subsequent time points. Curves were truncated after 50% of the animals in a group had exited the study due to tumor progression. Kaplan-Meier plots were constructed to show the percentage of animals remaining in the study as a function of time, and used the same data set as the logrank test. Prism (GraphPad) for Windows 3.03 was used for all graphic presentations and statistical analyses.

Treatment Response Summary

| Group | Median TTE | T – C | % TGD | Statistical Significance | MTV (n) Day 60 | Regressions PR | CR | TFS | Mean BW Nadir |
|---|---|---|---|---|---|---|---|---|---|
| 1 | 22.8 | — | — | — | — | 0 | 0 | 0 | — |
| 2 | 28.8 | 6.0 | 26 | ** | — | 0 | 0 | 0 | −5.3% Day 15 |
| 3 | 27.5 | 4.7 | 21 | ** | — | 1 | 0 | 0 | — |
| 4 | 59.9 | 37.1 | 163 | *** | 0 (4) | 4 | 5 | 4 | −0.6% Day 15 |

-continued

Treatment Response Summary

| Group | Median TTE | T − C | % TGD | Statistical Significance | MTV (n) Day 60 | Regressions PR | CR | TFS | Mean BW Nadir |
|---|---|---|---|---|---|---|---|---|---|
| 5 | 25.6 | 2.8 | 12 | Ns | — | 0 | 0 | 0 | — |
| 6 | 27.5 | 4.7 | 21 | * | — | 1 | 0 | 0 | — |

Growth of A375 Tumors in Control Mice (Group 1):

Animals in Group 1 received the 10% Cremophor EL/saline vehicle, po, qd×14. Tumors in the control mice grew progressively to the 2000 mm$^3$ endpoint volume with a median TTE of 22.8 days, establishing a maximum possible T-C in the study of 37.1 days, or 163% TGD.

Effect of Treatment with Paclitaxel (Group 2):

Group 2 animals were administered paclitaxel as a reference agent, 30 mg/kg, iv, god×5. All nine of the animals achieved the tumor volume endpoint. Tumor growth paralleled and was slightly right-shifted compared with the control group. The median TTE value was 28.8 days, corresponding to 26% TGD, a significant result by Logrank analysis (Table 2, P=0.0088 G1 vs. G2). No tumor regressions were associated with paclitaxel treatment.

Effect of Treatment with N—(S)-(3,4-difluoro-2-(2-fluoro-4-iodophenylamino)-6-methoxyphenyl)-1-(2,3-dihydroxypropyl)cyclopropane-1-sulfonamide (Groups 3-6):

Groups 3-6 received oral dosing with N—(S)-(3,4-difluoro-2-(2-fluoro-4-iodophenylamino)-6-methoxyphenyl)-1-(2,3-dihydroxypropyl)cyclopropane-1-sulfonamide as monotherapy. Group 3 animals were administered 50 mg/kg on a qd×14 schedule. The nine tumors in the group achieved the volume endpoint. Median tumor volume for the group underwent little net change for the first ~10 days, then increased for the duration of the study. A single animal experienced tumor PR. The median TTE value was 27.5 days, or 21% TGD, a significant result (P=0.0054 G1 vs. G).

Animals in Group 4 received 25 mg/kg N—(S)-(3,4-difluoro-2-(2-fluoro-4-iodophenylamino)-6-methoxyphenyl)-1-(2,3-dihydroxypropyl)cyclopropane-1-sulfonamide on a bid×14 schedule. Four of the nine animals in the group remained on Day 60, all TFS. An additional 2/9 animals had tumors reaching the volume endpoint on the day before study's end. The group had 4/9 PR, 5/9 CR and 4/9 TFS. Median tumor volume dropped beginning in the first few days of the study and continued for about 30 days. Tumor regrowth in 5/9 animals accounted for a resurgence of median tumor growth beginning on about Day 32 and continuing to the end of the study. The group median TTE value was 59.9 days, representing the maximum possible 163% TGD (P<0.0001, Table A1).

Mice in Group 5 also received 25 mg/kg N—(S)-(3,4-difluoro-2-(2-fluoro-4-iodophenylamino)-6-methoxyphenyl)-1-(2,3-dihydroxypropyl)cyclopropane-1-sulfonamide, but on a less intense qd×14 schedule. All nine animals in Group 5 reached the tumor volume endpoint, with no tumor regressions. Tumor growth tracked closely with that of the control group. The median TTE was 25.6 days, or 12% TGD, a non-significant result (P=0.0662 G1 vs. G5).

Group 6 animals were administered 12.5 mg/kg N—(S)-(3,4-difluoro-2-(2-fluoro-4-iodophenylamino)-6-methoxyphenyl)-1-(2,3-dihydroxypropyl)cyclopropane-1-sulfonamide on a bid×14 schedule. All tumors in the group achieved the volume endpoint. As with Group 4, median tumor volume in Group 6 dropped early in the study, but this reduction was sustained for only about nine days and was associated with a single PR response. Tumor volume increased from Day 10 to study end. The median TTE for the group was 27.5 days, corresponding to a significant 21% TGD (P 0.0424 G1 vs. G6).

In summary, N—(S)-(3,4-difluoro-2-(2-fluoro-4-iodophenylamino)-6-methoxyphenyl)-1-(2,3-dihydroxypropyl)cyclopropane-1-sulfonamide displayed dose-related antitumor activity against human A375 melanoma xenografts with both once-daily and twice-daily oral dosing. Twice-daily dosing was superior to once-daily in the magnitude of TGD produced and in the numbers of objective responses. Thus, N—(S)-(3,4-difluoro-2-(2-fluoro-4-iodophenylamino)-6-methoxyphenyl)-1-(2,3-dihydroxypropyl)cyclopropane-1-sulfonamide antitumor activity is both dose- and schedule-dependent.

Example 118

Activity Against Subcutaneous COLO 205 Human Colon Carcinoma Xenografts

Animals:

Female athymic nude mice (nu/nu, Harlan) were 12 to 13 weeks old and had a body weight (BW) range of 18.3 to 27.3 grams on Day 1 of the study. The animals were fed ad libitum water (reverse osmosis, 1 ppm CO and NIH 31 Modified and Irradiated Lab Diet® consisting of 18.0% crude protein, 5.0% crude fat, and 5.0% crude fiber. The mice were housed on irradiated ALPHA-Dri® Bed-O'Cobs® Laboratory Animal Bedding in static microisolators on a 12-hour light cycle at 21-22° C. (70-72° F.) and 40-60% humidity. The recommendations of the *Guide for Care and Use of Laboratory Animals* with respect to restraint, husbandry, surgical procedures, feed and fluid regulation, and veterinary care were adhered to.

Tumor Implantation:

Xenografts were initiated from COLO 205 human colon carcinoma cells. Tumor cells were cultured 10% heat-inactivated fetal bovine serum, 100 units/mL penicillin G sodium, 100 µg/mL streptomycin sulfate, 0.25 µg/mL amphotericin B, and 25 µg/mL gentamicin, 2 mM glutamine, 1 mM sodium pyruvate, 10 mM HEPES and 0.075% sodium bicarbonate. Cell cultures were maintained in tissue culture flasks in a humidified incubator at 37° C., in an atmosphere of 5% $CO_2$ and 95% air. On the day of tumor cell implant, Colo 205 cells were harvested during logarithmic growth and resuspended in 50% Matrigel matrix (BD Biosciences) in PBS at a concentration of 5×10$^6$ cells/mL. Each test mouse received 1×10$^6$ Colo 205 cells implanted subcutaneously in the right flank, and the growth of tumors was monitored as the average size approached 80-120 mm$^3$. Fourteen days later, designated as Day 1 of the study, animals were placed into eight groups (n=9) with individual tumor volumes ranging from 63 to 196 mm$^3$ and group mean tumor volumes of 118-119 mm$^3$. Tumor volume was calculated using the formula:

$$\text{Tumor Volume}(mm^3) = \frac{w^2 \times l}{2},$$

where w=width and l=length in mm of a COLO 205 tumor. Tumor weight may be estimated with the assumption that 1 mg is equivalent to 1 mm$^3$ of tumor volume.

Materials:

Dosing solutions of Compound A were prepared fresh daily by dissolving the required amount of compound in 100% Cremophor EL, and then diluting ten-fold with normal saline. Final dosing solution concentrations were 2.5, 5, 10, or 20 mg/mL, in order to provide respective doses of 25, 50, 100 or 200 mg/kg in a dosing volume of 10 mL/kg. Paclitaxel (Natural Pharmaceuticals, Inc.) was prepared fresh on each day of dosing in a vehicle consisting of 5% ethanol and 5% Cremophor EL in 90% D5W (5% EC vehicle).

Treatment: The table below shows the treatment regimen.

| Group | n | Agent | mg/kg | Route | Schedule |
|---|---|---|---|---|---|
| 1 | 9 | Vehicle | — | po | qd × 14 |
| 2 | 9 | Paclitaxel | 30 | iv | qod × 14 |
| 3 | 9 | Compound A | 50 | po | qd × 14 |
| 4 | 9 | Compound A | 25 | po | bid × 14 first day 1 dose |
| 5 | 9 | Compound A | 25 | po | qd × 14 |
| 6 | 9 | Compound A | 12.5 | po | bid × 14 first day 1 dose |

Group 1 received the formulation vehicle (10% Cremophor EL in saline), and served as the tumor growth control group. Group 2 received the reference drug paclitaxel administered on its optimal schedule in nude mice (30 mg/kg i.v. qod×5). Groups 3-6 received 25, 50, 100 and 200 mg/kg doses, respectively, of Compound A administered p.o. qd×14, with dosing in Group 6 (200 mg/kg) discontinued after six days due to toxicity. All doses were scaled to the weight of the animal (0.2 mL per 20 grams body weight).

Endpoint:

Tumors were measured twice each week using calipers. Each animal was euthanized when its tumor reached the pre-determined endpoint size of 2000 mm$^3$ or on the final day of the study (Day 74), whichever came first. However, control tumors did not exhibit logarithmic growth characteristics after attaining a size of approximately 800 mm$^3$. Therefore endpoint tumor size of 800 mm$^3$ was used for analysis of tumor growth delay (TGD). The time to endpoint (TTE) for each mouse was calculated from the following equation:

$$TTE(\text{days}) = \frac{\log_{10}(\text{endpoint volume, mm}^3) - b}{m},$$

where b is the intercept and m is the slope of the line obtained by linear regression of a log-transformed tumor growth data set. The data set was comprised of the first observation that exceeded the study endpoint volume and the three consecutive observations that immediately preceded the attainment of the endpoint volume. Animals that do not reach the endpoint are assigned a TTE value equal to the last day of the study. Animals classified as NTR (non-treatment-related) deaths due to accident (NTRa) or due unknown causes (NTRu) are excluded from TTE calculations (and all further analyses). Animals classified as TR (treatment-related) deaths or NTRm (non-treatment-related death due to metastasis) are assigned a TTE value equal to the day of death.

Treatment outcome was evaluated by tumor growth delay (TGD), which is defined as the increase in the median time to endpoint (TTE) in a treatment group compared to the control group: TGD=T−C, expressed in days, or as a percentage of the median TTE of the control group:

$$\% \; TGD = \frac{T-C}{C} \times 100,$$

where: T=median TTE for a treatment group, C=median TTE for the control group.

The control group was specified as Group 1 mice.

Treatment may cause partial regression (PR) or complete regression (CR) of the tumor in an animal. In a PR response, the tumor volume is 50% or less of its Day 1 volume for three consecutive measurements during the course of the study, and equal to or greater than 13.5 mm$^3$ for one or more of these three measurements. In a CR response, the tumor volume is less than 13.5 mm$^3$ for three consecutive measurements during the course of the study. Regression responses were monitored and recorded.

Side Effects:

Animals were weighed daily for the first five days of the study and then twice weekly. The mice were observed frequently for overt signs of any adverse, treatment-related side effects, and clinical signs of toxicity were recorded when observed. Acceptable toxicity is defined as a group mean body-weight loss of less than 20% during the study and not more than one treatment-related (TR) death among ten treated animals, and any dosing regimen that results in greater toxicity is considered above the maximum tolerated dose (MTD). A death is classified as TR if attributable to treatment side effects as evidenced by clinical signs and/or necropsy, or may be assessed as TR if due to unknown causes during the dosing period or within 10 days of the last dose. A death is classified as an NTR if there is no evidence that death was related to treatment side effects. Animals were monitored for side effects by frequent observation and BW measurements. BW changes were unremarkable, and all treatments were acceptably tolerated, except Group 6. Six once daily p.o. doses of 200 mg/kg Compound A resulted in one TR death assessed on Day 7 and two additional TR deaths on Day 8. All mice in Group 6 exhibited clinical symptoms of toxicity including hunched postures, hypoactivity, and loose stools.

Statistical and Graphical Analyses:

The logrank test was used to analyze the significance of the differences between the TTE values of treated and control groups. Two-tailed statistical analyses were conducted at significance level P=0.05.

Median tumor growth curves show group median tumor volumes plotted on a log scale as a function of time. When an animal exited the study due to tumor size or TR death, the final tumor volume recorded for the animal was included with the data used to calculate the group median tumor volume at subsequent time points. Curves were truncated after 50% of the animals in a group had exited the study due to tumor progression or after the second TR death in a group. Kaplan-Meier plots were constructed to show the percentage of animals remaining in the study as a function of time, and used the same data set as the logrank test. Prism (GraphPad) for Windows 3.03 was used for all graphic presentations and statistical analyses.

Treatment Response Summary

| Grp | Median | T − C | % TGD | SS | MTV (n) Day 74 | No of PR | CR | TFS | TR | NTR | Mean BW |
|---|---|---|---|---|---|---|---|---|---|---|---|
| 1 | 41.0 | — | — | — | 322 (2) | 0 | 0 | 0 | 0 | 0 | — |
| 2 | 60.0 | 19.0 | 46% | ns | 0 (3) | 1 | 0 | 0 | 2 | 2 | — |
| 3 | 47.9 | 6.9 | 17% | ns | 0 (3) | 1 | 0 | 0 | 2 | 2 | — |
| 4 | 59.1 | 18.1 | 44% | ns | 195 (1) | 4 | 0 | 0 | 0 | 0 | — |
| 5 | 74.0 | 33.0 | 80% | ns | 320 (5) | 4 | 0 | 0 | 1 | 0 | — |
| 6 | 57.8 | 16.8 | 41% | ne | 0 (3) | 1 | 3 | 0 | 2 | 2 | 0.1% Day 22 |

Growth of COLO 205 Tumors in Control Mice (Group 1)

Group 1 tumors exhibited slow, heterogeneous growth. The tumors of 7/9 vehicle-treated Group 1 control mice attained the 800 mm³ tumor volume endpoint and two mice remained at study's end. The Group 1 median TIE was 41.0 days, and therefore the maximum TGD possible in this 74-day study was 33.0 days (80%).

Effect of Treatment with Paclitaxel (Group 2)

Eight Group 2 mice (n=9) that received treatment with paclitaxel remained in the study on Day 74 with an MTV of 143 mm³. This corresponds to the maximum possible TGD (33.0 days or 80%) and statistically significant activity (P=0.002). Five PR responses were documented. The median tumor growth curve shows a decrease in MTV through Day 19, followed by little change until Day 47 when tumor growth resumed.

Effect of Treatment with Compound A (Groups 3-6)

Groups 3, 4, 5 produced median TTEs of 47.9, 59.1 and 74.0 days, respectively. Groups 3 and 4 had non-significant logrank results, and the Group 5 logrank test attained borderline significance (P=0.058). These treatments produced dose-dependent numbers of regressions, however, the type of regression response (PR vs. CR) and the numbers of 74-day survivors per group did not correlate with dose. The median tumor growth curves indicate similar activities for the three dose levels early in the study (through Day 29), followed by dose-dependent delays in tumor re-growth. Group 6 produced three TR deaths, and dosing was stopped after Day 6. The 200 mg/kg treatment was therefore deemed above the MTD and not evaluable for TGD.

Compound A demonstrated dose-dependent activity against COLO 205 colon carcinoma xenografts. When administered at 25 mg/kg, Compound A exhibited a TGD of 3%. At 50 mg/kg, Compound A produced a TGD of 46%. The 100 mg/kg treatment was acceptably tolerated and, like the paclitaxel treatment, resulted in the maximum TGD possible in the experiment with a similar number of regression responses. The 200 mg/kg treatment produced 3/9 TR deaths and was above the MTD. A more pronounced initial decrease in tumor burden for Compound A compared to paclitaxel was observed; however, the duration of the effect was shorter. Tumor re-growth in the 25 and 50 mg/kg groups initially proceeded at a more rapid pace compared to controls, and by the end of study, MTVs approached those of controls. The 100 mg/kg treatment did not exhibit this rapid re-growth, but did show faster tumor growth compared to that of paclitaxel.

Example 119

Human Clinical Trial

A randomized, Double-blind, open label, historical control, single group assignment, safety/efficacy human phase I clinical trial with compound A vs placebo in Patients with chemo-naive advanced or metastatic pancreatic cancer will be performed.

The primary purpose of the study is to evaluate the safety and tolerability of compound A. A secondary outcome will be to evaluate the response rate, clinical benefit, and tumor shrinkage after treatment with compound A. Further, the study will be designed to evaluate time to disease progression and overall survival of patients with the pancreatic cancer. In addition, pharmacodynamic changes in tumor vascular parameters will be evaluated (including, e.g. blood flow, blood volume, time to peak ROC-receiver operator characteristics curve) by DCE-MRI.

Moreover, the biologic markers such as MEK1 and MEK2 genetic plymorphisms and serum proteomics will be used to correlate outcomes. This will also permit the resectability rates of tumors after treatment to be determined, as well as the MTD for compound A to be evaluated.

During the study, compound A will be administered in varying does of about 1 mg, about 1.5 mg, about 2 mg, about 2.5 mg, about 3 mg, about 3.5 mg, about 4.0 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5, or about 15 mg.

Inclusion criteria for the study will be based on the following factors:

Histologically/pathologically confirmed locally advanced unresectable or borderline unresectable pancreatic cancer, and no evidence of metastatic disease.

Diagnosis of locally advanced unresectable pancreatic cancer based on assessment by dual-phase CT scan and/or endoscopic ultrasound (EUS) (EUS described in Appendix F).

Measurable disease according to RECIST and obtained by dual-phase CT scan within 14 days prior to being registered for protocol therapy.

Tumor size greater than or equal to 2 cm on dual-phase computed tomography scan.

Adequate organ function documented within 14 days of registration as evidenced by: absolute neutrophil count>1500/mm3; platelet count; 100,000/mm3; hemoglobin³ 9 gm/dL without transfusion requirement in the prior 4 weeks; total bilirubin≤1.5 times upper limit of normal (ULN); transaminases (AST and/or ALT)≤2.5× ULN; PT (or INR)≤1.5×ULN and aPTT within normal limits (patients who receive anticoagulation treatment with an agent such as warfarin or heparin will be allowed to participate; for patients on warfarin, close monitoring of at least weekly evaluations will be performed until INR is stable based on a measurement at predose, as defined by the local standard of care; Creatinine clearance of >60 ml/min calculated using the Cockcroft-Gault formula.

Exclusion Criteria will include: prior treatment with compound A within 6 months prior to registration; clinical evidence of duodenal mucosal invasion by tumor (as documented by endoscopy or endoscopic ultrasound); minor surgical procedure (e.g fine needle aspiration or needle biopsy) within 14 days of study registration; major surgical procedure, significant traumatic injury, or serious non-healing wound, ulcer or bone fracture within 21 days of study registration; any of the following within 6 months prior to study drug administration: severe/unstable angina (anginal symptoms at rest), new onset angina (began within the last 3 months) or myocardial infarction, congestive heart failure, cardiac ventricular arrhythmias requiring anti-arrhythmic therapy; history of thrombotic or embolic events such as cerebrovascular accident or transient ischemic attack within the past 6 months; history of aneurysm or arteriovenous malformation; known human immunodeficiency virus (HIV) infection or chronic Hepatitis B or C; active clinically serious infection greater than CTCAE grade 2; receipt of any investigational agent within 4 weeks of study registration; uncontrolled hypertension defined as systolic blood pressure greater than 150 mmHg or diastolic pressure greater than 90 mmHg, despite optimal medical management; pulmonary hemorrhage/bleeding event greater than CTCAE Grade 2 within 4 weeks of study registration; any other hemorrhage/bleeding event greater than CTCAE Grade 3 within 4 weeks of study registration; evidence or history of bleeding diathesis or coagulopathy; chronic, daily treatment with aspirin or other nonsteroidal anti-inflammatory medications; use of St. John's Wort, rifampin (rifampicin), ketoconazole, itraconazole, ritonavir, or grapefruit juice; known or suspected allergy to compound A; any condition that impairs patient's ability to swallow whole pill; any malabsorption problem; other severe, acute or chronic medical or psychiatric condition, or laboratory abnormality that may increase the risk associated with study participation or study drug administration, or may interfere with the interpretation of study results, and in the judgment of the investigator would make the patient inappropriate for entry into this study; history of collagen vascular disease; any contraindication to undergo magnetic resonance imaging.

Example 120

Human Clinical Trial

A randomized, Double-blind, open label, historical control, single group assignment, safety/efficacy human phase I clinical trial with compound A in Patients with chemo-naive advanced or metastatic stomach cancer will be performed in the same manner as that prescribed in Example 117, except the enrolled patients with be diagnosed either lymphoma, gastric stromal tumors, or carcinoid tumors of the stomach.

Example 121

Carrageenan-Induced Paw Edema (CPE) in Rats

Compound A (6, 20 & 60 mg/kg) or indomethacin (3 mg/kg) were administered orally 2 hr prior to injection of 1% suspension of carrageenan into the right hind foot pad of male Sprague-Dawley rats (N-6 per treatment group). The hind paw edema was measured 3 hr later by assessing paw volume by plethysmography. Reduction of hind paw edema by 30% or greater indicates significant acute anti-inflammatory activity. Indomethacin (Indo) was used as a positive control drug. The increases in paw volume in each of the treatment groups demonstrate that oral administration of Compound A resulted in significant anti-inflammatory activity in the rat carrageenan paw edema model in all dose groups.

Example 122

Rat Adjuvant Arthritis Inflammation Assay

In the rat adjuvant induced arthritis model, Complete Freund's Adjuvant (CFA) is injected into the right hind paw of rats to induce pathologies similar to rheumatoid arthritis in humans. Compound A was administered orally for 5 consecutive days at 2, 6, and 20 mg/kg. Dexamethasone at 5 m g/kg was also administered orally for 5 days. Enbrel at 10 mg/kg was administered by subcutaneous injection on days 1 and 4. CFA was injected into the right hind paw one hour after the first dose on day 1. The percent inhibition of right hind paw swelling relative to vehicle treated controls on days 1 and 5 were determined for the acute phase while the percent inhibition of left hind paw swelling relative to vehicle treated controls on days 14 and 18 were determined for the delayed phase. Polyarthritis was scored as the presence of swelling in front paws, tail, nose or ear.

The percent inhibition of swelling relative to control for the different treatment groups was determined. Compound A at 20 mg/kg showed significant reduction in swelling in both the acute and delayed phases. For the polyarthritis scoring, all 6 animals in the vehicle treated group had swelling in the front paws and tail. For the 20 mg/kg Compound A group, 2 of 6 did not have front paw swelling and 4 of 6 did not have swelling in the tail. For the enbrel group, no animals were protected from front paw swelling and 3 of 6 animals did not have swelling in the tail.

Example 123

Inhibition of Collagen-Antibody Induced-Arthritis (CAIA) in Mice

Male Balb/c mice (N=8 per treatment group) were injected intravenously (tail vein) with 2 mg of collagen antibody cocktail (Chondrex) on day 0. RDEA119 (1, 3 & 10 mg/kg QD) or dexamethasone (1 mg/kg QD) were administered orally from days 0-4, while Enbrel was injected subcutaneously on days 1 and 3. An intraperitoneal injection of LPS (50 µg) was given on day 3 to all mice except naïve animals. The determination of the arthritic scores on all limbs were determined (maximum score 16). Significant anti-inflammatory activity was noted for all test articles and reference drugs. Enbrel and dexamethasone were used as positive controls.

Example 124

In Vivo Cell Proliferation Assay

A method for determining cell proliferation counts in cancerous cells treated with a MEK protein kinase inhibitor, is understood in the art and is described in Kenny, L. M. et al., Positron Emission Tomography (PET) Imaging of Cell Proliferation in Oncology, Clinical Oncology, 16:176-185 (2004), which is hereby incorporated by reference in its entirety. A MEK protein kinase inhibitor (e.g. Compound A) is examined in vivo to determine their effect on proliferation of cancerous cells. 50 patients are voluntarily enrolled in the study, all of which are suffering from pancreatic cancer at a similar stage of cancerous development. 25 patients are administered a combination of compound A. The final 25 patients are administered placebo. Each patient is administered a daily dose for 14 days with a radio labeled tracer, e.g. labeled fluoro-2-deoxy-DF-glucose (FDG).

After 14 days of treatment, a trained physician using a non-invasive positron emission tomography (PET) imaging apparatus detects tumor cell proliferation. Moreover, the trained physician will determine cell proliferation counts of both tumor and normal cell tissue for patients treated with Compound A and placebo. The results will indicate a decrease in cell proliferation counts between the MEK protein kinase inhibitor (e.g. Compound A) and placebo. This assay for the determining cell proliferation counts using labeled tracers and PET imaging is referred to herein as an "in vivo cell proliferation method." Other in vivo cell proliferation methods are known in the art.

Similar analysis can be used to determine decrease in tumor size.

Example 125

In Vivo Apoptosis Assay

MEK inhibitor, e.g., Compound A is examined in vivo to determine its effect on apoptosis of cancer cells. 40 patients are voluntarily enrolled in the study, all of which are suffering from pancreatic cancer at a similar stage of cancerous development. 20 patients are administered compound A and 20 patients are administered placebo. Each patient is administered a daily dose for 14 days.

After 14 days, each patient will consume a detectable lipopolysaccharide binding protein (LBP) reagent coupled to a label. In accordance with WO/2006/054068, which is hereby incorporated by reference in its entirety, each patient is then placed in the field of a scanning apparatus whereby the waning apparatus detects the consumed reagent bound to dead cells. The number of dead cells can be correlated to a level apoptosis of each patient. The apoptosis levels in patients administered the combinations and those administered the single entity agents can be compared against each others, as well as with respect to the cohort group administered placebo. This assay for the detection of apoptosis levels using a lipopolysaccharide binding protein and scanning apparatus is referred to as the herein as an "in vivo apoptosis method."

Example 126

Dissolution Studies

Capsules containing Compound A were prepared as described in the above examples. The following dissolution data was obtained using the USP<711> method for dissolution.

| Time (min) | 1 mg from % Release (% RSD) | 10 mg form % Release (% RSD) |
|---|---|---|
| 15 | 78 (8.3) | 80 (7.3) |
| 30 | 82 (7.1) | 87 (9.2) |
| 45 | 82 (6.7) | 92 (9.6) |
| 60 | 88 (6.3) | 92 (7.2) |
| 70 | 86 (5.7) | 95 (5.4) |

What is claimed is:

1. A pharmaceutical composition comprising a pharmaceutically acceptable carrier and

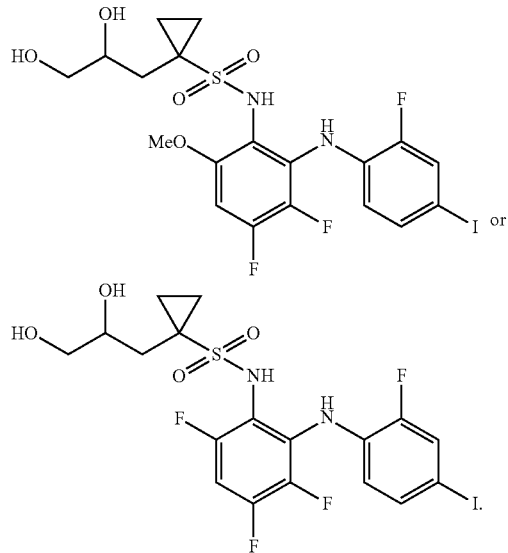

2. The pharmaceutical composition of claim 1, which is substantially free of the S-isomer of the compound

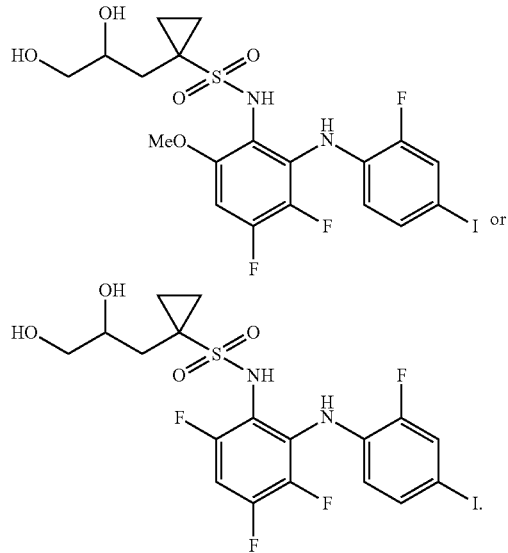

3. The pharmaceutical composition of claim 1, which is substantially free of the R-isomer of the compound

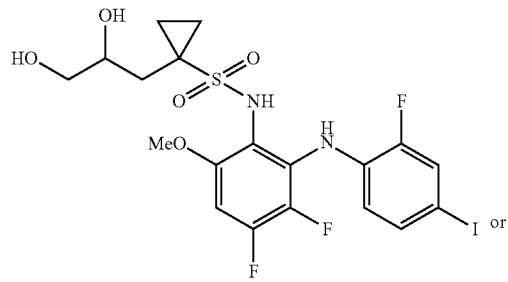

-continued

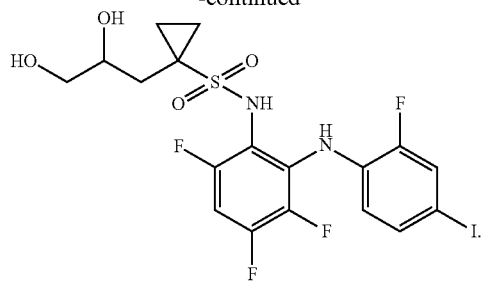

4. The pharmaceutical composition of claim 1, which contains less than 10% of the S-isomer of the compound

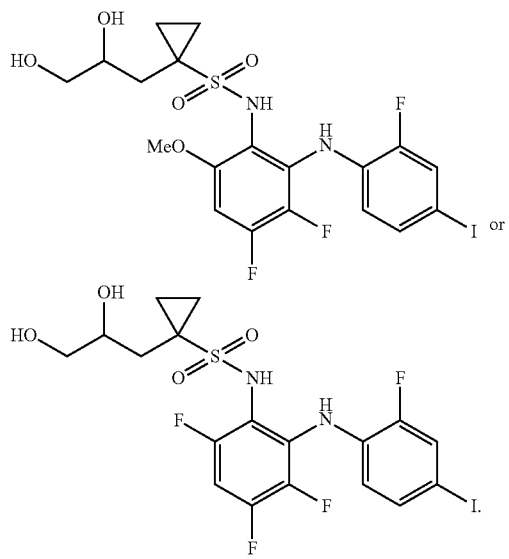

5. The pharmaceutical composition of claim 1, which contains less than 10% of the R-isomer of the compound

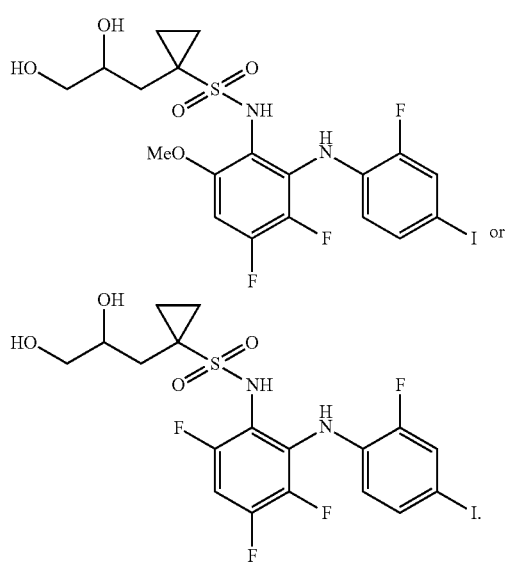

6. The pharmaceutical composition of claim 1, comprising about 1-100 mg of a compound having the following structure:

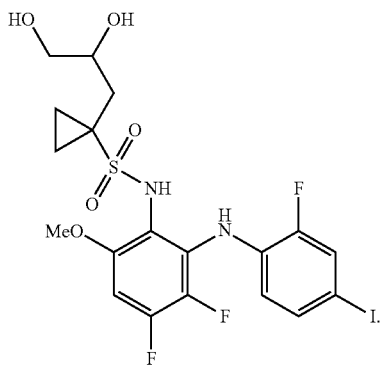

7. The pharmaceutical composition of claim 1, comprising: about 1-50 mg of a compound having the following structure

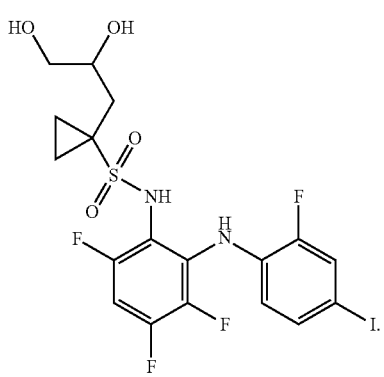

wherein the composition allows for modified release of the drug.

8. The pharmaceutical composition of claim 1, further comprising microcrystalline cellulose.

9. The pharmaceutical composition of claim 1, comprising about 1 mg of a compound of structure

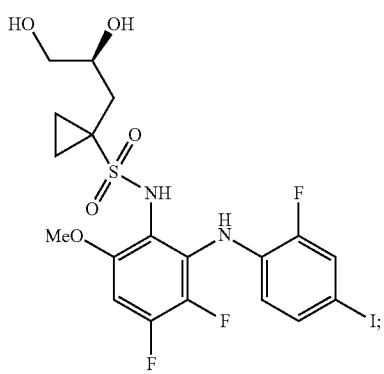 [SMILES: COc1cc(F)c(F)c(Nc2ccc(I)cc2F)c1NS(=O)(=O)C1(C[C@H](O)CO)CC1]

about 222.2 mg of microcrystalline cellulose;
about 12.0 mg of croscarmellose sodium;
about 2.4 mg of sodium lauryl sulfate; and
about 2.4 mg of magnesium stearate.

10. The pharmaceutical composition of claim 1, comprising about 10 mg of a compound of structure

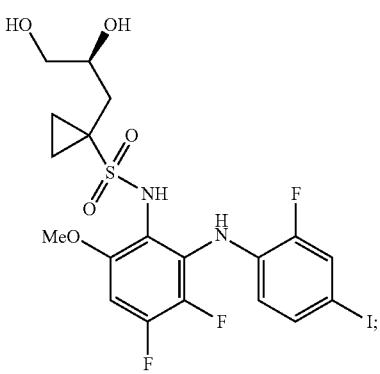 [SMILES: COc1cc(F)c(F)c(Nc2ccc(I)cc2F)c1NS(=O)(=O)C1(C[C@H](O)CO)CC1]

about 213.2 mg of microcrystalline cellulose;
about 12.0 mg of croscarmellose sodium;
about 2.4 mg of sodium lauryl sulfate; and
about 2.4 mg of magnesium stearate.

11. The pharmaceutical composition of claim 1, comprising about 20 mg of a compound of structure

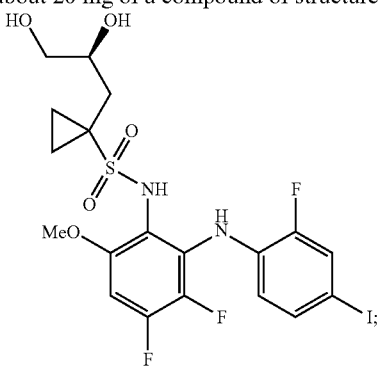

about 203.2 mg of microcrystalline cellulose;
about 12.0 mg of croscarmellose sodium;
about 2.4 mg of sodium lauryl sulfate; and
about 2.4 mg of magnesium stearate.

12. The pharmaceutical composition of claim 1, comprising about 40 mg of a compound of structure

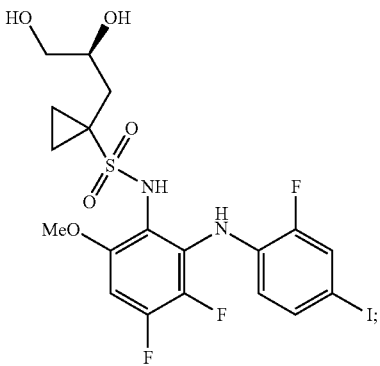 [SMILES: COc1cc(F)c(F)c(Nc2ccc(I)cc2F)c1NS(=O)(=O)C1(C[C@H](O)CO)CC1]

about 183.2 mg of microcrystalline cellulose;
about 12.0 mg of croscarmellose sodium;
about 2.4 mg of sodium lauryl sulfate; and
about 2.4 mg of magnesium stearate.

13. A method for inhibiting an MEK enzyme comprising contacting said MEK enzyme with an effective amount of a pharmaceutical composition according to claim 1 to inhibit said enzyme by at least 25%.

14. A method of treatment of a MEK mediated disorder in an individual suffering from said disorder, comprising administering to said individual an effective amount of a pharmaceutical composition according to claim 1.

15. A method for the treatment of a proliferative disease in an individual, wherein prophylaxis is excluded, comprising administering to said individual an effective amount of a pharmaceutical composition according to claim 1, wherein said proliferative disease is brain cancer, breast cancer, lung cancer, ovarian cancer, pancreatic cancer, prostate cancer, renal cancer, colorectal cancer, leukemia, myeloid leukemia, glioblastoma, follicular lymphoma, pre-B acute leukemia, chronic lymphocytic B-leukemia, stomach cancer, mesothelioma, non-small cell lung carcinoma, small cell lung cancer or liver cancer.

16. A method for the treatment of a proliferative disease in an individual, wherein prophylaxis is excluded, comprising administering to said individual an effective amount of a pharmaceutical composition according to claim 1, wherein said proliferative disease is lung cancer, pancreatic cancer, colorectal cancer, non-small cell lung carcinoma, small cell lung cancer or liver cancer.

17. A method for degrading, inhibiting the growth of or killing cancer cells comprising contacting the cells with an effective amount of a pharmaceutical composition according to claim 1 to degrade, inhibit the growth of or kill cancer cells.

18. A pharmaceutical composition according to claim 1, wherein upon administration to a subject, the compound

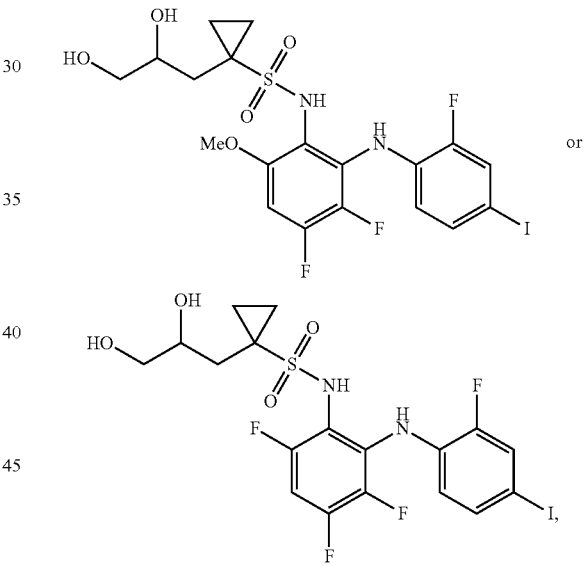

reaches a $C_{max}$ between about 0.01 µg/ml to about 1.0 µg/ml on day 1.

19. A pharmaceutical composition according to claim 1, wherein upon administration to a subject, the compound

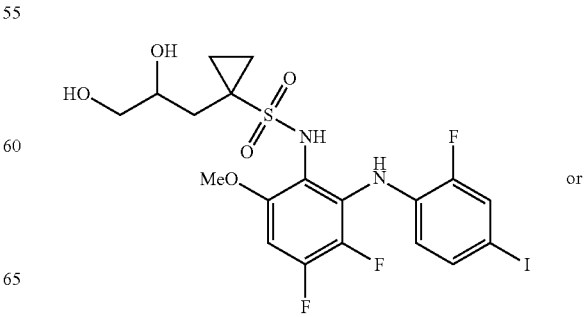

has an AUC between about 0.1 µg hr/mL to about 5.0 µg hr/mL from 0-12 hours.

20. A pharmaceutical composition according to claim 1, wherein upon administration to a subject, the compound has a T$_{max}$ between 0.5 and 5.0 hours.

21. A method for the treatment of stomach cancer, brain cancer, breast cancer, lung cancer, non small cell lung cancer, ovarian cancer, pancreatic cancer, liver cancer, prostate cancer, renal cancer, colorectal cancer or leukemia in an individual, wherein prophylaxis is excluded, comprising administering to said individual an effective amount of a pharmaceutical composition according to claim 1.

22. A method for the treatment of rheumatoid arthritis in an individual, wherein prophylaxis is excluded, comprising administering to said individual an effective amount of a pharmaceutical composition according to claim 1.

23. A pharmaceutical composition according to claim 1, wherein upon administration to a human subject, the compound reaches a C$_{max}$ between about 0.01 µg/ml to about 1.0 µg/ml on day 1.

24. A pharmaceutical composition according to claim 1, wherein upon administration to a human subject, the compound has an AUC between about 0.1 µg hr/mL to about 5.0 µg hr/mL from 0-12 hours.

25. A pharmaceutical composition according to claim 1, wherein upon administration to a human subject, the compound -continued
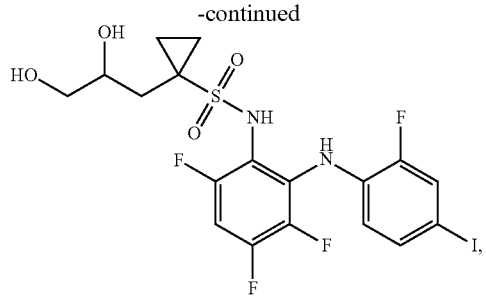
has a $T_{max}$ between 0.5 and 5.0 hours.
* * * * *

UNITED STATES PATENT AND TRADEMARK OFFICE
CERTIFICATE OF CORRECTION

PATENT NO. : 8,648,116 B2  
APPLICATION NO. : 12/671287  
DATED : February 11, 2014  
INVENTOR(S) : Jean-Michel Vernier et al.

Page 1 of 1

It is certified that error appears in the above-identified patent and that said Letters Patent is hereby corrected as shown below:

IN THE CLAIMS:

Column 300, Lines 21 - 35 (Claim 7), the structure presents as:

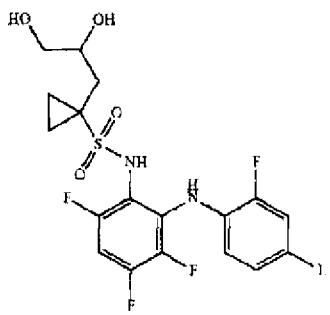

Should present as:

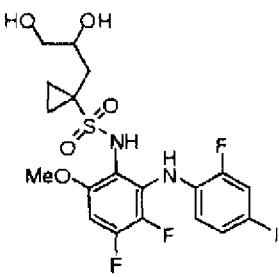

Signed and Sealed this  
Seventh Day of October, 2014

Michelle K. Lee  
*Deputy Director of the United States Patent and Trademark Office*